US010442819B2

(12) United States Patent
Fischer et al.

(10) Patent No.: US 10,442,819 B2
(45) Date of Patent: Oct. 15, 2019

(54) TRICYCLIC COMPOUNDS AS INHIBITORS OF MUTANT IDH ENZYMES

(71) Applicants: Christian Fischer, Natick, MA (US); Stephane L. Bogen, Somerset, NJ (US); Matthew L. Childers, Medfield, MA (US); Francesc Xavier Fradera Llinas, Brookline, MA (US); J. Michael Ellis, Needham, MA (US); Sara Esposite, Houston, PA (US); Qingmei Hong, Scotch Plains, NJ (US); Chunhui Huang, Arlington, MA (US); Alexander J. Kim, Eastvale, CA (US); John W. Lampe, Norfolk, MA (US); Michelle R. Machacek, Belmont, MA (US); Daniel R. McMasters, Brookline, MA (US); Ryan D. Otte, Natick, MA (US); Dann L. Parker, Jr., Cranford, NJ (US); Michael Reutershan, Brighton, MA (US); Nunzio Sciammetta, Sudbury, MA (US);
(Continued)

(72) Inventors: Christian Fischer, Natick, MA (US); Stephane L. Bogen, Somerset, NJ (US); Matthew L. Childers, Medfield, MA (US); Francesc Xavier Fradera Llinas, Brookline, MA (US); J. Michael Ellis, Needham, MA (US); Sara Esposite, Houston, PA (US); Qingmei Hong, Scotch Plains, NJ (US); Chunhui Huang, Arlington, MA (US); Alexander J. Kim, Eastvale, CA (US); John W. Lampe, Norfolk, MA (US); Michelle R. Machacek, Belmont, MA (US); Daniel R. McMasters, Brookline, MA (US); Ryan D. Otte, Natick, MA (US); Dann L. Parker, Jr., Cranford, NJ (US); Michael Reutershan, Brighton, MA (US); Nunzio Sciammetta, Sudbury, MA (US); Pengcheng P. Shao, Fanwood, NJ (US); David L. Sloman, Brookline, MA (US); Feroze Ujjainwalla, Ridgewood, NJ (US); Catherine White, Newton Center, MA (US); Zhicai Wu, Montvale, NJ (US); Yang Yu, Edison, NJ (US); Kake Zhao, Westfield, NJ (US); Craig Gibeau, Holliston, MA (US); Tesfaye Biftu, Freehold, NJ (US); Purakkattle Biju, Westwood, MA (US); Lei Chen, Basking Ridge, NJ (US); Joshua Close, Franklin, MA (US); Peter H. Fuller, Ashland, MA (US); Xianhai Huang, Warren, NJ (US); Min K. Park, Morristown, NJ (US); Valdimir Simov, Boston, MA (US); David J. Witter, Norfolk, MA (US); Hongjun Zhang, Boston, MA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 15/532,549

(22) PCT Filed: Dec. 1, 2015

(86) PCT No.: PCT/US2015/063061
§ 371 (c)(1),
(2) Date: Jun. 2, 2017

(87) PCT Pub. No.: WO2016/089797
PCT Pub. Date: Jun. 9, 2016

(65) Prior Publication Data
US 2017/0369507 A1    Dec. 28, 2017

Related U.S. Application Data

(60) Provisional application No. 62/088,262, filed on Dec. 5, 2014.

(51) Int. Cl.
*A61K 31/351* (2006.01)
*A61K 31/4353* (2006.01)
(Continued)

(52) U.S. Cl.
CPC .......... *C07D 498/08* (2013.01); *A61K 31/551* (2013.01); *C07D 471/04* (2013.01);
(Continued)

(58) Field of Classification Search
CPC .............. A61K 31/351; A61K 31/4353; A61K 31/5355; A61K 31/551; C07D 471/04; C07D 471/14
(Continued)

(56) References Cited

U.S. PATENT DOCUMENTS 6,235,900 B1   5/2001   Failli et al.
6,620,807 B1   9/2003   Steffan et al.
(Continued)

FOREIGN PATENT DOCUMENTS

WO   WO2000043398 A1   7/2000
WO   WO2003000692 A2   1/2003
(Continued)

*Primary Examiner* — Brenda L Coleman
(74) *Attorney, Agent, or Firm* — Yong Zhao; Catherine D. Fitch

(57) ABSTRACT

The present invention is directed to tricyclic compounds of formula (I) which are inhibitors of one or more mutant IDH enzymes: (I). The present invention is also directed to uses of the tricyclic compounds described herein in the potential treatment or prevention of cancers in which one or more mutant IDH enzymes are involved. The present invention is
(Continued)

also directed to compositions comprising these compounds. The present invention is also directed to uses of these compositions in the potential prevention or treatment of such cancers.

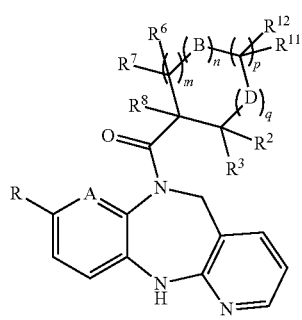

(I)

16 Claims, No Drawings

(71) Applicants: Pengcheng P. Shao, Fanwood, NJ (US); David L. Sloman, Brookline, MA (US); Feroze Ujjainwalla, Ridgewood, NJ (US); Catherine White, Newton Center, MA (US); Zhicai Wu, Montvale, NJ (US); Yang Yu, Edison, NJ (US); Kake Zhao, Westfield, NJ (US); Craig Gibeau, Holliston, MA (US); Tesfaye Biftu, Freehold, NJ (US); Purakkattle Biju, Westwood, MA (US); Lei Chen, Basking Ridge, NJ (US); Joshua Close, Franklin, MA (US); Peter H. Fuller, Ashland, MA (US); Xianhai Huang, Warren, NJ (US); Min K. Park, Morristown, NJ (US); Valdimir Simov, Boston, MA (US); David J. Witter, Norfolk, MA (US); Hongjun Zhang, Boston, MA (US)

(51) Int. Cl.
| | |
|---|---|
| *A61K 31/5355* | (2006.01) |
| *A61K 31/551* | (2006.01) |
| *C07D 471/04* | (2006.01) |
| *C07D 471/14* | (2006.01) |
| *C07D 498/08* | (2006.01) |
| *C07D 471/08* | (2006.01) |
| *C07D 498/04* | (2006.01) |
| *C07D 498/10* | (2006.01) |
| *A01N 43/00* | (2006.01) |

(52) U.S. Cl.
CPC ......... *C07D 471/08* (2013.01); *C07D 471/14* (2013.01); *C07D 498/04* (2013.01); *C07D 498/10* (2013.01); *A01N 43/00* (2013.01)

(58) Field of Classification Search
USPC .......................................... 514/220; 540/557
See application file for complete search history.

(56) References Cited

U.S. PATENT DOCUMENTS

| 7,022,699 B2 | 4/2006 | Failli et al. |
| 7,465,722 B2 | 12/2008 | Failli et al. |
| 7,790,739 B2 | 9/2010 | Lim et al. |
| 2009/0227565 A1 | 9/2009 | Failli et al. |

FOREIGN PATENT DOCUMENTS

| WO | WO2004069245 A1 | 8/2004 |
| WO | WO2006021213 | 3/2006 |
| WO | WO2006097449 | 9/2006 |
| WO | WO2009063993 A1 | 5/2009 |

TRICYCLIC COMPOUNDS AS INHIBITORS OF MUTANT IDH ENZYMES

CROSS REFERENCE TO RELATED APPLICATIONS

This application is a U.S. National Phase application under 35 U.S.C. § 371 of PCT Application No PCT/US2015/063061 filed Dec. 1, 2015, which claims priority from U.S. Provisional Application Ser. No. 62/088,262, filed Dec. 5, 2014.

BACKGROUND OF THE INVENTION

Isocitrate dehydrogenase (IDH) is a family of enzymes found in cellular metabolism. They are $NADP^+/NAD^+$ and metal dependent oxidoreductases of the enzyme class EC 1.1.1.42. The wild type proteins catalyze the oxidative decarboxylation of isocitrate to alpha-ketoglutarate, generating carbon dioxide and NADPH/NADH in the process. They are also known to convert oxalosuccinate into alpha-ketoglutarate. Mutations in IDH1 (cytosolic) and IDH2 (mitochondrial) have been identified in multiple cancer types including, but not limited to, glioma, glioblastoma multiforme, paraganglioma, supratentorial primordial neuroectodermal tumors, acute myeloid leukemia (AML), prostate cancer, thyroid cancer, colon cancer, chondrosarcoma, cholangiocarcinoma, peripheral T-cell lymphoma, and melanoma. (See L. Dang et al., Trends Mol. Med., 2010, 16, 387; T. Shibata et al., Am. J. Pathol., 2011, 178(3), 1395; Gaal et al., J. Clin. Endocrinol. Metab. 2010, 95(3), 1274; Balss et al., Acta Neuropathol., 2008, 116, 597). The mutations have been found at or near key residues in the active site: G97D, R100Q, R132H, H133Q, and A134D for IDH1, and R140 and R172 for IDH2. (See L. Dang et al., Nature, 2009, 462, 739; L. Sellner et al., Eur. J. Haematol., 2010, 85, 457).

These mutant forms of IDH are believed to have a neomorphic activity, reducing alpha-ketoglutarate to 2-hydroxyglutarate (2-HG). (See P. S. Ward et al., Cancer Cell, 2010, 17, 225) In general, production of 2-HG is enantio-specific, resulting in generation of the D-enantiomer (also known as the R enantiomer or R-2-HG). Normal cells generally have low native levels of 2-HG, whereas cells harboring these mutations in IDH1 or IDH2 show significantly elevated levels of 2-HG. High levels of 2-HG have also been detected in tumors harboring the mutations. High levels of 2-HG have been detected in the plasma of patients with mutant IDH containing AML. (See S. Gross et al., J. Exp. Med., 2010, 207(2), 339).

Mutations in IDH1 have been associated with multiple cancers and patients having these disorders often have increased levels of 2-HG in their urine, plasma or cerebrospinal fluid. (See M. Kranendijk et al., Science, 2010, 330, 336) There is a continuing need for small molecule inhibitors of mutant IDH enzymes, or more specifically IDH1 enzymes, for the treatment of diseases and disorders associated with these enzymes.

SUMMARY OF THE INVENTION

The present invention is directed to tricyclic compounds of formula (I) which are inhibitors of one or more mutant IDH enzymes. The present invention is also directed to uses of the tricyclic compounds described herein in the potential treatment or prevention of cancers in which one or more mutant IDH enzymes are involved. The present invention is also directed to compositions comprising these compounds. The present invention is further directed to uses of these compositions in the potential prevention or treatment of such cancers.

DETAILED DESCRIPTION OF THE INVENTION

Disclosed herein are compounds encompassed by formula I:

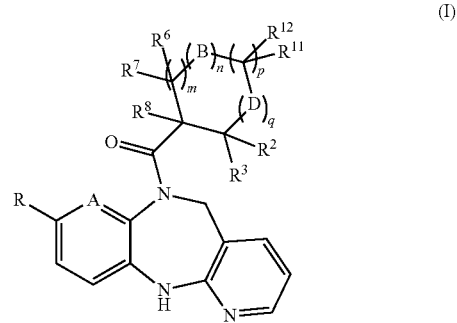

(I)

wherein A is $-C(R^1)=$ or $-N=$, and $R^1$ is hydrogen or hydroxyl;
B is $-C(R^9)(R^{10})-$, $-N(R^{10})-$, $-O-$, $-S-$ or $-S(O)_2-$;
D is $-C(R^4)(R^5)-$, $-N(R^5)-$, $-O-$ or $-S-$;
m is 0, 1 or 2; n is 0 or 1; p is 0, 1 or 2; q is 0 or 1; with the proviso that at least one of m, n, p and q is not 0;
R is selected from the group consisting of:
   (1) halogen,
   (2) $-CN$,
   (3) $-(C=O)_t-R^a$, wherein t is 0 or 1, and
   (4) $-S(O)_2R^a$;
each occurrence of $R^2$, $R^3$, $R^4$, $R^6$, $R^7$ and $R^9$ is independently selected from the group consisting of:
   (1) halogen,
   (2) $-CN$, and
   (3) $-(C=O)_t-R^a$, wherein t is 0 or 1;
each occurrence of $R^5$ and $R^{10}$ is independently selected from the group consisting of:
   (1) hydrogen,
   (2) $C_{1-6}$alkyl, optionally substituted with one to four substituents independently selected from $R^b$; and
   (3) $C_{3-7}$cycloalkyl, optionally substituted with one to four substituents independently selected from $R^b$;
$R^8$ is selected from the group consisting of:
   (1) hydrogen,
   (2) halogen,
   (3) $-CN$,
   (4) $-O-R^a$,
   (5) $-(C=O)-NR^jR^k$, wherein each of $R^j$ and $R^k$ is independently selected from the group consisting of hydrogen and $C_{1-6}$alkyl,
   (6) $C_{1-6}$alkyl, optionally substituted with one to four substituents independently selected from $R^b$,
   (7) $C_{2-6}$alkenyl, and
   (8) phenyl, optionally substituted with one to four substituents independently selected from $R^b$;
$R^{11}$ and $R^{12}$ together form an oxo; or alternatively, each occurrence of $R^{11}$ and $R^{12}$ is independently selected from the group consisting of:
   (1) halogen,
   (2) $-CN$, and
   (3) $-(C=O)_t-R^a$, wherein t is 0 or 1;

each occurrence of $R^a$ is independently selected from the group consisting of:
(1) hydrogen,
(2) —(O)$_t$—$R^d$, wherein t is 0 or 1; $R^d$ is selected from the group consisting of (a) hydrogen, (b) $C_{1-6}$alkyl, (c) $C_{3-7}$cycloalkyl, and (d) phenyl;
wherein each of the $C_{1-6}$alkyl of (b) and $C_{3-7}$cycloalkyl of (c) is optionally substituted with one to four substituents independently selected from $R^b$,
(3) —NR$^x$R$^y$, wherein each of R$^x$ and R$^y$ is independently selected from the group consisting of (a) hydrogen, (b) $C_{1-6}$alkyl, (c) $C_{3-6}$cycloalkyl, (d) —O—$C_{1-6}$alkyl, (e) phenyl optionally substituted with one to four halogens, and (f) heterocyclyl;
wherein the $C_{1-6}$alkyl of (b) is optionally substituted with one to four substituents independently selected from halogen, —O—$C_{1-4}$alkyl, $C_{3-6}$cycloalkyl, and heterocyclyl;
the $C_{3-6}$cycloalkyl of (c) is optionally substituted with one to four substituents independently selected from halogen, —O—$C_{1-4}$alkyl, $C_{3-6}$cycloalkyl, heterocyclyl, and $C_{1-4}$alkyl, which is optionally substituted with one to four halogens; and the heterocyclyl of (f) is optionally substituted with one to four substituents independently selected from halogen, $C_{1-4}$alkyl, —O—$C_{1-4}$alkyl, $C_{3-6}$cycloalkyl, and heterocyclyl,
(4) $C_{2-6}$alkenyl, optionally substituted with one to four substituents independently selected from $R^b$,
(5) $C_{5-6}$cycloalkenyl, optionally substituted with one to four substituents independently selected from $R^b$,
(6) aryl, optionally substituted with one to four substituents independently selected from $R^b$, and
(7) heterocyclyl, optionally substituted with one to four substituents independently selected from $R^b$;
each occurrence of $R^b$ is independently selected from the group consisting of:
(1) halogen,
(2) —CN,
(3) oxo,
(4) —(O)$_t$—$R^d$, wherein t is 0 or 1; $R^d$ is selected from the group consisting of (a) hydrogen, (b) $C_{1-6}$alkyl, (c) $C_{3-7}$cycloalkyl, and (d) heterocyclyl;
wherein the $C_{1-6}$alkyl of (b) is optionally substituted with one to four substituents independently selected from (i) halogen, (ii) hydroxyl, (iii) —O—$C_{1-6}$alkyl, (iv) $C_{3-6}$cycloalkyl optionally substituted with 1-3 halogens, (v) —NR$^x$R$^y$, wherein each of R$^x$ and R$^y$ is independently selected from the group consisting of hydrogen, $C_{1-6}$alkyl, $C_{3-6}$cycloalkyl, phenyl optionally substituted with one to four halogens, and heterocyclyl, and (vi) heterocyclyl;
the $C_{3-7}$cycloalkyl of (c) is optionally substituted with one to four substituents independently selected from (i) halogen, and (ii) $C_{1-6}$alkyl, which is optionally substituted with one to four halogens, and (iii) —CN; and
the heterocyclyl of (d) is optionally substituted with one to four substituents independently selected from (i) halogen, (ii) hydroxyl, (iii) oxo, (iv) $C_{1-6}$alkyl optionally substituted with one to four halogens, (v) —O—$C_{1-6}$alkyl, (vi) heterocyclyl optionally substituted with halogen or hydroxyl, and (vii) —NR$^j$R$^k$, wherein each of R$^j$ and R$^k$ is independently selected from the group consisting of hydrogen and $C_{1-6}$alkyl;
(5) —(C=O)$_t$—$R^c$, wherein t is 0 or 1; $R^c$ is selected from the group consisting of hydrogen, hydroxyl, $C_{1-6}$alkyl, $C_{2-6}$alkenyl, —O—$C_{1-6}$alkyl, —NR$^x$R$^y$, and heterocyclyl;
wherein each of R$^x$ and R$^y$ is independently selected from the group consisting of (a) hydrogen, (b) $C_{1-6}$alkyl, (c) $C_{2-6}$alkenyl, (d) $C_{3-6}$cycloalkyl, (e) phenyl optionally substituted with one to four halogens, and (f) heterocyclyl;
wherein the $C_{1-6}$alkyl of (b) is optionally substituted with one to four substituents independently selected from halogen, —O—$C_{1-4}$alkyl, $C_{3-6}$cycloalkyl, heterocyclyl, and —(C=O)—NR$^j$R$^k$, wherein each of R$^j$ and R$^k$ is independently hydrogen or $C_{1-6}$alkyl;
the $C_{3-6}$cycloalkyl of (d) is optionally substituted with one to four substituents independently selected from halogen and $C_{1-4}$alkyl, which is optionally substituted with one to four halogens; and
the heterocyclyl of (f) is optionally substituted with one to four substituents independently selected from halogen, —CN, $C_{1-6}$alkyl, and —O—$C_{1-6}$alkyl;
(6) —(P=O)R$^j$R$^k$, wherein each of R$^j$ and R$^k$ is independently hydrogen or $C_{1-6}$alkyl,
(7) $C_{2-6}$alkenyl, and
(8) phenyl, optionally substituted with one to four substituents independently selected from halogen, $C_{1-6}$alkyl, and —O—$C_{1-6}$alkyl;
or pharmaceutically acceptable salts thereof.
In an embodiment of the previous embodiment, compounds disclosed herein are of formula (Ia):

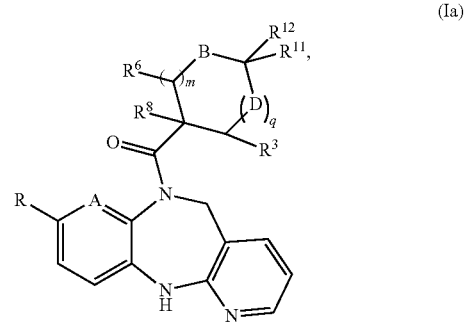

(Ia)

or a pharmaceutically acceptable salt thereof, wherein $R^3$, $R^6$, $R^8$, $R^{11}$, $R^{12}$, A, B, R, m and q are as previously described for formula (I).
In an embodiment of each previous embodiment of formula (I) and (Ia),
A is —CH= or —N=;
B is —CH(R$^9$)—, —O— or —N(R$^{10}$)—;
D is —CH(R$^5$)— or —N(R$^5$)—;
m is 0, 1 or 2; q is 0 or 1; and
$R^8$ is selected from the group consisting of hydrogen, $C_{1-4}$alkyl, —CN, and phenyl.
In an embodiment of each previous embodiment of formula (I) and (Ia), R is selected from the group consisting of:
(1) hydrogen,
(2) halogen,
(3) —CN,
(4) —S(O)$_2$—R$^f$, wherein R$^f$ is selected from the group consisting of (a) hydrogen, (b) $C_{1-4}$alkyl, (c) $C_{3-6}$cycloalkyl, (d) phenyl and (e) heterocyclyl;
wherein the $C_{1-4}$alkyl of (a) is optionally substituted with —NH$_2$ or —NH($C_{1-6}$alkyl); and each of the $C_{3-6}$cycloalkyl of (b), phenyl of (c) and heterocyclyl of (d) is optionally substituted with one to three substituents independently selected from halogen and $C_{1-4}$alkyl;

(5) —(C=O)$_t$—$R^h$, wherein t is 0 or 1; and $R^h$ is selected from the group consisting of (a) hydrogen, (b) $C_{1-6}$alkyl, (c) $C_{2-6}$alkenyl, (d) $C_{3-6}$cycloalkyl, (e) $C_{5-6}$cycloalkenyl, and (f) —O—$C_{1-6}$alkyl;

wherein the $C_{1-6}$alkyl of (a) is optionally substituted with one to four substituents independently selected from halogen, —CN, $C_{3-6}$cycloalkyl, —$OR^d$, —(C=O)—$R^e$, —$NR^xR^y$, and heterocyclyl optionally substituted with one to four substituents independently selected from halogen and $C_{1-6}$alkyl; wherein $R^d$ is hydrogen or $C_{1-4}$alkyl optionally substituted with heterocyclyl; $R^e$ is hydrogen, hydroxyl or heterocyclyl;

each of $R^x$ and $R^y$ is independently selected from the group consisting of (a) hydrogen, (b) $C_{1-6}$alkyl, which is optionally substituted with one to four substituents independently selected from halogen, —O—$C_{1-4}$alkyl, $C_{3-6}$cycloalkyl, and heterocyclyl, (c) $C_{3-6}$cycloalkyl, which is optionally substituted with one to four substituents independently selected from halogen and $C_{1-4}$alkyl, which is optionally substituted with one to four halogens, (d) phenyl, which is optionally substituted with one to four halogens, and (e) heterocyclyl;

the $C_{3-6}$cycloalkyl of (c) is optionally substituted with one to four substituents independently selected from halogen and $C_{1-4}$alkyl;

the $C_{5-6}$cycloalkenyl of (d) is optionally substituted with one to four substituents independently selected from halogen and —CN; and the —O—$C_{1-6}$alkyl of (e) is optionally substituted with one to four substituents independently selected from halogen and —CN;

(6) —(C=O)$_t$—$NR^xR^y$, wherein t is 0 or 1; each of $R^x$ and $R^y$ is independently selected from the group consisting of (a) hydrogen, (b) $C_{1-6}$alkyl, (c) $C_{3-6}$cycloalkyl, (d) —O—$C_{1-6}$alkyl, (e) phenyl, which is optionally substituted with one to four halogens, and (f) heterocyclyl, which is optionally substituted with $C_{1-4}$alkyl; wherein the $C_{1-6}$alkyl of (b) is optionally substituted with one to four substituents independently selected from halogen, —O—$C_{1-4}$alkyl, $C_{3-6}$cycloalkyl, and heterocyclyl; and the $C_{3-6}$cycloalkyl of (c) is optionally substituted with one to four substituents independently selected from halogen and $C_{1-4}$alkyl which is optionally substituted with one to four halogens, (7) aryl, optionally substituted with one to four substituents independently selected from halogen, $C_{1-6}$alkyl, and —O—$C_{1-6}$alkyl, and (8) —(C=O)$_t$-heterocyclyl, wherein t is 0 or 1; and the heterocyclyl is optionally substituted with one to four substituents independently selected from $R^b$.

In an embodiment of each previous embodiment of formula (I) and (Ia), R is selected from the group consisting of:
(1) hydrogen,
(2) halogen,
(3) —CN,
(4) —S(O)$_2$—$R^f$, wherein $R^f$ is selected from the group consisting of (a) $C_{1-4}$alkyl optionally substituted with —NH$_2$, (b) $C_{3-6}$cycloalkyl, and (c) phenyl optionally substituted with one to three halogens,
(5) $C_{1-6}$alkyl, optionally substituted with one to four substituents independently selected from (a) halogen, (b) —CN, (c) —$OR^d$, (d) —(C=O)—$R^e$, (e) —$NR^xR^y$, and (f) heterocyclyl; wherein $R^d$ is hydrogen or $C_{1-4}$alkyl optionally substituted with heterocyclyl; $R^e$ is hydroxyl or heterocyclyl;

each of $R^x$ and $R^y$ is independently selected from the group consisting of hydrogen, $C_{1-6}$alkyl, $C_{3-6}$cycloalkyl, and heterocyclyl; wherein the $C_{1-6}$alkyl is optionally substituted with one to four substituents independently selected from halogen, —O—$C_{1-4}$alkyl, $C_{3-6}$cycloalkyl, and heterocyclyl; and the $C_{3-6}$cycloalkyl is optionally substituted with one to four substituents independently selected from halogen and $C_{1-4}$alkyl optionally substituted with one to four halogens; and the heterocyclyl of (f) is optionally substituted with one to three substituents independently selected from halogen and $C_{1-6}$alkyl, (6) —O—$C_{1-6}$alkyl,
(7) $C_{5-6}$cycloalkenyl, optionally substituted with —CN,
(8) —(C=O)$_t$—$NR^xR^y$, wherein t is 0 or 1; each of $R^x$ and $R^y$ is independently selected from the group consisting of (a) hydrogen, (b) $C_{1-6}$alkyl, (c) $C_{3-6}$cycloalkyl, (d) —O—$C_{1-6}$alkyl, (e) phenyl optionally substituted with one to four halogens, and (f) heterocyclyl optionally substituted with $C_{1-4}$alkyl; wherein the $C_{1-6}$alkyl of (b) is optionally substituted with one to four substituents independently selected from halogen, —O—$C_{1-4}$alkyl, $C_{3-6}$cycloalkyl, and heterocyclyl; and the $C_{3-6}$cycloalkyl of (c) is optionally substituted with one to four substituents independently selected from halogen and $C_{1-4}$alkyl optionally substituted with one to four halogens,
(9) phenyl, optionally substituted with one to four halogens, and
(10) —(C=O)$_t$-heterocyclyl, wherein t is 0 or 1; and the heterocyclyl is optionally substituted with one to four substituents independently selected from $R^b$.

In an embodiment of each previous embodiment of formula (I) and (Ia), R is selected from the group consisting of:
(1) hydrogen,
(2) halogen,
(3) —CN,
(4) —S(O)$_2$—$R^f$, wherein $R^f$ is selected from the group consisting of (a) $C_{1-4}$alkyl optionally substituted with —NH$_2$, (b) $C_{3-6}$cycloalkyl, and (c) phenyl optionally substituted with one to three halogens;
(5) $C_{1-6}$alkyl, optionally substituted with one to four substituents independently selected from (a) halogen, (b) —CN, (c) —$OR^d$, (d) —(C=O)—$R^e$, (e) —$NR^xR^y$, and (f) heterocyclyl; wherein $R^d$ is hydrogen or $C_{1-4}$alkyl optionally substituted with heterocyclyl; $R^e$ is hydroxyl or heterocyclyl;

each of $R^x$ and $R^y$ is independently selected from the group consisting of hydrogen, $C_{1-6}$alkyl, and $C_{3-6}$cycloalkyl; wherein the $C_{3-6}$cycloalkyl is optionally substituted with one to four substituents independently selected from halogen and $C_{1-4}$alkyl optionally substituted with one to four halogens; and the heterocyclyl of (f) is optionally substituted with one to three substituents independently selected from halogen and $C_{1-6}$alkyl;

(6) —O—$C_{1-6}$alkyl,
(7) —$NR^xR^y$, wherein each of $R^x$ and $R^y$ is independently selected from the group consisting of (a) hydrogen, (b) $C_{1-6}$alkyl, (c) $C_{3-6}$cycloalkyl, (d) —O—$C_{1-6}$alkyl, (e) phenyl optionally substituted with one to four halogens, and (f) heterocyclyl optionally substituted with $C_{1-4}$alkyl; wherein the $C_{1-6}$alkyl of (b) is optionally substituted with one to four substituents independently selected from halogen, —O—$C_{1-4}$alkyl, $C_{3-6}$cycloalkyl, and heterocyclyl;
(8) —(C=O)—$NR^xR^y$, wherein each of $R^x$ and $R^y$ is independently selected from the group consisting of (a) hydrogen, (b) $C_{1-6}$alkyl, and (c) phenyl optionally substituted with one to three halogens,
(9) —(C=O)-heterocyclyl, wherein the heterocyclyl is optionally substituted with one to four substituents independently selected from halogen and $C_{1-6}$alkyl, and
(10) heterocyclyl, which is optionally substituted with one to four substituents independently selected from (a) halogen, (b) hydroxyl, (c) —CN, (d) oxo, (e) $C_{1-6}$alkyl optionally substituted with one to four substituents independently selected from halogen, —O—$C_{1-6}$alkyl, and heterocyclyl, (f) —O—$C_{1-6}$alkyl, (g) —(C=O)—$NH_2$, (h) —(C=O)—O—$C_{1-6}$alkyl, (i) —(C=O)—$C_{2-6}$alkenyl, (j) $C_{3-6}$cycloalkyl optionally substituted with one to four halogens, (k) —$NR^jR^k$, wherein each of $R^j$ and $R^k$ is independently selected from hydrogen and $C_{1-6}$alkyl optionally substituted with —(C=O)—N($C_{1-6}$alkyl)($C_{1-6}$alkyl), (l) phenyl optionally substituted with halogen or —O—$C_{1-6}$alkyl, and (m) heterocyclyl optionally substituted with halogen or $C_{1-6}$alkyl.

In an embodiment of each previous embodiment of formula (I) and (Ia), each occurrence of $R^3$, $R^4$, $R^6$, $R^7$ and $R^9$, when present, is independently selected from the group consisting of:
(1) hydrogen,
(2) halogen,
(3) —O—$C_{1-6}$alkyl, optionally substituted with one to four substituents independently selected from $R^b$,
(4) —O—$C_{3-6}$cycloalkyl, optionally substituted with one to four substituents independently selected from $R^b$,
(5) —$NR^xR^y$, wherein each of $R^x$ and $R^y$ is independently selected from the group consisting of (a) hydrogen, (b) $C_{1-6}$alkyl, (c) $C_{3-6}$cycloalkyl, (d) phenyl optionally substituted with one to four halogens, and (e) heterocyclyl;
wherein the $C_{1-6}$alkyl of (b) is optionally substituted with one to four substituents independently selected from halogen, —O—$C_{1-4}$alkyl, $C_{3-6}$cycloalkyl, and heterocyclyl; and
the $C_{3-6}$cycloalkyl of (c) is optionally substituted with one to four substituents independently selected from halogen and $C_{1-4}$alkyl, which is optionally substituted with one to four halogens,
(6) $C_{1-6}$alkyl, optionally substituted with one to four substituents independently selected from $R^b$,
(7) $C_{3-7}$cycloalkyl, optionally substituted with one to four substituents independently selected from $R^b$,
(8) —(C=O)—O—$C_{1-6}$alkyl,
(9) phenyl, optionally substituted with one to four halogens, and
(10) heterocyclyl, optionally substituted with one to four substituents independently selected from $R^b$.

In an embodiment of each previous embodiment of formula (I) and (Ia), each occurrence of $R^3$, $R^4$, $R^6$, $R^7$ and $R^9$, when present, is independently selected from the group consisting of:
(1) hydrogen,
(2) —O—$C_{1-6}$alkyl,
(3) $C_{1-6}$alkyl, optionally substituted with one to four halogens,
(4) $C_{3-7}$cycloalkyl,
(5) —(C=O)—O—$C_{1-6}$alkyl, and
(6) phenyl, optionally substituted with one to four halogens.

In an embodiment of each previous embodiment of formula (I) and (Ia), each occurrence of $R^5$ and $R^{10}$, when present, is independently selected from the group consisting of:
(1) hydrogen,
(2) $C_{1-4}$alkyl, optionally substituted with one to three halogens; and
(3) $C_{3-7}$cycloalkyl, optionally substituted with one to three halogens.

In an embodiment of each previous embodiment of formula (I) and (Ia), $R^8$ is selected from the group consisting of:
(1) hydrogen,
(2) —CN,
(3) $C_{1-4}$alkyl, optionally substituted with one to four substituents independently selected from halogen and —O—$C_{1-4}$alkyl; and
(4) phenyl.

In an embodiment of each previous embodiment of formula (I) and (Ia), $R^{11}$ and $R^{12}$ together form an oxo; or alternatively, each occurrence of $R^{11}$ and $R^{12}$ is independently selected from the group consisting of:
(1) hydrogen,
(2) halogen,
(3) —O—$C_{1-6}$alkyl, optionally substituted with one to four substituents independently selected from $R^b$,
(4) —O—$C_{3-6}$cycloalkyl, optionally substituted with one to four substituents independently selected from $R^b$,
(5) —$NR^xR^y$, wherein each of $R^x$ and $R^y$ is independently selected from the group consisting of (a) hydrogen, (b) $C_{1-6}$alkyl, (c) $C_{3-6}$cycloalkyl, (d) phenyl optionally substituted with one to four halogens, and (e) heterocyclyl;
wherein the $C_{1-6}$alkyl of (b) is optionally substituted with one to four substituents independently selected from halogen, —O—$C_{1-4}$alkyl, $C_{3-6}$cycloalkyl, and heterocyclyl; and
the $C_{3-6}$cycloalkyl of (c) is optionally substituted with one to four substituents independently selected from halogen and $C_{1-4}$alkyl, which is optionally substituted with one to four halogens,
(6) $C_{1-6}$alkyl, optionally substituted with one to four substituents independently selected from $R^b$,
(7) $C_{3-7}$cycloalkyl, optionally substituted with one to four substituents independently selected from $R^b$,
(8) —CN,
(9) hydroxyl,
(10) —(C=O)—$C_{1-6}$alkyl,
(11) $C_{2-6}$alkenyl,
(12) phenyl, optionally substituted with one to four halogens; and
(13) heterocyclyl, optionally substituted with one to four substituents independently selected from $R^b$.

In an embodiment of each previous embodiment of formula (I) and (Ia), $R^{11}$ and $R^{12}$ together form an oxo; or alternatively, each occurrence of $R^{11}$ and $R^{12}$ is independently selected from the group consisting of:
(1) hydrogen,
(2) halogen,
(3) —O—$C_{1-6}$alkyl, optionally substituted with one to three halogens,
(4) —O—$C_{3-6}$cycloalkyl, optionally substituted with one to three halogens,
(5) —$NR^xR^y$, wherein each of $R^x$ and $R^y$ is independently selected from the group consisting of (a) hydrogen, (b)

$C_{1-6}$alkyl, (c) $C_{3-6}$cycloalkyl, (d) phenyl optionally substituted with one to four halogens, and (e) heterocyclyl;
  wherein the $C_{1-6}$alkyl of (b) is optionally substituted with one to four substituents independently selected from halogen, —O—$C_{1-4}$alkyl, $C_{3-6}$cycloalkyl, and heterocyclyl; and
  the $C_{3-6}$cycloalkyl of (c) is optionally substituted with one to four substituents independently selected from halogen and $C_{1-4}$alkyl, which is optionally substituted with one to four halogens,
(6) $C_{1-6}$alkyl, optionally substituted with one to four substituents independently selected from (a) halogen, (b) hydroxyl, (c) —O—$C_{1-4}$alkyl, (d) $C_{3-6}$cycloalkyl, and (e) —NR$^x$R$^y$, wherein each of R$^x$ and R$^y$ is independently selected from the group consisting of hydrogen, $C_{1-6}$alkyl, $C_{3-6}$cycloalkyl, phenyl optionally substituted with one to four halogens, and heterocyclyl,
(7) —CN,
(8) hydroxyl,
(9) —(C=O)—$C_{1-6}$alkyl,
(10) $C_{2-6}$alkenyl,
(11) phenyl; optionally substituted with one to four halogens; and
(12) heterocyclyl, optionally substituted with one to four substituents independently selected from R$^b$.

In an embodiment of each previous embodiment of formula (I) and (Ia), R$^{11}$ and R$^{12}$ together form an oxo; or alternatively, each occurrence of R$^{11}$ and R$^{12}$ is independently selected from the group consisting of:
(1) hydrogen,
(2) halogen,
(3) —O—$C_{1-6}$alkyl, optionally substituted with one to three halogens,
(4) —O—$C_{3-6}$cycloalkyl, optionally substituted with one to three halogens,
(5) —NR$^x$R$^y$, wherein each of R$^x$ and R$^y$ is independently selected from the group consisting of (a) hydrogen, (b) $C_{1-6}$alkyl, and (c) $C_{3-6}$cycloalkyl;
  wherein the $C_{1-6}$alkyl of (b) is optionally substituted with one to four substituents independently selected from halogen, —O—$C_{1-6}$alkyl, and $C_{3-6}$cycloalkyl; and
  the $C_{3-6}$cycloalkyl of (c) is optionally substituted with one to four substituents independently selected from halogen and $C_{1-4}$alkyl, which is optionally substituted with one to four halogens,
(6) $C_{1-6}$alkyl, optionally substituted with one to four substituents independently selected from halogen, hydroxyl, —O—$C_{1-6}$alkyl, and $C_{3-6}$cycloalkyl,
(7) —CN,
(8) hydroxyl,
(9) —(C=O)—$C_{1-6}$alkyl,
(10) $C_{2-6}$alkenyl,
(11) phenyl, and
(12) heterocyclyl, optionally substituted with one to four substituents independently selected from halogen and $C_{1-6}$alkyl.

In an embodiment of each previous embodiment of formula (I) and (Ia), each occurrence of R$^b$ is independently selected from the group consisting of:
(1) halogen,
(2) hydroxyl,
(3) —CN,
(4) oxo,
(5) —O—$C_{1-6}$alkyl, wherein the alkyl is optionally substituted with one to four substituents independently selected from halogen and $C_{3-6}$cycloalkyl,
(6) $C_{1-6}$alkyl, optionally substituted with one to four substituents independently selected from (a) halogen, (b) hydroxyl, (c) —O—$C_{1-4}$alkyl, (d) $C_{3-6}$cycloalkyl, and (e) —NR$^x$R$^y$, wherein each of R$^x$ and R$^y$ is independently selected from the group consisting of hydrogen, $C_{1-6}$alkyl, $C_{3-6}$cycloalkyl, phenyl optionally substituted with one to four halogens, and heterocyclyl,
(7) $C_{3-7}$cycloalkyl, optionally substituted with one to four substituents independently selected from halogen and $C_{1-6}$alkyl,
(8) phenyl, optionally substituted with one to four halogens, and
(9) heterocyclyl, optionally substituted with one to four substituents independently selected halogen, $C_{1-6}$alkyl, and —O—$C_{1-6}$alkyl.

In an embodiment of each previous embodiment of formula (I) and (Ia), each occurrence of the heterocyclyl is independently a monocyclic or bicyclic saturated, partially unsaturated or aromatic ring moiety having at least one ring heteroatom and at least one ring carbon atom, wherein the heteroatom is selected from the group consisting of oxygen, sulfur, and nitrogen; and wherein the bicyclic ring moiety is a fused, spirocycle or bridged bicyclic ring moiety.

In an embodiment of each previous embodiment of formula (I) and (Ia), each occurrence of the heterocyclyl is independently a monocyclic saturated, partially unsaturated or aromatic 3-7 membered ring moiety having at least one ring heteroatom and at least one ring carbon atom, wherein the heteroatom is selected from the group consisting of oxygen, sulfur, and nitrogen.

In an embodiment of each previous embodiment of formula (I) and (Ia), each occurrence of the heterocyclyl is independently a 7-12 membered fused bicyclic ring moiety, wherein: a 4-6 membered heterocyclic ring comprising 1-4 heteroatoms selected from oxygen, sulfur and nitrogen and a 5-7 membered heterocyclic ring comprising 1-4 heteroatoms selected from oxygen, sulfur and nitrogen are connected through two ring atoms; or alternatively, a 4-6 membered heterocyclic ring comprising 1-4 heteroatoms selected from oxygen, sulfur and nitrogen and a $C_{5-10}$ carbocyclic ring are connected through two ring carbon atoms.

In an embodiment of each previous embodiment of formula (I) and (Ia), each occurrence of the heterocyclyl is independently a 7-12 membered spirocycle ("spiro") bicyclic moiety, wherein two 3-7 membered rings are connected through one common ring atom, and either or both of the 3-7 membered rings comprise at least one heteroatom selected from oxygen, sulfur and nitrogen.

In an embodiment of each previous embodiment of formula (I) and (Ia), each occurrence of the heterocyclyl is independently selected from the group consisting of: 8-azabicyclo[3.2.1]octanyl, 2-azaspiro[3.3]heptanyl, azaindolyl, azetidinyl, 2,5-diazabicyclo[2.2.2]octanyl, 1,6-diazaspiro[3.3]heptanyl, 2,6-diazaspiro[3.3]heptanyl, 2,3-dihydro-1,4-dioxinyl, 3,6-dihydro-pyranyl, 3,4-dihydro-2H-pyrido[3,2-b][1,4]oxazinyl, 5,6-dihydro-4H-pyrrolo[1,2-b]pyrazolyl, 3,9-dioxa-7-azabicyclo[3.3.1]nonanyl, 2,5-dioxabicyclo[4.1.0]heptanyl, 1,4-dioxanyl, hexahydro-1H-furo[3,4-c]pyrrolyl, 1,2,4,5,6,6a-hexahydropyrrolo[3,4-b]pyrrolyl, imidazolyl, 1H-imidazo[4,5-b]pyridinyl, isoindolinyl, isoxazolyl, morpholinyl, octahydrocyclopenta[1,4]oxazinyl, octahydro-1H-imidazo[4,5-c]pyridinyl, 2-oxa-5-azabicyclo[2.2.1]heptanyl, 3-oxa-6-azabicyclo

[3.2.0]heptanyl, 6-oxa-3-azabicyclo[3.1.1]heptanyl, 2-oxa-5-azabicyclo[2.2.2]octanyl, 3-oxa-8-azabicyclo[3.2.1]octanyl, 8-oxa-3-azabicyclo[3.2.1]octanyl, 1-oxa-8-azaspiro[4.5]decanyl, 2-oxa-6-azaspiro[3.3]heptanyl, 4-oxa-7-azaspiro[2.5]octanyl, 6-oxa-2-azaspiro[3.4]octanyl, 7-oxa-2,5-diazaspiro[3.4]octanyl, 3-oxa-1,7-diazaspiro[4.4]nonanyl, 1,4-oxazepanyl, oxazolidinyl, oxetanyl, piperazinyl, piperidinyl, pyrazolo[1,5-b]pyridazinyl, pyrazolyl, pyridazinyl, pyridinyl, pyrimidinyl, pyrrolidinyl, pyrrolyl, tetrahydrofuranyl, 5,6,7,8-tetrahydroimidazo[1,5-a]pyrazinyl, tetrahydropyranyl, 4,5,6,7-tetrahydropyrazolo[1,5-a]pyrazinyl, 4,5,6,7-tetrahydro-2H-pyrazolo[4,3-c]pyridinyl, 1,2,3,6-tetrahydropyridinyl, 1,2,3,4-tetrahydropyrrolo[1,2-a]pyrazinyl, 4,5,6,7-tetrahydro-[1,2,3]triazolo[1,5-a]pyrazinyl, 5,6,7,8-tetrahydro-[1,2,4]triazolo[4,3-a]pyrazinyl, 5,6,7,8-tetrahydro-[1,2,4]triazolo[1,5-a]pyrazinyl, thiazolyl, and thiophenyl.

In an embodiment of each previous embodiment of formula (I) and (Ia), a compound is of formula (Ib):

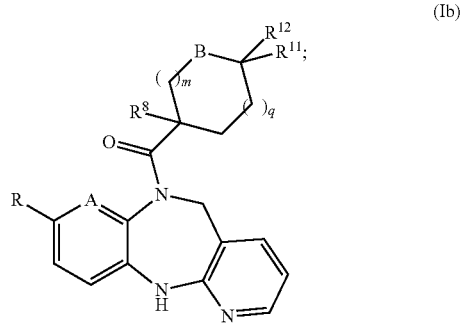

(Ib)

wherein A is —CH= or —N=;
B is —CH($R^9$)—, —O— or —N($R^{10}$)—;
m is 0, 1 or 2;
q is 0 or 1;
R is selected from the group consisting of:
(1) hydrogen;
(2) halogen;
(3) $C_{1-6}$alkyl, optionally substituted with one to three substituents independently selected from halogen, —$OR^d$, —CN, —(C=O)—$R^e$, —$NR^xR^y$, and heterocyclyl optionally substituted with $C_{1-4}$alkyl; wherein Rd is hydrogen or $C_{1-4}$alkyl optionally substituted with heterocyclyl; $R^e$ is hydroxyl or heterocyclyl; each of $R^x$ and $R^y$ is independently selected from the group consisting of (a) hydrogen, (b) $C_{1-6}$alkyl, (c) $C_{3-6}$cycloalkyl, (d) phenyl optionally substituted with one to four halogens, and (e) heterocyclyl;
wherein the $C_{1-6}$alkyl of (b) is optionally substituted with one to four substituents independently selected from halogen, —O—$C_{1-4}$alkyl, $C_{3-6}$cycloalkyl, and heterocyclyl; and
the $C_{3-6}$cycloalkyl of (c) is optionally substituted with one to four substituents independently selected from halogen and $C_{1-4}$alkyl, which is optionally substituted with one to four halogens;
(4) —(C=O)$_t$—$NR^xR^y$, wherein t is 0 or 1; each of $R^x$ and $R^y$ is independently selected from the group consisting of hydrogen, $C_{1-6}$alkyl, $C_{3-6}$cycloalkyl, phenyl optionally substituted with one to four halogens, and heterocyclyl; wherein each of the alkyl, cycloalkyl and heterocyclyl is optionally substituted with one to four substituents independently selected from halogen, —O—$C_{1-4}$alkyl, $C_{3-6}$cycloalkyl, and heterocyclyl; and
(5) —(C=O)$_t$-heterocyclyl, wherein t is 0 or 1; and the heterocyclyl is optionally substituted with one to four substituents independently selected from $R^b$;
each of $R^4$, $R^9$, $R^{11}$ and $R^{12}$ is independently selected from the group consisting of:
(1) hydrogen;
(2) halogen;
(3) —(O)$_t$—$R^d$, wherein t is 0 or 1; $R^d$ is (a) $C_{1-6}$alkyl or (b) $C_{3-6}$cycloalkyl, the alkyl of (a) is optionally substituted with one to four substituents independently selected from halogen, hydroxyl, —O—$C_{1-4}$alkyl and $C_{3-6}$cycloalkyl; and the cycloalkyl of (b) is optionally substituted with one to three halogens;
(4) —$NR^xR^y$, wherein each of $R^x$ and $R^y$ is independently selected from the group consisting of (a) hydrogen, (b) $C_{1-6}$alkyl, (c) $C_{3-6}$cycloalkyl, (d) phenyl optionally substituted with one to four halogens, and (e) heterocyclyl;
wherein the $C_{1-6}$alkyl of (b) is optionally substituted with one to four substituents independently selected from halogen, —O—$C_{1-4}$alkyl, $C_{3-6}$cycloalkyl, and heterocyclyl; and
the $C_{3-6}$cycloalkyl of (c) is optionally substituted with one to four substituents independently selected from halogen and $C_{1-4}$alkyl, which is optionally substituted with one to four halogens;
(5) phenyl; and
(6) —(C=O)$_t$-heterocyclyl, wherein t is 0 or 1; and the heterocyclyl is optionally substituted with one to four substituents independently selected from $R^b$;
$R^8$ is hydrogen or $C_{1-4}$alkyl;
$R^{10}$ is selected from the group consisting of:
(1) hydrogen,
(2) $C_{1-4}$alkyl, optionally substituted with one to three halogens; and
(3) $C_{3-7}$cycloalkyl, optionally substituted with one to three halogens;
each occurrence of $R^b$ is independently selected from the group consisting of:
(1) halogen;
(2) hydroxyl;
(3) —CN;
(4) oxo;
(5) —O—$C_{1-6}$alkyl, wherein the alkyl is optionally substituted with one to four substituents independently selected from halogen and $C_{3-6}$cycloalkyl;
(6) —(C=O)$_t$—$C_{1-6}$alkyl, wherein t is 0 or 1; and the alkyl is optionally substituted with one to four substituents independently selected from halogen, —O—$C_{1-6}$alkyl, and heterocycle; and
(7) —(C=O)$_t$-heterocyclyl, wherein t is 0 or 1; and the heterocyclyl is optionally substituted with one to four substituents independently selected from halogen, —CN, $C_{1-6}$alkyl, and —O—$C_{1-6}$alkyl; and
wherein each occurrence of the heterocyclyl in this claim is independently selected from the group consisting of azaindolyl, azetidinyl, 1,4-dioxanyl, imidazolyl, isoindolinyl, morpholinyl, oxazolidinyl, oxetanyl, piperazinyl, piperidinyl, pyrazolyl, pyridinyl, pyrimidinyl, pyrrolidinyl, tetrahydrofuranyl, tetrahydropyranyl, thiazolyl, 2-azaspiro[3.3]heptanyl, 2,5-diazabicyclo[2.2.2]octanyl, 1,6-diazaspiro[3.3]heptanyl, 2,6-diazaspiro[3.3]heptanyl, 2,3-dihydro-1,4-dioxinyl, 2,5-dioxabicyclo[4.1.0]heptanyl, 2-oxa-5-azabicyclo[2.2.2]octanyl, 1-oxa-8-azaspiro[4.5]decanyl, 2-oxa-6-azaspiro[3.3]heptanyl, 4-oxa-7-azaspiro[2.5]octanyl, 6-oxa-2-azaspiro[3.4]octanyl, 7-oxa-2,5-diazaspiro [3.4]octanyl, 3-oxa-1,7-diazaspiro[4.4]nonanyl, 3,6-dihydro-pyranyl, 3,4-dihydro-2H-pyrido[3,2-b][1,4]oxazinyl, 5,6-dihydro-4H-pyrrolo[1,2-b]pyrazolyl, hexahydro-1H-furo[3,4-c]pyrrolyl, 1,2,4,5,6,6a-hexahydropyrrolo[3,4-b] pyrrolyl, 1H-imidazo[4,5-b]pyridinyl, octahydrocyclopenta [1,4]oxazinyl, octahydro-1H-imidazo[4,5-c]pyridinyl, 3-oxa-6-azabicyclo[3.2.0]heptanyl, pyrazolo[1,5-b] pyridazinyl, 5,6,7,8-tetrahydroimidazo[1,5-a]pyrazinyl, 4,5, 6,7-tetrahydropyrazolo[1,5-a]pyrazinyl, 4,5,6,7-tetrahydro-2H-pyrazolo[4,3-c]pyridinyl, 1,2,3,4-tetrahydropyrrolo[1,2-a]pyrazinyl, 4,5,6,7-tetrahydro-[1,2,3]triazolo[1,5-a] pyrazinyl, 5,6,7,8-tetrahydro-[1,2,4]triazolo[4,3-a] pyrazinyl, and 5,6,7,8-tetrahydro-[1,2,4]triazolo[1,5-a] pyrazinyl;
or a pharmaceutically acceptable salt thereof.

In one embodiment, a compound is of formula (Ib):

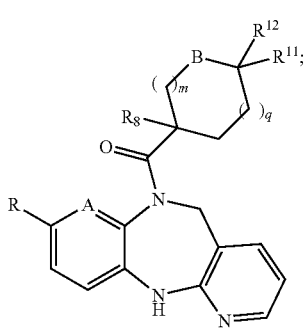

(Ib)

wherein
A is —CH═ or —N═;
B is —CH($R^9$)— or —O— or —N($R^{10}$)—;
m is 0, 1 or 2;
q is 0 or 1;
R is selected from the group consisting of:
 (1) hydrogen,
 (2) halogen,
 (3) $C_{1-4}$alkyl, which is optionally substituted with one to three substituents independently selected from halogen, —OH, —O—$C_{1-4}$alkyl, and —CN, and
 (4) heterocyclyl, which is optionally substituted with one to three substituents independently selected from $R^b$; wherein the heterocyclyl is selected from the group consisting of azaindolyl, azetidinyl, 2,5-dioxabicyclo [4.1.0]heptanyl, 1,4-dioxanyl, isoindolinyl, morpholinyl, oxazolidinyl, oxetanyl, piperazinyl, piperidinyl, pyridinyl, pyrazolyl, pyrrolidinyl, tetrahydrofuranyl, tetrahydropyranyl, and thiazolyl;
$R^8$ is hydrogen or $C_{1-4}$alkyl; and
each of $R^9$, $R^{11}$ and $R^{12}$ is selected from the group consisting of:
 (1) hydrogen,
 (2) halogen,
 (3) —O—$C_{1-6}$alkyl, which is optionally substituted with one to three halogens,
 (4) —N$R^xR^y$, wherein each of $R^x$ and $R^y$ is independently selected from hydrogen, and $C_{1-6}$alkyl, which is optionally substituted with one to three substituents independently selected from halogen and $C_{3-6}$cycloalkyl, and
 (5) $C_{1-6}$alkyl, which is optionally substituted with one to three substituents independently selected from halogen, hydroxyl, —CN, —O—$C_{1-4}$alkyl, $C_{3-6}$cycloalkyl, and —N$R^xR^y$, wherein each of $R^x$ and $R^y$ is independently selected from hydrogen, and $C_{1-6}$alkyl, which is optionally substituted with one to three substituents independently selected from halogen and $C_{3-6}$cycloalkyl $R^{10}$ is selected from the group consisting of:
 (1) hydrogen, and
 (2) $C_{1-4}$alkyl;
each occurrence of $R^b$ is independently selected from the group consisting of:
 (1) halogen,
 (2) hydroxyl,
 (3) —CN,
 (4) oxo,
 (5) —O—$C_{1-6}$alkyl, which is optionally substituted with one to four substituents independently selected from halogen and $C_{3-6}$cycloalkyl,
 (6) $C_{1-6}$alkyl, which is optionally substituted with one to four substituents independently selected from halogen, —O—$C_{1-6}$alkyl and heterocycle, and
 (7) heterocyclyl, which is optionally substituted with one to four substituents independently selected halogen, —CN, $C_{1-6}$alkyl, and —O—$C_{1-6}$alkyl;
 wherein each occurrence of the heterocyclyl of (6) and (7) is independently selected from the group consisting of azaindolyl, azetidinyl, 1,4-dioxanyl, isoindolinyl, morpholinyl, oxazolidinyl, oxetanyl, piperazinyl, piperidinyl, pyridinyl, pyrazolyl, pyrrolidinyl, tetrahydrofuranyl, tetrahydropyranyl, and thiazolyl;
or a pharmaceutically acceptable salt thereof.

In an embodiment of the previous embodiment of formula (Ib):
A is —CH═;
B is —CH($R^9$)— or —O—;
m is 1,
q is 0 or 1;
R is selected from the group consisting of
 (1) hydrogen,
 (2) halogen,
 (3) $C_{1-4}$alkyl, which is optionally substituted with one to three substituents independently selected from halogen, —OH, —O—$C_{1-4}$alkyl, and —CN, and
 (4) heterocyclyl, which is optionally substituted with one to three substituents independently selected from $R^b$; wherein the heterocyclyl is selected from the group consisting of azaindolyl, azetidinyl, 1,4-dioxanyl, isoindolinyl, morpholinyl, oxazolidinyl, oxetanyl, piperazinyl, piperidinyl, pyridinyl, pyrazolyl, pyrrolidinyl, tetrahydrofuranyl, tetrahydropyranyl, and thiazolyl;
$R^8$ is hydrogen; and
$R^9$, $R^{11}$, $R^{12}$, and $R^b$ are as previously described.

In one embodiment, a compound is selected from the subject compounds of the Examples herein, or a pharmaceutically acceptable salt thereof.

In one embodiment, a compound disclosed herein or a pharmaceutically acceptable salt thereof is used in medicine.

In one embodiment, disclosed herein is a composition which comprises an inert carrier or excipient and a compound of formula (I), or a pharmaceutically acceptable salt thereof.

In one embodiment, disclosed herein is a method for treating or preventing a disease or disorder associated with mutant IDH enzyme activity in a subject which comprises administering to the subject an effective amount of a compound of formula (I), or a pharmaceutically acceptable salt thereof.

In one embodiment, disclosed herein is the use of a compound of formula (I), or a pharmaceutically acceptable salt thereof, for the manufacture of a medicament for the treatment or prevention of a disease or disorder associated with mutant IDH enzyme activity.

In one embodiment, a method for treating a disease or disorder associated with mutant IDH enzyme activity in a subject comprises administering to the subject an effective amount of a compound of formula (I), or a pharmaceutically acceptable salt thereof, in combination with another anti-cancer agent.

In one embodiment, the disease or disorder associated with mutant IDH enzyme activity is cancer. In one embodiment, the cancer is selected from the group consisting of glioma, glioblastoma multiforme, paraganglioma, supratentorial primordial neuroectodermal tumors, acute myeloid leukemia (AML), breast cancer, prostate cancer, thyroid cancer, colon cancer, chondrosarcoma, cholangiocarcinoma, peripheral T-cell lymphoma, and melanoma. In one embodiment, the cancer is selected from glioma, glioblastoma multiforme, acute myeloid leukemia and breast cancer.

As used herein, "alkenyl" refers to both branched- and straight-chain unsaturated aliphatic hydrocarbon groups of 2 to 12 carbon atoms and having at least one carbon-carbon double bond. Alkenyl groups may be optionally substituted with one or more substituents as defined herein. Examples of such groups include, but are not limited to, ethenyl, propenyl, n-butenyl, 3-methylbut-2-enyl, n-pentenyl, octenyl and decenyl. "$C_{2-6}$alkenyl" refers to an alkenyl group as defined herein having 2 to 6 carbon atoms.

"Alkoxy" refers to any alkyl moiety attached through an oxygen bridge (e.g., a —O—$C_{1-6}$alkyl group wherein $C_{1-6}$alkyl is as defined herein). Examples of such groups include, but are not limited to, methoxy, ethoxy, propoxy, butyloxy and pentyloxy. Alkoxy groups may be optionally substituted with one or more substituents as defined herein. "$C_{1-6}$alkoxy" refers to an alkoxy group as defined herein having 1 to 6 carbon atoms.

"Alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "$C_{1-6}$alkyl" refers to an alkyl group as defined herein having 1 to 6 carbon atoms.

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$cycloalkenyl ring. Aryl groups may be optionally substituted with one or more substituents as defined herein. Bonding can be through any of the carbon atoms of any ring.

"Carbocycle" refers to a saturated, partially unsaturated or aromatic ring moiety having only ring carbon atoms. Carbocyclyl moieties include both monocyclic and multicyclic (e.g., bicyclic) ring moieties. Bicyclic carbocyclyl moieties include fused, spirocycle and bridged bicyclic rings. Examples of carbocyclyl moieties include, but are not limited to, cyclopentyl, cyclohexyl, cycloheptyl, cyclooctyl, cyclopentenyl, cyclohexenyl, cyclohexadienyl, phenyl, and naphthyl. Carbocyclic rings may be optionally substituted with one or more substituents as defined herein. "$C_{3-10}$carbocycle" refers to a carbocycle group as defined herein having 3 to 10 ring carbon atoms. In one embodiment, a carbocyclyl moiety is aryl.

In one embodiment, a carbocyclyl is a bridged bicyclic or multicyclic moiety. Non-limiting examples of these type of moieties include

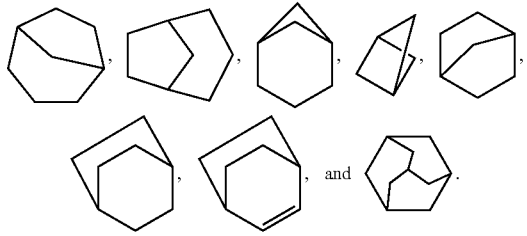

In one embodiment, a carbocycle is a $C_{3-7}$cycloalkyl. "Cycloalkyl" refers to a monocyclic saturated carbocyclic ring having the specified number of carbon atoms. For example, $C_{3-7}$ cycloalkyl refers to a cycloalkyl group as defined herein having 3 to 7 carbon atoms. Examples of cycloalkyl include, but are not limited to, cyclopropyl, cyclobutyl, cyclopentyl, cyclohexyl and cycloheptyl. Cycloalkyl groups may be optionally substituted with one or more substituents as defined herein.

In one embodiment, a carbocyclyl moiety is a $C_{4-7}$cycloalkenyl. "Cycloalkenyl" refers to a monocyclic partially unsaturated carbocyclic ring having the specified number of carbon atoms and at least one carbon-carbon double bond. Examples of cycloalkenyl include, but are not limited to, cyclobutenyl, cyclopentenyl, cyclohexenyl, cyclohexa-1,4-dienyl, and cycloheptenyl.

"Halo" or "halogen" refers to fluoro, chloro, bromo or iodo, unless otherwise noted.

"Heterocycle" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocycle and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, partially unsaturated and aromatic 4-7 membered monocyclic heterocyclyl moieties include, but are not limited to, 2,3-dihydro-1,4-dioxinyl, dihydropyranyl, dihydropyrazinyl, dihydropyridazinyl, dihydropyridinyl, dihydropyrimidinyl, furanyl, imidazolyl, isothiazolyl, isoxazolyl, oxadiazolyl, oxazolyl, pyranyl, pyrazinyl, pyrazolyl, pyridazinyl, pyridinyl, pyrimidinyl, pyrrolyl, tetrahydropyrazinyl, tetrahydropyridazinyl, tetrahydropyridinyl, tetrahydropyrimidinyl, tetrazolyl, thiadiazolyl, thiazolyl, thienyl, thiophenyl, and triazolyl.

In one embodiment, saturated 4-7 membered monocyclic heterocyclyl moieties include, but are not limited to, azetidinyl, 1,4-dioxanyl, hexahydroazepinyl, morpholinyl, 1,4-oxazepanyl, oxazolidinyl, oxetanyl, piperazinyl, piperidinyl, pyridin-2-onyl, pyrrolidinyl, tetrahydrofuranyl, tetrahydropyranyl, thiomorpholinyl, tetrahydrothienyl, and tetrahydrothiophenyl.

In one embodiment, a heterocyclyl is a fused bicyclic ring moiety wherein a 4-6 membered heterocyclic ring comprising 1-4 heteroatoms selected from oxygen, sulfur and nitrogen and a 5-6 membered heterocyclic ring comprising 1-4 heteroatoms selected from oxygen, sulfur and nitrogen are connected through two atoms. Exemplary heterocycles of this type include, but are not limited to, azaindolyl, dihydronaphthyridinyl, imidazopyridinyl, indolizinyl, naphthyridinyl, pteridinyl, purinyl, quinolizinyl, tetrahydroindolizinyl, tetrahydronaphthyridinyl, tetrahydroquinolizinyl,

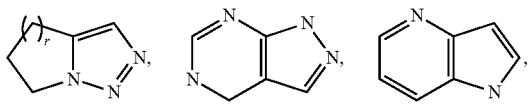
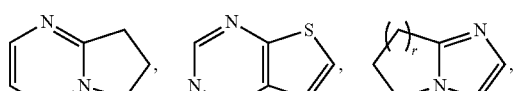
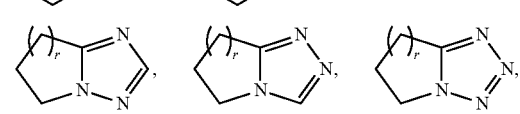
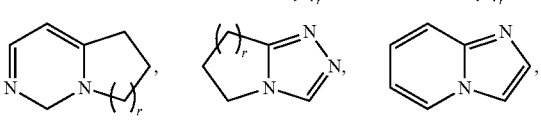
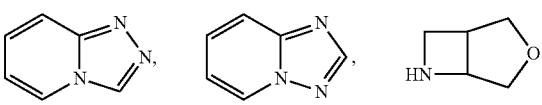

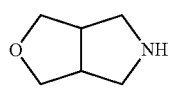

(3-oxa-6-azabicyclo[3.2.0]heptane),

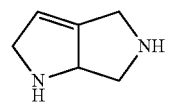

(hexahydro-1H-furo[3,4-c]pyrrole),

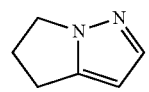

(1,2,4,5,6,6a-hexahydropyrrolo[3,4-b]pyrrole),

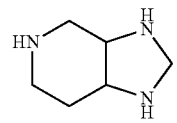

(5,6-dihydro-4H-pyrrolo[1,2-b]pyrazole),

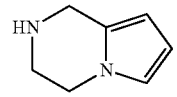

octahydro-1H-imidazo[4,5-c]pyridine),

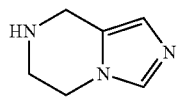

(1,2,3,4-tetrahydropyrrolo[1,2-a]pyrazine),

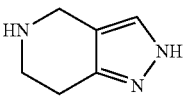

(5,6,7,8-tetrahydroimidazo[1,5-a]pyrazine),

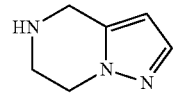

(4,5,6,7-tetrahydro-2H-pyrazolo[4,3-c]pyridine),

(4,5,6,7-tetrahydropyrazolo[1,5-a]pyrazine),

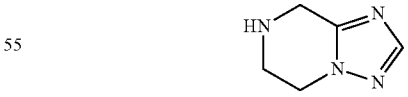

(5,6,7,8-tetrahydro-[1,2,4]triazolo[4,3-a]pyrazine), (5,6,7,8-tetrahydro-[1,2,4]triazolo[1,5-a]pyrazine),

(4,5,6,7-tetrahydro-[1,2,3]triazolo[1,5-a]pyrazine),

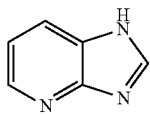

(1H-imidazo[4,5-b]pyridine),

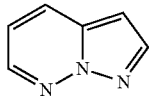

(pyrazolo[1,5-b]pyridazine), and

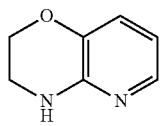

(3,4-dihydro-2H-pyrido[3,2-b][1,4]oxazine); wherein r is 1 or 2. In one embodiment, an azaindole is

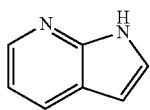

(1H-pyrrolo[2,3-b]pyridine),

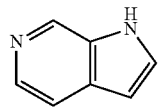

(1H-pyrrolo[2,3-c]pyridine),

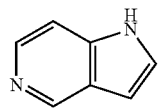

(1H-pyrrolo[3,2-c]pyridine), or

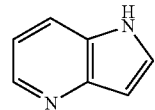

(1H-pyrrolo[3,2-b]pyridine). Such fused ring may be attached to the rest of the molecule via a carbon atom or a nitrogen atom on either ring. A heterocycle of this type includes a bicyclic ring comprising only one nitrogen as the sole heteroatom when the nitrogen is located at the bridgehead.

In one embodiment, a heterocyclyl is a fused bicyclic ring moiety wherein a 4-6 membered heterocyclic ring comprising 1-4 heteroatoms selected from oxygen, sulfur and nitrogen and a $C_{5-10}$ carbocyclic ring are connected through two carbon atoms. Exemplary heterocycles of this type include, but are not limited to, benzimidazolonyl, benzimidazolyl, benzisothiazolyl, benzisoxazolyl, benzofuranyl, benzofurazanyl, benzothienyl, benzotriazolyl, benzoxazolyl, benzthiazolyl, chromanyl, chromenyl, cinnolinyl, dihydroindazolyl, indazolyl, indolyl, isoindolyl, isoquinolinyl, quinazolinyl, quinolinyl, quinoxalinyl, tetrahydroindazolyl, tetrahydroquinolinyl,

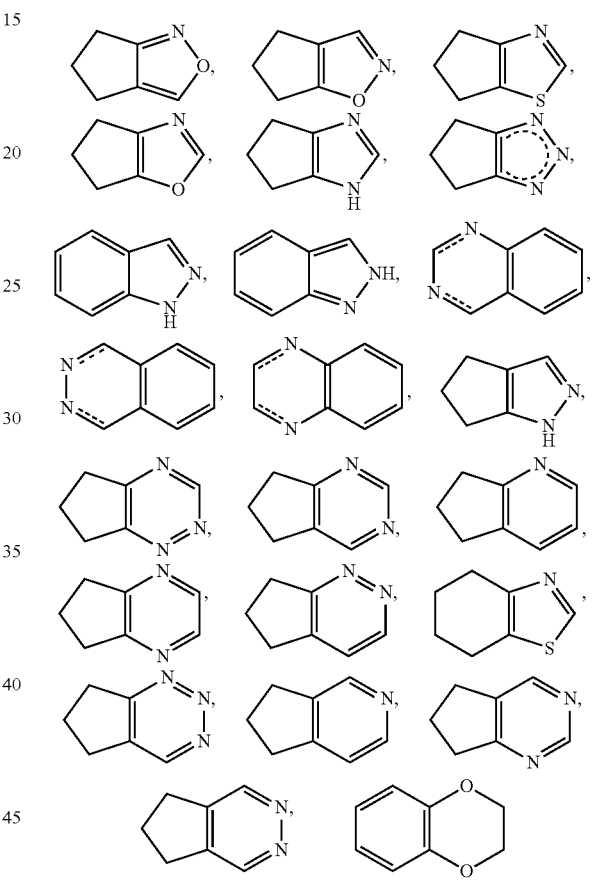

(2,3-dihydrobenzo[b][1,4]dioxine),

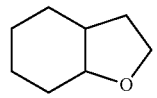

(octahydrobenzofuran)

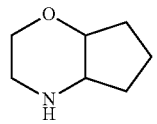

(octahydrocyclopenta[1,4]oxazine),

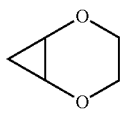

(2,5-dioxabicyclo[4.1.0]heptanyl) and

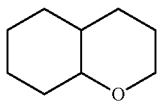

(octahydro-2H-chromene). Such fused ring may be attached to the rest of the molecule via a carbon atom or a nitrogen atom on either ring.

In one embodiment, a heterocyclyl is a spirocycle ("spiro") bicyclic moiety wherein two rings are connected through one atom, and either or both of the rings comprise at least one heteroatom. In one embodiment, a spiro bicyclic heterocycle comprises a 4-7 membered heterocyclic ring comprising 1-4 heteroatoms selected from oxygen, sulfur and nitrogen connected through a single atom to either a 3-6 membered ring comprising 1-2 heteroatoms selected from oxygen, sulfur and nitrogen or a 3-6 membered carbocyclic ring. Exemplary spiro heterocycles of this type include, but are not limited to:

(2-azaspiro[3.3]heptane),

(2-oxa-6-azaspiro[3.3]heptane),

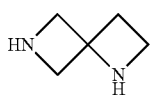

(1,6-diazaspiro[3.3]heptane),

(2,6-diazaspiro[3.3]heptane),

(6-oxa-2-azaspiro[3.4]octane),

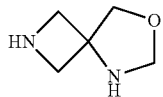

(7-oxa-2,5-diazaspiro[3.4]octane),

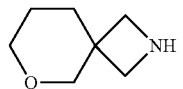

(6-oxa-2-azaspiro[3.5]nonanyl),

(3-oxa-1,7-diazaspiro[4.4]nonane),

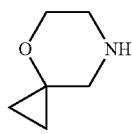

(4-oxa-7-azaspiro[2.5]octane), and

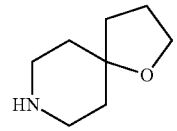

(1-oxa-8-azaspiro[4.5]decane).

Such spiro bicyclic moieties may be attached to the rest of the molecule via a carbon atom or a nitrogen atom on either ring.

In one embodiment, a heterocycle is a bridged bicyclic moiety selected from the group consisting of:

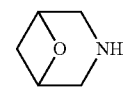

(6-oxa-3-azabicyclo[3.1.1]heptane),

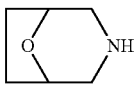

(8-oxa-3-azabicyclo[3.2.1]octane),

(2-oxa-5-azabicyclo[2.2.2]octane),

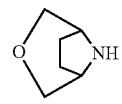

(3-oxa-8-azabicyclo[3.2.1]octane),

(2-oxa-5-azabicyclo[2.2.1]heptane),

(8-azabicyclo[3.2.1]octanyl),

(3,8-diazabicyclo[3.2.1]octane),

(2,5-diazabicyclo[2.2.2]octane),

(8-azabicyclo[3.2.1]octane),

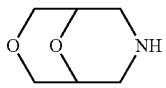

(3,9-dioxa-7-azabicyclo[3.3.1]nonanyl), and

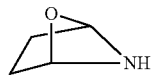

(5-oxa-6-azabicyclo[2.1.1]hexane). Such bridged bicyclic moieties may be attached to the rest of the molecule via a carbon atom or a nitrogen atom on either ring.

Heterocycles include ring moieties wherein a ring sulfur atom is oxidized to form SO and $SO_2$. In one embodiment, a heterocycle of this type is

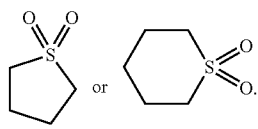

Heterocyclic groups may be optionally substituted with one or more substituents as defined herein.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

Polymorphism

A compound of formula (I), including a salt or solvate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound of formula (I).

Optical Isomers—Diastereomers—Geometric Isomers—Tautomers

Included herein are various isomers of the compounds of formula (I). The term "isomers" refers to compounds that have the same composition and molecular weight but differ in physical and/or chemical properties. The structural difference may be in constitution (geometric isomers) or in the ability to rotate the plane of polarized light (stereoisomers). With regard to stereoisomers, a compound of formula (I) may have one or more asymmetric carbon atom and may occur as a racemic mixture or as individual enantiomers or diastereomers. All such isomeric forms are included herein, including mixtures thereof. If a compound of formula (I) contains a double bond, the substituent may be in the E or Z configuration. If a compound of formula (I) contains a disubstituted cycloalkyl, the cycloalkyl substituent may have a cis- or trans-configuration. All tautomeric forms are also intended to be included.

Any asymmetric atom (e.g., carbon) of a compound of formula (I) can be present in racemic mixture or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

A compound of formula (I) can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Isotopic Variations

Compounds of formula (I) include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^2H$ (i.e., Deuterium or "D"), $^3H$, $^{11}C$, $^{13}C$, $^{14}C$, $^{13}N$, $^{15}N$, $^{15}O$, $^{17}O$, $^{18}O$, $^{32}P$, $^{35}S$, $^{18}F$, $^{123}I$, $^{125}I$ and $^{36}Cl$. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, substitution with positron emitting isotopes, such as $^{11}C$, $^{8}F$, $^{15}O$ and $^{13}N$, may be particularly desirable for PET or SPECT studies.

Isotopically-labeled compounds of formula (I) can generally be prepared by conventional techniques known to those skilled in the art. Furthermore, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound of formula (I) is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids. It will be understood that, as used herein, references to the compounds disclosed herein are meant to also include pharmaceutically acceptable salts thereof.

Methods of Use

The compounds disclosed herein are inhibitors of a mutant IDH enzyme. These compounds are potentially useful in treating diseases or disorders associated with such enzymes including, but not limited to, cell proliferation disorders, such as cancer.

Examples of these mutant IDH enzymes are mutant IDH1 and mutant IDH2. A mutation in human IDH1 enzyme includes a mutation at amino acid residue 97, 100, or 132, e.g. G97D, R100Q, R132H, R132C, R132S, R132G, R132L, or R132V. A mutation in human IDH2 enzyme includes a mutation at amino acid residue 140 or 172, e.g. R140Q, R140G, R172K, R172M, R172S, R172G, or R172W.

Cell-proliferation disorders that may be associated with a mutant IDH enzyme activity include, but are not limited to, cancer. Examples of such cancers include, but are not limited to, Acute Lymphoblastic Leukemia; Acute Myeloid Leukemia; Adrenocortical Carcinoma; AIDS-Related Lymphoma; AIDS-Related Malignancies; Anal Cancer; Astrocytoma; Bile Duct Cancer; Bladder Cancer; Bone Cancer, Osteosarcoma/Malignant Fibrous Histiocytoma; Brain Stem Glioma; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma; Breast Cancer; Bronchial Adenomas/Carcinoids; Carcinoid Tumor; Carcinoid Tumor, Gastrointestinal; Carcinoma, Adrenocortical; Carcinoma, Islet Cell; Central Nervous System Lymphoma, Primary; Cerebral Astrocytoma/ Malignant Glioma; Cervical Cancer; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer; Cutaneous T-Cell Lymphoma; Endometrial Cancer; Ependymoma; Epithelial Cancer, Ovarian; Esophageal Cancer; Esophageal Cancer; Ewing's Family of Tumors; Extracranial Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer; Hodgkin's Lymphoma; Hypopharyngeal Cancer; Hypothalamic and Visual Pathway Glioma; Intraocular Melanoma; Islet Cell Carcinoma (Endocrine Pancreas); Kaposi's Sarcoma; Kidney Cancer; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoblastic Leukemia; Lymphoma, AIDS-Related; Lymphoma, Central Nervous System (Primary); Lymphoma, Cutaneous T-Cell; Lymphoma, Hodgkin's; Lymphoma, Hodgkin's During Pregnancy; Lymphoma, Non-Hodgkin's; Lymphoma, Primary Central Nervous System; Macroglobulinemia, Waldenstrom's; Male Breast Cancer; Malignant Mesothelioma; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia; Myeloma, Multiple; Myeloproliferative Disorders, Chronic; Nasal Cavity and Paranasal Sinus Cancer; Nasopharyngeal Cancer; Neuroblastoma; Non-Hodgkin's Lymphoma; Non-Small Cell Lung Cancer; Oral Cancer; Oral Cavity and Lip Cancer; Oropharyngeal Cancer; steosarcoma/Malignant Fibrous Histiocytoma of Bone; Ovarian Epithelial Cancer; Ovarian Germ Cell Tumor; Ovarian Low Malignant Potential Tumor; Pancreatic Cancer; Paranasal Sinus and Nasal Cavity Cancer; Parathyroid Cancer; Penile Cancer; Pheochromocytoma; Pineal and Supratentorial Primitive Neuroectodermal Tumors; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer; Prostate Cancer; Rectal Cancer; Renal Cell (Kidney) Cancer; Renal Pelvis and Ureter, Transitional Cell Cancer; Retinoblastoma; Rhabdomyosarcoma; Salivary Gland Cancer; Sarcoma, Ewing's Family of Tumors; Sarcoma, Kaposi's; Sarcoma (Osteosarcoma)/Malignant Fibrous Histiocytoma of Bone; Sarcoma, Soft Tissue; Sezary Syndrome; Skin Cancer; Skin Cancer (Melanoma); Skin Carcinoma, Merkel Cell; Small Cell Lung Cancer; Small Intestine Cancer; Soft Tissue Sarcoma; Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Thymoma, Malignant; Thyroid Cancer; Transitional Cell Cancer of the Renal Pelvis and Ureter; Trophoblastic Tumor, Gestational; Ureter and Renal Pelvis, Transitional Cell Cancer; Urethral Cancer; Uterine Sarcoma; Vaginal Cancer; Visual Pathway and Hypothalamic Glioma; Vulvar Cancer; Waldenstrom's Macro globulinemia; and Wilms' Tumor.

In one embodiment, a cancer potentially associated with mutant IDH enzyme activity is brain cancer, such as an astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma); oligodendroglial tumor (e.g., oligodendroglioma, and anaplastic oligodendroglioma); oligoastrocytic tumor (e.g., oligoastrocytoma, and anaplastic oligoastrocytoma); ependymoma (e.g., myxopapillary ependymoma, and anaplastic ependymoma); medulloblastoma; primitive neuroectodermal tumor, schwannoma, meningioma, meatypical meningioma, anaplastic meningioma; and pituitary adenoma. In another embodiment, the brain cancer is glioma, glioblastoma multiforme, paraganglioma, or suprantentorial primordial neuroectodermal tumors (sPNET).

In another embodiment, a cancer potentially associated with mutant IDH enzyme activity is leukemia, such as acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blast-phase chronic myelogenous leukemia, angioimmunoblastic lymphoma and acute lymphoblastic leukemia.

In one embodiment, a cancer potentially associated with mutant IDH enzyme activity is skin cancer, including melanoma. In another embodiment, a cancer potentially associated with mutant IDH enzyme activity is prostate cancer, breast cancer, thyroid cancer, colon cancer, or lung cancer. In another embodiment, a cancer potentially associated with mutant IDH enzyme activity is sarcoma, including central chondrosarcoma, central and periosteal chondroma, and fibrosarcoma. In another embodiment, a cancer potentially associated with mutant IDH enzyme activity is cholangiocarcinoma.

A subject administered with a compound disclosed herein, or a pharmaceutically acceptable salt thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder described herein that may be associated with mutant IDH enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt thereof, and compositions of the foregoing to a subject.

The amount of a compound administered to a subject is an amount sufficient to inhibit mutant IDH enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an IDH mutation by treating a subject presently afflicted with the disorders, or by prophylactically treating a subject likely to be afflicted with the disorders, with an effective amount of a compound disclosed herein, or a pharmaceutically acceptable salt thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound of formula (I).

One embodiment of the present invention provides for a method of treating a disease or disorder associated with mutant IDH enzyme activity comprising administration of an effective amount of a compound of formula (I) to a subject in need of treatment thereof. In one embodiment, the disease or disorder associated with a mutant IDH enzyme is a cell proliferation disorder.

In one embodiment, the cell proliferation disorder is cancer. In another embodiment, the cancer is a cancer associated with mutant IDH1 enzyme activity. In another embodiment, the cancer is associated with human mutant IDH1 enzyme activity, having a mutation at amino acid residue 97, 100, or 132, such as G97D, R100Q, R132H, R132C, R132S, R132G, R132L, or R132V.

In one embodiment, the cancer is associated with human mutant IDH2 enzyme activity having a mutation at amino acid residue 140 or 172, e.g. R140Q, R140G, R172K, R172M, R172S, R172G, or R172W.

In one embodiment, the cancer is brain cancer, leukemia, skin cancer, prostate cancer, thyroid cancer, colon cancer, lung cancer or sarcoma. In another embodiment the cancer is glioma, glioblastoma multiforme, paraganglioma, suprantentorial primordial neuroectodermal tumors, acute myeloid leukemia, myelodysplastic syndrome, chronic myelogenous leukemia, melanoma, breast, prostate, thyroid, colon, lung, central chondrosarcoma, central and periosteal chondroma tumors, fibrosarcoma, and cholangiocarcinoma.

In one embodiment, disclosed herein is the use of a compound of formula (I) in a therapy. The compound may be useful in a method of inhibiting mutant IDH enzyme activity in a subject, such as a mammal in need of such inhibition, comprising administering an effective amount of the compound to the subject.

In one embodiment, disclosed herein is a pharmaceutical composition comprising at least one compound of formula (I), or a pharmaceutically acceptable salt thereof, for use in potential treatment of a disorder or disease related to mutant IDH1 enzyme activity.

In one embodiment, disclosed herein is the use of a compound of formula (I) in the manufacture of a medicament for the treatment of a disease or disorder associated with mutant IDH enzyme activity. In one embodiment, the disease or disorder associated with a mutant IDH is a cell proliferation disorder. In another embodiment, the cell proliferation disorder is cancer. In another embodiment, the cancer is brain cancer, leukemia, skin cancer, breast, prostate cancer, thyroid cancer, colon cancer, lung cancer or sarcoma. In another embodiment, the cancer is glioma, glioblastoma multiforme, paraganglioma, suprantentorial primordial neuroectodermal tumors, acute myeloid leukemia, myelodysplastic syndrome, chronic myelogenous leukemia, melanoma, breast, prostate, thyroid, colon, lung, central chondrosarcoma, central and periosteal chondroma tumors, fibrosarcoma, and/or cholangiocarcinoma.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound of formula (I), or a pharmaceutically acceptable salt thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound of formula (I), or a pharmaceutically acceptable salt thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound of formula (I). When prepared in unit dosage form, the composition of the invention typically contains from about 0.1 mg to 2 grams, or more specifically, 0.1 mg to 500 mg, or even more specifically, 0.2 mg to 100 mg, of a compound of formula (I), or a pharmaceutically acceptable salt thereof.

The compounds disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polyepsilon caprolactone, polyhydroxy butyric acid, polyorthoesters, polyacetals, polydihydropyrans, polycyanoacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound of formula (I) and one or more other active agent(s) together in the same pharmaceutical composition, or a compound of formula (I) and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, the invention provides a composition comprising a compound of formula (I) and at least one other therapeutic agent as a combined preparation for simultaneous, separate or sequential use in therapy. In one embodiment, the therapy is the treatment of a disease or disorder associated with mutant IDH enzyme activity.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

A kit of the invention may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound of formula (I) for treating a disease or disorder associated with mutant IDH enzyme activity, wherein the medicament is prepared for administration with another active agent. The invention also provides the use of another active agent for treating a disease or disorder associated with a mutant IDH enzyme, wherein the medicament is administered with a compound of formula (I).

The invention also provides the use of a compound of formula (I) for treating a disease or disorder associated with mutant IDH enzyme activity, wherein the patient has previously (e.g. within 24 hours) been treated with another active agent. The invention also provides the use of another therapeutic agent for treating a disease or disorder associated with mutant IDH enzyme activity, wherein the patient has previously (e.g. within 24 hours) been treated with a compound of formula (I). The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AGO 13736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4-pyridinylmethyl)amino]-3-pyridinecarboxamide. and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechlorethamine hydrochloride, sold under the tradename Mustargen®), streptozocin (sold under the tradename Zanosar®), thiotepa (also known as thiophosphoramide, TESPA and TSPA, and sold under the tradename Thioplex®).

Examples of anti-tumor antibiotics include, but are not limited to, doxorubicin (sold under the tradenames Adriamycin® and Rubex®), bleomycin (sold under the tradename Lenoxane®), daunorubicin (also known as daunorubicin hydrochloride, daunomycin, and rubidomycin hydrochloride, sold under the tradename Cerubidine®), daunorubicin liposomal (daunorubicin citrate liposome, sold under the tradename DaunoXome®), mitoxantrone (also known as DHAD, sold under the tradename Novantrone®), epirubicin (sold under the tradename Ellence™), idarubicin (sold under the tradenames Idamycin®, Idamycin PFS®), and mitomycin C (sold under the tradename Mutamycin®).

Examples of anti-metabolites include, but are not limited to, cladribine (2-chlorodeoxyadenosine, sold under the tradename Leustatin®), 5-fluorouracil (sold under the tradename Adrucil®), 6-thioguanine (sold under the tradename Purinethol®), pemetrexed (sold under the tradename Alimta®), cytarabine (also known as arabinosylcytosine (Ara-C), sold under the tradename Cytosar-U®), cytarabine liposomal (also known as Liposomal Ara-C, sold under the tradename DepoCyt™), decitabine (sold under the tradename Dacogen®), hydroxyurea (sold under the tradenames Hydrea®, Droxia™ and Mylocel™), fludarabine (sold under the tradename Fludara®), floxuridine (sold under the tradename FUDR®), cladribine (also known as 2-chlorodeoxyadenosine (2-CdA) sold under the tradename Leustatin™), methotrexate (also known as amethopterin, methotrexate sodium (MTX), sold under the tradenames Rheumatrex® and Trexall™), and pentostatin (sold under the tradename Nipent®).

Examples of retinoids include, but are not limited to, alitretinoin (sold under the tradename Panretin®), tretinoin (all-trans retinoic acid, also known as ATRA, sold under the tradename Vesanoid®), Isotretinoin (13-c/s-retinoic acid, sold under the tradenames Accutane® Amnesteem®, Claravis®, Clarus®, Decutan®, Isotane®, Izotech®, Oratane®, Isotret®, and Sotret®), and bexarotene (sold under the tradename Targretin®).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments. Examples of PD-1 antagonists include, but are not limited to Keytruda® and Opdivo®.

Examples of mAbs that bind to human PD-1, and useful in the treatment method, medicaments and uses of the present invention, are described in U.S. Pat. No. 7,488,802, U.S. Pat. No. 7,521,051, U.S. Pat. No. 8,008,449, U.S. Pat. No. 8,354,509, U.S. Pat. No. 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename Trisenox®), asparaginase (also known as L-asparaginase, and Erwinia L-asparaginase, sold under the tradenames Elspar® and Kidrolase®).

EXPERIMENTAL

The following examples are intended to be illustrative only and not limiting in any way. Abbreviations used are those conventional in the art or the following.
ACN=acetonitrile; BSA=bovine serum albumin; ° C.=degree Celsius; DMF=N,N-dimethylformamide; DMSO=dimethylsulfoxide; DTT=dithiothreitol; EtOAc=ethyl acetate; EtOH=ethanol; g=gram; h=hour(s); HMDS=hexamethyldisilazane; HPLC=high pressure liquid chromatography; kg=kilogram; L=liter; LC=liquid chromatography; LCMS=liquid chromatography and mass spectrometry; MeOH=methanol; MS=mass spectrometry;

MTBE=methyl tert-butyl ether; min=minutes; mL=milliliter(s); m/z=mass to charge ratio; nm=nanometer; nM=nanomolar; N=normal; NADPH nicotinamide adenine dinucleotide phosphate; NMR=nuclear magnetic resonance; PS-PPh$_3$=Polymer supported-triphenylphosphine; sat.=saturated; TEA=triethylamine; TFA=trifluoroacetic acid; THF=tetrahydrofuran; TLC=thin layer chromatography.

General Synthetic Schemes

The compounds of formula (I) may be prepared by methods known in the art of organic synthesis as set forth in part by the following synthetic schemes and synthetic procedures and conditions for the illustrative intermediates and examples.

In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art.

The compounds described herein may be made from commercially available starting materials or synthesized using known organic, inorganic, and/or enzymatic processes.

Scheme 1

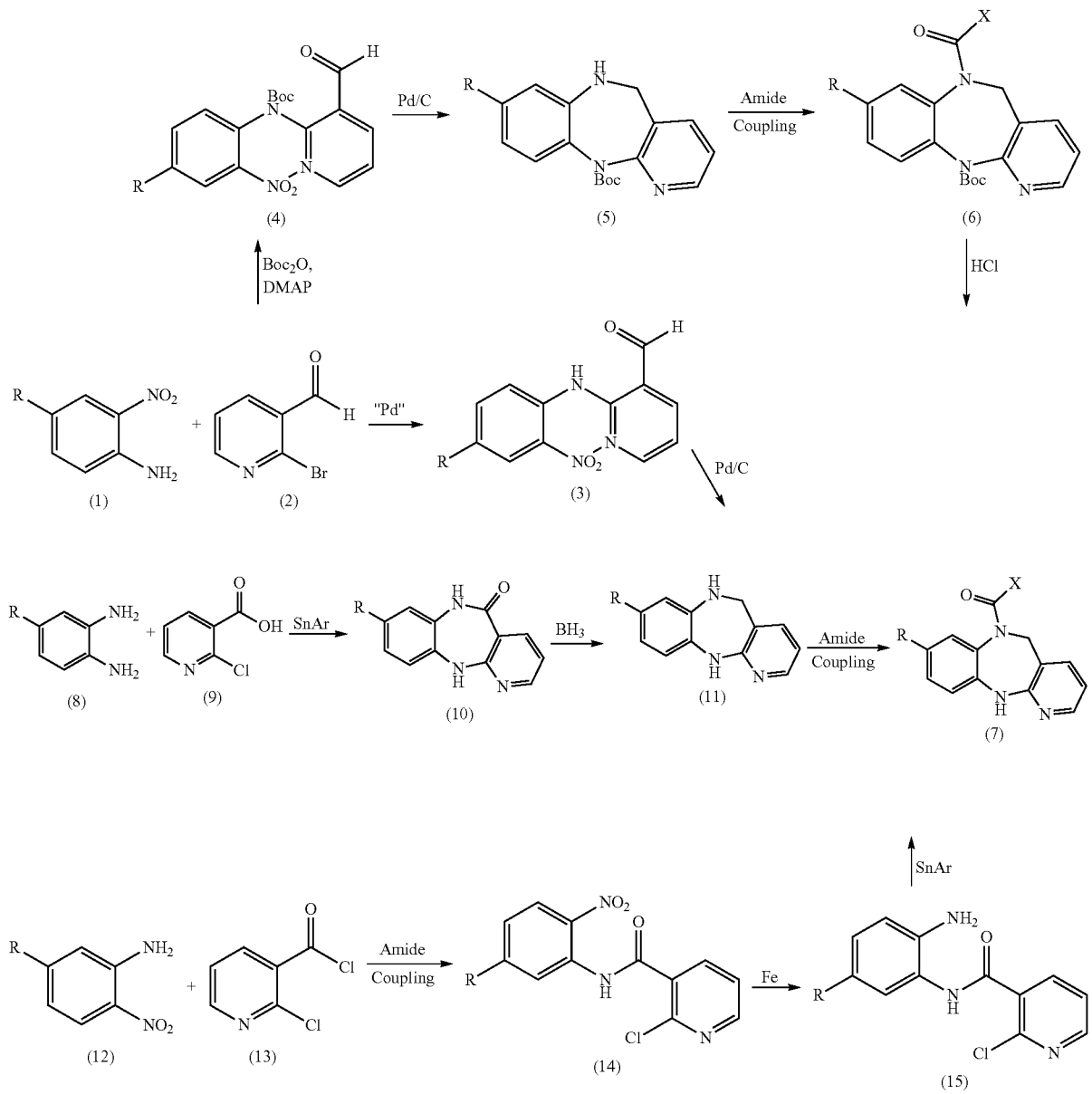

In general scheme 1, compounds of formula (7) can be formed in multiple ways. Substituted nitroaniline (1) and a formyl bromopyridine (2) can be combined in a palladium-mediated C—N coupling reaction to afford (3). Formation of a carbamate followed by reduction of the nitro group with palladium on carbon affords the substituted tricyclic compound (5). Amide coupling followed by deprotection affords the desired tricycle (7). Alternatively, a substituted diaminophenyl compound (8) can be reacted via an SnAr reaction with a substituted nicotinic acid (9) to afford the tricyclic compound (10). Borane reduction followed by amide coupling affords the desired tricycle (7). Alternatively, substituted nitroaniline (12) and acyl chloride (13) can be reacted via an amide coupling to afford (14). Reduction of the nitrobenzene (14) with iron affords the aniline (15). A one-pot cyclization and reduction with borane affords the desired tricyclic compound (11) that can undergo an amide coupling to afford (7).

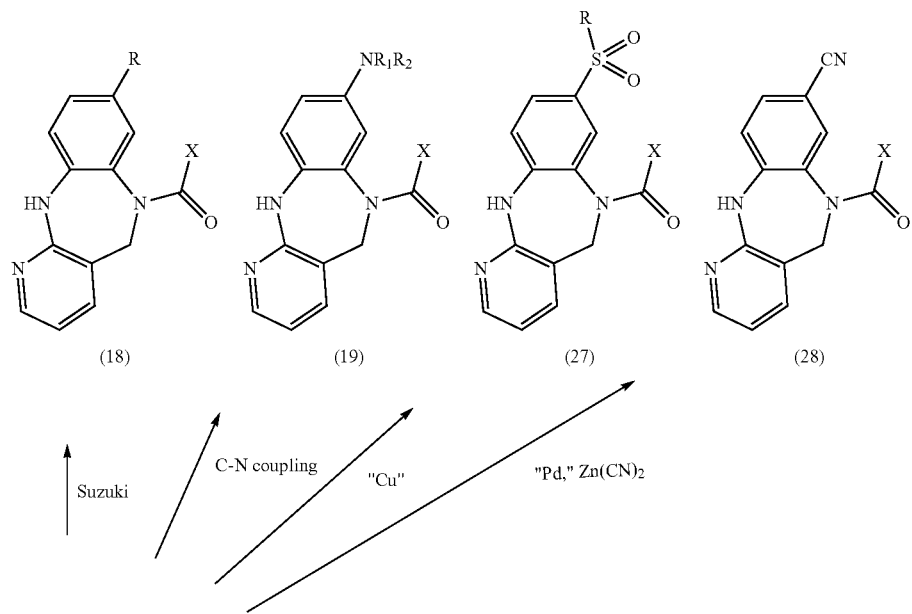

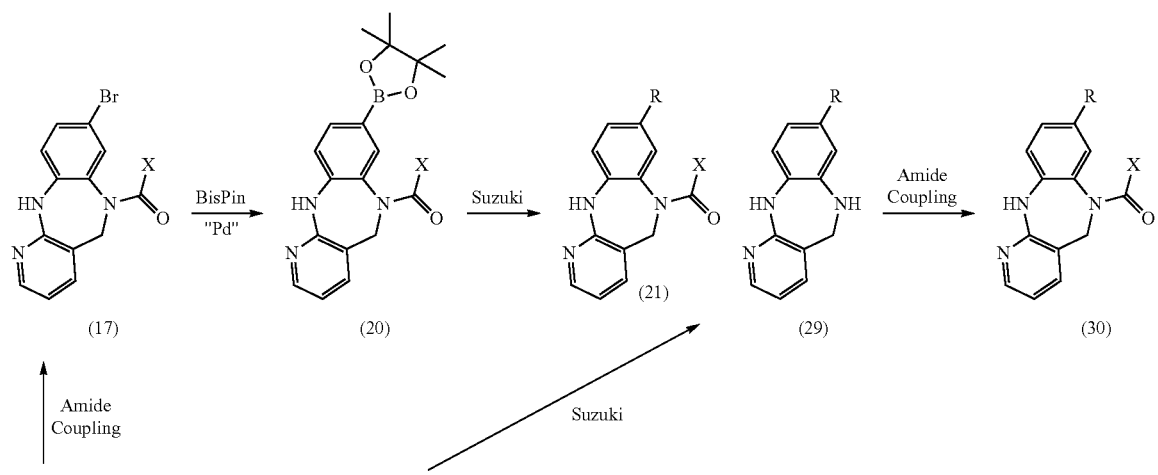

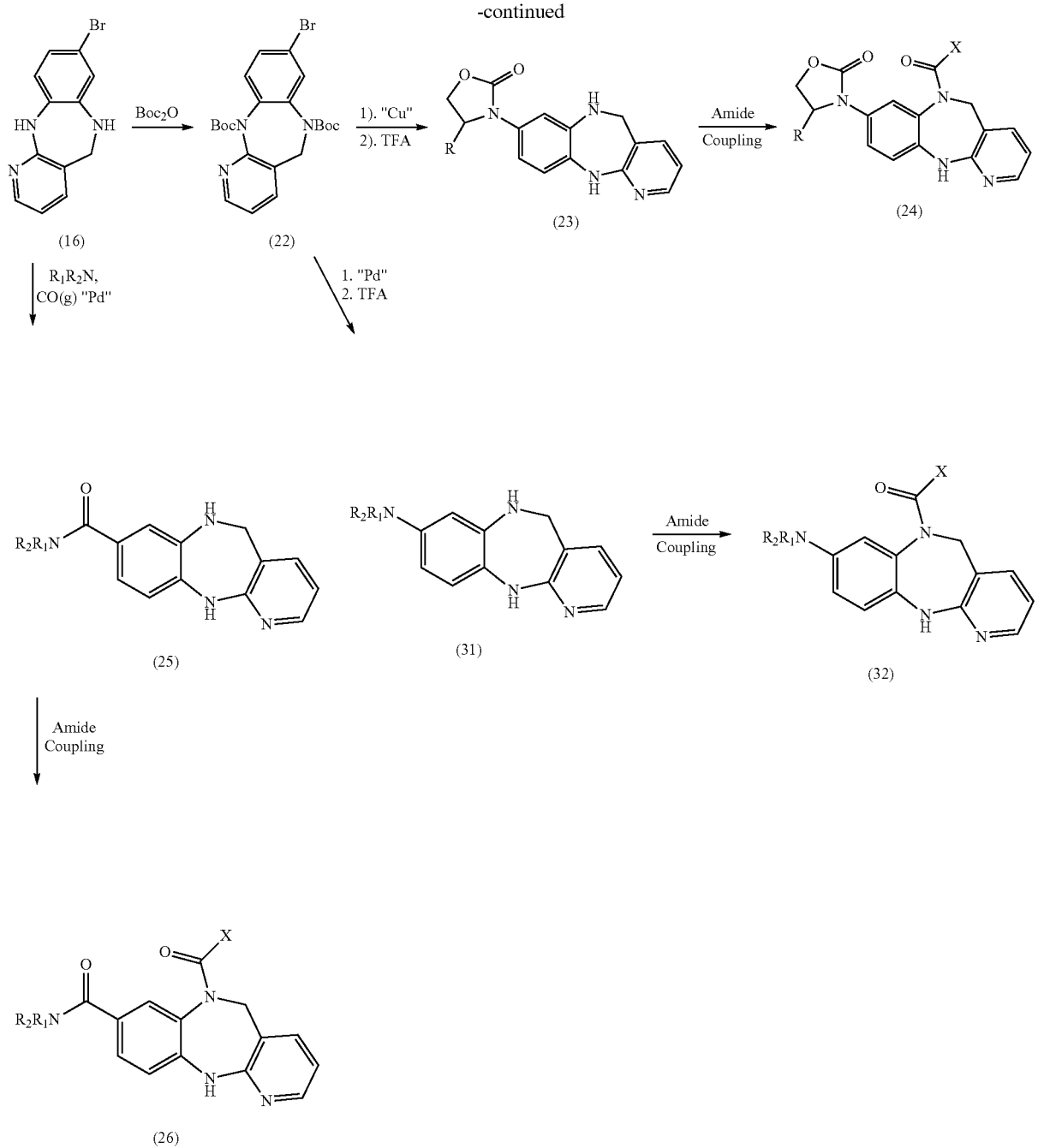

In general scheme 2, compound (16) can be used in a multitude of reactions. Amide coupling with (16) affords the tricycle (17). Suzuki reaction affords the final product (18). Alternatively, a palladium-mediated C—N coupling reaction between (17) and the appropriate amine affords (19). Alternatively, a copper-mediated coupling reaction with (17) affords the sulfone (27). Alternatively, a palladium-mediated cyanation between (17) and zinc cyanide affords (28). The aryl bromide (17) can also be converted to the boronate ester (20). Suzuki reaction affords the final product (21). Alternatively, a palladium-mediated C—N coupling reaction with compound (16) affords the C8 functionalized product (29), and amide coupling affords the final product (30). Alternatively, compound (16) can be protected to afford the bis-Boc protected tricycle (22). A copper-mediated C—N bond forming reaction followed by deprotection affords (23). Amide coupling affords the final product (24). Alternatively, a palladium-mediated carbonylation with (16) affords the amide (25). Amide coupling affords the final product (26). Alternatively, the bis-boc protected tricycle (22) can undergo a palladium-mediated CN coupling, followed by TFA deprotection and amide coupling to afford (32).

Scheme 3

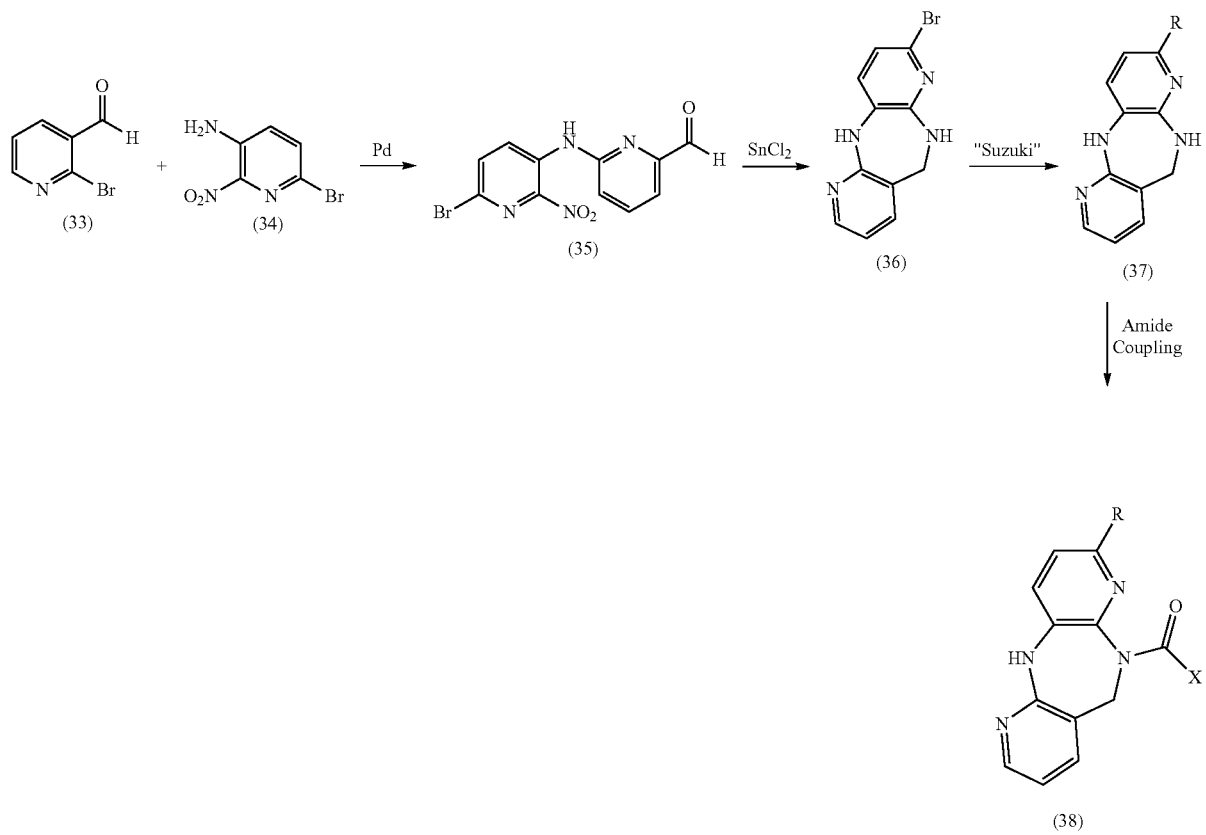

In general scheme 3, compounds of formula (38) can be prepared in the following sequence. A palladium-mediated C—N coupling between bromopyridine (33) and substituted aminopyridine (34) affords (35). Reduction with SnCl$_2$ and cyclization yields (36). Final product (38) can be prepared from (36) by utilizing a two-step sequence, an amide coupling and a palladium-mediated C—N coupling reaction.

Scheme 4

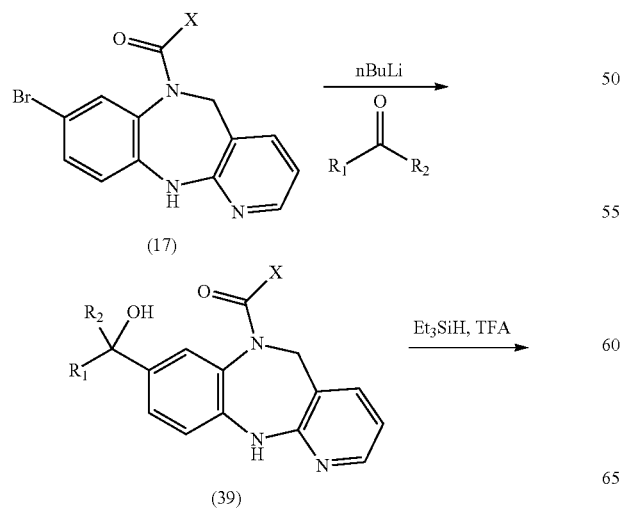

-continued

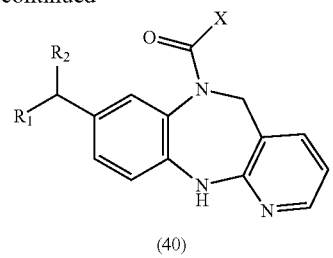

In general scheme 4, compounds of formula (40) can be prepared via a two-step sequence starting with aryl bromide (17). 1,2 Addition of the anion of (17) with an appropriately substituted carbonyl affords (39). A triethylsilane/TFA reduction affords the final product (40).

Scheme 5

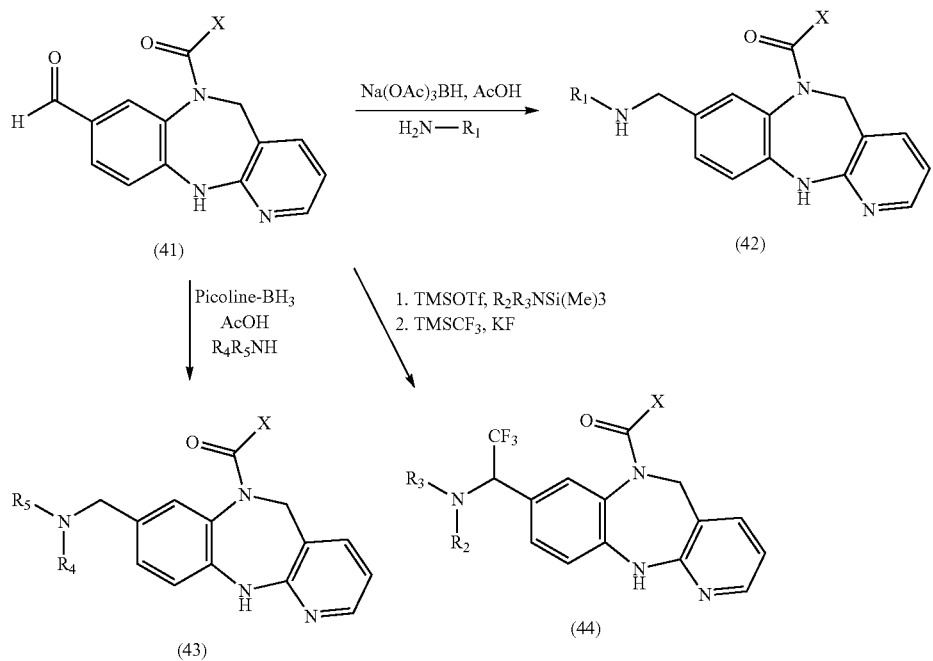

In general scheme 5, aldehyde compounds of formula (41) can be used in a multitude of reactions. Reductive amination with a primary amine affords (42). Reductive amination with a secondary amine affords (43). Reductive coupling of (41) followed by trifluoromethylation affords the final product (44).

Scheme 6

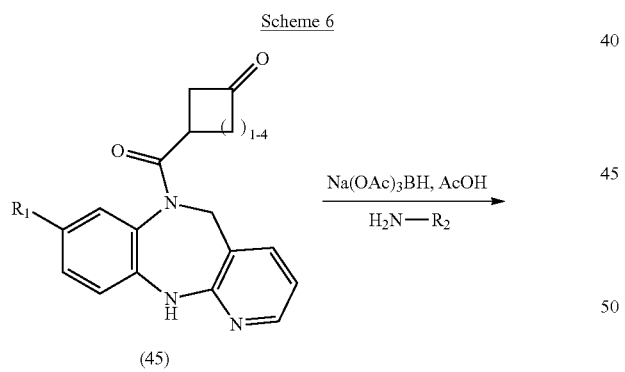

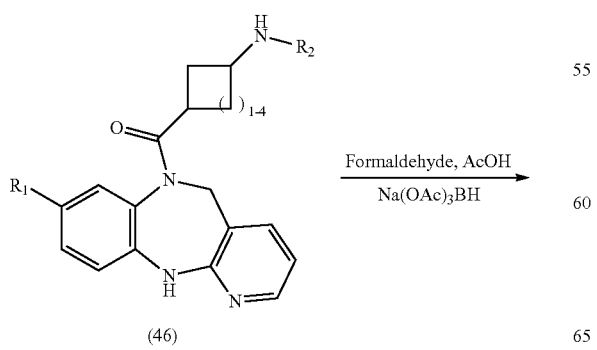

-continued

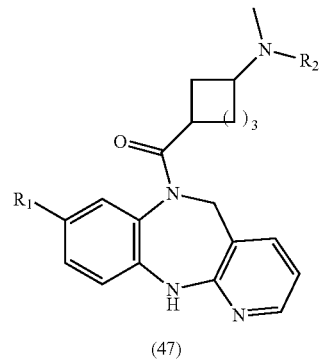

In general scheme 6, amine compounds of formula (47) can be prepared via a two-step process. Reductive amination of (45) affords (46). Amine (46) can be further functionalized by reductive amination with formaldehyde to afford the alkylated amine (47).

Scheme 7

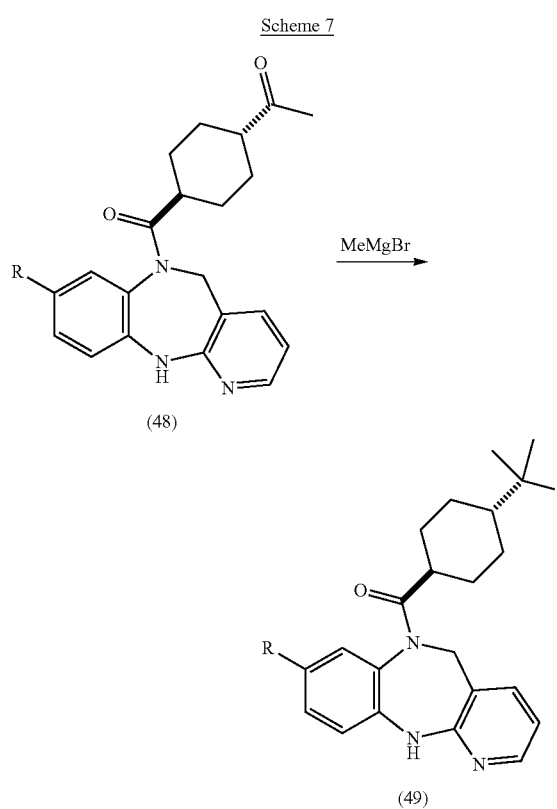

In general scheme 7, Grignard reaction with ketone compounds of formula (48) affords the tertiary alcohol (49).

Scheme 8

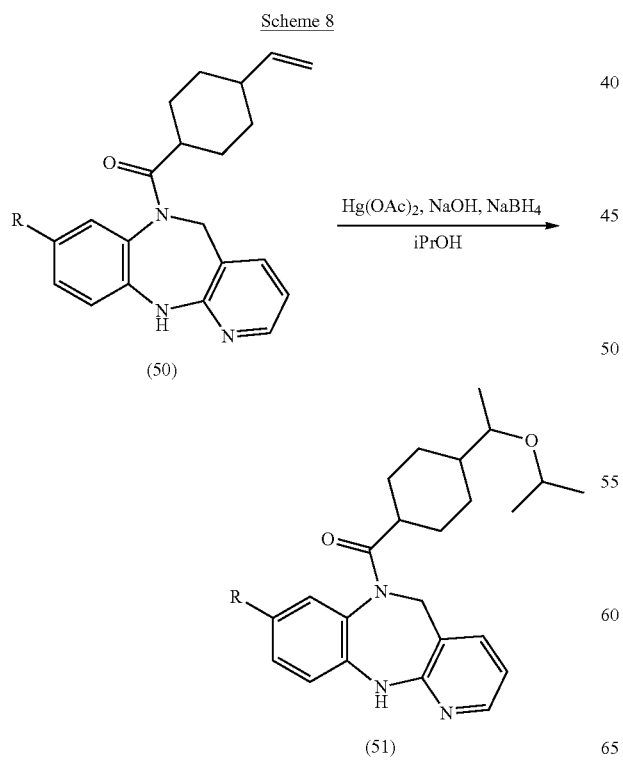

In general scheme 8, Markovnikov addition of an alcohol to alkene compounds of formula (50) via an oxymercuration-demercuration reaction affords ether (51).

Scheme 9

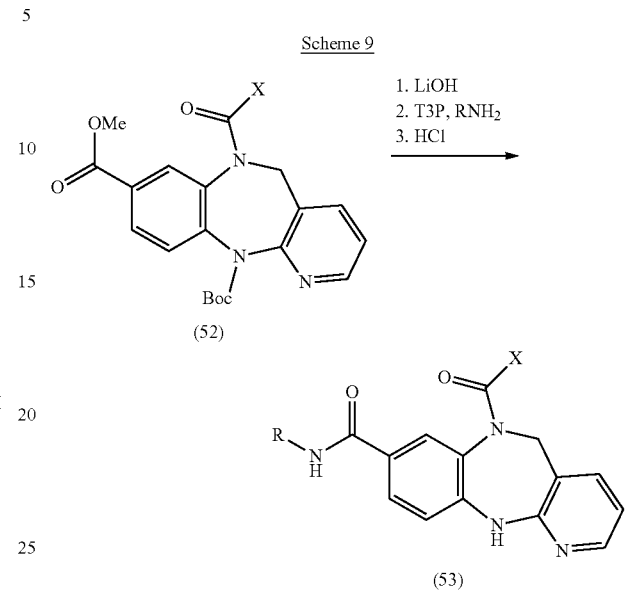

In general scheme 9, amide compounds of formula (53) can be prepared in three steps via ester (52). Hydrolysis of ester (52), followed by amide coupling gives the boc protected product. Acidic deprotection affords the final amide product (53).

Scheme 10

In general scheme 10, compounds of formula (55) can be prepared from ester (54) via reduction under an atmosphere of hydrogen followed by hydrolysis. Reductive coupling of (56) followed by hydrolysis affords carboxylic acid (57).

Scheme 11

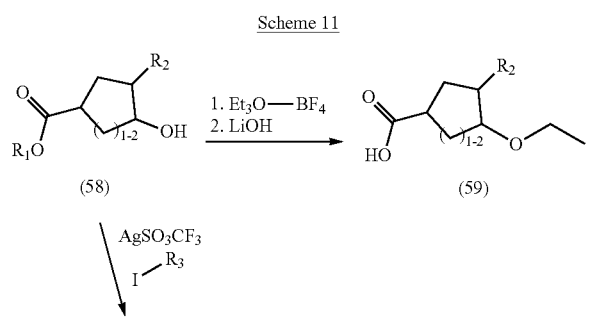

In general scheme 11, compounds of formula (58) can be used to prepare multiple intermediates. An alkylation reaction using Meerwein's reagent with (58) followed by hydrolysis of the ester affords carboxylic acid with general structure (59). Alternatively, a silver triflate-mediated alkylation of (58), followed by hydrolysis affords carboxylic acid (61).

In general scheme 12, a palladium-mediated hydrogenation of (62) affords keto ester (63), which can be used to make multiple intermediates. Ketone (63) can be reacted with DAST to afford the difluoro intermediate (64). Inversion of stereochemistry with KOtBu followed by hydrolysis affords intermediate (65). Alternatively, reduction of ketone (63) gives alcohol (66). Inversion of stereochemistry with KOtBu affords (67). Alkylation followed by hydrolysis affords intermediate (68).

Scheme 13

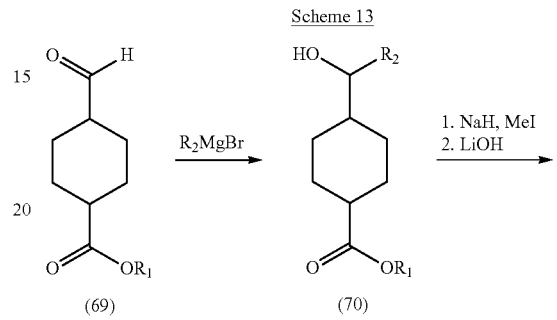

Scheme 12

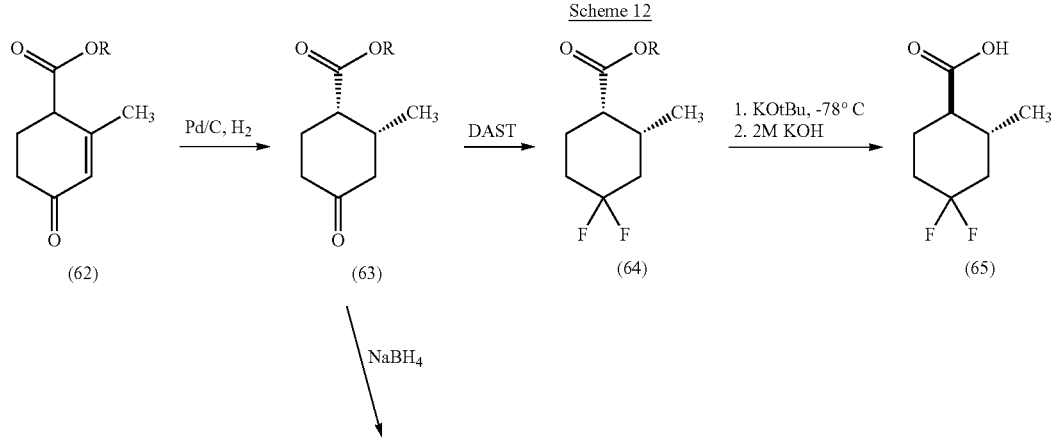

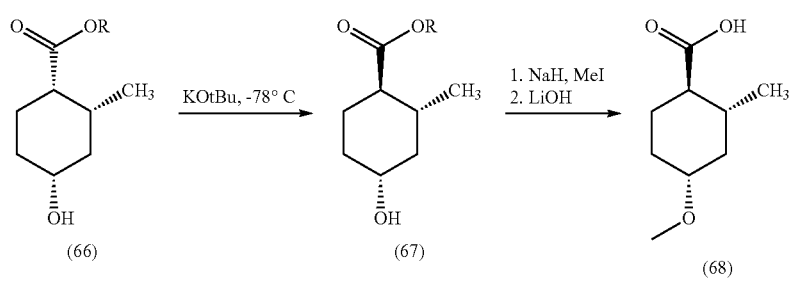

51
-continued

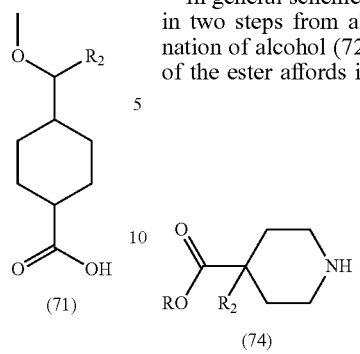

In general scheme 13, compound of formula (71) can be prepared in three steps from aldehyde (69). Grignard reaction with (69) gives secondary alcohol (70). Alkylation followed by hydrolysis affords intermediate (71).

Scheme 14

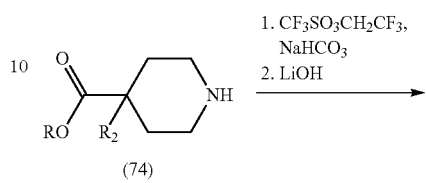

52

In general scheme 14, difluoro ether (73) can be prepared in two steps from alcohol (72). Copper-mediated difluorination of alcohol (72) affords the difluoro ether. Hydrolysis of the ester affords intermediate (73).

Scheme 15

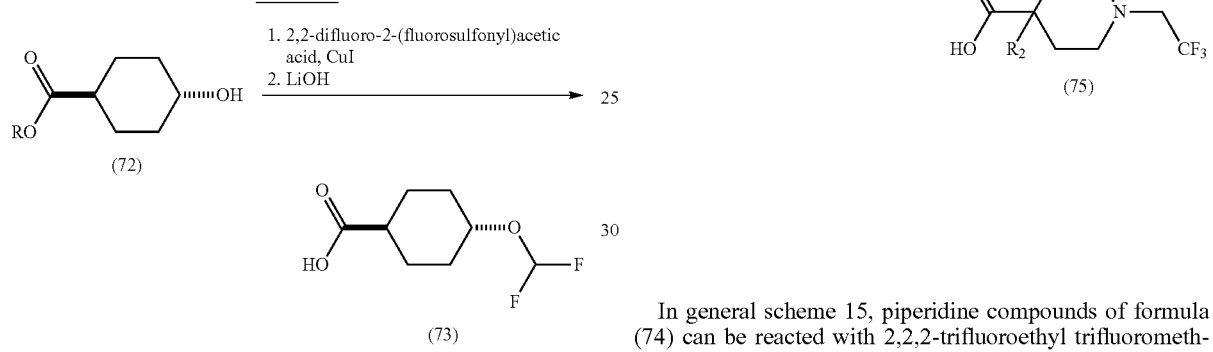

In general scheme 15, piperidine compounds of formula (74) can be reacted with 2,2,2-trifluoroethyl trifluoromethanesulfonate to give the trifluoroethyl amine. Hydrolysis of the ester gives the carboxylic acid intermediate (75).

Scheme 16

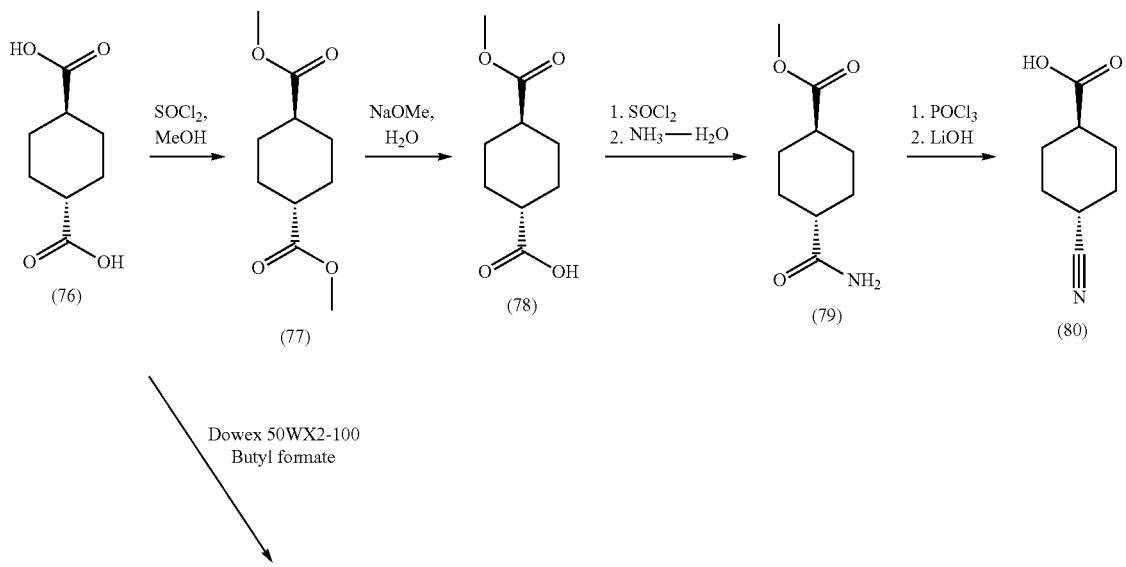

-continued

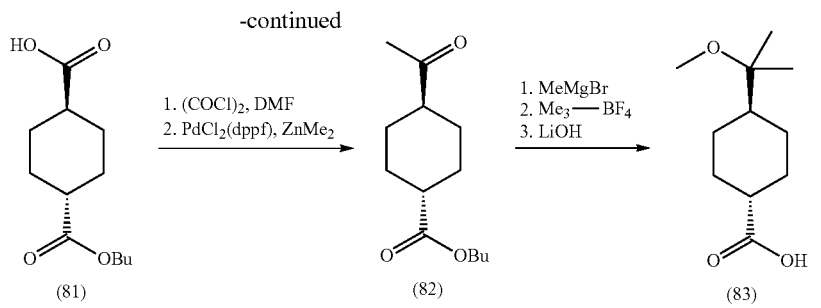

In general scheme 16, dicarboxylic acid (76) can be used to prepare multiple intermediates. Acylation of (76) with thionyl chloride in the presence of methanol gives diester (77). Hydrolysis with sodium methoxide gives carboxylic acid (78), followed by amide coupling to afford (79). Reduction of the amide with $PO_3$ gives the nitrile, followed by ester hydrolysis affords (80). Alternatively, mono-esterification of (76) gives intermediate (81). Acylation followed by a palladium-mediated methylation affords keto ester (82). Carboxylic acid (83) can be formed in three steps from keto ester (82). Grignard reaction with ketone (82) gives the tertiary alcohol. Alkylation with Meerwein's reagent gives the ether and hydrolysis of the ester gives carboxylic acid (83).

Scheme 17

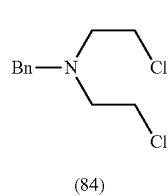

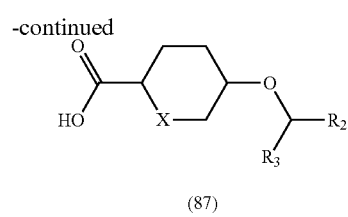

In general scheme 17, piperazine (85) can be obtained from dichloroamine (84) via cyclization with 1-(trifluoromethyl)cyclopropanamine to give the benzyl protected product. Palladium-mediated hydrogenation affords the final deprotected intermediate (85).

Scheme 18

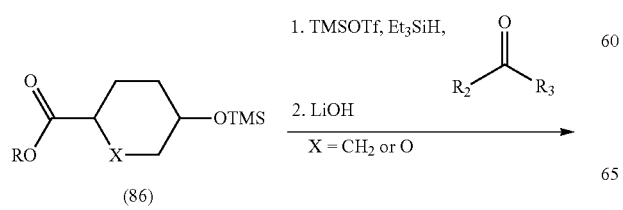

-continued

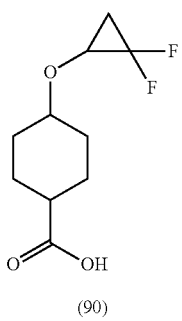

In general scheme 18, reductive coupling of silyl ether compounds of formula (86) with desired ketones, followed by ester hydrolysis gives carboxylic acid compounds with general structure (87).

Scheme 19

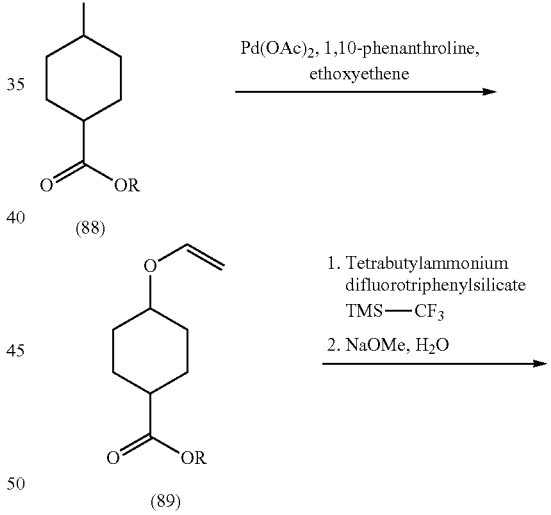

In general scheme 19, a palladium-mediated coupling of ethoxyethene with alcohols of general formula (88) affords alkene (89). Alkene (89) can be reacted with tetrabutylam-

Scheme 20

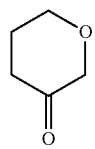
(105)

KHMDS, PhNTf₂ →

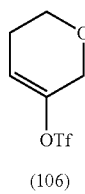
(106)

Bis-Pin, "Pd" →

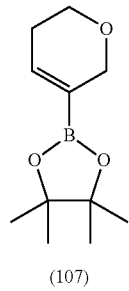
(107)

In general scheme 23, boronate ester (107) can be prepared by the following sequence. Vinyl triflate (106) can be prepared by reacting ketone (105) with PhNTf₂ in the presence of base. Conversion of the vinyl triflate (106) with bis(pinacolato)diboron affords the vinyl boronate ester (107).

Scheme 21

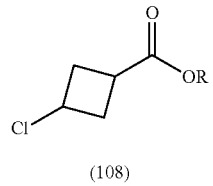
(108)

1. PhOH
2. NaOH →

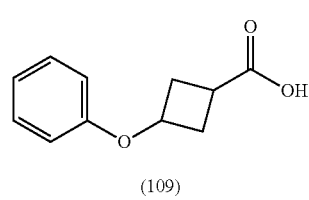
(109)

In general scheme 24, alkyl chloride (108) can be reacted with phenol to form an ether, followed by ester hydrolysis to give carboxylic acid (109).

Scheme 22

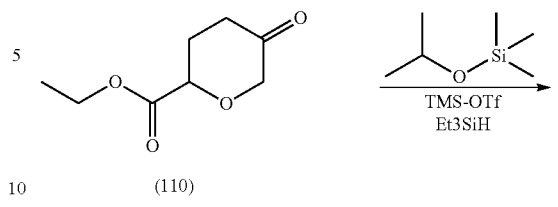
(110)

TMS-OTf, Et3SiH →

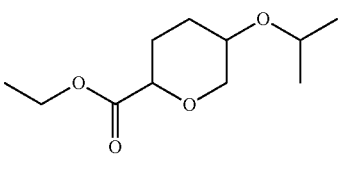
(111)

LiOH →

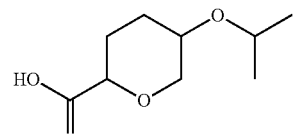
(112)

1) BnBr
2) chiral separation →

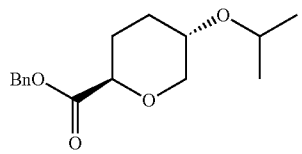
(113)

Pd/C, H₂ →

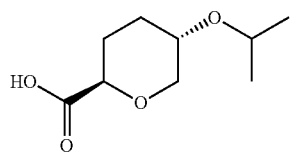
(114)

In general scheme 25, carboxylic acid (114) can be prepared from ketone (110) by the following sequence. Reductive coupling affords ether (111), and hydrolysis gives carboxylic acid (112). Benzylation of the carboxylic acid, followed by chiral separation gives enantiopure ester (113), and deprotection gives the enantiopure carboxylic acid (114).

Scheme 23

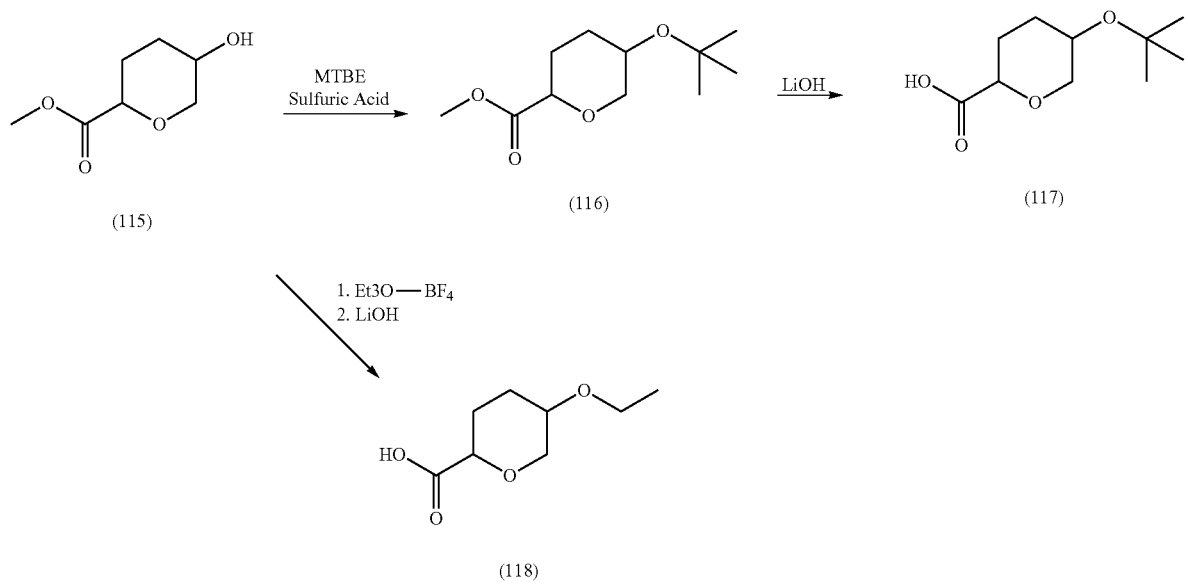

In general scheme 26, alcohol (115) can be used to prepare multiple intermediates. Etherification of (115) with MTBE and sulfuric acid gives t-Bu ether (116), and hydrolysis affords the final carboxylic acid (117). Alternatively, alkylation with Meerwein salt followed by hydrolysis gives carboxylic acid (118).

Scheme 24

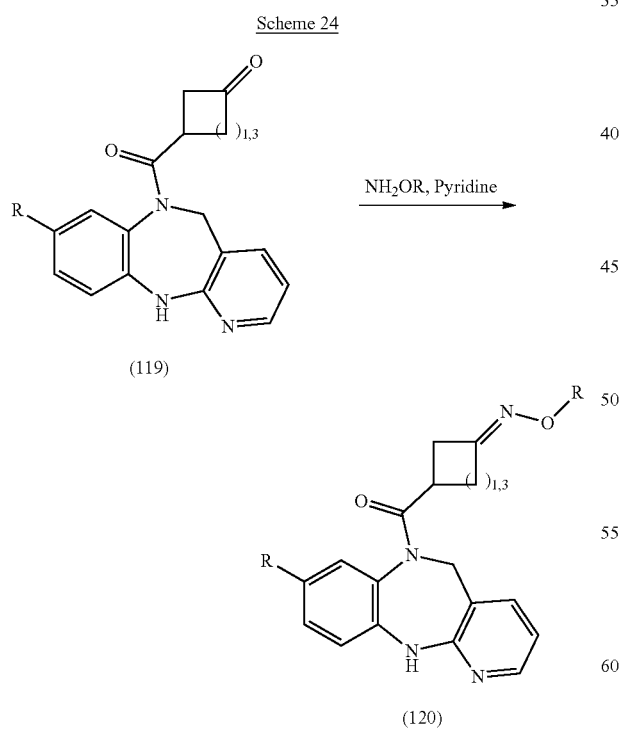

In general scheme 27, oxime compounds of formula (120) can be prepared via reaction with various O-substituted hydroxyl amines to give oxime (120).

Scheme 25

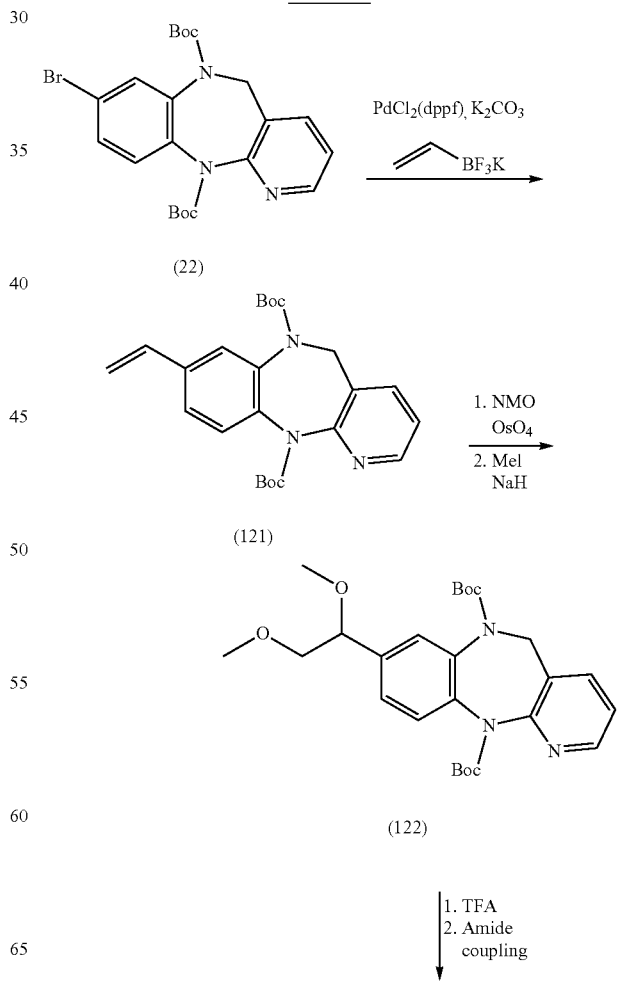

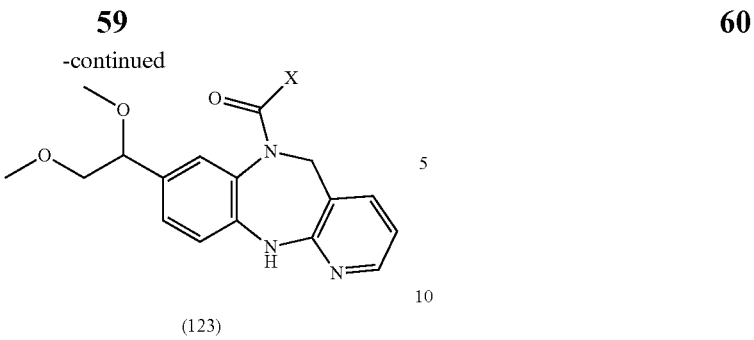
(123)
In general scheme 28, diether compounds of formula (123) can be prepared from the bis-boc protected tricycle core (22). Suzuki reaction gives styrene (121), and dihydroxylation followed by alkylation gives diether (122). TFA deprotection and amide coupling affords (123).
Scheme 26
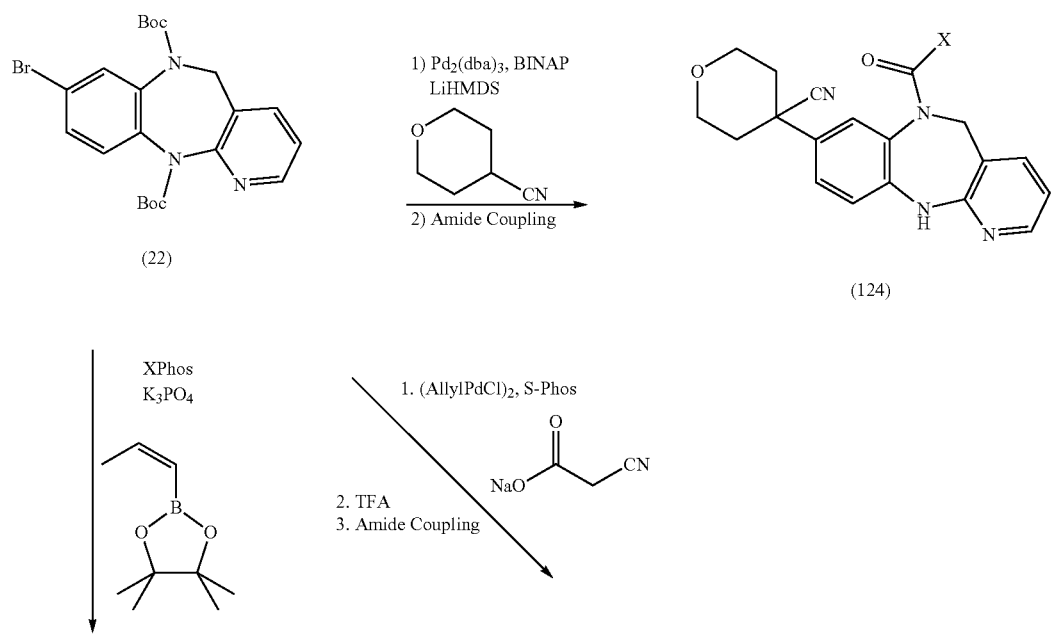

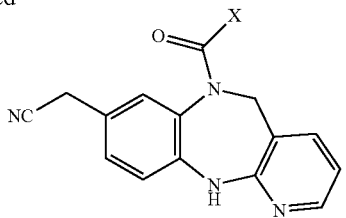

(125)

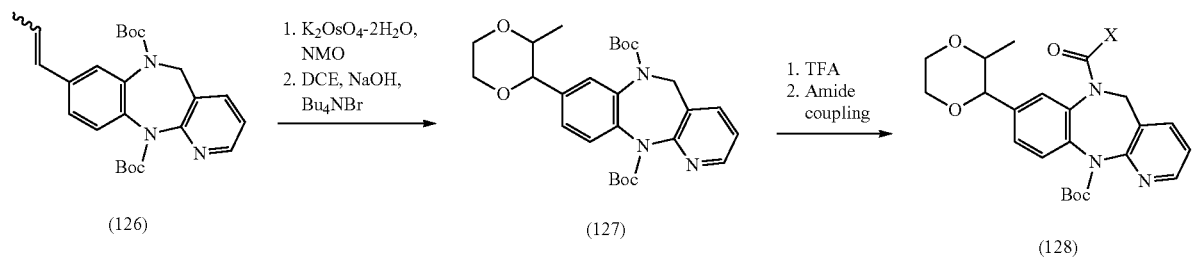

(126)   (127)   (128)

In general scheme 29, bis-boc tricycle (22) can be used to prepare multiple compounds. Alpha arylation of the nitrile building block, followed by amide coupling gives (124) and (125). Alternatively, a Suzuki reaction with (22) affords styrene (126), which is dihydroxylated and then cyclized to afford substituted dioxane (127). Deprotection followed by amide coupling affords (128).

-continued

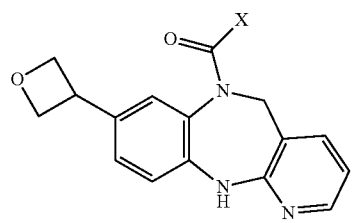

(130)

In general scheme 30, oxetane compounds of formula (130) can be prepared from bis-boc tricycle (22). Suzuki reaction, followed by hydroboration and hydrogenation affords diol (129). Tosylation in the presence of base gives the oxetane, and TFA deprotection followed by amide coupling affords (130).

Scheme 27

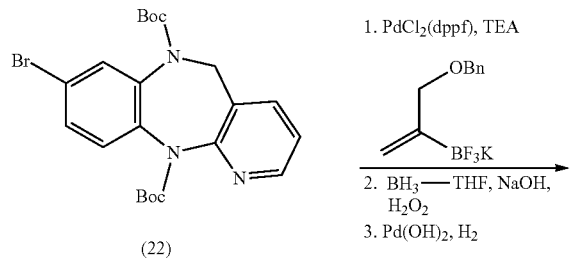

Scheme 28

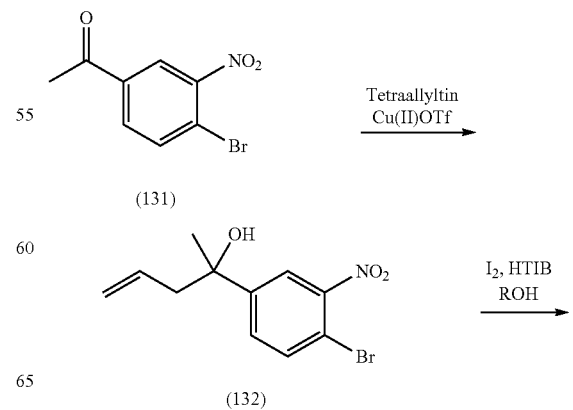

(131)

(132)

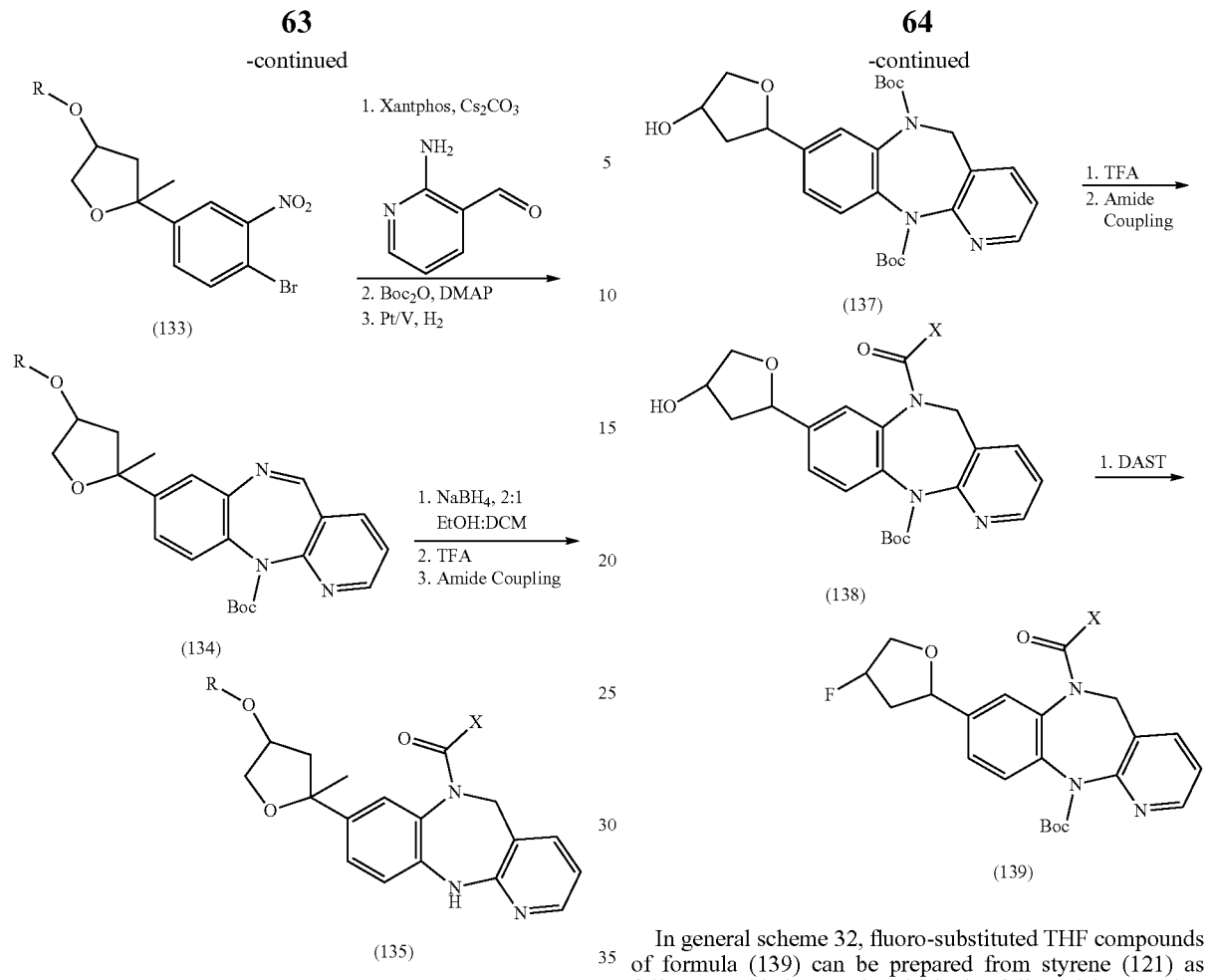

In general scheme 31, substituted THF compounds of formula (135) can be prepared from substituted acetophenone (131). Reaction with tetraallyltin affords alcohol (132), and cyclization affords substituted THF (133). C—N coupling, boc-protection, and cyclization afford tricycle (134). Imine reduction, followed by TFA deprotection and amide coupling afford (135).

In general scheme 32, fluoro-substituted THF compounds of formula (139) can be prepared from styrene (121) as follows. Oxidation to the aldehyde, followed by reaction with allylmagnesium chloride gives allyl alcohol (136). Dihydroxylation followed by cyclization gives hydroxyl THF (137). TFA deprotection and amide coupling afford (138). The hydroxyl THF derivative can be further derivatized by subjecting the alcohol to DAST to give the fluorinated derivative (139).

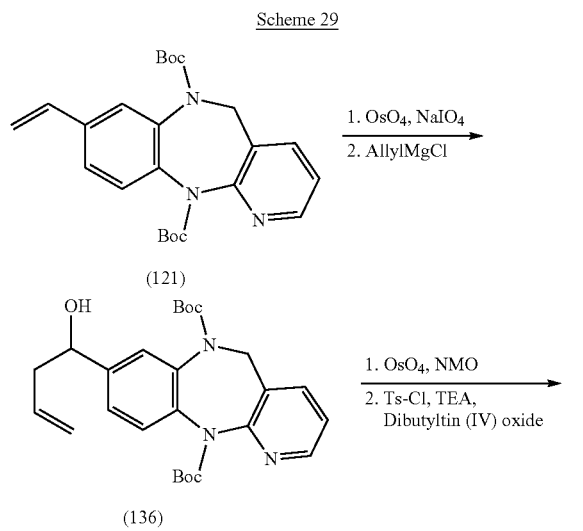

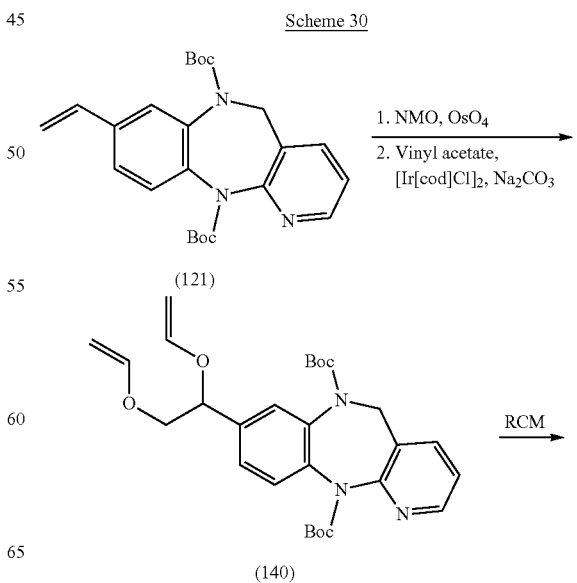

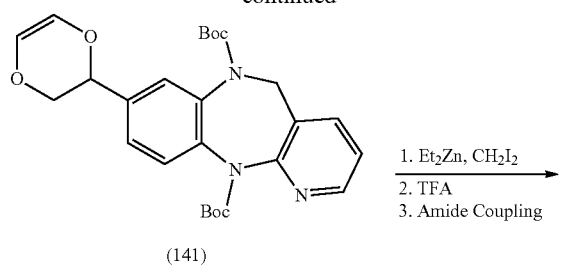

(141)

1. Et₂Zn, CH₂I₂
2. TFA
3. Amide Coupling

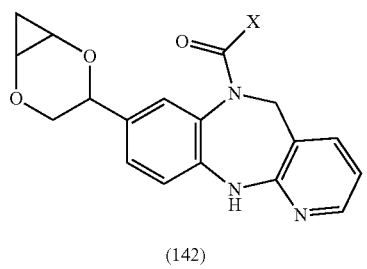

(142)

In general scheme 33, substituted dioxane compounds of formula (142) can be prepared from styrene (121) as follows. Dihydroxylation followed by vinylation gives (140). Ring closing metathesis affords dioxene (141), and cyclopropanation affords the cyclopropyl dioxane. TFA deprotection followed by amide coupling gives (142).

Scheme 31

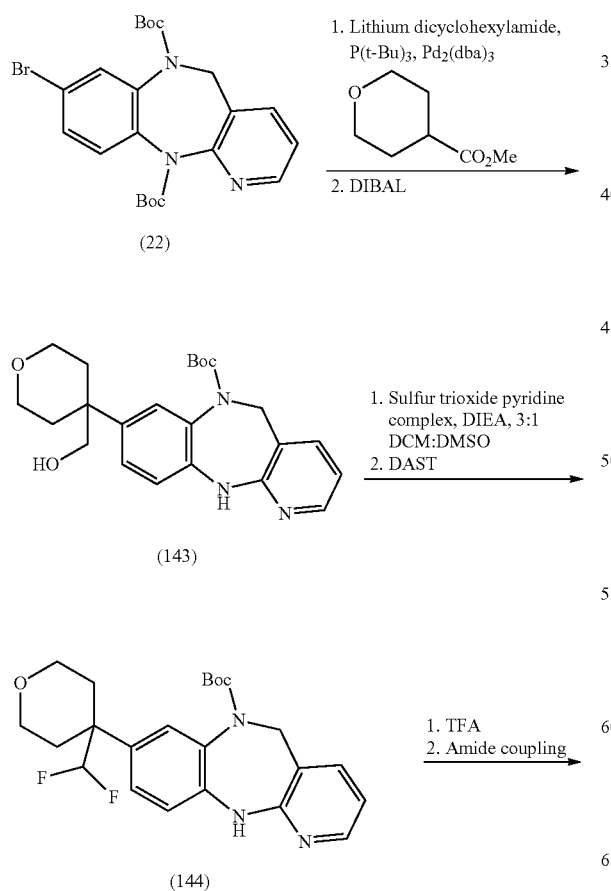

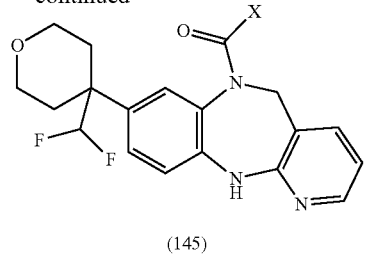

(145)

In general scheme 34, difluoro substituted tetrahydropyran compounds of formula (145) can be prepared from bis-boc tricycle (22). Alpha arylation of the ketone followed by DIBAL reduction gives alcohol (143). Oxidation followed by fluorination gives (144), and TFA deprotection and amide coupling affords (145).

Scheme 32

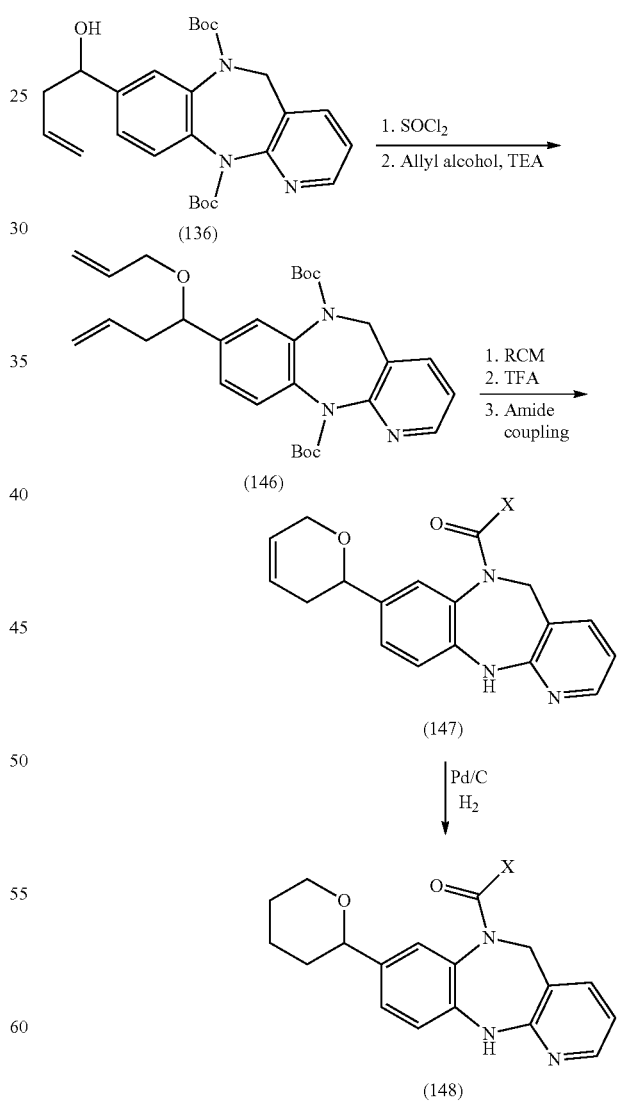

In general scheme 35, tetrahydropyran compounds of formula (148) can be prepared from allyl alcohol (136). Chlorination followed by reaction with allyl alcohol gives diene (146). Ring closing methathesis followed by TFA deprotection and amide coupling affords olefin (147). Hydrogenation affords the tetrahydropyran (148).

Scheme 33

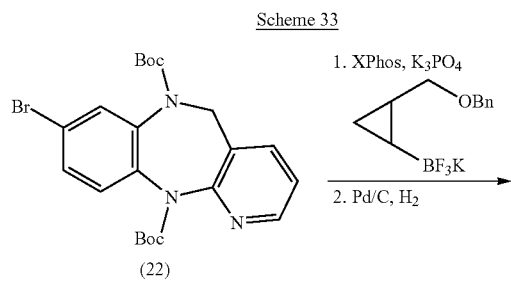

(22)

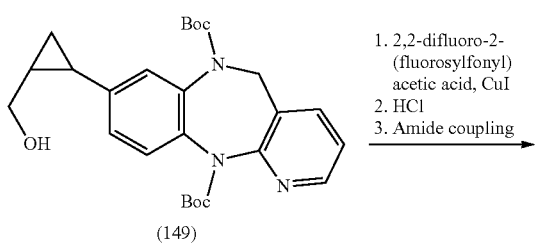

(149)

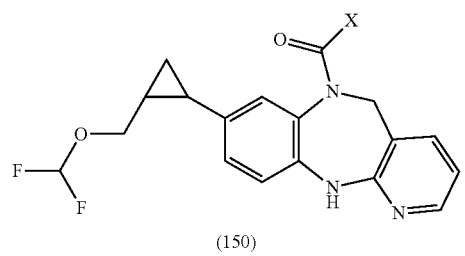

(150)

In general scheme 36, difluoroether compounds of formula (150) can be prepared from bis-boc tricycle (22). Suzuki reaction and deprotection affords cyclopropyl alcohol (149). Difluormethylation followed by deprotection and amide coupling affords (150).

Scheme 34

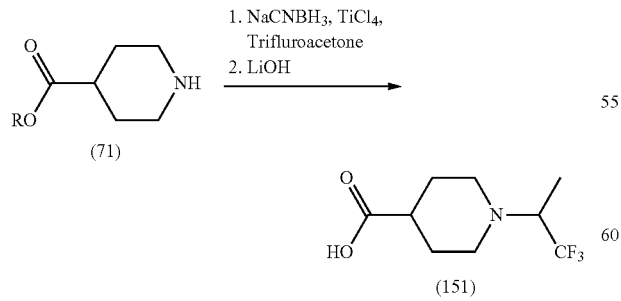

In general scheme 37, reductive amination of piperidine (71) with trifluoroacetone, followed by hydrolysis gives (151).

Scheme 35

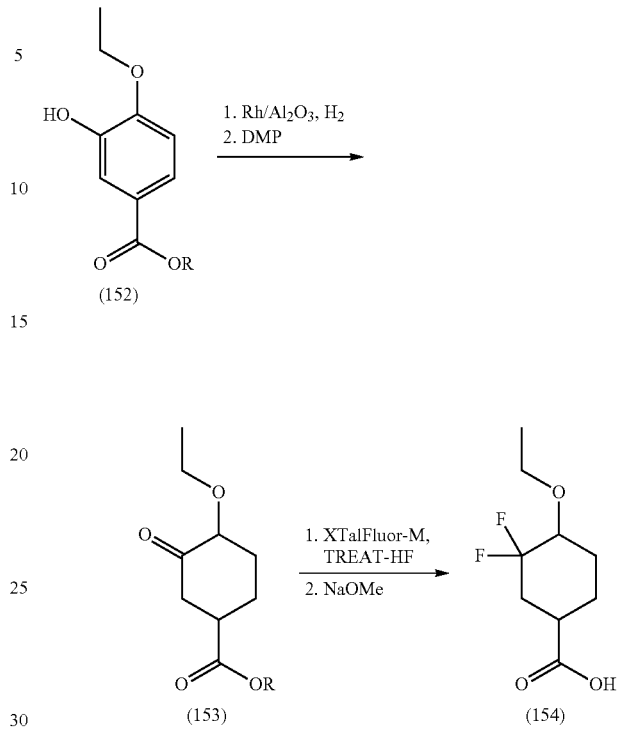

In general scheme 38, ketone (153) can be prepared from phenol (152) via reduction under an atmosphere of hydrogen followed by oxidation. Difluorination followed by hydrolysis affords carboxylic acid (154).

Scheme 36

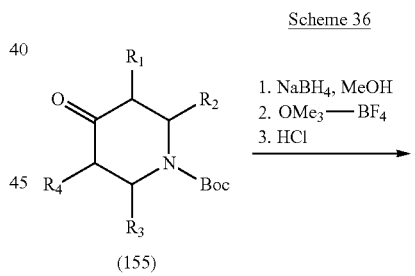

(155)

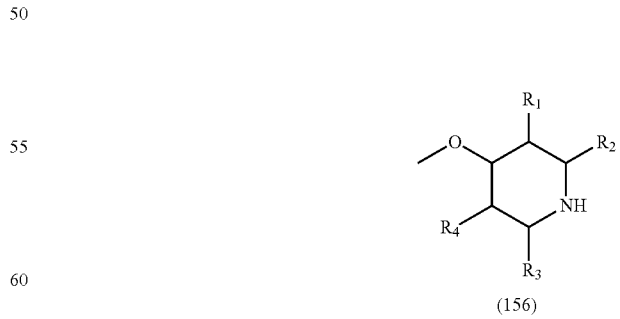

(156)

In general scheme 39, piperidine compounds of general structure (156) can be prepared from ketone (155). Reduction, followed by alkylation and boc deprotection affords amine (156).

Scheme 37

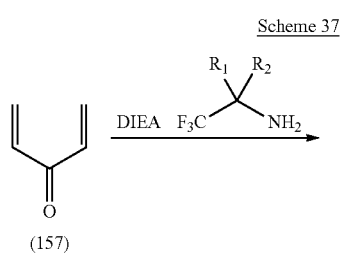

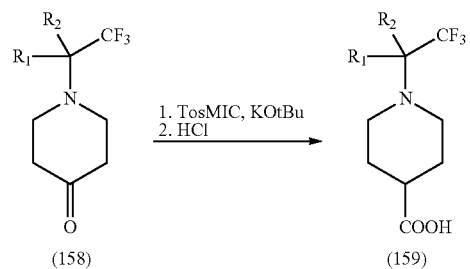

In general scheme 40, piperidine compounds of general structure (159) can be prepared from dienone (157) and substituted trifluoromethyl ethylamines to afford (158). Cyanation, followed by nitrile hydrolysis affords carboxylic acid (159).

Scheme 38

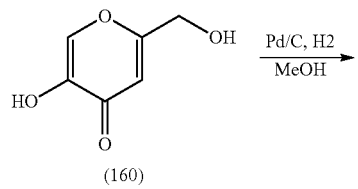

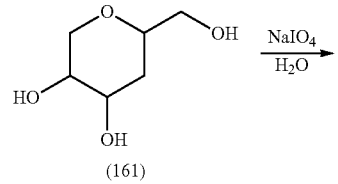

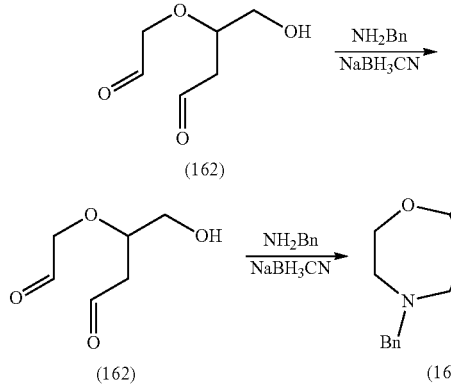

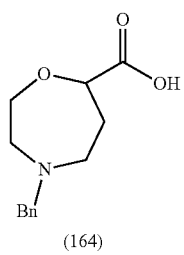

In general scheme 41, hydrogenation of dienone (160) affords triol (161), and oxidation affords dialdehyde (162). Reaction with benzylamine, followed by reductive amination affords cyclized product (163). Deprotection followed by boc-protection and oxidation affords carboxylic acid (164).

Scheme 39

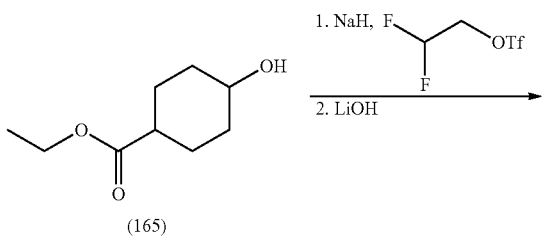

In general scheme 42, carboxylic acid (166) can be formed from alcohol (165) via alkylation to afford the difluoromethyl ethyl ether. Hydrolysis gives carboxylic acid (166).

Scheme 40

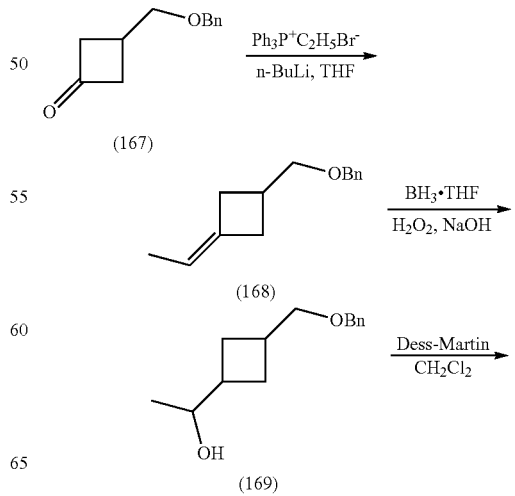

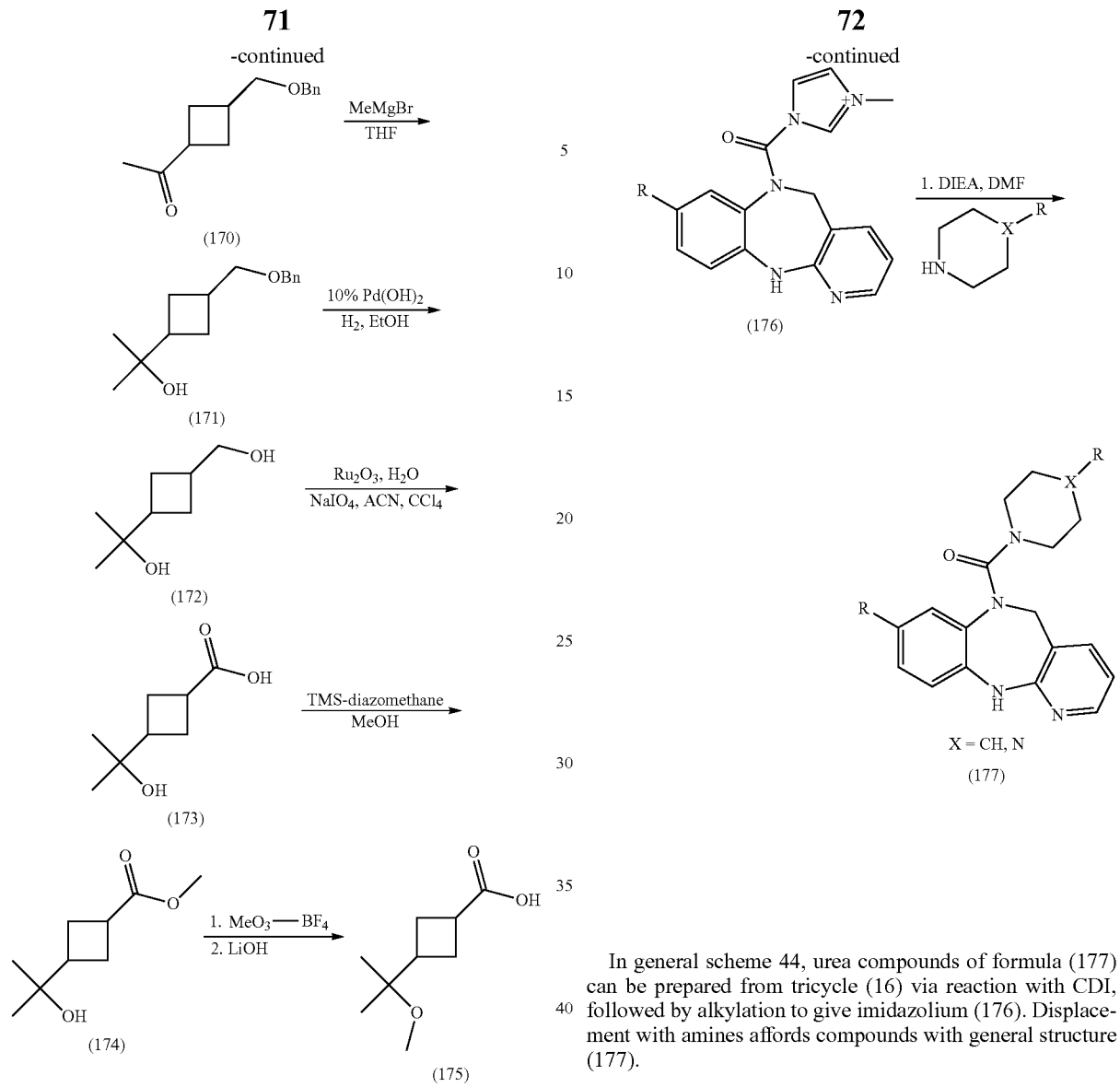

In general scheme 43, carboxylic acid (175) can be prepared from ketone (167) as follows. Wittig reaction gives olefin (168), and hydroboration gives alcohol (169). Oxidation gives ketone (170), and Grignard addition gives gem-dimethyl alcohol (171). Deprotection gives diol (172), followed by oxidation to afford carboxylic acid (173). Reaction with TMS-diazomethane affords ester (174), and alkylation followed by hydrolysis gives carboxylic acid (175).

Scheme 41

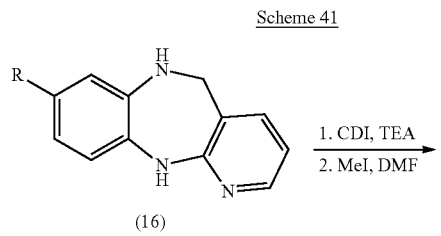

In general scheme 44, urea compounds of formula (177) can be prepared from tricycle (16) via reaction with CDI, followed by alkylation to give imidazolium (176). Displacement with amines affords compounds with general structure (177).

Scheme 42

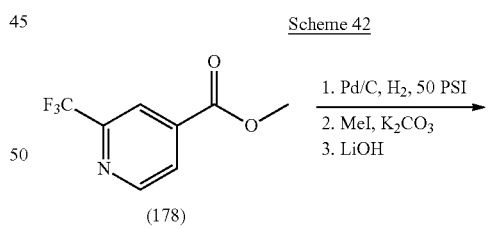

In general scheme 45, hydrogenation of (178) affords the piperidine, followed by alkylation and hydrolysis to afford carboxylic acid (179).

Scheme 43

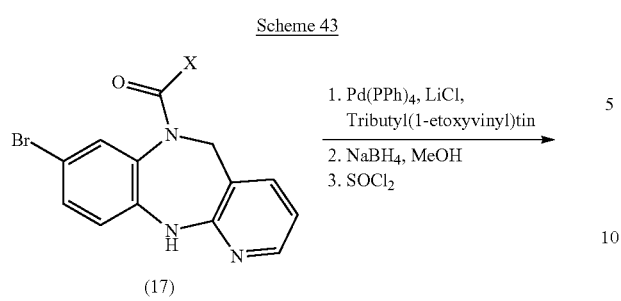

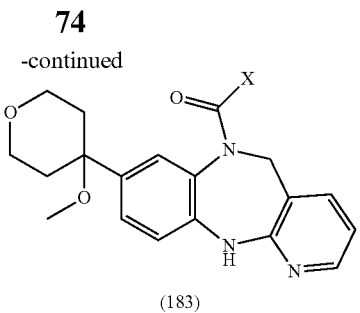

In general scheme 47, lithiation of (17) followed by fluorination gives (182). O-alkylation gives ether (183).

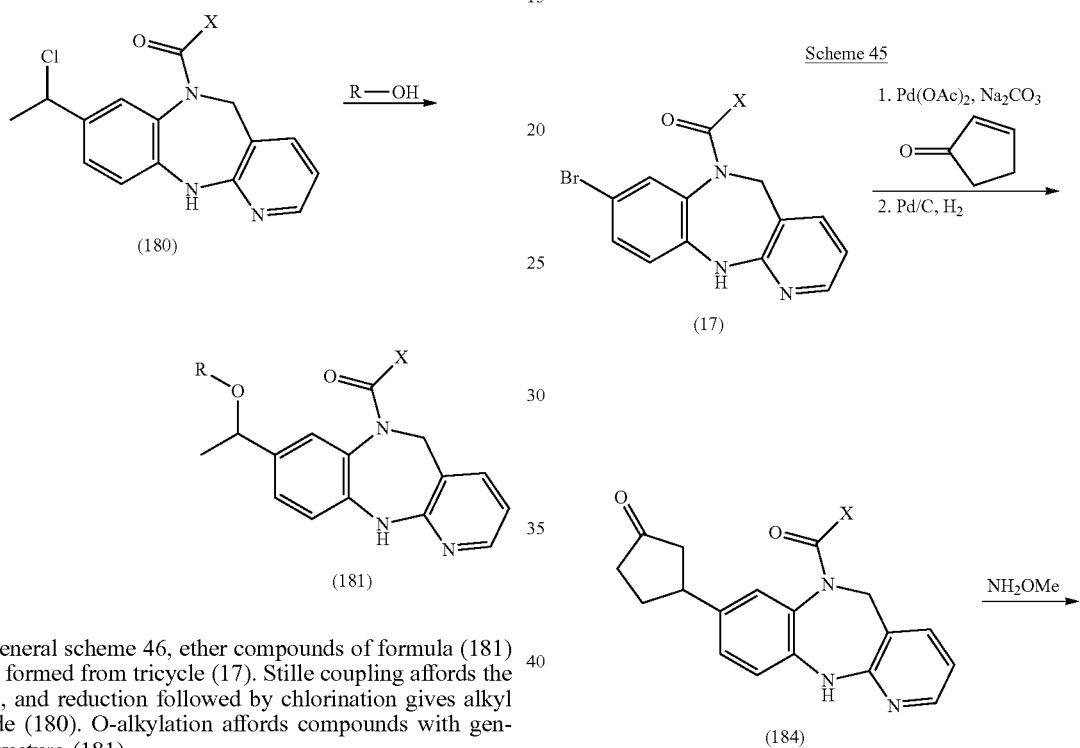

In general scheme 46, ether compounds of formula (181) can be formed from tricycle (17). Stille coupling affords the ketone, and reduction followed by chlorination gives alkyl chloride (180). O-alkylation affords compounds with general structure (181).

Scheme 44

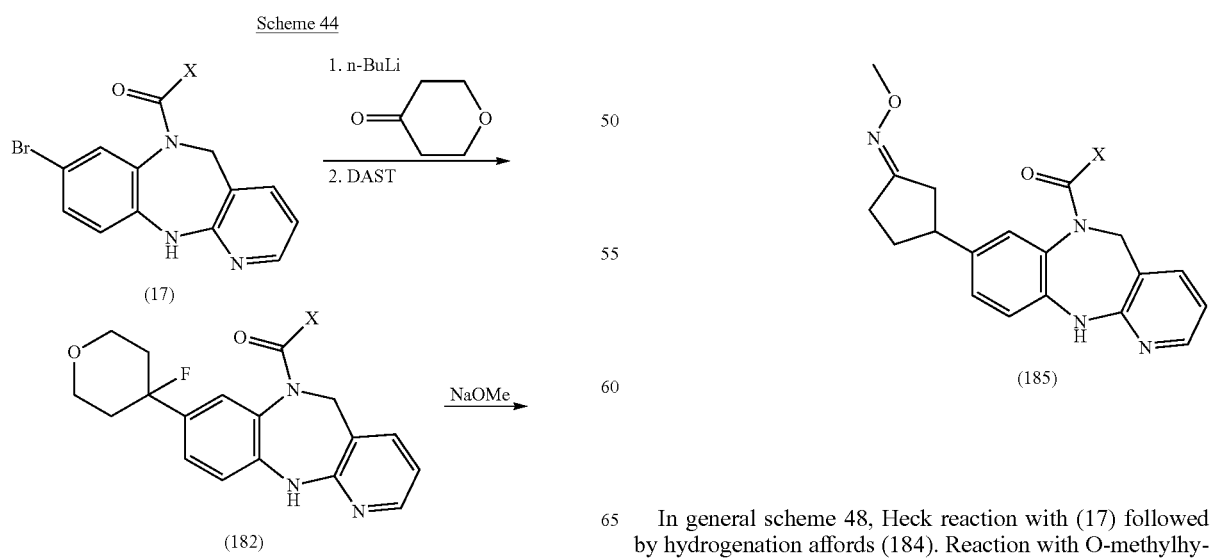

In general scheme 48, Heck reaction with (17) followed by hydrogenation affords (184). Reaction with O-methylhydroxylamine affords oxime (185).

Scheme 46

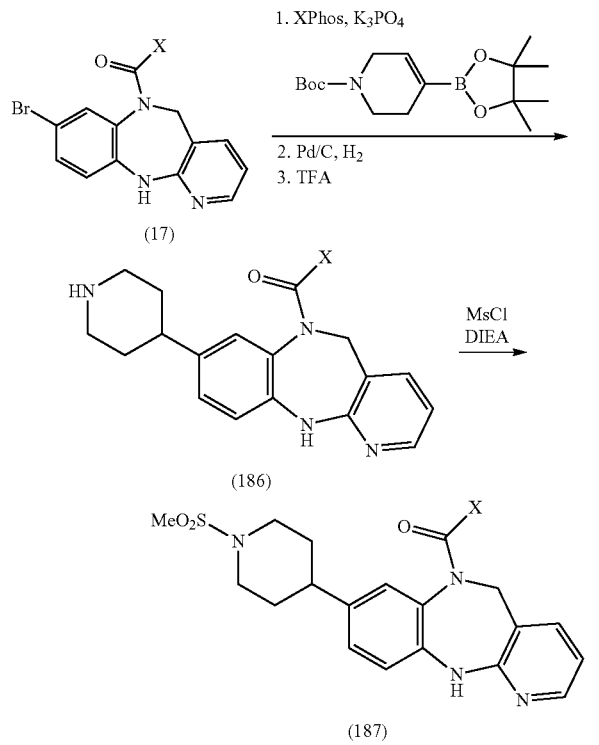

In general scheme 49, Suzuki reaction with (17), followed by hydrogenation and boc-deprotection gives (186). Reaction with mesyl chloride affords sulfonamide (187).

INTERMEDIATES

Intermediate 1: 6,11-Dihydro-5H-benzo[b]pyrido[2,3-e][1,4]diazepine

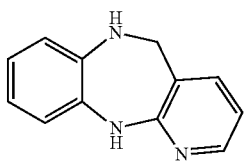 [SMILES: c1cnc2c(c1)CNc1ccccc1N2]

Step 1:
To a 10-L 4-necked round-bottom flask purged and maintained with an inert atmosphere of nitrogen was added a mixture of benzene-1,2-diamine (520 g, 4.81 mol) in cyclohexanol (4.8 L) followed by 4-chloropyridine-3-carboxylic acid (760 g, 4.82 mol). The resulting mixture was heated to 150° C. for 2.5 h. Upon cooling to room temperature, the mixture was diluted with DCM (10 L). The resulting solid was collected by filtration and washed with DCM (4×300 mL) to afford 6,11-dihydro-5H-benzo[b]pyrido[2,3-e][1,4]diazepin-5-one as the HCl salt that was taken on to the next step.

Step 2:
To a 10-L 4-necked round-bottom flask purged and maintained with an inert atmosphere of nitrogen was added a mixture of the HCl salt of 6,11-dihydro-5H-benzo[b]pyrido[2,3-e][1,4]diazepin-5-one (500 g, 2.02 mol) in 1,4-dioxane (4.6 L), followed by the dropwise addition of $BH_3$—$SMe_2$ (10M, 710 mL, 7.07 mol). The resulting mixture was stirred at room temperature for 10 h. The reaction was then quenched by the addition of aqueous HCl (2 M, 2000 mL) and MTBE (800 mL), and then stirred at room temperature for an additional 10 h. The pH of the solution was adjusted to 9-10 with aqueous sodium hydroxide (50%). The resulting mixture was extracted with ethyl acetate (3×1.5 L). The combined organic layers were washed with brine (1 L), dried over anhydrous magnesium sulfate, filtered, and concentrated under reduced pressure. The crude product was purified by re-crystallization from ether to afford the title compound as a solid. MS: 198 (M+1). $^1$H NMR (300 MHz, $CDCl_3$) δ 8.06-8.04 (m, 1H), 7.26-7.20 (m, 2H), 6.87-6.70 (m, 4H), 6.65-6.61 (m, 1H), 4.18 (s, 3H).

Intermediate 2: 8-Bromo-6,11-dihydro-5H-benzo[b]pyrido[2,3-e][1,4]diazepine (HCl Salt)

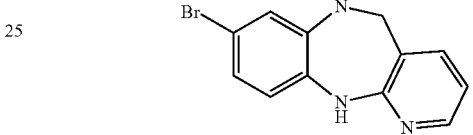

Step 1:
To a 20-L round-bottom flask was added potassium tert-butoxide (2198 g, 19.54 mol), ethylene glycol dimethyl ether (6 L) and cuprous chloride (45.5 g, 0.459 mol). A mixture of 1-bromo-4-nitrobenzene (929 g, 4.60 mol) and methoxylamine hydrochloride (480 g, 5.75 mol) in N,N-dimethylformamide (7.5 L) was added dropwise over 60 minutes. The resulting mixture was stirred at room temperature for 12 h and then diluted with ethyl acetate (4 L). The organic layer was washed with saturated aqueous ammonium chloride (2×12 L) and brine (3×8 L), dried over anhydrous magnesium sulfate, filtered, and concentrated under reduced pressure. The solid was washed with petroleum ether (3 L) to afford 5-bromo-2-nitroaniline as a solid that was used in the next reaction.

Step 2:
To a 20-L 4-necked round-bottom flask was added 5-bromo-2-nitroaniline (792 g, 3.65 mol), 1,4-dioxane (3 L), cyclohexane (9 L), and pyridine (289 g, 3.65 mol). 2-Chloropyridine-3-carbonyl chloride (738 g, 4.20 mol) in 1,4-dioxane (1 L) was added dropwise, and the resulting mixture was heated to 85° C. for 12 h. Upon cooling to room temperature, the solid was filtered. The filtrate was extracted with ethyl acetate (3×5 L) and the combined organic layers were dried over anhydrous sodium sulfate, filtered, and concentrated under reduced pressure. The solid was washed with petroleum ether (2 L) to afford N-(5-bromo-2-nitrophenyl)-2-chloropyridine-3-carboxamide as a solid that was used in the next reaction.

Step 3:
To a 20-L 4-necked round-bottom flask was added N-(5-bromo-2-nitrophenyl)-2-chloropyridine-3-carboxamide (800 g, 2.24 mol), ethanol/water (1:1 mixture, 10 L) and ammonium chloride (597 g, 11.3 mol). Iron was added (629 g, 11.3 mol) in portions, and the resulting mixture was heated to 80° C. for 1.5 h. Upon cooling to room temperature, the solid was filtered. The filtrate was concentrated under reduced pressure, and the residual mixture was extracted with ethyl acetate/tetrahydrofuran (1:3 mixture, 2×5 L). The combined organic layers were washed with brine (3 L), dried over anhydrous sodium sulfate, filtered, and concentrated under reduced pressure to afford N-(2-amino-5-bromophenyl)-2-chloropyridine-3-carboxamide as a solid that was used in the next reaction.

Step 4:
To a 20-L 4-necked round-bottom flask was added N-(2-amino-5-bromophenyl)-2-chloropyridine-3-carboxamide (330 g, 1.01 mol), tetrahydrofuran (5 L), and borane-THF complex (1M, 4.55 L, 4.55 mol). The resulting mixture was heated to 60° C. for 2 h. The reaction was then quenched with methanol (6.8 L) and heated to 70° C. for 2 h. Upon cooling to room temperature, the mixture was concentrated under reduced pressure. The residue was taken up in MTBE (800 mL) and the mixture was acidified to pH~2 with aqueous HCl (2N). The pH was then adjusted to 8-10 with aq. NaOH (2M). The resulting mixture was extracted with ethyl acetate/THF (1:3 mixture, 2×3 L), and the combined organic layers were washed with brine (1×2 L), dried over anhydrous sodium sulfate, filtered, and concentrated under reduced pressure. The resulting solid was washed with water (5×1 L) to afford 5-bromo-1-N-[(2-chloropyridin-3-yl)methyl]benzene-1,2-diamine as a solid that was used in the next reaction.

Step 5:
To a 10-L 4-necked round-bottom flask was added 5-bromo-1-N-[(2-chloropyridin-3-yl)methyl]benzene-1,2-diamine (465 g, 1.49 mol) and cyclohexanol (4.5 L). The resulting mixture was heated to 140° C. for 3 h. Upon cooling to room temperature, the mixture was concentrated under reduced pressure. The crude product was re-crystallized from dichloromethane and then washed with diethyl ether (2 L) to afford the title compound as a solid. MS: 276 (M+1). $^1$H NMR (300 MHz, DMSO-$d_6$) δ 10.75 (s, 1H), 8.16-8.13 (q, 1H), 7.88-7.82 (t, 1H), 7.15-6.70 (m, 4H), 4.20-4.16 (d, 2H).

Intermediate 3: 4-(6,11-Dihydro-5H-benzo[b]pyrido [2,3-e][1,4]diazepin-8-yl)morpholine

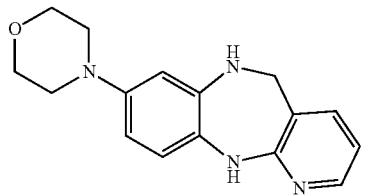

Step 1:
To a 5000-mL 3-necked round-bottom flask purged and maintained with an inert atmosphere of nitrogen was added 4-(morpholin-4-yl)-2-nitroaniline (65 g, 0.29 mol), 2-bromopyridine-3-carbaldehyde (53.8 g, 0.289 mol), tert-butanol (3000 mL), sodium carbonate (43.2 g, 0.407 mmol), Pd$_2$(dba)$_3$ (30.1 g, 0.0338 mol) and Xantphos (33.6 g, 0.0581 mol). The resulting mixture was heated to 80° C. for 18 h. Upon cooling to room temperature, the mixture was concentrated under reduced pressure. The residue was washed with ether (2×300 mL) and then purified by column chromatography on silica gel (100:1 DCM/methanol) to afford 2-[[4-(morpholin-4-yl)-2-nitrophenyl]amino]pyridine-3-carbaldehyde as a solid that was used in the next reaction.

Step 2:
To a 2000-mL round-bottom flask, was added 2-[[4-(morpholin-4-yl)-2-nitrophenyl]amino]pyridine-3-carbaldehyde (75 g, 0.23 mol), methanol (900 mL), THF (300 mL) and palladium on carbon (10 wt % loading, 7.5 g). The mixture was evacuated and then purged with hydrogen multiple times. The resulting mixture was stirred for 16 h at room temperature under a hydrogen atmosphere. The solids were then filtered and the filtrate was concentrated under reduced pressure. The residue was purified by column chromatography on silica gel (100:1 DCM/methanol) to afford the title compound as a solid. MS: 283 (M+1). $^1$H NMR (300 MHz, DMSO-$d_6$) δ 8.46 (s, 1H), 7.30 (d, 1H), 7.27 (d, 1H), 6.95 (d, 1H), 6.52 (s, 1H), 6.35 (m, 2H), 5.63 (s, 1H), 3.97 (m, 2H), 3.70 (m, 4H), 2.94 (m, 4H).

Intermediate 4: (8-Bromo-5,11-dihydro-6H-pyrido [2,3-b][1,5]benzodiazepin-6-yl)(trans-4-methoxycyclohexyl)methanone

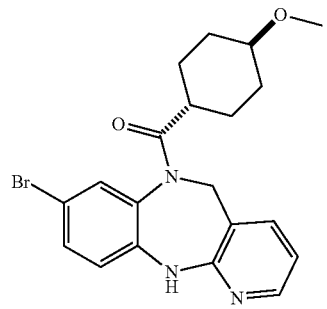

Step 1:
To a 2-L 4-necked round-bottom flask purged and maintained with an inert atmosphere of nitrogen, was placed a solution of trans-4-hydroxycyclohexanecarboxylic acid (20 g, 0.14 mol) in DMF (400 mL). Sodium hydride was added (60%, 14 g, 0.35 mol) in several batches at room temperature. The resulting solution was stirred for 2 h at 50° C. This was followed by the addition of iodomethane (27 mL) dropwise, while stirring at room temperature. The resulting solution was allowed to stir for an additional 10 h at room temperature. The reaction was quenched with saturated ammonium chloride (200 mL) and diluted with water/ether (1.2/1.0 L). The resulting solution was extracted with ether (2×500 mL) and the organic layers were combined. The resulting mixture was washed with water (2×1 L) and brine (2 L). The organic layer was dried over anhydrous sodium sulfate, filtered, and concentrated under reduced pressure to afford methyl trans-4-methoxycyclohexanecarboxylate as an oil.

Step 2:
To a 1-L 4-necked round-bottom flask purged and maintained with an inert atmosphere of nitrogen, was placed a solution of methyl trans-4-methoxycyclohexanecarboxylate (20.6 g, 0.120 mol) in dioxane (210 mL) and hydrogen chloride (6N, 140 mL). The resulting solution was stirred at 68° C. for 16 h. The mixture was diluted with brine (200 mL) and extracted with EtOAc (2×500 mL). The combined organic layers were dried over anhydrous sodium sulfate, filtered, and concentrated under reduced pressure. The residue was purified by column chromatography on silica (16/1 DCM/methanol) to afford trans-4-methoxycyclohexanecarboxylic acid as a solid.

Step 3:

To a flask purged and maintained with an inert atmosphere of nitrogen was placed a solution of trans-4-methoxycyclohexanecarboxylic acid (7.3 g, 46 mmol) in DCM (80 mL). One drop of DMF was added, followed by oxalyl chloride (8 mL) dropwise. The resulting solution was stirred for 3 h at 40° C. The mixture was concentrated under reduced pressure to afford trans-4-methoxycyclohexanecarbonyl chloride as an oil.

Step 4:

To a flask purged and maintained with an inert atmosphere of nitrogen, was placed a solution of 8-bromo-6,11-dihydro-5H-pyrido[2,3-b][1,5]benzodiazepine, HCl (12.8 g, 41.0 mmol) in DCE (130 mL). Trans-4-methoxycyclohexanecarbonyl chloride (8.0 g, 45 mmol) in DCE (65 mL) was added dropwise with stirring over 10 minutes. The resulting solution was stirred for 1.5 h at 85° C. To the mixture was added 4-dimethylaminopyridine (0.57 g), in portions, followed by DIEA (6 g) dropwise with stirring over 60 minutes. The resulting solution was stirred for 16 h at 85° C. The reaction mixture was cooled to room temperature, quenched with a water/ice mixture, and the resulting solution was extracted with DCE (2×200 mL). The combined organic layers were washed with saturated sodium bicarbonate (200 mL) and then brine (200 mL), and the mixture was dried over anhydrous sodium sulfate, filtered, and concentrated under reduced pressure. The residue was purified by column chromatography on silica gel (1:1 ethyl acetate:petroleum ether) to afford the title compound as a solid. MS: 416 (M+1). $^1$H NMR (300 MHz, DMSO-$d_6$,): δ 9.58 (s, 1H), 8.05 (dd, 1H), 7.53-7.40 (m, 3H), 7.29 (d, 1H), 6.75 (dd, 1H), 5.16 (d, 1H), 3.92 (d, 1H), 3.14 (d, 3H), 2.96-2.93 (m, 1H), 2.37-2.32 (m, 1H), 2.02-1.75 (m, 3H), 1.47-0.63 (m, 4H).

Intermediate 5: (8-Bromo-5,11-dihydro-6H-pyrido[2,3-b][1,5]benzodiazepin-6-yl)[trans-4-(propan-2-yloxy)cyclohexyl]methanone

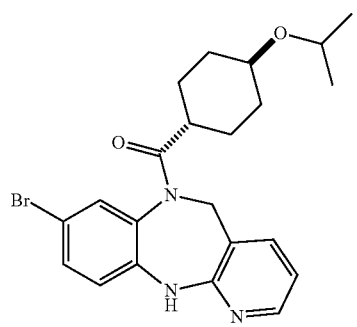

Intermediate 5 can be made using the procedure described for Intermediate 4. MS: 444 and 446 (M and M+2).

Intermediate 6: 2-(6,11-Dihydro-5H-benzo[b]pyrido[2,3-e][1,4]diazepin-8-yl)-2-methylpropanenitrile

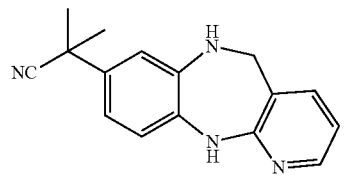 [SMILES: CC(C)(C#N)c1ccc2c(c1)NCc1cccnc1N2]

Step 1:

To a mixture of N-(4-(2-cyanopropane-2-yl)phenyl)acetamide (123 g, 0.610 mol) in concentrated sulfuric acid (494 mL) at −10° C. was added nitric acid (10 M, 73 mL, 0.73 mol) dropwise. The mixture was stirred at −5° C. for 20 minutes. The mixture was then poured into ice water (2 L) and extracted with MTBE (2 L×4). The combined organic layers were washed with saturated potassium carbonate and then brine. The organic layer was dried over sodium sulfate, filtered, and concentrated under reduced pressure to afford crude N-(4-(2-cyanopropane-2-yl)-2-nitrophenyl)acetamide as a solid.

Step 2:

To a mixture of crude N-(4-(2-cyanopropane-2-yl)-2-nitrophenyl)acetamide (250 g, 1.01 mol) in methanol (2.5 L) at 0° C. was added sodium hydroxide (243 g, 6.06 mol). The mixture was warmed to room temperature and stirred for 16 h. The mixture was concentrated and the residue was poured into water (1.5 L) and extracted with ethyl acetate (2 L×2). The combined organic layers were dried over sodium sulfate, filtered, and concentrated under reduced pressure. The residue was purified by column chromatography on silica gel (10/1 to 1/1 petroleum ether/ethyl acetate) to afford 2-(4-amino-3-nitrophenyl)-2-methylpropanenitrile as a solid.

Step 3:

To a mixture of 2-(4-amino-3-nitrophenyl)-2-methylpropanenitrile (100 g, 0.49 mol), 2-chloronicotinaldehyde (138 g, 0.980 mol), and cesium carbonate (397 g, 1.22 mol) in 1,4-dioxane (1.5 L) was added Pd$_2$(dba)$_3$ (45 g, 0.049 mol) and Xantphos (28 g, 0.049 mol) under a nitrogen atmosphere. The mixture was heated at reflux for 2 h. Upon cooling to room temperature, the mixture was diluted with water (1 L) and extracted with ethyl acetate (1 L×3). The combined organic layers were dried over sodium sulfate, filtered, and concentrated under reduced pressure. The residue was purified by column chromatography on silica gel (100/1 to 1/5 petroleum ether/ethyl acetate) to afford 2-(4-((3-formylpyridin-2-yl)amino)-3-nitrophenyl)-2-methylpropanenitrile as a solid.

Step 4:

To a mixture of 2-(4-((3-formylpyridin-2-yl)amino)-3-nitrophenyl)-2-methylpropanenitrile (25 g, 81 mmol) in ethyl acetate (1 L) and ethanol (1 L) was added palladium on carbon (10 wt % loading, 7.5 g). The flask was fitted with a hydrogen balloon and the mixture was evacuated and then purged multiple times with hydrogen. The mixture was stirred under a hydrogen atmosphere at room temperature for 30 h. The mixture was then filtered and the filtrate was concentrated under reduced pressure. The residue was purified by column chromatography on silica gel (10/1 to 3/1 petroleum ether/ethyl acetate) to afford the title compound as a solid. MS: 265 (M+1). $^1$H NMR (400 MHz, CDCl$_3$) δ 8.08 (dd, J=4.8 Hz, 1H), 7.27 (br, 1H), 7.19 (s, 1H), 6.88 (m, 2H), 6.85 (d, J=3.6 Hz, 1H), 6.79 (d, J=8.0 Hz, 1H), 4.27 (br, 1H), 4.20 (s, 2H), 1.71 (s, 6H).

Intermediate 7: 4-{[8-(Morpholin-4-yl)-5,11-dihydro-6H-pyrido[2,3-b][1,5]benzodiazepin-6-yl]carbonyl}cyclohexanone

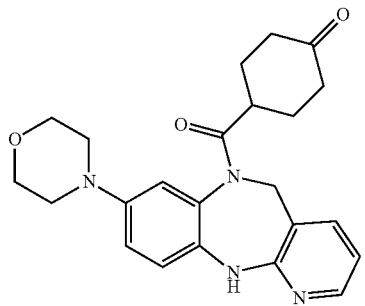 [SMILES: O=C1CCC(C(=O)N2Cc3cccnc3Nc3ccc(N4CCOCC4)cc32)CC1]

To a mixture of 4-oxocyclohexanecarboxylic acid (1.07 g, 7.51 mmol) in DCM (10 mL) was added 1 drop of DMF. Oxalyl chloride (0.670 mL, 7.65 mmol) was added and the mixture was stirred at room temperature for 1.5 h. The reaction mixture was concentrated under reduced pressure. The residue was dissolved in DCE (5 mL) and stirred at 80° C. 8-(Morpholin-4-yl)-6,11-dihydro-5H-pyrido[2,3-b][1,5]benzodiazepine (2.0 g, 7.1 mmol) dissolved in DCE (10 mL) was added dropwise to the reaction over a few minutes. 4-Dimethylaminopyridine (0.061 g, 0.50 mmol) was then added to the reaction and stirred at 80° C. for 16 h. The reaction was cooled to room temperature, diluted with DCM, and washed with saturated sodium bicarbonate. The layers were separated and the aqueous layer was washed with DCM (2×). The organic layers were combined and dried over sodium sulfate, filtered, and concentrated under reduced pressure. The residue was purified by column chromatography on silica gel (0-25% MeOH/DCM) to afford the title compound as a solid. MS: 407 (M+1). $^1$H NMR (600 MHz, DMSO-$d_6$) δ 9.10 (s, 1H), 7.95 (dd, J=1.6, 4.8 Hz, 1H), 7.39 (d, J=7.2 Hz, 1H), 7.21 (d, J=8.9 Hz, 1H), 6.90 (dd, J=2.8, 8.9 Hz, 1H), 6.86 (d, J=2.7 Hz, 1H), 6.61 (dd, J=4.8, 7.3 Hz, 1H), 5.18 (d, J=15.0 Hz, 1H), 3.89 (d, J=14.8 Hz, 1H), 3.72-3.68 (m, 4H), 3.09-3.03 (m, 2H), 3.02-2.91 (m, 3H), 2.23-2.21 (m, 2H), 2.11-2.06 (m, 1H), 2.02-1.89 (m, 2H), 1.85-1.76 (m, 1H), 1.49-1.42 (m, 1H), 1.38-1.32 (m, 1H).

The intermediates in the following table were prepared using the methodology herein and the general procedure described in Intermediate 7.

| Intermediate # | Structure | Chemical Name | [M + H]+ |
|---|---|---|---|
| 8 | 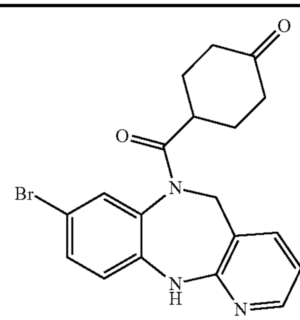 | 4-[(8-bromo-5,11-dihydro-6H-pyrido[2,3-b][1,5]benzodiazepin-6-yl)carbonyl]cyclohexanone | 400 |
| 9 | 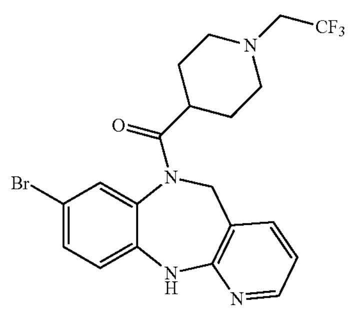 [SMILES: O=C(C1CCN(CC(F)(F)F)CC1)N1Cc2cccnc2Nc2ccc(Br)cc21] | (8-bromo-5,11-dihydro-6H-pyrido[2,3-b][1,5]benzodiazepin-6-yl)[1-(2,2,2-trifluoroethyl)piperidin-4-yl]methanone | 469 |
| 10 | 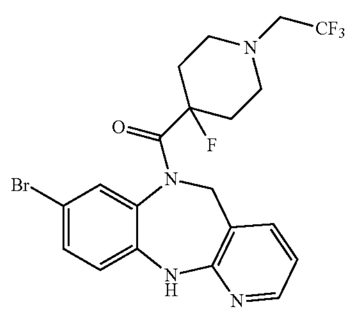 [SMILES: O=C(N1Cc2cccnc2Nc2ccc(Br)cc21)C1(F)CCN(CC(F)(F)F)CC1] | (8-bromo-5,11-dihydro-6H-pyrido[2,3-b][1,5]benzodiazepin-6-yl)[4-fluoro-1-(2,2,2-trifluoroethyl)piperidin-4-yl]methanone | 487 |

-continued

| Intermediate # | Structure | Chemical Name | [M + H]+ |
|---|---|---|---|
| 11 | 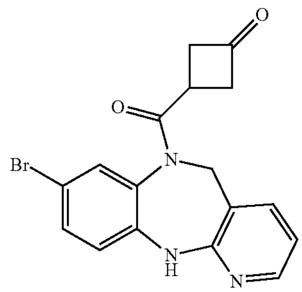 [SMILES: O=C1CC(C(=O)N2Cc3cccnc3Nc3ccc(Br)cc32)C1] | 3-[(8-bromo-5,11-dihydro-6H-pyrido[2,3-b][1,5]benzodiazepin-6-yl)carbonyl]cyclobutanone | 372 |
| 12 | 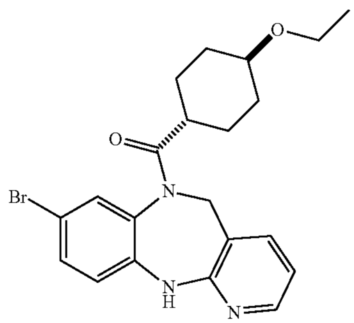 | (8-bromo-5,11-dihydro-6H-pyrido[2,3-b][1,5]benzodiazepin-6-yl)(trans-4-ethoxycyclohexyl)methanone | 430 |
| 13 | 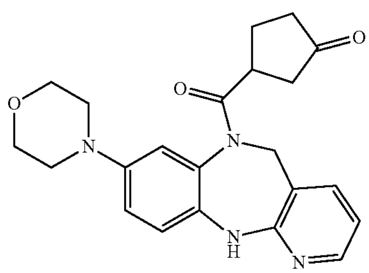 [SMILES: O=C1CCC(C(=O)N2Cc3cccnc3Nc3ccc(N4CCOCC4)cc32)C1] | 3-{[8-(morpholin-4-yl)-5,11-dihydro-6H-pyrido[2,3-b][1,5]benzodiazepin-6-yl]carbonyl}cyclopentanone | 393 |
| 14 | 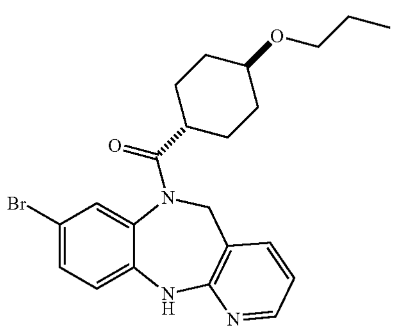 | (8-bromo-5,11-dihydro-6H-pyrido[2,3-b][1,5]benzodiazepin-6-yl)(trans-4-propoxycyclohexyl)methanone | 444 |
| 15 | 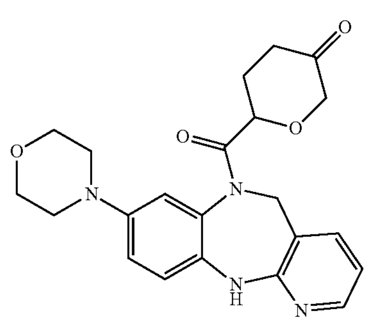 [SMILES: O=C1CCC(C(=O)N2Cc3cccnc3Nc3ccc(N4CCOCC4)cc32)OC1] | 6-{[8-(morpholin-4-yl)-5,11-dihydro-6H-pyrido[2,3-b][1,5]benzodiazepin-6-yl]carbonyl}dihydro-2H-pyran-3(4H)-one | 409 |

-continued

| Intermediate # | Structure | Chemical Name | [M + H]+ |
|---|---|---|---|
| 16 | 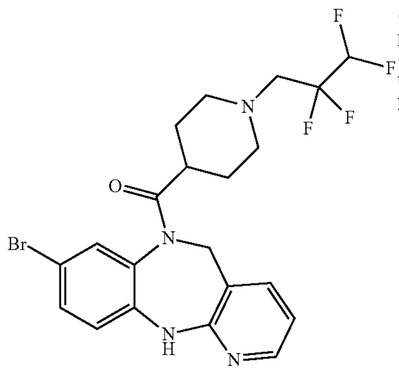 | (8-bromo-5,11-dihydro-6H-pyrido[2,3-b][1,5]benzodiazepin-6-yl)[1-(2,2,3,3-tetrafluoropropyl)piperidin-4-yl]methanone | 501 |
| 17 | 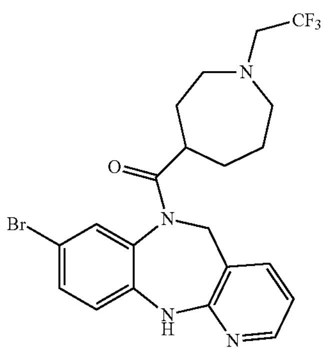 [SMILES: O=C(C1CCCN(CC(F)(F)F)CC1)N1Cc2cccnc2Nc2ccc(Br)cc21] | (8-bromo-5,11-dihydro-6H-pyrido[2,3-b][1,5]benzodiazepin-6-yl)[1-(2,2,2-trifluoroethyl)azepan-4-yl]methanone | 483 |
| 18 | 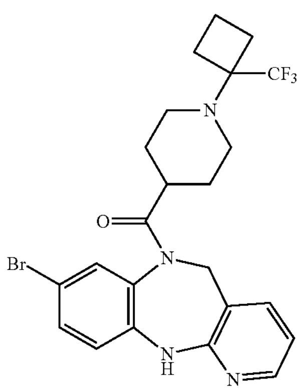 [SMILES: O=C(C1CCN(C2(C(F)(F)F)CCC2)CC1)N1Cc2cccnc2Nc2ccc(Br)cc21] | (8-bromo-5,11-dihydro-6H-pyrido[2,3-b][1,5]benzodiazepin-6-yl){1-[1-(trifluoromethyl)cyclobutyl]piperidin-4-yl}methanone | 509 |
| 19 | 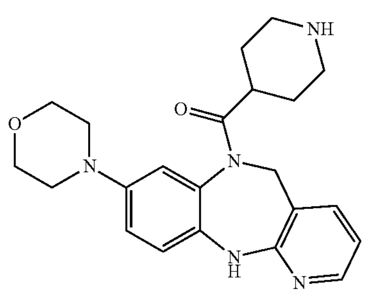 [SMILES: O=C(C1CCNCC1)N1Cc2cccnc2Nc2ccc(N3CCOCC3)cc21] | [8-(morpholin-4-yl)-5,11-dihydro-6H-pyrido[2,3-b][1,5]benzodiazepin-6-yl](piperidin-4-yl)methanone | 394 |

Intermediate 20: 2-Methyl-2-{6-[(4-oxocyclohexyl)carbonyl]-6,11-dihydro-5H-pyrido[2,3-b][1,5]benzodiazepin-8-yl}propanenitrile

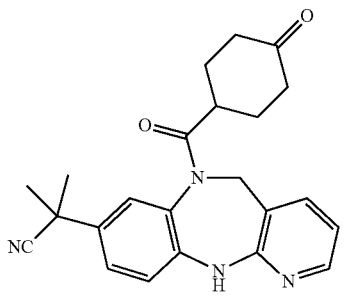 [SMILES: CC(C)(C#N)c1ccc2c(c1)N(C(=O)C1CCC(=O)CC1)Cc1cccnc1N2]

Step 1:
To a microwave vial equipped with a stir bar was added ethyl 4-oxocyclohexanecarboxylate (500 mg, 2.94 mmol), sodium hydroxide (587 mg, 14.7 mmol) and ethanol (12 mL). The reaction was stirred at room temperature for 2 h. The mixture was quenched via the dropwise addition of HCl (4N) to pH-1-3 and extracted with ethyl acetate. The organic layer was washed with brine, dried over sodium sulfate, filtered, and concentrated under reduced pressure to afford 4-oxocyclohexanecarboxylic acid as an oil. MS: 143 (M+1).

Step 2:
To a microwave vial was added 2-(6,11-dihydro-5H-benzo[b]pyrido[2,3-e][1,4]diazepin-8-yl)-2-methylpropanenitrile (80 mg, 0.30 mmol) and PS-PPh$_3$ (440 mg, 0.91 mmol). 4-Oxocyclohexanecarboxylic acid (52 mg, 0.36 mmol) dissolved in acetonitrile (2 mL) was added to the vial, followed by trichloroacetonitrile (152 µL, 1.51 mmol) and the vial was sealed and heated at 100° C. for 10 minutes in a microwave reactor. The reaction mixture was cooled to room temperature, dissolved in MeOH (3 mL), and stirred for 10 minutes. The mixture was filtered and concentrated under reduced pressure. The residue was diluted with ethyl acetate and washed with saturated sodium bicarbonate and then brine. The combined organic layers were dried over magnesium sulfate, filtered, and concentrated under reduced pressure. The residue was purified by column chromatography on silica gel (0-100% EtOAc/hexanes) to afford the title compound as a solid. MS: 389 (M+1).

Intermediate 21: tert-Butyl 8-methoxy-5,6-dihydro-11H-pyrido[2,3-b][1,5]benzodiazepine-11-carboxylate

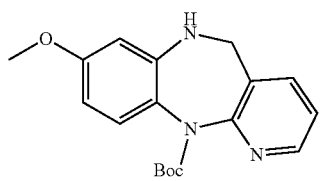 [SMILES: COc1ccc2c(c1)NCc1cccnc1N2C(=O)OC(C)(C)C]

Step 1:
To a flask was added 2-aminopyridine-3-carbaldehyde (2.35 g, 18.4 mmol), 1-bromo-4-methoxy-2-nitrobenzene (4.70 g, 20.3 mmol), Pd$_2$dba$_3$ (844 mg, 0.920 mmol), XantPhos (1.17 g, 2.03 mmol), and cesium carbonate (9.00 g, 27.6 mmol). THF (15 volumes) was added and the mixture was degassed by bubbling nitrogen through for 5 minutes. The reaction was then heated at reflux for 14 h. The material was cooled to room temperature, and then di-tert-butyl dicarbonate (5.23 g, 23.9 mmol) and DMAP (2.25 g, 18.4 mmol) were added to the reaction. The reaction was stirred at room temperature for 1 h. The mixture was diluted with DCM, absorbed on silica gel, and concentrated under reduced pressure. The residue was purified by column chromatography on silica gel (0-100% EtOAc/Hexanes) to afford tert-butyl (3-formylpyridin-2-yl)(4-methoxy-2-nitrophenyl)carbamate as an oil.

Step 2:
To tert-butyl (3-formylpyridin-2-yl)(4-methoxy-2-nitrophenyl)carbamate (5.3 g, 14 mmol) dissolved in MeOH (10 volumes) and EtOAc (5 volumes) under a nitrogen atmosphere was added palladium (10% on carbon, 1.51 g, 1.42 mmol). The mixture was placed under a hydrogen atmosphere (balloon) and stirred for 18 h at room temperature. The mixture was diluted with DCM, filtered through a pad of celite, and washed with DCM (3×). The combined organic layers were absorbed on silica gel and concentrated under reduced pressure. The residue was purified by column chromatography on silica gel (0-10% MeOH/DCM) to afford the title compound as a solid. MS: 328 (M+1). $^1$H NMR (600 MHz, DMSO-d$_6$) δ 8.34 (dd, J=1.7, 4.8 Hz, 1H), 7.82 (dd, J=1.6, 7.4 Hz, 1H), 7.34 (dd, J=4.9, 7.4 Hz, 1H), 6.95 (d, J=8.7 Hz, 1H), 6.32 (t, J=5.0 Hz, 1H), 6.09 (dd, J=2.7, 8.7 Hz, 1H), 6.04 (d, J=2.7 Hz, 1H), 4.18 (s, 2H), 3.57 (s, 3H), 1.29 (s, 9H).

Intermediate 22: Tert-butyl 8-(trifluoromethyl)-5,6-dihydro-11H-pyrido[2,3-b][1,5]benzodiazepine-11-carboxylate

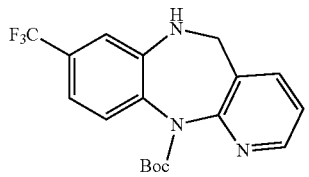 [SMILES: CC(C)(C)OC(=O)N1c2ccc(C(F)(F)F)cc2NCc2cccnc21]

Intermediate 23: Tert-butyl 8-formyl-5,6-dihydro-11H-pyrido[2,3-b][1,5]benzodiazepine-11-carboxylate

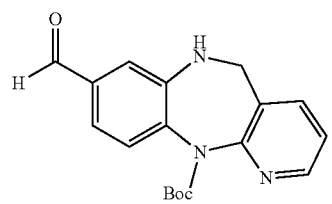 [SMILES: CC(C)(C)OC(=O)N1c2ccc(C=O)cc2NCc2cccnc21]

Intermediate 24: 11-Tert-butyl 8-methyl 5,6-di-hydro-11H-pyrido[2,3-b][1,5]benzodiazepine-8,11-dicarboxylate

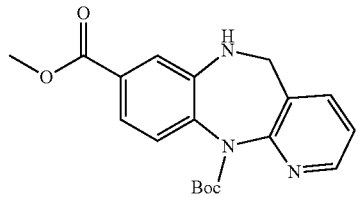 [SMILES: COC(=O)c1ccc2c(c1)NCc1cccnc1N2C(=O)OC(C)(C)C]

Intermediates 22-24 were made using the procedure described for Intermediate 21. Intermediate 22 MSL: 366 (M+1). Intermediate 23 MS: 326 (M+1). Intermediate 24 MS: 356 (M+1).

Intermediate 25: (8-Bromo-5,11-dihydro-6H-pyrido[2,3-b][1,5]benzodiazepin-6-yl)(3,3-dimethylcyclobutyl)methanone

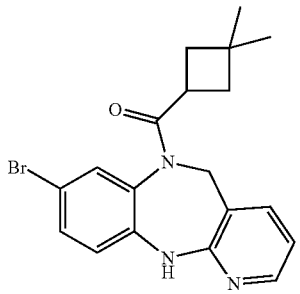 [SMILES: CC1(C)CC(C(=O)N2Cc3cccnc3Nc3ccc(Br)cc32)C1]

8-Bromo-6,11-dihydro-5H-pyrido[2,3-b][1,5]benzodiazepine, 2HCl (1.2 g, 3.4 mmol), 3,3-dimethylcyclobutanecarboxylic acid (0.441 g, 3.44 mmol), trichloroacetonitrile (1.0 mL, 10 mmol), PS-PPh$_3$ (5.61 g, 10.3 mmol), and acetonitrile (15 mL) were added to a microwave vial. The reaction was heated to 100° C. for 10 minutes in a microwave reactor. The reaction was washed with acetonitrile (40 mL) into a filter funnel, and the resin was washed with 1:1 DCM/MeOH (100 mL). The mixture was concentrated under reduced pressure and the residue was dissolved in EtOAc (200 mL) and free-based by washing with saturated sodium bicarbonate (100 mL). The organic layer was washed with brine, dried over sodium sulfate, filtered, and concentrated under reduced pressure. The residue was purified by column chromatography on silica gel (10-40% EtOAc/hexanes) to afford the title compound as a solid. MS: 386 (M+1). $^1$H NMR (500 MHz, CDCl$_3$) δ 8.08 (dd, J=1.2, 4.8 Hz, 1H), 7.52 (d, J=7.2 Hz, 1H), 7.33 (dd, J=2.2, 8.6 Hz, 1H), 7.30 (s, 1H), 7.22 (d, J=2.2 Hz, 1H), 6.84 (t, J=6.2 Hz, 1H), 6.79 (dd, J=4.9, 7.3 Hz, 1H), 5.40 (d, J=14.9 Hz, 1H), 3.89 (d, J=14.9 Hz, 1H), 3.08 (d, J=8.8 Hz, 1H), 2.14-2.10 (m, 1H), 1.94-1.77 (m, 2H), 1.42-1.30 (m, 1H), 1.03 (s, 3H), 0.99 (s, 3H).

The intermediates in the following table were prepared using the methodology herein and the general procedure described in Intermediate 25.

| Intermediate # | Structure | Chemical Name | [M + H]+ |
| --- | --- | --- | --- |
| 26 | 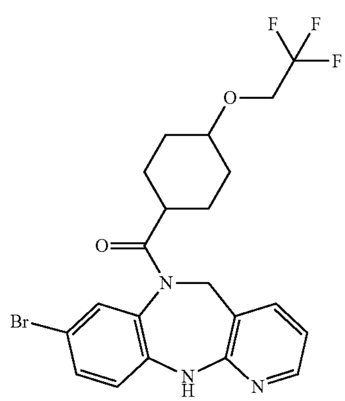 [SMILES: O=C(C1CCC(OCC(F)(F)F)CC1)N1Cc2cccnc2Nc2ccc(Br)cc21] | (8-bromo-5,11-dihydro-6H-pyrido[2,3-b][1,5]benzodiazepin-6-yl)[4-(2,2,2-trifluoroethoxy)cyclohexyl]methanone | 484 |

-continued

| Intermediate # | Structure | Chemical Name | [M + H]+ |
|---|---|---|---|
| 27 | 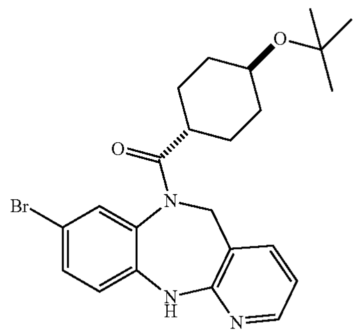 | (8-bromo-5,11-dihydro-6H-pyrido[2,3-b][1,5]benzodiazepin-6-yl)(trans-4-tert-butoxycyclohexyl)methanone | 458 |
| 28 | 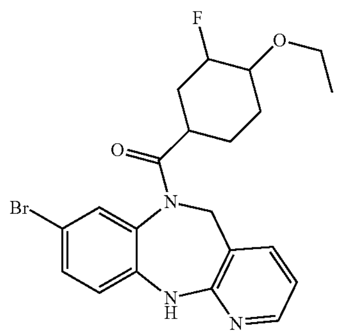 [SMILES: CCOC1CCC(C(=O)N2Cc3cccnc3Nc3ccc(Br)cc32)CC1F] | (8-bromo-5,11-dihydro-6H-pyrido[2,3-b][1,5]benzodiazepin-6-yl)(4-ethoxy-3-fluorocyclohexyl)methanone | 448 |
| 29 | 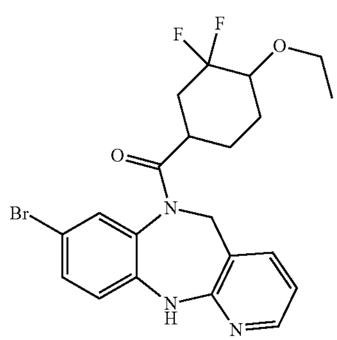 [SMILES: CCOC1CCC(C(=O)N2Cc3cccnc3Nc3ccc(Br)cc32)CC1(F)F] | (8-bromo-5,11-dihydro-6H-pyrido[2,3-b][1,5]benzodiazepin-6-yl)(4-ethoxy-3,3-difluorocyclohexyl)methanone | 466 |
| 30 | 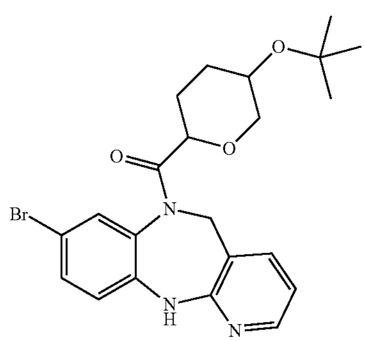 [SMILES: CC(C)(C)OC1CCC(C(=O)N2Cc3cccnc3Nc3ccc(Br)cc32)OC1] | (8-bromo-5,11-dihydro-6H-benzo[b]pyrido[2,3-e][1,4]diazepin-6-yl)(5-(tert-butoxy)tetrahydro-2H-pyran-2-yl)methanone | 460 |

-continued

| Intermediate # | Structure | Chemical Name | [M + H]+ |
|---|---|---|---|
| 31 | 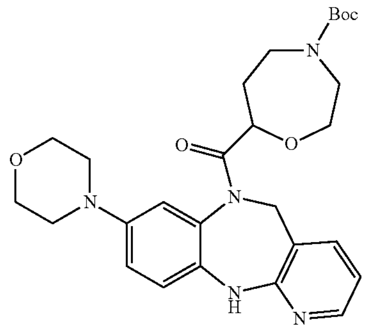 [SMILES: CC(C)(C)OC(=O)N1CCOC(C(=O)N2Cc3cccnc3Nc3ccc(N4CCOCC4)cc32)CC1] | tert-butyl 7-{[8-(morpholin-4-yl)-5,11-dihydro-6H-pyrido[2,3-b][1,5]benzodiazepin-6-yl]carbonyl}-1,4-oxazepane-4-carboxylate | 510 |
| 32 | 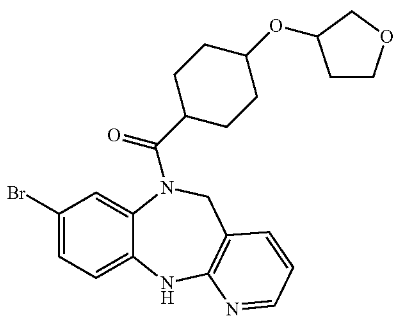 [SMILES: O=C(C1CCC(OC2CCOC2)CC1)N1Cc2cccnc2Nc2ccc(Br)cc21] | (8-bromo-5,11-dihydro-6H-pyrido[2,3-b][1,5]benzodiazepin-6-yl)[4-(tetrahydrofuran-3-yloxy)cyclohexyl]methanone | 472 |
| 33 | 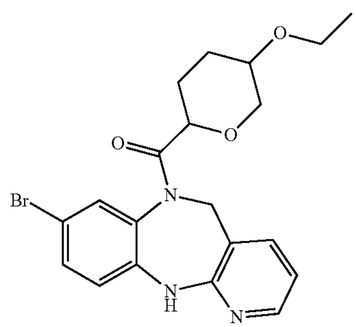 [SMILES: CCOC1CCC(C(=O)N2Cc3cccnc3Nc3ccc(Br)cc32)OC1] | (8-bromo-5,11-dihydro-6H-benzo[b]pyrido[2,3-e][1,4]diazepin-6-yl)(5-ethoxytetrahydro-2H-pyran-2-yl)methanone | 432 |

Intermediate 34: 1-(6,11-Dihydro-5H-pyrido[2,3-b][1,5]benzodiazepin-8-yl)piperidine-4-carbonitrile

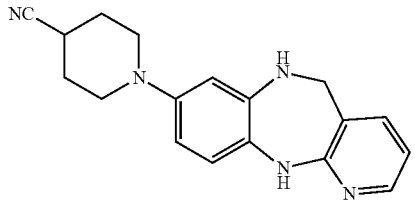 [SMILES: N#CC1CCN(c2ccc3c(c2)NCc2cccnc2N3)CC1]

To an oven-dried, nitrogen-cooled vial was added 8-bromo-6,11-dihydro-5H-pyrido[2,3-b][1,5]benzodiazepine, HCl (50.0 mg, 0.181 mmol), chloro(2-dicyclohexylphosphino-2',6'-di-i-propoxy-1,1'-biphenyl)[2-(2-aminoethylphenyl)]palladium(II), methyl-t-butylether adduct (7.4 mg, 9.1 µmol), and 2-dicyclohexylphosphino-2',6'-di-i-propoxy-1,1'-biphenyl (4.2 mg, 9.1 µmol). The mixture was placed under a nitrogen atmosphere by performing 3 vacuum/nitrogen cycles. LiHMDS (1.0 M in THF, 845 µL, 1.27 mmol) was added dropwise, followed by piperidine-4-carbonitrile (23.9 mg, 0.217 mmol), and the reaction mixture was heated to 100° C. for 16 h. The reaction was cooled to room temperature, quenched with methanol, filtered, and concentrated under reduced pressure to afford the title compound as a solid. MS: 306 (M+1).

Intermediate 35: Racemic trans (8-bromo-5,11-dihydro-6H-pyrido[2,3-b][1,5]benzodiazepin-6-yl)(4,4-difluoro-2-methylcyclohexyl)methanone

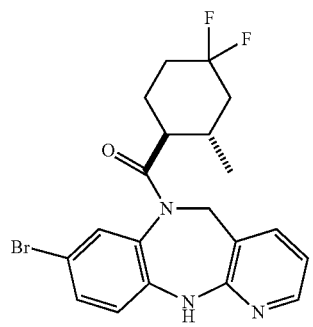

Step 1:
To a flask containing ethyl 2-methyl-4-oxocyclohex-2-ene-1-carboxylate (250 g, 1.37 mol) and ethanol (1.2 L) was added a slurry of 10% Pd/C (14.6 g, 0.05 wt %) in ethanol (70 mL). HCl (2 N, 44 mL) was added under nitrogen at room temperature, and the resulting slurry was stirred under hydrogen at 400 psi for 3 h. The reaction mixture was filtered through celite and washed with methanol (3×750 mL). The combined filtrates were concentrated under reduced pressure, and the residue was purified by column chromatography on silica gel (2-10% EtOAc/petroleum ether) to afford ethyl 2-methyl-4-oxocyclohexanecarboxylate as a liquid (mixture of cis isomers).

Step 2:
To a flask equipped with a magnetic stirrer and thermocouple connected to a nitrogen line was charged with ethyl 2-methyl-4-oxocyclohexanecarboxylate (200 g, 1.08 mol, mixture of cis isomers) and dichloromethane (2 L). The reaction mixture was cooled to −78° C. and DAST (350 mL, 2.16 mol) was added dropwise over 45 min while maintaining an internal temperature between −65 and −78° C. Once the addition was complete, the reaction mixture was gradually brought to room temperature and stirred for 15 h. The mixture was quenched with water (500 mL) and the organic layer was separated. The aqueous layer was extracted with dichloromethane (2×500 mL), washed with brine (2×100 mL), dried over sodium sulfate, filtered, and concentrated under reduced pressure to afford a mixture of three compounds: ethyl 4,4-difluoro-2-methylcyclohexanecarboxylate, ethyl 4-fluoro-6-methylcyclohex-3-ene-1-carboxylate, and ethyl 4-fluoro-2-methylcyclohex-3-ene-1-carboxylate as a liquid that are all mixtures of cis isomers.

Step 3:
To a flask equipped with a magnetic stirrer, thermocouple, and addition funnel connected to a nitrogen line was charged with a crude mixture of ethyl 4,4-difluoro-2-methylcyclohexanecarboxylate, ethyl 4-fluoro-6-methylcyclohex-3-ene-1-carboxylate, and ethyl 4-fluoro-2-methylcyclohex-3-ene-1-carboxylate (210 g, 1.01 mol, mixture of cis isomers), dioxane (2.5 L), and water (1.0 L). A solution of osmium tetroxide (2.5 wt % in tert-butyl alcohol, 37 g, 0.025 mol), sodium periodate (872 g, 4.07 mol), and 2,6-lutidine (56.7 g, 2.03 mol) were added sequentially. The reaction mixture was stirred at room temperature for 15 h. The mixture was diluted with water (200 mL) and extracted with dichloromethane (2×600 mL). The combined organic layers were washed with brine (2×300 mL), dried over sodium sulfate, filtered, and concentrated under reduced pressure. The residue was purified by column chromatography on silica gel (12-52% EtOAc/petroleum ether) to afford ethyl 4,4-difluoro-2-methylcyclohexanecarboxylate as an oil (mixture of cis isomers).

Step 4:
To a flask equipped with a temperature probe and nitrogen gas inlet was charged with ethyl 4,4-difluoro-2-methylcyclohexanecarboxylate (123 g, 5.37 mol, mixture of cis isomers) and THF (1.3 L). The reaction mixture was cooled to −78° C. and potassium tert-butoxide (73.6 g, 0.66 mol) was added portionwise over 30 minutes while maintaining an internal temperature between −65° C. and −78° C. Once the addition was complete, the reaction mixture was warmed to room temperature and stirred for 16 h. The reaction was cooled to 0° C. and quenched with water (50 mL). The organic layer was separated, and the aqueous layer was extracted with ethyl acetate (2×100 mL). The combined organic layers were washed with brine (100 mL) and dried over sodium sulfate, filtered, and concentrated under reduced pressure. The residue was purified by column chromatography on silica gel (0-5% EtOAc/petroleum ether) to afford ethyl 4,4-difluoro-2-methylcyclohexanecarboxylate as a liquid (mixture of trans isomers).

Step 5:
To a three-neck flask equipped with a magnetic stirrer and temperature probe was charged with ethyl 4,4-difluoro-2-methylcyclohexanecarboxylate (56 g, 0.27 mol, mixture of trans isomers) and methanol (230 mL). A solution of potassium hydroxide (2 N in water, 230 mL, 4 volumes) was added to the reaction, and the mixture was stirred at room temperature for 16 h. The mixture was concentrated under reduced pressure, and the residue was washed with MTBE (2×50 mL) and acidified with aqueous 2 N HCl solution to pH 2. The mixture was extracted with ethyl acetate (3×500 mL), and the combined organic layers were washed with brine (100 mL), dried over sodium sulfate, filtered, and concentrated under reduced pressure to afford 4,4-difluoro-2-methylcyclohexanecarboxylic acid as a solid (mixture of trans isomers).

Step 6:
To a vial was added 8-bromo-6,11-dihydro-5H-pyrido[2,3-b][1,5]benzodiazepine, HCl (0.25 g, 0.80 mmol), PS-PPh$_3$ (2.06 mmol/g loading, 1.2 g, 2.4 mmol), 4,4-difluoro-2-methylcyclohexanecarboxylic acid (0.14 g, 0.80 mmol, mixture of trans isomers), and acetonitrile (13.3 mL). Trichloroacetonitrile (0.40 mL, 4.0 mmol) was added and the reaction mixture was heated to 100° C. for 15 min in a microwave reactor. The material was filtered and concentrated under reduced pressure. The residue was purified by column chromatography on silica gel (0-100% 3:1 EtOAc:EtOH/Hexanes) to afford the title compound as an oil which is a mixture of trans isomers. MS: 436/438 (M/M+2).

Intermediate 36: 2-Bromo-10,11-dihydro-5H-dipyrido[2,3-b:2',3'-e][1,4]diazepine

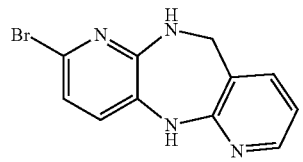 [SMILES: Brc1ccc2c(n1)NCc1cccnc1N2]

Step 1:
To a 10-L 4-necked round-bottom flask purged and maintained with an inert atmosphere of nitrogen was added a mixture of 2-bromopyridine-3-carbaldehyde (78.5 g, 422 mmol) in tert-butanol (6 L), 6-bromo-2-nitropyridin-3-amine (100 g, 422 mmol), XantPhos (24.43 g, 42.22 mmol), Pd$_2$(dba)$_3$ (19.35 g, 18.69 mmol), and sodium carbonate (56.48 g, 532.8 mmol). The resulting mixture was heated to 90° C. for 18 h. The mixture was cooled to room temperature and then quenched by the addition of water/ice (10 L). The solids were filtered and the filtrate was extracted with dichloromethane (3×3 L). The combined organic layers were dried over anhydrous sodium sulfate, filtered, and concentrated under reduced pressure. The residue was washed with methanol (2×500 mL) to afford 2-[(6-bromo-2-nitropyridin-3-yl)amino]pyridine-3-carbaldehyde as a solid that was taken on to the next step.

Step 2:
To a 2000-mL 4-necked round-bottom flask purged and maintained with an inert atmosphere of nitrogen was added a mixture of 2-[(6-bromo-2-nitropyridin-3-yl)amino]pyridine-3-carbaldehyde (70 g, 0.22 mol) in ethanol/EtOAc (700 mL). This was followed by the addition of SnCl$_2$.H$_2$O (195.5 g, 866.4 mmol) in several batches and the resulting mixture was stirred at room temperature for 18 h. The mixture was then concentrated under reduced pressure. The mixture was diluted with brine (300 mL) and then extracted with ethyl acetate (2×800 mL). The combined organic layers were dried over anhydrous sodium sulfate, filtered, and concentrated under reduced pressure. The residue was diluted with THF/MeOH (1:1 mixture, 400 mL), followed by the addition of sodium cyanoborohydride (38.12 g, 606.5 mmol) in several batches. The resulting mixture was stirred at room temperature for 2 h and then concentrated under reduced pressure. The residue was purified by column chromatography on silica gel (1:1 ethyl acetate/petroleum ether) to afford the title compound as solid. MS: 277 (M+1). $^1$H NMR (400 MHz, DMSO-d$_6$) δ 9.16 (s, 1H), 8.08-8.06 (m, 1H), 7.48-7.46 (d, 1H), 7.33-7.31 (d, 1H), 6.99-6.97 (d, 2H), 6.74-6.71 (m, 1H), 4.33 (s, 2H).

Intermediate 37:
Trans-4-(propan-2-yloxy)cyclohexanecarboxylic Acid

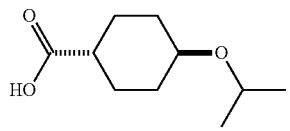

To a solution of ethyl trans-4-(propan-2-yloxy)cyclohexanecarboxylate (950 mg, 4.43 mmol) in THF (14 mL), water (3.5 mL) and MeOH (3.5 mL) was added lithium hydroxide (265 mg, 11.1 mmol). The reaction mixture was stirred at room temperature for 16 h. The reaction was quenched with 2 N HCl to pH 5~6 and extracted with EtOAc (2×50 mL). The combined organic layers were dried over sodium sulfate, filtered, and concentrated under reduced pressure to afford the title compound as a solid. $^1$H NMR (600 MHz, CDCl$_3$) δ 3.68 (hept, J=6.1 Hz, 1H), 3.28-3.22 (m, 1H), 2.30-2.23 (m, 1H), 2.06-1.96 (m, 4H), 1.50-1.41 (m, 2H), 1.30-1.20 (m, 2H), 1.12 (d, J=6.1 Hz, 6H).

Intermediate 38:
Trans-4-cyanocyclohexanecarboxylic Acid

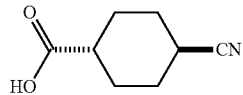 [SMILES: N#C[C@H]1CC[C@H](C(=O)O)CC1]

Step 1:
Thionyl chloride (127 mL, 1.80 mol) was added dropwise to methanol (750 mL) at −30° C. over 1 h. The mixture was stirred at room temperature for 0.5 h, and then trans-cyclohexane-1,4-dicarboxylic acid (250 g, 1.45 mol) was added and the mixture was stirred at room temperature for 17 h. The reaction was concentrated under reduced pressure. The residue was diluted with chloroform and the organic layer was washed with saturated aqueous sodium bicarbonate solution and brine. The organic layer was dried over sodium sulfate, filtered, and concentrated under reduced pressure. The resulting residue was crystallized from n-hexane, and the resulting solid was collected by filtration to give dimethyl trans-cyclohexane-1, 4-dicarboxylate as a solid.

Step 2:
To a solution of dimethyl trans-cyclohexane-1,4-dicarboxylate (150 g, 0.75 mol) in tetrahydrofuran (1500 mL) was added a mixture of 28% sodium methoxide in methanol (149 g, 0.770 mol) and water (13.2 mL) at 0° C. The reaction was warmed to room temperature and stirred for 3.5 hours. Hexane (1500 mL) was added and the mixture was filtered. The resulting solid was added to a mixture of concentrated hydrochloric acid (50 mL), water (450 mL) and chloroform (1000 mL) at 0° C. The resulting reaction mixture was stirred at room temperature for 20 minutes. The organic layer was separated and the aqueous layer was extracted with chloroform. The combined organic layers were dried over sodium sulfate, filtered, and concentrated under reduced pressure. The resulting residue was crystallized from n-hexane to afford trans-4-(methoxycarbonyl)cyclohexanecarboxylic acid as a solid.

Step 3:
A solution of trans-4-(methoxycarbonyl)cyclohexanecarboxylic acid (10 g, 54 mmol) in thionyl chloride (30 mL) was stirred at room temperature for 2 h. The mixture was concentrated under reduced pressure and the residue was dissolved in ether. A concentrated ammonia solution was added dropwise at 0° C. and the precipitate was filtered. The solid was dissolved in dichloromethane and the solution was dried over magnesium sulfate, filtered, and concentrated under reduced pressure to afford methyl trans-4-carbamoylcyclohexanecarboxylate as a solid.

Step 4:
A mixture of methyl trans-4-carbamoylcyclohexanecarboxylate (90 g, 0.49 mol) and phosphoryl trichloride (300 mL) was stirred at 60° C. for 1.5 h. The reaction mixture was concentrated under reduced pressure and the residue was poured slowly into ice water. The aqueous solution was extracted with ether and the organic layer was dried over sodium sulfate. The organic layer was concentrated and the product was recrystallized from ether to afford methyl trans-4-cyanocyclohexanecarboxylate as a solid.

Step 5:
To methyl trans-4-cyanocyclohexanecarboxylate (70 mg, 0.42 mmol) dissolved in THF (1.4 mL), water (0.35 mL) and MeOH (0.35 mL) was added lithium hydroxide (25 mg, 1.0 mmol). The mixture was stirred at room temperature for 16 h. The reaction mixture was quenched with 2 N HCl (to pH 5~6) and extracted with EtOAc (2×50 mL). The combined organic layers were dried over sodium sulfate, filtered and concentrated under reduced pressure to afford the title compound as a solid. $^1$H NMR (499 MHz, CDCl$_3$) δ 10.76 (bs, 1H), 2.58-2.47 (m, 1H), 2.46-2.40 (m, 1H), 2.19-2.07 (m, 4H), 1.75-1.62 (m, 2H), 1.61-1.50 (m, 2H).

Intermediate 39: Trans-4-(2-methoxypropan-2-yl)cyclohexanecarboxylic Acid

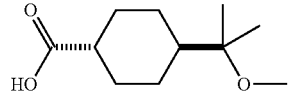

Step 1:

To trans-cyclohexane-1,4-dicarboxylic acid (150 g, 0.87 mol) and Dowex 50WX2-100 (800 g, 0.87 mol) in a 5 L three necked flask with overhead stirrer and reflux condenser was added n-octane (2 L) and butyl formate (1.0 L, 8.7 mol). The mixture was heated in 10-degree increments to 85° C. to control vigorous off gassing, and then stirred at 85° C. for 14 h. The reaction mixture was cooled to room temperature, filtered, and washed with EtOAc. The residue was absorbed on silica and purified by column chromatography on silica gel (30-70% EtOAc/Hexanes) to afford trans-4-(butoxycarbonyl)cyclohexanecarboxylic acid as a solid.

Step 2:

To trans-4-(butoxycarbonyl)cyclohexanecarboxylic acid (98.0 g, 429 mmol) in DCM (700 mL) at 0° C. was added 15 drops of DMF. Oxalyl chloride (39.5 mL, 451 mmol) was added via syringe, and the reaction mixture was warmed slowly to room temperature over 16 h. The mixture was concentrated under reduced pressure to afford the product as an oil. The oil was diluted with THF (750 mL) and cooled to 0° C. To the resulting solution was added $PdCl_2(dppf)$ (12.3 g, 15 mmol) and dimethyl zinc (1.2 M in toluene, 215 mL, 258 mmol) dropwise, keeping the internal temperature below 15° C. The reaction was warmed to room temperature and stirred for 2 h. The mixture was cooled to 0° C. and quenched with water. After the initial exotherm had subsided, 1N HCl was added until the mixture was homogenous. The mixture was extracted with EtOAc and the organic layer was washed a second time with water. The aqueous layer was back extracted with EtOAc. The combined organic layers were dried over magnesium sulfate, filtered, absorbed on silica, and concentrated under reduced pressure. The residue was purified by column chromatography on silica gel to afford butyl trans-4-acetylcyclohexanecarboxylate as an oil.

Step 3:

Methylmagnesium bromide (3.0 M in diethyl ether, 295 μL, 0.884 mmol) was added dropwise to a 0° C. solution of trans-4-acetylcyclohexanecarboxylate (200 mg, 0.884 mmol) in THF (1.8 mL) under a nitrogen atmosphere. The reaction was stirred for 1 hour at 0° C. The reaction mixture was quenched with saturated ammonium chloride and stirred for 10 minutes at room temperature. The mixture was partitioned between EtOAc and water, and the organic layer was washed with brine, dried over sodium sulfate, filtered, and concentrated under reduced pressure to afford butyl trans-4-(2-hydroxypropan-2-yl)cyclohexanecarboxylate as an oil.

Step 4:

To a solution of butyl trans-4-(2-hydroxypropan-2-yl) cyclohexanecarboxylate (71.7 mg, 0.296 mmol) in DCM (2.9 mL) was added 1,8-bis(dimethylamino)naphthalene (127 mg, 0.592 mmol) and trimethyloxonium tetrafluoroborate (87.6 mg, 0.592 mmol). The resulting reaction mixture was stirred at room temperature for 2 h. The reaction was quenched with water and extracted with DCM. The organic layer was dried over sodium sulfate, filtered, and concentrated under reduced pressure. The residue was purified by column chromatography on silica gel (0-50% EtOAc/ Hexanes) to afford butyl trans-4-(2-methoxypropan-2-yl) cyclohexanecarboxylate as a liquid.

Step 5:

To a solution of butyl trans-4-(2-methoxypropan-2-yl) cyclohexanecarboxylate (71.3 mg, 0.278 mmol) in THF (0.93 mL), water (0.23 mL) and MeOH (0.23 mL) was added lithium hydroxide (16.6 mg, 0.695 mmol). The mixture was stirred at room temperature for 16 h. The reaction was quenched with 2 N HCl to pH 5~6 and extracted with EtOAc (2×50 mL). The combined organic layers were dried over sodium sulfate, filtered, and concentrated under reduced pressure to afford the title compound as a solid. $^1$H NMR (500 MHz, $CDCl_3$) δ 3.18 (s, 3H), 2.31-2.23 (m, 1H), 2.12-2.06 (m, 2H), 1.88-1.82 (m, 2H), 1.50-1.37 (m, 4H), 1.10 (s, 6H), 1.08-1.04 (m, 1H).

Intermediate 40:

Trans-4-(difluoromethoxy)cyclohexanecarboxylic Acid

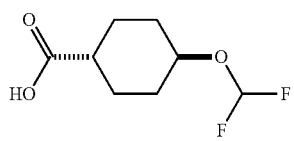

Step 1:

To a solution of ethyl trans-4-hydroxycyclohexanecarboxylate (1.03 g, 5.98 mmol) in acetonitrile (30 mL) was added copper(I) iodide (1.71 g, 8.97 mmol) and difluoro (fluorosulfonyl)acetic acid (0.930 mL, 8.97 mmol). The mixture was degassed under a nitrogen atmosphere, then heated to 80° C. for 1 h. The mixture was cooled in an ice bath, quenched with water (15 mL), and filtered through celite. The filtrate was concentrated under reduced pressure. The residue was dissolved in EtOAc and washed with water, saturated ammonium chloride and then brine. The organic layer was dried over sodium sulfate, filtered, and concentrated under reduced pressure. The residue was purified by column chromatography on silica gel (0-50% EtOAc/ Hexanes) to afford ethyl trans-4-(difluoromethoxy)cyclohexanecarboxylate as an oil.

Step 2:

To a solution of ethyl trans-4-(difluoromethoxy)cyclohexanecarboxylate (735 mg, 3.31 mmol) in THF (13.2 mL), water (3.3 mL) and MeOH (3.3 mL) was added lithium hydroxide hydrate (347 mg, 8.27 mmol). The mixture was stirred at room temperature for 16 h. The reaction was quenched with 2 N HCl to pH 5~6 and extracted with EtOAc (2×250 mL). The combined organic layers were dried over sodium sulfate, filtered and concentrated under reduced pressure to afford the title compound as a solid. $^1$H NMR (500 MHz, $CDCl_3$) δ 6.24 (t, J=75.2 Hz, 1H), 4.14-4.16 (m, 1H), 2.42-2.26 (m, 1H), 2.17-2.01 (m, 4H), 1.65-1.44 (m, 4H).

Intermediate 41:

4-(1-Methoxyethyl)cyclohexanecarboxylic Acid

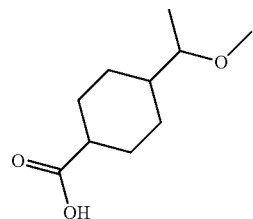

Step 1:

Methylmagnesium bromide (3.0 M in diethyl ether, 196 μL, 0.588 mmol) was added dropwise to a 0° C. solution of methyl 4-formylcyclohexanecarboxylate (100 mg, 0.588 mmol) in THF (1.2 mL) under a nitrogen atmosphere. The reaction was stirred for 1 hour at 0° C. The reaction mixture was quenched with saturated ammonium chloride and stirred for 10 minutes at room temperature. The mixture was partitioned between EtOAc and water, and the organic layer was washed with brine, dried over sodium sulfate, filtered, and concentrated under reduced pressure to afford methyl 4-(1-hydroxyethyl)cyclohexanecarboxylate as an oil.

Step 2:

To a 0° C. solution of methyl 4-(1-hydroxyethyl)cyclohexanecarboxylate (98 mg, 0.53 mmol) in DMF (2.6 mL) was added sodium hydride (23.2 mg, 0.579 mmol). The resulting slurry was stirred at 0° C. for 5 minutes. Iodomethane was added (36 μL, 0.58 mmol) and the mixture was slowly warmed to room temperature and stirred for 16 h. The reaction was diluted with EtOAc, washed with water and brine, and the organic layer was dried over sodium sulfate, filtered, and concentrated under reduced pressure to afford methyl 4-(1-methoxyethyl)cyclohexanecarboxylate as an oil.

Step 3:

To methyl 4-(1-methoxyethyl)cyclohexanecarboxylate (105 mg, 0.524 mmol), dissolved in THF (1.7 mL), water (0.44 mL), and MeOH (0.44 mL) was added lithium hydroxide (31.4 mg, 1.31 mmol). The mixture was stirred at room temperature for 16 h. The reaction was quenched with 2 N HCl to pH 5~6 and extracted with EtOAc (2×). The combined organic layers were dried over sodium sulfate, filtered, and concentrated under reduced pressure to afford the title compound as an oil. $^1$H NMR (500 MHz, CDCl$_3$) δ 3.32 (s, 3H), 3.12-3.03 (m, 1H), 2.32-2.23 (m, 1H), 2.14-2.01 (m, 3H), 1.50-1.36 (m, 4H), 1.21-1.14 (m, 2H), 1.10 (d, J=6.2 Hz, 3H).

Intermediate 42: 5-Bromopyridine-2-carboxamide

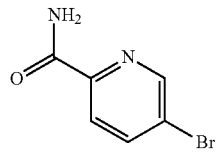

To 5-bromopyridine-2-carboxylic acid (200 mg, 0.99 mmol) dissolved in DMF (3.3 mL) was added DIEA (380 μL, 2.18 mmol), ammonia (0.5 M in MeOH, 2.37 mL, 1.19 mmol), and 2,4,6-tripropyl-1,3,5,2,4,6-trioxatriphosphinane 2,4,6-trioxide (50% in DMF, 694 μL, 1.19 mmol).

The reaction mixture was stirred for 16 h at room temperature. The mixture was filtered, rinsed with EtOAc, and the filtrate was concentrated under reduced pressure. The residue was purified by mass triggered reverse phase HPLC (ACN/water with 0.1% TFA modifier) to afford the title compound as a solid TFA salt. MS: 201/203 (M/M+2). $^1$H NMR (500 MHz, DMSO-d$_6$) δ 8.77-8.74 (m, 1H), 8.23 (dd, J=2.3, 8.4 Hz, 1H), 8.14 (s, 1H), 7.96 (d, J=8.4 Hz, 1H), 7.73 (s, 1H).

Intermediate 43:
4-(Methoxymethyl)cyclohexanecarboxylic Acid

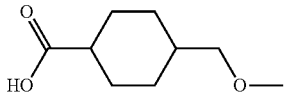

Step 1:

To a 0° C. solution of ethyl 4-(hydroxymethyl)cyclohexanecarboxylate (100 mg, 0.537 mmol) in DMF (2.7 mL) was added sodium hydride (22 mg, 0.54 mmol). The mixture was stirred at 0° C. for 5 min, and then iodomethane (35 μL, 0.56 mmol) was added. The reaction mixture was allowed to slowly warm to room temperature and stir for 16 h. The mixture was carefully quenched with water and then 2N HCl to pH 5~6. The mixture was extracted with EtOAc and the organic layer was dried over sodium sulfate, filtered, and concentrated under reduced pressure to afford ethyl 4-(methoxymethyl)cyclohexanecarboxylate as an oil.

Step 2:

To ethyl 4-(methoxymethyl)cyclohexanecarboxylate (108 mg, 0.539 mmol) dissolved in THF (1.8 mL), water (0.45 mL), and MeOH (0.45 mL) was added lithium hydroxide (32.3 mg, 1.35 mmol). The mixture was stirred at room temperature for 16 h. The reaction mixture was quenched with 2 N HCl to pH 5~6 and extracted with EtOAc (2×). The combined organic layers were dried over sodium sulfate, filtered and concentrated under reduced pressure to afford the title compound as an oil. $^1$H NMR (500 MHz, CDCl$_3$) δ 3.34 (s, 3H), 3.21 (d, J=6.4 Hz, 2H), 2.34-2.23 (m, 1H), 2.13-2.02 (m, 2H), 1.94-1.82 (m, 2H), 1.66-1.40 (m, 3H), 1.08-0.93 (m, 2H).

Intermediate 44: 3-Fluoro-4-methoxypiperidine

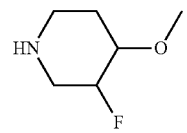

Step 1:

Sodium hydride (40 mg, 1.0 mmol) was added to a 0° C. solution of tert-butyl 3-fluoro-4-hydroxypiperidine-1-carboxylate (200 mg, 0.912 mmol) in DMF (3.0 mL). The reaction mixture was stirred at 0° C. for 5 minutes, and then iodomethane (63 μL, 1.0 mmol) was added. The mixture was slowly warmed to room temperature and stirred for 16 h. The mixture was diluted with EtOAc and washed with water and then brine. The organic layer was dried over sodium sulfate, filtered, and concentrated under reduced pressure. The residue was purified by column chromatography on silica gel (0-70% EtOAc/Hexanes) to afford tert-butyl 3-fluoro-4-methoxypiperidine-1-carboxylate as an oil.

Step 2:

To a solution of tert-butyl 3-fluoro-4-methoxypiperidine-1-carboxylate (186 mg, 0.796 mmol) dissolved in EtOAc (1.6 mL) was added HCl (4.0 M in dioxane, 2 mL, 7.96 mmol). The reaction mixture was stirred at room temperature for 16 h, and then concentrated under reduced pressure to afford the title compound as a solid HCl salt. $^1$H NMR (500 MHz, CDCl$_3$) δ 10.04 (s, 1H), 9.73 (s, 1H), 5.11-4.97

(m, 1H), 3.78-3.71 (m, 1H), 3.48 (s, 3H), 3.42-3.31 (m, 1H), 3.31-3.21 (m, 1H), 3.21-3.11 (m, 1H), 2.23-2.13 (m, 1H), 2.13-2.01 (m, 1H).

Intermediate 45: 3,3-Difluoro-4-methoxypiperidine

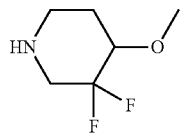

Intermediate 46: 4,4-Difluoro-3-methoxypiperidine

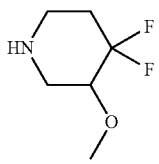

Intermediate 47: Racemic trans-4-fluoro-3-methoxypiperidine

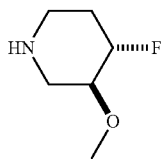

Intermediate 48: Racemic cis-4-fluoro-3-methoxypiperidine

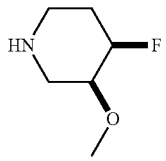

Intermediate 49: 3-Fluoro-4-methoxypyrrolidine

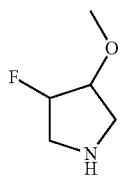

Intermediates 45-49 were prepared using the procedure described for Intermediate 44.

Intermediate 50: 1-(2,2,2-Trifluoroethyl)piperidine-4-carboxylic Acid

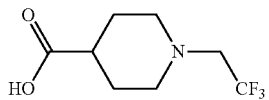

Step 1:
To the solution of ethyl piperidine-4-carboxylate (500 mg, 3.18 mmol) in ethanol (6.4 mL) was added 2,2,2-trifluoroethyl trifluoromethanesulfonate (369 mg, 1.59 mmol) and sodium bicarbonate (267 mg, 3.18 mmol) at room temperature. The reaction mixture was refluxed for 16 h. The reaction mixture was cooled to room temperature and concentrated under reduced pressure. The residue was partitioned between DCM and water, dried over sodium sulfate, filtered, and concentrated under reduced pressure. The crude product was purified by column chromatography on silica gel (0-50% EtOAc/hexane) to give ethyl 1-(2,2,2-trifluoroethyl)piperidine-4-carboxylate as an oil. MS: 240 (M+1).

Step 2:
To a solution of ethyl 1-(2,2,2-trifluoroethyl)piperidine-4-carboxylate (200 mg, 0.84 mmol) in tetrahydrofuran (4.5 mL) and MeOH (1.1 mL) was added lithium hydroxide (1.8 mL, 1.8 mmol, 1M solution) at room temperature. The reaction was stirred at room temperature for 16 h. The mixture was quenched with HCl (1.4 mL, 1.8 mmol, 1.25M in MeOH), extracted with EtOAc, and the organic layer was dried over sodium sulfate, filtered, and concentrated under reduced pressure to afford the title compound as a solid. MS: 212 (M+1). $^1$H NMR (500 MHz, CD$_3$OD) δ 6.91-6.84 (m, 1H), 3.09-2.98 (m, 2H), 2.98-2.85 (m, 2H), 2.50-2.32 (m, 2H), 2.30-2.15 (m, 1H), 1.92-1.80 (m, 2H), 1.80-1.62 (m, 2H).

The intermediates in the following table were prepared using the methodology herein and the general procedure described in Intermediate 50.

| Intermediate # | Structure | Chemical Name | [M + H]+ |
|---|---|---|---|
| 51 | 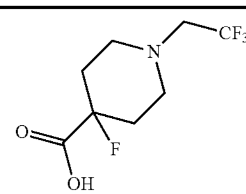 | 4-fluoro-1-(2,2,2-trifluoroethyl)piperidine-4-carboxylic acid | 230 |
| 52 | 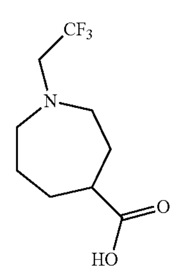 [SMILES: O=C(O)C1CCCN(CC(F)(F)F)CC1] | 1-(2,2,2-trifluoroethyl)azepane-4-carboxylic acid | 226 |

Intermediate 53: 1-[1-(Trifluoromethyl)cyclopropyl]piperazine

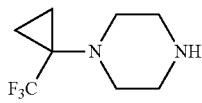

Step 1:

To a microwave vial was added N-benzyl-2-chloro-N-(2-chloroethyl)ethanamine, HCl (300 mg, 1.12 mmol), 1-(trifluoromethyl)cyclopropanamine (140 mg, 1.12 mmol), and DIPEA (2 mL). The mixture was heated to 120° C. for 2 days. The reaction was cooled to room temperature and concentrated under reduced pressure. The residue was diluted with EtOAc and washed with water and then brine. The organic layer was dried over sodium sulfate, filtered, and concentrated under reduced pressure. The residue was purified by column chromatography on silica gel (0-60% EtOAc/hexanes) to afford 1-benzyl-4-(1-(trifluoromethyl)cyclopropyl)piperazine. MS: 285 (M+1).

Step 2:

1-Benzyl-4-(1-(trifluoromethyl)cyclopropyl)piperazine (102 mg, 0.359 mmol) and palladium on carbon (11 mg, 0.1 mmol) were suspended in MeOH (7 mL). The reaction mixture was placed on a Parr shaker under 50 psi hydrogen for 6 h. The mixture was filtered over celite and the filtrate was concentrated under reduced pressure to afford the title compound. MS: 195 (M+1).

Intermediate 54: 3-Ethoxycyclopentanecarboxylic Acid

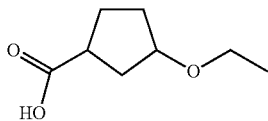

Step 1:

Bis(dimethylamino)naphthalene (1.76 g, 8.22 mmol) and triethyloxonium tetrafluoroborate (1.56 g, 8.22 mmol) were added to a solution containing ethyl 3-hydroxycyclopentanecarboxylate (1.0 g, 6.3 mmol) dissolved in DCM (63 mL). The reaction was stirred at room temperature for 18 h. Citric acid (1N) was added and the mixture was stirred for 45 minutes. The organic layer was separated and dried with sodium sulfate, filtered, and concentrated under reduced pressure. The product was purified by column chromatography on silica gel (25% EtOAc/Hexanes) to afford ethyl 3-ethoxycyclopentanecarboxylate as a liquid. MS: 187 (M+1).

Step 2:

Lithium hydroxide (0.219 g, 9.13 mmol) was added to a solution containing ethyl 3-ethoxycyclopentanecarboxylate (0.68 g, 3.6 mmol) in THF (2 mL) and water (10 mL). The reaction was allowed to stir for 18 h at room temperature. The reaction was quenched with 1 N HCl (to pH 4) and extracted with EtOAc (2×). The combined organic layers were dried over sodium sulfate, filtered, and concentrated to the title compound as a solid. 1H NMR (600 MHz, DMSO-d6) δ 11.97 (s, 1H), 3.89-3.75 (m, 1H), 3.35-3.26 (m, 2H), 2.76-2.55 (m, 1H), 2.06-1.98 (m, 1H), 1.89-1.49 (m, 5H), 1.06-0.97 (m, 3H).

The intermediates in the following table were prepared using the methodology herein and the general procedure described in Intermediate 54.

| Intermediate # | Structure | Chemical Name | [M + H]+ |
| --- | --- | --- | --- |
| 55 | 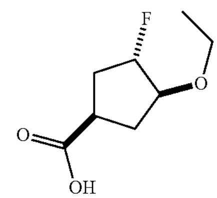 | (1R,3S,4S)-3-ethoxy-4-fluoro-cyclopentane-carboxylic acid | 177 |
| 56 | 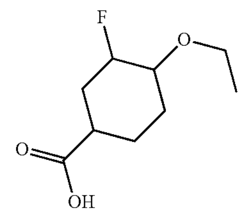 | 4-ethoxy-3-fluorocyclo-hexane-carboxylic acid | 191 |
| 57 | 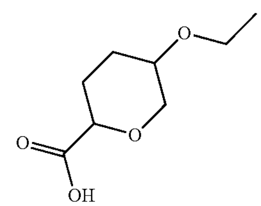 | 2,6-anhydro-3,4-dideoxy-5-O-ethyl-hexonic acid | |

Intermediate 58: 3-(Propan-2-yloxy)cyclopentanecarboxylic Acid

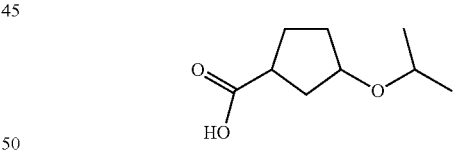

Silver trifluoromethanesulfonate (4.06 g, 15.8 mmol) and dried 4 Å sieves (1 g) were added to a solution of ethyl 3-hydroxycyclopentanecarboxylate (1.0 g, 6.3 mmol) in DCM (3.2 mL) followed by the addition of 2-iodopropane (1.6 mL, 16 mmol) in DCM (0.79 mL) over 15 minutes. The mixture was stirred at room temperature for 18 h. The mixture was diluted with DCM and filtered through a pad of celite. The mixture was concentrated under reduced pressure and the material was purified by column chromatography on silica gel (0-60% EtOAc/Hex) to afford the title compound as an oil. MS: 201 (M+1). 1H NMR (600 MHz, DMSO-d6) δ 4.07-3.86 (m, 2H), 3.54-3.42 (m, 1H), 3.12-2.17 (m, 3H), 2.07-1.46 (m, 5H), 1.16-1.08 (m, 6H), 1.02-0.97 (m, 3H). The material was hydrolyzed per the conditions described above.

Intermediate 59:
4-(Cyclopropyloxy)cyclohexanecarboxylic Acid

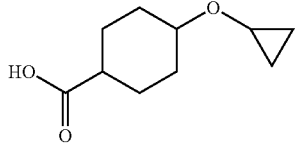 [SMILES: O=C(O)C1CCC(OC2CC2)CC1]

Step 1:

1-bromo-4-(cyclopropyloxy)benzene (9.5 g, 45 mmol), DMA (66 mL), and MeOH (33 mL) were added to a bomb reactor and degassed by bubbling through argon for ~5 minutes. The degassed mixture was charged with DPPF (1.85 g, 3.34 mmol) and Pd(OAc)$_2$ (0.50 g, 2.2 mmol) and degassed under CO. The reaction was heated in the bomb at 15 psi CO at 80° C. for 18 h. The crude reaction mixture was filtered through celite and concentrated under reduced pressure. The residue was purified by column chromatography on silica gel (5-25% EtOAc/hexane) to afford methyl 4-cyclopropoxybenzoate.

Step 2:

Methyl 4-cyclopropoxybenzoate (2.7 g, 14 mmol) was dissolved in MeOH (60 mL) and the solution was degassed by bubbling through argon for 10 minutes. The degassed mixture was charged with 5% Rhodium/Alumina (0.576 g, 2.81 mmol) and backfilled with hydrogen (2×). The mixture was allowed to react at 55 psi hydrogen for 72 h on a Parr shaker. The reaction was filtered through celite and concentrated under reduced pressure. The residue was purified by column chromatography on silica gel (0-10% EtOAc/DCM) to afford methyl 4-cyclopropoxycyclohexanecarboxylate.

Step 3:

Methyl 4-cyclopropoxycyclohexanecarboxylate (800 mg, 4.04 mmol) was dissolved in 0.5 M sodium methoxide in methanol (2.42 mL, 12.1 mmol) and heated to 50° C. for 18 h. The reaction was cooled to room temperature and concentrated under reduced pressure. The residue was diluted with water (10 mL) and allowed to stir for 15 minutes. The solution was acidified with 1N HCl (10 mL), extracted with EtOAc (2×50 mL), and the combined organic layers were washed with brine, dried over sodium sulfate, filtered, and concentrated under reduced pressure to afford the title compound as a mixture of cis/trans isomers. MS: 185 (M+1). $^1$H NMR (500 MHz, CDCl$_3$) δ 11.35 (s, 1H), 3.47-3.35 (m, 1H), 2.49-2.25 (m, 1H), 2.19-2.02 (m, 2H), 1.97-1.81 (m, 2H), 1.75-1.63 (m, 1H), 1.63-1.44 (m, 2H), 1.37-1.21 (m, 2H), 0.56 (s, 2H), 0.51-0.43 (m, 2H).

Intermediate 60:
4-Methoxy-3-methylcyclohexanecarboxylic Acid as a Mixture of Cis Isomers

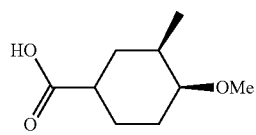

Intermediate 61:
4-Methoxy-3-(trifluoromethyl)cyclohexanecarboxylic Acid as a Mixture of Cis Isomers

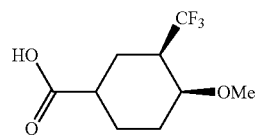 [SMILES: CO[C@H]1CCC(C(=O)O)C[C@H]1C(F)(F)F]

Intermediate 62:
(3aS,7aS)-Octahydro-1-benzofuran-5-carboxylic Acid as a Mixture of Isomers

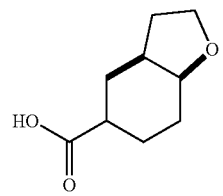

Intermediate 63:
4-Ethoxy-3-methylcyclohexanecarboxylic Acid

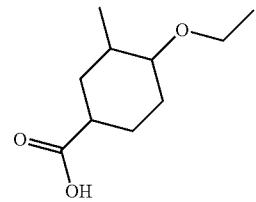

Intermediate 64: Ethyl 4-ethoxy-3-hydroxycyclohexanecarboxylate

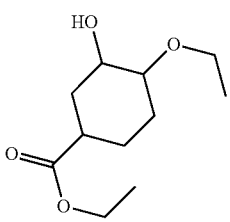

Intermediates 60-64 were prepared using the procedure described for Intermediate 60 via Rh/Al$_2$O$_3$ condition and NaOMe/MeOH saponification.

Intermediate 65:
4-(Tetrahydro-2H-pyran-4-yl)cyclohexanecarboxylic Acid

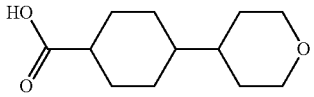 [SMILES: O=C(O)C1CCC(C2CCOCC2)CC1]

Step 1:

To a dry flask was added 4-(tetrahydro-2H-pyran-4-yl)benzoic acid (1.7 g, 8.2 mmol) and methanol (30 mL). Thionyl chloride (3.0 mL, 41 mmol) was added dropwise and the reaction was allowed to stir at room temperature for 16 h. The mixture was concentrated under reduced pressure to afford methyl 4-(tetrahydro-2H-pyran-4-yl)benzoate.

Step 2:

Methyl 4-(tetrahydro-2H-pyran-4-yl)benzoate (1.8 g, 8.2 mmol) was added to a dry 250 mL Parr flask charged with AcOH (100 mL). The mixture was degassed by bubbling argon through for 5 minutes. The flask was charged with platinum(IV) oxide (186 mg, 0.817 mmol), and backfilled with hydrogen (2×). The mixture was allowed to react at 55 psi hydrogen for 72 h on a Parr shaker. The mixture was filtered through celite and concentrated under reduced pressure to afford crude methyl 4-(tetrahydro-2H-pyran-4-yl)cyclohexanecarboxylate that was used crude in the next step without further purification.

Step 3:

Methyl 4-(tetrahydro-2H-pyran-4-yl)cyclohexanecarboxylate (1.2 g, 5.2 mmol) was dissolved in MeOH (20 mL) and charged with potassium tert-butoxide (1.74 g, 15.5 mmol). The mixture was stirred at room temperature for 18 h. The reaction was concentrated under reduced pressure to ~5 mL MeOH, and the flask was charged with water (3 mL) and allowed to stir for 10 min at room temperature. The reaction was acidified with HCl (10.3 ml, 20.7 mmol), and partitioned with ethyl acetate. The organic layer was washed with brine, dried over sodium sulfate, filtered, and concentrated under reduced pressure to afford the title compound as a mixture of cis/trans isomers. $^1$H NMR (500 MHz, CDCl$_3$) δ 4.04-3.93 (m, 2H), 3.35 (t, J=11.7 Hz, 2H), 2.67-2.53 (m, 1H), 2.10-2.03 (m, 1H), 1.87-1.83 (m, 1H), 1.68-1.46 (m, 5H), 1.46-1.23 (m, 6H), 1.20-1.05 (m, 1H).

Intermediate 66:
4-Methoxy-2,3-dimethylcyclohexanecarboxylic Acid as a Mixture of Isomers

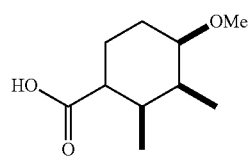

Intermediate 67 can be made using the procedure described for Intermediate 66 via SOCl$_2$/MeOH, PtO$_2$/AcOH and NaOMe/MeOH saponification.

Intermediate 67:
4-Methoxy-2,5-dimethylcyclohexanecarboxylic Acid as a Mixture of Isomers

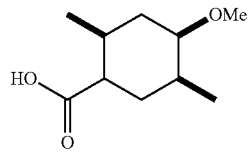

Intermediate 68 can be made using the procedure described for Intermediate 66 via PtO$_2$/AcOH and NaOMe/MeOH saponification.

Intermediates 68 and 69:
4-Methoxy-3,5-dimethylcyclohexanecarboxylic Acid as a Mixture of Isomers (69) and 3,5-dimethylcyclohexanecarboxylic Acid as a Mixture of Isomers (70)

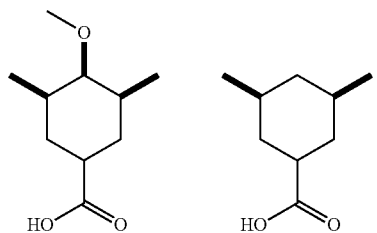

(Elimination product formed in hydrogenation and carried through to final coupling)

Intermediates 68 and 69 were prepared using the procedure described for Intermediate 65 via PtO$_2$/AcOH and KOtBu/MeOH saponification.

Intermediate 70:
4-(2,2,2-Trifluoroethoxy)cyclohexanecarboxylic Acid as a Mixture of Cis/Trans Isomers

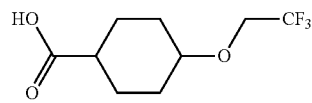

Intermediate 71:
4-(Tetrahydrofuran-3-yloxy)cyclohexanecarboxylic Acid

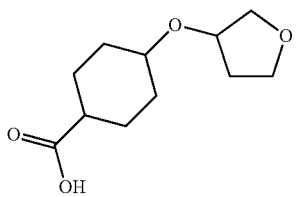 [SMILES: O=C(O)C1CCC(OC2CCOC2)CC1]

Intermediates 70 and 71 were prepared using the procedure described for Intermediate 66 via PtO$_2$/AcOH and NaOMe/MeOH saponification.

Intermediate 72:
(4R)-4-Methoxy-2-methylcyclohexanecarboxylic Acid as a Mixture of Trans Isomers

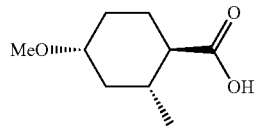

Step 1:

To a flask charged with ethyl 2-methyl-4-oxocyclohex-2-ene-1-carboxylate (50 g, 0.28 mol) and ethanol (430 mL) was added a slurry of palladium (10% on carbon, 2.0 g, 0.04 wt %) in ethanol (70 mL) and 2 N HCl solution (10 mL) under a nitrogen atmosphere at room temperature. The resulting slurry was stirred under hydrogen at 50 psi for 15 h at room temperature. The reaction mixture was filtered through a pad of celite and the pad was washed with methanol (3×200 mL). The combined filtrates were concentrated under reduced pressure. The residue was purified by column chromatography on silica gel (2-10% EtOAc/petroleum ether) to afford ethyl 2-methyl-4-oxocyclohexanecarboxylate as a liquid. The material was isolated as a racemic mixture of cis isomers.

Step 2:

A flask equipped with a mechanical stirrer and thermocouple, and connected to a nitrogen line was charged with ethyl 2-methyl-4-oxocyclohexanecarboxylate (50 g, 0.27 mol, mixture of cis isomers) and methanol (500 mL). The reaction mixture was cooled to 0° C. and sodium borohydride (12.3 g, 0.32 mol) was added portion wise over 45 minutes while maintaining the internal temperature between 0 and 5° C. The reaction mixture was held at 0° C. for 2 h. The mixture was quenched with water (50 mL) and methanol was removed under reduced pressure. The residue was diluted with MTBE (500 mL), washed with water (2×100 mL) and brine (100 mL), and dried over anhydrous sodium sulfate, filtered, and concentrated under reduced pressure. The residue was purified by column chromatography on silica gel (2-10% EtOAc/petroleum ether) to afford ethyl (4R)-4-hydroxy-2-methylcyclohexanecarboxylate as an oil. The material was isolated as a racemic mixture of cis isomers.

Step 3:

A three-neck flask equipped with a temperature probe and nitrogen gas inlet was charged with ethyl (4R)-4-hydroxy-2-methylcyclohexanecarboxylate (74 g, 0.39 mol, mixture of cis isomers) and THF (540 mL). The reaction mixture was cooled to −75° C. and a solution of potassium tert-butoxide (89 g, 0.79 mol) in THF (200 mL) was added dropwise over 45 minutes while maintaining an internal temperature between −65 and −75° C. The reaction mixture was held at −65 to −75° C. for 1 h. The mixture was then warmed to room temperature and stirred for 15 h. The reaction was cooled to −20° C. and quenched with water (50 mL). The organic layer was separated, and the aqueous layer was extracted with ethyl acetate (2×100 mL). The combined organic layers were washed with brine (100 mL) and dried over anhydrous sodium sulfate, filtered, and concentrated under reduced pressure. The residue was purified by column chromatography on silica gel (10% EtOAc in hexane) to afford racemic trans ethyl (4R)-4-hydroxy-2-methylcyclohexanecarboxylate as a liquid.

Step 4:

Racemic trans ethyl (4R)-4-hydroxy-2-methylcyclohexanecarboxylate (1.53 g, 8.23 mmol) was dissolved in THF (40 mL) and cooled to 0° C. Sodium hydride (0.362 g, 9.05 mmol) was added and the mixture was stirred for 20 minutes. The reaction was charged with iodomethane (0.566 mL, 9.05 mmol) and stirred for 2 h as the solution slowly warmed to room temperature. The reaction was then heated at reflux for 16 h. The reaction was cooled to room temperature and quenched with water. The mixture was extracted with ethyl acetate, and the organic layer was dried over sodium sulfate, filtered, and concentrated under reduced pressure. The residue was purified by column chromatography on silica gel (10-40% EtOAc/hexanes) to afford provided racemic trans (4R)-ethyl 4-methoxy-2-methylcyclohexanecarboxylate.

Step 5:

To a mixture of racemic trans (4R)-ethyl 4-methoxy-2-methylcyclohexanecarboxylate (296 mg, 1.48 mmol) dissolved in THF (6 mL), water (1.5 mL), and MeOH (1.5 mL) was added lithium hydroxide (133 mg, 5.55 mmol). The mixture was heated to 60° C. for 48 h. The reaction was cooled to room temperature and quenched with 2 N HCl (5.34 mL to pH 5~6) and extracted with EtOAc (2×). The combined organic layers were dried over sodium sulfate, filtered and concentrated under reduced pressure to afford the title compound as an oil that is a mixture of trans isomers. $^1$H NMR (500 MHz, CDCl$_3$) δ 3.37 (s, 3H), 3.24-3.12 (m, 1H), 2.18-2.07 (m, 2H), 2.05-1.99 (m, 1H), 1.97-1.93 (m, 1H), 1.80-1.75 (m, 1H), 1.61-1.48 (m, 1H), 1.20-1.16 (m, 1H), 1.01 (d, J=7.5 Hz, 3H), 0.98-0.90 (m, 1H).

Intermediate 73:
4-(Cyclobutyloxy)cyclohexanecarboxylic Acid

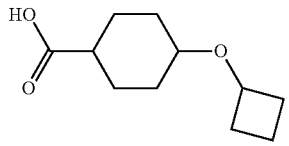 [SMILES: O=C(O)C1CCC(OC2CCC2)CC1]

Step 1:

To ethyl 4-((trimethylsilyl)oxy)cyclohexanecarboxylate (1.5 g, 6.1 mmol) dissolved in DCM (30 mL) at −78° C. was added cyclobutanone (0.4 mL, 5.5 mmol) followed by TMS-OTf (0.1 mL, 0.6 mmol). The reaction was stirred at −78° C. for 20 minutes and then triethylsilane (1.1 mL, 6.7 mmol) was added. The dry ice bath was removed and the reaction was stirred at room temperature for 16 h. The reaction was quenched with MeOH (5 mL) and concentrated under reduced pressure. The residue was purified by column chromatography on silica gel (0-5% EtOAc/DCM) to afford ethyl 4-cyclobutoxycyclohexanecarboxylate.

Step 2:

Ethyl 4-cyclobutoxycyclohexanecarboxylate (811 mg, 3.58 mmol) was dissolved in sodium methoxide (0.5 M in MeOH, 3.87 g, 17.9 mmol) and the mixture was heated to 50° C. for 18 h. The reaction was concentrated under reduced pressure and then diluted with water (10 mL) and allowed to stir at room temperature for 10 minutes. The water layer was acidified with 1N HCl (15 mL) and extracted with EtOAc (2×50 mL). The combined organic layers were washed with brine, dried over sodium sulfate, filtered, and concentrated under reduced pressure to afford the title compound as a mixture of cis/trans isomers. MS: 199 (M+1). $^1$H NMR (500 MHz, CDCl$_3$) δ 4.09-3.90 (m, 1H), 3.52-3.17 (m, 1H), 2.47-2.25 (m, 1H), 2.25-2.15 (m, 2H), 2.09-1.87 (m, 5H), 1.81-1.60 (m, 3H), 1.60-1.40 (m, 2H), 1.35-1.20 (m, 2H).

Intermediate 74:
4-((Propan-2yl-d7)oxy)cyclohexane-1-carboxylic Acid

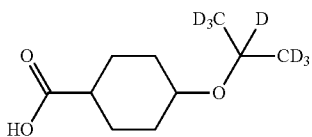 [SMILES: [2H]C([2H])([2H])C([2H])(OC1CCC(C(=O)O)CC1)C([2H])([2H])[2H]]

Intermediate 75: 4-Methoxycycloheptanecarboxylic Acid

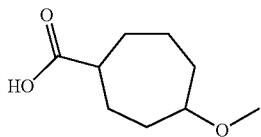

Intermediates 74-75 were prepared using the procedure described for Intermediate 73.

Intermediate 76: 4-[(2,2-Difluorocyclopropyl)oxy]cyclohexanecarboxylic Acid

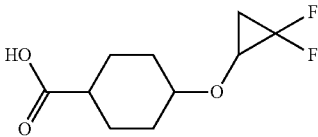 [SMILES: O=C(O)C1CCC(OC2CC2(F)F)CC1]

Step 1:
Diacetoxypalladium (336 mg, 1.50 mmol) was added to a solution of 1,10-phenanthroline (270 mg, 1.50 mmol) in ethoxyethene (20 mL) in a 100 mL pressure vessel. The mixture was stirred at room temperature for 15 minutes and then a solution of ethyl 4-hydroxycyclohexanecarboxylate (2.58 g, 14.9 mmol) in ethyl vinyl ether (10 mL) was added. The vessel was sealed and heated at 60° C. for 18 h. The mixture was cooled to room temperature and concentrated under reduced pressure. The residue was purified by column chromatography on silica gel (0-10% EtOAc/hexanes) to afford ethyl 4-(vinyloxy)cyclohexanecarboxylate as an oil.

Step 2:
Ethyl 4-(vinyloxy)cyclohexanecarboxylate (850 mg, 4.29 mmol) was added to an oven-dried flask. The flask was charged with tetrabutylammonium difluorotriphenylsilicate (116 mg, 0.21 mmol), the mixture was cooled to −40° C. for 10 minutes, and then charged with (trifluoromethyl) trimethylsilane (2 M in THF, 5.36 mL, 10.7 mmol) over 10 minutes. The reaction was allowed to stir for 2 h at −40° C., and then the mixture was warmed to room temperature and stirred for 18 h. The reaction was concentrated under reduced pressure and the residue was purified by column chromatography on silica gel (0-10% EtOAc/hexanes) to afford ethyl 4-(2,2-difluorocyclopropoxy)cyclohexanecarboxylate.

Step 3:
Ethyl 4-(2,2-difluorocyclopropoxy)cyclohexanecarboxylate (300 mg, 1.21 mmol) was dissolved in sodium methoxide (0.5 M in MeOH, 7.25 mL, 3.63 mmol) and heated to 50° C. for 18 h. The reaction was cooled to room temperature and concentrated under reduced pressure. The residue was diluted with water (10 mL) and allowed to stir 10 minutes at room temperature. The water layer was acidified with 1N HCl (15 mL) and extracted with EtOAc (2×50 mL). The combined organic layers were washed with brine, dried over sodium sulfate, filtered, and concentrated under reduced pressure to afford the title compound as a cis/trans mixture. MS: 221 (M+1). $^1$H NMR (500 MHz, CDCl$_3$) δ 3.70-3.67 (m, 1H), 3.65-3.60 (m, 1H), 3.53-3.41 (m, 1H), 2.48-2.42 (m, 1H), 2.39-2.26 (m, 1H), 2.20-2.09 (m, 1H), 1.99-1.85 (m, 2H), 1.79-1.71 (m, 1H), 1.68-1.58 (m, 1H), 1.59-1.48 (m, 1H), 1.47-1.37 (m, 1H), 1.28-1.24 (m, 1H).

Intermediate 77: Racemic cis 4,4-difluoro-2-methylcyclohexanecarboxylic Acid

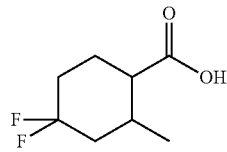

Step 1:
To a flask containing ethyl 2-methyl-4-oxocyclohex-2-ene-1-carboxylate (275 g, 1.43 mol) and ethanol (1.2 L) was added a slurry of 10% Pd/C (16.0 g, 0.05 wt %) in ethanol (70 mL). Hydrochloric acid (2 N, 40 mL) was added under nitrogen at room temperature, and the resulting slurry was stirred under hydrogen at 800 psi for 3 h. The reaction mixture was filtered through celite and washed with methanol (3×750 mL). The combined filtrates were concentrated under reduced pressure, and the residue was purified by column chromatography on silica gel (2-10% EtOAc/petroleum ether) to afford ethyl 2-methyl-4-oxocyclohexanecarboxylate as a liquid, that is a mixture of cis isomers.

Step 2:
To a flask equipped with a magnetic stirrer and thermocouple connected to a nitrogen line was charged with ethyl 2-methyl-4-oxocyclohexanecarboxylate (200 g, 1.03 mol, a mixture of cis isomers) and dichloromethane (500 mL). The reaction mixture was cooled to −78° C. and DAST (350 mL, 2.16 mol) was added dropwise over 45 minutes while maintaining an internal temperature between −65 and −78° C. Once the addition was complete, the reaction mixture was gradually brought to room temperature and stirred for 15 h. The mixture was quenched with water (500 mL) and the organic layer was separated. The aqueous layer was extracted with dichloromethane (2×500 mL), and the combined organic layers were washed with brine (2×100 mL), dried over sodium sulfate, filtered, and concentrated under reduced pressure. The residue was purified by column chromatography on silica gel (2-10% EtOAc/petroleum ether) to afford ethyl 4,4-difluoro-2-methylcyclohexanecarboxylate as a liquid (mixture of cis isomers).

Step 3:

To a flask equipped with a magnetic stirrer and temperature probe was charged with ethyl 4,4-difluoro-2-methylcyclohexanecarboxylate (120 g, 0.58 mol, mixture of cis isomers) and ethanol (540 mL). Potassium hydroxide (2N in water, 400 mL, 6 volumes) was added, and the reaction was stirred at room temperature for 3 h. The mixture was concentrated under reduced pressure, and the residue was acidified with aqueous 2N HCl to pH 3. The mixture was extracted with EtOAc (3×500 mL), and the combined organic layers were washed with brine (100 mL), dried over anhydrous sodium sulfate, filtered, and concentrated under reduced pressure. The residue was dissolved in a mixture of water and dioxane (1:7, 400 mL) and was added to a solution of osmium tetroxide (2.5 wt % in tert-butanol, 3.8 mL, 0.014 mol), sodium periodate (494 g, 2.32 mol), and 2,6-lutidine (125 g, 1.16 mol). The reaction mixture was stirred at room temperature for 3 h. The mixture was diluted with water (200 mL) and extracted with dichloromethane (2×600 mL). The combined organic layers were washed with brine (2×300 mL), dried over sodium sulfate, filtered, and concentrated under reduced pressure. The residue was purified by column chromatography on silica gel (10% EtOAc in hexanes) to afford racemic cis 4,4-difluoro-2-methylcyclohexanecarboxylic acid as an oil. $^1$H NMR (400 MHz, CDCl$_3$) δ: 12.33 (bs, 1H), 2.49 (s, 1H), 2.26-1.82 (m, 7H), 1.1 (d, J=7.2 Hz, 3H).

Intermediate 78: Racemic Trans Ethyl (4R)-4-hydroxy-2-methylcyclohexanecarboxylate

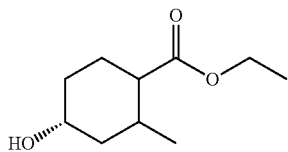

Step 1:

To a flask charged with ethyl 2-methyl-4-oxocyclohex-2-ene-1-carboxylate (50 g, 0.28 mol) and ethanol (430 mL) was added a slurry of palladium (10% on carbon, 2.0 g, 0.04 wt %) in ethanol (70 mL) and 2 N HCl solution (10 mL) under a nitrogen atmosphere at room temperature. The resulting slurry was stirred under hydrogen at 50 psi for 15 h at room temperature. The reaction mixture was filtered through a pad of celite and the pad was washed with methanol (3×200 mL). The combined filtrates were concentrated under reduced pressure. The residue was purified by column chromatography on silica gel (2-10% EtOAc/petroleum ether) to afford ethyl 2-methyl-4-oxocyclohexanecarboxylate as a liquid. The material was isolated as a racemic mixture of cis isomers.

Step 2:

A flask equipped with a mechanical stirrer and thermocouple, and connected to a nitrogen line was charged with ethyl 2-methyl-4-oxocyclohexanecarboxylate (50 g, 0.27 mol, mixture of cis isomers) and methanol (500 mL). The reaction mixture was cooled to 0° C. and sodium borohydride (12.3 g, 0.32 mol) was added portion wise over 45 minutes while maintaining the internal temperature between 0 and 5° C. The reaction mixture was held at 0° C. for 2 h. The mixture was quenched with water (50 mL) and methanol was removed under reduced pressure. The residue was diluted with MTBE (500 mL), washed with water (2×100 mL) and brine (100 mL), and dried over anhydrous sodium sulfate, filtered, and concentrated under reduced pressure. The residue was purified by column chromatography on silica gel (2-10% EtOAc/petroleum ether) to afford ethyl (4R)-4-hydroxy-2-methylcyclohexanecarboxylate as an oil. The material was isolated as a racemic mixture of cis isomers.

Step 3:

A three-neck flask equipped with a temperature probe and nitrogen gas inlet was charged with ethyl (4R)-4-hydroxy-2-methylcyclohexanecarboxylate (74 g, 0.39 mol, mixture of cis isomers) and THF (540 mL). The reaction mixture was cooled to -75° C. and a solution of potassium tert-butoxide (89 g, 0.79 mol) in THF (200 mL) was added dropwise over 45 minutes while maintaining an internal temperature between -65 and -75° C. The reaction mixture was held at -65 to -75° C. for 1 h. The mixture was then warmed to room temperature and stirred for 15 h. The reaction was cooled to -20° C. and quenched with water (50 mL). The organic layer was separated, and the aqueous layer was extracted with ethyl acetate (2×100 mL). The combined organic layers were washed with brine (100 mL) and dried over anhydrous sodium sulfate, filtered, and concentrated under reduced pressure. The residue was purified by column chromatography on silica gel (10% EtOAc in hexane) to afford racemic trans ethyl (4R)-4-hydroxy-2-methylcyclohexanecarboxylate as a liquid. $^1$H NMR (400 MHz, CDCl$_3$) δ: 4.14 (q, J=7.2 Hz, 2H), 3.72-3.64 (m, 1H), 2.08-1.42 (m, 8H), 1.26 (t, J=7.2 Hz, 3H), 1.04-0.98 (m, 1H), 0.94 (d, J=6.4 Hz, 3H).

Intermediate 79: 5-(4,4,5,5-Tetramethyl-1,3,2-dioxaborolan-2-yl)-3,6-dihydro-2H-pyran

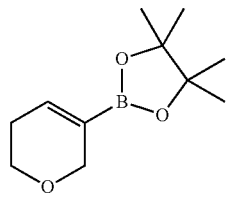

Step 1:

To a 3-neck flask purged and maintained with an inert atmosphere of nitrogen was placed KHMDS (32 ml, 1.40 equiv, 21%). A solution of dihydro-2H-pyran-3(4H)-one (2 g, 0.02 mol) in THF (8 mL) was added dropwise with stirring at -78° C., and the resulting solution was stirred for 2 h at -78° C. A solution of 1,1,1-trifluoro-N-phenyl-N-[(trifluoromethyl)sulfonyl]methanesulfonamide (7.9 g, 0.022 mmol) in anhydrous THF (25 mL) was added dropwise with stirring at -78° C., and the resulting solution was stirred for 2 h at -78° C. The reaction mixture was quenched with water (10 mL), and concentrated under reduced pressure. The residue was dissolved in DCM (100 mL), washed with 5% NaHCO$_3$/H$_2$O (3×1000 mL), 15% NaHSO$_4$/H$_2$O (3×1000 mL), and 5% Na$_2$CO$_3$/H$_2$O (3×1000 mL). The organic layer was dried over magnesium sulfate, filtered, and concentrated under reduced pressure. The residue was purified by column chromatography on silica gel (1:50

EtOAc/petroleum ether) to afford 5,6-dihydro-2H-pyran-3-yl trifluoromethanesulfonate as an oil.

Step 2:

To a 4-neck flask purged and maintained with an inert atmosphere of nitrogen was placed a solution of 5,6-dihydro-2H-pyran-3-yl trifluoromethanesulfonate (80 g, 0.34 mol) in dioxane (800 mL), potassium acetate (102 g, 1.04 mol), 4,4,5,5-tetramethyl-2-(4,4,5,5-tetramethyl-1,3,2-dioxaborolan-2-yl)-1,3,2-dioxaborolane (88.3 g, 0.347 mol), and PdCl$_2$(dppf) (14.2 g, 0.0174 mol). The resulting mixture was stirred for 1 h at 80° C. The reaction mixture was cooled to room temperature, filtered, and concentrated under reduced pressure. The residue was dissolved in DCM (2000 mL), washed with water (2×2000 mL), dried over magnesium sulfate, filtered, and concentrated under reduced pressure. The residue was purified by column chromatography on silica gel (1:150 MeOH:DCM) to afford the title compound as an oil. $^1$H-NMR (400 MHz, CDCl$_3$) δ: 6.65 (s, 1H) 4.23 (s, 2H), 3.78-3.76 (m, 2H), 2.19 (s, 2H), 1.25 (s, 12H).

Intermediate 80: 3-Phenoxycyclobutanecarboxylic Acid

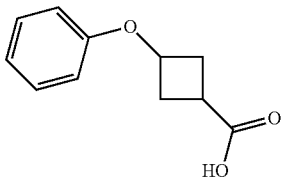 [SMILES: O=C(O)C1CC(Oc2ccccc2)C1]

Step 1:

To a 3-neck flask that had been purged and maintained with an inert atmosphere of nitrogen, was placed a solution of phenol (111 g, 1.18 mol) in DMSO (2000 mL). To this solution was added potassium tert-butoxide (240 g, 2.14 mol), and the mixture was heated to 80° C. with vigorous stirring under an argon atmosphere for 15 minutes. To the above solution was added methyl 3-chlorocyclobutanecarboxylate (160 g, 1.08 mol) dropwise with stirring followed by tetrabutylammonium iodide (238 g, 0.646 mol). The reaction mixture was stirred for 1.5 h at 80° C. The mixture was cooled to 10° C., quenched with water (30 mL), and the aqueous layer was extracted with EtOAc (3×1000 mL). The combined organic layers were washed with brine (200 mL), dried over sodium sulfate, filtered, and concentrated under reduced pressure. The residue was purified by column chromatography on silica gel (1:40 EtOAc:petroleum ether) to afford methyl 3-phenoxycyclobutanecarboxylate as a solid.

Step 2:

To a flask was placed a solution of methyl 3-phenoxycyclobutanecarboxylate (60 g, 0.29 mol) in MeOH (200 mL). Sodium hydroxide (22 g, 0.55 mol) was added, and the solution was stirred for 2 h at reflux. The solution was cooled to room temperature and concentrated under reduced pressure. The resulting solid was diluted with EtOAc, water, and HCl (12 N) to pH 2. The resulting solution was extracted with EtOAc (2×1000 mL). The combined organic layers were dried over sodium sulfate, filtered, and concentrated under reduced pressure to afford the title compound as a solid. $^1$H-NMR (400 MHz, DMSO-d$_6$) δ: 12 (s, 1H), 7.2-6.8 (m, 5H), 4.6-4.5 (m, 1H), 2.76-2.67 (m, 2H), 2.16-2.10 (m, 3H).

Intermediate 81: (8-Bromo-5,11-dihydro-6H-benzo[b]pyrido[2,3-e][1,4]diazepin-6-yl)(4-((1-(trifluoromethyl)cyclopropyl)amino)cyclohexyl)methanone

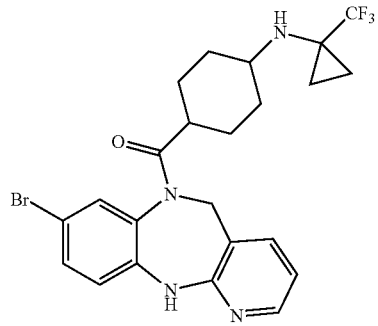 [SMILES: O=C(C1CCC(NC2(C(F)(F)F)CC2)CC1)N1Cc2cccnc2Nc2ccc(Br)cc21]

To a flask was added 4-(8-bromo-6,11-dihydro-5H-benzo[b]pyrido[2,3-e][1,4]diazepine-6-carbonyl)cyclohexanone (464 mg, 1.16 mmol), 1-(trifluoromethyl)cyclopropanamine (580 mg, 4.64 mmol) and DCE (15 mL). Acetic acid (0.13 mL, 2.3 mmol) was added followed by the addition of sodium triacetoxyhydroborate (590 mg, 2.78 mmol). The mixture was stirred at room temperature overnight, and the reaction mixture was quenched with water. The mixture was extracted with EtOAc and the organic layer was washed by brine, dried over sodium sulfate, filtered, and concentrated under reduced pressure. The residue was purified by column chromatography on silica gel (0-80% EtOAc/DCM) to afford the title compound as a mixture of cis/trans isomers. MS: 509 and 511 (M+1, M+3).

Intermediate 82: Di-tert-butyl 8-bromo-5H-benzo[b]pyrido[2,3-e][1,4]diazepine-6,11-dicarboxylate

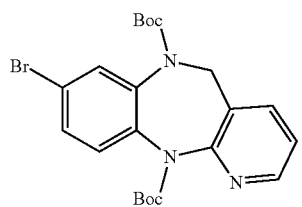 [SMILES: CC(C)(C)OC(=O)N1Cc2cccnc2N(C(=O)OC(C)(C)C)c2ccc(Br)cc21]

Step 1:

To a mixture of 8-bromo-6,11-dihydro-5H-pyrido[2,3-b][1,5]benzodiazepine, HCl (5.0 g, 16 mmol) in THF (300 mL) was added triethylamine (17.9 mL, 128 mmol), di-tert-butyl dicarbonate (14 g, 64 mmol) and DMAP (2.3 g, 19 mmol). The mixture was heated to 70° C. for 18 h. Upon cooling to room temperature, the mixture was diluted with ethyl acetate, washed with water, dried over magnesium sulfate, filtered and concentrated under reduced pressure. The mixture was purified by column chromatography to afford the title compound. MS: 376, 378 (M−C$_5$H$_8$O$_2$, M−C$_5$H$_8$O$_2$+2). $^1$H NMR (600 MHz, DMSO-d$_6$) δ 8.31 (dd, J=4.8, 1.8 Hz, 1H), 7.66 (dd, J=7.7, 1.8 Hz, 1H), 7.62 (d, J=2.3 Hz, 1H), 7.49 (dd, J=8.6, 2.3 Hz, 1H), 7.36 (d, J=8.5 Hz, 1H), 7.27 (dd, J=7.7, 4.6 Hz, 1H), 4.89 (s, 2H), 1.32 (s, 9H), 1.29 (s, 9H).

Intermediate 83: (2R,5S)-5-Isopropoxytetrahydro-2H-pyran-2-carboxylic Acid

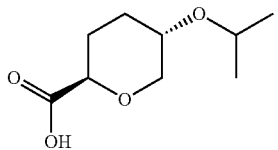

Step 1:
A flask containing ethyl 5-oxotetrahydro-2H-pyran-2-carboxylate (2.0 g, 12 mmol) and dichloromethane (100 mL) was cooled to −78° C. Isopropoxytrimethylsilane (2.5 mL, 14 mmol), followed by trimethylsilyl trifluoromethanesulfonate (0.53 mL, 2.9 mmol) were added and the mixture was stirred for 1 h at −78° C. Triethylsilane (2.0 mL, 13 mmol) was added, the dry ice bath was removed and the reaction was allowed to warm to RT for 18 h. The mixture was quenched with methanol (5 mL), concentrated under reduced pressure and purified by column chromatography on silica gel to afford trans ethyl 5-isopropoxytetrahydro-2H-pyran-2-carboxylate as a mixture of isomers that was taken on to the next step.

Step 2:
To a mixture of trans ethyl 5-isopropoxytetrahydro-2H-pyran-2-carboxylate (8.4 g, 39 mmol) in THF (100 mL), water (32 mL) and ethanol (32 mL) was added lithium hydroxide (3.5 g, 0.15 mol) and the mixture was stirred at RT for 18 h. HCl (2.0 M in water, 78 mL, 0.16 mmol) was added and then the mixture was extracted with ethyl acetate (2×150 mL). The organic extracts were combined, dried over sodium sulfate, filtered and concentrated to afford trans 5-isopropoxytetrahydro-2H-pyran-2-carboxylic acid that was taken on to the next step without further purification.

Step 3:
To a mixture of trans 5-isopropoxytetrahydro-2H-pyran-2-carboxylic acid (10.3 g, 54.5 mmol), potassium carbonate (15.1 g, 109 mmol) and sodium iodide (1.6 g, 11 mmol) in DMF (160 mL) was added benzyl bromide (7.1 mL, 60 mmol). The reaction mixture was stirred for 16 h. The reaction mixture was diluted with ethyl acetate (500 mL) and washed with water (6×100 mL) and brine (1×50 mL). The organic layer was dried over sodium sulfate, filtered, and concentrated under reduced pressure to afford the crude product. The residue was purified by column chromatography on silica gel to afford trans benzyl 5-isopropoxytetrahydro-2H-pyran-2-carboxylate. The purified product was then further purified by chiral SFC (IC, 2.1×25 cm, methanol with 0.25% DMEA and 10% modifier in $CO_2$) to separate the enantiomers.

Characterization data for the first peak isolated from SFC: MS: 279 (M+1).

Characterization data for the second peak isolated from SFC: MS: 279 (M+1).

Step 4:
To a mixture of trans benzyl 5-isopropoxytetrahydro-2H-pyran-2-carboxylate (peak 2 from SFC, 3.4 g, 12 mmol) in ethyl acetate (120 mL) was added palladium on carbon (10% by weight, 2.60 g, 2.4 mmol) under an atmosphere of argon. The flask was fitted with a hydrogen balloon and the mixture was evacuated and purged 5 times with hydrogen. The mixture was stirred overnight at RT, then filtered through celite and the celite was washed with ethyl acetate. The filtrate was concentrated under reduced pressure to afford the title compound as a single enantiomer (2R,5S)-5-isopropoxytetrahydro-2H-pyran-2-carboxylic acid. $^1$H NMR (500 MHz, DMSO-$d_6$) δ 12.61 (s, 1H), 3.89 (ddd, 1H), 3.82 (dd, 1H), 3.68 (hept, 1H), 3.39-3.31 (m, 1H), 3.05 (dd, 1H), 2.02-1.95 (m, 1H), 1.95-1.88 (m, 1H), 1.55-1.45 (m, 1H), 1.41-1.31 (m, 1H), 1.06 (d, 3H), 1.04 (d, 3H).

Trans benzyl 5-isopropoxytetrahydro-2H-pyran-2-carboxylate (peak 1 from SFC) can be hydrogenated as described in Step 4 to afford trans 5-isopropoxytetrahydro-2H-pyran-2-carboxylic acid as a single enantiomer.

Intermediate 84: (8-Bromo-5,11-dihydro-6H-pyrido[2,3-b][1,5]benzodiazepin-6-yl)[4-(methoxyimino)cyclohexyl]methanone

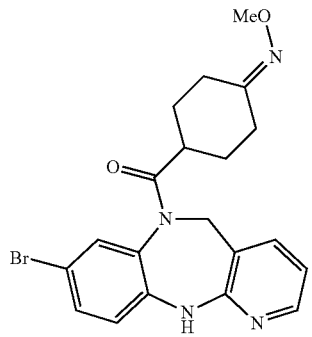 [SMILES: CON=C1CCC(C(=O)N2Cc3cccnc3Nc3ccc(Br)cc32)CC1]

A solution of 4-(8-bromo-6,11-dihydro-5H-benzo[b]pyrido[2,3-e][1,4]diazepine-6-carbonyl)cyclohexanone (1.13 g, 2.82 mmol) and O-methylhydroxylamine hydrochloride (0.472 g, 5.65 mmol) in pyridine (5 mL) was stirred at room temperature overnight. Saturated aqueous sodium bicarbonate was added and the mixture was diluted with water and then extracted with EtOAc (3×). The organic layer was washed with water and then brine, dried over sodium sulfate, filtered and concentrated under reduced pressure. The residue was purified by column chromatography on silica gel (0-100% EtOAc/Hexanes) to afford the title compound as a solid. MS: 429 and 431 (M+1 and M+3).

Intermediate 85: (8-Bromo-5,11-dihydro-6H-pyrido[2,3-b][1,5]benzodiazepin-6-yl)[3-(ethoxyimino)cyclobutyl]methanone

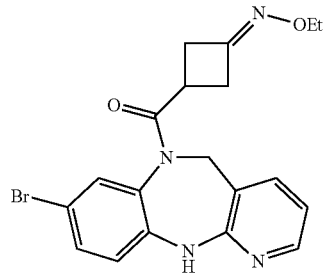 [SMILES: CCON=C1CC(C(=O)N2Cc3cccnc3Nc3ccc(Br)cc32)C1]

Intermediate 85 was prepared using the procedure described for Intermediate 84. MS: 415 and 417 (M+1 and M+3).

Intermediates 86 and 87: (R or S) 8-(Tetrahydro-furan-3-yl)-6,11-dihydro-5H-pyrido[2,3-b][1,5]benzodiazepine and (R or S) 8-(tetrahydrofuran-3-yl)-6,11-dihydro-5H-pyrido[2,3-b][1,5]benzodiazepine

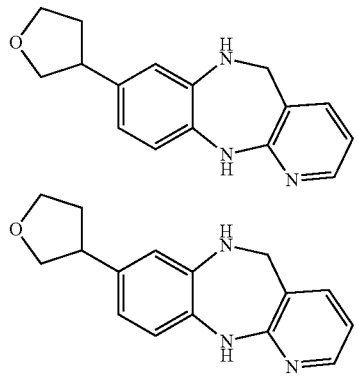

Step 1:

To an oven-dried, nitrogen-cooled vial was added di-tert-butyl 8-bromo-5H-pyrido[2,3-b][1,5]benzodiazepine-6,11-dicarboxylate (450 mg, 0.94 mmol), 3rd generation x-phos palladacycle (80 mg, 0.094 mmol), and 2-(2,5-dihydrofuran-3-yl)-4,4,5,5-tetramethyl-1,3,2-dioxaborolane (223 mg, 1.14 mmol). THF (5 mL) and then potassium phosphate, tribasic (0.5 M in water, 9.5 mL, 4.7 mmol) were added and the reaction was heated to 50° C. for 2 h. The mixture was cooled to room temperature, and diluted with EtOAc. The mixture was washed with water, and the organic layer was dried over sodium sulfate, filtered, and concentrated under reduced pressure. The residue was purified by column chromatography on silica gel (5-40% 3:1 EtOAc:EtOH/Hexanes) to afford di-tert-butyl 8-(2,5-dihydrofuran-3-yl)-5H-pyrido[2,3-b][1,5]benzodiazepine-6,11-dicarboxylate as a solid. MS: 466 (M+1).

Step 2:

To a flask containing palladium on carbon (10% weight loading, 97 mg, 0.091 mmol) under a nitrogen atmosphere was added MeOH (18 mL). Added di-tert-butyl 8-(2,5-dihydrofuran-3-yl)-5H-pyrido[2,3-b][1,5]benzodiazepine-6,11-dicarboxylate (420 mg, 0.91 mmol) to the flask and then evacuated and back-filled 3× with hydrogen gas via a balloon. The mixture was stirred under a hydrogen atmosphere at room temperature for 16 h. The reaction mixture was filtered over a pad of Celite and the filtrate was concentrated under reduced pressure. The residue was then purified by chiral SFC (Chiralcel AD-H column, 10%/90% EtOH/CO$_2$ with 0.25% N,N-dimethylethylamine modifier) to afford (R or S) di-tert-butyl 8-(tetrahydrofuran-3-yl)-5H-pyrido[2,3-b][1,5]benzodiazepine-6,11-dicarboxylate and (R or S) di-tert-butyl 8-(tetrahydrofuran-3-yl)-5H-pyrido[2,3-b][1,5]benzodiazepine-6,11-dicarboxylate both as solids. MS: 468 (M+1) for both peaks.

Step 3:

To a mixture of (R or S) di-tert-butyl 8-(tetrahydrofuran-3-yl)-5H-pyrido[2,3-b][1,5]benzodiazepine-6,11-dicarboxylate (early eluting peak 1, 167 mg, 0.357 mmol) and DCM (2 mL) was added TFA (0.55 mL, 7.1 mmol). The mixture was stirred at room temperature for 16 h. The mixture was concentrated and the residue was dissolved in EtOAc. The mixture was washed with aqueous saturated sodium bicarbonate and extracted with EtOAc (2×). The combined organic layers were dried over sodium sulfate, filtered, and concentrated under reduced pressure to afford the title compound as a solid. MS: 268 (M+1).

Intermediate 87 (slower eluting peak 2) was prepared using the procedure described in step 3. MS: 268 (M+1).

The intermediates in the following table were prepared using the methodology herein and the general procedure described in Intermediates 86 and 87.

| Intermediate # | Structure | Chemical Name | [M + H]+ |
| --- | --- | --- | --- |
| 88 | 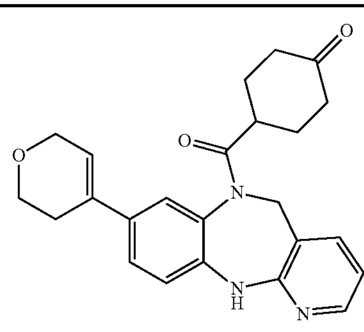 | 4-{[8-(3,6-dihydro-2H-pyran-4-yl)-5,11-dihydro-6H-pyrido[2,3-b][1,5]benzodiazepin-6-yl]carbonyl}cyclohexanone | 404 |
| 89 | 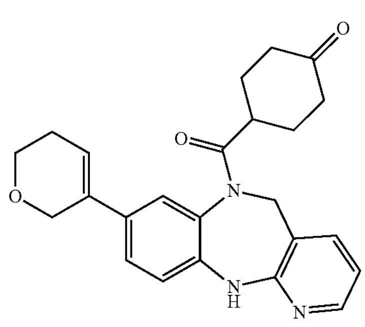 [SMILES: O=C1CCC(C(=O)N2Cc3cccnc3Nc3ccc(C4=CCCOC4)cc32)CC1] | 4-{[8-(5,6-dihydro-2H-pyran-3-yl)-5,11-dihydro-6H-pyrido[2,3-b][1,5]benzodiazepin-6-yl]carbonyl}cyclohexanone | 404 |

-continued

| Intermediate # | Structure | Chemical Name | [M + H]+ |
| --- | --- | --- | --- |
| 90 | 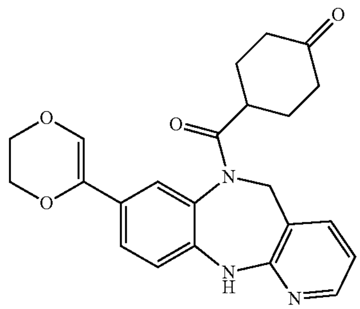 [SMILES: O=C1CCC(C(=O)N2Cc3cccnc3Nc3ccc(C4=COCCO4)cc32)CC1] | 4-{[8-(5,6-dihydro-1,4-dioxin-2-yl)-5,11-dihydro-6H-pyrido[2,3-b][1,5]benzodiazepin-6-yl]carbonyl}cyclohexanone | 406 |
| 91 | 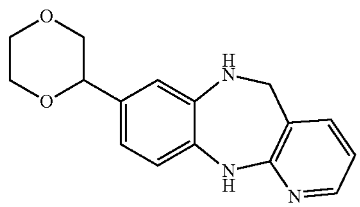 [SMILES: c1cnc2c(c1)CNc1cc(C3COCCO3)ccc1N2] | 8-(1,4-dioxan-2-yl)-6,11-dihydro-5H-pyrido[2,3-b][1,5]benzodiazepine | 284 |
| 92 | 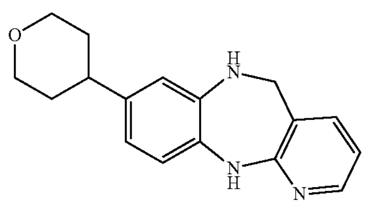 [SMILES: c1cnc2c(c1)CNc1cc(C3CCOCC3)ccc1N2] | 8-(tetrahydro-2H-pyran-4-yl)-6,11-dihydro-5H-pyrido[2,3-b][1,5]benzodiazepine | 282 |
| 93 | 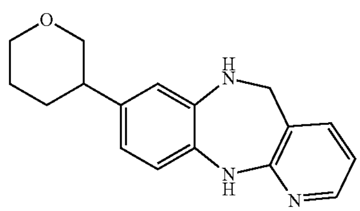 [SMILES: c1cnc2c(c1)CNc1cc(C3CCCOC3)ccc1N2] | 8-(tetrahydro-2H-pyran-3-yl)-6,11-dihydro-5H-pyrido[2,3-b][1,5]benzodiazepine | 282 |
| 94 | 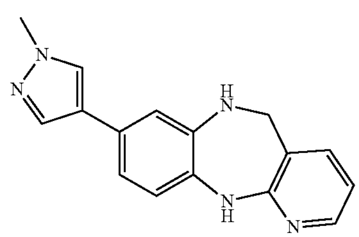 [SMILES: Cn1cc(-c2ccc3c(c2)NCc2cccnc2N3)cn1] | 8-(1-methyl-1H-pyrazol-4-yl)-6,11-dihydro-5H-pyrido[2,3-b][1,5]benzodiazepine | 278 |
| 95 | 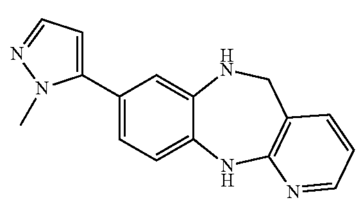 [SMILES: Cn1nccc1-c1ccc2c(c1)NCc1cccnc1N2] | 8-(1-methyl-1H-pyrazol-5-yl)-6,11-dihydro-5H-pyrido[2,3-b][1,5]benzodiazepine | 278 |
| 96 | 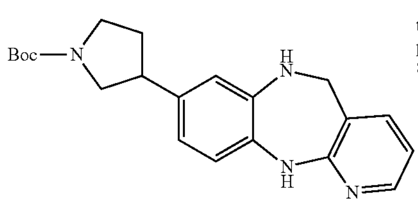 | tert-butyl 3-(6,11-dihydro-5H-pyrido[2,3-b][1,5]benzodiazepin-8-yl)pyrrolidine-1-carboxylate | 367 |

Intermediate 97: 8-(Isopropoxymethyl)-6,11-dihydro-5H-benzo[b]pyrido[2,3-e][1,4]diazepine

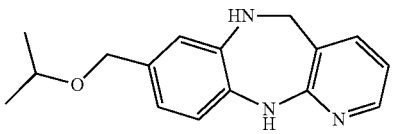 [SMILES: CC(C)OCc1ccc2c(c1)NCc1cccnc1N2]

Step 1:

A vial was charged with di-tert-butyl 8-bromo-5H-benzo[b]pyrido[2,3-e][1,4]diazepine-6,11-dicarboxylate (150 mg, 0.32 mmol), potassium trifluoro(isopropoxymethyl)borate (113 mg, 0.630 mmol), CataCXin A Pd G3 (23 mg, 0.031 mmol) and cesium carbonate (310 mg, 0.95 mmol). Added tert-Amyl Alcohol (1.3 mL) and Water (0.32 mL), and the vial was purged under argon for five minutes and heated to 110° C. for 24 h. The reaction was cooled to room temperature and diluted with EtOAc and saturated aqueous sodium bicarbonate. The combined organic layers were dried over magnesium sulfate, filtered, and concentrated under reduced pressure. The residue was purified by column chromatography on silica gel (0-100% Ethyl Acetate/Hexanes) to afford di-tert-butyl 8-(isopropoxymethyl)-5H-benzo[b]pyrido[2,3-e][1,4]diazepine-6,11-dicarboxylate. MS: 470 (M+1).

Step 2:

To a vial was added di-tert-butyl 8-(isopropoxymethyl)-5H-benzo[b]pyrido[2,3-e][1,4]diazepine-6,11-dicarboxylate (128 mg, 0.273 mmol), ethyl acetate (1.4 mL), and HCl (4.0 M in 1,4-dioxane, 1.4 mL, 5.45 mmol). The reaction was stirred at room temperature for 4.5 h and then 50° C. for 2 h. The mixture was cooled to room temperature and then concentrated under reduced pressure. The residue was dissolved in EtOAc and washed with saturated aqueous sodium bicarbonate. The organic layer was dried over magnesium sulfate, filtered, and concentrated under reduced pressure to afford the title compound. MS: 270 (M+1).

Intermediate 98 and 99: (R or S)-8-(1,2-Dimethoxyethyl)-6,11-dihydro-5H-benzo[b]pyrido[2,3-e][1,4]diazepine and (R or S)-8-(1,2-dimethoxyethyl)-6,11-dihydro-5H-benzo[b]pyrido[2,3-e][1,4]diazepine

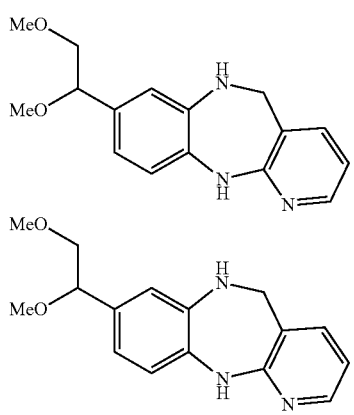

Step 1:

To a mixture of di-tert-butyl 8-bromo-5H-benzo[b]pyrido[2,3-e][1,4]diazepine-6,11-dicarboxylate (0.50 g, 1.1 mmol), potassium trifluoro(vinyl)borate (0.21 g, 1.6 mmol) in 1,4-dioxane (2.6 mL) was added $K_2CO_3$ (2.0 M in water, 1.57 ml, 3.15 mmol) and $PdCl_2(dppf)$ (0.077 g, 0.11 mmol). The mixture was stirred at 100° C. for 3 hours. Upon cooling to room temperature, the mixture was diluted with water and extracted with EtOAc. The organic layer was separated, washed with brine, dried over magnesium sulfate, filtered, and concentrated under reduced pressure. The residue was purified by column chromatography on silica gel (0-60% EtOAc/hexanes) to afford di-tert-butyl 8-vinyl-5H-benzo[b]pyrido[2,3-e][1,4]diazepine-6,11-dicarboxylate. MS: 324 (M–$C_5H_8O_2$+H).

Step 2:

To a solution of di-tert-butyl 8-vinyl-5H-benzo[b]pyrido[2,3-e][1,4]diazepine-6,11-dicarboxylate (370 mg, 0.86 mmol) in acetonitrile (3.9 mL) and water (0.4 ml) at room temperature was added NMO (202 mg, 1.73 mmol). Osmium tetroxide (220 mg, 0.035 mmol) was added, and the mixture was stirred at room temperature for 14 h. The reaction was quenched with saturated aqueous $Na_2SO_3$ and extracted with EtOAc. The organic layer was separated, washed with brine, dried over magnesium sulfate, filtered, and concentrated under reduced pressure to afford di-tert-butyl 8-(1,2-dihydroxyethyl)-5H-benzo[b]pyrido[2,3-e][1,4]diazepine-6,11-dicarboxylate. This material was used without further purification in next step. MS: 480 (M+Na).

Step 3:

To a solution of di-tert-butyl 8-(1,2-dihydroxyethyl)-5H-benzo[b]pyrido[2,3-e][1,4]diazepine-6,11-dicarboxylate (120 mg, 0.26 mmol) in THF (0.90 mL) at –30° C. was added KHMDS (1.0 M in THF, 0.79 mL, 0.79 mmol). The mixture was stirred for 15 min, followed by the addition of MeI (66 µl, 1.1 mmol). The mixture was stirred for 20 min and then the cooling bath was removed and the mixture was stirred at room temperature for 30 min. The reaction mixture was diluted with saturate aqueous ammonium chloride, and extracted with EtOAc. The organic layer was separated, washed with brine, dried over magnesium sulfate, filtered, and concentrated under reduced pressure. The residue was purified by column chromatography on silica gel (0-50% EtOAc/hexanes) to afford racemic di-tert-butyl 8-(1,2-dimethoxyethyl)-5H-benzo[b]pyrido[2,3-e][1,4]diazepine-6,11-dicarboxylate. This material was then purified by chiral SFC (Chiralcel AD-H column, 10%/90% iPrOH/$CO_2$ [with 0.25% N,N-dimethyl ethyl amine modifier]) to afford di-tert-butyl (R or S) 8-(1,2-dimethoxyethyl)-5H-benzo[b]pyrido[2,3-e][1,4]diazepine-6,11-dicarboxylate and di-tert-butyl (R or S) 8-(1,2-dimethoxyethyl)-5H-benzo[b]pyrido[2,3-e][1,4]diazepine-6,11-dicarboxylate. MS: 508 (M+Na) for both peaks.

Step 4:

To a solution of di-tert-butyl (R or S) 8-(1,2-dimethoxyethyl)-5H-benzo[b]pyrido[2,3-e][1,4]diazepine-6,11-dicarboxylate (early eluting peak 1, 22 mg, 0.045 mmol) in DCM (1 mL) was added TFA (0.33 mL). The mixture was stirred at room temperature for 4 h. The reaction was quenched with saturated aqueous sodium bicarbonate and extracted with EtOAc. The organic layer was separated, washed with brine, dried over magnesium sulfate, filtered, and concentrated to afford the title compound. MS: 286 (M+1).

Intermediate 99 (slower eluting peak 2) was prepared using the procedure described in step 4. MS: 286 (M+1)

Intermediate 100: 4-(6,11-Dihydro-5H-pyrido[2,3-b][1,5]benzodiazepin-8-yl)tetrahydro-2H-pyran-4-carbonitrile

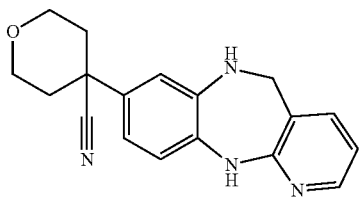 [SMILES: N#CC1(c2ccc3c(c2)NCc2cccnc2N3)CCOCC1]

Step 1:
To an oven-dried, nitrogen-cooled flask was added Pd$_2$(dba)$_3$ (96 mg, 0.10 mmol), BINAP (131 mg, 0.210 mmol), and THF (2 mL). The mixture was stirred for 10 min followed by the addition of di-tert-butyl 8-bromo-5H-benzo[b]pyrido[2,3-e][1,4]diazepine-6,11-dicarboxylate (500 mg, 1.05 mmol), tetrahydro-2H-pyran-4-carbonitrile (520 mg, 4.68 mmol), and lithium hexamethyldisilazide (0.5 M in THF, 9.2 mL, 4.6 mmol). The reaction mixture was heated to 80° C. for 24 h, and then cooled to room temperature. The reaction mixture was diluted with 1:1 DCM:EtOAc (50 mL), and filtered through Celite. The filtrate was concentrated under reduced pressure. The residue was dissolved in DCM (2 mL), and TFA (2 mL) was added. The reaction mixture was stirred for an 3 h, and then concentrate under reduced pressure. The residue was purified by reverse phase HPLC (acetonitrile/water, with 0.1% TFA modifier) to the title compound. MS: 307 (M+1).

Intermediate 101: 6,11-Dihydro-5H-pyrido[2,3-b][1,5]benzodiazepin-8-ylacetonitrile

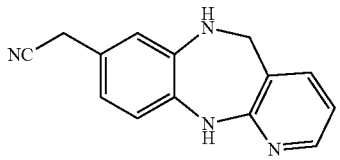 [SMILES: N#CCc1ccc2c(c1)NCc1cccnc1N2]

Step 1:
To a solution of 2-cyanoacetic acid (1.00 g, 11.8 mmol) in ethanol (15 mL) was added sodium tert-butoxide (1.13 g, 11.8 mmol) in ethanol (15 mL) dropwise. The reaction was stirred for 1 h at room temperature. After removing most of the ethanol solvent (~4/5) by concentrating under reduced pressure, diethyl ether was added and the solid was collected by filtration. The solid was dried in vacuo to afford sodium 2-cyanoacetate. $^1$H NMR (500 MHz, DMSO-d$_6$) δ 3.35 (s, 2H).
Step 2:
A mixture of di-tert-butyl 8-bromo-5H-pyrido[2,3-b][1,5]benzodiazepine-6,11-dicarboxylate (0.20 g, 0.42 mmol), sodium 2-cyanoacetate, (0.090 g, 0.84 mmol), allylpalladium chloride dimer (0.015 g, 0.042 mmol) and 2-dicyclohexylphosphino-2',6'-dimethoxybiphenyl (0.052 g, 0.13 mmol) in mesitylene (2.1 mL) was heated to 140° C. and stirred for 5 h. The mixture was cooled to room temperature, diluted with DCM, and filtered through Celite. The filtrate was concentrated under reduced pressure and the residue was purified by column chromatography on silica gel (0-70% EtOAc/Hexanes) to afford di-tert-butyl 8-(cyanomethyl)-5H-pyrido[2,3-b][1,5]benzodiazepine-6,11-dicarboxylate as a solid. MS: 437 (M+1), $^1$H NMR (500 MHz, CDCl$_3$) δ 8.43 (s, 1H), 7.55 (m, 1H), 7.49-7.45 (m, 1H), 7.35 (s, 1H), 7.28-7.19 (m, 1H), 7.17 (dd, J=7.8, 4.6 Hz, 1H), 4.98 (s, 2H), 3.76 (d, J=4.1 Hz, 2H), 1.41 (dd, J=15.4, 4.1 Hz, 18H).
Step 3:
To a solution of di-tert-butyl 8-(cyanomethyl)-5H-pyrido[2,3-b][1,5]benzodiazepine-6,11-dicarboxylate (40 mg, 0.092 mmol) dissolved in DCM (0.5 mL) was added TFA (0.5 mL). The mixture was stirred at room temperature for 1 h. The reaction was then concentrated under reduced pressure, diluted with DCM, and washed with saturated aqueous sodium bicarbonate. The organic layer was dried over magnesium sulfate, filtered, and concentrated under reduced pressure to afford the title compound which was used without purification in the next step. MS: 237 (M+H).

Intermediate 102: 8-(3-Methyl-1,4-dioxan-2-yl)-6,11-dihydro-5H-benzo[b]pyrido[2,3-e][1,4]diazepine

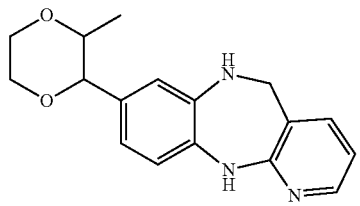 [SMILES: CC1OCCOC1c1ccc2c(c1)NCc1cccnc1N2]

Step 1:
To a flask was added di-tert-butyl 8-bromo-5H-benzo[b]pyrido[2,3-e][1,4]diazepine-6,11-dicarboxylate (500 mg, 1.05 mmol), (E)-4,4,5,5-tetramethyl-2-(prop-1-en-1-yl)-1,3,2-dioxaborolane (353 mg, 2.10 mmol), potassium phosphate tribasic (0.5 M in water, 6.30 mL, 3.15 mmol) and THF (6.3 mL). Methanesulfonato(2-dicyclohexylphosphino-2',4',6'-tri-i-propyl-1,1'-biphenyl)(2'-amino-1,1'-biphenyl-2-yl)palladium(II) (44 mg, 0.052 mmol) was added and the reaction vessel was sealed and the reaction mixture was bubbled with nitrogen gas for 10 min before it was allowed to stir at 100° C. for 1 h. The reaction mixture was cooled to room temperature, quenched with water, and extracted with EtOAc. The organic layer was washed with brine, dried over sodium sulfate, filtered, and concentrated under reduced pressure. The residue was purified by column chromatography on silica gel (0-40% EtOAc:EtOH 3:1 in hexane) to afford (E)-di-tert-butyl 8-(prop-1-en-1-yl)-5H-benzo[b]pyrido[2,3-e][1,4]diazepine-6,11-dicarboxylate as a solid. MS: 438 (M+H).
Step 2:
To a stirred solution of (E)-di-tert-butyl 8-(prop-1-en-1-yl)-5H-benzo[b]pyrido[2,3-e][1,4]diazepine-6,11-dicarboxylate (470 mg, 1.07 mmol) in acetonitrile/water (10/1, 5.4 mL) was added NMO (177 mg, 1.51 mmol) and potassium osmate(VI) dihydrate (20 mg, 0.054 mmol) at 0° C. The resulting mixture was allowed to warm to room temperature and stirred for 2 h. The mixture was poured into a solution of Na$_2$SO$_3$ (50 mL) and then extracted with EtOAc (50 mL×3). The combined organic layers were dried over sodium sulfate, and filtered, and concentrated under reduced pressure. The residue was purified by column chromatography on silica gel (0-100% 3:1 EtOAc:EtOH in hexane) to afford di-tert-butyl 8-(1,2-dihydroxypropyl)-5H-benzo[b]pyrido[2,3-e][1,4]diazepine-6,11-dicarboxylate as a solid. MS: 472 (M+H).

Step 3:

Di-tert-butyl 8-(1,2-dihydroxypropyl)-5H-benzo[b]pyrido[2,3-e][1,4]diazepine-6,11-dicarboxylate (465 mg, 0.986 mmol), tetrabutylammonium bromide (64 mg, 0.19 mmol), DCE (20 mL, 254 mmol) and NaOH (35% aqueous solution, 20 mL, 0.99 mmol) were combined in a flask and heated to 55° C. for three days. Upon cooling, the mixture was neutralized with HCl (6N), diluted with water, and extracted with EtOAc. The organic layer was dried over sodium sulfate, filtered, and concentrated under reduced pressure. The residue was purified by column chromatography on silica gel (0-70% 3:1 EtOAc: EtOH in hexane) to afford di-tert-butyl 8-(3-methyl-1,4-dioxan-2-yl)-5H-benzo[b]pyrido[2,3-e][1,4]diazepine-6,11-dicarboxylate as a solid. MS: 498 (M+H).

Step 4:

To a stirred solution of di-tert-butyl 8-(3-methyl-1,4-dioxan-2-yl)-5H-benzo[b]pyrido[2,3-e][1,4]diazepine-6,11-dicarboxylate (279 mg, 0.561 mmol) in DCM (1.5 mL) was added TFA (1.5 mL, 19 mmol) at room temperature. The reaction mixture was stirred for 1 h at room temperature. The mixture was concentrated under reduced pressure, and the residue was diluted with EtOAc and quenched with saturated aqueous sodium bicarbonate. The organic layer was washed with brine, dried over sodium sulfate, filtered, and concentrated to afford the title compound, which was used in subsequent steps without further purification. MS: 298 (M+H).

Intermediate 103: 8-(Oxetan-3-yl)-6,11-dihydro-5H-benzo[b]pyrido[2,3-e][1,4]diazepine

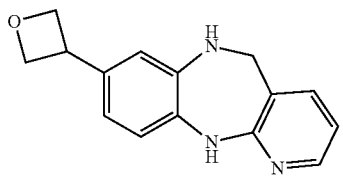 [SMILES: c1cnc2c(c1)CNc1cc(C3COC3)ccc1N2]

Step 1:

To a vial was added di-tert-butyl 8-bromo-5H-benzo[b]pyrido[2,3-e][1,4]diazepine-6,11-dicarboxylate (1.5 g, 3.2 mmol), potassium (3-(benzyloxy)prop-1-en-2-yl)trifluoroborate (800 mg, 3.2 mmol), 1,4-dioxane (10.5 mL) and K$_2$CO$_3$ (2.0 M in water, 4.7 mL, 9.5 mmol). Added PdCl$_2$(dppf)-CH$_2$Cl$_2$ Adduct (51 mg, 0.063 mmol) and the mixture was heated at 100° C. for 3 h. The mixture was cooled to room temperature, diluted with water, and extracted with EtOAc. The organic layer was separated, washed with brine, dried over magnesium sulfate, filtered, and concentrated under reduced pressure. The residue was purified by column chromatography on silica gel (0-60% EtOAc/hexanes) to afford di-tert-butyl 8-(3-(benzyloxy)prop-1-en-2-yl)-5H-benzo[b]pyrido[2,3-e][1,4]diazepine-6,11-dicarboxylate. MS: 444 (M−C$_5$H$_8$O$_2$+H).

Step 2:

To a solution of di-tert-butyl 8-(3-(benzyloxy)prop-1-en-2-yl)-5H-benzo[b]pyrido[2,3-e][1,4]diazepine-6,11-dicarboxylate (1.1 g, 2.0 mmol) in THF (10 mL) at room temperature was added borane-tetrahydrofuran complex (1.0 M in THF, 4.1 mL, 4.1 mmol) dropwise. The resulting mixture was stirred at room temperature for 30 mins. To the reaction mixture was added NaOH (16.2 mL, 16 mmol), followed by slow addition of H$_2$O$_2$ (35% in water, 2.8 mL, 32 mmol). The mixture was stirred at room temperature for 40 mins. The reaction mixture was diluted with water and extracted with EtOAc. The organic layer was separated, washed with brine, dried over magnesium sulfate, filtered, and concentrated. The residue was purified by column chromatography on silica gel (20-80% EtOAc/hexanes) to afford di-tert-butyl 8-(1-(benzyloxy)-3-hydroxypropan-2-yl)-5H-benzo[b]pyrido[2,3-e][1,4]diazepine-6,11-dicarboxylate. MS: 462 (M−C$_5$H$_8$O$_2$+H).

Step 3:

To a solution of di-tert-butyl 8-(1-(benzyloxy)-3-hydroxypropan-2-yl)-5H-benzo[b]pyrido[2,3-e][1,4]diazepine-6,11-dicarboxylate (350 mg, 0.623 mmol) in MeOH (2.0 mL) was added palladium hydroxide on carbon (20% wt, 66 mg, 0.093 mmol). The mixture was evacuated and back-filled with N$_2$ three times, then connected to a hydrogen balloon and stirred under an atmosphere of hydrogen for 14 h. An additional 0.20 equivalents of palladium hydroxide on carbon were added and the mixture was stirred at room temperature for an additional 24 h. The mixture was filtered through Celite, rinsed with EtOAc, and concentrated under reduced pressure. The residue was purified by column chromatography on silica gel (0-10% MeOH/EtOAc) to give di-tert-butyl 8-(1,3-dihydroxypropan-2-yl)-5H-benzo[b]pyrido[2,3-e][1,4]diazepine-6,11-dicarboxylate. MS: 372 (M−C$_5$H$_8$O$_2$+H).

Step 4:

To a suspension of di-tert-butyl 8-(1,3-dihydroxypropan-2-yl)-5H-benzo[b]pyrido[2,3-e][1,4]diazepine-6,11-dicarboxylate (90 mg, 0.19 mmol) in THF (1.0 mL) at room temperature was added KHMDS (1.0 M in THF, 0.23 mL, 0.23 mmol) dropwise. After addition, the mixture was stirred at room temperature for 5 mins. Then a solution of Ts-Cl (33 mg, 0.17 mmol) in 0.5 mL of THF was added. The mixture was stirred at room temperature for 15 mins, then additional KHMDS (1.0 M in THF, 0.23 ml, 0.23 mmol) was added. The mixture was stirred at room temperature for 1 h, then heated at 50° C. for 30 mins. The mixture was cooled to room temperature, diluted with saturated aqueous ammonium chloride, and extracted with EtOAc. The organic layer was washed with brine, dried over sodium sulfate, filtered, and concentrated. The residue was purified by column chromatography on silica gel (10-80% EtOAc/hexanes) to afford di-tert-butyl 8-(oxetan-3-yl)-5H-benzo[b]pyrido[2,3-e][1,4]diazepine-6,11-dicarboxylate. MS: 354 (M−C$_5$H$_8$O$_2$+H).

Step 5:

To a solution of di-tert-butyl 8-(oxetan-3-yl)-5H-benzo[b]pyrido[2,3-e][1,4]diazepine-6,11-dicarboxylate (20 mg, 0.044 mmol) in DMC (1.0 mL) was added TFA (0.33 mL). The mixture was stirred at room temperature for 2 h. The mixture was quenched with saturated aqueous sodium bicarbonate and extracted with EtOAc. The organic layer was separated, washed with brine, dried over magnesium sulfate, filtered, and concentrated to give the title compound. This material was used without further purification in next step. MS: 254 (M+1).

Intermediate 104: Tert-butyl 8-(4-methoxy-2-methyltetrahydrofuran-2-yl)-5,6-dihydro-11H-benzo[b]pyrido[2,3-e][1,4]diazepine-11-carboxylate

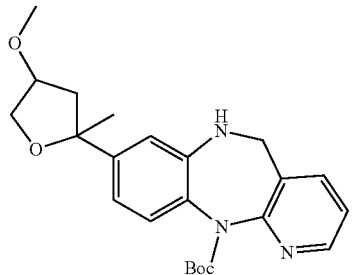 [SMILES: COC1COC(C)(c2ccc3c(c2)NCc2cccnc2N3C(=O)OC(C)(C)C)C1]

Step 1:

1-(4-Bromo-3-nitrophenyl)ethanone (10 g, 41 mmol) was stirred in DCM (200 mL) and copper (II) trifluoromethanesulfonate (1.48 g, 4.10 mmol) was added followed by tetraallyltin (9.9 mL, 41 mmol). The resulting mixture was stirred at room temperature for 16 h. The reaction mixture was concentrated under reduced pressure and then diluted with diethyl ether and washed with ~0.5 N aqueous HCl (2×). The aqueous layer was extracted with diethyl ether, and then the combined organic layers were washed with saturated aqueous sodium bicarbonate, washed with brine, dried over anhydrous magnesium sulfate, filtered, and concentrated under reduced pressure. The residue was purified by column chromatography on silica gel (0-35% EtOAc:hexanes) to afford 2-(4-bromo-3-nitrophenyl)pent-4-en-2-ol as an oil. $^1$H NMR (499 MHz, CDCl$_3$): δ 7.95 (d, J=2.2 Hz, 1H); 7.70 (d, J=8.4 Hz, 1H); 7.50 (dd, J=8.4, 2.2 Hz, 1H); 5.57-5.65 (m, 1H); 5.10-5.18 (m, 2H); 2.64 (dd, J=13.9, 6.7 Hz, 1H); 2.52 (dd, J=13.9, 8.1 Hz, 1H); 2.20 (s, 1H); 1.57 (s, 3H).

Step 2:

2-(4-Bromo-3-nitrophenyl)pent-4-en-2-ol (12 g, 42 mmol) was stirred in methanol (210 mL) and to this mixture was added [hydroxy(tosyloxy)iodo]benzene (33 g, 84 mmol) followed by iodine (2.1 g, 8.4 mmol). The resulting mixture was stirred at ambient temperature for 2 days. The reaction mixture was then concentrated under reduced pressure, diluted with diethylether, and washed with saturated aqueous sodium thiosulfate. The organic layer was washed with saturated aqueous sodium bicarbonate, brine, then dried over anhydrous magnesium sulfate, filtered, and concentrated under reduced pressure. The residue was purified by column chromatography on silica gel (0-30% EtOAc:hexanes) to afford 2-(4-bromo-3-nitrophenyl)-4-methoxy-2-methyltetrahydrofuran as the following mixture of diastereomers:

(2S,4R and 2R,4S)-2-(4-bromo-3-nitrophenyl)-4-methoxy-2-methyltetrahydrofuran $^1$H NMR (499 MHz, CDCl$_3$): δ 7.87 (d, J=2.2 Hz, 1H); 7.69 (d, J=8.4 Hz, 1H); 7.43-7.47 (m, 1H); 4.08-4.12 (m, 1H); 3.98-4.00 (m, 1H); 3.90 (dd, J=9.9, 4.8 Hz, 1H); 3.34 (s, 3H); 2.29-2.31 (m, 2H); 1.61 (s, 3H).

(2R,4R and 2S,4S)-2-(4-bromo-3-nitrophenyl)-4-methoxy-2-methyltetrahydrofuran $^1$H NMR (499 MHz, CDCl$_3$): δ 7.92 (d, J=2.1 Hz, 1H); 7.65-7.70 (m, 1H); 7.47-7.54 (m, 1H); 4.11-4.14 (m, 2H); 3.95 (d, J=9.2 Hz, 1H); 3.15 (s, 3H); 2.37 (d, J=13.5 Hz, 1H); 2.23 (dd, J=13.6, 5.9 Hz, 1H); 1.53 (s, 3H).

Step 3:

2-(4-Bromo-3-nitrophenyl)-4-methoxy-2-methyltetrahydrofuran (2.8 g, 8.9 mmol), 2-aminonicotinaldehyde (1.1 g, 8.9 mmol), [(4,5-bis(diphenylphosphino)-9,9-dimethyxanthene)-2-(2'-amino-1,1'-biphenyl)]palladium(II) methanesulfonate (0.42 g, 0.45 mmol), and cesium carbonate (4.4 g, 13 mmol) were combined in dioxane (45 mL). The resulting mixture was stirred at 80° C. for 2 h. The reaction mixture was cooled to ambient temperature, then di-tert-butyl dicarbonate (2.3 g, 11 mmol), and N,N-dimethylpyridin-4-amine (0.11 g, 0.89 mmol) was added. The reaction mixture was heated at 80° C. for 3 h. The reaction mixture was cooled to ambient temperature, diluted with saturated aqueous sodium bicarbonate and extracted with EtOAc (2×). The combined organic layers were washed with brine, dried over anhydrous magnesium sulfate, filtered, and concentrated under reduced pressure. The residue was purified by column chromatography on silica gel (0-75% EtOAc:hexanes) to afford tert-butyl (3-formylpyridin-2-yl)(4-(4-methoxy-2-methyltetrahydrofuran-2-yl)-2-nitrophenyl)carbamate. MS: 458 and 402 (M+1; M-t-Bu+1).

Step 4:

tert-Butyl (3-formylpyridin-2-yl)(4-(4-methoxy-2-methyltetrahydrofuran-2-yl)-2-nitrophenyl)carbamate (1.64 g, 3.58 mmol) and platinum and vanadium on activated carbon (1.18 g, 0.143 mmol, 1% Pt, 2% V) were added to a reaction vessel. The vessel was sealed and purged with nitrogen. The mixture was then suspended in 2:1 MeOH:EtOAc (36 mL) and was evacuated and backfilled with hydrogen gas (3×). The reaction was stirred at room temperature for 16 h under a hydrogen atmosphere. The mixture was evacuated and backfilled with nitrogen gas (3×), and then purged with nitrogen. The mixture was diluted with DCM, and carefully filtered through celite under a stream of argon. The celite was flushed with DCM:MeOH, and the filtrate was concentrated under reduced pressure to afford tert-butyl 8-(4-methoxy-2-methyltetrahydrofuran-2-yl)-11H-benzo[b]pyrido[2,3-e][1,4]diazepine-11-carboxylate. MS: 410 (M+1).

Step 5:

tert-Butyl 8-(4-methoxy-2-methyltetrahydrofuran-2-yl)-11H-benzo[b]pyrido[2,3-e][1,4]diazepine-11-carboxylate (0.35 g, 0.85 mmol) was stirred in THF (4.3 mL) at room temperature. Sodium borohydride (0.097 g, 2.6 mmol) was added carefully, and the mixture was stirred at room temperature for 3 h. The reaction mixture was carefully diluted with saturated aqueous sodium bicarbonate and extracted with EtOAc (2×). The combined organic layers were washed with brine, dried over anhydrous magnesium sulfate, filtered, and concentrated under reduced pressure. The residue was purified by column chromatography on silica gel (35-100% EtOAc:hexanes) to afford the title compound. MS: 412 (M+1).

Intermediate 105: Tert-butyl 8-(4-isopropoxy-2-methyltetrahydrofuran-2-yl)-5,6-dihydro-11H-benzo[b]pyrido[2,3-e][1,4]diazepine-11-carboxylate

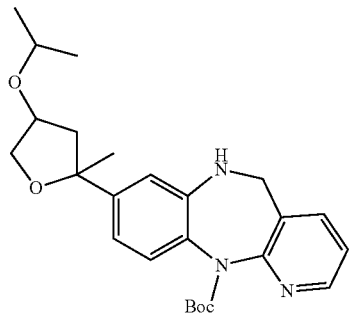 [SMILES: CC(C)OC1COC(C)(c2ccc3c(c2)NCc2cccnc2N3C(=O)OC(C)(C)C)C1]

Intermediate 105 was prepared using the procedure described for Intermediate 104. MS: 440 (M+1).

Intermediate 106: 5-(6,11-Dihydro-5H-pyrido[2,3-b][1,5]benzodiazepin-8-yl)tetrahydrofuran-3-ol

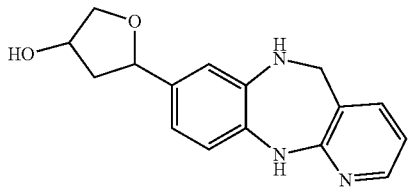 [SMILES: OC1COC(c2ccc3c(c2)NCc2cccnc2N3)C1]

Step 1:

To a solution of di-tert-butyl 8-bromo-5H-pyrido[2,3-b][1,5]benzodiazepine-6,11-dicarboxylate (3.0 g, 6.3 mmol) in EtOH (63 mL) was added potassium vinyltrifluoroborate (1.26 g, 9.45 mmol), triethylamine (1.32 ml, 9.45 mmol), and PdCl$_2$(dppf)-CH$_2$Cl$_2$ adduct (0.26 g, 0.32 mmol). The mixture was heated to reflux for 4 h. Upon cooling to room temperature, the mixture was filtered through Celite, washing with DCM. The filtrate was concentrated under reduced pressure and the residue was purified by column chromatography on silica gel (0-50% EtOAc/isohexane) to afford di-tert-butyl 8-ethenyl-5H-pyrido[2,3-b][1,5]benzodiazepine-6,11-dicarboxylate as a solid. MS: 424 (M+1).

Step 2:

To the mixture of di-tert-butyl 8-ethenyl-5H-pyrido[2,3-b][1,5]benzodiazepine-6,11-dicarboxylate (1.44 g, 3.40 mmol) and osmium tetroxide in 2.5% t-BuOH (2.13 ml, 0.170 mmol) in THF (43 mL) and water (43 ml) was added sodium periodate (2.18 g, 10.2 mmol). The mixture was stirred at room temperature overnight. Saturated aqueous sodium thiosulfate solution and saturated aqueous sodium bicarbonate were added, and the mixture was stirred at room temperature for 10 min. The mixture was then extracted with dichloromethane (2×), and the combined organic layers were dried over magnesium sulfate, filtered, and concentrated under reduced pressure. The residue was purified by column chromatography on silica gel (0-50% EtOAc/isohexane) to afford di-tert-butyl 8-formyl-5H-pyrido[2,3-b][1,5]benzodiazepine-6,11-dicarboxylate. MS: 426 (M+1).

Step 3:

Di-tert-butyl 8-formyl-5H-pyrido[2,3-b][1,5]benzodiazepine-6,11-dicarboxylate (1.33 g, 3.12 mmol) was dissolved in THF (21 mL) and cooled to 0° C. Allylmagnesium chloride (2.0 M in THF, 1.95 mL, 3.90 mmol) was added slowly, and the solution was maintained at 0° C. for 1.5 h. This mixture was quenched with saturated aqueous ammonium chloride and extracted with EtOAc. The organic layer was dried over magnesium sulfate, filtered, and concentrated under reduced pressure. The residue was purified by column chromatography on silica gel (0-70% EtOAc/isohexane) to afford di-tert-butyl 8-(1-hydroxybut-3-en-1-yl)-5H-pyrido[2,3-b][1,5]benzodiazepine-6,11-dicarboxylate as a solid. MS: 468 (M+1).

Step 4:

Di-tert-butyl 8-(1-hydroxybut-3-en-1-yl)-5H-pyrido[2,3-b][1,5]benzodiazepine-6,11-dicarboxylate (0.44 g, 0.94 mmol) was dissolved in THF (5.3 mL) and water (2.7 mL). Osmium tetroxide in 2.5% t-BuOH (0.48 mL, 0.047 mmol) was added followed by NMO (0.13 g, 1.1 mmol). The reaction was stirred at room temperature overnight. The mixture was quenched with saturated aqueous sodium thiosulfate and the mixture was stirred for 10 minutes. The mixture was extracted with EtOAc (2×), and the combined organic layers were dried over magnesium sulfate, filtered, and concentrated under reduced pressure. The residue was purified by column chromatography on silica gel (0-60% 3:1 EtOAc:EtOH/isohexane) to afford di-tert-butyl 8-(1,3,4-trihydroxybutyl)-5H-pyrido[2,3-b][1,5]benzodiazepine-6,11-dicarboxylate as a solid. MS: 502 (M+1).

Step 5:

A mixture of di-tert-butyl 8-(1,3,4-trihydroxybutyl)-5H-pyrido[2,3-b][1,5]benzodiazepine-6,11-dicarboxylate (0.347 g, 0.691 mmol), p-toluenesulfonyl chloride (0.145 g, 0.760 mmol), dibutyltin oxide (8.6 mg, 0.035 mmol), and triethylamine (0.11 ml, 0.76 mmol) in DCM (7 mL) was heated at reflux for 3 h. The reaction was quenched with saturated aqueous ammonium chloride and diluted with EtOAc. The organic layer was washed with water and brine, dried over magnesium sulfate, filtered, and concentrated under reduced pressure. The residue was purified by reverse phase HPLC (acetonitrile/water, with 0.1% TFA modifier). The collected fractions were concentrated under reduced pressure, diluted with DCM, and washed with saturated aqueous sodium bicarbonate, dried over magnesium sulfate, filtered, and concentrated under reduced pressure to afford di-tert-butyl 8-(4-hydroxytetrahydrofuran-2-yl)-5H-pyrido[2,3-b][1,5]benzodiazepine-6,11-dicarboxylate. MS: 484 (M+1).

Step 6:

To a solution of di-tert-butyl 8-(4-hydroxytetrahydrofuran-2-yl)-5H-pyrido[2,3-b][1,5]benzodiazepine-6,11-dicarboxylate (58 mg, 0.12 mmol) dissolved in DCM (0.5 mL) was added TFA (0.5 mL). The mixture was stirred at room temperature for 1 h. The reaction was then concentrated under reduced pressure, diluted with DCM, and washed with saturated aqueous sodium bicarbonate. The organic layer was dried over magnesium sulfate, filtered, and concentrated under reduced pressure to the title compound which was used without purification in the next step. MS: 284 (M+H).

Intermediate 107: 8-(2,5-Dioxabicyclo[4.1.0]heptan-3-yl)-6,11-dihydro-5H-benzo[b]pyrido[2,3-e][1,4]diazepine

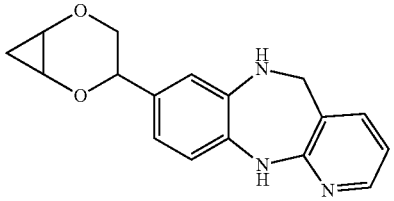 [SMILES: c1cnc2c(c1)CNc1cc(C3COC4CC4O3)ccc1N2]

Step 1:
To a solution of di-tert-butyl 8-bromo-5H-benzo[b]pyrido[2,3-e][1,4]diazepine-6,11-dicarboxylate (3.33 g, 6.99 mmol) in EtOH (70 mL) was added potassium vinyltrifluoroborate (1.40 g, 10.5 mmol), triethylamine (1.46 mL, 10.5 mmol), and PdCl$_2$(dppf)-DCM adduct (0.285 g, 0.350 mmol). The mixture evacuated and backfilled with nitrogen (3×) and then heated to reflux for 3 h. Upon cooling, the mixture was filtered through Celite and washed with DCM. The filtrate was concentrated under reduced pressure, and the residue was purified by column chromatography on silica gel (0-50% EtOAc/hexane) to afford di-tert-butyl 8-vinyl-5H-benzo[b]pyrido[2,3-e][1,4]diazepine-6,11-dicarboxylate as a solid. MS: 424 (M+H).

Step 2:
To a mixture of di-tert-butyl 8-vinyl-5H-benzo[b]pyrido[2,3-e][1,4]diazepine-6,11-dicarboxylate (0.83 g, 2.0 mmol) in THF and water (17 mL, 2:1) was added NMO (0.276 g, 2.35 mmol) and osmium tetroxide (2.5% t-BuOH, 1.0 mL, 0.098 mmol). The reaction mixture was stirred at room temperature for 3 h. The reaction cooled to 0° C. and quenched with Na$_2$S$_2$O$_3$. The mixture was stirred for 10 minutes, and then extracted with EtOAc. The organic layer was dried over sodium sulfate, filtered, and concentrated under reduces pressure. The residue was purified by column chromatography on silica gel (0-100% 3:1 EtOAc:EtOH in hexane) to afford di-tert-butyl 8-(1,2-dihydroxyethyl)-5H-benzo[b]pyrido[2,3-e][1,4]diazepine-6,11-dicarboxylate as a solid. MS: 458 (M+H).

Step 3:
To a vial was added di-tert-butyl 8-(1,2-dihydroxyethyl)-5H-benzo[b]pyrido[2,3-e][1,4]diazepine-6,11-dicarboxylate (500 mg, 1.09 mmol) and sodium carbonate (116 mg, 1.09 mmol). The mixture was brought to glovebox and added [Ir(cod)Cl]$_2$ (15 mg, 0.022 mmol), vinyl propionate (656 mg, 6.56 mmol), and toluene (2 mL). The mixture was heated to 100° C. for 16 h. Upon cooling, the residue was purified by column chromatography on silica gel (0-50% EtOAc in hexane) to afford di-tert-butyl 8-(1,2-bis(vinyloxy)ethyl)-5H-benzo[b]pyrido[2,3-e][1,4]diazepine-6,11-dicarboxylate as a solid. MS: 510 (M+H).

Step 4:
Grubbs 2$^{nd}$ generation catalyst (14 mg, 0.017 mmol) was added to a solution of di-tert-butyl 8-(1,2-bis(vinyloxy)ethyl)-5H-benzo[b]pyrido[2,3-e][1,4]diazepine-6,11-dicarboxylate (170 mg, 0.334 mmol) in toluene (18 mL) under a nitrogen atmosphere. The reaction mixture was heated at 60° C. for 5 h and then another portion of Grubbs 2$^{nd}$ generation catalyst (14 mg, 0.017 mmol) was added. The reaction was heated at 60° C. for 16 h. Upon cooling to room temperature, the mixture was concentrated under reduced pressure. The residue was purified by column chromatography on silica gel (0-70% EtOAc in hexane) to afford di-tert-butyl 8-(2,3-dihydro-1,4-dioxin-2-yl)-5H-benzo[b]pyrido[2,3-e][1,4]diazepine-6,11-dicarboxylate as a solid. MS: 482 (M+H).

Step 5:
To a vial under an inert atmosphere of nitrogen containing DCM (1.5 mL) was added diethylzinc (1 M in heptane, 0.50 mL, 0.50 mmol) at 0° C. After 20 min, chloroiodomethane (0.072 mL, 0.99 mmol) was added over 5 min, followed by addition of a solution of di-tert-butyl 8-(2,3-dihydro-1,4-dioxin-2-yl)-5H-benzo[b]pyrido[2,3-e][1,4]diazepine-6,11-dicarboxylate (120 mg, 0.249 mmol) in THF/DCM (2 mL, 1:1). The cooling bath was removed and the reaction mixture was stirred at room temperature overnight. To a separate flask containing DCM (1.5 mL) was added diethylzinc (1 M in heptane, 0.50 mL, 0.50 mmol) at 0° C. under an inert atmosphere of nitrogen. Diiodomethane (0.080 mL, 0.99 mmol) was added and the mixture was stirred for 15 min. The reaction mixture in the first flask was added to the second flask via syringe. The cooling bath was removed and the mixture was stirred at room temperature for two days. The reaction was quenched with saturated aqueous ammonium chloride (25 mL) and extracted with EtOAc. The organic layer was washed with brine, dried over sodium sulfate, filtered, and concentrated under reduced pressure to afford di-tert-butyl 8-(2,5-dioxabicyclo[4.1.0]heptan-3-yl)-5H-benzo[b]pyrido[2,3-e][1,4]diazepine-6,11-dicarboxylate. MS: 382 and 482 (M–C$_5$H$_8$O$_2$+H, M+H).

Step 6:
To a solution of di-tert-butyl 8-(2,5-dioxabicyclo[4.1.0]heptan-3-yl)-5H-benzo[b]pyrido[2,3-e][1,4]diazepine-6,11-dicarboxylate (124 mg, 0.250 mmol) in DCM (1 mL) was added TFA (1.0 mL, 13 mmol). The mixture was stirred for 1 h. The reaction was concentrated under reduced pressure, and the residue was purified by reverse phase HPLC (acetonitrile/water, with 0.1% TFA modifier). The fractions were concentrated, diluted with EtOAc, and quenched with saturated aqueous sodium bicarbonate. The organic layer was dried over sodium sulfate, filtered, and concentrated under reduced pressure to afford the title compound as a solid. MS: 296 (M+H).

Intermediate 108: 8-[4-(Difluoromethyl)tetrahydro-2H-pyran-4-yl]-6,11-dihydro-5H-pyrido[2,3-b][1,5]benzodiazepine

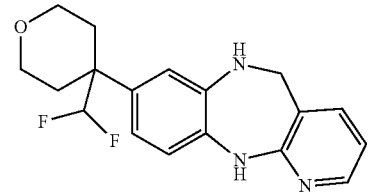 [SMILES: FC(F)C1(c2ccc3c(c2)NCc2cccnc2N3)CCOCC1]

Step 1:
To an oven-dried, nitrogen-cooled flask was added lithium dicyclohexylamide (4.7 g, 25 mmol) and toluene (9.4 mL). The mixture was cooled to 0° C. and then methyl tetrahydro-2H-pyran-4-carboxylate (3.4 g, 26 mmol) was added. The mixture was stirred for 10 min at 0° C., and then it was warmed to room temperature. Added di-tert-butyl 8-bromo-5H-benzo[b]pyrido[2,3-e][1,4]diazepine-6,11-dicarboxylate (2.25 g, 4.72 mmol), Pd$_2$(dba)$_3$ (433 mg, 0.472 mmol), and tri-tert-butyl phosphine (1.0 M in toluene, 472 uL, 0.472 mmol). The reaction mixture was stirred at room temperature for 1 h, and then the reaction was diluted with ethyl acetate and purified by column chromatography on silica gel (0-80% 3:1 EtOAc:EtOH/hexanes) to give di-tert-butyl 8-(4-(methoxycarbonyl)tetrahydro-2H-pyran-4-yl)-5H-benzo[b]pyrido[2,3-e][1,4]diazepine-6,11-dicarboxylate. MS: 440 and 540 (M–C₅H₈O₂+H, M+H).

Step 2:

To an oven-dried, nitrogen-cooled flask was added di-tert-butyl 8-(4-(methoxycarbonyl)tetrahydro-2H-pyran-4-yl)-5H-benzo[b]pyrido[2,3-e][1,4]diazepine-6,11-dicarboxylate (2.9 g, 5.4 mmol) and THF (5.4 mL). The solution was cooled to 0° C. and diisobutyl aluminum hydride (1.0 M THF, 45 mL, 45 mmol) was added. The reaction mixture was stirred for 12 h at room temperature. The mixture was diluted with ethyl acetate (25 mL), and then Rochelle's salt (100 mL) was added. The mixture was vigorously stirred for an additional 24 h, followed by phase separation. The resulting aqueous layer was extracted with EtOAc (3×50 mL). The combined organic layers were washed with brine, dried over sodium sulfate, filtered, and concentrated under reduced pressure. The residue was purified by column chromatography on silica gel (0-80% 3:1 EtOAc:EtOH/ hexanes) to afford tert-butyl 8-(4-(hydroxymethyl)tetrahydro-2H-pyran-4-yl)-5H-benzo[b]pyrido[2,3-e][1,4]diazepine-6(11H)-carboxylate. MS: 412 (M+1).

Step 3:

To an oven-dried, nitrogen-cooled flask was added tert-butyl 8-(4-(hydroxymethyl)tetrahydro-2H-pyran-4-yl)-5H-benzo[b]pyrido[2,3-e][1,4]diazepine-6(11H)-carboxylate (400 mg, 0.972 mol), DCM (2.4 mL), DMSO (0.81 mL), and Hunig's base (0.68 mL, 3.9 mmol). The solution was cooled to 0° C. and sulfur trioxide pyridine complex (0.62 g, 3.9 mmol) was added. The reaction mixture was slowly warmed to room temperature over 3 h. The crude reaction mixture was purified by column chromatography on silica gel (0-80% 3:1 EtOAc:EtOH/hexanes) to afford tert-butyl 8-(4-formyltetrahydro-2H-pyran-4-yl)-5,11-dihydro-6H-benzo[b]pyrido[2,3-e][1,4]diazepine-6-carboxylate, MS: 410 (M+1).

Step 4:

To an oven-dried, nitrogen-cooled flask was added tert-butyl 8-(4-formyltetrahydro-2H-pyran-4-yl)-5,11-dihydro-6H-benzo[b]pyrido[2,3-e][1,4]diazepine-6-carboxylate (0.32 g, 0.78 mmol), DCM (1.6 mL), and DAST (516 uL, 3.91 mmol). The reaction mixture was stirred at room temperature for 4 h. The crude reaction mixture was purified column chromatography on silica gel (0-80% 3:1 EtOAc: EtOH/Hexanes) to afford tert-butyl 8-(4-(difluoromethyl) tetrahydro-2H-pyran-4-yl)-5,11-dihydro-6H-benzo[b] pyrido[2,3-e][1,4]diazepine-6-carboxylate. MS: 432 (M+1).

Step 5:

To a flask was added tert-butyl 8-(4-(difluoromethyl) tetrahydro-2H-pyran-4-yl)-5,11-dihydro-6H-benzo[b] pyrido[2,3-e][1,4]diazepine-6-carboxylate (0.23 g, 0.53 mmol), DCM (2.7 mL), and TFA (2.7 mL). The reaction mixture was stirred at room temperature for 1 h, and then concentrated under reduced pressure. The residue was purified by reverse phase HPLC (acetonitrile/water, with 0.1% TFA modifier) to afford the title compound. MS: 332 (M+1).

Intermediate 109: 8-(3,6-Dihydro-2H-pyran-2-yl)-6, 11-dihydro-5H-pyrido[2,3-b][1,5]benzodiazepine

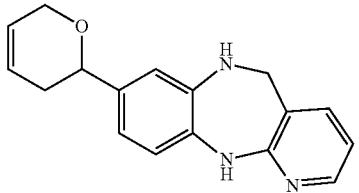 [SMILES: C1=CCC(c2ccc3c(c2)NCc2cccnc2N3)OC1]

Step 1:

To a solution of di-tert-butyl 8-(1-hydroxybut-3-en-1-yl)-5H-pyrido[2,3-b][1,5]benzodiazepine-6,11-dicarboxylate (0.10 g, 0.21 mmol) in DCM (1.1 mL) at 0° C. was added thionyl chloride (0.047 mL, 0.64 mmol). The reaction was stirred at 0° C. for 1 h. The reaction was partitioned between water and EtOAc. The organic layer was washed with saturated aqueous sodium bicarbonate and then brine. The organic layer was dried over sodium sulfate, filtered, and concentrated under reduced pressure. The residue was purified by column chromatography on silica gel (0-50% EtOAc/hexanes) to afford di-tert-butyl 8-(1-chlorobut-3-en-1-yl)-5H-pyrido[2,3-b][1,5]benzodiazepine-6,11-dicarboxylate MS: 486 (M+1).

Step 2:

To a mixture of di-tert-butyl 8-(1-chlorobut-3-en-1-yl)-5H-pyrido[2,3-b][1,5]benzodiazepine-6,11-dicarboxylate (0.100 g, 0.222 mmol) and allyl alcohol (0.302 ml, 4.44 mmol) was added triethylamine (0.062 mL, 0.44 mmol). The reaction was heated to 80° C. overnight. The mixture was cooled to room temperature and concentrated under reduced pressure. The residue was purified by reverse phase chromatography (acetonitrile/water, with 0.1% TFA modifier). The fractions were concentrated under reduced pressure, diluted with DCM, and washed with saturated aqueous sodium bicarbonate. The organic layer was dried over magnesium sulfate, filtered, and concentrated under reduced pressure to afford di-tert-butyl 8-[1-(prop-2-en-1-yloxy)but-3-en-1-yl]-5H-pyrido[2,3-b][1,5]benzodiazepine-6,11-dicarboxylate. MS: 508 (M+1).

Step 3:

To a solution of di-tert-butyl 8-[1-(prop-2-en-1-yloxy) but-3-en-1-yl]-5H-pyrido[2,3-b][1,5]benzodiazepine-6,11-dicarboxylate (0.049 g, 0.096 mmol) in DCM (1.0 mL) was added 1,3-bis(2,4,6-trimethylphenyl)-4,5-dihydroimidazol-2-ylidene[2-(i-propoxy)-5-(N,N-dimethylaminosulfonyl) phenyl]methyleneruthenium(II) dichloride (3.5 mg, 4.8 μmol) under a stream of nitrogen gas. The reaction mixture was heated to 50° C. for 2 h under a nitrogen atmosphere. The mixture was cooled to room temperate and concentrated under reduced pressure. The residue was purified by column chromatography on silica gel (0-50% EtOAc/isohexane) to afford di-tert-butyl 8-(3,6-dihydro-2H-pyran-2-yl)-5H-pyrido[2,3-b][1,5]benzodiazepine-6,11-dicarboxylate as a solid. MS: 480 (M+1).

Step 4:

To a solution of di-tert-butyl 8-(3,6-dihydro-2H-pyran-2-yl)-5H-pyrido[2,3-b][1,5]benzodiazepine-6,11-dicarboxylate (36 mg, 0.074 mmol) dissolved in DCM (0.5 mL) was added TFA (0.5 mL). The mixture was stirred at room temperature for 1 h. The reaction was then concentrated under reduced pressure, diluted with DCM, and washed with saturated aqueous sodium bicarbonate. The organic layer was dried over magnesium sulfate, filtered, and concentrated under reduced pressure to afford the title compound which was used without purification in the next step. MS: 280 (M+H).

Intermediate 110: 8-(2-((Difluoromethoxy)methyl)cyclopropyl)-6,11-dihydro-5H-benzo[b]pyrido[2,3-e][1,4]diazepine

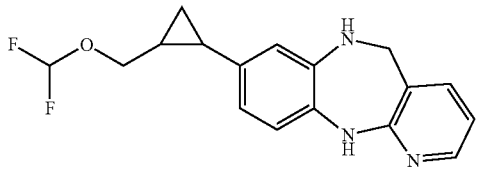 [SMILES: FC(F)OCC1CC1c1ccc2c(c1)NCc1cccnc1N2]

Step 1:
To a vial under an inert atmosphere of nitrogen was added di-tert-butyl 8-bromo-5H-benzo[b]pyrido[2,3-e][1,4]diazepine-6,11-dicarboxylate (400 mg, 0.840 mmol), X-Phos 3$^{rd}$ Generation precatalyst (71 mg, 0.084 mmol), potassium phosphate (535 mg, 2.52 mmol), dioxane (2.1 mL) and water (2.1 mL). The reaction was heated to 80° C. for 16 h. Upon cooling to room temperature, the reaction was diluted with EtOAc and washed with saturated aqueous sodium bicarbonate. The organic layer was dried over sodium sulfate, filtered, and concentrated under reduced pressure. The residue was purified by column chromatography on silica gel (0-50% EtOAc/Hexanes) to afford di-tert-butyl 8-(2-((benzyloxy)methyl)cyclopropyl)-5H-benzo[b]pyrido[2,3-e][1,4]diazepine-6,11-dicarboxylate. MS: 458 (M–C$_5$H$_8$O$_2$+H).

Step 2:
Under nitrogen gas flow, palladium on carbon (59 mg, 0.056 mmol) was added to di-tert-butyl 8-(2-((benzyloxy)methyl)cyclopropyl)-5H-benzo[b]pyrido[2,3-e][1,4]diazepine-6,11-dicarboxylate (310 mg, 0.556 mmol). MeOH (4 mL) was added, and the reaction mixture was purged with hydrogen (3×) and stirred under a hydrogen atmosphere at room temperature for 4 h. The reaction was filtered over Celite, washed with MeOH, and concentrated under reduced pressure to afford di-tert-butyl 8-(2-(hydroxymethyl)cyclopropyl)-5H-benzo[b]pyrido[2,3-e][1,4]diazepine-6,11-dicarboxylate which was used as is without further purification. MS: 468 (M+H).

Step 3:
Under nitrogen gas flow, 2,2-difluoro-2-(fluorosulfonyl)acetic acid (22.8 mg, 0.128 mmol) was added di-tert-butyl 8-(2-(hydroxymethyl)cyclopropyl)-5H-benzo[b]pyrido[2,3-e][1,4]diazepine-6,11-dicarboxylate (30 mg, 0.064 mmol) and copper(I) iodide (3.7 mg, 0.019 mmol) in acetonitrile (650 µL). The reaction mixture was stirred at 50° C. for 1 h, and then quenched with saturated aqueous sodium bicarbonate and extracted with EtOAc (3×). The combined organic layers were dried over sodium sulfate, filtered, and concentrated under reduced pressure. The crude product (33 mg, 0.064 mmol) was dissolved in HCl (4.0 M in 1,4-dioxane, 650 µL, 2.55 mmol) and stirred at room temperature for 0.5 h. The reaction was concentrated under reduced pressure to afford the title compound as an HCl salt, which was used as is without further purification. MS: 318 (M+H).

Intermediate 111: 1-(1,1,1-Trifluoropropan-2-yl)piperidine-4-carboxylic Acid

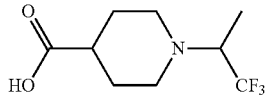

Step 1:
To a solution of ethyl piperidine-4-carboxylate (500 mg, 3.18 mmol) and 1,1,1-trifluoropropan-2-one (0.28 ml, 3.2 mmol) in DCM (16 mL) was added triethylamine (1.33 mL, 9.54 mmol) and titanium(IV) chloride (0.350 mL, 3.18 mmol). The reaction mixture was stirred at room temperature under an inert atmosphere of nitrogen for 18 h. A methanolic solution of sodium cyanoborohydride (600 mg, 9.54 mmol) in methanol (7.6 mL) was added and the mixture was stirred for 0.5 h. The reaction was basified with the addition of NaOH (3N), and the mixture was extracted with EtOAc. The organic layer was dried over anhydrous sodium sulfate, filtered, and concentrated under reduced pressure. The residue was purified by column chromatography on silica gel (0-70% EtOAc/hexanes) to afford ethyl 1-(1, 1, 1-trifluoropropan-2-yl) piperidine-4-carboxylate. MS: 254 (M+1).

Step 2:
To a solution of ethyl 1-(1,1,1-trifluoropropan-2-yl)piperidine-4-carboxylate (200 mg, 0.790 mmol) in THF (4 mL) and MeOH (1 mL) was added lithium hydroxide (1.0 M in water, 2.0 mL, 2.0 mmol) at room temperature. The reaction mixture was stirred at room temperature for 18 h. The reaction mixture was concentrated under reduced pressure, and then diluted with water and acidified with HCl (1.25 M, 1.6 mL, 2.0 mmol). The mixture was extracted with EtOAc, and the organic layer was dried over anhydrous sodium sulfate, filtered, and concentrated under reduced pressure to afford the title compound as a solid. MS: 226 (M+1).

Intermediate 112: 4-Ethoxy-3,3-difluorocyclohexane-1-carboxylic Acid

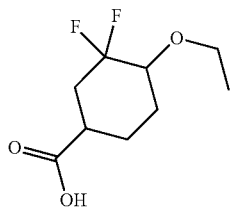

Step 1:
Ethyl 4-ethoxy-3-hydroxycyclohexanecarboxylate (2.25 g, 10.4 mmol) was dissolved in DCM (150 mL) and 1 drop of water was added. The mixture was cooled to 0° C. and charged with Dess-Martin periodinane (5.74 g, 13.5 mmol). The mixture was slowly warmed to room temperature over 1.5 h. The reaction was quenched with sodium thiosulfate (1N, 50 mL) and saturated sodium bicarbonate (50 mL) and the mixture was stirred vigorously for 30 minutes. The aqueous layer was extracted with DCM (50 mL), washed with brine, dried over sodium sulfate, filtered, and concentrated under reduced pressure to afford crude ethyl 4-ethoxy- 3-oxocyclohexanecarboxylate, which was used without further purification. MS: 215 (M+H).

Step 2:

To a solution of triethylamine trihydrofluoride (1.38 mL, 8.47 mmol) in DCE (20 mL) at room temperature was added difluoro(morpholino)sulfonium tetrafluoroborate (2.06 g, 8.47 mmol) followed by ethyl 4-ethoxy-3-oxocyclohexanecarboxylate (1.65 g, 7.70 mmol). The reaction was heated to reflux for 3 h, then cooled to 0° C. and quenched with a 5% aqueous sodium bicarbonate solution. The mixture was stirred for 15 min. The resulting mixture was extracted twice with dichloromethane and the combined organic layers were dried over sodium sulfate, filtered, and concentrated under reduced pressure. The residue was purified by column chromatography on silica gel (0-15% EtOAc/hexanes) to afford ethyl 4-ethoxy-3,3-difluorocyclohexanecarboxylate as a clear oil. MS: 237 (M+H).

Step 3:

Ethyl 4-ethoxy-3,3-difluorocyclohexanecarboxylate (135 mg, 0.571 mmol) was dissolved in sodium methoxide (0.5 M in MeOH, 4.6 mL, 2.3 mmol) and heated to 50° C. for 4 h. The reaction was concentrated under reduced pressure, and water (10 mL) was added and the mixture was stirred for 10 minutes at room temperature. The water layer was acidified with HCl and then extracted with EtOAc (2×50 mL), and the combined organic layers were washed with brine, dried over sodium sulfate, filtered and concentrated under reduced pressure to afford the title compound as a mixture of cis and trans isomers that was used without further purification. MS: 209 (M+H).

Intermediate 113: 7-Methoxy-3-oxa-9-azabicyclo[3.3.1]nonane

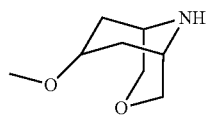

Step 1:

Sodium borohydride (47 mg, 1.3 mmol) was added to tert-butyl 7-oxo-3-oxa-9-azabicyclo[3.3.1]nonane-9-carboxylate (200 mg, 0.835 mmol) dissolved in MeOH (2 mL) at 0° C. The mixture was slowly warmed to room temperature and stirred for 16 h. The reaction was quenched with saturated aqueous ammonium chloride and concentrated under reduced pressure. The resulting mixture was extracted with DCM (3×) and the combined extracts were dried over sodium sulfate, filtered, and concentrated under reduced pressure to afford tert-butyl 7-hydroxy-3-oxa-9-azabicyclo[3.3.1]nonane-9-carboxylate as a solid.

Step 2:

To a solution of tert-butyl 7-hydroxy-3-oxa-9-azabicyclo[3.3.1]nonane-9-carboxylate (200 mg, 0.822 mmol) dissolved in DCM (4 mL) was added N,N,N',N'-tetramethylnaphthalene-1,8-diamine (350 mg, 1.64 mmol). Trimethyloxonium tetrafluoroborate (240 mg, 1.64 mmol) was added and the reaction was stirred at room temperature for 16 h. Citric acid (1N) was added, and the mixture was stirred for 45 minutes. The organic layer was separated, dried over sodium sulfate, filtered, and concentrated under reduced pressure. The residue was purified by column chromatograph on silica gel (5-50% EtOAc/hexanes) to afford tert-butyl 7-methoxy-3-oxa-9-azabicyclo[3.3.1]nonane-9-carboxylate as a liquid.

Step 3:

To a solution of tert-butyl 7-methoxy-3-oxa-9-azabicyclo[3.3.1]nonane-9-carboxylate (120 mg, 0.472 mmol) dissolved in EtOAc (1 mL) was added HCl (4.0 M in dioxane, 1.2 mL, 4.7 mmol). The reaction was stirred at room temperature for 16 h and then concentrated under reduced pressure to afford the title compound as a solid. $^1$H NMR (499 MHz, DMSO-$d_6$) δ 3.81 (d, J=11.0 Hz, 2H), 3.68 (d, J=12.3 Hz, 2H), 3.59 (p, J=5.6 Hz, 1H), 3.49 (d, J=7.7 Hz, 2H), 3.21 (s, 3H), 2.31 (dt, J=14.3, 6.9 Hz, 2H), 1.84-1.74 (m, 2H).

Intermediate 114:
5-Methoxy-2-azabicyclo[2.2.2]octane

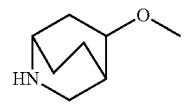

Intermediate 115:
(2R)-4-Methoxy-2-methylpiperidine

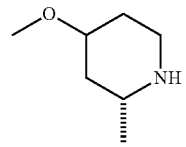

Intermediate 116:
(2S)-4-Methoxy-2-methylpiperidine

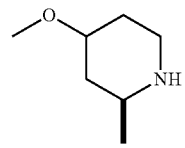

Intermediates 114 to 116 were prepared using the procedure described for Intermediate 113.

Intermediate 117: 1-[1-(Trifluoromethyl)cyclobutyl]piperidine-4-carboxylic Acid

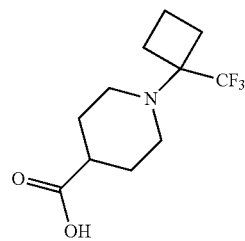 [SMILES: O=C(O)C1CCN(C2(C(F)(F)F)CCC2)CC1]

Step 1:

To a solution of 1-(trifluoromethyl)cyclobutanamine hydrochloride (1.05 g, 5.97 mmol) in MeOH (10 mL) was added N,N-diisopropylethylamine (1.0 mL, 5.9 mmol) and penta-1,4-dien-3-one (735 mg, 8.95 mmol) in 1,2-dichloroethane (10 mL). The reaction was heated at 80° C. for 3 h, and stirred at room temperature overnight. The mixture was concentrated under reduced pressure to afford 1-(1-(trifluoromethyl)cyclobutyl)piperidin-4-one as an oil which was used in next step without purification. MS: 222 (M+H).

Step 2:

To a stirred solution of 1-(1-(trifluoromethyl)cyclobutyl)piperidin-4-one (2.4 g, 11 mmol) in 1,2-dimethoxyethane (50 mL) and ethanol (1.8 mL) cooled to 0° C. was added tosylmethyl isocyanide (4.24 g, 21.7 mmol). Potassium tert-butoxide (3.65 g, 32.5 mmol) was added over a period of 1 h (~1 g every 15 min). The mixture was stirred at 0° C. for 1 h and then the mixture was gradually warmed to room temperature and stirred for 2 h. The mixture was cooled to 0° C. and quenched with brine. The mixture was extracted with EtOAc (3×30 mL). The combined organic layers were dried over sodium sulfate, filtered, and concentrated under reduced pressure. The residue was purified by column chromatography on silica gel (0-100% EtOAc/isohexane) to afford 1-(1-(trifluoromethyl)cyclobutyl)piperidine-4-carbonitrile as a solid. MS: 232 (M+H).

Step 3:

Hydrochloric acid (6 M in water, 8.0 mL, 48 mmol) was added to 1-(1-(trifluoromethyl)cyclobutyl)piperidine-4-carbonitrile (345 mg, 1.49 mmol). The reaction was refluxed overnight. The mixture was cooled to room temperature, and concentrated under reduced pressure. The mixture was then azeotroped with toluene (4×25 mL) to afford the title compound as a solid. MS: 252 (M+H).

Intermediate 118: 1-[1-(Trifluoromethyl)cyclopropyl]piperidine-4-carboxylic Acid

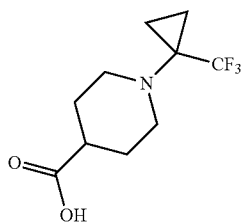 [SMILES: O=C(O)C1CCN(C2(C(F)(F)F)CC2)CC1]

Intermediate 119: 1-(1,1,1-Trifluoro-2-methylpropan-2-yl)piperidine-4-carboxylic Acid

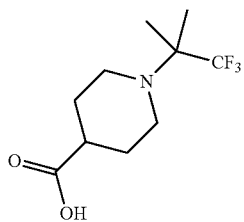 [SMILES: CC(C)(N1CCC(C(=O)O)CC1)C(F)(F)F]

Intermediates 118-119 can be made using the procedure described for Intermediate 117.

Intermediate 120: 5-(Tert-butoxy)tetrahydro-2H-pyran-2-carboxylic Acid

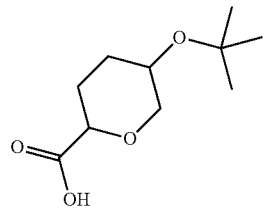

Step 1:

To a flask was added methyl 5-hydroxytetrahydro-2H-pyran-2-carboxylate (0.8 g, 5 mmol), MTBE (15 mL, 125 mmol), and 2 g activated 4 Å 1.5 mm molecular sieves. Sulfuric acid (0.53 mL, 10 mmol) was added dropwise, and the reaction was stirred overnight at room temperature. The reaction was quenched slowly with saturated aqueous sodium bicarbonate (20 mL) and filtered through a small pad of Celite. The organic layer was washed with water (2×20 mL), dried over sodium sulfate, filtered, and concentrated under reduced pressure. The residue was purified by column chromatography on silica gel (0-25% EtOAc/DCM) to afford methyl 5-(tert-butoxy)tetrahydro-2H-pyran-2-carboxylate. MS: 217 (M+H).

Step 2:

To a mixture of methyl 5-(tert-butoxy)tetrahydro-2H-pyran-2-carboxylate (250 mg, 1.16 mmol) dissolved in THF (4 mL), water (1 mL), and MeOH (1 mL) was added lithium hydroxide (69 mg, 2.9 mmol). The mixture was stirred at room temperature for 18 h. The reaction was quenched with HCl (6 M in water, 482 µL, 2.89 mmol) and the mixture was extracted with EtOAc (2×25 mL). The combined organic layers were dried over sodium sulfate, filtered, and concentrated to the title compound. MS: 225 (M+Na).

Intermediate 121 and 122: (1R,4R)-5-(6,11-Dihydro-5H-benzo[b]pyrido[2,3-e][1,4]diazepin-8-yl)-2-oxa-5-azabicyclo[2.2.2]octane and (1S,4S)-5-(6,11-dihydro-5H-benzo[b]pyrido[2,3-e][1,4]diazepin-8-yl)-2-oxa-5-azabicyclo[2.2.2]octane

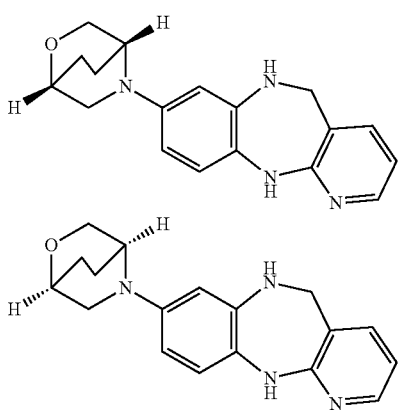

Step 1:

To a mixture of 8-bromo-6,11-dihydro-5H-pyrido[2,3-b][1,5]benzodiazepine, HCl (5.0 g, 16 mmol) in THF (300 mL) was added triethylamine (17.9 mL, 128 mmol), di-tert-butyl dicarbonate (14 g, 64 mmol) and DMAP (2.3 g, 19 mmol). The mixture was heated to 70° C. for 18 h. Upon cooling to room temperature, the mixture was diluted with ethyl acetate, washed with water, dried over magnesium sulfate, filtered and concentrated under reduced pressure. The mixture was purified by column chromatography to afford di-tert-butyl 8-bromo-5H-benzo[b]pyrido[2,3-e][1,4]diazepine-6,11-dicarboxylate. MS: 376, 378 ($M-C_5H_8O_2$, $M-C_5H_8O_2+2$).

Step 2:

To a mixture of di-tert-butyl 8-bromo-5H-benzo[b]pyrido[2,3-e][1,4]diazepine-6,11-dicarboxylate (1.0 g, 2.1 mmol), RuPhos-G1-palladacycle (171 mg, 0.210 mmol), 2-oxa-5-azabicyclo[2.2.2]octane (309 mg, 2.73 mmol), and sodium tert-butoxide (1.0 g, 11 mmol) was added THF (22 mL) and water (5 mL). The mixture was evacuated and then purged with nitrogen and then heated to 80° C. for 18 h. Upon cooling to room temperature, the mixture was diluted with ethyl acetate and water. The organic layer was separated, dried over magnesium sulfate, filtered and concentrated under reduced pressure. The mixture was purified by column chromatography to afford di-tert-butyl 8-(2-oxa-5-azabicyclo[2.2.2]octan-5-yl)-5H-benzo[b]pyrido[2,3-e][1,4]diazepine-6,11-dicarboxylate as a mixture of enantiomers. The enantiomers were separated by SFC (Chiralcel OD-H column, 10%/90% methanol/$CO_2$ with 0.25% N,N-dimethylethanamine modifier) to afford di-tert-butyl 8-((1R,4R)-2-oxa-5-azabicyclo[2.2.2]octan-5-yl)-5H-benzo[b]pyrido[2,3-e][1,4]diazepine-6,11-dicarboxylate and di-tert-butyl 8-((1S,4S)-2-oxa-5-azabicyclo[2.2.2]octan-5-yl)-5H-benzo[b]pyrido[2,3-e][1,4]diazepine-6,11-dicarboxylate.

Characterization data for di-tert-butyl 8-((1R,4R)-2-oxa-5-azabicyclo[2.2.2]octan-5-yl)-5H-benzo[b]pyrido[2,3-e][1,4]diazepine-6,11-dicarboxylate (early eluting): MS: 409 ($M-C_5H_8O_2+H$)

Characterization data for di-tert-butyl 8-((1S,4S)-2-oxa-5-azabicyclo[2.2.2]octan-5-yl)-5H-benzo[b]pyrido[2,3-e][1,4]diazepine-6,11-dicarboxylate (late eluting): MS: 409 ($M-C_5H_8O_2+H$)

Step 3:

To a mixture of di-tert-butyl 8-((1R,4R)-2-oxa-5-azabicyclo[2.2.2]octan-5-yl)-5H-benzo[b]pyrido[2,3-e][1,4]diazepine-6,11-dicarboxylate (177 mg, 0.348 mmol) in dichloromethane (2 mL) was added trifluoroacetic acid (200 μL, 2.61 mmol) and the mixture was allowed to stir overnight at room temperature. The mixture was concentrated and then taken up in ethyl acetate. The mixture was washed with saturated aqueous sodium bicarbonate, dried over magnesium sulfate, filtered and concentrated to afford (1R,4R)-5-(6,11-dihydro-5H-benzo[b]pyrido[2,3-e][1,4]diazepin-8-yl)-2-oxa-5-azabicyclo[2.2.2]octane. MS: 309 (M+H).

1S,4S)-5-(6,11-dihydro-5H-benzo[b]pyrido[2,3-e][1,4]diazepin-8-yl)-2-oxa-5-azabicyclo[2.2.2]octane can be prepared using the procedure described in Step 3. MS: 309 (M+H).

The intermediates in the following table were prepared using the methodology herein and the general procedure described in Intermediates 121 and 122.

| Intermediate # | Structure | Chemical Name | [M + H]+ |
|---|---|---|---|
| 123 | 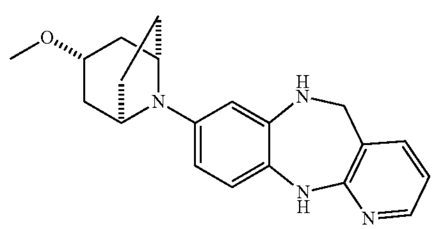 [SMILES: CO[C@H]1C[C@H]2CC[C@@H](C1)N2c1ccc2c(c1)NCc1cccnc1N2] | 8-[(3-endo)-3-methoxy-8-azabicyclo[3.2.1]oct-8-yl]-6,11-dihydro-5H-pyrido[2,3-b][1,5]benzodiazepine | 337 |
| 124 | 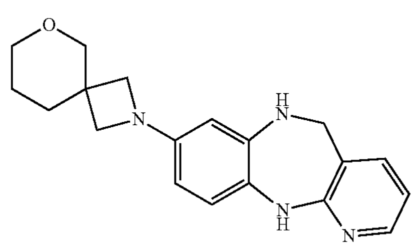 [SMILES: c1cnc2c(c1)CNc1cc(N3CC4(CCCOC4)C3)ccc1N2] | 8-(6-oxa-2-azaspiro[3.5]non-2-yl)-6,11-dihydro-5H-pyrido[2,3-b][1,5]benzodiazepine | 323 |
| 125 | 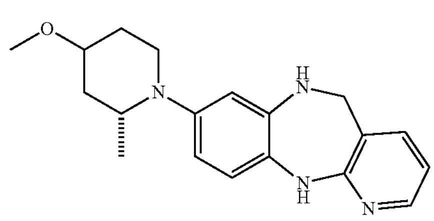 [SMILES: COC1CCN(c2ccc3c(c2)NCc2cccnc2N3)[C@H](C)C1] | 8-[(2R)-4-methoxy-2-methyl-piperidin-1-yl]-6,11-dihydro-5H-pyrido[2,3-b][1,5]benzodiazepine | 325 |

| Intermediate # | Structure | Chemical Name | [M + H]+ |
|---|---|---|---|
| 126 | 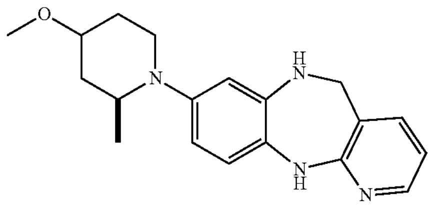 [SMILES: COC1CCN(c2ccc3c(c2)NCc2cccnc2N3)[C@@H](C)C1] | 8-[(2S)-4-methoxy-2-methyl-piperidin-1-yl]-6,11-dihydro-5H-pyrido[2,3-b][1,5]benzo-diazepine | 325 |
| 127 | 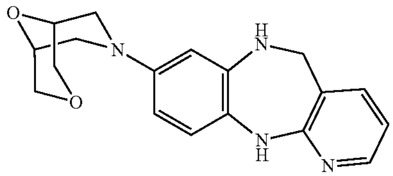 [SMILES: c1cnc2c(c1)CNc1cc(N3CC4COCC(C3)O4)ccc1N2] | 8-(3,9-dioxa-7-azabicyclo[3.3.1]non-7-yl)-6,11-dihydro-5H-pyrido[2,3-b][1,5]benzo-diazepine | 325 |
| 128 | 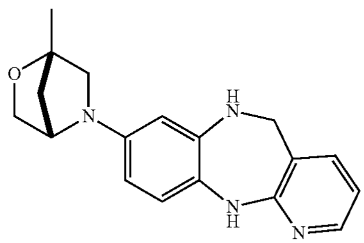 | 8-[(1S,4S)-1-methyl-2-oxa-5-azabicyclo[2.2.1]hept-5-yl]-6,11-dihydro-5H-pyrido[2,3-b][1,5]benzodiazepine | 309 |
| 129 | 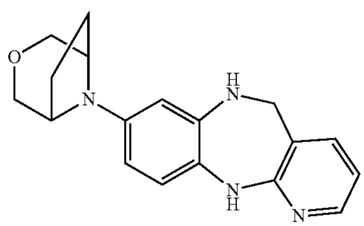 [SMILES: c1cnc2c(c1)CNc1cc(N3C4CCC3COC4)ccc1N2] | 8-(3-oxa-8-azabicyclo[3.2.1]oct-8-yl)-6,11-dihydro-5H-pyrido[2,3-b][1,5]benzo-diazepine | 309 |
| 130 | 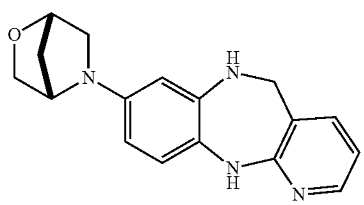 | 8-[(1S,4S)-2-oxa-5-azabicyclo[2.2.1]hept-5-yl]-6,11-dihydro-5H-pyrido[2,3-b][1,5]benzodiazepine | 295 |

Intermediate 131:
4-(Tert-butoxycarbonyl)-1,4-oxazepane-7-carboxylic Acid

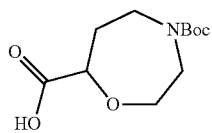 [SMILES: CC(C)(C)OC(=O)N1CCOC(C(=O)O)CC1]

Step 1:

A solution of 5-hydroxy-2-(hydroxymethyl)-4H-pyran-4-one (30 g, 0.21 mol) in MeOH (1.2 L) was added to 10% Pd/C (3.0 g). The mixture was stirred under hydrogen (3 Mpa) at 110° C. for 17 h. Upon cooling to room temperature, the reaction was filtered and the solvent was concentrated under reduced pressure. The residue was purified by column chromatography to give 6-(hydroxymethyl)tetrahydro-2H-pyran-3,4-diol as an oil.

Step 2:

A solution of sodium periodate (282 g, 1.30 mol) in distilled water was added dropwise to a stirred solution of 6-(hydroxymethyl)tetrahydro-2H-pyran-3,4-diol (163 g, 1.10 mol) in water at 0° C. The reaction mixture was stirred at room temperature for 15 h, and then it was filtered through Celite and concentrated under reduced pressure to afford crude 4-hydroxy-3-(2-oxoethoxy)butanal which was subjected to the next step without further purification.

Step 3:

Sodium cyanoborohydride (119 g, 1.80 mol) was added to a stirred solution of 1-phenylmethanamine (39 g, 0.40 mol), 4-hydroxy-3-(2-oxoethoxy)butanal (107 g, 0.70 mol), and 4 Å molecular sieves in methanol. The reaction was stirred at room temperature for 24 h, and then concentrated under reduced pressure. The residue was dissolved in DCM, and then washed with water. The organic phase was dried over magnesium sulfate, filtered, and concentrated under reduced pressure. The residue was purified by column chromatography to afford (4-benzyl-1,4-oxazepan-7-yl)methanol as an oil.

Step 4:

To (4-benzyl-1,4-oxazepan-7-yl)methanol (4.07 g, 18.4 mmol) in MeOH (92 mL) was added 20% palladium hydroxide on carbon (2.58 g, 3.68 mmol) and then stirred under an atmosphere of hydrogen overnight. The reaction was filtered through Celite and rinsed with DCM. The filtrate was concentrated under reduced pressure and then diluted with 3:1 DCM:EtOH (92 mL). Di-tert-butyl dicarbonate (4.01 g, 18.4 mmol) and DIEA (3.15 mL, 18.4 mmol) were added and the mixture was stirred at room temperature overnight. The mixture was concentrated under reduced pressure and then diluted with DCM, washed with aqueous HCl (1N), and brine. The organic layer was dried over magnesium sulfate, filtered, and concentrated under reduced pressure to afford tert-butyl 7-(hydroxymethyl)-1,4-oxazepane-4-carboxylate as an oil. MS: 232 (M+1).

Step 5:

To tert-butyl 7-(hydroxymethyl)-1,4-oxazepane-4-carboxylate (3.33 g, 14.4 mmol) in acetone (72 mL) was added Jones reagent (21.6 ml, 43.2 mmol) dropwise at 0° C. The reaction was stirred for 0.5 h at room temperature. IPA (6.7 mL, 86 mmol) was added at 0° C., and the mixture was stirred for 10 min at room temperature. Sodium sulfate (24 g) was added and the mixture was stirred for 10 min. The mixture was filtered, and the filtrate was washed with brine, dried over magnesium sulfate, filtered, and concentrated under reduced pressure to afford the title compound as an oil. MS: 246 (M+1).

Intermediate 132: 3-(6,11-Dihydro-5H-benzo[b]pyrido[2,3-e][1,4]diazepin-8-yl)-8-oxa-3-azabicyclo[3.2.1]octane

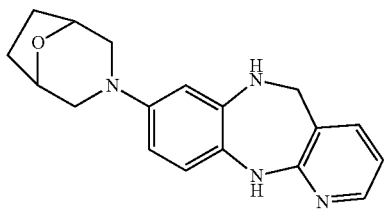 [SMILES: c1cnc2c(c1)CNc1cc(N3CC4CCC(C3)O4)ccc1N2]

A reaction vessel was charged with lithium bis(trimethylsilyl)amide (1.0 M in THF, 64.0 mL, 64.0 mmol) followed by 8-bromo-6,11-dihydro-5H-benzo[b]pyrido[2,3-e][1,4]diazepin-11-ium chloride (2.0 g, 6.4 mmol), 8-oxa-3-azabicyclo[3.2.1]octane hydrochloride (1.4 g, 9.6 mmol), and (2-dicyclohexylphosphino-2',6'-diisopropoxy-1,1'-biphenyl)[2-(2'-amino-1,1'-biphenyl)]palladium(II) methanesulfonate (RuPhos G3) (0.53 g, 0.64 mmol). The vessel was sealed and heated at 80° C. for 16 h. The reaction mixture was cooled to room temperature, and diluted with saturated aqueous sodium bicarbonate and extracted with EtOAc (2×). The combined organic layers were washed with brine, dried over anhydrous magnesium sulfate, filtered, and concentrated under reduced pressure. The residue was purified by column chromatography on silica gel (30-100% EtOAc:Hex) to afford the title compound. MS: 309 (M+1).

Intermediate 133: 4-{[8-(8-Oxa-3-azabicyclo[3.2.1]oct-3-yl)-5,11-dihydro-6H-pyrido[2,3-b][1,5]benzodiazepin-6-yl]carbonyl}cyclohexanone

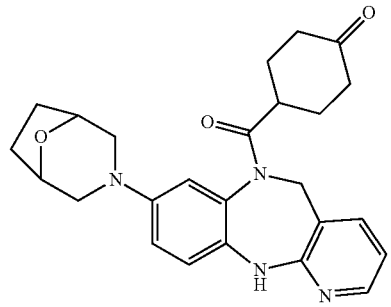 [SMILES: O=C1CCC(C(=O)N2Cc3cccnc3Nc3ccc(N4CC5CCC(C4)O5)cc32)CC1]

Intermediate 133 was made using the procedure described for Intermediate 132. MS: 433 (M+1)

Intermediate 134: 4-(2,2-Difluoroethoxy)cyclohexane-1-carboxylic Acid

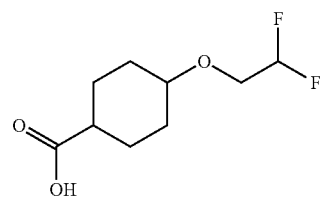 [SMILES: O=C(O)C1CCC(OCC(F)F)CC1]

Step 1:

Ethyl 4-hydroxycyclohexanecarboxylate (2.1 g, 12 mmol) was dissolved in THF (100 mL) and the mixture was cooled to 0° C. The reaction was charged with 2,2-difluoroethyl trifluoromethanesulfonate (2.86 g, 13.4 mmol) and sodium hydride (0.534 g, 13.4 mmol) and allowed to warm to room temperature overnight. The reaction was quenched with saturated aqueous ammonium chloride (50 mL) and extracted with EtOAc (2×50 mL). The combined organic layers were washed with brine, dried over sodium sulfate, filtered, and concentrated under reduced pressure. The residue was purified by column chromatography on silica gel (5-40% EtOAc/hexanes) to afford ethyl 4-(2,2-difluoroethoxy)cyclohexanecarboxylate as an oil.

Step 2:

Ethyl 4-(2,2-difluoroethoxy)cyclohexanecarboxylate (550 mg, 2.33 mmol) was dissolved in THF (10 mL) and a solution of lithium hydroxide (223 mg, 9.31 mmol) in water (1.0 mL) was added. The reaction was stirred overnight at room temperature. The reaction was quenched with HCl (2.0 M in water, 5.82 ml, 11.6 mmol) and extracted with EtOAc (50 mL). The organic layer was washed with brine, dried over sodium sulfate, filtered, and concentrated under reduced pressure to afford the title compound as a solid. MS: 225 (M+Na).

Intermediate 135:
3-(2-Methoxypropan-2-yl)cyclobutanecarboxylic Acid

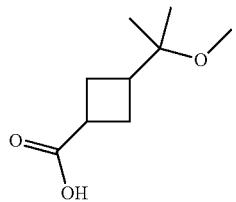

Step 1:

A 10 L round-bottom flask equipped with a mechanical stirrer, addition funnel, and thermocouple, and connected to a nitrogen line was charged with ethyltriphenylphosphonium bromide (310 g, 3.57 mol) and fresh tetrahydrofuran (1.2 L). The solution was cooled to 0-5° C. A solution of n-BuLi (930 mL, 0.21 mol) in tetrahydrofuran was added dropwise over 30 min while maintaining the internal temperature at 5-10° C. The reaction mixture was stirred at 18-22° C. for 30 min. The reaction mixture was re-cooled to 5-10° C. and a solution of 3-[(benzyloxy)methyl]cyclobutanone (300 g, 0.21 mol) in tetrahydrofuran (500 mL) was added over 45 min while maintaining the internal temperature at 5-10° C. Once the addition was complete, the reaction mixture was held at 18-22° C. for 2 h. The reaction mixture was cooled to 0° C. and was quenched by adding 2 N HCl solution (5 L) slowly while maintaining the temperature of the mixture below 15° C. The reaction mixture was extracted with ethyl acetate (3×1 L). The combined organic layer was washed with brine (3×1 L) and dried over anhydrous sodium sulfate. The filtrate was concentrated under reduced pressure. The residue was purified by column chromatography on silica gel (10-30% EtOAc in petroleum ether) to afford {[(3-ethylidenecyclobutyl)methoxy]methyl}benzene as an oil.

Step 2:

A 10 L round-bottom flask equipped with a mechanical stirrer, thermocouple, and addition funnel, and connected to a nitrogen line was charged with {[(3-ethylidenecyclobutyl)methoxy]methyl}benzene (146 g, 0.710 mol) and tetrahydrofuran (1.4 L). The reaction mixture was cooled to −5° C. and a solution of borane-tetrahydrofuran complex (1.3 L, 1.1 mol) was added dropwise over 30 min while maintaining the internal temperature between 0 and 5° C. The resulting solution was held at 0-5° C. for 3 h. The reaction was quenched by adding aqueous NaOH (2N, 2.4 L, 4.3 mol) solution dropwise over 30 min followed by hydrogen peroxide (30%, 0.55 L, 4.3 mol) solution while maintaining the internal temperature between 0 and 5° C. Once the addition was complete, the reaction mixture was stirred again for 30 min and extracted with ethyl acetate (2×700 mL). The combined extracts were washed with brine (3×700 mL), dried over anhydrous sodium sulfate, and filtered. The filtrate was concentrated under reduced pressure. The residue was purified by column chromatography on silica gel (50-20% EtOAc in petroleum ether) to give 1-{3-[(benzyloxy)methyl]cyclobutyl}ethanol as an oil.

Step 3:

A three-neck 5 L flask equipped with a temperature probe, $N_2$ inlet, and mechanical stirrer was charged with 1-{3-[(benzyloxy)methyl]cyclobutyl}ethanol (148 g, 0.670 mol) and dichloromethane (2 L). The reaction mixture was cooled to 0° C. and Dess-Martin periodinane (450 g, 1.00 mol) was added portionwise over 45 min while maintaining the internal temperature between 5 and 15° C. Once the addition was complete, the reaction mixture was warmed to room temperature and stirred for 15 h. The reaction was diluted with dichloromethane (750 mL) and was cooled to 0° C. The resulting slurry was quenched with saturated aqueous sodium bicarbonate (3 L). The layers were separated and the organic phase was washed with saturated aqueous sodium bicarbonate (3 L) followed by brine (3×700 mL). The organic phase was dried over sodium sulfate, filtered, and concentrated under reduced pressure. The residue was purified by column chromatography on silica gel (20-60% EtOAc in petroleum ether) to afford 1-{3-[(benzyloxy)methyl]cyclobutyl}ethanone as an oil and a 70:30 mixture of cis:trans isomers.

Step 4:

A 5 L round-bottom flask equipped with a mechanical stirrer and thermocouple was charged with 1-{3-[(benzyloxy)methyl]cyclobutyl}ethanone (103 g, 0.470 mol) and tetrahydrofuran (600 mL). The reaction mixture was cooled to −5° C. and a solution of methylmagnesium bromide (240 mL, 0.70 mol) in tetrahydrofuran was added dropwise over 30 min while maintaining the internal temperature between 0 and 5° C. Once the addition was complete, the reaction mixture was warmed to room temperature and the mixture was stirred for 15 h. The reaction was cooled to 0° C. and quenched by adding aqueous 1 N HCl solution (250 mL) slowly while maintaining the internal temperature of the mixture below 15° C. The aqueous layer was extracted with ethyl acetate (3×450 mL), and the combined organic phase was washed with brine (3×300 mL), dried over anhydrous sodium sulfate, filtered, and concentrated under reduced pressure. The residue was purified by column chromatography on silica gel (30-80% EtOAc in petroleum ether) to afford 2-{3-[(benzyloxy)methyl]cyclobutyl}propan-2-ol as an oil and a 84:16 mixture of cs:trans isomers.

Step 5:

A 500 mL flask was charged with 2-{3-[(benzyloxy)methyl]cyclobutyl}propan-2-ol (93 g, 0.39 mol) and ethyl acetate (200 mL). A slurry of 5% $Pd(OH)_2$ (50% wet, 17 g, 0.11 mol) in ethyl acetate (50 mL) was added under a nitrogen atmosphere. The vessel was closed and stirred under $H_2$ (50 psi) at ambient temperature for 15 h. The reaction mixture was filtered through a Celite pad and the pad was washed with ethyl acetate (3×250 mL). The combined organic phase was concentrated under reduced pressure. The residue was purified by column chromatography on silica gel (30-90% EtOAc in petroleum ether) to afford 2-[3-(hydroxymethyl)cyclobutyl]propan-2-ol as an oil and mixture of cis/trans isomers.

Step 6:

A 3.0 L round-bottom flask equipped with a magnetic stirrer and thermocouple, and connected to a nitrogen line was charged with 2-[3-(hydroxymethyl)cyclobutyl]propan-2-ol (26 g, 0.18 mol), acetonitrile (2.6 L), and carbon tetrachloride (2.6 L). A mixture of ruthenium(III) chloride (5.6 g, 0.020 mol) and sodium periodate (110 g, 0.410 mol) in water (2.3 L) was added at room temperature. The reaction mixture was stirred for 20 h at room temperature. The reaction was diluted with dichloromethane (2 L), and charcoal (7 g) was added. The mixture was stirred for 45 min. The reaction mixture was filtered through a Celite pad and the Celite pad was washed with dichloromethane (3×250 mL). The organic phase was separated and collected, and then washed with brine (150 mL). The organic phase was dried over anhydrous sodium sulfate, filtered, and concentrated under reduced pressure. The residue was purified by column chromatography on silica gel (30-80% EtOAc in petroleum ether) to afford 3-(2-hydroxypropan-2-yl)cyclobutanecarboxylic acid as a liquid and mixture of cis/trans isomers.
Step 7:
To a solution of 3-(2-hydroxypropan-2-yl)cyclobutanecarboxylic acid (400 mg, 2.53 mmol) in DCM (2.4 mL) and MeOH (0.7 mL) at 0° C. was added (diazomethyl)trimethylsilane (2.0 M, 1.9 mL, 3.8 mmol) dropwise. The resulting mixture was warmed to room temperature and stirred for 45 min. The mixture was cooled to 0° C. and quenched by the dropwise addition of acetic acid (1 mL). The mixture was diluted with water (10 mL) and extracted with DCM (3×20 mL). The combined organic layers were washed with saturated aqueous sodium bicarbonate and then brine, dried over sodium sulfate, filtered, and concentrated under reduced pressure to afford methyl 3-(2-hydroxypropan-2-yl)cyclobutanecarboxylate as a liquid.
Step 8:
To a solution of methyl 3-(2-hydroxypropan-2-yl)cyclobutanecarboxylate (400 mg, 2.35 mmol) dissolved in DCM (12 mL) was added N,N,N',N'-tetramethylnaphthalene-1,8-diamine (1 g, 4.7 mmol). Trimethyloxonium tetrafluoroborate (700 mg, 4.7 mmol) was added and the reaction was stirred at room temperature for 2 h. The mixture was quenched with water and extracted with DCM. The organic layer was dried over sodium sulfate, filtered, and concentrated under reduced pressure. The residue was diluted with DCM (11 mL) and the remaining base was scavenged with resin bound MP-p-toluenesulfonic acid (4.44 mmol/g loading, 3.2 g, 14 mmol). The mixture was stirred gently for 2 h and then filtered and concentrated under reduced pressure. The residue was purified by column chromatography on silica gel (5-50% EtOAc:Hexanes) to afford methyl 3-(2-methoxypropan-2-yl)cyclobutanecarboxylate as a liquid.
Step 9:
To methyl 3-(2-methoxypropan-2-yl)cyclobutanecarboxylate (55 mg, 0.29 mmol) dissolved in THF (1.2 mL), water (0.30 mL), and MeOH (0.30 mL) was added lithium hydroxide (31 mg, 0.74 mmol). The mixture was stirred at room temperature for 16 h. The reaction mixture was quenched with 2 N HCl to pH 5~6 and extracted with EtOAc (2×). The combined organic layers were dried over sodium sulfate, filtered and concentrated under reduced pressure to afford the title compound as a solid. $^1$H NMR (499 MHz, CDCl$_3$) δ 3.27 and 3.21 (s, 3H), 3.06-2.96 (m, 1H), 2.65-2.56 (m, 1H), 2.45-2.16 (m, 4H), 1.08 (d, J=10.4 Hz, 6H).

Intermediate 136: 3-Methyl-1-(8-morpholino-6,11-dihydro-5H-benzo[b]pyrido[2,3-e][1,4]diazepine-6-carbonyl)-1H-imidazol-3-ium Iodide

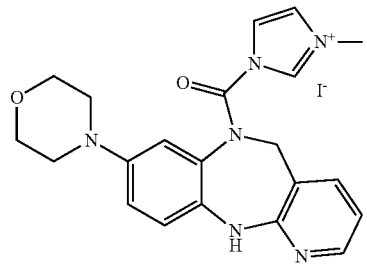 [SMILES: C[n+]1ccn(C(=O)N2Cc3cccnc3Nc3ccc(N4CCOCC4)cc32)c1 ; [I-]]

Step 1:
To a mixture of 4-(6,11-dihydro-5H-benzo[b]pyrido[2,3-e][1,4]diazepin-8-yl)morpholine (1.0 g, 3.1 mmol) in THF (13 mL) was added 1,1'-carbonyldiimidazole (1.5 g, 9.4 mmol) and triethylamine (1.3 mL, 9.4 mmol). The reaction was stirred at room temperature for 18 h. The mixture was then diluted with ethyl acetate, washed with saturated aqueous sodium bicarbonate (2×30 mL), washed with brine (30 mL), dried over magnesium sulfate, filtered and concentrated under reduced pressure. The residue was purified by column chromatography on silica gel to afford (1H-imidazol-1-yl)(8-morpholino-5,11-dihydro-6H-benzo[b]pyrido[2,3-e][1,4]diazepin-6-yl)methanone. MS: 377 (M+H).
Step 2:
To a mixture of (1H-imidazol-1-yl)(8-morpholino-5,11-dihydro-6H-benzo[b]pyrido[2,3-e][1,4]diazepin-6-yl)methanone (0.44 g, 1.2 mmol) in DMF (6.0 mL) was added iodomethane (0.29 mL, 4.7 mmol) and the mixture was allowed to stir for 18 h. To the mixture was added a minimal amount of diethyl ether to crash out the product. The liquids were decanted off to afford the title compound as a solid that was used in the further reactions without further purification. MS: 391 (M).

Intermediate 137: 1-Methyl-2-(trifluoromethyl)piperidine-4-carboxylic Acid

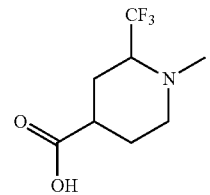

Step 1:
A mixture of methyl 2-(trifluoromethyl)isonicotinate (1.0 g, 4.9 mmol) and 10% Pd—C (1.04 g, 0.975 mmol) in 25 mL EtOH was degassed and backfilled with H$_2$. The mixture was stirred under a hydrogen atmosphere at 50 psi for 18 h at room temperature. The reaction was filtered and the filtrate was concentrated under reduced pressure to afford crude methyl 2-(trifluoromethyl)piperidine-4-carboxylate as solid which was used directly in the next step. MS: 212 (M+H).
Step 2:
To methyl 2-(trifluoromethyl)piperidine-4-carboxylate (0.35 g, 1.6 mmol) in DCE (16 ml) was added potassium carbonate (1.1 g, 8.3 mmol) and iodomethane (0.24 g, 1.6 mmol) at room temperature. The reaction was to stirred for 18 h at 40° C. The reaction was cooled to room temperature and diluted with water (20 mL). The aqueous layer was extracted with 25% IPA/CHCl$_3$ (2×25 mL), and the combined organic layer was washed with brine and dried over sodium sulfate. The material was filtered through a plug of silica gel, and the filtrate was concentrated under reduced pressure to afford crude methyl 1-methyl-2-(trifluoromethyl)piperidine-4-carboxylate which was used directly in the next step without further purification. MS: 226 (M+H).
Step 3:
To methyl 1-methyl-2-(trifluoromethyl)piperidine-4-carboxylate (0.16 g, 0.71 mmol) in THF (0.300 mL) and water (1.5 mL) was added lithium hydroxide (0.043 g, 1.8 mmol). The reaction was stirred at room temperature for 18 h. The reaction was quenched with HCl (1N, to pH ~4), and the aqueous layer was extracted with 25% IPA/CHCl₃ (2×50 mL). The aqueous layer was concentrated under reduced pressure to afford the title compound. MS: 212 (M+H).

Intermediate 138: [8-(1-Chloroethyl)-5,11-dihydro-6H-pyrido[2,3-b][1,5]benzodiazepin-6-yl][trans-4-(propan-2-yloxy)cyclohexyl]methanone

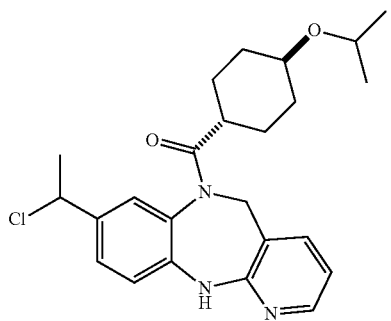

Step 1:
A mixture of lithium chloride (382 mg, 9.00 mmol), tetrakis(triphenylphosphine)palladium(0) (260 mg, 0.225 mmol), (8-bromo-5,11-dihydro-6H-pyrido[2,3-b][1,5]benzodiazepin-6-yl)[trans-4-(propan-2-yloxy)cyclohexyl]methanone (1.0 g, 2.3 mmol), and tributyl(1-ethoxyvinyl)stannane (1.6 g, 4.5 mmol) in dioxane (10 mL) was vacuum/N₂ exchanged (3×) and stirred at 80° C. overnight. HCl (1N, 5 mL) was added and the mixture was stirred for 10 minutes. The mixture was diluted with EtOAc, and washed with saturated aqueous sodium bicarbonate. The organic layer was washed with water and then brine, dried over magnesium sulfate, filtered, and concentrated under reduced pressure. The residue was purified column chromatography on silica gel (0-100% EtOAc/hexane) to afford 1-(6-{[trans-4-(propan-2-yloxy)cyclohexyl]carbonyl}-6,11-dihydro-5H-pyrido[2,3-b][1,5]benzodiazepin-8-yl)ethanone as a solid. MS: 408 (M+H).

Step 2:
Sodium borohydride (35 mg, 0.92 mmol) was added to a stirred room temperature mixture of 1-(6-{[trans-4-(propan-2-yloxy)cyclohexyl]carbonyl}-6,11-dihydro-5H-pyrido[2,3-b][1,5]benzodiazepin-8-yl)ethanone (250 mg, 0.613 mmol) in MeOH (4 mL) and DCM (2 mL). The mixture was stirred at room temperature for 2 h. The mixture was concentrated under reduced pressure and the residue was purified by column chromatography on silica gel (0-100% EtOAc/hexanes) to afford [8-(1-hydroxyethyl)-5,11-dihydro-6H-pyrido[2,3-b][1,5]benzodiazepin-6-yl][trans-4-(propan-2-yloxy)cyclohexyl]methanone as a solid. MS: 410 (M+H).

Step 3:
Thionyl chloride (0.178 mL, 2.44 mmol) was added to a stirred, cooled 0° C. solution of [8-(1-hydroxyethyl)-5,11-dihydro-6H-pyrido[2,3-b][1,5]benzodiazepin-6-yl][trans-4-(propan-2-yloxy)cyclohexyl]methanone (100 mg, 0.244 mmol) dissolved in DCE (3 mL). The mixture was slowly warmed to room temperature and stirred overnight. The reaction was concentrated under reduced pressure to afford the title compound, HCl as a solid. The material was used directly for next reaction. MS: 424 (M-Cl+MeOH).

EXAMPLES

Example 1: 6-[(3-Phenylcyclobutyl)carbonyl]-6,11-dihydro-5H-pyrido[2,3-b][1,5]benzodiazepine

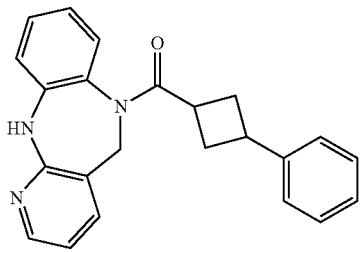 [SMILES: O=C(C1CC(c2ccccc2)C1)N1Cc2cccnc2Nc2ccccc21]

3-Phenylcyclobutanecarboxylic acid (50 mg, 0.28 mmol) was placed in a vial and dissolved in dichloromethane (0.75 mL). Thionyl chloride (0.025 mL, 0.34 mmol) was added and the reaction mixture was stirred for 2 hours at room temperature. The crude acid chloride was added to 6,11-dihydro-5H-benzo[b]pyrido[2,3-e][1,4]diazepine (50 mg, 0.254 mmol) and cesium carbonate (124 mg, 0.380 mmol) in DMF (1 mL) at −78° C. The reaction mixture was allowed to warm to room temperature. The reaction mixture was filtered and purified by mass-triggered reverse phase HPLC (C18; acetonitrile/water with 0.1% TFA) followed by a $2^{nd}$ purification using a Gemini Luna PFP, 20×150 mm, 5 uM column with a water/methanol 0.1% TFA gradient 25-90% in acetonitrile over 30 min using a flow rate of 25 mL/min over a 25 min run time collecting on 220 nm absorbance to afford the title compound as a solid TFA salt (1.7:1 mixture of cis/trans isomers). MS: 356 (M+1). ¹H NMR (600 MHz, DMSO-d₆) δ 9.42-9.41 (m, 1H), 8.03-8.00 (m, 1H), 7.52-7.47 (m, 1H), 7.30-7.08 (m, 7H), 7.03-7.01 (m, 1H), 6.91-6.84 (m, 1H), 6.74-6.70 (m, 1H), 5.29-5.18 (m, 2H), 3.92-3.89 (m, 1H), 3.24-3.09 (m, 3H), 2.40-2.10 (m, 2H).

The compound in the following table was prepared using the methodology herein and the general procedure described in Example 1.

| Ex. No. | Structure | Chemical Name | [M + H]+ |
|---|---|---|---|
| 2 | 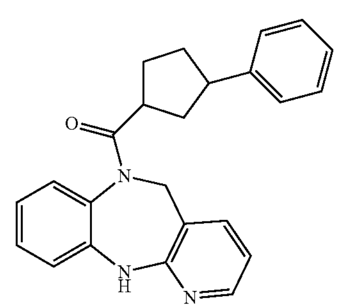 [SMILES: O=C(C1CCC(c2ccccc2)C1)N1Cc2cccnc2Nc2ccccc21] | 6-[(3-phenyl-cyclopentyl)carbonyl]-6,11-dihydro-5H-pyrido-[2,3-b][1,5]benzo-diazepine | 370 |

Examples 3 and 4: 6-[(Trans-4-methoxycyclohexyl)carbonyl]-8-(pyrrolidin-1-ylcarbonyl)-6,11-dihydro-5H-pyrido[2,3-b][1,5]benzodiazepine and 6-[(Cis-4-methoxycyclohexyl)carbonyl]-8-(pyrrolidin-1-ylcarbonyl)-6,11-dihydro-5H-pyrido[2,3-b][1,5]benzodiazepine Examples 5 and 6: 1-Cyclopropyl-2,2,2-trifluoro-N-({6-[(trans-4-methoxycyclohexyl)carbonyl]-6,11-dihydro-5H-pyrido[2,3-b][1,5]benzodiazepin-8-yl}methyl)-N-methylethanamine and 1-Cyclopropyl-2,2,2-trifluoro-N-({6-[(cis-4-methoxycyclohexyl)carbonyl]-6,11-dihydro-5H-pyrido[2,3-b][1,5]benzodiazepin-8-yl}methyl)-N-methylethanamine

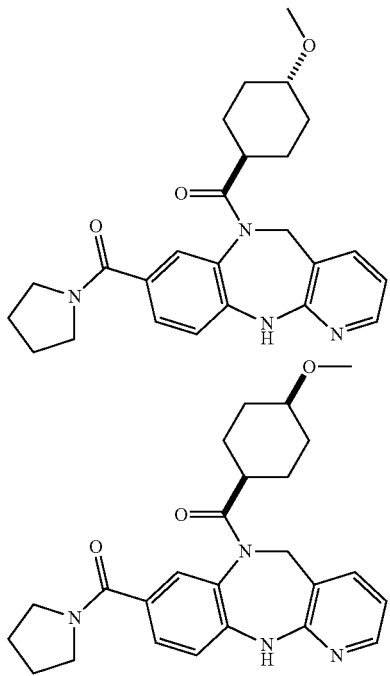

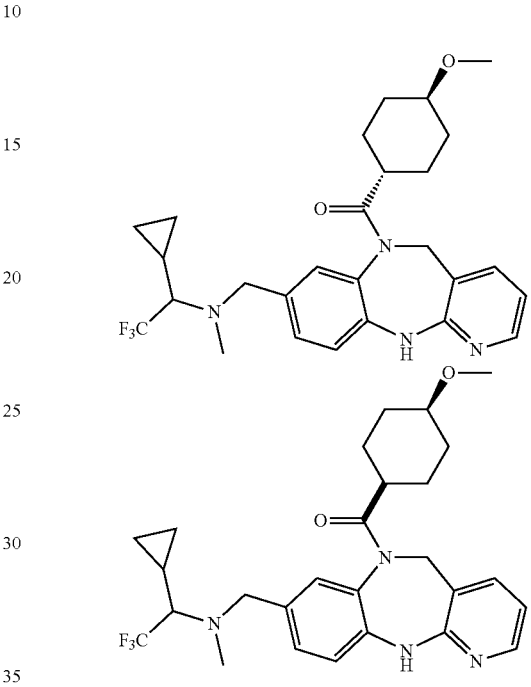

To a vial was added with (8-bromo-5H-benzo[b]pyrido[2,3-e][1,4]diazepin-6(11H)-yl)(4-methoxycyclohexyl)methanone (25 mg, 0.06 mmol, trans/cis: ~10:1), pyrrolidine (22 mg, 0.30 mmol), palladium acetate (1.35 mg, 10 mol %), Xantphos (5.2 mg, 15 mol %), sodium carbonate (31.8 mg, 0.302 mmol) and dioxane (0.52 mL). The reaction mixture was stirred at 80° C. with 15 PSIG carbon monoxide for 18 hours. After completion, the reaction mixture was diluted with methanol, filtered, and concentrated under reduced pressure. The residue was purified by mass triggered reverse phase HPLC (ACN/water with 0.1% $NH_4OH$) to afford the title compounds, both as solid TFA salts.

Trans:

MS 435 (M+1). $^1$H NMR (400 MHz, $CH_3OH$-$d_4$) δ 8.05 (d, J=4.9 Hz, 1H), 7.53-7.46 (m, 3H), 7.30-7.28 (m, 1H), 6.79 (dd, J=7.4, 4.9 Hz, 1H), 5.28 (d, J=14.9 Hz, 1H), 3.97 (d, J=14.8 Hz, 1H), 3.59-3.54 (m, 4H), 3.23 (s, 3H), 3.05-2.98 (m, 1H), 2.57-2.49 (m, 1H), 2.10-2.05 (m, 1H), 1.99-1.84 (m, 7H), 1.64-1.53 (m, 1H), 1.34-1.30 (m, 1H), 1.13-0.93 (m, 2H), 0.79-0.69 (m, 1H).

Cis:

MS: 435 (M+1). $^1$H NMR (500 MHz, $CH_3OH$-$d_4$): δ 8.08 (d, J=4.9 Hz, 1H), 7.56 (d, J=7.4 Hz, 1H), 7.50 (d, J=10.6 Hz, 2H), 7.31 (d, J=8.3 Hz, 1H), 6.82 (dd, J=7.3, 4.9 Hz, 1H), 5.31 (d, J=14.9 Hz, 1H), 3.99 (d, J=14.9 Hz, 1H), 3.61 (t, J=7.1 Hz, 4H), 3.21 (s, 3H), 2.67-2.63 (m, 2H), 2.00-1.86 (m, 7H), 1.70-1.59 (m, 2H), 1.37-1.27 (m, 2H), 1.09-1.02 (m, 2H).

To a vial equipped with a stir bar was added tert-butyl 8-formyl-6-(4-methoxycyclohexanecarbonyl)-5H-benzo[b]pyrido[2,3-e][1,4]diazepine-11(6H)-carboxylate (15 mg, 0.032 mmol) and 1-cyclopropyl-2,2,2-trifluoro-N-methylethanamine, HCl (12 mg, 0.064 mmol). The mixture was dissolved in MeOH/acetic acid (0.5 mL, 10:1) and then 2-picoline-borane complex (8.0 mg, 0.074 mmol) was added. The reaction was stirred at room temperature for 16 h. After completion, the mixture was concentrated under reduced pressure. The residue was treated with TFA/DCM (1 mL, 1:1) at room temperature for 30 min. The reaction mixture was concentrated under reduced pressure and the residue was purified by mass triggered reverse phase HPLC (ACN/water with 0.1% $NH_4OH$) to afford the title compounds, both as solid TFA salts.

Trans:

MS: 503 (M+1). $^1$H NMR (500 MHz, $CH_3OH$-$d_4$): δ 8.03 (d, J=4.9 Hz, 1H), 7.52 (d, J=7.3 Hz, 1H), 7.25-7.18 (m, 3H), 6.76 (dd, J=7.3, 5.0, 1H), 5.32 (d, J=14.9 Hz, 1H), 3.99 (d, J=14.9 Hz, 1H), 3.90-3.80 (m, 2H), 3.28-3.25 (m, 3H), 3.10-3.00 (m, 1H), 2.57-2.50 (m, 2H), 2.45-2.42 (m, 3H), 2.09 (s, 1H), 1.96-1.92 (m, 1H), 1.90-1.87 (m, 1H), 1.66-1.58 (m, 1H), 1.38-1.35 (m, 1H), 1.20-1.15 (m, 2H), 1.04-0.96 (m, 1H), 0.78-0.72 (m, 3H), 0.55-0.44 (m, 2H).

Cis:

MS: 503 (M+1). $^1$H NMR (500 MHz, $CH_3OH$-$d_4$): δ 8.03 (d, J=4.9 Hz, 1H), 7.52 (d, J=7.3 Hz, 1H), 7.22-7.17 (m, 3H), 6.76 (dd, J=7.3, 5.0 Hz, 1H), 5.32 (d, J=14.9 Hz, 1H), 3.98 (d, J=14.8 Hz, 1H), 3.90-3.80 (m, 2H), 3.25-3.21 (m, 3H), 3.20-3.17 (m, 1H), 2.64-2.52 (m, 2H), 2.48-2.43 (m, 3H), 1.98-1.86 (m, 2H), 1.71 (s, 1H), 1.60 (s, 1H), 1.44-1.38 (m,

1H), 1.30-1.23 (m, 1H), 1.22-1.16 (m, 1H), 1.05-0.99 (m, 2H), 0.78-0.72 (m, 2H), 0.48-0.43 (m, 2H).

Examples 7 and 8: 6-[(Trans-4-methoxycyclohexyl)carbonyl]-8-(2,2,2-trifluoro-1-pyrrolidin-1-ylethyl)-6,11-dihydro-5H-pyrido[2,3-b][1,5]benzodiazepine and 6-[(Cis-4-methoxycyclohexyl)carbonyl]-8-(2,2,2-trifluoro-1-pyrrolidin-1-ylethyl)-6,11-dihydro-5H-pyrido[2,3-b][1,5]benzodiazepine

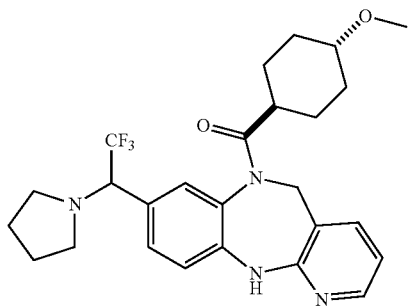

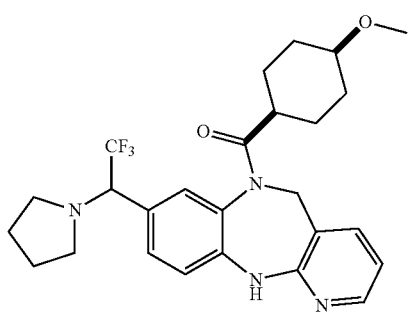

Step 1:

4-Methoxycyclohexanecarboxylic acid (153 mg, 0.968 mmol) was dissolved in DCM (1.8 mL) and one drop of DMF was added. Oxalyl chloride (129 mg, 1.01 mmol) was added to the reaction mixture. The reaction was stirred at room temperature for 1 h, and then concentrated under reduced pressure. To a separate flask was added tert-butyl 8-formyl-5H-benzo[b]pyrido[2,3-e][1,4]diazepine-11(6H)-carboxylate (300 mg, 0.922 mmol) and N,N-dimethylpyridin-4-amine (5.6 mg, 0.046 mmol) in DCE (4 mL). The mixture was heated to 82° C., and to this hot mixture was added freshly prepared acyl chloride in DCE (1.5 mL). The reaction was heated at 82° C. for 16 h and then cooled to room temperature. The mixture was concentrated under reduced pressure. The residue was purified by column chromatography on silica gel (0-40% EtOAc/Hexane) to give tert-butyl 8-formyl-6-(4-methoxycyclohexanecarbonyl)-5H-benzo[b]pyrido[2,3-e][1,4]diazepine-11(6H)-carboxylate. MS: 466 (M+1).

Step 2:

To a solution of tert-butyl 8-formyl-6-(4-methoxycyclohexanecarbonyl)-5H-benzo[b]pyrido[2,3-e][1,4]diazepine-11(6H)-carboxylate (48.6 mg, 0.104 mmol) in DCM (0.3 mL) at 0° C. was added 1-(trimethylsilyl)pyrrolidine (0.036 mL, 0.21 mmol) and trimethylsilyl trifluoromethanesulfonate (42 µL, 0.23 mmol). The cooling bath was removed, and the mixture was stirred for 1 h at room temperature. The reaction mixture was concentrated under reduced pressure, and the residue was dissolved in DMF (0.3 mL). Trimethyl (trifluoromethyl)silane (0.5 M in THF, 460 µL) and potassium fluoride (30 mg, 0.52 mmol) were added. The reaction was stirred at room temperature for 16 h. The residue was purified by mass triggered reverse phase HPLC (ACN/water with 0.1% NH$_4$OH) to afford title compounds both as solid TFA salts.

Trans:

MS: 489 (M+1). $^1$H NMR (500 MHz, CH$_3$OH-d$_4$): δ 8.05 (d, J=4.8 Hz, 1H), 7.54 (d, J=7.4 Hz, 1H), 7.38-7.33 (m, 2H), 7.26 (d, J=8.3 Hz, 1H), 6.80-6.76 (m, 1H), 5.32 (d, J=14.9 Hz, 1H), 4.03-3.96 (m, 2H), 3.26 (s, 3H), 3.10-3.04 (m, 1H), 2.69 (s, 2H), 2.61-2.58 (m, 2H), 2.56-2.48 (m, 1H), 2.12-2.07 (m, 1H), 1.97-1.92 (m, 1H), 1.90-1.87 (m, 1H), 1.83-1.80 (m, 4H), 1.65-1.59 (m, 1H), 1.34-1.29 (m, 1H), 1.19-1.10 (m, 1H), 1.02-0.95 (m, 1H), 0.75-0.69 (m, 1H).

Cis:

MS: 489 (M+1). $^1$H NMR (500 MHz, CH$_3$OH-d$_4$): δ 8.05 (d, J=4.9 Hz, 1H), 7.54 (d, J=7.4 Hz, 1H), 7.38-7.32 (m, 2H), 7.26 (d, J=8.4 Hz, 1H), 6.80-6.76 (m, 1H), 5.32 (d, J=14.9 Hz, 1H), 4.03-3.97 (m, 2H), 3.22 (s, 3H), 2.69 (s, 2H), 2.59 (s, 3H), 2.01-1.96 (m, 1H), 1.89-1.87 (m, 1H), 1.82-1.80 (m, 4H), 1.74-1.70 (m, 1H), 1.61 (br s, 2H), 1.41-1.33 (m, 1H), 1.25-1.21 (m, 1H), 1.02-0.93 (m, 2H).

Example 9: 8-(5,6-Dihydro-1,4-dioxin-2-yl)-6-[(trans-4-methoxycyclohexyl)carbonyl]-6,11-dihydro-5H-pyrido[2,3-b][1,5]benzodiazepine

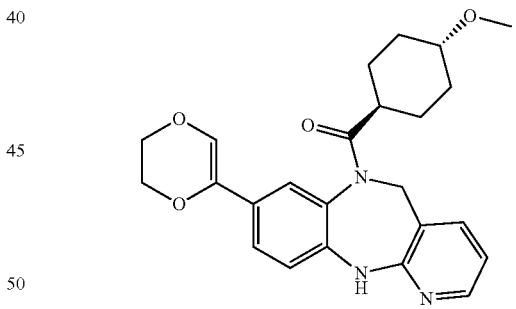

To a microwave vial was added palladium(II) hexafluoroacetylacetonate (3 mg, 0.006 mmol), tri-tert-butylphosphonium tetrafluoroborate (3.5 mg, 0.012 mmol), and 1,3-dimethyl-3,4,5,6-tetrahydro-2(1H)-pyrimidinone (0.5 mL). The reaction mixture was evacuated and refilled with nitrogen gas three times. After stirring at room temperature for 10 minutes, (8-bromo-5,11-dihydro-6H-pyrido[2,3-b][1,5]benzodiazepin-6-yl)(trans-4-methoxycyclohexyl)methanone (50 mg, 0.12 mmol), N,N-diisopropylethylamine (0.031 mL, 0.180 mmol), and 1,4-dioxene (0.096 mL, 1.2 mmol) were added sequentially. The reaction mixture was heated at 120° C. for 16 h. The reaction was quenched with methanol, filtered, and concentrated under reduced pressure. The residue was purified by mass triggered reverse phase HPLC (ACN/water with 0.1% NH$_4$OH) to afford the title compound as a solid TFA salt. MS: 422 (M+1). ¹H NMR (500 MHz, CH₃OH-d₄): δ 8.03 (d, J=4.9 Hz, 1H), 7.52 (d, J=7.5 Hz, 1H), 7.34 (d, J=8.6 Hz, 1H), 7.27 (s, 1H), 7.17 (d, J=8.6 Hz, 1H), 6.78-6.75 (m, 1H), 6.73 (s, 1H), 5.30 (d, J=14.9 Hz, 1H), 4.28-4.25 (m, 2H), 4.16-4.12 (m, 2H), 3.99 (d, J=14.9 Hz, 1H), 3.22 (s, 3H), 3.09-3.02 (m, 1H), 2.53-2.49 (m, 1H), 2.12-2.09 (m, 1H), 1.95-1.86 (m, 3H), 1.63-1.58 (m, 1H), 1.40-1.37 (m, 1H), 1.19-1.12 (m, 1H), 1.06-0.98 (m, 1H), 0.81-0.74 (m, 1H).

Example 10: 8-(1,4-Dioxan-2-yl)-6-[(trans-4-methoxycyclohexyl)carbonyl]-6,11-dihydro-5H-pyrido[2,3-b][1,5]benzodiazepine

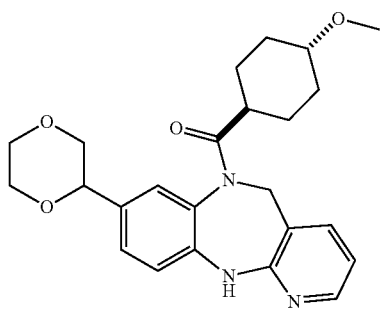

To as flask containing Example 12 (42.5 mg, 0.101 mmol) and palladium on carbon (10 mol %, 10 mg, 0.01 mmol) was added methanol (5 mL). The mixture was stirred at room temperature under an atmosphere of hydrogen (balloon) for 16 h. The mixture was filtered over celite and concentrated under reduced pressure. The residue was purified by mass triggered reverse phase HPLC (ACN/water with 0.1% NH₄OH) to afford the title compound as a solid. MS: 424 (M+1). ¹H NMR (500 MHz, CH₃OH-d₄): δ 8.04 (s, 1H), 7.52 (d, J=7.3 Hz, 1H), 7.29-7.20 (m, 3H), 6.79-6.75 (m, 1H), 5.31 (d, J=14.9 Hz, 1H), 4.66-4.61 (m, 1H), 4.01-3.78 (m, 5H), 3.73-3.68 (m, 1H), 3.45-3.41 (m, 1H), 3.27 (s, 3H), 3.07-3.04 (m, 1H), 2.51-245 (m, 1H), 2.15-2.10 (m, 1H), 1.97 (br s, 1H), 1.87 (br s, 1H), 1.66-1.56 (m, 1H), 1.36-1.32 (m, 1H), 1.16-1.13 (m, 1H), 1.04-0.99 (m, 1H), 0.79-0.71 (m, 1H).

Example 11: Tert-butyl 4-(8-morpholino-6,11-dihydro-5H-benzo[b]pyrido[2,3-e][1,4]diazepine-6-carbonyl)piperidine-1-carboxylate

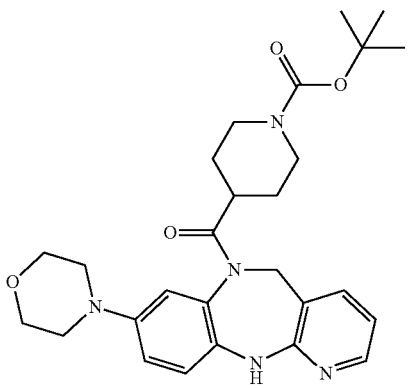 [SMILES: CC(C)(C)OC(=O)N1CCC(C(=O)N2Cc3cccnc3Nc3ccc(N4CCOCC4)cc32)CC1]

To a solution of 1-(tert-butoxycarbonyl) piperidine-4-carboxylic acid (1 g, 4.36 mmol) in dichloromethane (44 mL) was added one drop of DMF. The solution was cooled to 0° C. and oxalyl chloride (0.40 mL, 4.6 mmol) was added. The reaction mixture was warmed to room temperature and stirred for 2.5 h. The mixture was concentrated under reduced pressure to afford crude tert-butyl 4-(chlorocarbonyl)piperidine-1-carboxylate (1.1 g, 4.3 mmol). The acid chloride (0.53 g, 2.1 mmol) which was taken up in DCE (5 mL) and added to a suspension of 4-(6,11-dihydro-5H-benzo[b]pyrido[2,3-e][1,4]diazepin-8-yl)morpholine (0.6 g, 2.13 mmol) in DCE (15 mL) at 80° C. via syringe. DMAP (0.026 g, 0.21 mmol) was added, and the reaction was heated at 80° C. for 18 h. Another equivalent of tert-butyl 4-(chlorocarbonyl)piperidine-1-carboxylate (0.53 g, 2.1 mmol) was added and the mixture was heated at 80° C. for another 18 h. The reaction mixture was cooled to room temperature, diluted with DCM, and washed with aqueous sodium bicarbonate. The aqueous layer was extracted with DCM (2×), and the combined organic layers were dried over sodium sulfate, filtered, and concentrated under reduced pressure. The residue was purified by column chromatography on silica gel (0-5% MeOH/DCM), followed by a second purification using reverse phase HPLC (10-90% ACN/water with 0.05% TFA over 10 min.) to afford the title compound as a solid TFA salt. MS: 495 (M+1). ¹H NMR (500 MHz, CD₃OD) δ 7.98 (d, J=6.2 Hz, 2H), 7.31 (d, J=8.8 Hz, 1H), 7.15-7.05 (m, 1H), 7.01 (s, 1H) 7.05-6.95 (m, 1H), 5.45-5.35 (m, 1H), 4.15-4.02 (m, 1H), 3.90-3.80 (m, 4H), 3.25-3.12 (m, 5H), 3.05-2.91 (m, 1H), 2.88-2.71 (m, 1H), 2.15-2.06 (m, 1H), 2.05-1.98 (m, 1H), 1.89-1.82 (m, 1H), 1.75-1.60 (m, 1H), 1.60-1.45 (m, 1H), 1.38 (s, 9H), 1.20-1.10 (m, 1H).

The compounds in the following table were prepared using the methodology herein and the general procedure described in Example 11.

| Ex. No. | Structure | Compound Name | [M + H]+ |
|---|---|---|---|
| 12 | Isomer 1 | (8-(1,4-dioxan-2-yl)-5,11-dihydro-6H-benzo[b]pyrido[2,3-e][1,4]diazepin-6-yl)((2R,5S)-5-isopropoxytetrahydro-2H-pyran-2-yl)methanone | 454 |
| 13 | Isomer 2 | (8-(1,4-dioxan-2-yl)-5,11-dihydro-6H-benzo[b]pyrido[2,3-e][1,4]diazepin-6-yl)((2R,5S)-5-isopropoxytetrahydro-2H-pyran-2-yl)methanone | 454 |
| 14 | 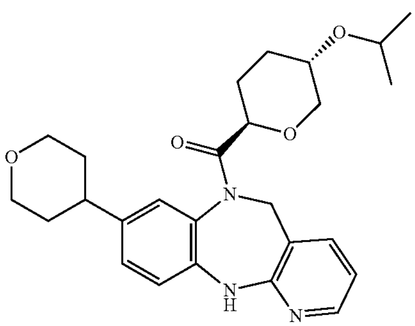 [SMILES: CC(C)O[C@H]1CC[C@H](C(=O)N2Cc3cccnc3Nc3ccc(C4CCOCC4)cc32)OC1] | ((2R,5S)-5-isopropoxytetrahydro-2H-pyran-2-yl)(8-(tetrahydro-2H-pyran-4-yl)-5,11-dihydro-6H-benzo[b]pyrido[2,3-e][1,4]diazepin-6-yl)methanone | 452 |
| 15 | Isomer 1 | ((2R,5S)-5-isopropoxytetrahydro-2H-pyran-2-yl)(8-(tetrahydrofuran-3-yl)-5,11-dihydro-6H-benzo[b]pyrido[2,3-e][1,4]diazepin-6-yl)methanone | 438 |

-continued

| Ex. No. | Structure | Compound Name | [M + H]+ |
|---|---|---|---|
| 16 | Isomer 2 | ((2R,5S)-5-isopropoxytetrahydro-2H-pyran-2-yl)(8-(tetrahydrofuran-3-yl)-5,11-dihydro-6H-benzo[b]pyrido[2,3-e][1,4]diazepin-6-yl)methanone | 438 |
| 17 | 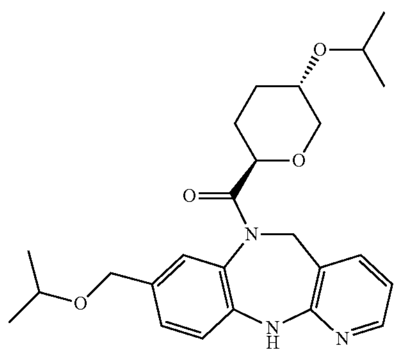 [SMILES: CC(C)OCc1ccc2c(c1)N(C(=O)[C@H]1CC[C@H](OC(C)C)CO1)Cc1cccnc1N2] | (8-(isopropoxymethyl)-5,11-dihydro-6H-benzo[b]pyrido[2,3-e][1,4]diazepin-6-yl)((2R,5S)-5-isopropoxytetrahydro-2H-pyran-2-yl)methanone | 440 |
| 18 | and diastereomer | (8-(1,2-dimethoxyethyl)-5,11-dihydro-6H-benzo[b]pyrido[2,3-e][1,4]diazepin-6-yl)((2R,5S)-5-isopropoxytetrahydro-2H-pyran-2-yl)methanone | 456 |
| 19 | 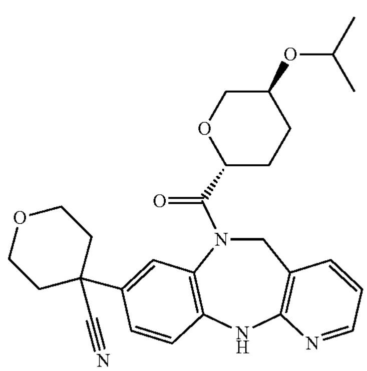 [SMILES: CC(C)O[C@H]1CC[C@H](C(=O)N2Cc3cccnc3Nc3ccc(C4(C#N)CCOCC4)cc32)OC1] | 4-(6-((2R,5S)-5-isopropoxytetrahydro-2H-pyran-2-carbonyl)-6,11-dihydro-5H-benzo[b]pyrido[2,3-e][1,4]diazepin-8-yl)tetrahydro-2H-pyran-4-carbonitrile | 477 |

| Ex. No. | Structure | Compound Name | [M + H]+ |
|---|---|---|---|
| 20 | Isomer 1 | (8-(1,2-dimethoxyethyl)-5,11-dihydro-6H-benzo[b]pyrido[2,3-e][1,4]diazepin-6-yl)((2R,5S)-5-isopropoxytetrahydro-2H-pyran-2-yl)methanone | 456 |
| 21 | Isomer 2 | (8-(1,2-dimethoxyethyl)-5,11-dihydro-6H-benzo[b]pyrido[2,3-e][1,4]diazepin-6-yl)((2R,5S)-5-isopropoxytetrahydro-2H-pyran-2-yl)methanone | 456 |
| 22 | 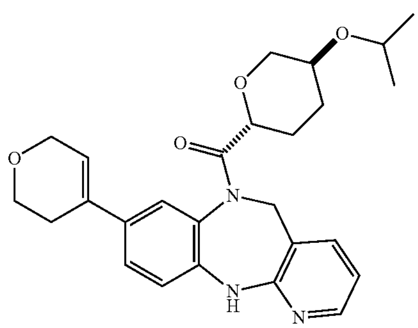 | (8-(3,6-dihydro-2H-pyran-4-yl)-5,11-dihydro-6H-benzo[b]pyrido[2,3-e][1,4]diazepin-6-yl)((2R,5S)-5-isopropoxytetrahydro-2H-pyran-2-yl)methanone | 450 |
| 23 | 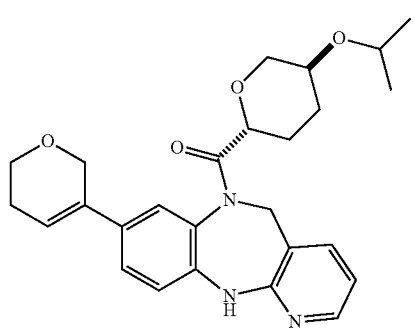 | (8-(5,6-dihydro-2H-pyran-3-yl)-5,11-dihydro-6H-benzo[b]pyrido[2,3-e][1,4]diazepin-6-yl)((2R,5S)-5-isopropoxytetrahydro-2H-pyran-2-yl)methanone | 450 |

| Ex. No. | Structure | Compound Name | [M + H]+ |
| --- | --- | --- | --- |
| 24 | Isomer 1 | ((2R,5S)-5-isopropoxytetrahydro-2H-pyran-2-yl)(8-(3-methyl-1,4-dioxan-2-yl)-5,11-dihydro-6H-benzo[b]pyrido[2,3-e][1,4]diazepin-6-yl)methanone | 468 |
| 25 | Isomer 2 | ((2R,5S)-5-isopropoxytetrahydro-2H-pyran-2-yl)(8-(3-methyl-1,4-dioxan-2-yl)-5,11-dihydro-6H-benzo[b]pyrido[2,3-e][1,4]diazepin-6-yl)methanone | 468 |
| 26 | 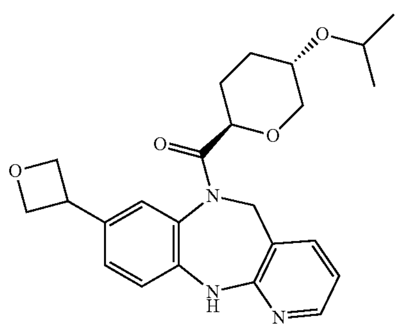 [SMILES: CC(C)O[C@H]1CC[C@H](C(=O)N2Cc3cccnc3Nc3ccc(C4COC4)cc32)OC1] | ((2R,5S)-5-isopropoxytetrahydro-2H-pyran-2-yl)(8-(oxetan-3-yl)-5,11-dihydro-6H-benzo[b]pyrido[2,3-e][1,4]diazepin-6-yl)methanone | 424 |
| 27 | Isomer 1 | ((2R,5S)-5-isopropoxytetrahydro-2H-pyran-2-yl)(8-(tetrahydro-2H-pyran-3-yl)-5,11-dihydro-6H-benzo[b]pyrido[2,3-e][1,4]diazepin-6-yl)methanone | 452 |

| Ex. No. | Structure | Compound Name | [M + H]+ |
| --- | --- | --- | --- |
| 28 | Isomer 2 | ((2R,5S)-5-isopropoxytetrahydro-2H-pyran-2-yl)(8-(tetrahydro-2H-pyran-3-yl)-5,11-dihydro-6H-benzo[b]pyrido[2,3-e][1,4]diazepin-6-yl)methanone | 452 |
| 29 | Isomer 1 | (8-(2,5-dioxabicyclo[4.1.0]heptan-3-yl)-5,11-dihydro-6H-benzo[b]pyrido[2,3-e][1,4]diazepin-6-yl)((2R,5S)-5-isopropoxytetrahydro-2H-pyran-2-yl)methanone | 466 |
| 30 | Isomer 2 | (8-(2,5-dioxabicyclo[4.1.0]heptan-3-yl)-5,11-dihydro-6H-benzo[b]pyrido[2,3-e][1,4]diazepin-6-yl)((2R,5S)-5-isopropoxytetrahydro-2H-pyran-2-yl)methanone | 466 |
| 31 | Isomer 3 | (8-(2,5-dioxabicyclo[4.1.0]heptan-3-yl)-5,11-dihydro-6H-benzo[b]pyrido[2,3-e][1,4]diazepin-6-yl)((2R,5S)-5-isopropoxytetrahydro-2H-pyran-2-yl)methanone | 466 |

| Ex. No. | Structure | Compound Name | [M + H]+ |
|---|---|---|---|
| 32 | 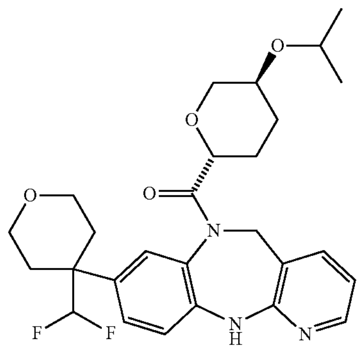 | (8-(4-(difluoromethyl)tetrahydro-2H-pyran-4-yl)-5,11-dihydro-6H-benzo[b]pyrido[2,3-e][1,4]diazepin-6-yl)((2R,5S)-5-isopropoxytetrahydro-2H-pyran-2-yl)methanone | 502 |
| 33 | Isomer 3 | ((2R,5S)-5-isopropoxytetrahydro-2H-pyran-2-yl)(8-(3-methyl-1,4-dioxan-2-yl)-5,11-dihydro-6H-benzo[b]pyrido[2,3-e][1,4]diazepin-6-yl)methanone | 468 |
| 34 | Isomer 4 | ((2R,5S)-5-isopropoxytetrahydro-2H-pyran-2-yl)(8-(3-methyl-1,4-dioxan-2-yl)-5,11-dihydro-6H-benzo[b]pyrido[2,3-e][1,4]diazepin-6-yl)methanone | 468 |
| 35 | Isomer 5 | ((2R,5S)-5-isopropoxytetrahydro-2H-pyran-2-yl)(8-(3-methyl-1,4-dioxan-2-yl)-5,11-dihydro-6H-benzo[b]pyrido[2,3-e][1,4]diazepin-6-yl)methanone | 468 |

| Ex. No. | Structure | Compound Name | [M + H]+ |
|---|---|---|---|
| 36 | 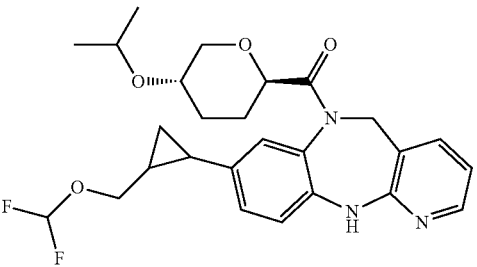 and diastereomers | (8-(2-((difluoromethoxy)methyl)cyclopropyl)-5,11-dihydro-6H-benzo[b]pyrido[2,3-e][1,4]diazepin-6-yl)((2R,5S)-5-isopropoxytetrahydro-2H-pyran-2-yl)methanone | 488 |
| 37 | 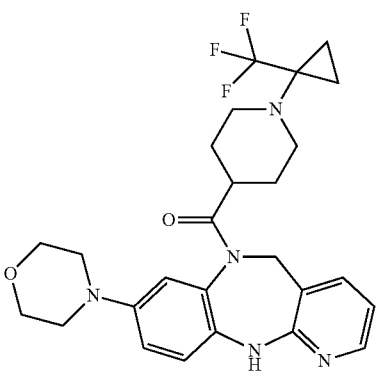 [SMILES: O=C(C1CCN(C2(C(F)(F)F)CC2)CC1)N1Cc2cccnc2Nc2ccc(N3CCOCC3)cc21] | 8-morpholin-4-yl-6-({1-[1-(trifluoromethyl)cyclopropyl]piperidin-4-yl}carbonyl)-6,11-dihydro-5H-pyrido[2,3-b][1,5]benzodiazepine | 502 |
| 38 | 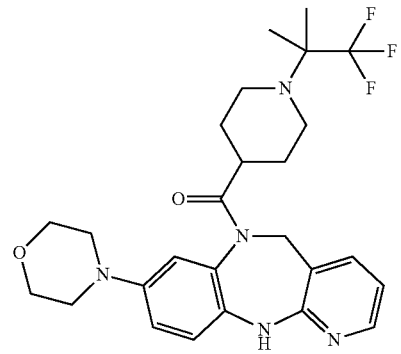 [SMILES: CC(C)(N1CCC(C(=O)N2Cc3cccnc3Nc3ccc(N4CCOCC4)cc32)CC1)C(F)(F)F] | 8-morpholin-4-yl-6-{[1-(2,2,2-trifluoro-1,1-dimethylethyl)piperidin-4-yl]carbonyl}-6,11-dihydro-5H-pyrido[2,3-b][1,5]benzodiazepine | 504 |
| 39 | 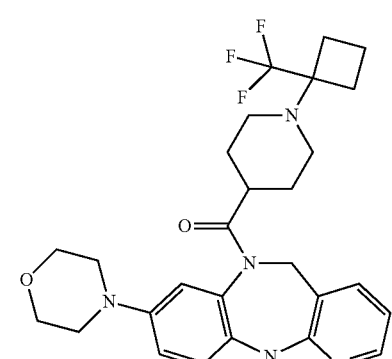 | 8-morpholin-4-yl-6-({1-[1-(trifluoromethyl)cyclobutyl]piperidin-4-yl}carbonyl)-6,11-dihydro-5H-pyrido[2,3-b][1,5]benzodiazepine | 516 |

| Ex. No. | Structure | Compound Name | [M + H]+ |
|---|---|---|---|
| 40 | Isomer 1 | (8-((1S,4S)-2-oxa-5-azabicyclo[2.2.2]octan-5-yl)-5,11-dihydro-6H-benzo[b]pyrido[2,3-e][1,4]diazepin-6-yl)((2R,5S)-5-isopropoxytetrahydro-2H-pyran-2-yl)methanone | 479 |
| 41 | Isomer 2 | (8-((1R,4R)-2-oxa-5-azabicyclo[2.2.2]octan-5-yl)-5,11-dihydro-6H-benzo[b]pyrido[2,3-e][1,4]diazepin-6-yl)((2R,5S)-5-isopropoxytetrahydro-2H-pyran-2-yl)methanone | 479 |
| 42 | 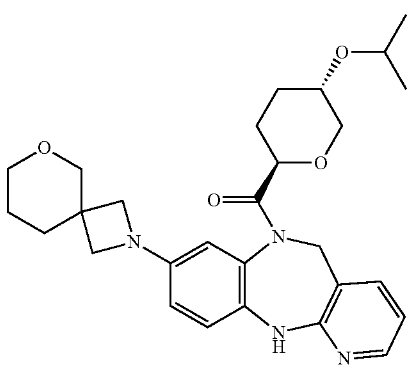 [SMILES: CC(C)O[C@H]1CC[C@H](C(=O)N2Cc3cccnc3Nc3ccc(N4CC5(CCCOC5)C4)cc32)OC1] | (8-(6-oxa-2-azaspiro[3.5]nonan-2-yl)-5,11-dihydro-6H-benzo[b]pyrido[2,3-e][1,4]diazepin-6-yl)((2R,5S)-5-isopropoxytetrahydro-2H-pyran-2-yl)methanone | 493 |
| 43 | Isomer 1 | ((2R,5S)-5-isopropoxytetrahydro-2H-pyran-2-yl)(8-((2R,4S)-4-methoxy-2-methylpiperidin-1-yl)-5,11-dihydro-6H-benzo[b]pyrido[2,3-e][1,4]diazepin-6-yl)methanone | 495 |

| Ex. No. | Structure | Compound Name | [M + H]+ |
| --- | --- | --- | --- |
| 44 | Isomer 2 | ((2R,5S)-5-isopropoxytetrahydro-2H-pyran-2-yl)(8-((2R,4R)-4-methoxy-2-methylpiperidin-1-yl)-5,11-dihydro-6H-benzo[b]pyrido[2,3-e][1,4]diazepin-6-yl)methanone | 495 |
| 45 | Isomer 1 | ((2R,5S)-5-isopropoxytetrahydro-2H-pyran-2-yl)(8-((2S,4R)-4-methoxy-2-methylpiperidin-1-yl)-5,11-dihydro-6H-benzo[b]pyrido[2,3-e][1,4]diazepin-6-yl)methanone | 495 |
| 46 | Isomer 2 | ((2R,5S)-5-isopropoxytetrahydro-2H-pyran-2-yl)(8-((2S,4S)-4-methoxy-2-methylpiperidin-1-yl)-5,11-dihydro-6H-benzo[b]pyrido[2,3-e][1,4]diazepin-6-yl)methanone | 495 |
| 47 | 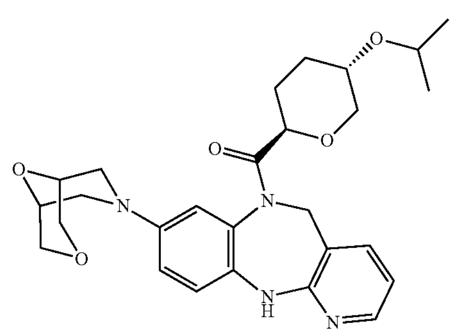 [SMILES: CC(C)O[C@H]1CC[C@H](C(=O)N2Cc3cccnc3Nc3ccc(N4CC5COCC(C4)O5)cc32)OC1] | (8-(3,9-dioxa-7-azabicyclo[3.3.1]nonan-7-yl)-5,11-dihydro-6H-benzo[b]pyrido[2,3-e][1,4]diazepin-6-yl)((2R,5S)-5-isopropoxytetrahydro-2H-pyran-2-yl)methanone | 495 |

| Ex. No. | Structure | Compound Name | [M + H]+ |
|---|---|---|---|
| 48 | 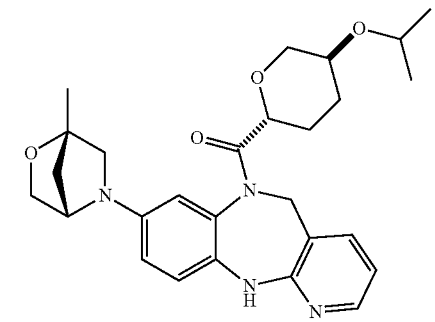 | ((2R,5S)-5-isopropoxytetrahydro-2H-pyran-2-yl)(8-((1S,4S)-1-methyl-2-oxa-5-azabicyclo[2.2.1]heptan-5-yl)-5,11-dihydro-6H-benzo[b]pyrido[2,3-e][1,4]diazepin-6-yl)methanone | 479 |
| 49 | 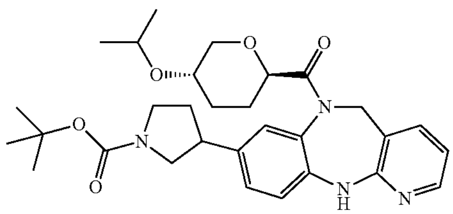 [SMILES: CC(C)O[C@H]1CC[C@H](C(=O)N2Cc3cccnc3Nc3ccc(C4CCN(C(=O)OC(C)(C)C)C4)cc32)OC1] | tert-butyl 3-(6-((2R,5S)-5-isopropoxytetrahydro-2H-pyran-2-carbonyl)-6,11-dihydro-5H-benzo[b]pyrido[2,3-e][1,4]diazepin-8-yl)pyrrolidine-1-carboxylate | 537 |
| 50 | Single isomer | 8-morpholin-4-yl-6-{[1-(2,2,2-trifluoroethyl)pyrrolidin-3-yl]carbonyl}-6,11-dihydro-5H-pyrido[2,3-b][1,5]benzodiazepine | 462 |
| 51 | Single isomer | 8-morpholin-4-yl-6-{[(3S)-1-(2,2,2-trifluoroethyl)piperidin-3-yl]carbonyl}-6,11-dihydro-5H-pyrido[2,3-b][1,5]benzodiazepine | 476 |

Examples 52 and 53: 6-[(Trans-4-methoxycyclohexyl)carbonyl]-8-morpholin-4-yl-6,11-dihydro-5H-pyrido[2,3-b][1,5]benzodiazepine and 6-[(Cis-4-methoxycyclohexyl)carbonyl]-8-morpholin-4-yl-6,11-dihydro-5H-pyrido[2,3-b][1,5]benzodiazepine

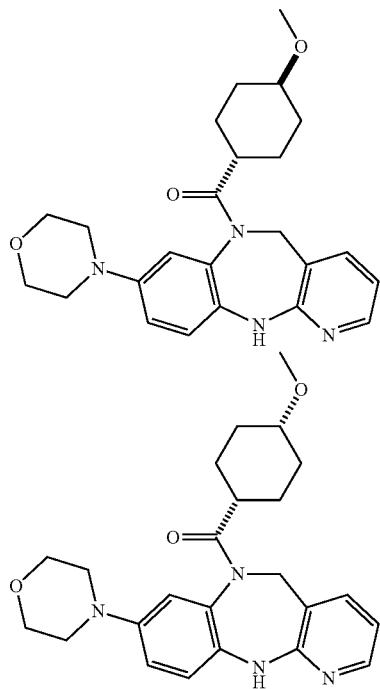

To a vial was added 8-(morpholin-4-yl)-6,11-dihydro-5H-pyrido[2,3-b][1,5]benzodiazepine (27 mg, 0.096 mmol), PS-PPh$_3$ (2.06 mmol/g loading, 139 mg, 0.287 mmol), 1,4-methoxycyclohexanecarboxylic acid (15 mg, 0.098 mmol), and acetonitrile (1.6 mL). Trichloroacetonitrile (48 µL, 0.48 mmol) was added and the reaction mixture was heated to 100° C. for 10 minutes in a microwave reactor. The material was filtered through celite and washed with methanol. The filtrate was concentrated under reduced pressure and the residue was purified by mass triggered reverse phase HPLC (ACN/water with 0.1% TFA modifier) to afford both isomers as follows:

Peak 1: Ex. 52 as a solid TFA salt. MS: 423 (M+1). $^1$H NMR (500 MHz, DMSO-d$_6$) δ 9.72 (s, 1H), 8.03 (d, J=5.0 Hz, 1H), 7.63 (d, J=7.3 Hz, 1H), 7.23 (d, J=8.9 Hz, 1H), 7.00-6.96 (m, 1H), 6.90 (s, 1H), 6.80-6.76 (m, 1H), 5.22 (d, J=15.1 Hz, 1H), 3.93 (d, J=14.9 Hz, 1H), 3.79-3.68 (m, 2H), 3.14 (s, 3H), 3.12-3.08 (m, 2H), 3.07-3.00 (m, 2H), 3.00-2.92 (m, 1H), 2.48-2.38 (m, 1H), 2.03-1.95 (m, 1H), 1.95-1.87 (m, 1H), 1.83-1.72 (m, 1H), 1.50-1.37 (m, 1H), 1.27-1.16 (m, 2H), 1.09-0.96 (m, 1H), 0.95-0.80 (m, 2H), 0.71-0.60 (m, 1H).

Peak 2: Ex. 53 as a solid TFA salt. MS: 423 (M+1). $^1$H NMR (500 MHz, DMSO-d$_6$) δ 9.70 (s, 1H), 8.03 (d, J=4.4 Hz, 1H), 7.64 (d, J=7.0 Hz, 1H), 7.22 (d, J=8.9 Hz, 1H), 7.00-6.94 (m, 1H), 6.89 (s, 1H), 6.82-6.75 (m, 1H), 5.22 (d, J=15.0 Hz, 1H), 3.91 (d, J=15.0 Hz, 1H), 3.77-3.68 (m, 5H), 3.23 (s, 1H), 3.11 (s, 3H), 3.07-3.00 (m, 2H), 2.57-2.52 (m, 1H), 1.86-1.78 (m, 1H), 1.75-1.66 (m, 1H), 1.60-1.52 (m, 2H), 1.29-1.16 (m, 2H), 1.03-0.80 (m, 3H).

The compounds in the following table were prepared using the methodology herein and the general procedure described in Examples 52 and 53.

| Ex. No. | Structure | Chemical Name | [M + H]+ |
|---|---|---|---|
| 54 | 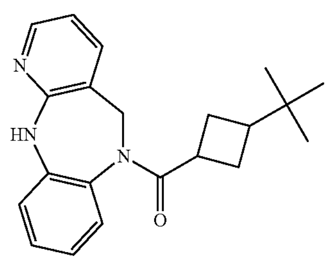 [SMILES: CC(C)(C)C1CC(C(=O)N2Cc3cccnc3Nc3ccccc32)C1] | 6-[(3-tert-butylcyclobutyl)carbonyl]-6,11-dihydro-5H-pyrido[2,3-b][1,5]benzodiazepine | 336 |
| 55 | 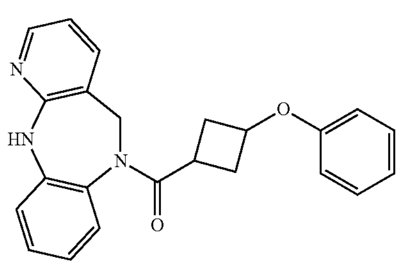 [SMILES: O=C(C1CC(Oc2ccccc2)C1)N1Cc2cccnc2Nc2ccccc21] | 6-[(3-phenoxycyclobutyl)carbonyl]-6,11-dihydro-5H-pyrido[2,3-b][1,5]benzodiazepine | 372 |

-continued

| Ex. No. | Structure | Chemical Name | [M + H]+ |
| --- | --- | --- | --- |
| 56 | 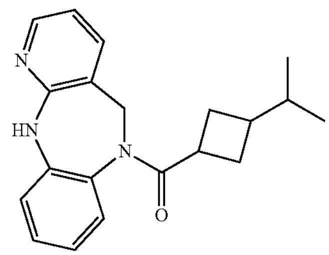 [SMILES: CC(C)C1CC(C(=O)N2Cc3cccnc3Nc3ccccc32)C1] | 6-{[3-(1-methylethyl)cyclobutyl]carbonyl}-6,11-dihydro-5H-pyrido[2,3-b][1,5]benzodiazepine | 322 |
| 57 | 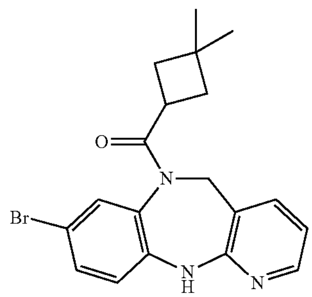 [SMILES: CC1(C)CC(C(=O)N2Cc3cccnc3Nc3ccc(Br)cc32)C1] | 8-bromo-6-[(3,3-dimethylcyclobutyl)carbonyl]-6,11-dihydro-5H-pyrido[2,3-b][1,5]benzodiazepine | 386 |
| 58 | 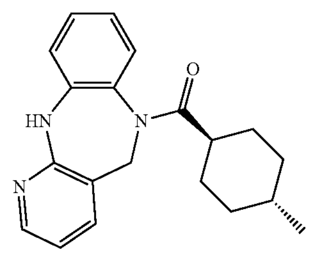 [SMILES: C[C@H]1CC[C@H](C(=O)N2Cc3cccnc3Nc3ccccc32)CC1] | 6-[(trans-4-methylcyclohexyl)carbonyl]-6,11-dihydro-5H-pyrido[2,3-b][1,5]benzodiazepine | 322 |
| 59 | 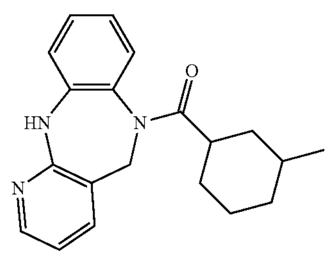 [SMILES: CC1CCCC(C(=O)N2Cc3cccnc3Nc3ccccc32)C1] | 6-[(3-methylcyclohexyl)carbonyl]-6,11-dihydro-5H-pyrido[2,3-b][1,5]benzodiazepine | 322 |
| 60 | 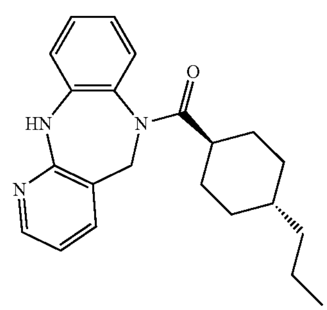 [SMILES: CCC[C@H]1CC[C@H](C(=O)N2Cc3cccnc3Nc3ccccc32)CC1] | 6-[(trans-4-propylcyclohexyl)carbonyl]-6,11-dihydro-5H-pyrido[2,3-b][1,5]benzodiazepine | 350 |

-continued

| Ex. No. | Structure | Chemical Name | [M + H]+ |
|---|---|---|---|
| 61 | 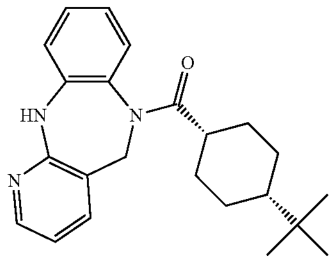 [SMILES: CC(C)(C)[C@H]1CC[C@@H](C(=O)N2Cc3cccnc3Nc3ccccc32)CC1] | 6-[(cis-4-tert-butylcyclohexyl)carbonyl]-6,11-dihydro-5H-pyrido[2,3-b][1,5]benzodiazepine | 364 |
| 62 | 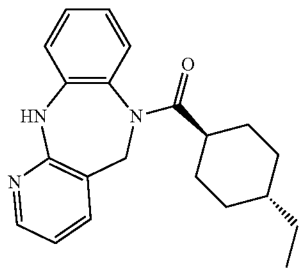 [SMILES: CC[C@H]1CC[C@H](C(=O)N2Cc3cccnc3Nc3ccccc32)CC1] | 6-[(trans-4-ethylcyclohexyl)carbonyl]-6,11-dihydro-5H-pyrido[2,3-b][1,5]benzodiazepine | 336 |
| 63 | Single Trans Isomer | 6-{[(1S,3S)-3-ethoxycyclopentyl]carbonyl}-8-morpholin-4-yl-6,11-dihydro-5H-pyrido[2,3-b][1,5]benzodiazepine | 423 |
| 64 | Single Trans Isomer | 6-{[(1R,3R)-3-(1-methylethoxy)cyclopentyl]carbonyl}-8-morpholin-4-yl-6,11-dihydro-5H-pyrido[2,3-b][1,5]benzodiazepine | 437 |

| Ex. No. | Structure | Chemical Name | [M + H]+ |
|---|---|---|---|
| 65 | Cis Isomer | 6-{[(1S,3R)-3-ethoxycyclopentyl]carbonyl}-8-morpholin-4-yl-6,11-dihydro-5H-pyrido[2,3-b][1,5]benzodiazepine | 423 |
| 66 | Cis Isomer | 6-{[(1S,3R)-3-(1-methylethoxy)cyclopentyl]carbonyl}-8-morpholin-4-yl-6,11-dihydro-5H-pyrido[2,3-b][1,5]benzodiazepine | 437 |
| 67 | 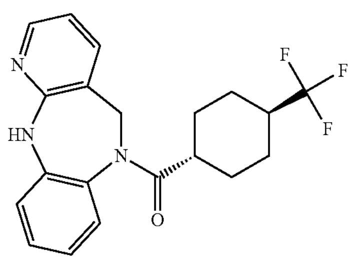 [SMILES: O=C([C@H]1CC[C@H](C(F)(F)F)CC1)N1Cc2cccnc2Nc2ccccc21] | 6-{[trans-4-(trifluoromethyl)cyclohexyl]carbonyl}-6,11-dihydro-5H-pyrido[2,3-b][1,5]benzodiazepine | 376 |
| 68 | 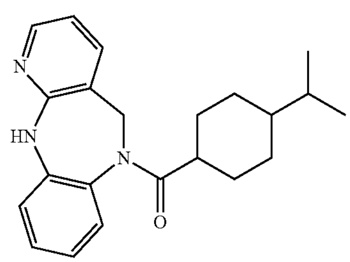 [SMILES: CC(C)C1CCC(C(=O)N2Cc3cccnc3Nc3ccccc32)CC1] | 6-{[4-(1-methylethyl)cyclohexyl]carbonyl}-6,11-dihydro-5H-pyrido[2,3-b][1,5]benzodiazepine | 350 |
| 69 | 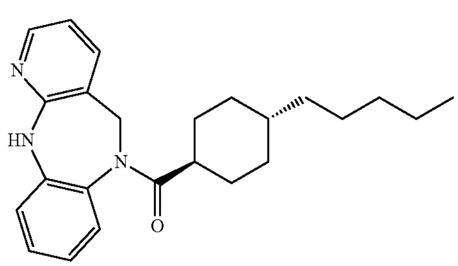 [SMILES: CCCCC[C@H]1CC[C@H](C(=O)N2Cc3cccnc3Nc3ccccc32)CC1] | 6-[(trans-4-pentylcyclohexyl)carbonyl]-6,11-dihydro-5H-pyrido[2,3-b][1,5]benzodiazepine | 378 |

| Ex. No. | Structure | Chemical Name | [M + H]+ |
|---|---|---|---|
| 70 | 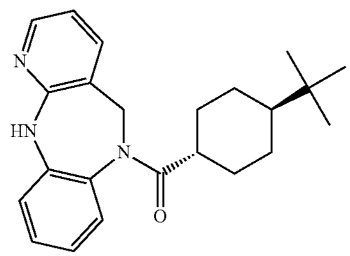 [SMILES: CC(C)(C)[C@H]1CC[C@H](C(=O)N2Cc3cccnc3Nc3ccccc32)CC1] | 6-[(trans-4-tert-butylcyclohexyl)carbonyl]-6,11-dihydro-5H-pyrido[2,3-b][1,5]benzodiazepine | 364 |
| 71 | 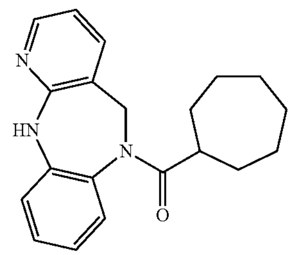 [SMILES: O=C(C1CCCCCC1)N1Cc2cccnc2Nc2ccccc21] | 6-(cycloheptylcarbonyl)-6,11-dihydro-5H-pyrido[2,3-b][1,5]benzodiazepine | 322 |
| 72 | 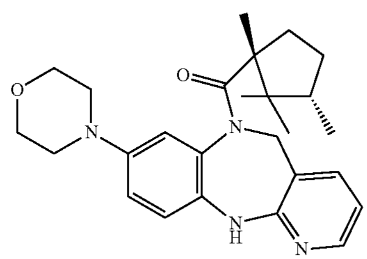 [SMILES: C[C@H]1CC[C@@](C)(C(=O)N2Cc3cccnc3Nc3ccc(N4CCOCC4)cc32)C1(C)C] | 8-morpholin-4-yl-6-{[(1R,3S)-1,2,2,3-tetramethylcyclopentyl]carbonyl}-6,11-dihydro-5H-pyrido[2,3-b][1,5]benzodiazepine | 435 |
| 73 | 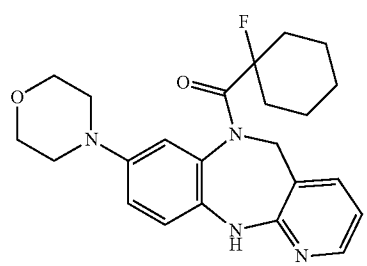 [SMILES: O=C(N1Cc2cccnc2Nc2ccc(N3CCOCC3)cc21)C1(F)CCCCC1] | 6-[(1-fluorocyclohexyl)carbonyl]-8-morpholin-4-yl-6,11-dihydro-5H-pyrido[2,3-b][1,5]benzodiazepine | 411 |
| 74 | 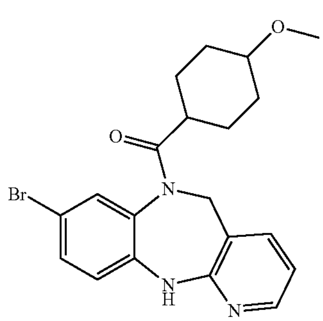 [SMILES: COC1CCC(C(=O)N2Cc3cccnc3Nc3ccc(Br)cc32)CC1] | 8-bromo-6-[(4-methoxycyclohexyl)carbonyl]-6,11-dihydro-5H-pyrido[2,3-b][1,5]benzodiazepine | 416 |

| Ex. No. | Structure | Chemical Name | [M + H]+ |
|---|---|---|---|
| 75 | 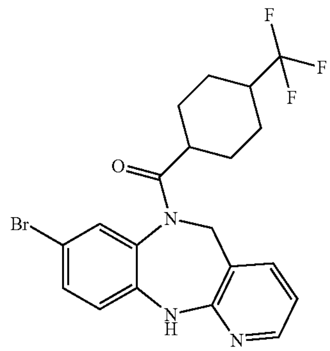 [SMILES: O=C(C1CCC(C(F)(F)F)CC1)N1Cc2cccnc2Nc2ccc(Br)cc21] | 8-bromo-6-{[4-(trifluoromethyl)cyclohexyl]carbonyl}-6,11-dihydro-5H-pyrido[2,3-b][1,5]benzodiazepine | 454 |
| 76 | 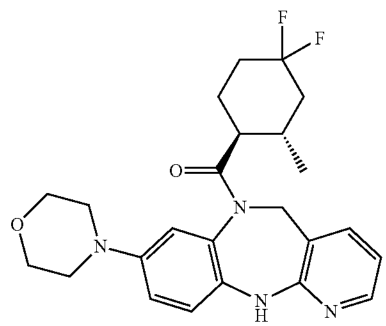 [SMILES: C[C@H]1CC(F)(F)CC[C@@H]1C(=O)N1Cc2cccnc2Nc2ccc(N3CCOCC3)cc21] | 6-{[(1S,2S)-4,4-difluoro-2-methylcyclohexyl]carbonyl}-8-morpholin-4-yl-6,11-dihydro-5H-pyrido[2,3-b][1,5]benzodiazepine | 443 |
| 77 | 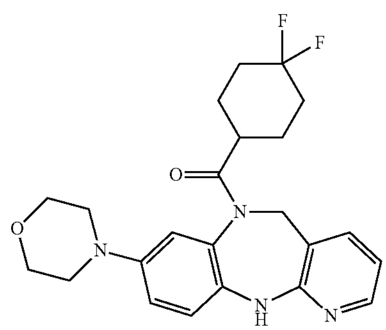 [SMILES: O=C(C1CCC(F)(F)CC1)N1Cc2cccnc2Nc2ccc(N3CCOCC3)cc21] | 6-[(4,4-difluorocyclohexyl)carbonyl]-8-morpholin-4-yl-6,11-dihydro-5H-pyrido[2,3-b][1,5]benzodiazepine | 429 |
| 78 | Isomer 1 | 6-{[4-(1-methylethoxy)cyclohexyl]carbonyl}-8-morpholin-4-yl-6,11-dihydro-5H-pyrido[2,3-b][1,5]benzodiazepine | 451 |

| Ex. No. | Structure | Chemical Name | [M + H]+ |
|---|---|---|---|
| 79 | 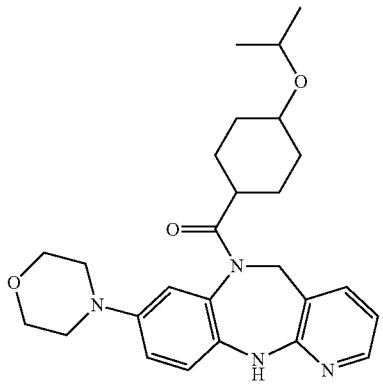<br>Isomer 2 | 6-{[4-(1-methylethoxy)cyclohexyl]carbonyl}-8-morpholin-4-yl-6,11-dihydro-5H-pyrido[2,3-b][1,5]benzodiazepine | 451 |
| 80 | 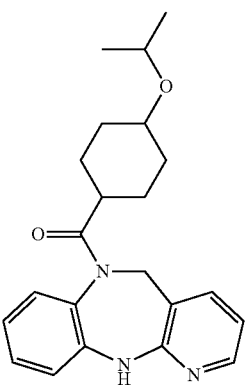<br>Isomer 1 | 6-{[4-(1-methylethoxy)cyclohexyl]carbonyl}-6,11-dihydro-5H-pyrido[2,3-b][1,5]benzodiazepine | 366 |
| 81 | 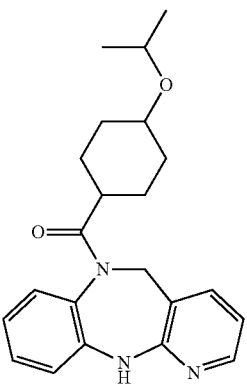<br>Isomer 2 | 6-{[4-(1-methylethoxy)cyclohexyl]carbonyl}-6,11-dihydro-5H-pyrido[2,3-b][1,5]benzodiazepine | 366 |

-continued

| Ex. No. | Structure | Chemical Name | [M + H]+ |
|---|---|---|---|
| 82 | Isomer 1 | 6-[(4-tert-butoxycyclohexyl)carbonyl]-8-morpholin-4-yl-6,11-dihydro-5H-pyrido[2,3-b][1,5]benzodiazepine | 465 |
| 83 | Isomer 2 | 6-[(4-tert-butoxycyclohexyl)carbonyl]-8-morpholin-4-yl-6,11-dihydro-5H-pyrido[2,3-b][1,5]benzodiazepine | 465 |
| 84 | 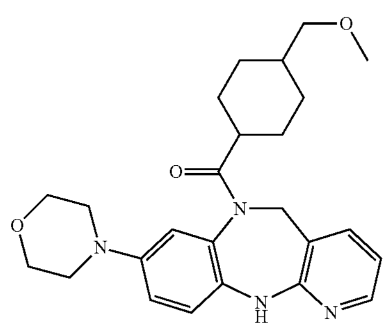 [SMILES: COCC1CCC(C(=O)N2Cc3cccnc3Nc3ccc(N4CCOCC4)cc32)CC1] | 6-{[4-(methoxymethyl)cyclohexyl]carbonyl}-8-morpholin-4-yl-6,11-dihydro-5H-pyrido[2,3-b][1,5]benzodiazepine | 437 |
| 85 | 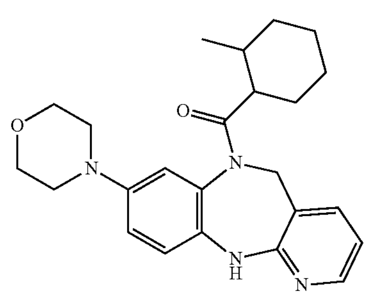 [SMILES: CC1CCCCC1C(=O)N1Cc2cccnc2Nc2ccc(N3CCOCC3)cc21] | 6-[(2-methylcyclohexyl)carbonyl]-8-morpholin-4-yl-6,11-dihydro-5H-pyrido[2,3-b][1,5]benzodiazepine | 407 |

| Ex. No. | Structure | Chemical Name | [M + H]+ |
| --- | --- | --- | --- |
| 86 | 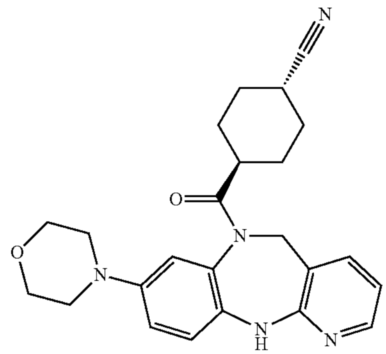 [SMILES: N#C[C@H]1CC[C@H](C(=O)N2Cc3cccnc3Nc3ccc(N4CCOCC4)cc32)CC1] | trans-4-[(8-morpholin-4-yl-5,11-dihydro-6H-pyrido[2,3-b][1,5]benzodiazepin-6-yl)carbonyl]cyclohexane carbonitrile | 418 |
| 87 | 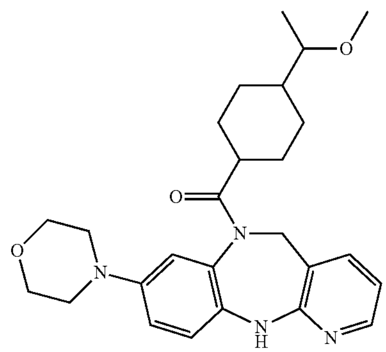 [SMILES: COC(C)C1CCC(C(=O)N2Cc3cccnc3Nc3ccc(N4CCOCC4)cc32)CC1] | 6-{[4-(1-methoxyethyl)cyclohexyl]-carbonyl}-8-morpholin-4-yl-6,11-dihydro-5H-pyrido[2,3-b][1,5]benzodiazepine | 451 |
| 88 | 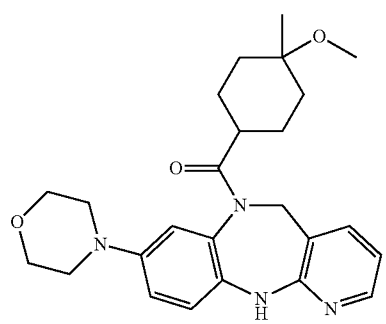 [SMILES: COC1(C)CCC(C(=O)N2Cc3cccnc3Nc3ccc(N4CCOCC4)cc32)CC1] | 6-[(4-methoxy-4-methylcyclohexyl)carbonyl]-8-morpholin-4-yl-6,11-dihydro-5H-pyrido[2,3-b][1,5]benzodiazepine | 437 |
| 89 | 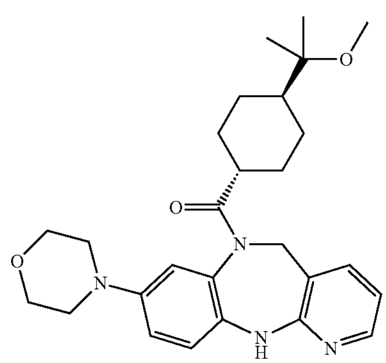 [SMILES: COC(C)(C)[C@H]1CC[C@H](C(=O)N2Cc3cccnc3Nc3ccc(N4CCOCC4)cc32)CC1] | 6-{[trans-4-(1-methoxy-1-methylethyl)cyclohexyl]-carbonyl}-8-morpholin-4-yl-6,11-dihydro-5H-pyrido[2,3-b][1,5]benzodiazepine | 465 |

-continued

| Ex. No. | Structure | Chemical Name | [M + H]+ |
|---|---|---|---|
| 90 | 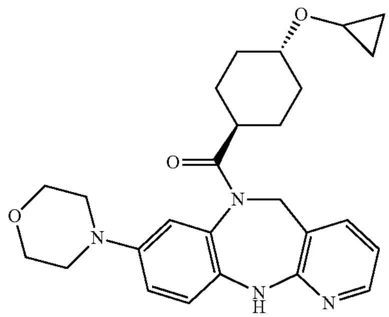 [SMILES: O=C([C@H]1CC[C@H](OC2CC2)CC1)N1Cc2cccnc2Nc2ccc(N3CCOCC3)cc21] | 6-{[trans-4-(cyclopropyloxy)cyclo-hexyl]carbonyl}-8-morpholin-4-yl-6,11-dihydro-5H-pyrido[2,3-b][1,5]benzodiazepine | 449 |
| 91 | 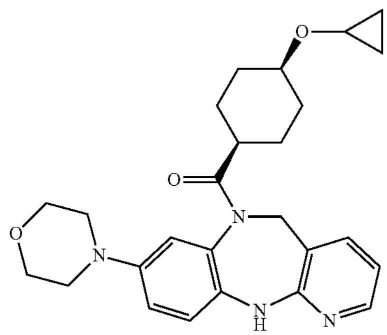 [SMILES: O=C([C@H]1CC[C@@H](OC2CC2)CC1)N1Cc2cccnc2Nc2ccc(N3CCOCC3)cc21] | 6-{[cis-4-(cyclopropyloxy)cyclo-hexyl]carbonyl}-8-morpholin-4-yl-6,11-dihydro-5H-pyrido[2,3-b][1,5]benzodiazepine | 449 |
| 92 | 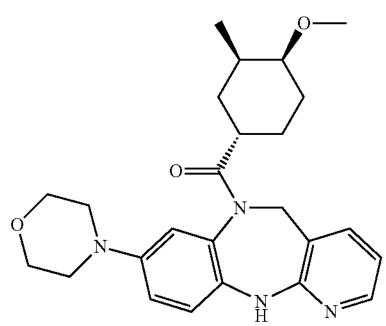 [SMILES: CO[C@H]1CC[C@H](C(=O)N2Cc3cccnc3Nc3ccc(N4CCOCC4)cc32)C[C@H]1C] | 6-{[(1S,3R,4S)-4-methoxy-3-methylcyclohexyl]carbon-yl}-8-morpholin-4-yl-6,11-dihydro-5H-pyrido[2,3-b][1,5]benzodiazepine | 437 |
| 93 | 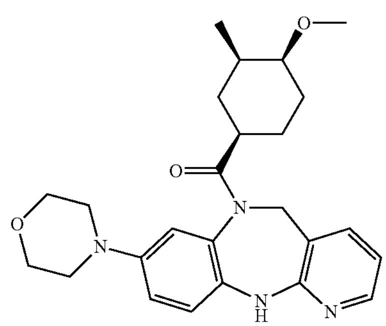 [SMILES: CO[C@H]1CC[C@@H](C(=O)N2Cc3cccnc3Nc3ccc(N4CCOCC4)cc32)C[C@H]1C] | 6-{[(1R,3R,4S)-4-methoxy-3-methylcyclohexyl]carbon-yl}-8-morpholin-4-yl-6,11-dihydro-5H-pyrido[2,3-b][1,5]benzodiazepine | 437 |
| 94 | 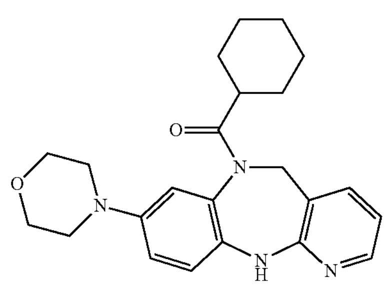 [SMILES: O=C(C1CCCCC1)N1Cc2cccnc2Nc2ccc(N3CCOCC3)cc21] | 6-(cyclohexylcarbonyl)-8-morpholin-4-yl-6,11-dihydro-5H-pyrido[2,3-b][1,5]benzodiazepine | 393 |

-continued

| Ex. No. | Structure | Chemical Name | [M + H]+ |
|---|---|---|---|
| 95 | 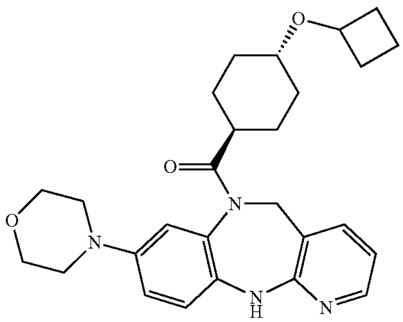 [SMILES: O=C([C@H]1CC[C@H](OC2CCC2)CC1)N1Cc2cccnc2Nc2ccc(N3CCOCC3)cc21] | 6-{[trans-4-(cyclobutyloxy)cyclohexyl]carbonyl}-8-morpholin-4-yl-6,11-dihydro-5H-pyrido[2,3-b][1,5]benzodiazepine | 463 |
| 96 | 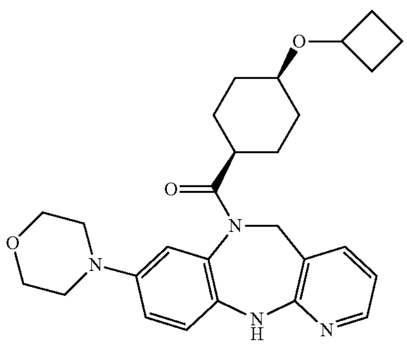 [SMILES: O=C([C@H]1CC[C@@H](OC2CCC2)CC1)N1Cc2cccnc2Nc2ccc(N3CCOCC3)cc21] | 6-{[cis-4-(cyclobutyloxy)cyclohexyl]carbonyl}-8-morpholin-4-yl-6,11-dihydro-5H-pyrido[2,3-b][1,5]benzodiazepine | 463 |
| 97 | Isomer 1 | 6-{[(1R,3R,4S)-4-methoxy-3-methylcyclohexyl]carbonyl}-8-morpholin-4-yl-6,11-dihydro-5H-pyrido[2,3-b][1,5]benzodiazepine | 437 |
| 98 | Isomer 2 | 6-{[(1S,3S,4R)-4-methoxy-3-methylcyclohexyl]carbonyl}-8-morpholin-4-yl-6,11-dihydro-5H-pyrido[2,3-b][1,5]benzodiazepine | 437 |

-continued

| Ex. No. | Structure | Chemical Name | [M + H]+ |
|---|---|---|---|
| 99 | Isomer 1 | 6-{[(1R,3S,4R)-4-methoxy-3-(trifluoromethyl)cyclohexyl]carbonyl}-8-morpholin-4-yl-6,11-dihydro-5H-pyrido[2,3-b][1,5]benzodiazepine | 491 |
| 100 | Isomer 2 | 6-{[(1R,3R,4S)-4-methoxy-3-(trifluoromethyl)cyclohexyl]carbonyl}-8-morpholin-4-yl-6,11-dihydro-5H-pyrido[2,3-b][1,5]benzodiazepine | 491 |
| 101 | Isomer 3 | 6-{[(1S,3S,4R)-4-methoxy-3-(trifluoromethyl)cyclohexyl]carbonyl}-8-morpholin-4-yl-6,11-dihydro-5H-pyrido[2,3-b][1,5]benzodiazepine | 491 |
| 102 | 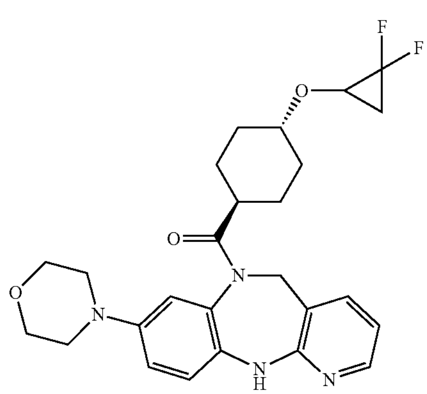 [SMILES: O=C([C@H]1CC[C@H](OC2CC2(F)F)CC1)N1Cc2cccnc2Nc2ccc(N3CCOCC3)cc21] | 6-[(trans-4-{[(1S)-2,2-difluorocyclopropyl]oxy}-cyclohexyl)carbonyl]-8-morpholin-4-yl-6,11-dihydro-5H-pyrido[2,3-b][1,5]benzodiazepine | 485 |

| Ex. No. | Structure | Chemical Name | [M + H]+ |
|---|---|---|---|
| 103 | 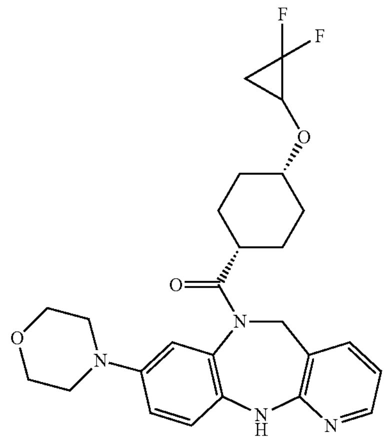 [SMILES: O=C([C@H]1CC[C@@H](OC2CC2(F)F)CC1)N1Cc2cccnc2Nc2ccc(N3CCOCC3)cc21] | 6-[(cis-4-{[(1R)-2,2-difluorocyclopropyl]oxy}-cyclohexyl)carbonyl]-8-morpholin-4-yl-6,11-dihydro-5H-pyrido[2,3-b][1,5]benzodiazepine | 485 |
| 104 | Isomer 1 | 6-[(cis-4-{[(1S)-2,2-difluorocyclopropyl]oxy}-cyclohexyl)carbonyl]-8-morpholin-4-yl-6,11-dihydro-5H-pyrido[2,3-b][1,5]benzodiazepine | 485 |
| 105 | 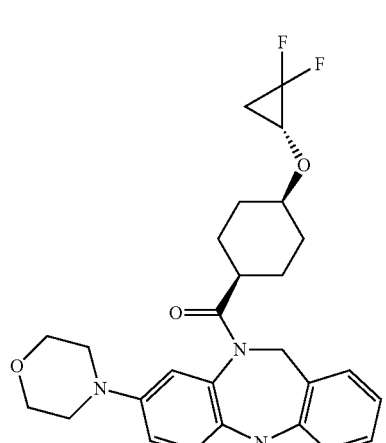Isomer 2 | 6-[(cis-4-{[(1S)-2,2-difluorocyclopropyl]oxy}-cyclohexyl)carbonyl]-8-morpholin-4-yl-6,11-dihydro-5H-pyrido[2,3-b][1,5]benzodiazepine | 485 |

-continued

| Ex. No. | Structure | Chemical Name | [M + H]+ |
|---|---|---|---|
| 106 | 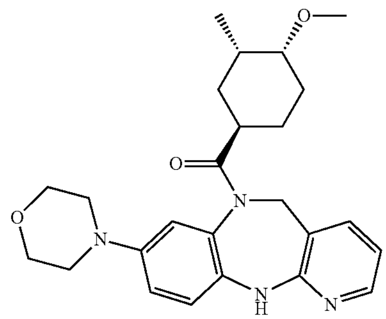 [SMILES: CO[C@@H]1CC[C@@H](C(=O)N2Cc3cccnc3Nc3ccc(N4CCOCC4)cc32)C[C@@H]1C] | 6-{[(1R,3S,4R)-4-methoxy-3-methylcyclohexyl]carbonyl}-8-morpholin-4-yl-6,11-dihydro-5H-pyrido[2,3-b][1,5]benzodiazepine | 437 |
| 107 | 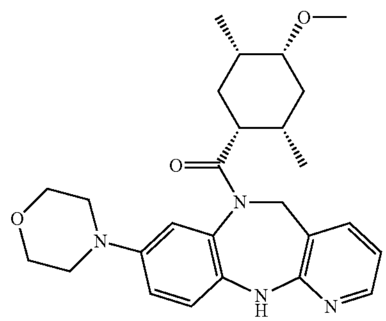 [SMILES: CO[C@@H]1C[C@H](C)[C@H](C(=O)N2Cc3cccnc3Nc3ccc(N4CCOCC4)cc32)C[C@@H]1C] | 6-{[(1R,2S,4R,5S)-4-methoxy-2,5-dimethylcyclohexyl]carbonyl}-8-morpholin-4-yl-6,11-dihydro-5H-pyrido[2,3-b][1,5]benzodiazepine | 451 |
| 108 | Isomer 1 | 6-{[(1R,2S,3R,4S)-4-methoxy-2,3-dimethylcyclohexyl]carbonyl}-8-morpholin-4-yl-6,11-dihydro-5H-pyrido[2,3-b][1,5]benzodiazepine | 451 |
| 109 | Isomer 2 | 6-{[(1S,2R,3S,4R)-4-methoxy-2,3-dimethylcyclohexyl]carbonyl}-8-morpholin-4-yl-6,11-dihydro-5H-pyrido[2,3-b][1,5]benzodiazepine | 451 |

| Ex. No. | Structure | Chemical Name | [M + H]+ |
|---|---|---|---|
| 110 | 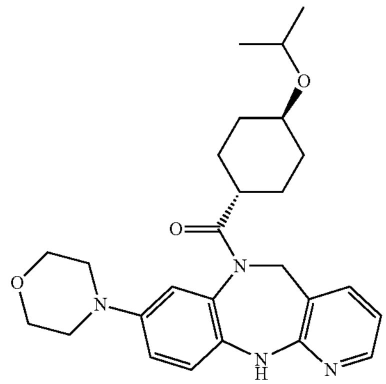 [SMILES: CC(C)O[C@H]1CC[C@H](C(=O)N2Cc3cccnc3Nc3ccc(N4CCOCC4)cc32)CC1] | 6-{[trans-4-(1-methylethoxy)cyclohexyl]-carbonyl}-8-morpholin-4-yl-6,11-dihydro-5H-pyrido[2,3-b][1,5]benzodiazepine | 451 |
| 111 | 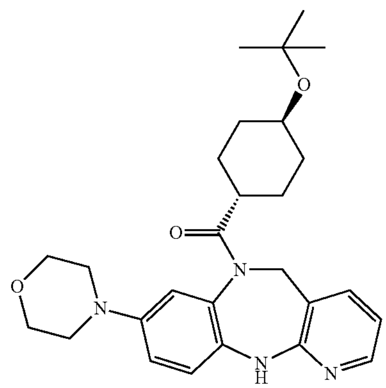 [SMILES: CC(C)(C)O[C@H]1CC[C@H](C(=O)N2Cc3cccnc3Nc3ccc(N4CCOCC4)cc32)CC1] | 6-[(trans-4-tert-butoxycyclohexyl)carbonyl]-8-morpholin-4-yl-6,11-dihydro-5H-pyrido[2,3-b][1,5]benzodiazepine | 465 |
| 112 | 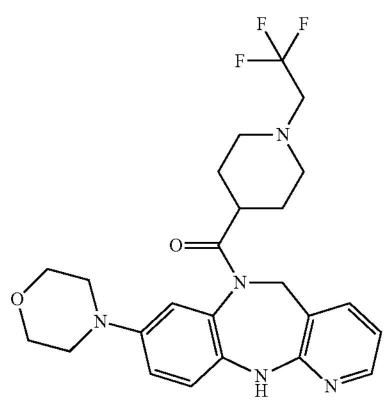 | 8-morpholin-4-yl-6-{[1-(2,2,2-trifluoroethyl)piperidin-4-yl]carbonyl}-6,11-dihydro-5H-pyrido[2,3-b][1,5]benzodiazepine | 476 |
| 113 | 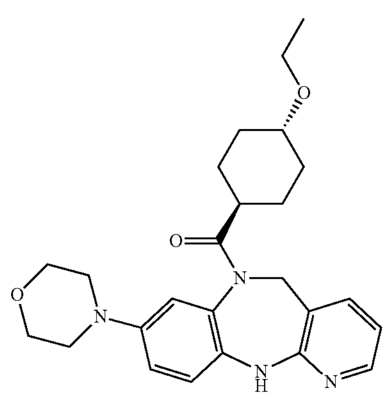 [SMILES: CCO[C@H]1CC[C@H](C(=O)N2Cc3cccnc3Nc3ccc(N4CCOCC4)cc32)CC1] | 6-[(trans-4-ethoxycyclohexyl)carbonyl]-8-morpholin-4-yl-6,11-dihydro-5H-pyrido[2,3-b][1,5]benzodiazepine | 437 |

| Ex. No. | Structure | Chemical Name | [M + H]+ |
|---|---|---|---|
| 114 | 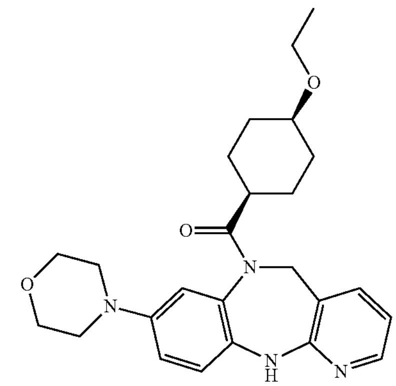 [SMILES: CCO[C@H]1CC[C@@H](C(=O)N2Cc3cccnc3Nc3ccc(N4CCOCC4)cc32)CC1] | 6-[(cis-4-ethoxycyclohexyl)carbonyl]-8-morpholin-4-yl-6,11-dihydro-5H-pyrido[2,3-b][1,5]benzodiazepine | 437 |
| 115 | 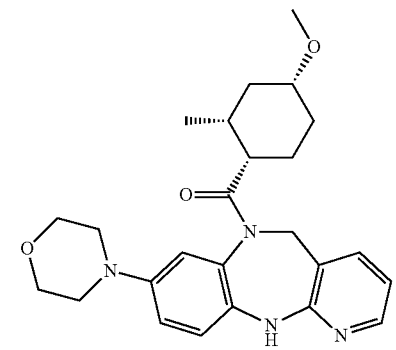 [SMILES: CO[C@@H]1CC[C@H](C(=O)N2Cc3cccnc3Nc3ccc(N4CCOCC4)cc32)[C@H](C)C1] | 6-{[(1S,2R,4R)-4-methoxy-2-methylcyclohexyl]carbonyl}-8-morpholin-4-yl-6,11-dihydro-5H-pyrido[2,3-b][1,5]benzodiazepine | 437 |
| 116 | Isomer 1 | 6-({cis-4-[(1S)-1-methoxy-2-methylpropyl]cyclohexyl}carbonyl)-8-morpholin-4-yl-6,11-dihydro-5H-pyrido[2,3-b][1,5]benzodiazepine | 479 |
| 117 | Isomer 2 | 6-({cis-4-[(1R)-1-methoxy-2-methylpropyl]cyclohexyl}carbonyl)-8-morpholin-4-yl-6,11-dihydro-5H-pyrido[2,3-b][1,5]benzodiazepine | 479 |

-continued

| Ex. No. | Structure | Chemical Name | [M + H]+ |
|---|---|---|---|
| 118 | Isomer 1 | 6-({trans-4-[(1S)-1-methoxy-2-methylpropyl]cyclohexyl}-carbonyl)-8-morpholin-4-yl-6,11-dihydro-5H-pyrido[2,3-b][1,5]benzodiazepine | 479 |
| 119 | Isomer 2 | 6-({trans-4-[(1R)-1-methoxy-2-methylpropyl]cyclohexyl}-carbonyl)-8-morpholin-4-yl-6,11-dihydro-5H-pyrido[2,3-b][1,5]benzodiazepine | 479 |
| 120 | 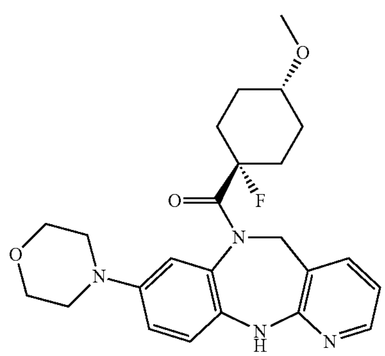 [SMILES: CO[C@H]1CC[C@](F)(C(=O)N2Cc3cccnc3Nc3ccc(N4CCOCC4)cc32)CC1] | 6-[(cis-1-fluoro-4-methoxycyclohexyl)carbonyl]-8-morpholin-4-yl-6,11-dihydro-5H-pyrido[2,3-b][1,5]benzodiazepine | 441 |
| 121 | 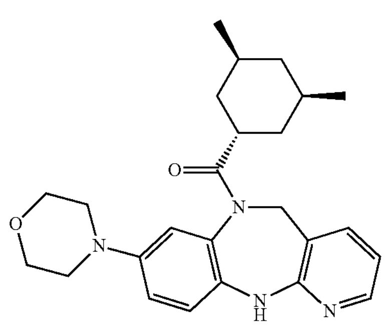 [SMILES: C[C@@H]1C[C@H](C)C[C@@H](C(=O)N2Cc3cccnc3Nc3ccc(N4CCOCC4)cc32)C1] | 6-{[(1r,3R,5S)-3,5-dimethylcyclohexyl]carbonyl}-8-morpholin-4-yl-6,11-dihydro-5H-pyrido[2,3-b][1,5]benzodiazepine | 421 |

-continued

| Ex. No. | Structure | Chemical Name | [M + H]+ |
|---|---|---|---|
| 122 | 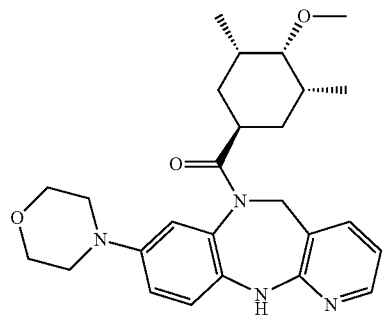 [SMILES: CO[C@@H]1[C@H](C)C[C@@H](C(=O)N2Cc3cccnc3Nc3ccc(N4CCOCC4)cc32)C[C@@H]1C] | 6-{[(1s,3R,4s,5S)-4-methoxy-3,5-dimethylcyclohexyl]carbonyl}-8-morpholin-4-yl-6,11-dihydro-5H-pyrido[2,3-b][1,5]benzodiazepine | 451 |
| 123 | 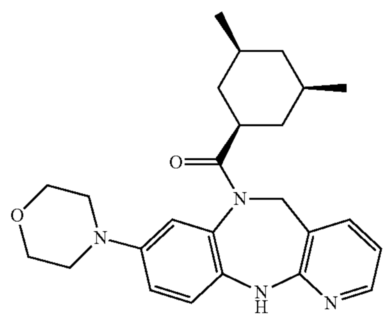 [SMILES: C[C@@H]1C[C@H](C)C[C@H](C(=O)N2Cc3cccnc3Nc3ccc(N4CCOCC4)cc32)C1] | 6-{[(1s,3R,5S)-3,5-dimethylcyclohexyl]carbonyl}-8-morpholin-4-yl-6,11-dihydro-5H-pyrido[2,3-b][1,5]benzodiazepine | 421 |
| 124 | 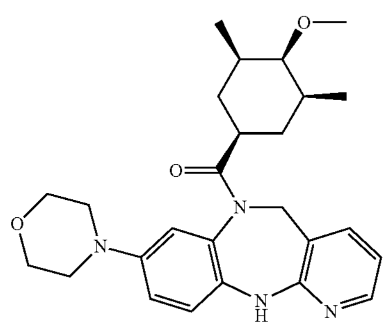 [SMILES: CO[C@@H]1[C@H](C)C[C@H](C(=O)N2Cc3cccnc3Nc3ccc(N4CCOCC4)cc32)C[C@@H]1C] | 6-{[(1r,3R,4s,5S)-4-methoxy-3,5-dimethylcyclohexyl]carbonyl}-8-morpholin-4-yl-6,11-dihydro-5H-pyrido[2,3-b][1,5]benzodiazepine | 451 |
| 125 | 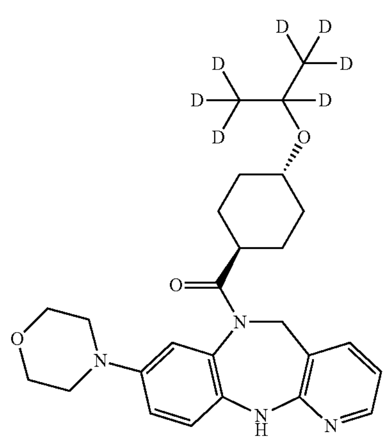 [SMILES: [2H]C([2H])([2H])C([2H])(O[C@H]1CC[C@H](C(=O)N2Cc3cccnc3Nc3ccc(N4CCOCC4)cc32)CC1)C([2H])([2H])[2H]] | [8-(morpholin-4-yl)-5,11-dihydro-6H-pyrido[2,3-b][1,5]benzodiazepin-6-yl]{trans-4-[($^2$H$_7$)propan-2-yloxy]cyclohexyl}methanone | 458 |

| Ex. No. | Structure | Chemical Name | [M + H]+ |
|---|---|---|---|
| 126 | 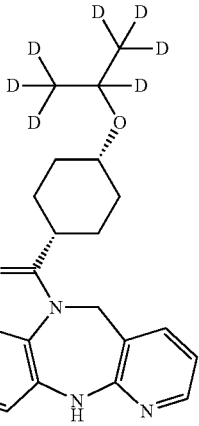 | [8-(morpholin-4-yl)-5,11-dihydro-6H-pyrido[2,3-b][1,5]benzodiazepin-6-yl]{cis-4-[($^2$H$_7$)propan-2-yloxy]cyclohexyl}methanone | 458 |
| 127 | 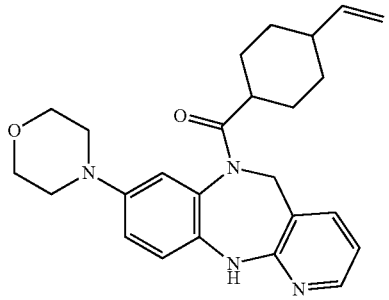 [SMILES: C=CC1CCC(C(=O)N2Cc3cccnc3Nc3ccc(N4CCOCC4)cc32)CC1] | 6-[(4-ethenylcyclohexyl)carbonyl]-8-morpholin-4-yl-6,11-dihydro-5H-pyrido[2,3-b][1,5]benzodiazepine | 419 |
| 128 | 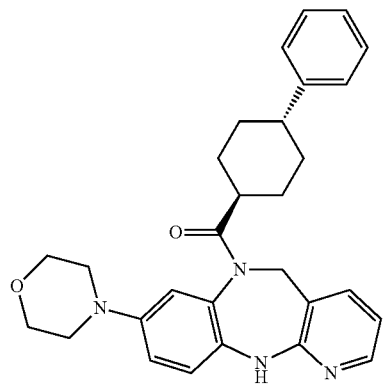 [SMILES: O=C([C@H]1CC[C@H](c2ccccc2)CC1)N1Cc2cccnc2Nc2ccc(N3CCOCC3)cc21] | 8-morpholin-4-yl-6-[(trans-4-phenylcyclohexyl)carbonyl]-6,11-dihydro-5H-pyrido[2,3-b][1,5]benzodiazepine | 469 |
| 129 | 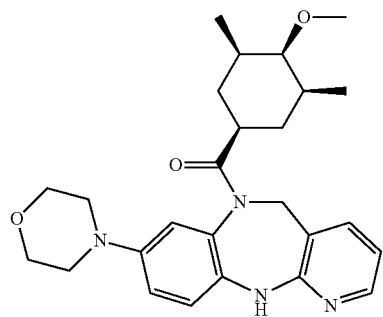
Isomer 1 | 6-{[(1r,3R,4s,5S)-4-methoxy-3,5-dimethylcyclohexyl]carbonyl}-8-morpholin-4-yl-6,11-dihydro-5H-pyrido[2,3-b][1,5]benzodiazepine | 451 |

| Ex. No. | Structure | Chemical Name | [M + H]+ |
|---|---|---|---|
| 130 | 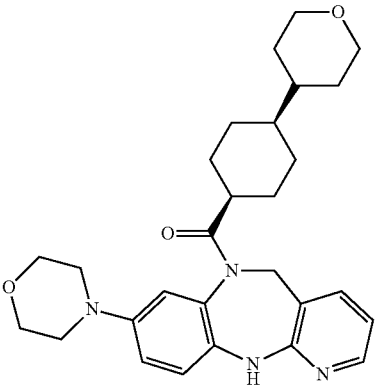 [SMILES: O=C([C@H]1CC[C@@H](C2CCOCC2)CC1)N1Cc2cccnc2Nc2ccc(N3CCOCC3)cc21] | 8-morpholin-4-yl-6-{[cis-4-(tetrahydro-2H-pyran-4-yl)cyclohexyl]carbonyl}-6,11-dihydro-5H-pyrido[2,3-b][1,5]benzodiazepine | 477 |
| 131 | 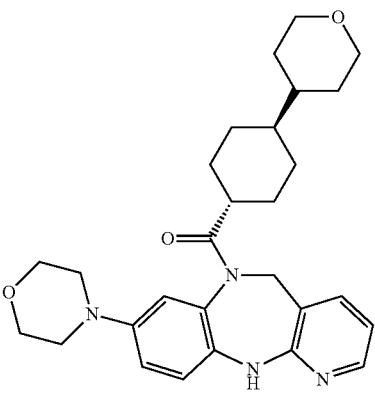 [SMILES: O=C([C@H]1CC[C@H](C2CCOCC2)CC1)N1Cc2cccnc2Nc2ccc(N3CCOCC3)cc21] | 8-morpholin-4-yl-6-{[trans-4-(tetrahydro-2H-pyran-4-yl)cyclohexyl]carbonyl}-6,11-dihydro-5H-pyrido[2,3-b][1,5]benzodiazepine | 477 |
| 132 | 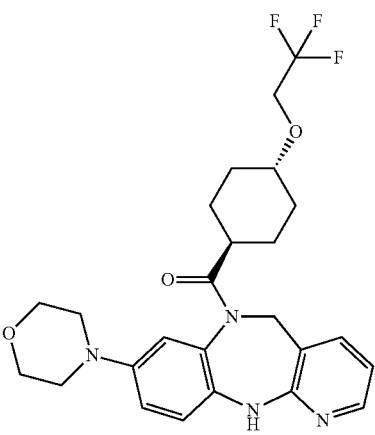 [SMILES: O=C([C@H]1CC[C@H](OCC(F)(F)F)CC1)N1Cc2cccnc2Nc2ccc(N3CCOCC3)cc21] | 8-morpholin-4-yl-6-{[trans-4-(2,2,2-trifluoroethoxy)cyclohexyl]carbonyl}-6,11-dihydro-5H-pyrido[2,3-b][1,5]benzodiazepine | 491 |

-continued

| Ex. No. | Structure | Chemical Name | [M + H]+ |
|---|---|---|---|
| 133 | 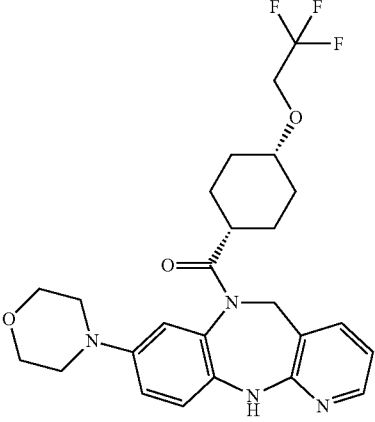 | 8-morpholin-4-yl-6-{[cis-4-(2,2,2-trifluoroethoxy)cyclohexyl]carbonyl}-6,11-dihydro-5H-pyrido[2,3-b][1,5]benzodiazepine | 491 |
| 134 | 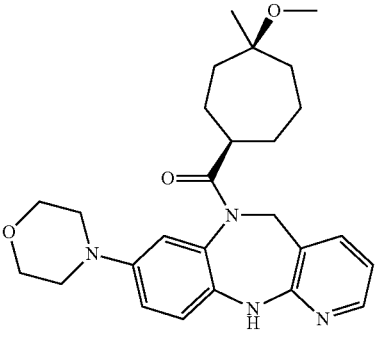 [SMILES: CO[C@@]1(C)CCC[C@@H](C(=O)N2Cc3cccnc3Nc3ccc(N4CCOCC4)cc32)CC1] | 6-{[(1R,4S)-4-methoxy-4-methylcycloheptyl]carbonyl}-8-morpholin-4-yl-6,11-dihydro-5H-pyrido[2,3-b][1,5]benzodiazepine | 451 |
| 135 | 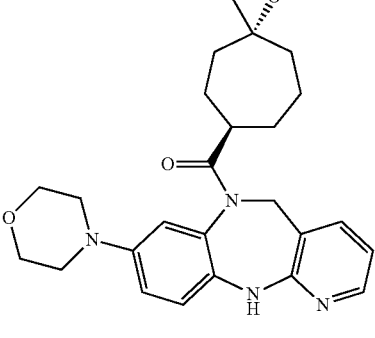 | 6-{[(1R,4R)-4-methoxy-4-methylcycloheptyl]carbonyl}-8-morpholin-4-yl-6,11-dihydro-5H-pyrido[2,3-b][1,5]benzodiazepine | 451 |
| 136 | 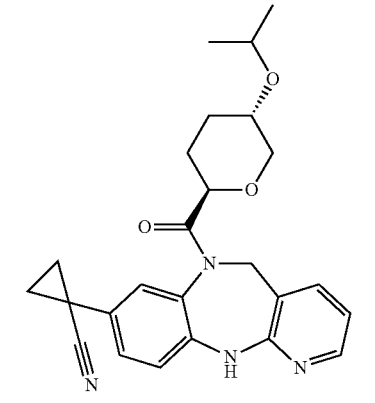 [SMILES: CC(C)O[C@H]1CC[C@H](C(=O)N2Cc3cccnc3Nc3ccc(C4(C#N)CC4)cc32)OC1] | 1-(6-((2R,5S)-5-isopropoxytetrahydro-2H-pyran-2-carbonyl)-6,11-dihydro-5H-benzo[b]pyrido[2,3-e][1,4]diazepin-8-yl)cyclopropane-1-carbonitrile | 433 |

-continued

| Ex. No. | Structure | Chemical Name | [M + H]+ |
| --- | --- | --- | --- |
| 137 | 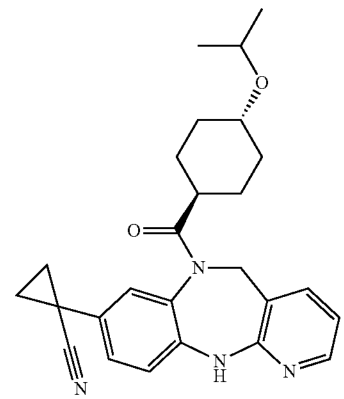 [SMILES: CC(C)O[C@H]1CC[C@H](C(=O)N2Cc3cccnc3Nc3ccc(C4(C#N)CC4)cc32)CC1] | 1-(6-{[trans-4-(1-methylethoxy)cyclohexyl]-carbonyl}-6,11-dihydro-5H-pyrido[2,3-b][1,5]benzodiazepin-8-yl)cyclopropanecarbonitrile | 431 |
| 138 | 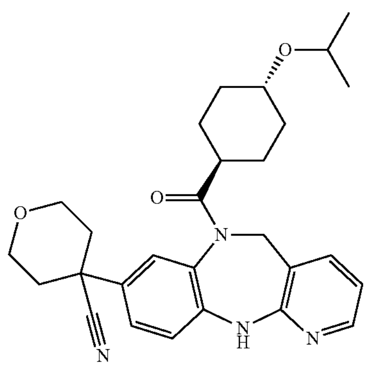 [SMILES: CC(C)O[C@H]1CC[C@H](C(=O)N2Cc3cccnc3Nc3ccc(C4(C#N)CCOCC4)cc32)CC1] | 4-(6-{[trans-4-(1-methylethoxy)cyclohexyl]-carbonyl}-6,11-dihydro-5H-pyrido[2,3-b][1,5]benzodiazepin-8-yl)tetrahydro-2H-pyran-4-carbonitrile | 475 |
| 139 | 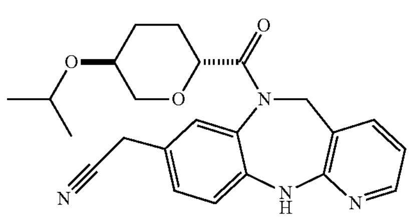 | 2-(6-((2R,5S)-5-isopropoxytetrahydro-2H-pyran-2-carbonyl)-6,11-dihydro-5H-benzo[b]pyrido[2,3-e][1,4]diazepin-8-yl)acetonitrile | 407 |
| 140 | 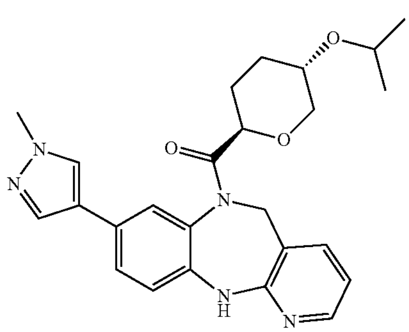 [SMILES: CC(C)O[C@H]1CC[C@H](C(=O)N2Cc3cccnc3Nc3ccc(-c4cnn(C)c4)cc32)OC1] | ((2R,5S)-5-isopropoxytetrahydro-2H-pyran-2-yl)(8-(1-methyl-1H-pyrazol-4-yl)-5,11-dihydro-6H-benzo[b]pyrido[2,3-e][1,4]diazepin-6-yl)methanone | 448 |

| Ex. No. | Structure | Chemical Name | [M + H]+ |
|---|---|---|---|
| 141 | 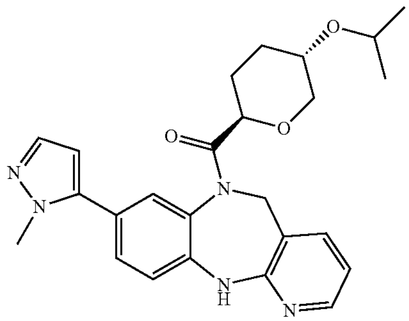 [SMILES: CC(C)O[C@H]1CC[C@H](C(=O)N2Cc3cccnc3Nc3ccc(-c4ccnn4C)cc32)OC1] | ((2R,5S)-5-isopropoxytetrahydro-2H-pyran-2-yl)(8-(1-methyl-1H-pyrazol-5-yl)-5,11-dihydro-6H-benzo[b]pyrido[2,3-e][1,4]diazepin-6-yl)methanone | 448 |
| 142 | Cis isomer 1 | ((2R,5S)-5-isopropoxytetrahydro-2H-pyran-2-yl)(8-((2R,4S)-4-methoxy-2-methyltetrahydrofuran-2-yl)-5,11-dihydro-6H-benzo[b]pyrido[2,3-e][1,4]diazepin-6-yl)methanone | 482 |
| 143 | Cis isomer 2 | ((2R,5S)-5-isopropoxytetrahydro-2H-pyran-2-yl)(8-((2S,4R)-4-methoxy-2-methyltetrahydrofuran-2-yl)-5,11-dihydro-6H-benzo[b]pyrido[2,3-e][1,4]diazepin-6-yl)methanone | 482 |
| 144 | Trans isomer | ((2R,5S)-5-isopropoxytetrahydro-2H-pyran-2-yl)(8-((2S,4S)-4-methoxy-2-methyltetrahydrofuran-2-yl)-5,11-dihydro-6H-benzo[b]pyrido[2,3-e][1,4]diazepin-6-yl)methanone | 482 |

| Ex. No. | Structure | Chemical Name | [M + H]+ |
|---|---|---|---|
| 145 | 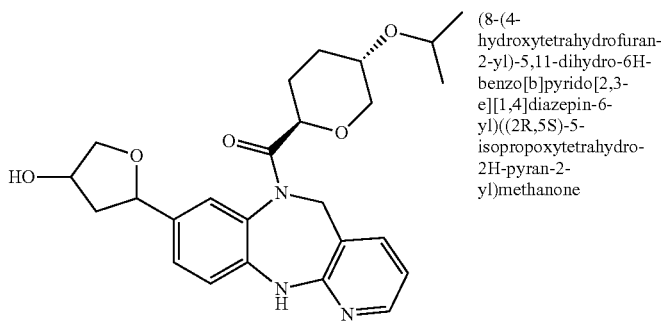<br>And diastereomer | (8-(4-hydroxytetrahydrofuran-2-yl)-5,11-dihydro-6H-benzo[b]pyrido[2,3-e][1,4]diazepin-6-yl)((2R,5S)-5-isopropoxytetrahydro-2H-pyran-2-yl)methanone | 454 |
| 146 | 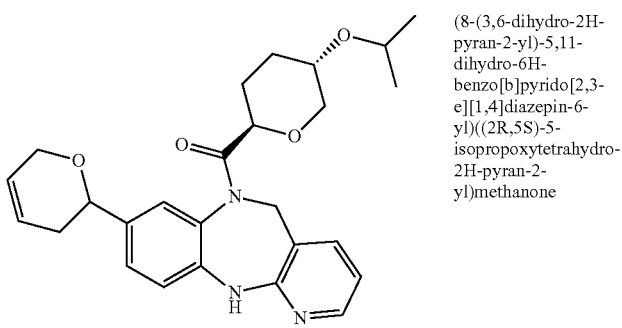<br>And diastereomer | (8-(3,6-dihydro-2H-pyran-2-yl)-5,11-dihydro-6H-benzo[b]pyrido[2,3-e][1,4]diazepin-6-yl)((2R,5S)-5-isopropoxytetrahydro-2H-pyran-2-yl)methanone | 450 |
| 147 | 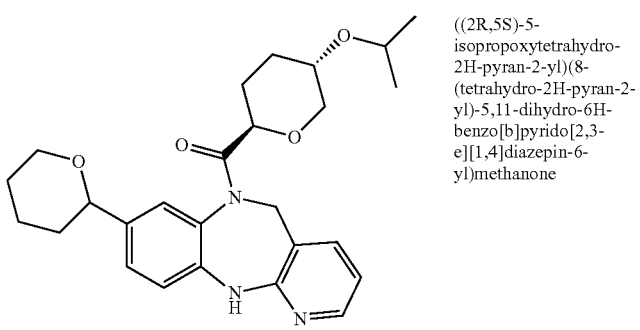<br>And diastereomer | ((2R,5S)-5-isopropoxytetrahydro-2H-pyran-2-yl)(8-(tetrahydro-2H-pyran-2-yl)-5,11-dihydro-6H-benzo[b]pyrido[2,3-e][1,4]diazepin-6-yl)methanone | 452 |
| 148 | 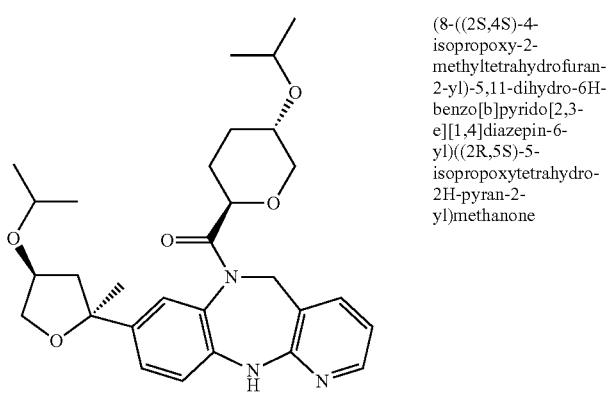<br>Trans isomer 1 | (8-((2S,4S)-4-isopropoxy-2-methyltetrahydrofuran-2-yl)-5,11-dihydro-6H-benzo[b]pyrido[2,3-e][1,4]diazepin-6-yl)((2R,5S)-5-isopropoxytetrahydro-2H-pyran-2-yl)methanone | 510 |

-continued

| Ex. No. | Structure | Chemical Name | [M + H]+ |
|---|---|---|---|
| 149 | Trans isomer 2 | (8-((2R,4R)-4-isopropoxy-2-methyltetrahydrofuran-2-yl)-5,11-dihydro-6H-benzo[b]pyrido[2,3-e][1,4]diazepin-6-yl)((2R,5S)-5-isopropoxytetrahydro-2H-pyran-2-yl)methanone | 510 |
| 150 | 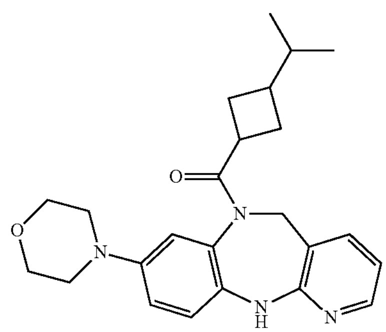 [SMILES: CC(C)C1CC(C(=O)N2Cc3cccnc3Nc3ccc(N4CCOCC4)cc32)C1] | 6-{[3-(1-methylethyl)cyclobutyl]carbonyl}-8-morpholin-4-yl-6,11-dihydro-5H-pyrido[2,3-b][1,5]benzodiazepine | 407 |
| 151 | Racemic | 8-morpholin-4-yl-6-{[1-(2,2,2-trifluoro-1-methylethyl)piperidin-4-yl]carbonyl}-6,11-dihydro-5H-pyrido[2,3-b][1,5]benzodiazepine | 490 |
| 152 | Cis isomer, single enantiomer | 6-{[(1R,3R,4S)-4-ethoxy-3-methylcyclohexyl]carbonyl}-8-morpholin-4-yl-6,11-dihydro-5H-pyrido[2,3-b][1,5]benzodiazepine | 451 |

-continued

| Ex. No. | Structure | Chemical Name | [M + H]+ |
|---|---|---|---|
| 153 | Isomer 1 | 8-morpholin-4-yl-6-{[1-(2,2,2-trifluoro-1-methylethyl)piperidin-4-yl]carbonyl}-6,11-dihydro-5H-pyrido[2,3-b][1,5]benzodiazepine | 490 |
| 154 | Isomer 2 | 8-morpholin-4-yl-6-{[1-(2,2,2-trifluoro-1-methylethyl)piperidin-4-yl]carbonyl}-6,11-dihydro-5H-pyrido[2,3-b][1,5]benzodiazepine | 490 |
| 155 | Cis isomer | 6-{[(1S,3R)-3-ethoxycyclopentyl]carbonyl}-8-(8-oxa-3-azabicyclo[3.2.1]oct-3-yl)-6,11-dihydro-5H-pyrido[2,3-b][1,5]benzodiazepine | 449 |
| 156 | And diastereomer | 6-[(trans-4-{[1-methylpropyl]oxy}cyclohexyl)carbonyl]-8-morpholin-4-yl-6,11-dihydro-5H-pyrido[2,3-b][1,5]benzodiazepine | 465 |

| Ex. No. | Structure | Chemical Name | [M + H]+ |
| --- | --- | --- | --- |
| 157 | Single cis isomer | 6-{[(1R,3S,4S)-3-ethoxy-4-fluorocyclopentyl]carbonyl}-8-[(1S,4S)-2-oxa-5-azabicyclo[2.2.2]oct-5-yl]-6,11-dihydro-5H-pyrido[2,3-b][1,5]benzodiazepine | 467 |
| 158 | Single cis isomer | 6-{[(1R,3S,4S)-3-ethoxy-4-fluorocyclopentyl]carbonyl}-8-[(1R,4R)-2-oxa-5-azabicyclo[2.2.2]oct-5-yl]-6,11-dihydro-5H-pyrido[2,3-b][1,5]benzodiazepine | 467 |
| 159 | 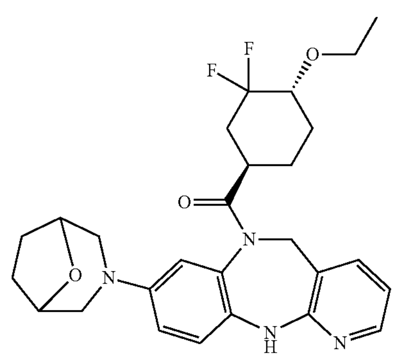 [SMILES: CCO[C@@H]1CC[C@@H](C(=O)N2Cc3cccnc3Nc3ccc(N4CC5CCC(C4)O5)cc32)CC1(F)F] | 6-{[(1R,4R)-4-ethoxy-3,3-difluorocyclohexyl]carbonyl}-8-(8-oxa-3-azabicyclo[3.2.1]oct-3-yl)-6,11-dihydro-5H-pyrido[2,3-b][1,5]benzodiazepine | 499 |
| 160 | 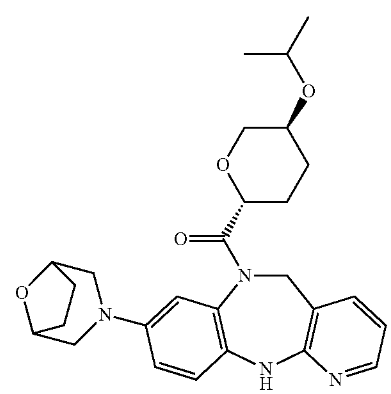 [SMILES: CC(C)O[C@H]1CC[C@H](C(=O)N2Cc3cccnc3Nc3ccc(N4CC5CCC(C4)O5)cc32)OC1] | (8-(8-oxa-3-azabicyclo[3.2.1]octan-3-yl)-5,11-dihydro-6H-benzo[b]pyrido[2,3-e][1,4]diazepin-6-yl)((2R,5S)-5-isopropoxytetrahydro-2H-pyran-2-yl)methanone | 479 |

-continued

| Ex. No. | Structure | Chemical Name | [M + H]+ |
|---|---|---|---|
| 161 | 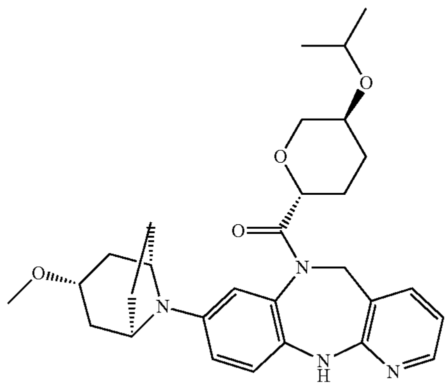 [SMILES: CO[C@H]1C[C@H]2CC[C@@H](C1)N2c1ccc2c(c1)N(C(=O)[C@H]1CC[C@H](OC(C)C)CO1)Cc1cccnc1N2] | ((2R,5S)-5-isopropoxytetrahydro-2H-pyran-2-yl)(8-((1R,3R,5S)-3-methoxy-8-azabicyclo[3.2.1]octan-8-yl)-5,11-dihydro-6H-benzo[b]pyrido[2,3-e][1,4]diazepin-6-yl)methanone | 507 |
| 162 | 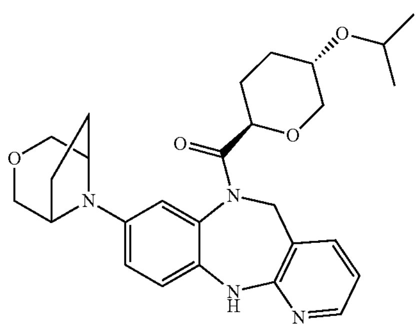 [SMILES: CC(C)O[C@H]1CC[C@H](C(=O)N2Cc3cccnc3Nc3ccc(N4C5CCC4COC5)cc32)OC1] | (8-(3-oxa-8-azabicyclo[3.2.1]octan-8-yl)-5,11-dihydro-6H-benzo[b]pyrido[2,3-e][1,4]diazepin-6-yl)((2R,5S)-5-isopropoxytetrahydro-2H-pyran-2-yl)methanone | 479 |
| 163 | 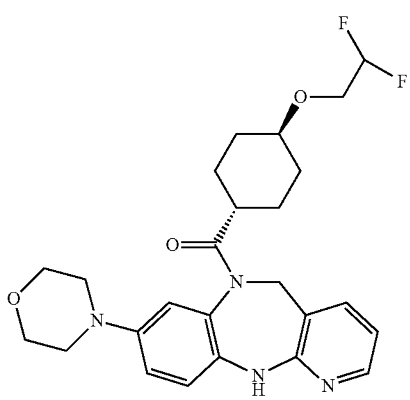 [SMILES: O=C([C@H]1CC[C@H](OCC(F)F)CC1)N1Cc2cccnc2Nc2ccc(N3CCOCC3)cc21] | 6-{[trans-4-(2,2-difluoroethoxy)cyclohexyl]carbonyl}-8-morpholin-4-yl-6,11-dihydro-5H-pyrido[2,3-b][1,5]benzodiazepine | 473 |

-continued

| Ex. No. | Structure | Chemical Name | [M + H]+ |
|---|---|---|---|
| 164 | 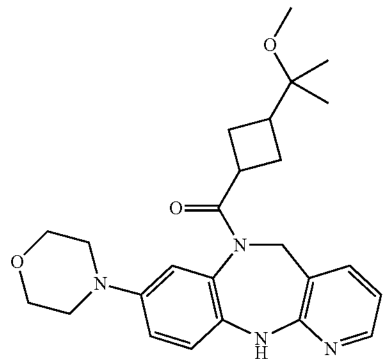 [SMILES: COC(C)(C)C1CC(C(=O)N2Cc3cccnc3Nc3ccc(N4CCOCC4)cc32)C1] | 6-{[3-(1-methoxy-1-methylethyl)cyclobutyl]carbonyl}-8-morpholin-4-yl-6,11-dihydro-5H-pyrido[2,3-b][1,5]benzodiazepine | 437 |
| 165 | Single isomer | 6-[(4-methoxycycloheptyl)carbonyl]-8-morpholin-4-yl-6,11-dihydro-5H-pyrido[2,3-b][1,5]benzodiazepine | 437 |
| 166 | Cis isomer | 6-{[(2S,4R)-1-methyl-2-(trifluoromethyl)piperidin-4-yl]carbonyl}-8-morpholin-4-yl-6,11-dihydro-5H-pyrido[2,3-b][1,5]benzodiazepine | 476 |

241

Examples 167-170: 6-({Cis-4-[(R)-cyclopropyl (methoxy)methyl]cyclohexyl}carbonyl)-8-morpholin-4-yl-6,11-dihydro-5H-pyrido[2,3-b][1,5]benzodiazepine isomer 1

6-({Cis-4-[(S)-cyclopropyl(methoxy)methyl] cyclohexyl}carbonyl)-8-morpholin-4-yl-6,11-dihydro-5H-pyrido[2,3-b][1,5]benzodiazepine isomer 2

6-({Trans-4-[(R)-cyclopropyl(methoxy)methyl] cyclohexyl}carbonyl)-8-morpholin-4-yl-6,11-dihydro-5H-pyrido[2,3-b][1,5]benzodiazepine isomer 1, and 6-({Trans-4-[(S)-cyclopropyl(methoxy)methyl] cyclohexyl}carbonyl)-8-morpholin-4-yl-6,11-dihydro-5H-pyrido[2,3-b][1,5]benzodiazepine isomer 2

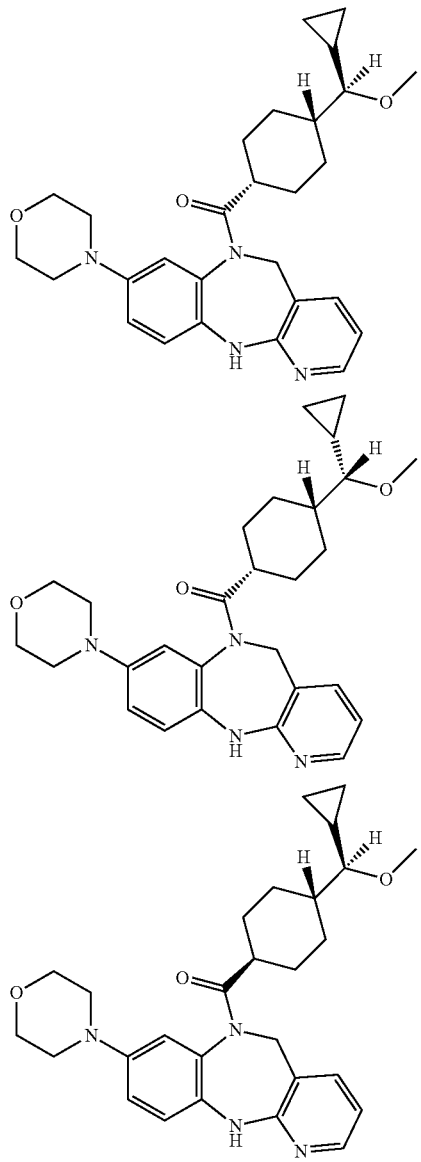

242

-continued

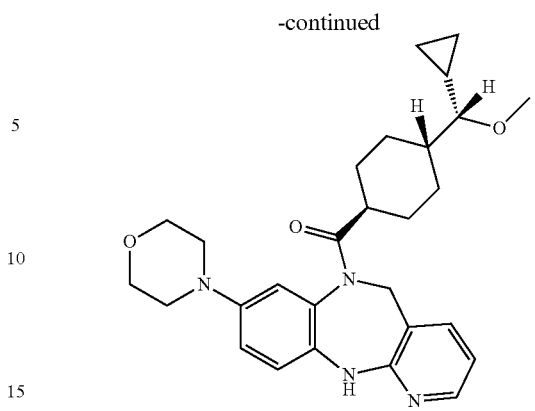

Step 1:
To a mixture of methyl 4-formylcyclohexanecarboxylate (1.0 g, 5.9 mmol) in THF (12 mL) at 0° C. was added cyclopropylmagnesium bromide (1.0 M in 2-methyltetrahydrofuran, 5.9 mL, 5.9 mmol) and the mixture was then allowed to warm to room temperature for 2 h. The mixture was then quenched slowly with water and then ethyl acetate was added. The organic layer was separated, dried over magnesium sulfate, filtered, and concentrated under reduced pressure. The residue was purified by column chromatography on silica gel to afford methyl 4-(cyclopropyl(hydroxy) methyl)cyclohexanecarboxylate.

Step 2:
To a mixture of methyl 4-(cyclopropyl(hydroxy)methyl) cyclohexanecarboxylate (354 mg, 1.67 mmol) in DMF (1.0 mL) at 0° C. was added sodium hydride (60% dispersion in mineral oil, 100 mg, 2.50 mmol). After stirring for 5 minutes at 0° C., iodomethane (260 μL, 4.17 mmol) was added dropwise. The mixture was then heated to 60° C. for 2 hours. Upon cooling to room temperature, the mixture was quenched with water and then ethyl acetate was added. The organic layer was separated, dried over magnesium sulfate, filtered, and concentrated under reduced pressure. The residue was purified by column chromatography on silica gel to afford methyl 4-(cyclopropyl(methoxy)methyl)cyclohexanecarboxylate.

Step 3:
To a mixture of methyl 4-(cyclopropyl(methoxy)methyl) cyclohexanecarboxylate (224 mg, 0.990 mmol) in THF (3.30 mL), water (0.80 mL) and methanol (0.80 mL) was added lithium hydroxide (59 mg, 2.5 mmol) and the mixture was stirred at room temperature for 16 h. The mixture was then quenched with aqueous HCl (6 M, 0.40 mL, 2.5 mmol) and then extracted with ethyl acetate (2×). The combined organic layers were dried over magnesium sulfate, filtered, and concentrated under reduced pressure to afford 4-(cyclopropyl(methoxy)methyl)cyclohexanecarboxylic acid that was used without further purification or characterization.

Step 4:
To a microwave vial containing 4-(cyclopropyl(methoxy) methyl)cyclohexanecarboxylic acid (132 mg, 0.620 mmol) and 4-(6,11-dihydro-5H-benzo[b]pyrido[2,3-e][1,4]diazepin-8-yl)morpholine (175 mg, 0.620 mmol) was added acetonitrile (6.0 mL). PS-PPh$_3$ (2.06 mmol/g loading, 129 mg, 0.492 mmol) and trichloroacetonitrile (0.31 mL, 3.1 mmol) were added and the mixture was irradiated in the microwave to 100° C. for 10 minutes. Upon cooling to room temperature, the mixture was filtered and then concentrated under reduced pressure. The residue was taken up in ethyl acetate and saturated aqueous sodium bicarbonate. The organic layer was separated, dried over magnesium sulfate, filtered, and concentrated under reduced pressure. The residue was purified by column chromatography on silica gel to afford the title compounds as a mixture of 4 isomers. The product was then separated into the 4 isomers by SFC (IC, 2.1×25 cm, methanol with 0.25% DMEA and 40% modifier in $CO_2$). The first run separated two isomers. The fractions that contained a mixture of isomers were concentrated and then purified again by SFC (IC, 2.1×25 cm, isopropanol with 0.25% DMEA and 30% modifier in $CO_2$) to afford the remaining two pure fractions.

Characterization data for the first peak isolated from SFC: MS: 477 (M+1). $^1$H NMR (500 MHz, DMSO-$d_6$) δ 9.11 (s, 1H), 7.98 (d, J=3.9 Hz, 1H), 7.40 (d, J=7.3 Hz, 1H), 7.20 (d, J=8.8 Hz, 1H), 6.92-6.86 (m, 1H), 6.79 (s, 1H), 6.64 (dd, J=7.1, 5.0 Hz, 1H), 5.19 (d, J=14.9 Hz, 1H), 3.84 (d, J=14.3 Hz, 1H), 3.76-3.68 (m, 4H), 3.11-3.02 (m, 4H), 3.03-2.91 (m, 3H), 2.76-2.66 (m, 1H), 2.42-2.29 (m, 1H), 1.92-1.79 (m, 2H), 1.79-1.66 (m, 1H), 1.51-1.39 (m, 2H), 1.39-0.95 (m, 4H), 0.67-0.50 (m, 1H), 0.48-0.31 (m, 2H), 0.31-0.22 (m, 1H), 0.08--0.10 (m, 1H).

Characterization data for the second peak isolated from SFC: MS: 477 (M+1). $^1$H NMR (600 MHz, DMSO-$d_6$) δ 9.07 (s, 1H), 7.95 (d, J=4.7 Hz, 1H), 7.37 (d, J=7.1 Hz, 1H), 7.17 (dd, J=8.9, 1.3 Hz, 1H), 6.85 (dd, J=8.9, 2.7 Hz, 1H), 6.76 (t, J=2.7 Hz, 1H), 6.61 (dd, J=7.2, 4.8 Hz, 1H), 5.16 (d, J=14.9 Hz, 1H), 3.80 (d, J=14.8 Hz, 1H), 3.76-3.62 (m, 4H), 3.09-2.99 (m, 4H), 2.99-2.91 (m, 3H), 2.73-2.63 (m, 1H), 2.39-2.27 (m, 1H), 1.87-1.65 (m, 3H), 1.46-1.36 (m, 2H), 1.37-1.05 (m, 4H), 0.61-0.48 (m, 1H), 0.44-0.28 (m, 2H), 0.28-0.17 (m, 1H), 0.03--0.12 (m, 1H).

Characterization data for the third peak isolated from SFC: MS: 477 (M+1). $^1$H NMR (500 MHz, DMSO-$d_6$) δ 9.11 (s, 1H), 7.98 (d, J=3.4 Hz, 1H), 7.40 (d, J=6.6 Hz, 1H), 7.21 (d, J=8.9 Hz, 1H), 6.91 (dd, J=9.0, 2.7 Hz, 1H), 6.78 (s, 1H), 6.64 (dd, J=7.2, 4.8 Hz, 1H), 5.18 (d, J=15.0 Hz, 1H), 3.88 (d, J=14.9 Hz, 1H), 3.79-3.67 (m, 4H), 3.20 (s, 3H), 3.09-3.05 (m, 2H), 3.02-2.94 (m, 2H), 2.43-2.32 (m, 1H), 2.18-2.12 (m, 1H), 1.89 (d, J=12.2 Hz, 1H), 1.79 (d, J=13.6 Hz, 1H), 1.69 (d, J=11.0 Hz, 1H), 1.59 (d, J=13.0 Hz, 1H), 1.49 (d, J=14.2 Hz, 1H), 1.44-1.32 (m, 2H), 1.31-1.17 (m, 2H), 0.67-0.57 (m, 1H), 0.50-0.40 (m, 1H), 0.39-0.28 (m, 1H), 0.28-0.20 (m, 1H), 0.02--0.08 (m, 1H).

Characterization data for the fourth peak isolated from SFC: MS: 477 (M+1). $^1$H NMR (600 MHz, DMSO-$d_6$) δ 9.06 (s, 1H), 7.95 (dd, J=4.8, 1.6 Hz, 1H), 7.37 (d, J=6.1 Hz, 1H), 7.18 (d, J=8.9 Hz, 1H), 6.88 (dd, J=8.9, 2.8 Hz, 1H), 6.74 (t, J=2.3 Hz, 1H), 6.61 (dd, J=7.2, 4.8 Hz, 1H), 5.15 (d, J=15.0 Hz, 1H), 3.85 (d, J=14.8 Hz, 1H), 3.76-3.65 (m, 4H), 3.17 (s, 3H), 3.10-3.00 (m, 2H), 3.00-2.91 (m, 2H), 2.35 (t, J=11.1 Hz, 1H), 2.16-2.08 (m, 1H), 1.91-1.81 (m, 1H), 1.80-1.72 (m, 1H), 1.71-1.62 (m, 1H), 1.56 (d, J=11.9 Hz, 1H), 1.47 (d, J=12.6 Hz, 1H), 1.41-1.29 (m, 2H), 1.28-1.16 (m, 2H), 0.63-0.53 (m, 1H), 0.46-0.36 (m, 1H), 0.34-0.26 (m, 1H), 0.26-0.18 (m, 1H), −0.02--0.11 (m, 1H).

Examples 171-174: [8-(Morpholin-4-yl)-5,11-dihydro-6H-pyrido[2,3-b][1,5]benzodiazepin-6-yl]{cis-4-[(1R)-1-(propan-2-yloxy)ethyl]cyclohexyl}methanone isomer 1, [8-(Morpholin-4-yl)-5,11-dihydro-6H-pyrido[2,3-b][1,5]benzodiazepin-6-yl]{cis-4-[(1S)-1-(propan-2-yloxy)ethyl]cyclohexyl}methanone isomer 2, [8-(Morpholin-4-yl)-5,11-dihydro-6H-pyrido[2,3-b][1,5]benzodiazepin-6-yl]{trans-4-[(1R)-1-(propan-2-yloxy)ethyl]cyclohexyl}methanone isomer 1, and [8-(Morpholin-4-yl)-5,11-dihydro-6H-pyrido[2,3-b][1,5]benzodiazepin-6-yl]{trans-4-[(1S)-1-(propan-2-yloxy)ethyl]cyclohexyl}methanone isomer 2

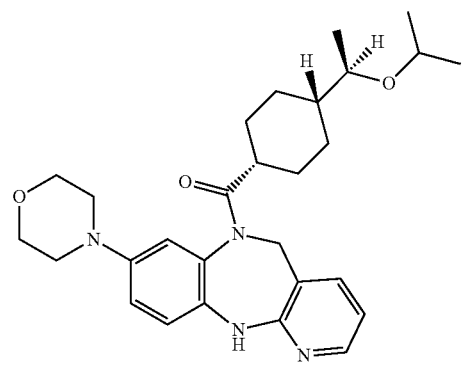

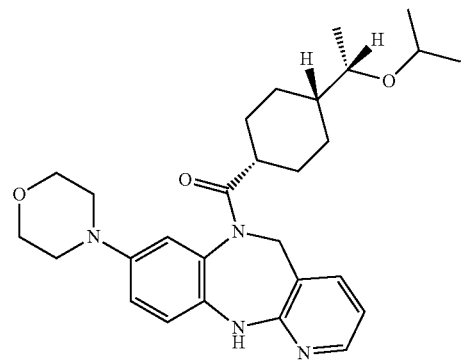

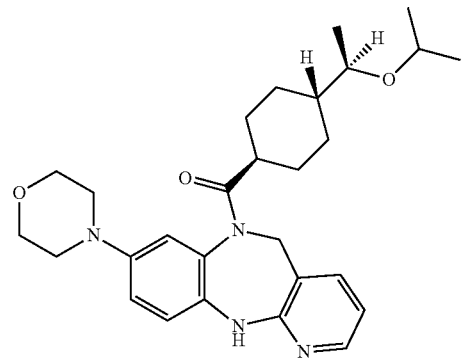

-continued

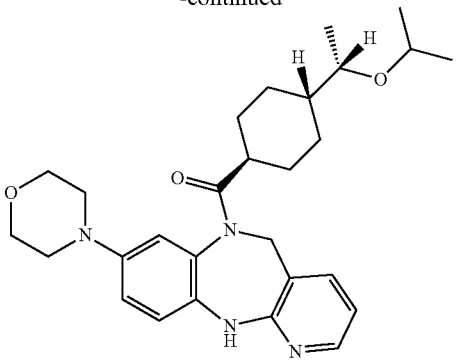

Step 1:

To a microwave vial containing 4-vinylcyclohexanecarboxylic acid (124 mg, 0.806 mmol) and 4-(6,11-dihydro-5H-benzo[b]pyrido[2,3-e][1,4]diazepin-8-yl)morpholine (175 mg, 0.620 mmol) was added acetonitrile (6.0 mL). PS-PPh$_3$ (2.06 mmol/g loading, 490 mg, 1.86 mmol) and trichloroacetonitrile (300 μL, 3.00 mmol) were added and the mixture was irradiated in the microwave to 100° C. for 10 minutes. Upon cooling to room temperature, the mixture was diluted with methanol, filtered, and then purified by reverse phase HPLC (acetonitrile/water with 0.1% TFA modifier) to afford (8-morpholino-5H-benzo[b]pyrido[2,3-e][1,4]diazepin-6(11H)-yl)(4-vinylcyclohexyl)methanone as the TFA salt. MS: 419 (M+1).

Step 2:

To a mixture of mercuric acetate (55 mg, 0.17 mmol) in 2-propanol (170 μL) was added (8-morpholino-5H-benzo[b]pyrido[2,3-e][1,4]diazepin-6(11H)-yl)(4-vinylcyclohexyl)methanone, TFA salt (92 mg, 0.17 mmol) and the mixture was stirred for 1 h. Aqueous sodium hydroxide (1.0 M, 0.35 mL, 0.35 mmol) was added and the mixture was stirred for 2 minutes. Sodium borohydride (3.0 mg, 0.086 mmol) was added and the mixture was stirred for 15 minutes. The mixture was diluted with ethyl acetate and then washed with water. The organic layer was separated, dried over magnesium sulfate, filtered and concentrated. The residue was purified by column chromatography on silica gel to afford two spots containing [8-(morpholin-4-yl)-5,11-dihydro-6H-pyrido[2,3-b][1,5]benzodiazepin-6-yl]{4-[1-(propan-2-yloxy)ethyl]cyclohexyl}methanone. The two spots (top spot and bottom spot) were then separately purified by chiral SFC to afford all 4 isomers. SFC conditions to separate top spot: (IC, 2.1×25 cm, methanol with 0.25% DMEA and 35% modifier in CO$_2$). SFC conditions to separate bottom spot: (IC, 2.1×25 cm, isopropanol with 0.25% DMEA and 25% modifier in CO$_2$).

Characterization data for the first peak isolated from SFC (top spot): MS: 479 (M+1). $^1$H NMR (500 MHz, DMSO-d$_6$) δ 9.11 (d, J=7.5 Hz, 1H), 8.02-7.94 (m, 1H), 7.40 (d, J=7.1 Hz, 1H), 7.22-7.18 (m, 1H), 6.95-6.85 (m, 1H), 6.79 (t, J=2.9 Hz, 1H), 6.63 (dd, J=7.3, 4.7 Hz, 1H), 5.19 (d, J=14.9 Hz, 1H), 3.84 (d, J=14.9 Hz, 1H), 3.76-3.68 (m, 4H), 3.55-3.42 (m, 1H), 3.21-3.12 (m, 1H), 3.09-3.02 (m, 2H), 3.02-2.94 (m, 2H), 2.75-2.64 (m, 1H), 1.77 (d, J=11.7 Hz, 1H), 1.72-1.54 (m, 1H), 1.54-1.37 (m, 2H), 1.32-1.10 (m, 5H), 0.98 (d, J=6.1 Hz, 3H), 0.94-0.86 (m, 6H).

Characterization data for the second peak isolated from SFC (top spot): MS: 479 (M+1). $^1$H NMR (500 MHz, DMSO-d$_6$) δ 9.20 (s, 1H), 7.99 (d, J=4.7 Hz, 1H), 7.43 (d, J=7.1 Hz, 1H), 7.21 (d, J=8.9 Hz, 1H), 6.92 (d, J=6.8 Hz, 1H), 6.79 (s, 1H), 6.68-6.62 (m, 1H), 5.18 (d, J=15.0 Hz, 1H), 3.88 (d, J=14.9 Hz, 1H), 3.79-3.66 (m, 4H), 3.51-3.42 (m, 1H), 3.11-3.01 (m, 4H), 3.01-2.95 (m, 1H), 2.43-2.32 (m, 1H), 1.89 (d, J=13.6 Hz, 1H), 1.81 (d, J=13.3 Hz, 1H), 1.62 (s, 1H), 1.46-1.31 (m, 2H), 1.21 (d, J=11.7 Hz, 2H), 1.14-1.01 (m, 2H), 1.01-0.87 (m, 9H).

Characterization data for the first peak isolated from SFC (bottom spot): MS: 479 (M+1). $^1$H NMR (500 MHz, DMSO-d$_6$) δ 9.11 (s, 1H), 7.98 (d, J=4.3 Hz, 1H), 7.40 (d, J=7.2 Hz, 1H), 7.21 (d, J=8.9 Hz, 1H), 6.91 (dd, J=9.0, 2.7 Hz, 1H), 6.82-6.75 (m, 1H), 6.64 (dd, J=7.2, 4.8 Hz, 1H), 5.18 (d, J=15.0 Hz, 1H), 3.87 (d, J=14.9 Hz, 1H), 3.77-3.67 (m, 4H), 3.52-3.41 (m, 1H), 3.11-3.01 (m, 3H), 3.01-2.92 (m, 2H), 2.43-2.33 (m, 1H), 1.88 (d, J=12.9 Hz, 1H), 1.66-1.56 (m, 1H), 1.45-1.33 (m, 2H), 1.30-1.14 (m, 3H), 1.13-1.02 (m, 2H), 1.01-0.87 (m, 9H).

Characterization data for the second peak isolated from SFC (bottom spot): MS: 479 (M+1). $^1$H NMR (500 MHz, DMSO-d$_6$) δ 9.11 (s, 1H), 7.98 (d, J=4.0 Hz, 1H), 7.40 (d, J=7.4 Hz, 1H), 7.21 (d, J=8.9 Hz, 1H), 6.91 (dd, J=9.0, 2.6 Hz, 1H), 6.78 (d, J=2.2 Hz, 1H), 6.64 (dd, J=7.2, 4.9 Hz, 1H), 5.18 (d, J=14.9 Hz, 1H), 3.87 (d, J=14.9 Hz, 1H), 3.77-3.66 (m, 4H), 3.53-3.40 (m, 1H), 3.11-3.01 (m, 3H), 3.01-2.92 (m, 2H), 2.43-2.33 (m, 1H), 1.89 (d, J=12.7 Hz, 1H), 1.67-1.56 (m, 1H), 1.46-1.32 (m, 2H), 1.27-1.16 (m, 3H), 1.15-1.02 (m, 2H), 1.01-0.87 (m, 9H).

Example 175: 2-Methyl-2-(6-{[trans-4-(propan-2-yloxy)cyclohexyl]carbonyl}-6,11-dihydro-5H-pyrido[2,3-b][1,5]benzodiazepin-8-yl)propanenitrile

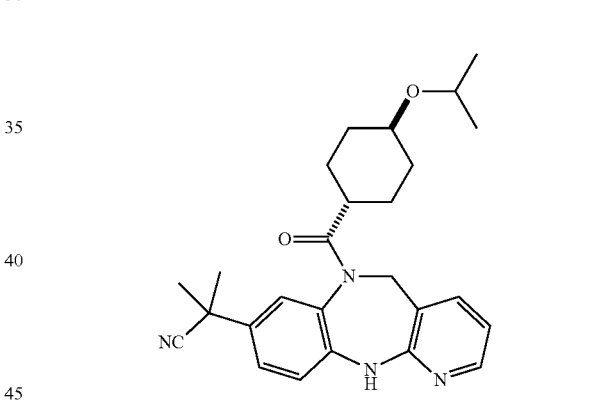

To a vial was added 2-(6,11-dihydro-5H-pyrido[2,3-b][1,5]benzodiazepin-8-yl)-2-methylpropanenitrile (30 mg, 0.11 mmol), PS-PPh$_3$ (2.06 mmol/g loading, 165 mg, 0.340 mmol), trans-4-(propan-2-yloxy)cyclohexanecarboxylic acid (21 mg, 0.11 mmol), and acetonitrile (1.9 mL). Trichloroacetonitrile (57 μL, 0.57 mmol) was added and the vial was sealed and heated to 100° C. for 15 min in a microwave reactor. Upon cooling to room temperature, the material was filtered and the solids were rinsed with 1:1 MeOH/DCM (20 mL). The filtrate was concentrated under reduced pressure, and the residue was purified by mass triggered reverse phase HPLC (ACN/water with 0.1% TFA modifier) to afford the title compound as a solid TFA salt. MS: 433 (M+1). $^1$H NMR (500 MHz, DMSO-d$_6$) δ 9.64 (s, 1H), 8.09-8.03 (m, 1H), 7.52 (d, J=7.0 Hz, 1H), 7.40 (s, 1H), 7.37 (d, J=1.8 Hz, 2H), 6.79-6.72 (m, 1H), 5.20 (d, J=15.0 Hz, 1H), 3.94 (d, J=14.8 Hz, 1H), 3.60-3.52 (m, 1H), 3.18-3.05 (m, 1H), 2.37-2.26 (m, 1H), 1.96-1.82 (m, 2H), 1.68 (d, J=6.2 Hz, 6H), 1.63 (s, 1H), 1.51-1.39 (m, 1H), 1.14-1.06 (m, 1H), 1.05-1.00 (m, 1H), 0.98-0.94 (m, 6H), 0.92-0.87 (m, 1H), 0.70-0.56 (m, 1H).

Example 176: Racemic trans 1-{6-[(4,4-difluoro-2-methylcyclohexyl)carbonyl]-6,11-dihydro-5H-pyrido[2,3-b][1,5]benzodiazepin-8-yl}piperidine-4-carbonitrile

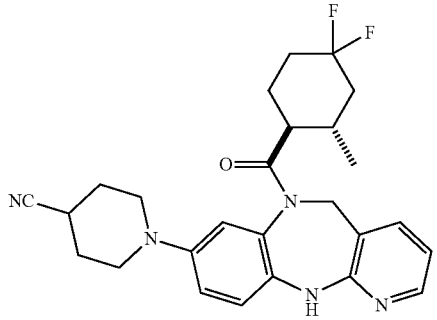

To a vial was added 1-(6,11-dihydro-5H-pyrido[2,3-b][1,5]benzodiazepin-8-yl)piperidine-4-carbonitrile (40 mg, 0.13 mmol), PS-PPh₃ (2.06 mmol/g loading, 191 mg, 0.394 mmol), 4,4-difluoro-2-methylcyclohexanecarboxylic acid (23 mg, 0.13 mmol, mixture of trans isomers), and acetonitrile (1.3 mL). Trichloroacetonitrile (66 μL, 0.66 mmol) was added and the vial was sealed and heated to 100° C. for 15 min in a microwave reactor. Upon cooling to room temperature, the material was filtered and concentrated under reduced pressure. The residue was purified by mass triggered reverse phase HPLC (ACN/water with 0.1% TFA modifier) to afford the title compound as a solid TFA salt. MS: 466 (M+1). $^1$H NMR (500 MHz, DMSO-$d_6$) δ 9.93 (s, 1H), 8.04 (d, J=5.3 Hz, 1H), 7.73-7.61 (m, 1H), 7.28-7.21 (m, 1H), 7.08-6.98 (m, 1H), 6.88 (s, 1H), 6.84-6.77 (m, 1H), 5.27 (d, J=14.9 Hz, 1H), 3.98 (d, J=15.0 Hz, 1H), 3.41-3.25 (m, 2H), 3.17-2.98 (m, 2H), 2.21-2.06 (m, 2H), 2.06-1.90 (m, 4H), 1.90-1.77 (m, 3H), 1.77-1.59 (m, 2H), 1.03-0.91 (m, 2H), 0.28 (d, J=6.5 Hz, 3H).

Example 177: 6-[(Trans-4-methoxycyclohexyl)carbonyl]-8-(1,3-thiazol-5-yl)-6,11-dihydro-5H-pyrido[2,3-b][1,5]benzodiazepine

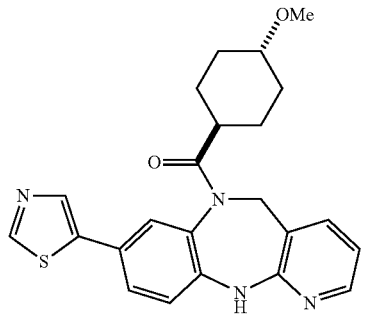

Thiazole-5-boronic acid pinacol ester (10 mg, 0.048 mmol) was added to a reaction vessel containing (8-bromo-5H-benzo[b]pyrido[2,3-e][1,4]diazepin-6(11H)-yl)(trans-4-methoxycyclohexyl)methanone (20 mg, 0.048 mmol), potassium phosphate, tribasic (1.0 M in water, 0.19 mL, 0.19 mmol), and 1,1'-bis(diphenylphosphino)ferrocene-palladium(II)dichloride dichloromethane complex (4.0 mg, 4.8 μmol). The mixture was degassed under nitrogen and charged with DMA (1 mL). The reaction was heated to 80° C. for 18 h. Upon cooling to room temperature, the mixture was filtered and purified by mass triggered reverse phase HPLC (ACN/water with 0.1% TFA modifier) to afford the title compound as a solid TFA salt. MS: 421 (M+1). $^1$H NMR (600 MHz, DMSO-$d_6$) δ 9.79 (s, 1H), 8.99 (d, J=13.8 Hz, 1H), 8.24 (s, 1H), 8.08-8.01 (m, 1H), 7.63 (d, J=2.1 Hz, 1H), 7.59-7.50 (m, 2H), 7.37 (d, J=8.5 Hz, 1H), 6.77 (dd, J=7.3, 5.0 Hz, 1H), 5.19 (d, J=15.1 Hz, 1H), 3.95 (d, J=14.9 Hz, 1H), 3.08 (s, 3H), 2.95-2.87 (m, 1H), 2.44-2.36 (m, 1H), 2.01-1.87 (m, 2H), 1.77-1.68 (m, 1H), 1.49-1.37 (m, 1H), 1.23-1.12 (m, 1H), 1.02-0.91 (m, 1H), 0.88-0.78 (m, 1H), 0.65-0.54 (m, 1H).

The compounds in the following table were prepared using the methodology herein and the general procedure described in Example 177.

| Ex. No. | Structure | Chemical Name | [M + H]+ |
|---|---|---|---|
| 178 | 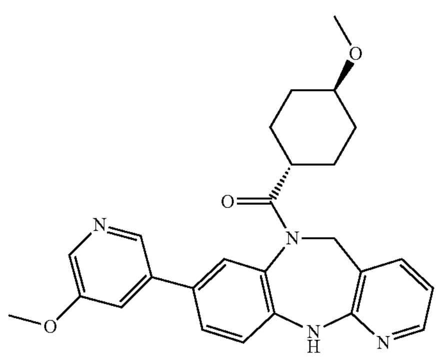 [SMILES: COc1cncc(-c2ccc3c(c2)N(C(=O)[C@H]2CC[C@H](OC)CC2)Cc2cccnc2N3)c1] | 6-[(trans-4-methoxycyclohexyl)carbonyl]-8-(5-methoxypyridin-3-yl)-6,11-dihydro-5H-pyrido[2,3-b][1,5]benzodiazepine | 445 |

-continued

| Ex. No. | Structure | Chemical Name | [M + H]+ |
|---|---|---|---|
| 179 | 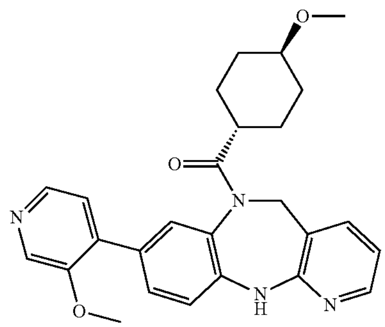 [SMILES: COc1cnccc1-c1ccc2c(c1)N(C(=O)[C@H]1CC[C@H](OC)CC1)Cc1cccnc1N2] | 6-[(trans-4-methoxycyclohexyl)carbonyl]-8-(3-methoxypyridin-4-yl)-6,11-dihydro-5H-pyrido[2,3-b][1,5]benzodiazepine | 445 |
| 180 | 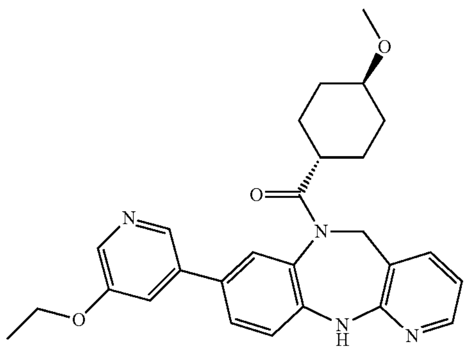 [SMILES: CCOc1cncc(-c2ccc3c(c2)N(C(=O)[C@H]2CC[C@H](OC)CC2)Cc2cccnc2N3)c1] | 8-(5-ethoxypyridin-3-yl)-6-[(trans-4-methoxycyclohexyl)carbonyl]-6,11-dihydro-5H-pyrido[2,3-b][1,5]benzodiazepine | 459 |
| 181 | 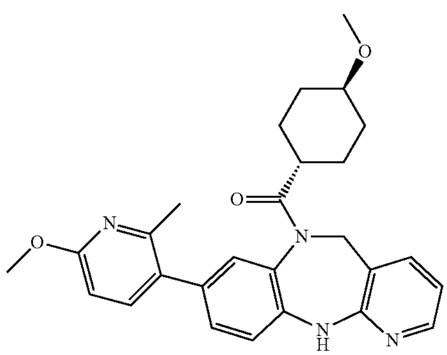 [SMILES: COc1ccc(-c2ccc3c(c2)N(C(=O)[C@H]2CC[C@H](OC)CC2)Cc2cccnc2N3)c(C)n1] | 6-[(trans-4-methoxycyclohexyl)carbonyl]-8-(6-methoxy-2-methylpyridin-3-yl)-6,11-dihydro-5H-pyrido[2,3-b][1,5]benzodiazepine | 459 |
| 182 | 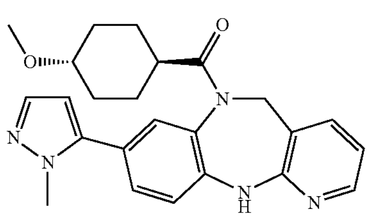 [SMILES: CO[C@H]1CC[C@H](C(=O)N2Cc3cccnc3Nc3ccc(-c4ccnn4C)cc32)CC1] | 6-[(trans-4-methoxycyclohexyl)carbonyl]-8-(1-methyl-1H-pyrazol-5-yl)-6,11-dihydro-5H-pyrido[2,3-b][1,5]benzodiazepine | 418 |
| 183 | 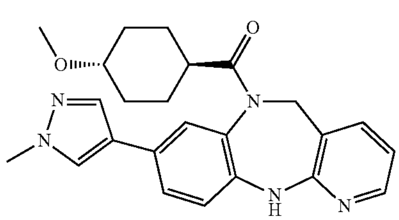 [SMILES: CO[C@H]1CC[C@H](C(=O)N2Cc3cccnc3Nc3ccc(-c4cnn(C)c4)cc32)CC1] | 6-[(trans-4-methoxycyclohexyl)carbonyl]-8-(1-methyl-1H-pyrazol-4-yl)-6,11-dihydro-5H-pyrido[2,3-b][1,5]benzodiazepine | 418 |

-continued

| Ex. No. | Structure | Chemical Name | [M + H]+ |
|---|---|---|---|
| 184 | 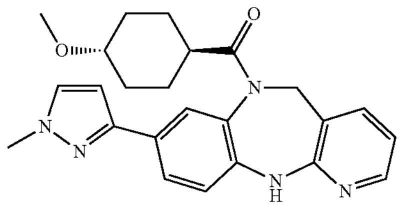 [SMILES: CO[C@H]1CC[C@H](C(=O)N2Cc3cccnc3Nc3ccc(-c4ccn(C)n4)cc32)CC1] | 6-[(trans-4-methoxycyclohexyl)carbonyl]-8-(1-methyl-1H-pyrazol-3-yl)-6,11-dihydro-5H-pyrido[2,3-b][1,5]benzodiazepine | 418 |
| 185 | 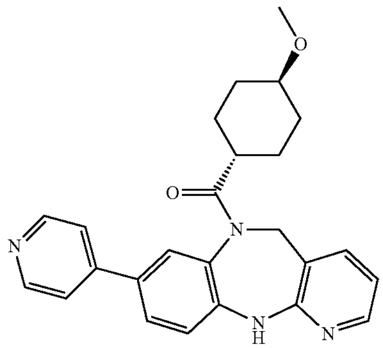 [SMILES: CO[C@H]1CC[C@H](C(=O)N2Cc3cccnc3Nc3ccc(-c4ccncc4)cc32)CC1] | 6-[(trans-4-methoxycyclohexyl)carbonyl]-8-pyridin-4-yl-6,11-dihydro-5H-pyrido[2,3-b][1,5]benzodiazepine | 415 |
| 186 | 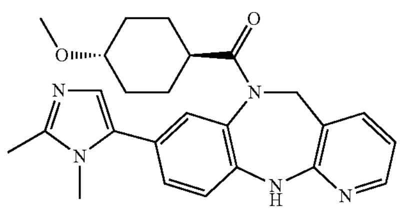 [SMILES: CO[C@H]1CC[C@H](C(=O)N2Cc3cccnc3Nc3ccc(-c4cnc(C)n4C)cc32)CC1] | 8-(1,2-dimethyl-1H-imidazol-5-yl)-6-[(trans-4-methoxycyclohexyl)carbonyl]-6,11-dihydro-5H-pyrido[2,3-b][1,5]benzodiazepine | 432 |
| 187 | 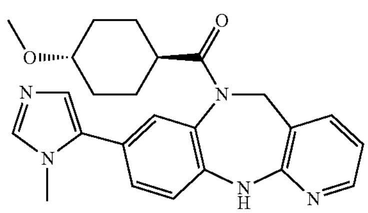 [SMILES: CO[C@H]1CC[C@H](C(=O)N2Cc3cccnc3Nc3ccc(-c4cncn4C)cc32)CC1] | 6-[(trans-4-methoxycyclohexyl)carbonyl]-8-(1-methyl-1H-imidazol-5-yl)-6,11-dihydro-5H-pyrido[2,3-b][1,5]benzodiazepine | 418 |

Example 188: Trans 5-{6-[(4,4-difluoro-2-methyl-cyclohexyl)carbonyl]-6,11-dihydro-5H-pyrido[2,3-b][1,5]benzodiazepin-8-yl}pyridine-2-carboxamide

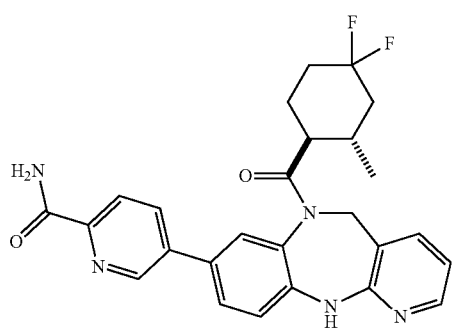

Step 1:

To an oven-dried, nitrogen cooled vial was added racemic trans (8-bromo-5,11-dihydro-6H-pyrido[2,3-b][1,5]benzodiazepin-6-yl)(4,4-difluoro-2-methylcyclohexyl)methanone (65 mg, 0.15 mmol), bis(pinacolato)diboron (76 mg, 0.30 mmol), potassium acetate (29 mg, 0.30 mmol), and 1,1'-bis(di-tert-butylphosphino)ferrocene palladium dichloride (10 mg, 0.015 mmol). DMA (0.75 mL) was added, the mixture was degassed under a nitrogen atmosphere for 10 minutes, and then heated to 90° C. for 16 h. The reaction mixture was allowed to cool to room temperature, filtered over a pad of celite, diluted with water, and extracted with EtOAc (3×). The combined organic layers were washed with brine, dried over sodium sulfate, filtered, and concentrated under reduced pressure. The residue was purified by column chromatography on silica gel (0-50% 3:1 EtOAc:EtOH/Hexanes to afford racemic trans (4,4-difluoro-2-methylcyclohexyl)[8-(4,4,5,5-tetramethyl-1,3,2-dioxaborolan-2-yl)-5,11-dihydro-6H-pyrido[2,3-b][1,5]benzodiazepin-6-yl]methanone as a solid. MS: 484 (M+1).

Step 2:

To an oven-dried, nitrogen cooled vial was added trans (4,4-difluoro-2-methylcyclohexyl)[8-(4,4,5,5-tetramethyl-1,3,2-dioxaborolan-2-yl)-5,11-dihydro-6H-pyrido[2,3-b][1,5]benzodiazepin-6-yl]methanone (66 mg, 0.14 mmol), methyl 5-bromopyridine-2-carboxylate (35 mg, 0.16 mmol), and 3$^{rd}$ generation x-phos palladacycle (12 mg, 0.014 mmol). THF (0.68 mL) was added, followed by potassium phosphate, tribasic (0.5 M in water, 1.4 mL, 0.70 mmol), and the reaction mixture was heated to 50° C. for 16 hours. The reaction was allowed to cool to room temperature, washed with water, and extracted with EtOAc (2×). The combined organic layers were dried over sodium sulfate, filtered, and concentrated under reduced pressure. The residue was purified by column chromatography on silica gel (0-100% 3:1 EtOAc:EtOH/Hexanes) to afford trans methyl 5-{6-[(4,4-difluoro-2-methylcyclohexyl)carbonyl]-6,11-dihydro-5H-pyrido[2,3-b][1,5]benzodiazepin-8-yl}pyridine-2-carboxylate as an oil. MS: 493 (M+1).

Step 3:

To a mixture of trans methyl 5-{6-[(4,4-difluoro-2-methylcyclohexyl)carbonyl]-6,11-dihydro-5H-pyrido[2,3-b][1,5]benzodiazepin-8-yl}pyridine-2-carboxylate (18 mg, 0.037 mmol), dissolved in THF (1.0 mL), water (0.25 mL), and MeOH (0.25 mL) was added lithium hydroxide (2 mg, 0.09 mmol). The mixture was stirred at room temperature for 16 h. The reaction was quenched with aqueous HCl (2N) to pH 5~6 and extracted with EtOAc (2×). The combined organic layers were dried over sodium sulfate, filtered, and concentrated under reduced pressure to afford trans 5-{6-[(4,4-difluoro-2-methylcyclohexyl)carbonyl]-6,11-dihydro-5H-pyrido[2,3-b][1,5]benzodiazepin-8-yl}pyridine-2-carboxylic acid as a solid. MS: 479 (M+1).

Step 4:

To trans 5-{6-[(4,4-difluoro-2-methylcyclohexyl)carbonyl]-6,11-dihydro-5H-pyrido[2,3-b][1,5]benzodiazepin-8-yl}pyridine-2-carboxylic acid (15 mg, 0.031 mmol) dissolved in DMF (0.31 mL) was added DIEA (16 µL, 0.093 mmol), ammonium chloride (3 mg, 0.06 mmol), and 2,4,6-tripropyl-1,3,5,2,4,6-trioxatriphosphinane 2,4,6-trioxide (50% in DMF, 22 µL, 0.037 mmol). The reaction mixture was stirred for 16 h at room temperature. The mixture was quenched with aqueous HCl (1N) to pH 5~6, and extracted with EtOAc (2×). The combined organic layers were dried over sodium sulfate, filtered, and concentrated under reduced pressure. The residue was purified by mass triggered reverse phase HPLC (ACN/water with 0.1% TFA modifier) to afford the title compound as a solid TFA salt. MS: 478 (M+1). $^1$H NMR (600 MHz, DMSO-d$_6$) δ 9.86 (s, 1H), 8.89 (s, 1H), 8.25-8.20 (m, 1H), 8.12-8.01 (m, 3H), 7.77-7.69 (m, 2H), 7.61 (s, 1H), 7.58-7.52 (m, 1H), 7.49-7.42 (m, 1H), 6.80-6.75 (m, 1H), 5.26 (d, J=14.8 Hz, 1H), 3.99 (d, J=14.8 Hz, 1H), 2.24-2.16 (m, 1H), 2.02-1.87 (m, 1H), 1.78-1.70 (m, 1H), 1.69-1.43 (m, 3H), 1.40-1.25 (m, 1H), 1.02-0.97 (m, 1H), 0.22 (d, J=6.4 Hz, 3H).

Example 189: 5-(6-{[4-(Propan-2-yloxy)cyclohexyl]carbonyl}-6,11-dihydro-5H-pyrido[2,3-b][1,5]benzodiazepin-8-yl)pyridine-2-carboxamide

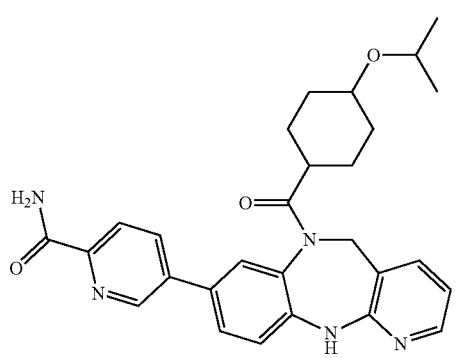 [SMILES: CC(C)OC1CCC(C(=O)N2Cc3cccnc3Nc3ccc(-c4ccc(C(N)=O)nc4)cc32)CC1]

Step 1:

To an oven-dried, nitrogen cooled vial was added (8-bromo-5,11-dihydro-6H-pyrido[2,3-b][1,5]benzodiazepin-6-yl)[4-(propan-2-yloxy)cyclohexyl]methanone (103 mg, 0.232 mmol), bis(pinacolato)diboron (118 mg, 0.464 mmol), potassium acetate (46 mg, 0.46 mmol), and 1,1'-bis(di-tert-butylphosphino)ferrocene palladium dichloride (15 mg, 0.023 mmol). DMA (1.2 mL) was added, the mixture was degassed under a nitrogen atmosphere for 10 minutes, and then heated to 90° C. for 16 h. The reaction mixture was cooled to room temperature, filtered over a pad of celite, diluted with water, and extracted with EtOAc (3×). The combined organic layers were washed with brine, dried over sodium sulfate, filtered, and concentrated under reduced pressure. The residue was purified by column chromatography on silica gel (0-50% 3:1 EtOAc:EtOH/Hexanes) to afford [4-(propan-2-yloxy)cyclohexyl][8-(4,4,5,5-tetramethyl-1,3,2-dioxaborolan-2-yl)-5,11-dihydro-6H-pyrido[2,3-b][1,5]benzodiazepin-6-yl]methanone as an oil. MS: 492 (M+1).

Step 2:

To an oven-dried, nitrogen cooled vial was added [4-(propan-2-yloxy)cyclohexyl][8-(4,4,5,5-tetramethyl-1,3,2-dioxaborolan-2-yl)-5,11-dihydro-6H-pyrido[2,3-b][1,5]benzodiazepin-6-yl]methanone (114 mg, 0.232 mmol), 5-bromopyridine-2-carboxamide, TFA (88 mg, 0.28 mmol), and 3$^{rd}$ generation x-phos palladacycle (20 mg, 0.023 mmol). THF (1.2 mL) was added, followed by potassium phosphate, tribasic (0.5 M in water, 2.3 mL, 1.2 mmol), and the reaction mixture was heated to 50° C. for 16 h. The reaction was allowed to cool to room temperature, washed with water, and extracted with EtOAc (2×). The combined organic layers were dried over sodium sulfate, filtered, and concentrated under reduced pressure. The residue was purified by mass triggered reverse phase HPLC (ACN/water with 0.1% TFA modifier) to afford the title compound as a solid. MS: 486 (M+1). $^1$H NMR (500 MHz, DMSO-d$_6$) δ 9.71 (s, 1H), 8.95-8.93 (m, 1H), 8.28-8.25 (m, 1H), 8.11 (s, 1H), 8.09-8.04 (m, 2H), 7.83-7.81 (m, 1H), 7.75-7.72 (m, 1H), 7.65 (s, 1H), 7.52 (d, J=7.5 Hz, 1H), 7.47 (d, J=8.6 Hz, 1H), 6.81-6.75 (m, 1H), 5.23 (d, J=14.9 Hz, 1H), 3.95 (d, J=14.5 Hz, 1H), 2.61-2.53 (m, 1H), 1.82-1.66 (m, 2H), 1.61-1.53 (m, 1H), 1.44-1.34 (m, 1H), 1.29-1.24 (m, 1H), 1.24-1.12 (m, 3H), 1.01-0.94 (m, 6H), 0.94-0.85 (m, 2H).

Example 190: 8-(1,6-Diazaspiro[3.3]hept-1-yl)-6-[(3,3-dimethylcyclobutyl)carbonyl]-6,11-dihydro-5H-pyrido[2,3-b][1,5]benzodiazepine

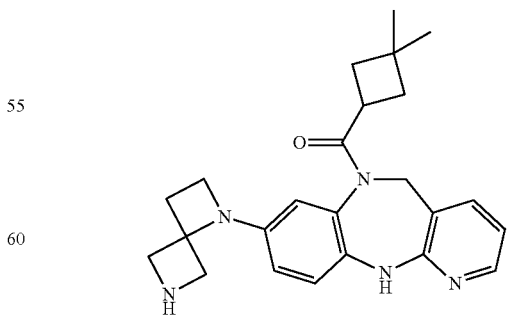

Step 1:

To an oven-dried, nitrogen cooled microwave vial was added (8-bromo-5,11-dihydro-6H-pyrido[2,3-b][1,5]benzodiazepin-6-yl)(3,3-dimethylcyclobutyl)methanone (250 mg, 0.647 mmol), tert-butyl 1,6-diazaspiro[3.3]heptane-6-carboxylate, oxalate salt (220 mg, 0.768 mmol), RuPhos-G1-palladacycle (26 mg, 0.032 mmol) and Ruphos (15 mg, 0.032 mmol). The vial was evacuated and filled with nitrogen and then THF (750 µL) and lithium bis(trimethylsilyl)amide (1.0 M in THF, 2.1 mL, 2.1 mmol) was added via syringe. The reaction was heated to 100° C. for 16 h. Upon cooling to room temperature, the mixture was diluted with water, extracted with ethyl acetate (2×) and the combined organic layers were washed with brine, dried over sodium sulfate, filtered, and concentrated under reduced pressure. The residue was purified by column chromatography on silica gel (10-50% EtOAc/DCM) to afford tert-butyl 1-{6-[(3,3-dimethylcyclobutyl)carbonyl]-6,11-dihydro-5H-pyrido[2,3-b][1,5]benzodiazepin-8-yl}-1,6-diazaspiro[3.3]heptane-6-carboxylate as a solid. MS: 504 (M+1). IDH1 R132H: 484.8 nM Step 2:

To a mixture of tert-butyl 1-{6-[(3,3-dimethylcyclobutyl)carbonyl]-6,11-dihydro-5H-pyrido[2,3-b][1,5]benzodiazepin-8-yl}-1,6-diazaspiro[3.3]heptane-6-carboxylate (162 mg, 0.322 mmol) in DCM (1 mL) was added TFA (1 mL) and the mixture was stirred for 1 h at room temperature. The mixture was concentrated under reduced pressure, and the residue was free-based by passing through PS-bicarbonate cartridges (2×500 mg columns) to afford the title compound as a solid. MS: 404 (M+1). $^1$H NMR (500 MHz, DMSO-d$_6$) 8.99 (s, 1H), 7.98 (d, J=3.5 Hz, 1H), 7.41 (d, J=6.6 Hz, 1H), 7.17 (d, J=8.7 Hz, 1H), 6.72-6.69 (m, 1H), 6.65-6.57 (m, 2H), 5.18 (d, J=15.0 Hz, 1H), 3.97-3.85 (m, 3H), 3.62-3.48 (m, 4H), 3.30-3.23 (m, 1H), 2.43-2.29 (m, 2H), 2.00-1.91 (m, 1H), 1.79-1.71 (m, 1H), 1.57-1.48 (m, 1H), 1.24-1.12 (m, 1H), 0.94 (s, 3H), 0.88 (s, 3H).

Examples 191-192: 6-{[Trans-4-(1-methylethoxy)cyclohexyl]carbonyl}-8-(2-oxa-5-azabicyclo[2.2.2]oct-5-yl)-6,11-dihydro-5H-pyrido[2,3-b][1,5]benzodiazepine Isomer 1 and 6-{[Trans-4-(1-methylethoxy)cyclohexyl]carbonyl}-8-(2-oxa-5-azabicyclo[2.2.2]oct-5-yl)-6,11-dihydro-5H-pyrido[2,3-b][1,5]benzodiazepine Isomer 2 isomer 1

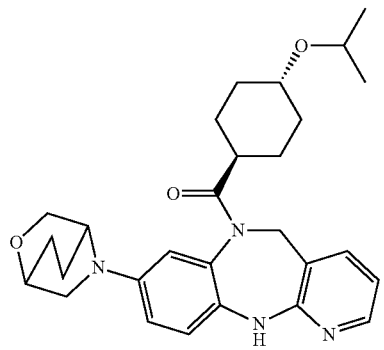

isomer 2

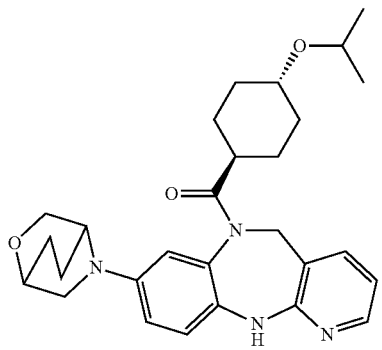

To a mixture of (8-bromo-5,11-dihydro-6H-pyrido[2,3-b][1,5]benzodiazepin-6-yl)(trans-4-isopropoxycyclohexyl)methanone (790 mg, 1.78 mmol), 2-oxa-5-azabicyclo[2.2.2]octane, hemioxalate salt (402 mg, 3.56 mmol), and (2-dicyclohexylphosphino-2',6'-diisopropoxy-1,1'-biphenyl)[2-(2'-amino-1,1'-biphenyl)]palladium(II) methanesulfonate (149 mg, 0.178 mmol) was added lithium bis(trimethylsilyl)amide (1 M THF, 18 mL, 18 mmol) and the flask was evacuated and then purged 5 times with argon. The mixture was heated to 80° C. overnight. Upon cooling to room temperature, the mixture was diluted with ethyl acetate and water. The organic layer was separated, dried over magnesium sulfate, filtered, and concentrated. The solid was taken up in DMSO (6 mL) and purified by reverse phase HPLC (acetonitrile and water with a TFA modifier). The fractions containing product were combined, diluted with ethyl acetate, and washed with saturated aqueous sodium bicarbonate. The organic layer was then dried over magnesium sulfate, filtered, and concentrated. The residue was then purified by chiral SFC (Chiralcel OD-H column, 25%/70% methanol/CO$_2$ with 0.25% N,N-dimethylethanamine modifier) to afford two isomers of the title compound.

Characterization data for isomer 1 (early eluting): MS 477 (M+1). 1H NMR (500 MHz, DMSO-d6) δ 8.95 (d, J=2.9 Hz, 1H), 7.96 (d, J=3.4 Hz, 1H), 7.38 (d, J=6.9 Hz, 1H), 7.18 (d, J=8.8 Hz, 1H), 6.64 (dt, J=9.0, 2.6 Hz, 1H), 6.61 (dd, J=7.2, 4.8 Hz, 1H), 6.55 (s, 1H), 5.18 (d, J=15.0 Hz, 1H), 4.04-3.84 (m, 5H), 3.62-3.54 (m, 2H), 3.19-3.04 (m, 1H), 2.07-1.92 (m, 2H), 1.92-1.79 (m, 4H), 1.77-1.62 (m, 2H), 1.55-1.38 (m, 1H), 1.30-1.19 (m, 2H), 1.15-1.01 (m, 1H), 1.01-0.94 (m, 6H), 0.93-0.81 (m, 1H), 0.75-0.61 (m, 1H).

Characterization data for isomer 2 (late eluting): MS 477 (M+1). 1H NMR (500 MHz, DMSO-d6) δ 8.96 (s, 1H), 7.96 (d, J=4.1 Hz, 1H), 7.38 (d, J=7.2 Hz, 1H), 7.18 (d, J=8.9 Hz, 1H), 6.67-6.62 (m, 1H), 6.61 (dd, J=6.9, 5.1 Hz, 1H), 6.55 (s, 1H), 5.18 (d, J=15.0 Hz, 1H), 4.01-3.85 (m, 5H), 3.62-3.53 (m, 2H), 3.19-3.09 (m, 1H), 2.05-1.95 (m, 2H), 1.93-1.80 (m, 4H), 1.76-1.61 (m, 2H), 1.54-1.39 (m, 1H), 1.28-1.18 (m, 2H), 1.15-1.01 (m, 1H), 1.01-0.94 (m, 6H), 0.94-0.80 (m, 1H), 0.75-0.61 (m, 1H).

The compounds in the following table were prepared using the methodology herein and the general procedure described in Examples 191-192.

| Ex. No. | Structure | Chemical Name | [M + H]+ |
|---|---|---|---|
| 193 | 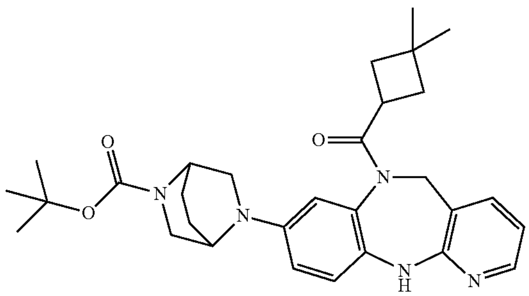 [SMILES: CC1(C)CC(C(=O)N2Cc3cccnc3Nc3ccc(N4CC5CCC4CN5C(=O)OC(C)(C)C)cc32)C1] | tert-butyl 5-{6-[(3,3-dimethylcyclobutyl)carbonyl]-6,11-dihydro-5H-pyrido[2,3-b][1,5]benzodiazepin-8-yl}-2,5-diazabicyclo[2.2.2]octane-2-carboxylate | 518 |
| 194 | 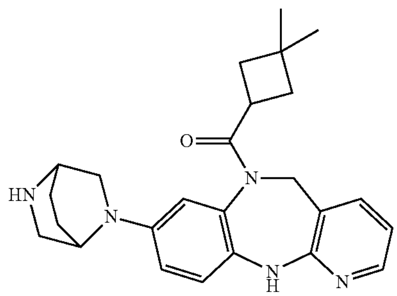 [SMILES: CC1(C)CC(C(=O)N2Cc3cccnc3Nc3ccc(N4CC5CCC4CN5)cc32)C1] | 8-(2,5-diazabicyclo[2.2.2]oct-2-yl)-6-[(3,3-dimethylcyclobutyl)carbonyl]-6,11-dihydro-5H-pyrido[2,3-b][1,5]benzodiazepine | 418 |
| 195 | 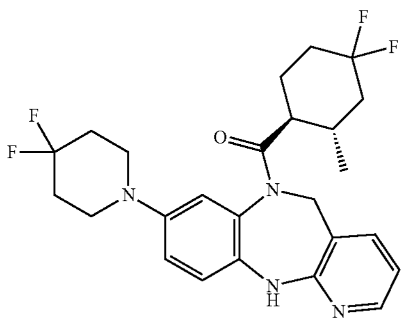 [SMILES: C[C@H]1CC(F)(F)CC[C@@H]1C(=O)N1Cc2cccnc2Nc2ccc(N3CCC(F)(F)CC3)cc21] | 6-{[(1S,2S)-4,4-difluoro-2-methylcyclohexyl]carbonyl}-8-(4,4-difluoropiperidin-1-yl)-6,11-dihydro-5H-pyrido[2,3-b][1,5]benzodiazepine | 477 |
| 196 | 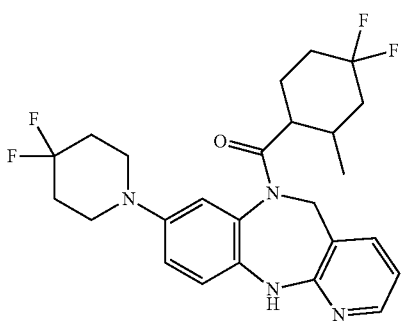 [SMILES: CC1CC(F)(F)CCC1C(=O)N1Cc2cccnc2Nc2ccc(N3CCC(F)(F)CC3)cc21] | 6-[(4,4-difluoro-2-methylcyclohexyl)carbonyl]-8-(4,4-difluoropiperidin-1-yl)-6,11-dihydro-5H-pyrido[2,3-b][1,5]benzodiazepine | 477 |
| 197 | 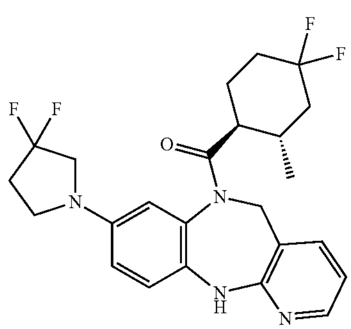 [SMILES: C[C@H]1CC(F)(F)CC[C@@H]1C(=O)N1Cc2cccnc2Nc2ccc(N3CCC(F)(F)C3)cc21] | 6-{[(1S,2S)-4,4-difluoro-2-methylcyclohexyl]carbonyl}-8-(3,3-difluoropyrrolidin-1-yl)-6,11-dihydro-5H-pyrido[2,3-b][1,5]benzodiazepine | 463 |

| Ex. No. | Structure | Chemical Name | [M + H]+ |
|---|---|---|---|
| 198 | 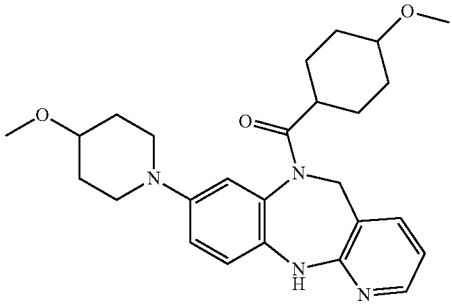<br>Isomer 1 | 6-[(4-methoxycyclohexyl)carbonyl]-8-(4-methoxypiperidin-1-yl)-6,11-dihydro-5H-pyrido[2,3-b][1,5]benzodiazepine | 451 |
| 199 | 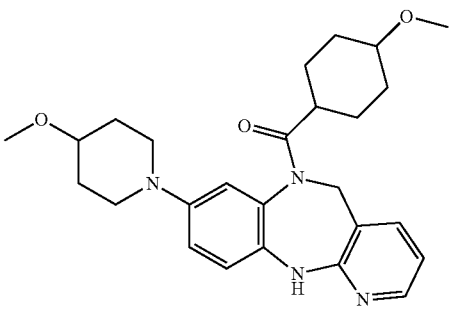<br>Isomer 2 | 6-[(4-methoxycyclohexyl)carbonyl]-8-(4-methoxypiperidin-1-yl)-6,11-dihydro-5H-pyrido[2,3-b][1,5]benzodiazepine | 451 |
| 200 | 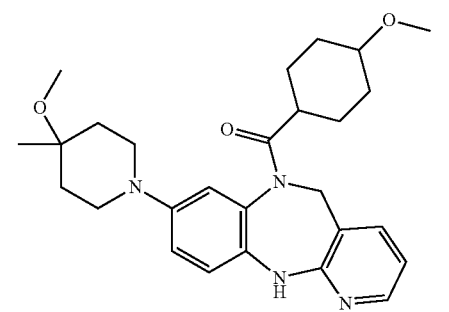<br>Isomer 1 | 6-[(4-methoxycyclohexyl)carbonyl]-8-(4-methoxy-4-methylpiperidin-1-yl)-6,11-dihydro-5H-pyrido[2,3-b][1,5]benzodiazepine | 465 |
| 201 | 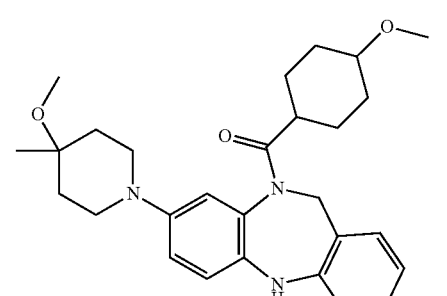<br>Isomer 2 | 6-[(4-methoxycyclohexyl)carbonyl]-8-(4-methoxy-4-methylpiperidin-1-yl)-6,11-dihydro-5H-pyrido[2,3-b][1,5]benzodiazepine | 465 |

-continued

| Ex. No. | Structure | Chemical Name | [M + H]+ |
|---|---|---|---|
| 202 | Isomer 1 | 6-[(4-methoxycyclohexyl)carbonyl]-8-(3-methoxypiperidin-1-yl)-6,11-dihydro-5H-pyrido[2,3-b][1,5]benzodiazepine | 451 |
| 203 | Isomer 2 | 6-[(4-methoxycyclohexyl)carbonyl]-8-(3-methoxypiperidin-1-yl)-6,11-dihydro-5H-pyrido[2,3-b][1,5]benzodiazepine | 451 |
| 204 | Cis/trans Isomer | 6-[(4-methoxycyclohexyl)carbonyl]-8-[(3S)-3-methoxypyrrolidin-1-yl]-6,11-dihydro-5H-pyrido[2,3-b][1,5]benzodiazepine | 437 |
| 205 | Isomer 1 | 6-[(4-methoxycyclohexyl)carbonyl]-8-[(3R)-3-methoxypyrrolidin-1-yl]-6,11-dihydro-5H-pyrido[2,3-b][1,5]benzodiazepine | 437 |

| Ex. No. | Structure | Chemical Name | [M + H]+ |
|---|---|---|---|
| 206 | Isomer 2 | 6-[(4-methoxycyclohexyl)carbonyl]-8-[(3R)-3-methoxypyrrolidin-1-yl]-6,11-dihydro-5H-pyrido[2,3-b][1,5]benzodiazepine | 437 |
| 207 | 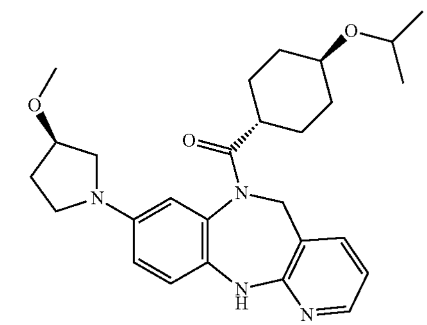 [SMILES: CO[C@@H]1CCN(c2ccc3c(c2)N(C(=O)[C@H]2CC[C@H](OC(C)C)CC2)Cc2cccnc2N3)C1] | 8-[(3R)-3-methoxypyrrolidin-1-yl]-6-{[trans-4-(1-methylethoxy)cyclohexyl]carbonyl}-6,11-dihydro-5H-pyrido[2,3-b][1,5]benzodiazepine | 465 |
| 208 | 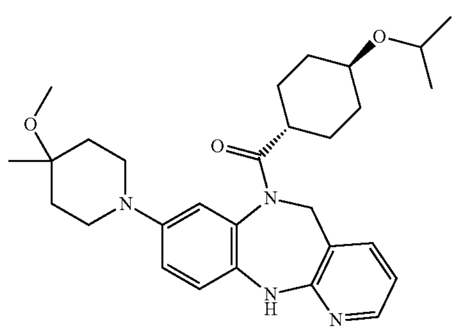 [SMILES: COC1(C)CCN(c2ccc3c(c2)N(C(=O)[C@H]2CC[C@H](OC(C)C)CC2)Cc2cccnc2N3)CC1] | 8-(4-methoxy-4-methylpiperidin-1-yl)-6-{[trans-4-(1-methylethoxy)cyclohexyl]carbonyl}-6,11-dihydro-5H-pyrido[2,3-b][1,5]benzodiazepine | 493 |
| 209 | 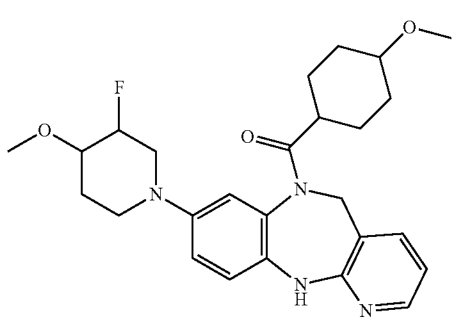 | 8-(3-fluoro-4-methoxypiperidin-1-yl)-6-[(4-methoxycyclohexyl)carbonyl]-6,11-dihydro-5H-pyrido[2,3-b][1,5]benzodiazepine | 469 |

-continued

| Ex. No. | Structure | Chemical Name | [M + H]+ |
| --- | --- | --- | --- |
| 210 | Isomer 1 | 8-(3,3-difluoro-4-methoxypiperidin-1-yl)-6-[(trans-4-methoxycyclohexyl)carbonyl]-6,11-dihydro-5H-pyrido[2,3-b][1,5]benzodiazepine | 487 |
| 211 | Isomer 2 | 8-(3,3-difluoro-4-methoxypiperidin-1-yl)-6-[(trans-4-methoxycyclohexyl)carbonyl]-6,11-dihydro-5H-pyrido[2,3-b][1,5]benzodiazepine | 487 |
| 212 | Isomer 1 | 8-(4,4-difluoro-3-methoxypiperidin-1-yl)-6-[(trans-4-methoxycyclohexyl)carbonyl]-6,11-dihydro-5H-pyrido[2,3-b][1,5]benzodiazepine | 487 |
| 213 | Isomer 2 | 8-(4,4-difluoro-3-methoxypiperidin-1-yl)-6-[(trans-4-methoxycyclohexyl)carbonyl]-6,11-dihydro-5H-pyrido[2,3-b][1,5]benzodiazepine | 487 |

| Ex. No. | Structure | Chemical Name | [M + H]+ |
|---|---|---|---|
| 214 | Isomer 1 | 8-[(3S,4S)-4-fluoro-3-methoxypiperidin-1-yl]-6-[(trans-4-methoxycyclohexyl)carbonyl]-6,11-dihydro-5H-pyrido[2,3-b][1,5]benzodiazepine | 469 |
| 215 | Isomer 2 | 8-[(3S,4S)-4-fluoro-3-methoxypiperidin-1-yl]-6-[(trans-4-methoxycyclohexyl)carbonyl]-6,11-dihydro-5H-pyrido[2,3-b][1,5]benzodiazepine | 469 |
| 216 | Isomer 1 | 8-[(3S,4R)-4-fluoro-3-methoxypiperidin-1-yl]-6-[(trans-4-methoxycyclohexyl)carbonyl]-6,11-dihydro-5H-pyrido[2,3-b][1,5]benzodiazepine | 469 |
| 217 | Isomer 2 | 8-[(3S,4R)-4-fluoro-3-methoxypiperidin-1-yl]-6-[(trans-4-methoxycyclohexyl)carbonyl]-6,11-dihydro-5H-pyrido[2,3-b][1,5]benzodiazepine | 469 |

| Ex. No. | Structure | Chemical Name | [M + H]+ |
|---|---|---|---|
| 218 | Isomer 1 | 8-(3-fluoro-4-methoxypyrrolidin-1-yl)-6-[(trans-4-methoxycyclohexyl)carbonyl]-6,11-dihydro-5H-pyrido[2,3-b][1,5]benzodiazepine | 455 |
| 219 | Isomer 2 | 8-(3-fluoro-4-methoxypyrrolidin-1-yl)-6-[(trans-4-methoxycyclohexyl)carbonyl]-6,11-dihydro-5H-pyrido[2,3-b][1,5]benzodiazepine | 455 |
| 220 | 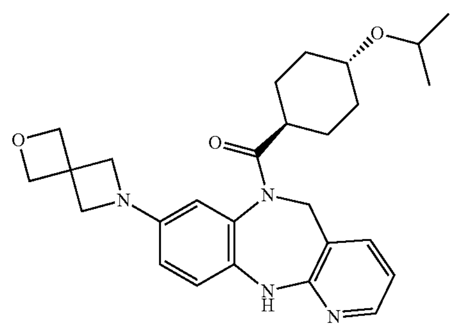 [SMILES: CC(C)O[C@H]1CC[C@H](C(=O)N2Cc3cccnc3Nc3ccc(N4CC5(COC5)C4)cc32)CC1] | 6-{[trans-4-(1-methylethoxy)cyclohexyl]carbonyl}-8-(2-oxa-6-azaspiro[3.3]hept-6-yl)-6,11-dihydro-5H-pyrido[2,3-b][1,5]benzodiazepine | 463 |
| 221 | 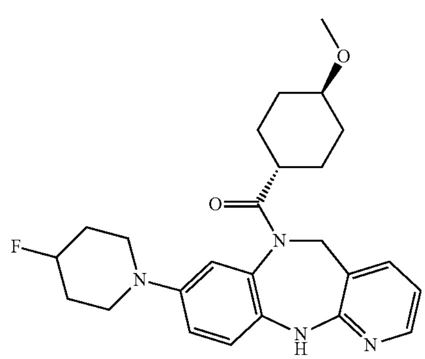 [SMILES: CO[C@H]1CC[C@H](C(=O)N2Cc3cccnc3Nc3ccc(N4CCC(F)CC4)cc32)CC1] | 8-(4-fluoropiperidin-1-yl)-6-[(trans-4-methoxycyclohexyl)carbonyl]-6,11-dihydro-5H-pyrido[2,3-b][1,5]benzodiazepine | 439 |

| Ex. No. | Structure | Chemical Name | [M + H]+ |
| --- | --- | --- | --- |
| 222 | 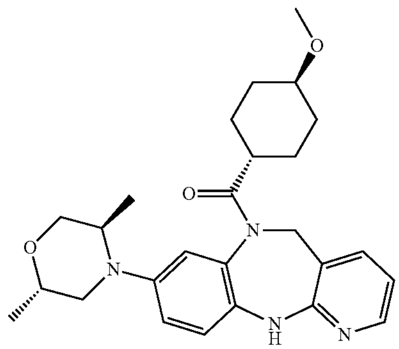 [SMILES: CO[C@H]1CC[C@H](C(=O)N2Cc3cccnc3Nc3ccc(N4C[C@H](C)OC[C@H]4C)cc32)CC1] | 8-[(2S,5R)-2,5-dimethylmorpholin-4-yl]-6-[(trans-4-methoxycyclohexyl)carbonyl]-6,11-dihydro-5H-pyrido[2,3-b][1,5]benzodiazepine | 451 |
| 223 | 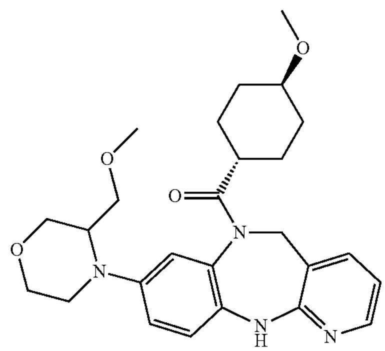 [SMILES: COCC1COCCN1c1ccc2c(c1)N(C(=O)[C@H]1CC[C@H](OC)CC1)Cc1cccnc1N2] | 6-[(trans-4-methoxycyclohexyl)carbonyl]-8-[3-(methoxymethyl)morpholin-4-yl]-6,11-dihydro-5H-pyrido[2,3-b][1,5]benzodiazepine | 467 |
| 224 | 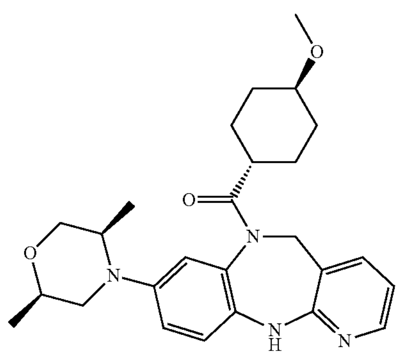 [SMILES: CO[C@H]1CC[C@H](C(=O)N2Cc3cccnc3Nc3ccc(N4C[C@@H](C)OC[C@H]4C)cc32)CC1] | 8-[(2R,5R)-2,5-dimethylmorpholin-4-yl]-6-[(trans-4-methoxycyclohexyl)carbonyl]-6,11-dihydro-5H-pyrido[2,3-b][1,5]benzodiazepine | 451 |
| 225 | 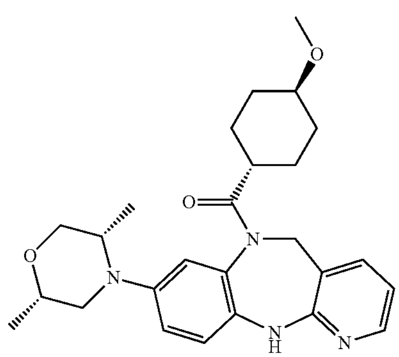 [SMILES: CO[C@H]1CC[C@H](C(=O)N2Cc3cccnc3Nc3ccc(N4C[C@H](C)OC[C@@H]4C)cc32)CC1] | 8-[(2S,5S)-2,5-dimethylmorpholin-4-yl]-6-[(trans-4-methoxycyclohexyl)carbonyl]-6,11-dihydro-5H-pyrido[2,3-b][1,5]benzodiazepine | 451 |

-continued

| Ex. No. | Structure | Chemical Name | [M + H]+ |
|---|---|---|---|
| 226 | 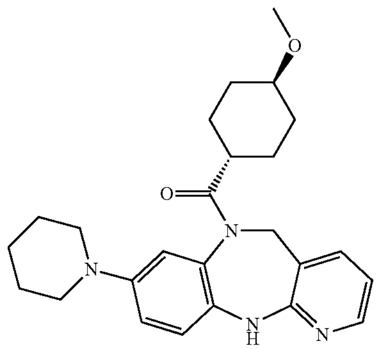 [SMILES: CO[C@H]1CC[C@H](C(=O)N2Cc3cccnc3Nc3ccc(N4CCCCC4)cc32)CC1] | 6-[(trans-4-methoxycyclohexyl)carbonyl]-8-piperidin-1-yl-6,11-dihydro-5H-pyrido[2,3-b][1,5]benzodiazepine | 421 |
| 227 | 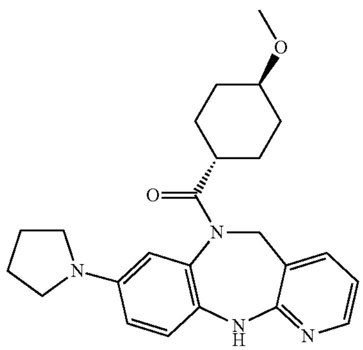 [SMILES: CO[C@H]1CC[C@H](C(=O)N2Cc3cccnc3Nc3ccc(N4CCCC4)cc32)CC1] | 6-[(trans-4-methoxycyclohexyl)carbonyl]-8-pyrrolidin-1-yl-6,11-dihydro-5H-pyrido[2,3-b][1,5]benzodiazepine | 407 |
| 228 | 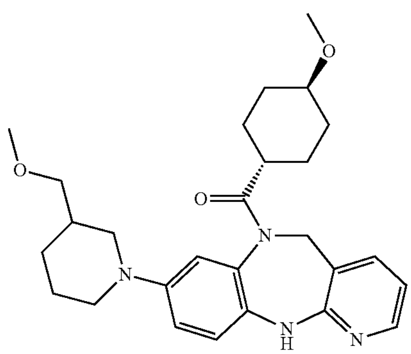 [SMILES: COCC1CCCN(c2ccc3c(c2)N(C(=O)[C@H]2CC[C@H](OC)CC2)Cc2cccnc2N3)C1] | 6-[(trans-4-methoxycyclohexyl)carbonyl]-8-[3-(methoxymethyl)piperidin-1-yl]-6,11-dihydro-5H-pyrido[2,3-b][1,5]benzodiazepine | 465 |
| 229 | 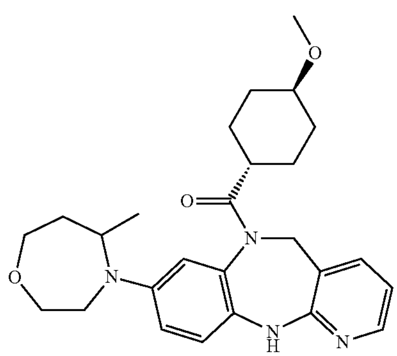 [SMILES: CO[C@H]1CC[C@H](C(=O)N2Cc3cccnc3Nc3ccc(N4CCOCCC4C)cc32)CC1] | 6-[(trans-4-methoxycyclohexyl)carbonyl]-8-(5-methyl-1,4-oxazepan-4-yl)-6,11-dihydro-5H-pyrido[2,3-b][1,5]benzodiazepine | 451 |

| Ex. No. | Structure | Chemical Name | [M + H]+ |
|---|---|---|---|
| 230 | 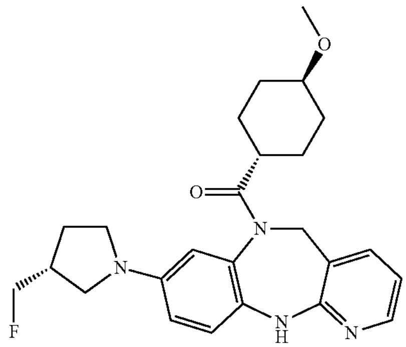 [SMILES: CO[C@H]1CC[C@H](C(=O)N2Cc3cccnc3Nc3ccc(N4CC[C@@H](CF)C4)cc32)CC1] | 8-[(3R)-3-(fluoromethyl)pyrrolidin-1-yl]-6-[(trans-4-methoxycyclohexyl)carbonyl]-6,11-dihydro-5H-pyrido[2,3-b][1,5]benzodiazepine | 439 |
| 231 | 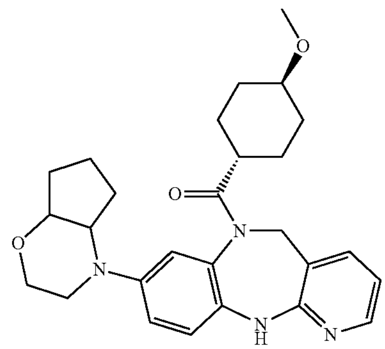 [SMILES: CO[C@H]1CC[C@H](C(=O)N2Cc3cccnc3Nc3ccc(N4CCOC5CCCC54)cc32)CC1] | 8-(hexahydrocyclopenta[b][1,4]oxazin-4(4aH)-yl)-6-[(trans-4-methoxycyclohexyl)carbonyl]-6,11-dihydro-5H-pyrido[2,3-b][1,5]benzodiazepine | 463 |
| 232 | 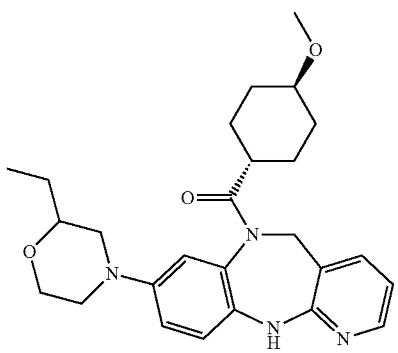 [SMILES: CCC1CN(c2ccc3c(c2)N(C(=O)[C@H]2CC[C@H](OC)CC2)Cc2cccnc2N3)CCO1] | 8-(2-ethylmorpholin-4-yl)-6-[(trans-4-methoxycyclohexyl)carbonyl]-6,11-dihydro-5H-pyrido[2,3-b][1,5]benzodiazepine | 451 |
| 233 | Isomer 1 | 6-[(trans-4-methoxycyclohexyl)carbonyl]-8-(6-methyl-1,4-oxazepan-4-yl)-6,11-dihydro-5H-pyrido[2,3-b][1,5]benzodiazepine | 451 |

| Ex. No. | Structure | Chemical Name | [M + H]+ |
|---|---|---|---|
| 234 | 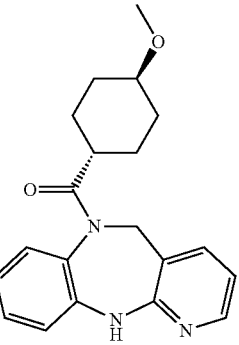<br>Isomer 2 | 6-[(trans-4-methoxycyclohexyl)carbonyl]-8-(2-methyl-1,4-oxazepan-4-yl)-6,11-dihydro-5H-pyrido[2,3-b][1,5]benzodiazepine | 451 |
| 235 | 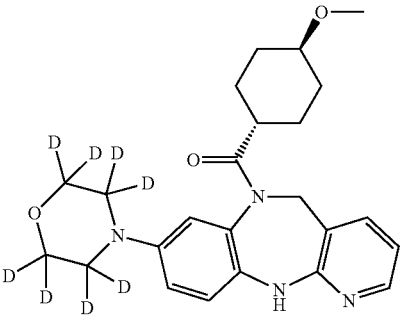 [SMILES: [2H]C1([2H])OC([2H])([2H])C([2H])([2H])N(c2ccc3c(c2)N(C(=O)[C@H]2CC[C@H](OC)CC2)Cc2cccnc2N3)C1([2H])[2H]] | (trans-4-methoxycyclohexyl){8-[($^2$H$_8$)morpholin-4-yl]-5,11-dihydro-6H-pyrido[2,3-b][1,5]benzodiazepin-6-yl}methanone | 431 |
| 236 | 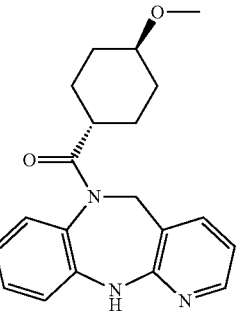 | 6-[(trans-4-methoxycyclohexyl)carbonyl]-N-(2-methoxyethyl)-N-methyl-6,11-dihydro-5H-pyrido[2,3-b][1,5]benzodiazepin-8-amine | 425 |
| 237 | 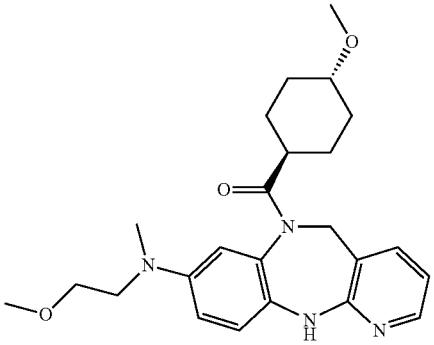 [SMILES: COCCN(C)c1ccc2c(c1)N(C(=O)[C@H]1CC[C@H](OC)CC1)Cc1cccnc1N2] | 6-[(cis-4-methoxycyclohexyl)carbonyl]-N-(2-methoxyethyl)-N-methyl-6,11-dihydro-5H-pyrido[2,3-b][1,5]benzodiazepin-8-amine | 425 |

| Ex. No. | Structure | Chemical Name | [M + H]+ |
| --- | --- | --- | --- |
| 238 | 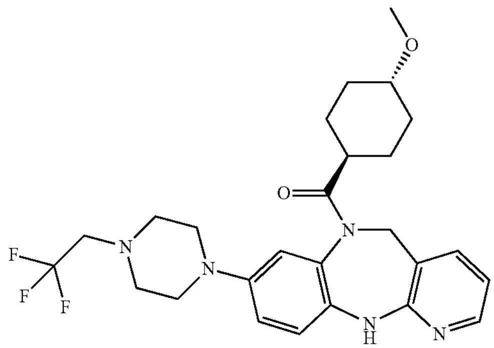 [SMILES: CO[C@H]1CC[C@H](C(=O)N2Cc3cccnc3Nc3ccc(N4CCN(CC(F)(F)F)CC4)cc32)CC1] | 6-[(trans-4-methoxycyclohexyl)carbonyl]-8-[4-(2,2,2-trifluoroethyl)piperazin-1-yl]-6,11-dihydro-5H-pyrido[2,3-b][1,5]benzodiazepine | 504 |
| 239 | 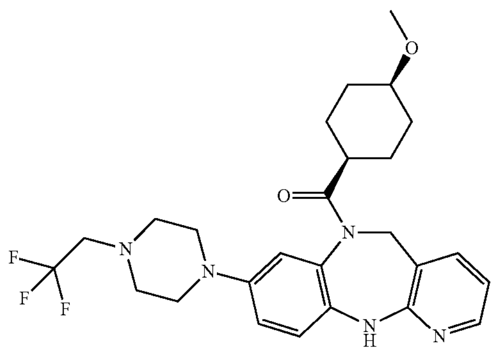 [SMILES: CO[C@H]1CC[C@@H](C(=O)N2Cc3cccnc3Nc3ccc(N4CCN(CC(F)(F)F)CC4)cc32)CC1] | 6-[(cis-4-methoxycyclohexyl)carbonyl]-8-[4-(2,2,2-trifluoroethyl)piperazin-1-yl]-6,11-dihydro-5H-pyrido[2,3-b][1,5]benzodiazepine | 504 |
| 240 | 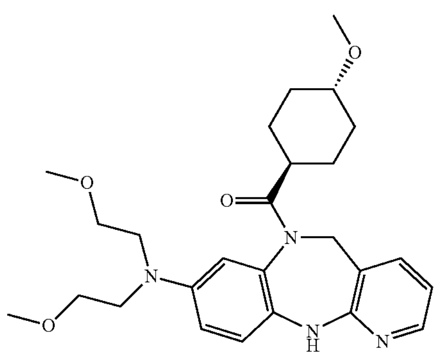 [SMILES: COCCN(CCOC)c1ccc2c(c1)N(C(=O)[C@H]1CC[C@H](OC)CC1)Cc1cccnc1N2] | 6-[(trans-4-methoxycyclohexyl)carbonyl]-N,N-bis(2-methoxyethyl)-6,11-dihydro-5H-pyrido[2,3-b][1,5]benzodiazepin-8-amine | 469 |
| 241 | 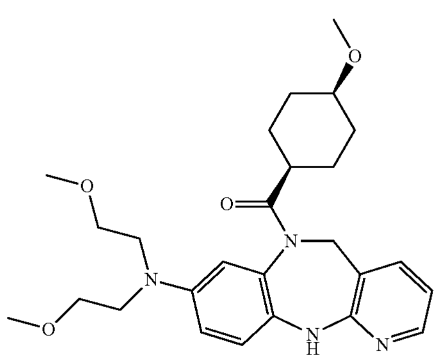 [SMILES: COCCN(CCOC)c1ccc2c(c1)N(C(=O)[C@H]1CC[C@@H](OC)CC1)Cc1cccnc1N2] | 6-[(cis-4-methoxycyclohexyl)carbonyl]-N,N-bis(2-methoxyethyl)-6,11-dihydro-5H-pyrido[2,3-b][1,5]benzodiazepin-8-amine | 469 |

-continued

| Ex. No. | Structure | Chemical Name | [M + H]+ |
|---|---|---|---|
| 242 | 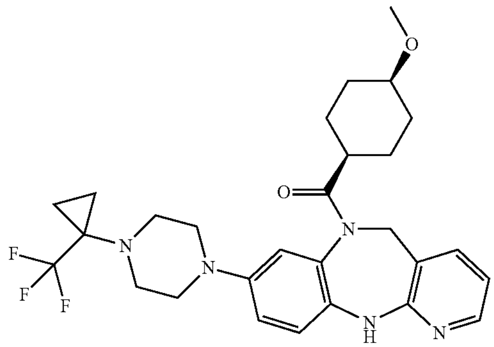 [SMILES: CO[C@H]1CC[C@@H](C(=O)N2Cc3cccnc3Nc3ccc(N4CCN(C5(C(F)(F)F)CC5)CC4)cc32)CC1] | 6-[(cis-4-methoxycyclohexyl)carbonyl]-8-{4-[1-(trifluoromethyl)cyclopropyl]piperazin-1-yl}-6,11-dihydro-5H-pyrido[2,3-b][1,5]benzodiazepine | 530 |
| 243 | 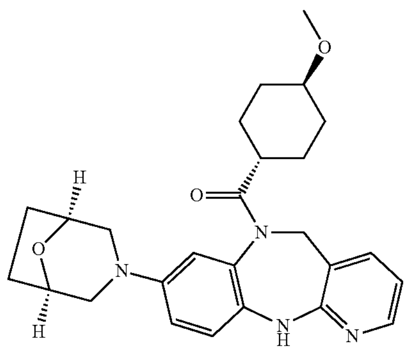 [SMILES: CO[C@H]1CC[C@H](C(=O)N2Cc3cccnc3Nc3ccc(N4C[C@H]5CC[C@@H](C4)O5)cc32)CC1] | 6-[(trans-4-methoxycyclohexyl)carbonyl]-8-[(1R,5S)-8-oxa-3-azabicyclo[3.2.1]oct-3-yl]-6,11-dihydro-5H-pyrido[2,3-b][1,5]benzodiazepine | 449 |
| 244 | 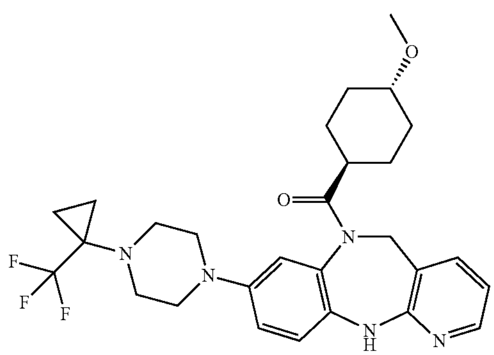 [SMILES: CO[C@H]1CC[C@H](C(=O)N2Cc3cccnc3Nc3ccc(N4CCN(C5(C(F)(F)F)CC5)CC4)cc32)CC1] | 6-[(trans-4-methoxycyclohexyl)carbonyl]-8-{4-[1-(trifluoromethyl)cyclopropyl]piperazin-1-yl}-6,11-dihydro-5H-pyrido[2,3-b][1,5]benzodiazepine | 530 |
| 245 | 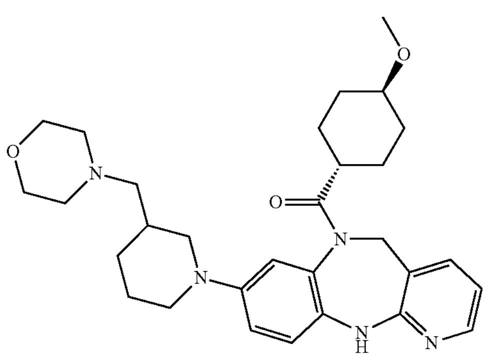 [SMILES: CO[C@H]1CC[C@H](C(=O)N2Cc3cccnc3Nc3ccc(N4CCCC(CN5CCOCC5)C4)cc32)CC1] | 6-[(trans-4-methoxycyclohexyl)carbonyl]-8-[3-(morpholin-4-ylmethyl)piperidin-1-yl]-6,11-dihydro-5H-pyrido[2,3-b][1,5]benzodiazepine | 520 |

-continued

| Ex. No. | Structure | Chemical Name | [M + H]+ |
| --- | --- | --- | --- |
| 246 | 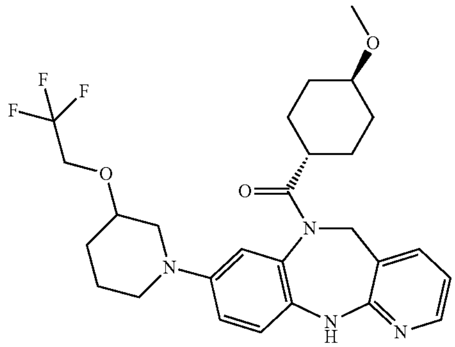 [SMILES: CO[C@H]1CC[C@H](C(=O)N2Cc3cccnc3Nc3ccc(N4CCCC(OCC(F)(F)F)C4)cc32)CC1] | 6-[(trans-4-methoxycyclohexyl)carbonyl]-8-[3-(2,2,2-trifluoroethoxy)piperidin-1-yl]-6,11-dihydro-5H-pyrido[2,3-b][1,5]benzodiazepine | 519 |
| 247 | 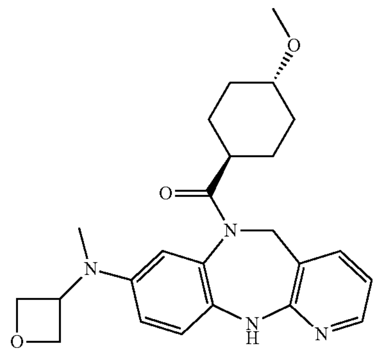 [SMILES: CO[C@H]1CC[C@H](C(=O)N2Cc3cccnc3Nc3ccc(N(C)C4COC4)cc32)CC1] | 6-[(trans-4-methoxycyclohexyl)carbonyl]-N-methyl-N-oxetan-3-yl-6,11-dihydro-5H-pyrido[2,3-b][1,5]benzodiazepin-8-amine | 423 |
| 248 | 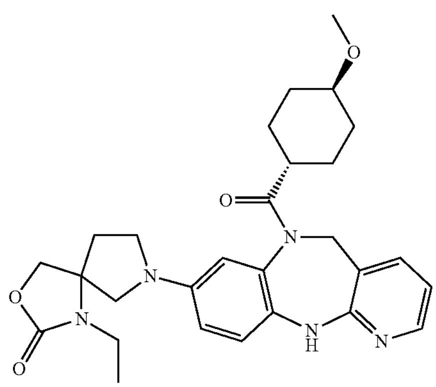 [SMILES: CCN1C(=O)OCC12CCN(c1ccc3c(c1)N(C(=O)[C@H]1CC[C@H](OC)CC1)Cc1cccnc1N3)C2] | 1-ethyl-7-{6-[(trans-4-methoxycyclohexyl)carbonyl]-6,11-dihydro-5H-pyrido[2,3-b][1,5]benzodiazepin-8-yl}-3-oxa-1,7-diazaspiro[4.4]nonan-2-one | 506 |
| 249 | 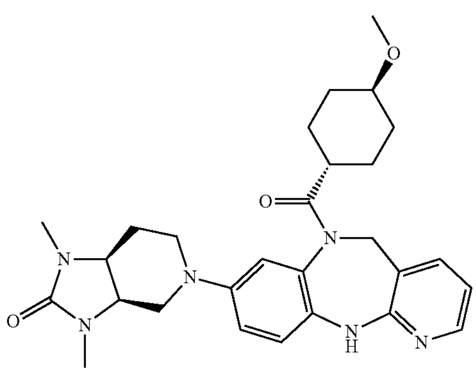 [SMILES: CO[C@H]1CC[C@H](C(=O)N2Cc3cccnc3Nc3ccc(N4CC[C@H]5[C@@H](C4)N(C)C(=O)N5C)cc32)CC1] | (3aR,7aS)-5-{6-[(trans-4-methoxycyclohexyl)carbonyl]-6,11-dihydro-5H-pyrido[2,3-b][1,5]benzodiazepin-8-yl}-1,3-dimethyloctahydro-2H-imidazo[4,5-c]pyridin-2-one | 505 |

-continued

| Ex. No. | Structure | Chemical Name | [M + H]+ |
| --- | --- | --- | --- |
| 250 | 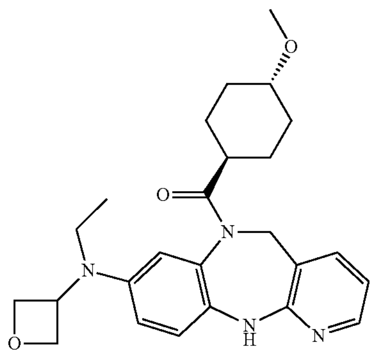 [SMILES: CCN(c1ccc2c(c1)N(C(=O)[C@H]1CC[C@H](OC)CC1)Cc1cccnc1N2)C1COC1] | N-ethyl-6-[(trans-4-methoxycyclohexyl)carbonyl]-N-oxetan-3-yl-6,11-dihydro-5H-pyrido[2,3-b][1,5]benzodiazepin-8-amine | 437 |
| 251 | 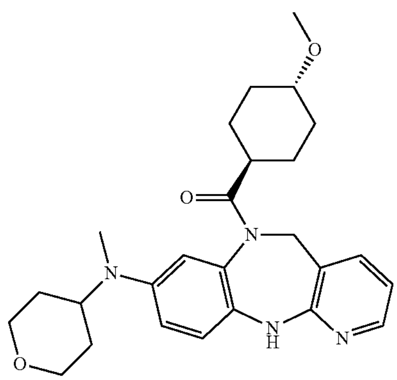 [SMILES: CO[C@H]1CC[C@H](C(=O)N2Cc3cccnc3Nc3ccc(N(C)C4CCOCC4)cc32)CC1] | 6-[(trans-4-methoxycyclohexyl)carbonyl]-N-methyl-N-(tetrahydro-2H-pyran-4-yl)-6,11-dihydro-5H-pyrido[2,3-b][1,5]benzodiazepin-8-amine | 451 |
| 252 | 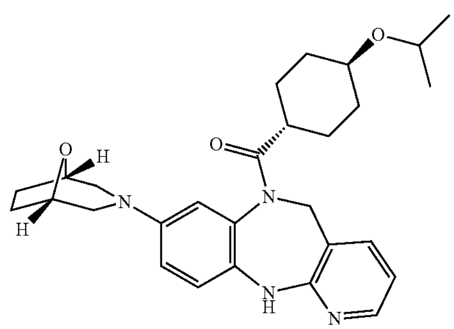 [SMILES: CC(C)O[C@H]1CC[C@H](C(=O)N2Cc3cccnc3Nc3ccc(N4C[C@@H]5CC[C@@H](C4)O5)cc32)CC1] | 6-{[trans-4-(1-methylethoxy)cyclohexyl]carbonyl}-8-[(1S,5S)-8-oxa-3-azabicyclo[3.2.1]oct-3-yl]-6,11-dihydro-5H-pyrido[2,3-b][1,5]benzodiazepine | 477 |
| 253 | 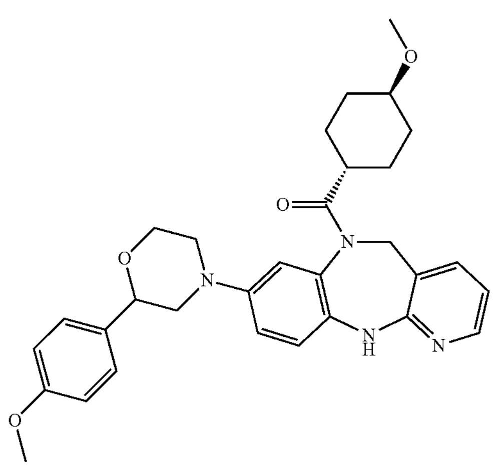 [SMILES: COc1ccc(C2CN(c3ccc4c(c3)N(C(=O)[C@H]3CC[C@H](OC)CC3)Cc3cccnc3N4)CCO2)cc1] | 6-[(trans-4-methoxycyclohexyl)carbonyl]-8-[2-(4-methoxyphenyl)morpholin-4-yl]-6,11-dihydro-5H-pyrido[2,3-b][1,5]benzodiazepine | 529 |

| Ex. No. | Structure | Chemical Name | [M + H]+ |
| --- | --- | --- | --- |
| 254 | 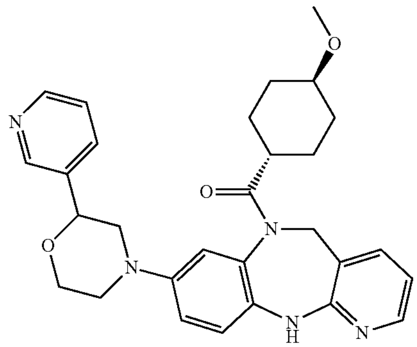 [SMILES: CO[C@H]1CC[C@H](C(=O)N2Cc3cccnc3Nc3ccc(N4CCOC(c5cccnc5)C4)cc32)CC1] | 6-[(trans-4-methoxycyclohexyl)carbonyl]-8-(2-pyridin-3-ylmorpholin-4-yl)-6,11-dihydro-5H-pyrido[2,3-b][1,5]benzodiazepine | 500 |
| 255 | 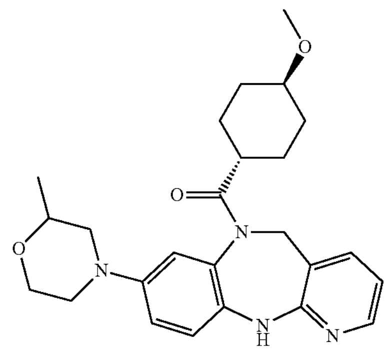 [SMILES: CO[C@H]1CC[C@H](C(=O)N2Cc3cccnc3Nc3ccc(N4CCOC(C)C4)cc32)CC1] | 6-[(trans-4-methoxycyclohexyl)carbonyl]-8-(2-methylmorpholin-4-yl)-6,11-dihydro-5H-pyrido[2,3-b][1,5]benzodiazepine | 437 |
| 256 | 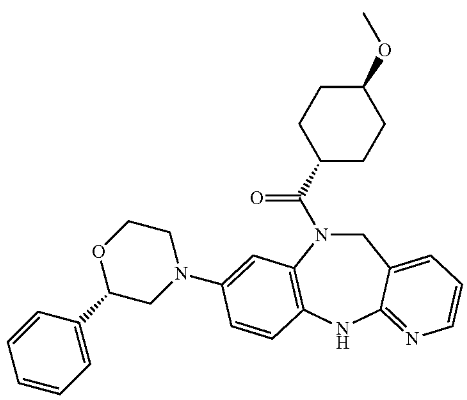 [SMILES: CO[C@H]1CC[C@H](C(=O)N2Cc3cccnc3Nc3ccc(N4CCO[C@@H](c5ccccc5)C4)cc32)CC1] | 6-[(trans-4-methoxycyclohexyl)carbonyl]-8-[(2S)-2-phenylmorpholin-4-yl]-6,11-dihydro-5H-pyrido[2,3-b][1,5]benzodiazepine | 499 |
| 257 | 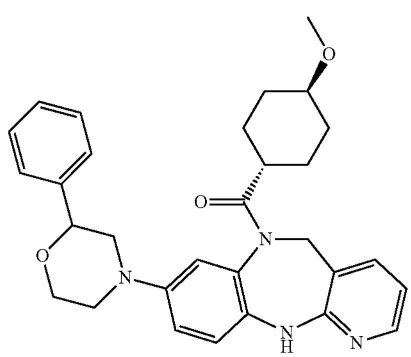 [SMILES: CO[C@H]1CC[C@H](C(=O)N2Cc3cccnc3Nc3ccc(N4CCOC(c5ccccc5)C4)cc32)CC1] | 6-[(trans-4-methoxycyclohexyl)carbonyl]-8-(2-phenylmorpholin-4-yl)-6,11-dihydro-5H-pyrido[2,3-b][1,5]benzodiazepine | 499 |

| Ex. No. | Structure | Chemical Name | [M + H]+ |
| --- | --- | --- | --- |
| 258 | 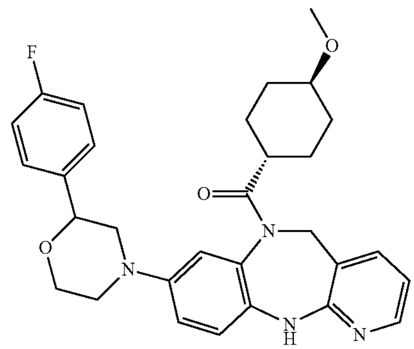 [SMILES: CO[C@H]1CC[C@H](C(=O)N2Cc3cccnc3Nc3ccc(N4CCOC(c5ccc(F)cc5)C4)cc32)CC1] | 8-[2-(4-fluorophenyl)morpholin-4-yl]-6-[(trans-4-methoxycyclohexyl)carbonyl]-6,11-dihydro-5H-pyrido[2,3-b][1,5]benzodiazepine | 517 |
| 259 | 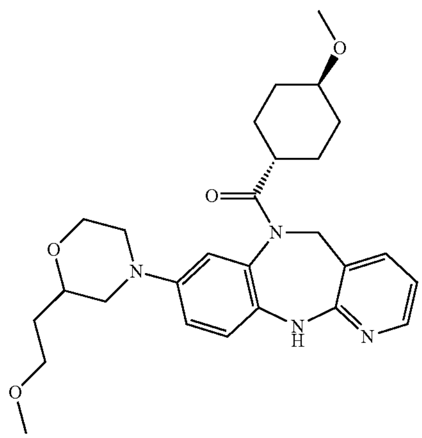 [SMILES: COCCC1CN(c2ccc3c(c2)N(C(=O)[C@H]2CC[C@H](OC)CC2)Cc2cccnc2N3)CCO1] | 6-[(trans-4-methoxycyclohexyl)carbonyl]-8-[2-(2-methoxyethyl)morpholin-4-yl]-6,11-dihydro-5H-pyrido[2,3-b][1,5]benzodiazepine | 481 |
| 260 | 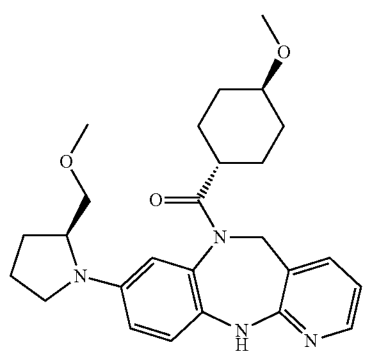 [SMILES: COC[C@@H]1CCCN1c1ccc2c(c1)N(C(=O)[C@H]1CC[C@H](OC)CC1)Cc1cccnc1N2] | 6-[(trans-4-methoxycyclohexyl)carbonyl]-8-[(2S)-2-(methoxymethyl)pyrrolidin-1-yl]-6,11-dihydro-5H-pyrido[2,3-b][1,5]benzodiazepine | 451 |
| 261 | 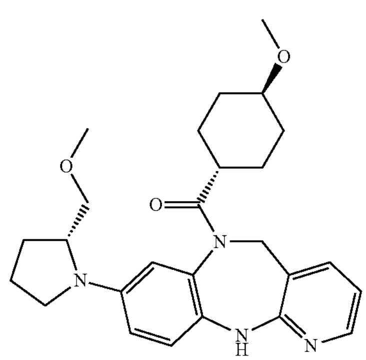 [SMILES: COC[C@H]1CCCN1c1ccc2c(c1)N(C(=O)[C@H]1CC[C@H](OC)CC1)Cc1cccnc1N2] | 6-[(trans-4-methoxycyclohexyl)carbonyl]-8-[(2R)-2-(methoxymethyl)pyrrolidin-1-yl]-6,11-dihydro-5H-pyrido[2,3-b][1,5]benzodiazepine | 451 |

| Ex. No. | Structure | Chemical Name | [M + H]+ |
|---|---|---|---|
| 262 | 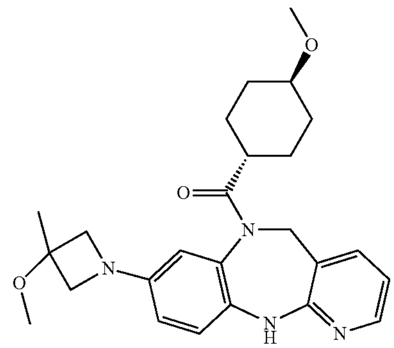 [SMILES: COC1(C)CN(c2ccc3c(c2)N(C(=O)[C@H]2CC[C@H](OC)CC2)Cc2cccnc2N3)C1] | 6-[(trans-4-methoxycyclohexyl)carbonyl]-8-(3-methoxy-3-methylazetidin-1-yl)-6,11-dihydro-5H-pyrido[2,3-b][1,5]benzodiazepine | 437 |
| 263 | 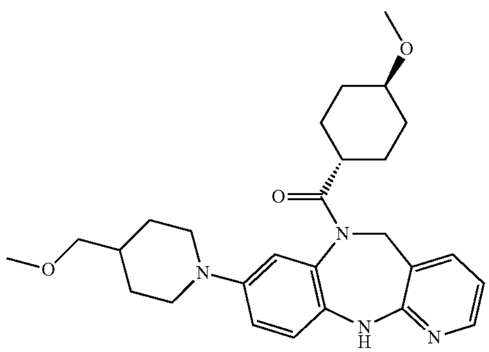 [SMILES: COCC1CCN(c2ccc3c(c2)N(C(=O)[C@H]2CC[C@H](OC)CC2)Cc2cccnc2N3)CC1] | 6-[(trans-4-methoxycyclohexyl)carbonyl]-8-[4-(methoxymethyl)piperidin-1-yl]-6,11-dihydro-5H-pyrido[2,3-b][1,5]benzodiazepine | 465 |
| 264 | 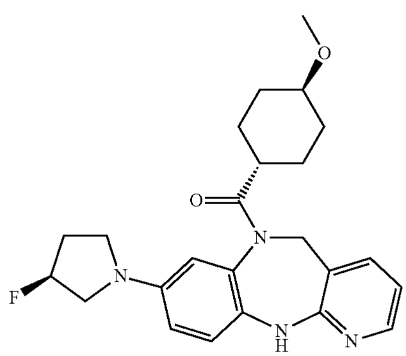 [SMILES: CO[C@H]1CC[C@H](C(=O)N2Cc3cccnc3Nc3ccc(N4CC[C@H](F)C4)cc32)CC1] | 8-[(3S)-3-fluoropyrrolidin-1-yl]-6-[(trans-4-methoxycyclohexyl)carbonyl]-6,11-dihydro-5H-pyrido[2,3-b][1,5]benzodiazepine | 425 |
| 265 | 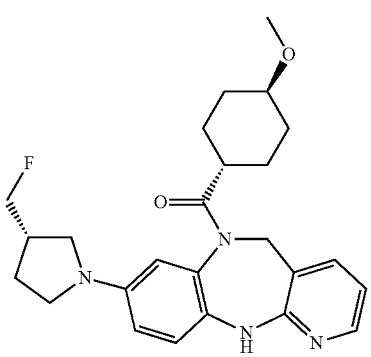 [SMILES: CO[C@H]1CC[C@H](C(=O)N2Cc3cccnc3Nc3ccc(N4CC[C@H](CF)C4)cc32)CC1] | 8-[(3S)-3-(fluoromethyl)pyrrolidin-1-yl]-6-[(trans-4-methoxycyclohexyl)carbonyl]-6,11-dihydro-5H-pyrido[2,3-b][1,5]benzodiazepine | 439 |

| Ex. No. | Structure | Chemical Name | [M + H]+ |
|---|---|---|---|
| 266 | 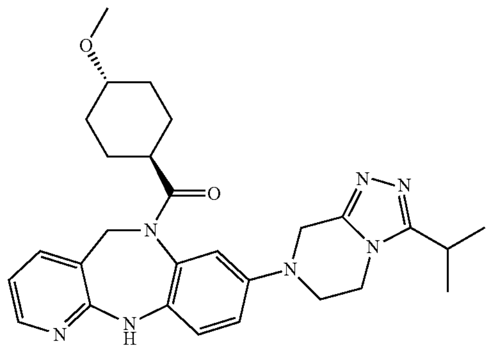 [SMILES: CO[C@H]1CC[C@H](C(=O)N2Cc3cccnc3Nc3ccc(N4CCn5c(nnc5C(C)C)C4)cc32)CC1] | 6-[(trans-4-methoxycyclohexyl)carbonyl]-8-[3-(1-methylethyl)-5,6-dihydro[1,2,4]triazolo[4,3-a]pyrazin-7(8H)-yl]-6,11-dihydro-5H-pyrido[2,3-b][1,5]benzodiazepine | 502 |
| 267 | 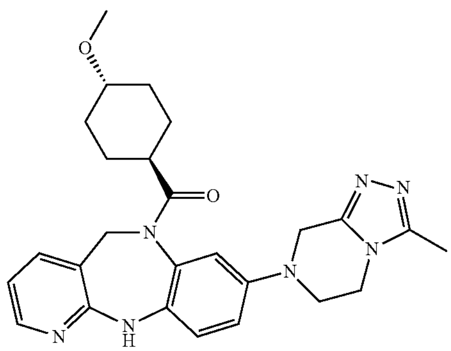 [SMILES: CO[C@H]1CC[C@H](C(=O)N2Cc3cccnc3Nc3ccc(N4CCn5c(C)nnc5C4)cc32)CC1] | 6-[(trans-4-methoxycyclohexyl)carbonyl]-8-(3-methyl-5,6-dihydro[1,2,4]triazolo[4,3-a]pyrazin-7(8H)-yl)-6,11-dihydro-5H-pyrido[2,3-b][1,5]benzodiazepine | 474 |
| 268 | 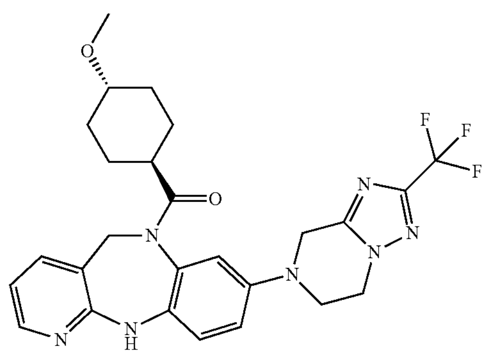 [SMILES: CO[C@H]1CC[C@H](C(=O)N2Cc3cccnc3Nc3ccc(N4CCn5nc(C(F)(F)F)nc5C4)cc32)CC1] | 6-[(trans-4-methoxycyclohexyl)carbonyl]-8-[2-(trifluoromethyl)-5,6-dihydro[1,2,4]triazolo[1,5-a]pyrazin-7(8H)-yl]-6,11-dihydro-5H-pyrido[2,3-b][1,5]benzodiazepine | 528 |
| 269 | 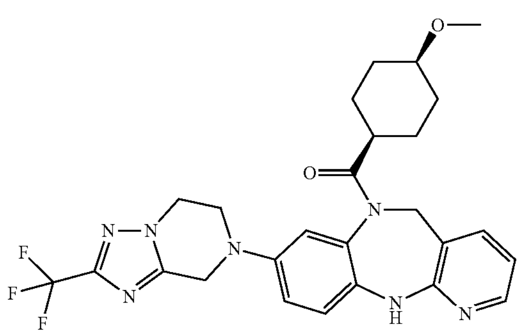 [SMILES: CO[C@H]1CC[C@@H](C(=O)N2Cc3cccnc3Nc3ccc(N4CCn5nc(C(F)(F)F)nc5C4)cc32)CC1] | 6-[(cis-4-methoxycyclohexyl)carbonyl]-8-[2-(trifluoromethyl)-5,6-dihydro[1,2,4]triazolo[1,5-a]pyrazin-7(8H)-yl]-6,11-dihydro-5H-pyrido[2,3-b][1,5]benzodiazepine | 528 |

| Ex. No. | Structure | Chemical Name | [M + H]+ |
|---|---|---|---|
| 270 | 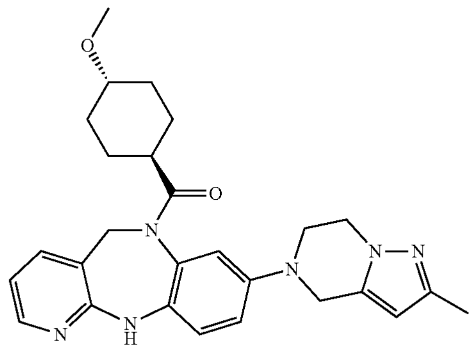 [SMILES: CO[C@H]1CC[C@H](C(=O)N2Cc3cccnc3Nc3ccc(N4CCn5nc(C)cc5C4)cc32)CC1] | 6-[(trans-4-methoxycyclohexyl)carbonyl]-8-(2-methyl-6,7-dihydropyrazolo[1,5-a]pyrazin-5(4H)-yl)-6,11-dihydro-5H-pyrido[2,3-b][1,5]benzodiazepine | 473 |
| 271 | 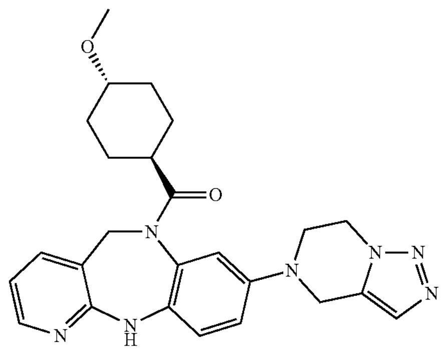 [SMILES: CO[C@H]1CC[C@H](C(=O)N2Cc3cccnc3Nc3ccc(N4CCn5nncc5C4)cc32)CC1] | 8-(6,7-dihydro[1,2,3]triazolo[1,5-a]pyrazin-5(4H)-yl)-6-[(trans-4-methoxycyclohexyl)carbonyl]-6,11-dihydro-5H-pyrido[2,3-b][1,5]benzodiazepine | 460 |
| 272 | 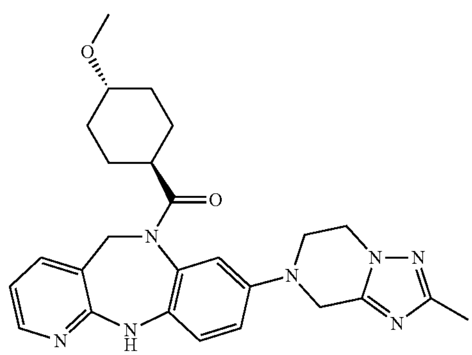 [SMILES: CO[C@H]1CC[C@H](C(=O)N2Cc3cccnc3Nc3ccc(N4CCn5nc(C)nc5C4)cc32)CC1] | 6-[(trans-4-methoxycyclohexyl)carbonyl]-8-(2-methyl-5,6-dihydro[1,2,4]triazolo[1,5-a]pyrazin-7(8H)-yl)-6,11-dihydro-5H-pyrido[2,3-b][1,5]benzodiazepine | 474 |
| 273 | 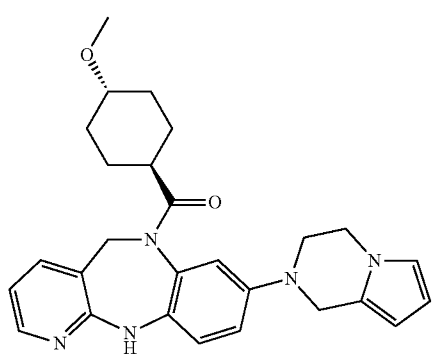 [SMILES: CO[C@H]1CC[C@H](C(=O)N2Cc3cccnc3Nc3ccc(N4CCn5cccc5C4)cc32)CC1] | 8-(3,4-dihydropyrrolo[1,2-a]pyrazin-2(1H)-yl)-6-[(trans-4-methoxycyclohexyl)carbonyl]-6,11-dihydro-5H-pyrido[2,3-b][1,5]benzodiazepine | 458 |

-continued

| Ex. No. | Structure | Chemical Name | [M + H]+ |
| --- | --- | --- | --- |
| 274 | 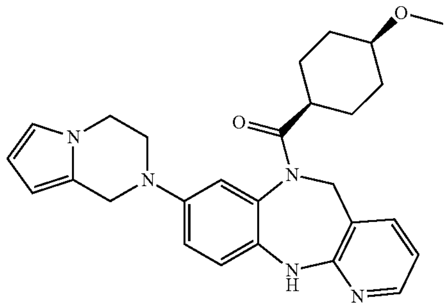 [SMILES: CO[C@H]1CC[C@@H](C(=O)N2Cc3cccnc3Nc3ccc(N4CCn5cccc5C4)cc32)CC1] | 8-(3,4-dihydropyrrolo[1,2-a]pyrazin-2(1H)-yl)-6-[(cis-4-methoxycyclohexyl)carbonyl]-6,11-dihydro-5H-pyrido[2,3-b][1,5]benzodiazepine | 458 |
| 275 | 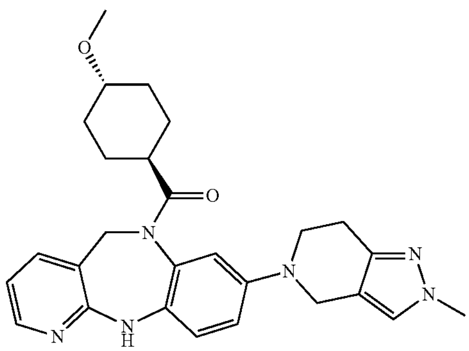 [SMILES: CO[C@H]1CC[C@H](C(=O)N2Cc3cccnc3Nc3ccc(N4CCc5nn(C)cc5C4)cc32)CC1] | 6-[(trans-4-methoxycyclohexyl)carbonyl]-8-(2-methyl-2,4,6,7-tetrahydro-5H-pyrazolo[4,3-c]pyridin-5-yl)-6,11-dihydro-5H-pyrido[2,3-b][1,5]benzodiazepine | 473 |
| 276 | 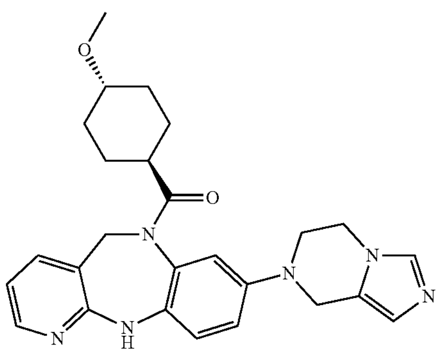 [SMILES: CO[C@H]1CC[C@H](C(=O)N2Cc3cccnc3Nc3ccc(N4CCn5cncc5C4)cc32)CC1] | 8-(5,6-dihydroimidazo[1,5-a]pyrazin-7(8H)-yl)-6-[(trans-4-methoxycyclohexyl)carbonyl]-6,11-dihydro-5H-pyrido[2,3-b][1,5]benzodiazepine | 459 |
| 277 | 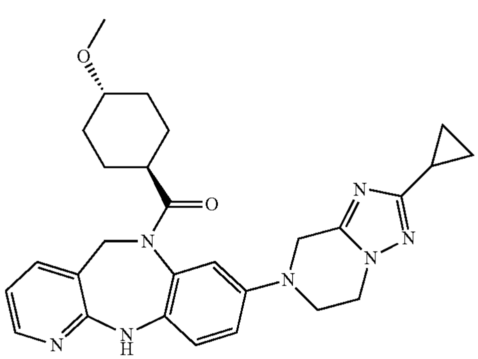 [SMILES: CO[C@H]1CC[C@H](C(=O)N2Cc3cccnc3Nc3ccc(N4CCn5nc(C6CC6)nc5C4)cc32)CC1] | 8-(2-cyclopropyl-5,6-dihydro[1,2,4]triazolo[1,5-a]pyrazin-7(8H)-yl)-6-[(trans-4-methoxycyclohexyl)carbonyl]-6,11-dihydro-5H-pyrido[2,3-b][1,5]benzodiazepine | 500 |

| Ex. No. | Structure | Chemical Name | [M + H]+ |
|---|---|---|---|
| 278 | 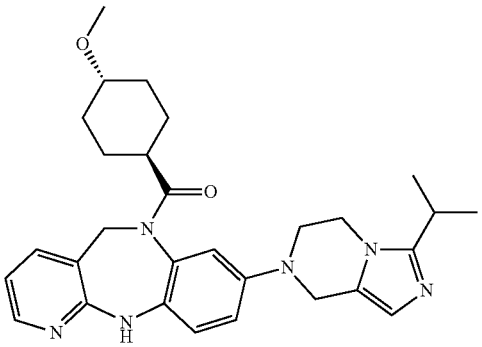 [SMILES: CO[C@H]1CC[C@H](C(=O)N2Cc3cccnc3Nc3ccc(N4CCn5c(cnc5C(C)C)C4)cc32)CC1] | 6-[(trans-4-methoxycyclohexyl)carbonyl]-8-[3-(1-methylethyl)-5,6-dihydroimidazo[1,5-a]pyrazin-7(8H)-yl]-6,11-dihydro-5H-pyrido[2,3-b][1,5]benzodiazepine | 501 |
| 279 | 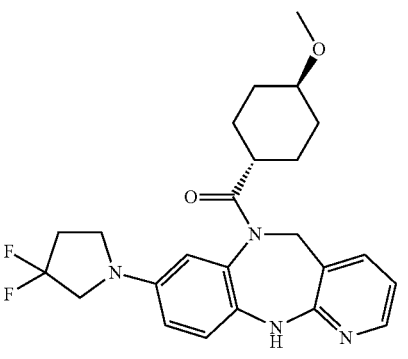 [SMILES: CO[C@H]1CC[C@H](C(=O)N2Cc3cccnc3Nc3ccc(N4CCC(F)(F)C4)cc32)CC1] | 8-(3,3-difluoropyrrolidin-1-yl)-6-[(trans-4-methoxycyclohexyl)carbonyl]-6,11-dihydro-5H-pyrido[2,3-b][1,5]benzodiazepine | 443 |
| 280 | 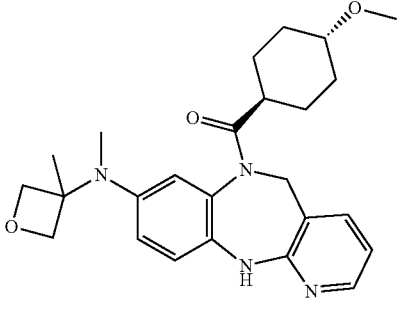 [SMILES: CO[C@H]1CC[C@H](C(=O)N2Cc3cccnc3Nc3ccc(N(C)C4(C)COC4)cc32)CC1] | 6-[(trans-4-methoxycyclohexyl)carbonyl]-N-methyl-N-(3-methyloxetan-3-yl)-6,11-dihydro-5H-pyrido[2,3-b][1,5]benzodiazepin-8-amine | 437 |
| 281 | 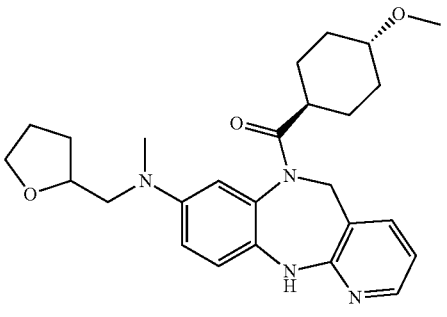 [SMILES: CO[C@H]1CC[C@H](C(=O)N2Cc3cccnc3Nc3ccc(N(C)CC4CCCO4)cc32)CC1] | 6-[(trans-4-methoxycyclohexyl)carbonyl]-N-methyl-N-(tetrahydro furan-2-ylmethyl)-6,11-dihydro-5H-pyrido[2,3-b][1,5]benzodiazepin-8-amine | 451 |

-continued

| Ex. No. | Structure | Chemical Name | [M + H]+ |
|---|---|---|---|
| 282 | 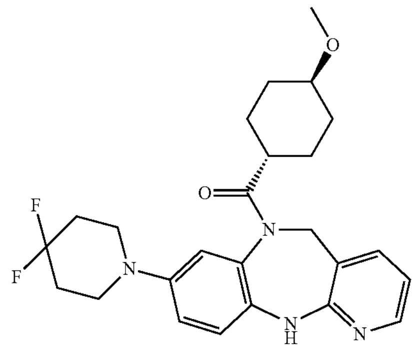 [SMILES: CO[C@H]1CC[C@H](C(=O)N2Cc3cccnc3Nc3ccc(N4CCC(F)(F)CC4)cc32)CC1] | 8-(4,4-difluoropiperidin-1-yl)-6-[(trans-4-methoxycyclohexyl)carbonyl]-6,11-dihydro-5H-pyrido[2,3-b][1,5]benzodiazepine | 457 |
| 283 | 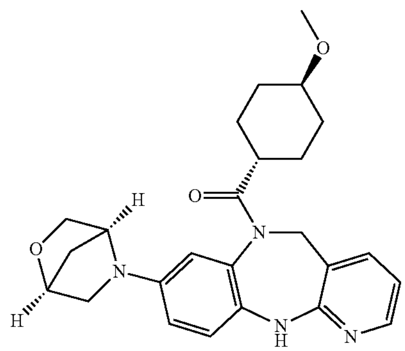 [SMILES: CO[C@H]1CC[C@H](C(=O)N2Cc3cccnc3Nc3ccc(N4C[C@@H]5C[C@H]4CO5)cc32)CC1] | 6-[(trans-4-methoxycyclohexyl)carbonyl]-8-[(1S,4S)-2-oxa-5-azabicyclo[2.2.1]hept-5-yl]-6,11-dihydro-5H-pyrido[2,3-b][1,5]benzodiazepine | 435 |
| 284 | 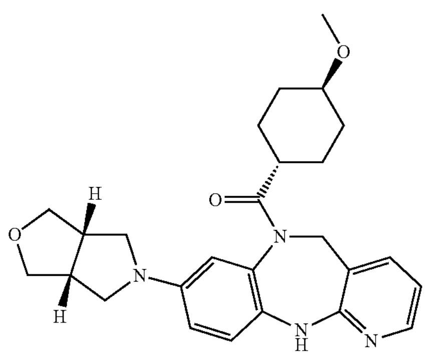 [SMILES: CO[C@H]1CC[C@H](C(=O)N2Cc3cccnc3Nc3ccc(N4C[C@H]5COC[C@H]5C4)cc32)CC1] | 6-[(trans-4-methoxycyclohexyl)carbonyl]-8-[(3aR,6aS)-tetrahydro-1H-furo[3,4-c]pyrrol-5(3H)-yl]-6,11-dihydro-5H-pyrido[2,3-b][1,5]benzodiazepine | 449 |
| 285 | 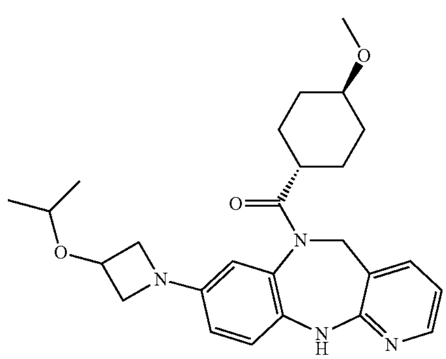 [SMILES: CO[C@H]1CC[C@H](C(=O)N2Cc3cccnc3Nc3ccc(N4CC(OC(C)C)C4)cc32)CC1] | 6-[(trans-4-methoxycyclohexyl)carbonyl]-8-[3-(1-methylethoxy)azetidin-1-yl]-6,11-dihydro-5H-pyrido[2,3-b][1,5]benzodiazepine | 451 |

| Ex. No. | Structure | Chemical Name | [M + H]+ |
| --- | --- | --- | --- |
| 286 | 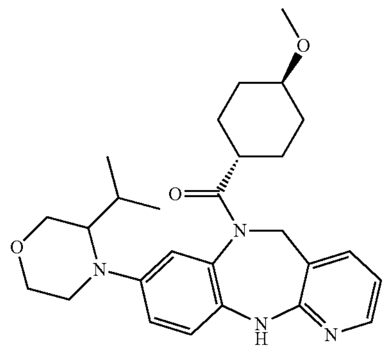 [SMILES: CO[C@H]1CC[C@H](C(=O)N2Cc3cccnc3Nc3ccc(N4CCOCC4C(C)C)cc32)CC1] | 6-[(trans-4-methoxycyclohexyl)carbonyl]-8-[3-(1-methylethyl)morpholin-4-yl]-6,11-dihydro-5H-pyrido[2,3-b][1,5]benzodiazepine | 465 |
| 287 | 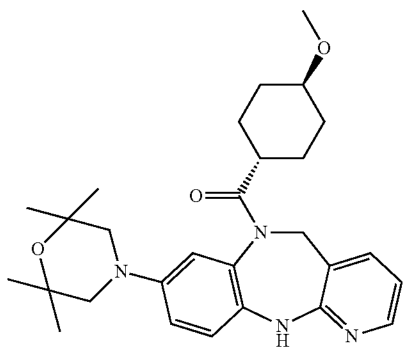 [SMILES: CO[C@H]1CC[C@H](C(=O)N2Cc3cccnc3Nc3ccc(N4CC(C)(C)OC(C)(C)C4)cc32)CC1] | 6-[(trans-4-methoxycyclohexyl)carbonyl]-8-(2,2,6,6-tetramethylmorpholin-4-yl)-6,11-dihydro-5H-pyrido[2,3-b][1,5]benzodiazepine | 479 |
| 288 | 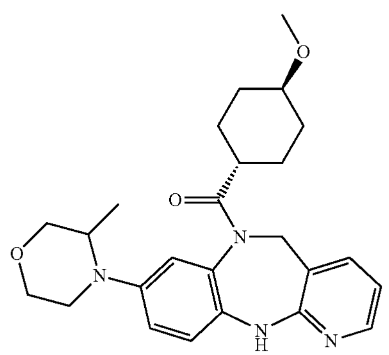 [SMILES: CO[C@H]1CC[C@H](C(=O)N2Cc3cccnc3Nc3ccc(N4CCOCC4C)cc32)CC1] | 6-[(trans-4-methoxycyclohexyl)carbonyl]-8-(3-methylmorpholin-4-yl)-6,11-dihydro-5H-pyrido[2,3-b][1,5]benzodiazepine | 437 |
| 289 | 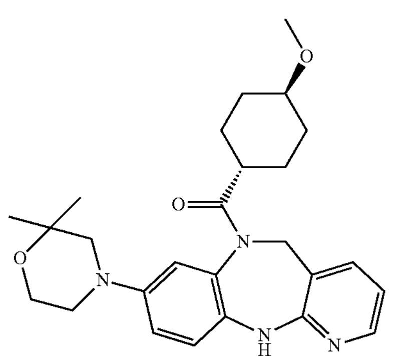 [SMILES: CO[C@H]1CC[C@H](C(=O)N2Cc3cccnc3Nc3ccc(N4CCOC(C)(C)C4)cc32)CC1] | 8-(2,2-dimethylmorpholin-4-yl)-6-[(trans-4-methoxycyclohexyl)carbonyl]-6,11-dihydro-5H-pyrido[2,3-b][1,5]benzodiazepine | 451 |

-continued

| Ex. No. | Structure | Chemical Name | [M + H]+ |
| --- | --- | --- | --- |
| 290 | 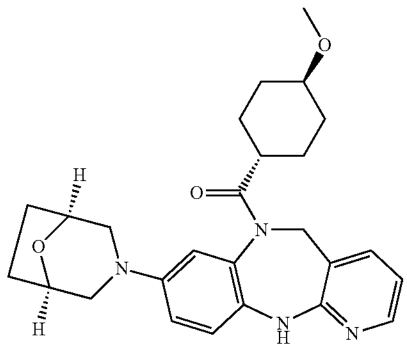 [SMILES: CO[C@H]1CC[C@H](C(=O)N2Cc3cccnc3Nc3ccc(N4C[C@H]5CC[C@@H](C4)O5)cc32)CC1] | 6-[(trans-4-methoxycyclohexyl)carbonyl]-8-[(1R,5S)-8-oxa-3-azabicyclo[3.2.1]oct-3-yl]-6,11-dihydro-5H-pyrido[2,3-b][1,5]benzodiazepine | 449 |
| 291 | 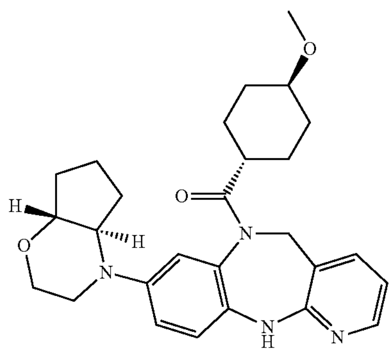 [SMILES: CO[C@H]1CC[C@H](C(=O)N2Cc3cccnc3Nc3ccc(N4CCO[C@@H]5CCC[C@H]54)cc32)CC1] | 8-[(4aR,7aR)-hexahydrocyclopenta[b][1,4]oxazin-4(4aH)-yl]-6-[(trans-4-methoxycyclohexyl)carbonyl]-6,11-dihydro-5H-pyrido[2,3-b][1,5]benzodiazepine | 463 |
| 292 | 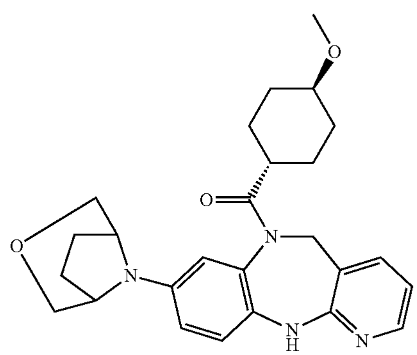 [SMILES: CO[C@H]1CC[C@H](C(=O)N2Cc3cccnc3Nc3ccc(N4C5CCC4COC5)cc32)CC1] | 6-[(trans-4-methoxycyclohexyl)carbonyl]-8-(3-oxa-8-azabicyclo[3.2.1]oct-8-yl)-6,11-dihydro-5H-pyrido[2,3-b][1,5]benzodiazepine | 449 |
| 293 | 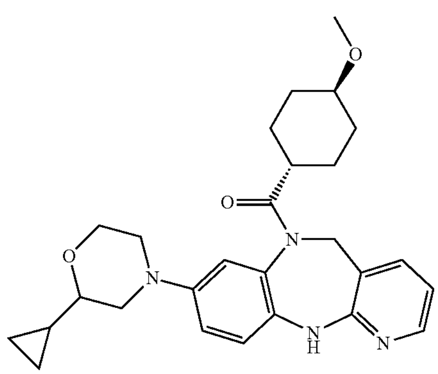 [SMILES: CO[C@H]1CC[C@H](C(=O)N2Cc3cccnc3Nc3ccc(N4CCOC(C5CC5)C4)cc32)CC1] | 8-(2-cyclopropylmorpholin-4-yl)-6-[(trans-4-methoxycyclohexyl)carbonyl]-6,11-dihydro-5H-pyrido[2,3-b][1,5]benzodiazepine | 463 |

-continued

| Ex. No. | Structure | Chemical Name | [M + H]+ |
|---|---|---|---|
| 294 | 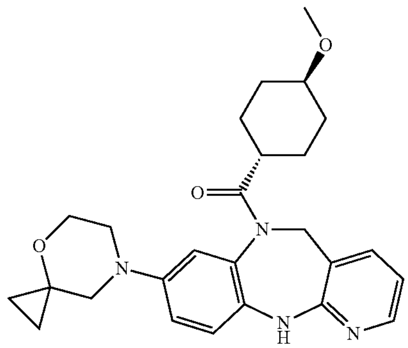 [SMILES: CO[C@H]1CC[C@H](C(=O)N2Cc3cccnc3Nc3ccc(N4CCOC5(CC5)C4)cc32)CC1] | 6-[(trans-4-methoxycyclohexyl)carbonyl]-8-(4-oxa-7-azaspiro[2.5]oct-7-yl)-6,11-dihydro-5H-pyrido[2,3-b][1,5]benzodiazepine | 449 |
| 295 | 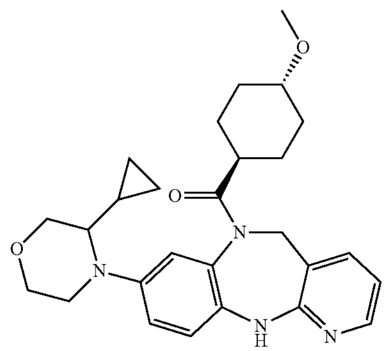 [SMILES: CO[C@H]1CC[C@H](C(=O)N2Cc3cccnc3Nc3ccc(N4CCOCC4C4CC4)cc32)CC1] | 8-(3-cyclopropylmorpholin-4-yl)-6-[(trans-4-methoxycyclohexyl)carbonyl]-6,11-dihydro-5H-pyrido[2,3-b][1,5]benzodiazepine | 463 |
| 296 | 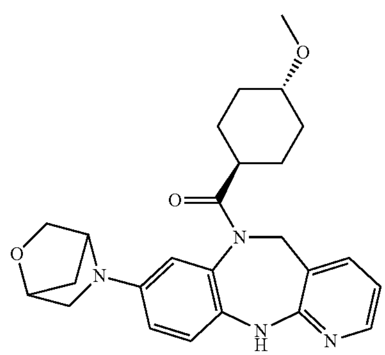 [SMILES: CO[C@H]1CC[C@H](C(=O)N2Cc3cccnc3Nc3ccc(N4CC5CC4CO5)cc32)CC1] | 6-[(trans-4-methoxycyclohexyl)carbonyl]-8-(2-oxa-5-azabicyclo[2.2.1]hept-5-yl)-6,11-dihydro-5H-pyrido[2,3-b][1,5]benzodiazepine | 435 |
| 297 | Isomer 2 | 8-(3-fluoro-4-methoxypiperidin-1-yl)-6-[(4-methoxycyclohexyl)carbonyl]-6,11-dihydro-5H-pyrido[2,3-b][1,5]benzodiazepine | 469 |

-continued

| Ex. No. | Structure | Chemical Name | [M + H]+ |
|---|---|---|---|
| 298 | 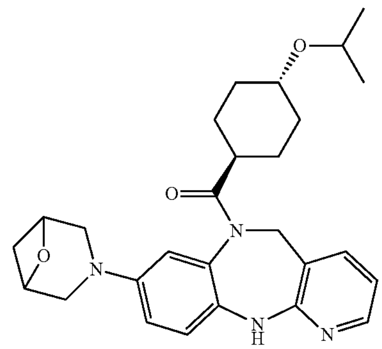 [SMILES: CC(C)O[C@H]1CC[C@H](C(=O)N2Cc3cccnc3Nc3ccc(N4CC5CC(C4)O5)cc32)CC1] | 6-{[trans-4-(1-methylethoxy)cyclohexyl]carbonyl}-8-(6-oxa-3-azabicyclo[3.1.1]hept-3-yl)-6,11-dihydro-5H-pyrido[2,3-b][1,5]benzodiazepine | 463 |
| 299 | 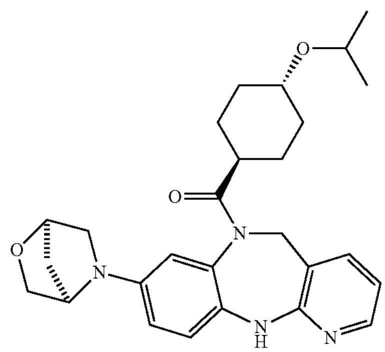 | 6-{[trans-4-(1-methylethoxy)cyclohexyl]carbonyl}-8-[(1R,4R)-2-oxa-5-azabicyclo[2.2.1]hept-5-yl]-6,11-dihydro-5H-pyrido[2,3-b][1,5]benzodiazepine | 463 |
| 300 | 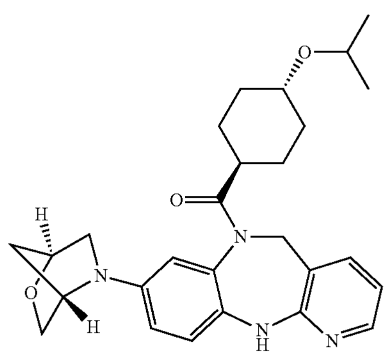 [SMILES: CC(C)O[C@H]1CC[C@H](C(=O)N2Cc3cccnc3Nc3ccc(N4C[C@@H]5C[C@H]4CO5)cc32)CC1] | 6-{[trans-4-(1-methylethoxy)cyclohexyl]carbonyl}-8-[(1S,4S)-2-oxa-5-azabicyclo[2.2.1]hept-5-yl]-6,11-dihydro-5H-pyrido[2,3-b][1,5]benzodiazepine | 463 |
| 301 | 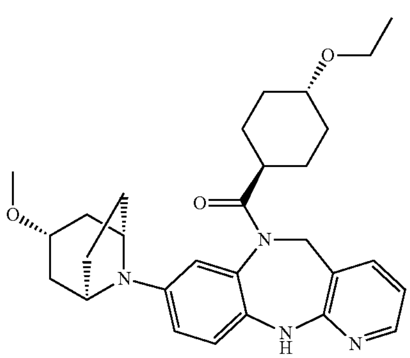 | 6-[(trans-4-ethoxycyclohexyl)carbonyl]-8-[(3-endo)-3-methoxy-8-azabicyclo[3.2.1]oct-8-yl]-6,11-dihydro-5H-pyrido[2,3-b][1,5]benzodiazepine | 491 |

-continued

| Ex. No. | Structure | Chemical Name | [M + H]+ |
| --- | --- | --- | --- |
| 302 | 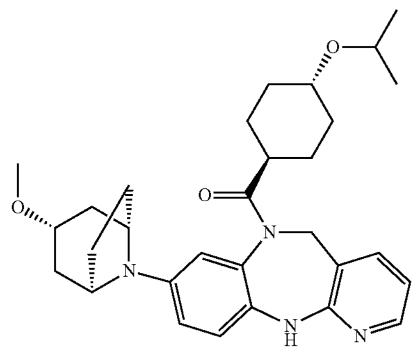 [SMILES: CO[C@H]1C[C@H]2CC[C@@H](C1)N2c1ccc2c(c1)N(C(=O)[C@H]1CC[C@H](OC(C)C)CC1)Cc1cccnc1N2] | 8-[(3-endo)-3-methoxy-8-azabicyclo[3.2.1]oct-8-yl]-6-{[trans-4-(1-methylethoxy)cyclohexyl]carbonyl}-6,11-dihydro-5H-pyrido[2,3-b][1,5]benzodiazepine | 505 |
| 303 | 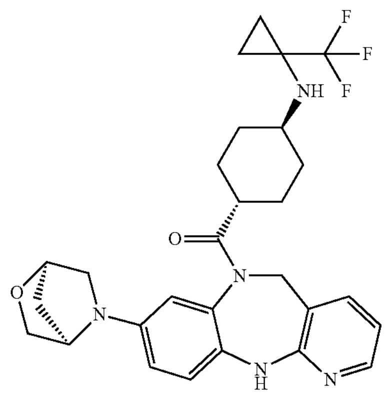 [SMILES: O=C([C@H]1CC[C@H](NC2(C(F)(F)F)CC2)CC1)N1Cc2cccnc2Nc2ccc(N3C[C@H]4C[C@@H]3CO4)cc21] | trans-4-({8-[(1R,4R)-2-oxa-5-azabicyclo[2.2.1]hept-5-yl]-5,11-dihydro-6H-pyrido[2,3-b][1,5]benzodiazepin-6-yl}carbonyl)-N-[1-(trifluoromethyl)cyclopropyl]cyclohexanamine | 528 |
| 304 | 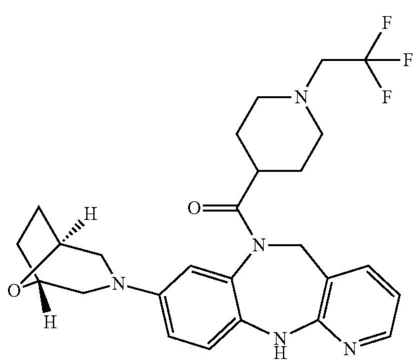 [SMILES: O=C(C1CCN(CC(F)(F)F)CC1)N1Cc2cccnc2Nc2ccc(N3C[C@H]4CC[C@@H](C3)O4)cc21] | 8-[(1R,5S)-8-oxa-3-azabicyclo[3.2.1]oct-3-yl]-6-{[1-(2,2,2-trifluoroethyl)piperidin-4-yl]carbonyl}-6,11-dihydro-5H-pyrido[2,3-b][1,5]benzodiazepine | 502 |
| 305 | 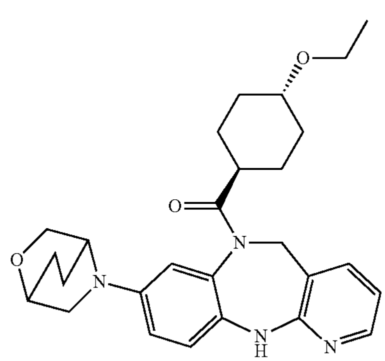 [SMILES: CCO[C@H]1CC[C@H](C(=O)N2Cc3cccnc3Nc3ccc(N4CC5CCC4CO5)cc32)CC1] | 6-[(trans-4-ethoxycyclohexyl)carbonyl]-8-(2-oxa-5-azabicyclo[2.2.2]oct-5-yl)-6,11-dihydro-5H-pyrido[2,3-b][1,5]benzodiazepine | 463 |

| Ex. No. | Structure | Chemical Name | [M + H]+ |
| --- | --- | --- | --- |
| 306 | 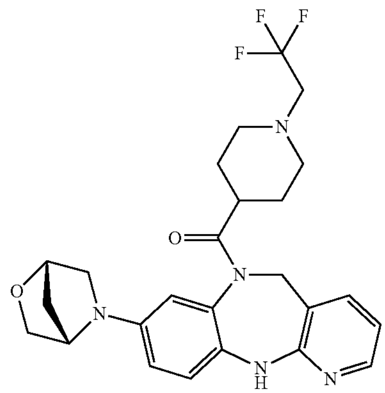 [SMILES: O=C(C1CCN(CC(F)(F)F)CC1)N1Cc2cccnc2Nc2ccc(N3C[C@@H]4C[C@H]3CO4)cc21] | 8-[(1S,4S)-2-oxa-5-azabicyclo[2.2.1]hept-5-yl]-6-{[1-(2,2,2-trifluoroethyl)piperidin-4-yl]carbonyl}-6,11-dihydro-5H-pyrido[2,3-b][1,5]benzodiazepine | 488 |
| 307 | 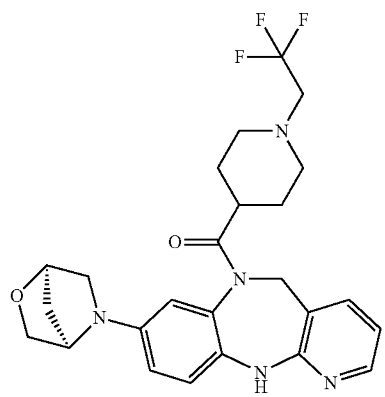 [SMILES: O=C(C1CCN(CC(F)(F)F)CC1)N1Cc2cccnc2Nc2ccc(N3C[C@H]4C[C@@H]3CO4)cc21] | 8-[(1R,4R)-2-oxa-5-azabicyclo[2.2.1]hept-5-yl]-6-{[1-(2,2,2-trifluoroethyl)piperidin-4-yl]carbonyl}-6,11-dihydro-5H-pyrido[2,3-b][1,5]benzodiazepine | 488 |
| 308 | 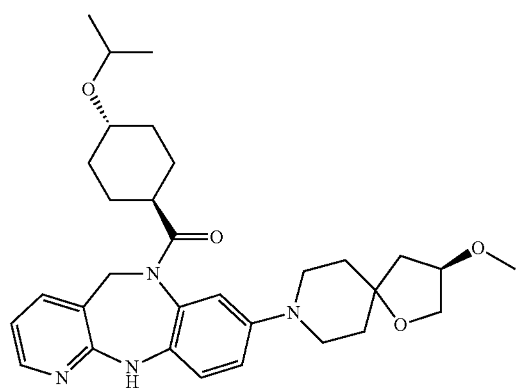 [SMILES: CO[C@H]1COC2(CCN(c3ccc4c(c3)N(C(=O)[C@H]3CC[C@H](OC(C)C)CC3)Cc3cccnc3N4)CC2)C1] | 8-[(3R)-3-methoxy-1-oxa-8-azaspiro[4.5]dec-8-yl]-6-{[trans-4-(1-methylethoxy)cyclohexyl]carbonyl}-6,11-dihydro-5H-pyrido[2,3-b][1,5]benzodiazepine | 535 |
| 309 | 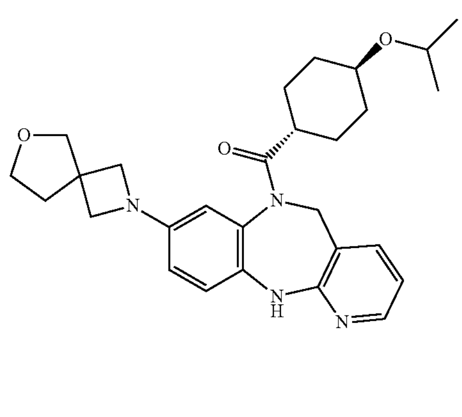 [SMILES: CC(C)O[C@H]1CC[C@H](C(=O)N2Cc3cccnc3Nc3ccc(N4CC5(CCOC5)C4)cc32)CC1] | 6-{[trans-4-(1-methylethoxy)cyclohexyl]carbonyl}-8-(6-oxa-2-azaspiro[3.4]oct-2-yl)-6,11-dihydro-5H-pyrido[2,3-b][1,5]benzodiazepine | 477 |

-continued

| Ex. No. | Structure | Chemical Name | [M + H]+ |
|---|---|---|---|
| 310 | 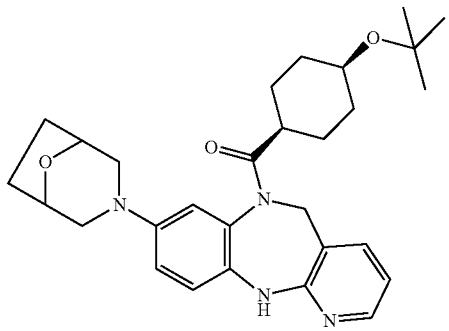 [SMILES: CC(C)(C)O[C@H]1CC[C@@H](C(=O)N2Cc3cccnc3Nc3ccc(N4CC5CCC(C4)O5)cc32)CC1] | 6-[(cis-4-tert-butoxycyclohexyl)carbonyl]-8-(8-oxa-3-azabicyclo[3.2.1]oct-3-yl)-6,11-dihydro-5H-pyrido[2,3-b][1,5]benzodiazepine | 491 |
| 311 | 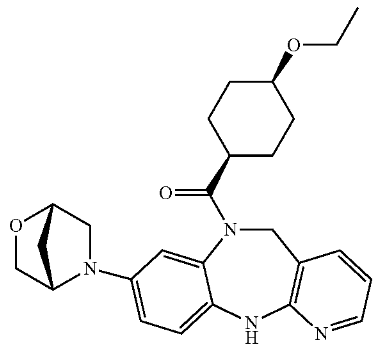 [SMILES: CCO[C@H]1CC[C@@H](C(=O)N2Cc3cccnc3Nc3ccc(N4C[C@@H]5C[C@H]4CO5)cc32)CC1] | 6-[(cis-4-ethoxycyclohexyl)carbonyl]-8-[(1S,4S)-2-oxa-5-azabicyclo[2.2.1]hept-5-yl]-6,11-dihydro-5H-pyrido[2,3-b][1,5]benzodiazepine | 449 |
| 312 | And enantiomer | trans-4-{[8-(2-oxa-5-azabicyclo[2.2.2]oct-5-yl)-5,11-dihydro-6H-pyrido[2,3-b][1,5]benzodiazepin-6-yl]carbonyl}-N-[1-(trifluoromethyl)cyclopropyl]cyclohexanamine | 542 |
| 313 | 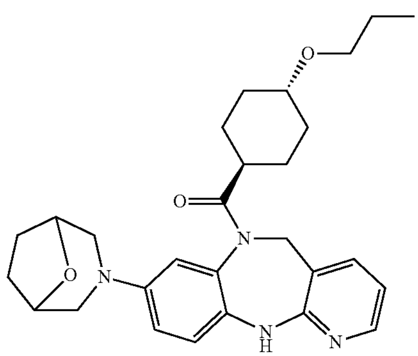 [SMILES: CCCO[C@H]1CC[C@H](C(=O)N2Cc3cccnc3Nc3ccc(N4CC5CCC(C4)O5)cc32)CC1] | 8-[8-oxa-3-azabicyclo[3.2.1]oct-3-yl]-6-[(trans-4-propoxycyclohexyl)carbonyl]-6,11-dihydro-5H-pyrido[2,3-b][1,5]benzodiazepine | 477 |

-continued

| Ex. No. | Structure | Chemical Name | [M + H]+ |
|---|---|---|---|
| 314 | 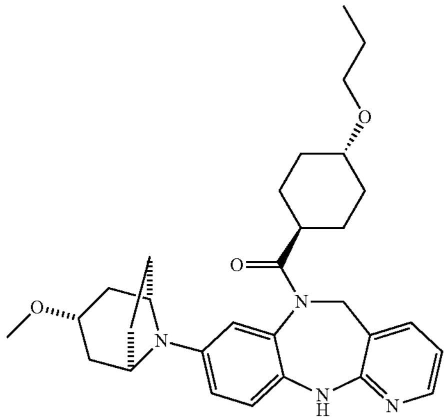 [SMILES: CCCO[C@H]1CC[C@H](C(=O)N2Cc3cccnc3Nc3ccc(N4[C@@H]5CC[C@H]4C[C@@H](OC)C5)cc32)CC1] | 8-[(3-endo)-3-methoxy-8-azabicyclo[3.2.1]oct-8-yl]-6-[(trans-4-propoxycyclohexyl)carbonyl]-6,11-dihydro-5H-pyrido[2,3-b][1,5]benzodiazepine | 505 |
| 315 | 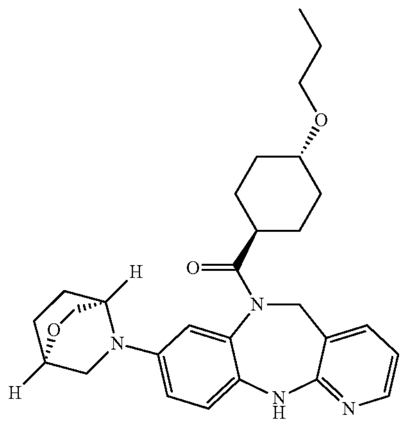 [SMILES: CCCO[C@H]1CC[C@H](C(=O)N2Cc3cccnc3Nc3ccc(N4C[C@H]5CC[C@@H]4CO5)cc32)CC1] | 8-[(1R,4R)-2-oxa-5-azabicyclo[2.2.2]oct-5-yl]-6-[(trans-4-propoxycyclohexyl)carbonyl]-6,11-dihydro-5H-pyrido[2,3-b][1,5]benzodiazepine | 477 |
| 316 | 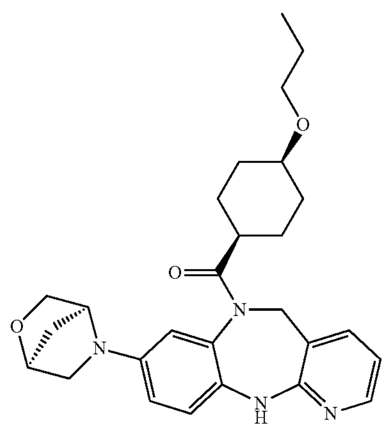 [SMILES: CCCO[C@H]1CC[C@@H](C(=O)N2Cc3cccnc3Nc3ccc(N4C[C@@H]5C[C@H]4CO5)cc32)CC1] | 8-[(1S,4S)-2-oxa-5-azabicyclo[2.2.1]hept-5-yl]-6-[(cis-4-propoxycyclohexyl)carbonyl]-6,11-dihydro-5H-pyrido[2,3-b][1,5]benzodiazepine | 463 |
| 317 | 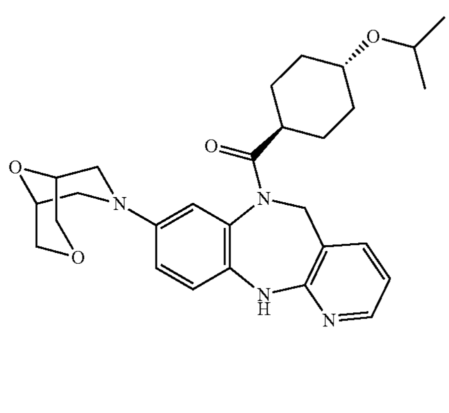 [SMILES: CC(C)O[C@H]1CC[C@H](C(=O)N2Cc3cccnc3Nc3ccc(N4CC5COCC(C4)O5)cc32)CC1] | 8-(3,9-dioxa-7-azabicyclo[3.3.1]non-7-yl)-6-{[trans-4-(1-methylethoxy)cyclohexyl]carbonyl}-6,11-dihydro-5H-pyrido[2,3-b][1,5]benzodiazepine | 493 |

| Ex. No. | Structure | Chemical Name | [M + H]+ |
|---|---|---|---|
| 318 | 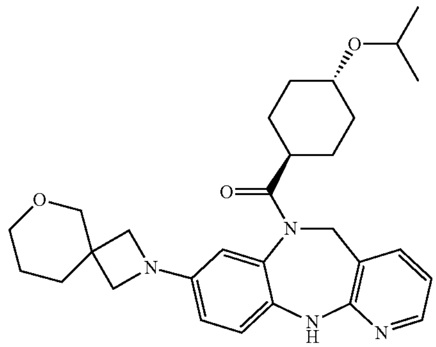 [SMILES: CC(C)O[C@H]1CC[C@H](C(=O)N2Cc3cccnc3Nc3ccc(N4CC5(CCCOC5)C4)cc32)CC1] | 6-{[trans-4-(1-methylethoxy)cyclohexyl]carbonyl}-8-(6-oxa-2-azaspiro[3.5]non-2-yl)-6,11-dihydro-5H-pyrido[2,3-b][1,5]benzodiazepine | 491 |
| 319 | 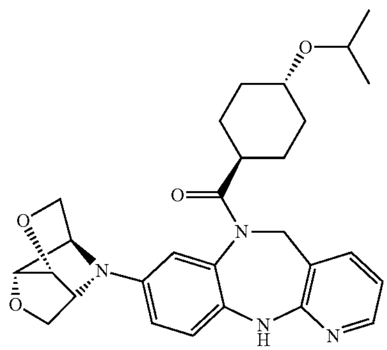 | 8-[(3R,3aR,6S,6aR)-hexahydro-3,6-epiminofuro[3,2-b]furan-7-yl]-6-{[trans-4-(1-methylethoxy)cyclohexyl]carbonyl}-6,11-dihydro-5H-pyrido[2,3-b][1,5]benzodiazepine | 491 |
| 320 | Isomer 1 | 8-(2-oxa-5-azabicyclo[2.2.2]oct-5-yl)-6-{[1-(2,2,2-trifluoroethyl)piperidin-4-yl]carbonyl}-6,11-dihydro-5H-pyrido[2,3-b][1,5]benzodiazepine | 502 |
| 321 | Isomer 2 | 8-(2-oxa-5-azabicyclo[2.2.2]oct-5-yl)-6-{[1-(2,2,2-trifluoroethyl)piperidin-4-yl]carbonyl}-6,11-dihydro-5H-pyrido[2,3-b][1,5]benzodiazepine | 502 |

| Ex. No. | Structure | Chemical Name | [M + H]+ |
|---|---|---|---|
| 322 | 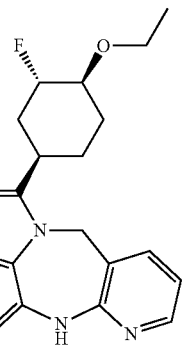<br>Isomer 1 | 6-{[(1R,3S,4S)-4-ethoxy-3-fluorocyclohexyl]carbonyl}-8-[(1S,4S)-2-oxa-5-azabicyclo[2.2.2]oct-5-yl]-6,11-dihydro-5H-pyrido[2,3-b][1,5]benzodiazepine | 481 |
| 323 | 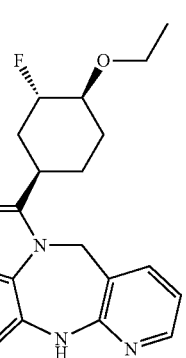<br>Isomer 2 | 6-{[(1R,3S,4S)-4-ethoxy-3-fluorocyclohexyl]carbonyl}-8-[(1R,4R)-2-oxa-5-azabicyclo[2.2.2]oct-5-yl]-6,11-dihydro-5H-pyrido[2,3-b][1,5]benzodiazepine | 481 |
| 324 | 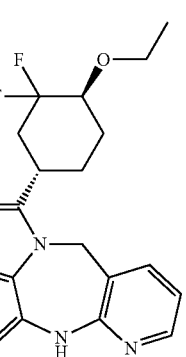<br>Isomer 1 | 6-{[(1S,4S)-4-ethoxy-3,3-difluorocyclohexyl]carbonyl}-8-[(1S,4S)-2-oxa-5-azabicyclo[2.2.2]oct-5-yl]-6,11-dihydro-5H-pyrido[2,3-b][1,5]benzodiazepine | 499 |
| 325 | 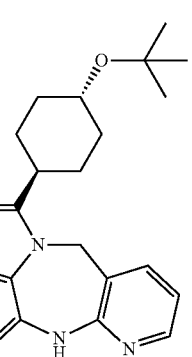 | 6-[(trans-4-tert-butoxycyclohexyl)carbonyl]-8-[(3R,3aR,6S,6aR)-hexahydro-3,6-epiminofuro[3,2-b]furan-7-yl]-6,11-dihydro-5H-pyrido[2,3-b][1,5]benzodiazepine | 505 |

-continued

| Ex. No. | Structure | Chemical Name | [M + H]+ |
|---|---|---|---|
| 326 | 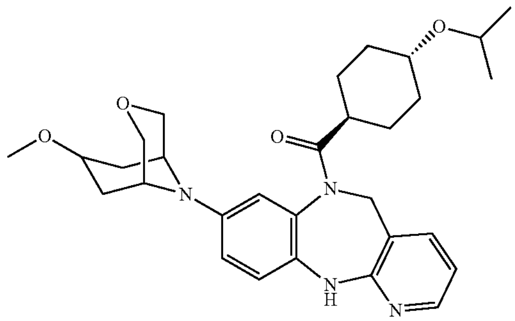 [SMILES: COC1CC2COCC(C1)N2c1ccc2c(c1)N(C(=O)[C@H]1CC[C@H](OC(C)C)CC1)Cc1cccnc1N2] | 8-(7-methoxy-3-oxa-9-azabicyclo[3.3.1]non-9-yl)-6-{[trans-4-(1-methylethoxy)cyclohexyl]carbonyl}-6,11-dihydro-5H-pyrido[2,3-b][1,5]benzodiazepine | 521 |
| 327 | 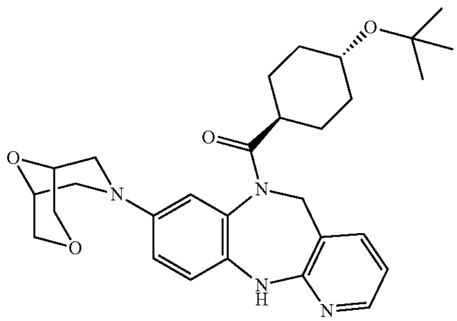 [SMILES: CC(C)(C)O[C@H]1CC[C@H](C(=O)N2Cc3cccnc3Nc3ccc(N4CC5COCC(C4)O5)cc32)CC1] | 6-[(trans-4-tert-butoxycyclohexyl)carbonyl]-8-(3,9-dioxa-7-azabicyclo[3.3.1]non-7-yl)-6,11-dihydro-5H-pyrido[2,3-b][1,5]benzodiazepine | 507 |
| 328 | 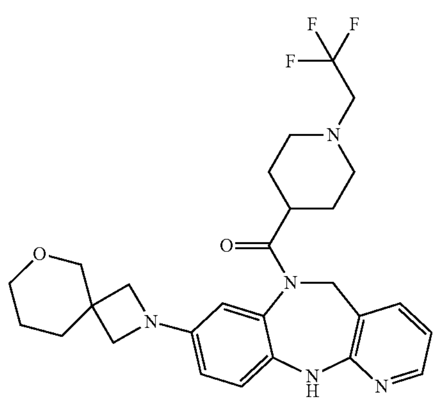 [SMILES: O=C(C1CCN(CC(F)(F)F)CC1)N1Cc2cccnc2Nc2ccc(N3CC4(CCCOC4)C3)cc21] | 8-(6-oxa-2-azaspiro[3.5]non-2-yl)-6-{[1-(2,2,2-trifluoroethyl)piperidin-4-yl]carbonyl}-6,11-dihydro-5H-pyrido[2,3-b][1,5]benzodiazepine | 516 |
| 329 | Isomer 1 | (8-((1S,4S)-2-oxa-5-azabicyclo[2.2.2]octan-5-yl)-5,11-dihydro-6H-benzo[b]pyrido[2,3-e][1,4]diazepin-6-yl)((2R,5S)-5-(tert-butoxy)tetrahydro-2H-pyran-2-yl)methanone | 493 |

-continued

| Ex. No. | Structure | Chemical Name | [M + H]+ |
|---|---|---|---|
| 330 | 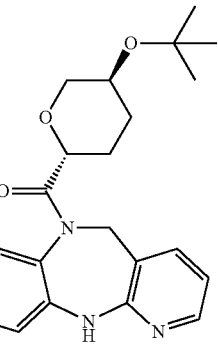 Isomer 2 | (8-((1R,4R)-2-oxa-5-azabicyclo[2.2.2]octan-5-yl)-5,11-dihydro-6H-benzo[b]pyrido[2,3-e][1,4]diazepin-6-yl)((2R,5S)-5-(tert-butoxy)tetrahydro-2H-pyran-2-yl)methanone | 493 |
| 331 | 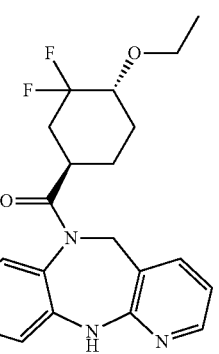 Isomer 2 | 6-{[(1R,4R)-4-ethoxy-3,3-difluorocyclohexyl]carbonyl}-8-[(1R,4R)-2-oxa-5-azabicyclo[2.2.2]oct-5-yl]-6,11-dihydro-5H-pyrido[2,3-b][1,5]benzodiazepine | 499 |
| 332 | 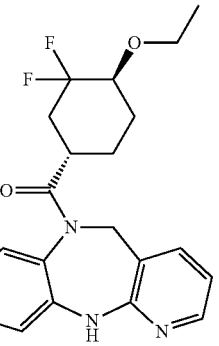 Isomer 3 | 6-{[(1S,4S)-4-ethoxy-3,3-difluorocyclohexyl]carbonyl}-8-[(1R,4R)-2-oxa-5-azabicyclo[2.2.2]oct-5-yl]-6,11-dihydro-5H-pyrido[2,3-b][1,5]benzodiazepine | 499 |
| 333 | 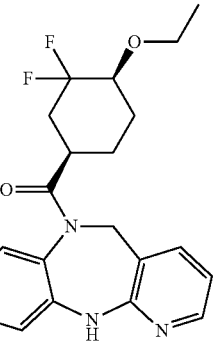 Isomer 4 | 6-{[(1R,4S)-4-ethoxy-3,3-difluorocyclohexyl]carbonyl}-8-[(1R,4R)-2-oxa-5-azabicyclo[2.2.2]oct-5-yl]-6,11-dihydro-5H-pyrido[2,3-b][1,5]benzodiazepine | 499 |

-continued

| Ex. No. | Structure | Chemical Name | [M + H]+ |
|---|---|---|---|
| 334 | Isomer 1, single diastereomer | (8-((1S,4S)-2-oxa-5-azabicyclo[2.2.2]octan-5-yl)-5,11-dihydro-6H-benzo[b]pyrido[2,3-e][1,4]diazepin-6-yl)((2R,5S)-5-ethoxytetrahydro-2H-pyran-2-yl)methanone | 465 |
| 335 | Isomer 2, single diastereomer | (8-((1R,4R)-2-oxa-5-azabicyclo[2.2.2]octan-5-yl)-5,11-dihydro-6H-benzo[b]pyrido[2,3-e][1,4]diazepin-6-yl)((2S,5R)-5-ethoxytetrahydro-2H-pyran-2-yl)methanone | 465 |
| 336 | Isomer 1 | 8-(3,9-dioxa-7-azabicyclo[3.3.1]non-7-yl)-6-{[(1S,4S)-4-ethoxy-3,3-difluorocyclohexyl]carbonyl}-6,11-dihydro-5H-pyrido[2,3-b][1,5]benzodiazepine | 515 |
| 337 | Isomer 2 | 8-(3,9-dioxa-7-azabicyclo[3.3.1]non-7-yl)-6-{[(1R,4S)-4-ethoxy-3,3-difluorocyclohexyl]carbonyl}-6,11-dihydro-5H-pyrido[2,3-b][1,5]benzodiazepine | 515 |

-continued

| Ex. No. | Structure | Chemical Name | [M + H]+ |
|---|---|---|---|
| 338 | 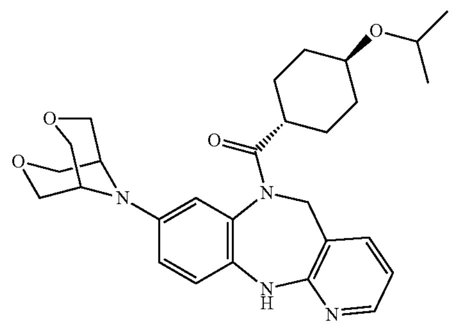 [SMILES: CC(C)O[C@H]1CC[C@H](C(=O)N2Cc3cccnc3Nc3ccc(N4C5COCC4COC5)cc32)CC1] | 8-(3,7-dioxa-9-azabicyclo[3.3.1]non-9-yl)-6-{[trans-4-(1-methylethoxy)cyclohexyl]carbonyl}-6,11-dihydro-5H-pyrido[2,3-b][1,5]benzodiazepine | 493 |
| 339 | Isomer 1 | 8-[(1S,4S)-5-methoxy-2-azabicyclo[2.2.2]oct-2-yl]-6-{[trans-4-(1-methylethoxy)cyclohexyl]carbonyl}-6,11-dihydro-5H-pyrido[2,3-b][1,5]benzodiazepine | 505 |
| 340 | Isomer 2 | 8-[(1R,4R)-5-methoxy-2-azabicyclo[2.2.2]oct-2-yl]-6-{[trans-4-(1-methylethoxy)cyclohexyl]carbonyl}-6,11-dihydro-5H-pyrido[2,3-b][1,5]benzodiazepine | 505 |
| 341 | And enantiomer | 8-(2-oxa-5-azabicyclo[2.2.2]oct-5-yl)-6-{[1-(2,2,3,3-tetrafluoropropyl)piperidin-4-yl]carbonyl}-6,11-dihydro-5H-pyrido[2,3-b][1,5]benzodiazepine | 534 |

-continued

| Ex. No. | Structure | Chemical Name | [M + H]+ |
|---|---|---|---|
| 342 | 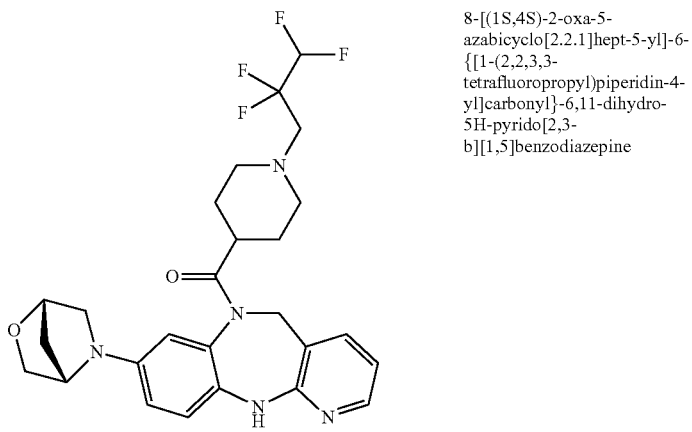 | 8-[(1S,4S)-2-oxa-5-azabicyclo[2.2.1]hept-5-yl]-6-{[1-(2,2,3,3-tetrafluoropropyl)piperidin-4-yl]carbonyl}-6,11-dihydro-5H-pyrido[2,3-b][1,5]benzodiazepine | 520 |
| 343 | 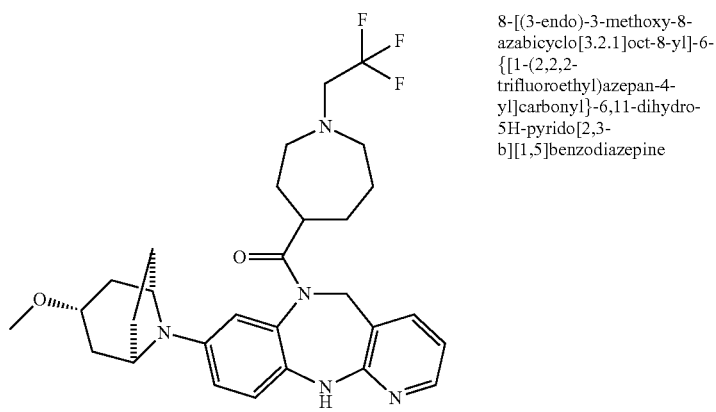  Single diastereomer | 8-[(3-endo)-3-methoxy-8-azabicyclo[3.2.1]oct-8-yl]-6-{[1-(2,2,2-trifluoroethyl)azepan-4-yl]carbonyl}-6,11-dihydro-5H-pyrido[2,3-b][1,5]benzodiazepine | 544 |
| 344 | 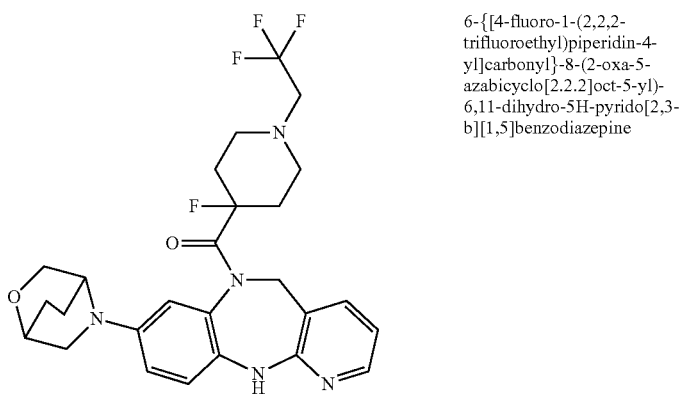  Isomer 1 | 6-{[4-fluoro-1-(2,2,2-trifluoroethyl)piperidin-4-yl]carbonyl}-8-(2-oxa-5-azabicyclo[2.2.2]oct-5-yl)-6,11-dihydro-5H-pyrido[2,3-b][1,5]benzodiazepine | 520 |

| Ex. No. | Structure | Chemical Name | [M + H]+ |
|---|---|---|---|
| 345 | 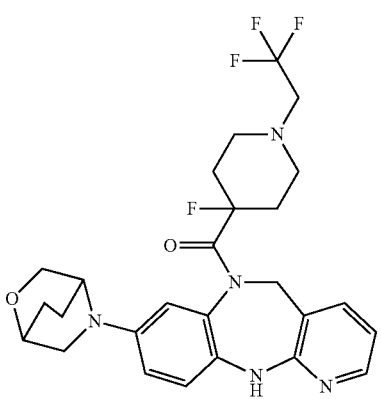<br>Isomer 2 | 6-{[4-fluoro-1-(2,2,2-trifluoroethyl)piperidin-4-yl]carbonyl}-8-(2-oxa-5-azabicyclo[2.2.2]oct-5-yl)-6,11-dihydro-5H-pyrido[2,3-b][1,5]benzodiazepine | 520 |
| 346 | 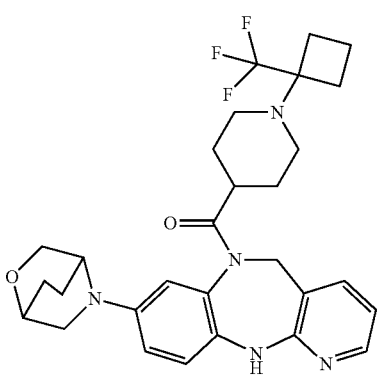<br>Isomer 1 | 8-(2-oxa-5-azabicyclo[2.2.2]oct-5-yl)-6-({1-[1-(trifluoromethyl)cyclobutyl]piperidin-4-yl}carbonyl)-6,11-dihydro-5H-pyrido[2,3-b][1,5]benzodiazepine | 542 |
| 347 | 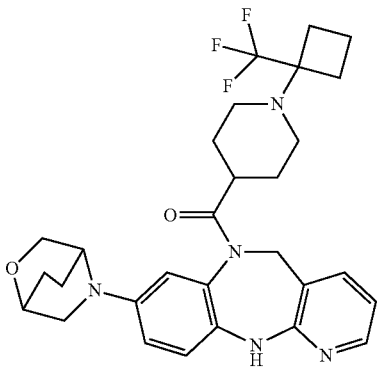<br>Isomer 2 | 8-(2-oxa-5-azabicyclo[2.2.2]oct-5-yl)-6-({1-[1-(trifluoromethyl)cyclobutyl]piperidin-4-yl}carbonyl)-6,11-dihydro-5H-pyrido[2,3-b][1,5]benzodiazepine | 542 |

| Ex. No. | Structure | Chemical Name | [M + H]+ |
|---|---|---|---|
| 348 | 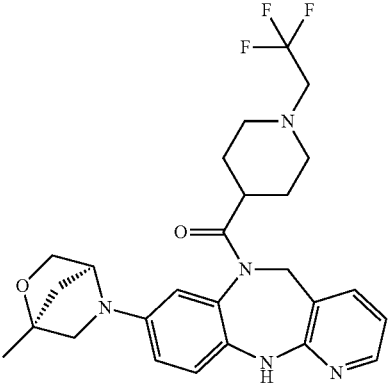 [SMILES: C[C@@]12C[C@@H](CO1)N(c1ccc3c(c1)N(C(=O)C1CCN(CC(F)(F)F)CC1)Cc1cccnc1N3)C2] | 8-[(1S,4S)-1-methyl-2-oxa-5-azabicyclo[2.2.1]hept-5-yl]-6-{[1-(2,2,2-trifluoroethyl)piperidin-4-yl]carbonyl}-6,11-dihydro-5H-pyrido[2,3-b][1,5]benzodiazepine | 502 |
| 349 | 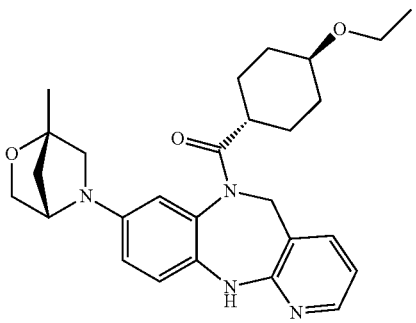 [SMILES: CCO[C@H]1CC[C@H](C(=O)N2Cc3cccnc3Nc3ccc(N4C[C@]5(C)C[C@H]4CO5)cc32)CC1] | 6-{[trans-4-(1-methylethoxy)cyclohexyl]carbonyl}-8-[(1S,4S)-1-methyl-2-oxa-5-azabicyclo[2.2.1]hept-5-yl]-6,11-dihydro-5H-pyrido[2,3-b][1,5]benzodiazepine | 477 |
| 350 | 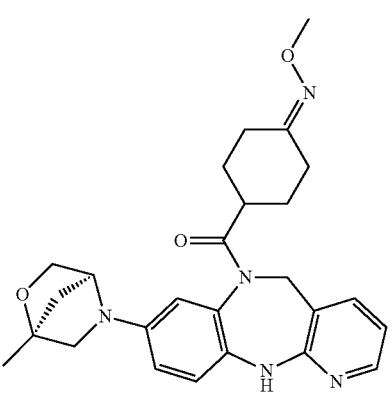 [SMILES: CON=C1CCC(C(=O)N2Cc3cccnc3Nc3ccc(N4C[C@]5(C)C[C@H]4CO5)cc32)CC1] | 4-({8-[(1S,4S)-1-methyl-2-oxa-5-azabicyclo[2.2.1]hept-5-yl]-5,11-dihydro-6H-pyrido[2,3-b][1,5]benzodiazepin-6-yl}carbonyl)cyclohexanone O-methyloxime | 462 |

Example 351: 6-{[Trans-4-(1-methylethoxy)cyclohexyl]carbonyl}-8-(tetrahydro-2H-pyran-4-yl)-6,11-dihydro-5H-pyrido[2,3-b][1,5]benzodiazepine

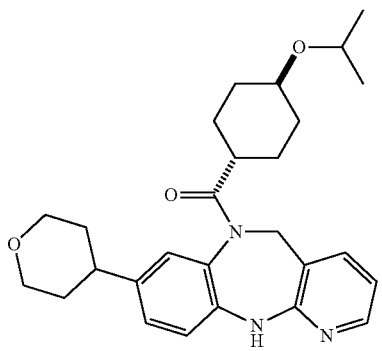

Step 1:

To an oven-dried, nitrogen-cooled vial was added (8-bromo-5,11-dihydro-6H-pyrido[2,3-b][1,5]benzodiazepin-6-yl)[trans-4-(propan-2-yloxy)cyclohexyl]methanone (50 mg, 0.11 mmol), 4-(4,4,5,5-tetramethyl-1,3,2-dioxaborolan-2-yl)-3,6-dihydro-2H-pyran (28 mg, 0.14 mmol), and 3$^{rd}$ generation x-phos palladacycle (10 mg, 0.011 mmol). THF (0.56 mL) and then potassium phosphate, tribasic (0.5 M in water, 1.1 mL, 0.56 mmol) were added and the reaction mixture was heated to 50° C. for 16 h. The mixture was allowed to cool to room temperature and diluted with EtOAc. The mixture was washed with water, and the organic layer was dried over sodium sulfate, filtered, and concentrated under reduced pressure. The residue was purified by column chromatography on silica gel (0-40% 3:1 EtOAc:EtOH/Hexanes) to afford [8-(3,6-dihydro-2H-pyran-4-yl)-5,11-dihydro-6H-pyrido[2,3-b][1,5]benzodiazepin-6-yl][trans-4-(propan-2-yloxy)cyclohexyl]methanone as an oil. MS: 448 (M+1).

Step 2:

To a flask containing palladium on carbon (10% weight loading, 7 mg, 7 μmol) under a nitrogen atmosphere was added MeOH (1 mL). [8-(3,6-Dihydro-2H-pyran-4-yl)-5,11-dihydro-6H-pyrido[2,3-b][1,5]benzodiazepin-6-yl][trans-4-(propan-2-yloxy)cyclohexyl]methanone (30 mg, 0.067 mmol) was added and the flask was evacuated and back-filled 3× with hydrogen gas via a balloon. The mixture was stirred under a hydrogen atmosphere at room temperature for 16 h. The reaction mixture was then filtered over a pad of celite and the filtrate was concentrated under reduced pressure. The residue was purified by mass triggered reverse phase HPLC (ACN/water with 0.1% TFA modifier) to afford the title compound as a solid TFA salt. MS: 450 (M+1). $^1$H NMR (500 MHz, DMSO-d$_6$) δ 9.55 (s, 1H), 8.06-8.00 (m, 1H), 7.53 (d, J=7.2 Hz, 1H), 7.26 (d, J=8.2 Hz, 1H), 7.17-7.12 (m, 2H), 6.78-6.71 (m, 1H), 5.19 (d, J=15.0 Hz, 1H), 3.98-3.87 (m, 1H), 3.61-3.53 (m, 1H), 3.47-3.37 (m, 2H), 3.16-3.07 (m, 1H), 2.78-2.69 (m, 1H), 2.39-2.29 (m, 1H), 1.93-1.87 (m, 2H), 1.72-1.58 (m, 6H), 1.52-1.41 (m, 1H), 1.15-1.08 (m, 1H), 1.07-0.99 (m, 2H), 0.99-0.93 (m, 6H), 0.92-0.81 (m, 1H), 0.65-0.55 (m, 1H).

The compounds in the following table were prepared using the methodology herein and the general procedure described in Example 351.

| Ex. No. | Structure | Chemical Name | [M + H]+ |
|---|---|---|---|
| 352 | 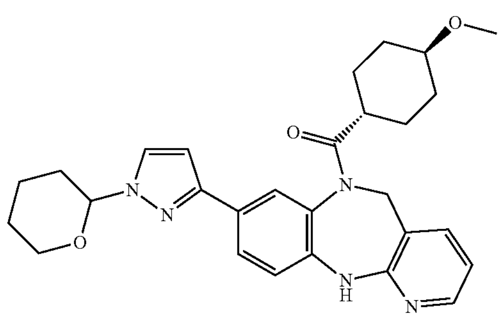 [SMILES: CO[C@H]1CC[C@H](C(=O)N2Cc3cccnc3Nc3ccc(-c4ccn(C5CCCCO5)n4)cc32)CC1] | 6-[(trans-4-methoxycyclohexyl)carbonyl]-8-[1-(tetrahydro-2H-pyran-2-yl)-1H-pyrazol-3-yl]-6,11-dihydro-5H-pyrido[2,3-b][1,5]benzodiazepine | 488 |
| 353 | 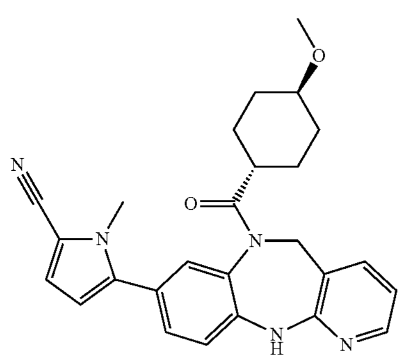 [SMILES: CO[C@H]1CC[C@H](C(=O)N2Cc3cccnc3Nc3ccc(-c4ccc(C#N)n4C)cc32)CC1] | 5-{6-[(trans-4-methoxycyclohexyl)carbonyl]-6,11-dihydro-5H-pyrido[2,3-b][1,5]benzodiazepin-8-yl}-1-methyl-1H-pyrrole-2-carbonitrile | 442 |

| Ex. No. | Structure | Chemical Name | [M + H]+ |
|---|---|---|---|
| 354 | 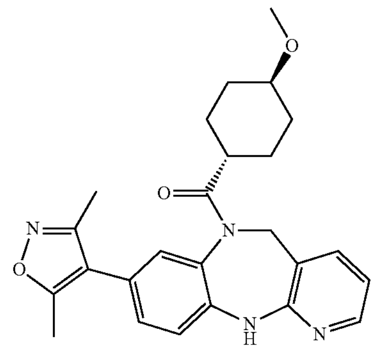 [SMILES: CO[C@H]1CC[C@H](C(=O)N2Cc3cccnc3Nc3ccc(-c4c(C)noc4C)cc32)CC1] | 8-(3,5-dimethylisoxazol-4-yl)-6-[(trans-4-methoxycyclohexyl)carbonyl]-6,11-dihydro-5H-pyrido[2,3-b][1,5]benzodiazepine | 433 |
| 355 | 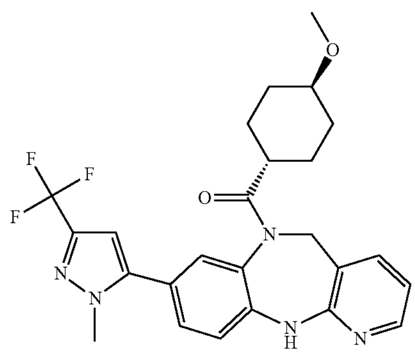 [SMILES: CO[C@H]1CC[C@H](C(=O)N2Cc3cccnc3Nc3ccc(-c4cc(C(F)(F)F)nn4C)cc32)CC1] | 6-[(trans-4-methoxycyclohexyl)carbonyl]-8-[1-methyl-3-(trifluoromethyl)-1H-pyrazol-5-yl]-6,11-dihydro-5H-pyrido[2,3-b][1,3]benzodiazepine | 486 |
| 356 | 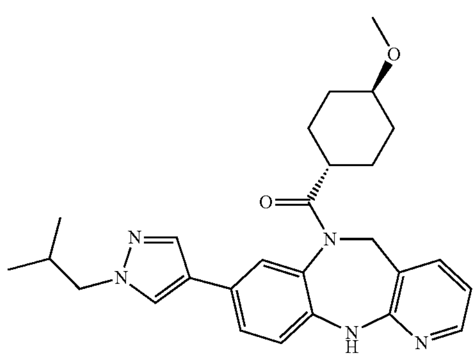 [SMILES: CO[C@H]1CC[C@H](C(=O)N2Cc3cccnc3Nc3ccc(-c4cnn(CC(C)C)c4)cc32)CC1] | 6-[(trans-4-methoxycyclohexyl)carbonyl]-8-[1-(2-methylpropyl)-1H-pyrazol-4-yl]-6,11-dihydro-5H-pyrido[2,3-b][1,5]benzodiazepine | 460 |
| 357 | 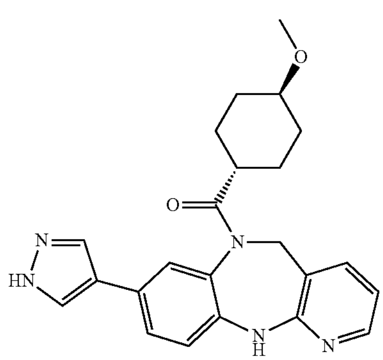 [SMILES: CO[C@H]1CC[C@H](C(=O)N2Cc3cccnc3Nc3ccc(-c4cn[nH]c4)cc32)CC1] | 6-[(trans-4-methoxycyclohexyl)carbonyl]-8-(1H-pyrazol-4-yl)-6,11-dihydro-5H-pyrido[2,3-b][1,5]benzodiazepine | 404 |

-continued

| Ex. No. | Structure | Chemical Name | [M + H]+ |
|---|---|---|---|
| 358 | 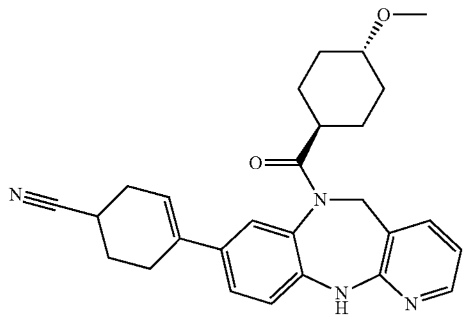 [SMILES: CO[C@H]1CC[C@H](C(=O)N2Cc3cccnc3Nc3ccc(C4=CCC(C#N)CC4)cc32)CC1] | 4-{6-[(trans-4-methoxycyclohexyl)carbonyl]-6,11-dihydro-5H-pyrido[2,3-b][1,5]benzodiazepin-8-yl}cyclohex-3-ene-1-carbonitrile | 443 |
| 359 | 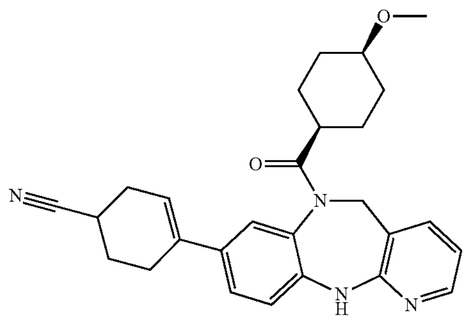 [SMILES: CO[C@H]1CC[C@@H](C(=O)N2Cc3cccnc3Nc3ccc(C4=CCC(C#N)CC4)cc32)CC1] | 4-{6-[(cis-4-methoxycyclohexyl)carbonyl]-6,11-dihydro-5H-pyrido[2,3-b][1,5]benzodiazepin-8-yl}cyclohex-3-ene-1-carbonitrile | 443 |
| 360 | 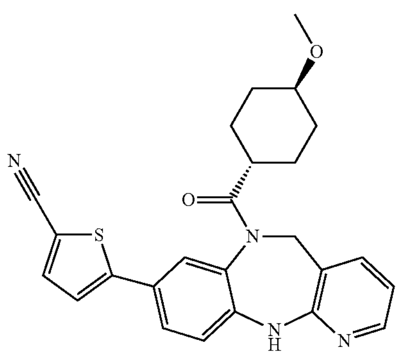 [SMILES: CO[C@H]1CC[C@H](C(=O)N2Cc3cccnc3Nc3ccc(-c4ccc(C#N)s4)cc32)CC1] | 5-{6-[(trans-4-methoxycyclohexyl)carbonyl]-6,11-dihydro-5H-pyrido[2,3-b][1,5]benzodiazepin-8-yl}thiophene-2-carbonitrile | 445 |
| 361 | 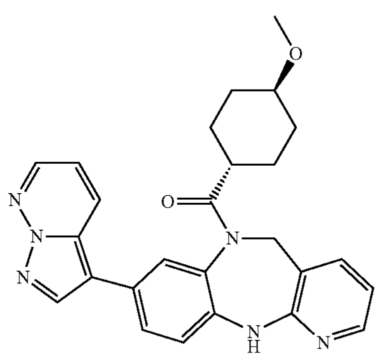 [SMILES: CO[C@H]1CC[C@H](C(=O)N2Cc3cccnc3Nc3ccc(-c4cnn5ncccc45)cc32)CC1] | 6-[(trans-4-methoxycyclohexyl)carbonyl]-8-pyrazolo[1,5-b]pyridazin-3-yl-6,11-dihydro-5H-pyrido[2,3-b][1,5]benzodiazepine | 455 |

| Ex. No. | Structure | Chemical Name | [M + H]+ |
| --- | --- | --- | --- |
| 362 | 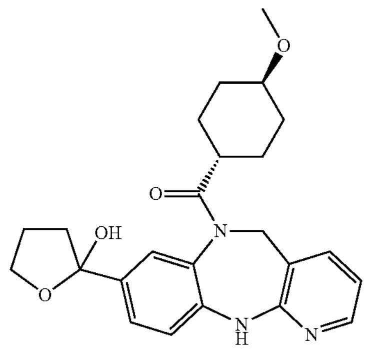 [SMILES: CO[C@H]1CC[C@H](C(=O)N2Cc3cccnc3Nc3ccc(C4(O)CCCO4)cc32)CC1] | 2-{6-[(trans-4-methoxycyclohexyl)carbonyl]-6,11-dihydro-5H-pyrido[2,3-b][1,5]benzodiazepin-8-yl}tetrahydrofuran-2-ol | 424 |
| 363 | 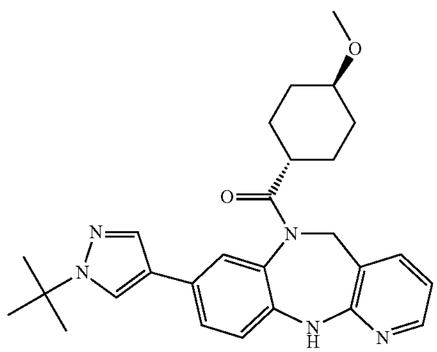 [SMILES: CO[C@H]1CC[C@H](C(=O)N2Cc3cccnc3Nc3ccc(-c4cnn(C(C)(C)C)c4)cc32)CC1] | 8-(1-tert-butyl-1H-pyrazol-4-yl)-6-[(trans-4-methoxycyclohexyl)carbonyl]-6,11-dihydro-5H-pyrido[2,3-b][1,5]benzodiazepine | 460 |
| 364 | 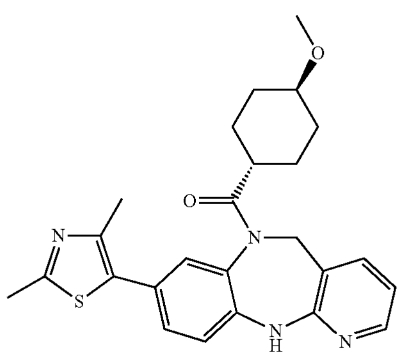 [SMILES: CO[C@H]1CC[C@H](C(=O)N2Cc3cccnc3Nc3ccc(-c4sc(C)nc4C)cc32)CC1] | 8-(2,4-dimethyl-1,3-thiazol-5-yl)-6-[(trans-4-methoxycyclohexyl)carbonyl]-6,11-dihydro-5H-pyrido[2,3-b][1,5]benzodiazepine | 449 |
| 365 | 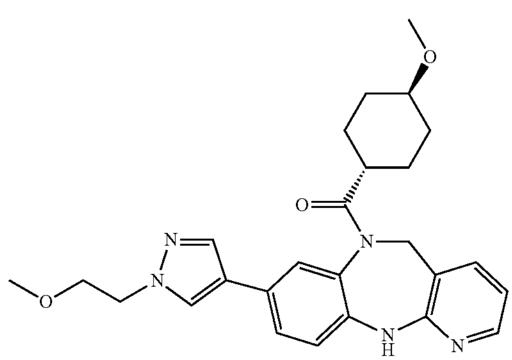 [SMILES: COCCn1cc(-c2ccc3c(c2)N(C(=O)[C@H]2CC[C@H](OC)CC2)Cc2cccnc2N3)cn1] | 6-[(trans-4-methoxycyclohexyl)carbonyl]-8-[1-(2-methoxyethyl)-1H-pyrazol-4-yl]-6,11-dihydro-5H-pyrido[2,3-b][1,5]benzodiazepine | 462 |

-continued

| Ex. No. | Structure | Chemical Name | [M + H]+ |
|---|---|---|---|
| 366 | 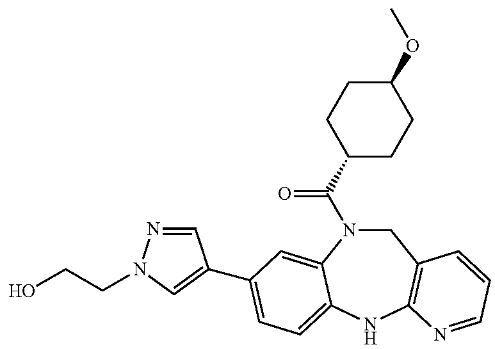 [SMILES: CO[C@H]1CC[C@H](C(=O)N2Cc3cccnc3Nc3ccc(-c4cnn(CCO)c4)cc32)CC1] | 2-(4-{6-[(trans-4-methoxycyclohexyl)carbonyl]-6,11-dihydro-5H-pyrido[2,3-b][1,5]benzodiazepin-8-yl}-1H-pyrazol-1-yl)ethanol | 448 |
| 367 | 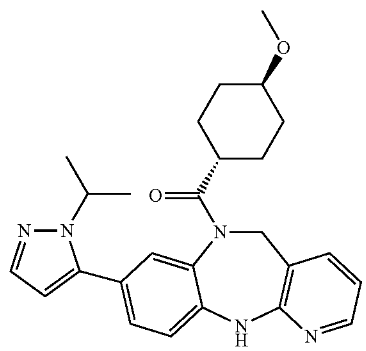 [SMILES: CO[C@H]1CC[C@H](C(=O)N2Cc3cccnc3Nc3ccc(-c4ccnn4C(C)C)cc32)CC1] | 6-[(trans-4-methoxycyclohexyl)carbonyl]-8-[1-(1-methyethyl)-1H-pyrazol-5-yl]-6,11-dihydro-5H-pyrido[2,3-b][1,5]benzodiazepine | 446 |
| 368 | 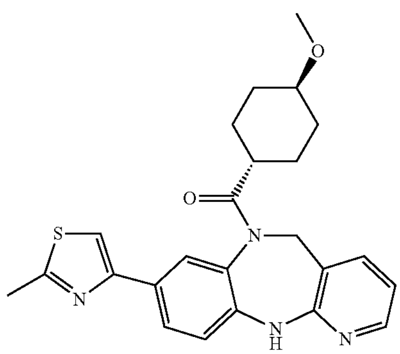 [SMILES: CO[C@H]1CC[C@H](C(=O)N2Cc3cccnc3Nc3ccc(-c4csc(C)n4)cc32)CC1] | 6-[(trans-4-methoxycyclohexyl)carbonyl]-8-(2-methyl-1,3-thiazol-4-yl)-6,11-dihydro-5H-pyrido[2,3-b][1,5]benzodiazepine | 435 |
| 369 | 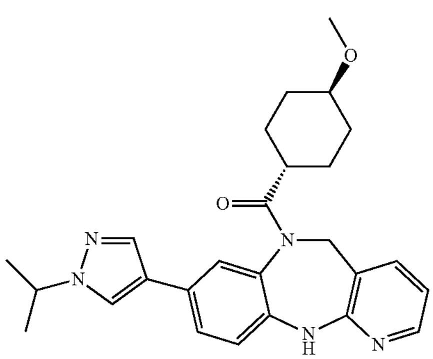 [SMILES: CO[C@H]1CC[C@H](C(=O)N2Cc3cccnc3Nc3ccc(-c4cnn(C(C)C)c4)cc32)CC1] | 6-[(trans-4-methoxycyclohexyl)carbonyl]-8-[1-(1-methylethyl)-1H-pyrazol-4-yl]-6,11-dihydro-5H-pyrido[2,3-b][1,5]benzodiazepine | 446 |

| Ex. No. | Structure | Chemical Name | [M + H]+ |
|---|---|---|---|
| 370 | 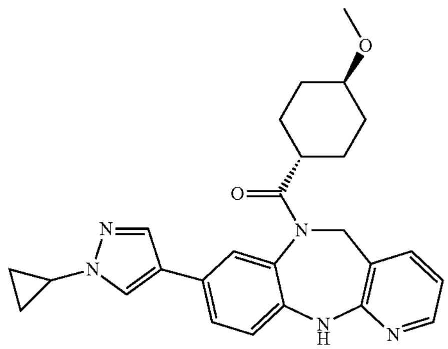 [SMILES: CO[C@H]1CC[C@H](C(=O)N2Cc3cccnc3Nc3ccc(-c4cnn(C5CC5)c4)cc32)CC1] | 8-(1-cyclopropyl-1H-pyrazol-4-yl)-6-[(trans-4-methoxycyclohexyl)carbonyl]-6,11-dihydro-5H-pyrido[2,3-b][1,5]benzodiazepine | 444 |
| 371 | 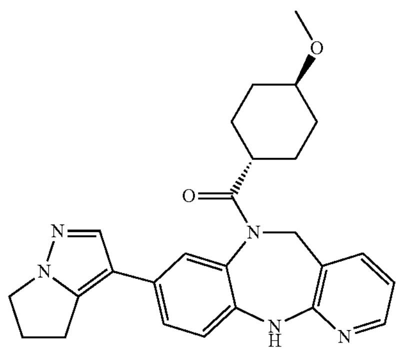 [SMILES: CO[C@H]1CC[C@H](C(=O)N2Cc3cccnc3Nc3ccc(-c4cnn5c4CCC5)cc32)CC1] | 8-(5,6-dihydro-4H-pyrrolo[1,2-b]pyrazol-3-yl)-6-[(trans-4-methoxycyclohexyl)carbonyl]-6,11-dihydro-5H-pyrido[2,3-b][1,5]benzodiazepine | 444 |
| 372 | 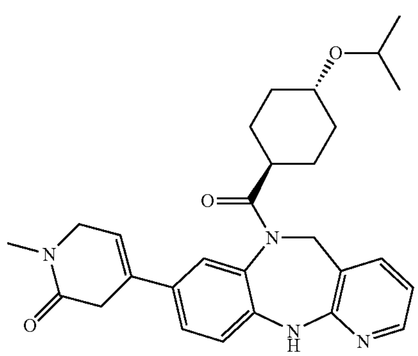 [SMILES: CC(C)O[C@H]1CC[C@H](C(=O)N2Cc3cccnc3Nc3ccc(C4=CCN(C)C(=O)C4)cc32)CC1] | 1-methyl-4-(6-{[trans-4-(1-methylethoxy)cyclohexyl]carbonyl}-6,11-dihydro-5H-pyrido[2,3-b][1,5]benzodiazepin-8-yl)-3,6-dihydropyridin-2(1H)-one | 475 |
| 373 | 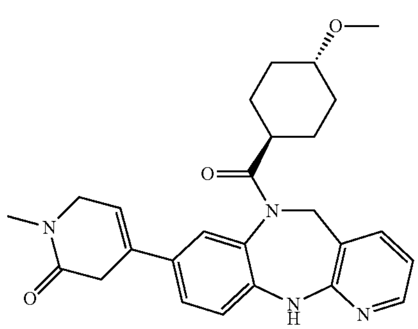 [SMILES: CO[C@H]1CC[C@H](C(=O)N2Cc3cccnc3Nc3ccc(C4=CCN(C)C(=O)C4)cc32)CC1] | 4-{6-[(trans-4-methoxycyclohexyl)carbonyl]-6,11-dihydro-5H-pyrido[2,3-b][1,5]benzodiazepin-8-yl}-1-methyl-3,6-dihydropyridin-2(1H)-one | 447 |

| Ex. No. | Structure | Chemical Name | [M + H]+ |
|---|---|---|---|
| 374 | 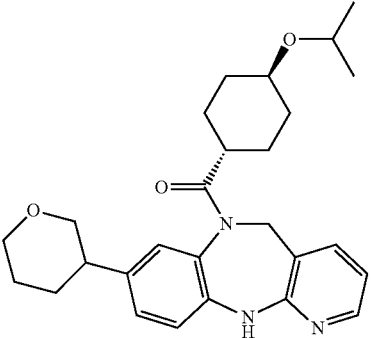 [SMILES: CC(C)O[C@H]1CC[C@H](C(=O)N2Cc3cccnc3Nc3ccc(C4CCCOC4)cc32)CC1] | 6-{[trans-4-(1-methylethoxy)cyclohexyl]carbonyl}-8-(tetrahydro-2H-pyran-3-yl)-6,11-dihydro-5H-pyrido[2,3-b][1,5]benzodiazepine | 450 |
| 375 | 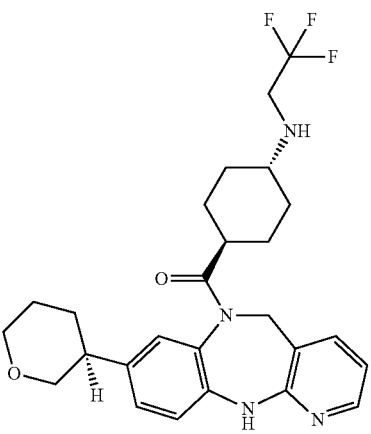 Isomer 1 | trans-4-({8-[(3S)-tetrahydro-2H-pyran-3-yl]-5,11-dihydro-6H-pyrido[2,3-b][1,5]benzodiazepin-6-yl}carbonyl)-N-(2,2,2-trifluoroethyl)cyclohexanamine | 489 |
| 376 | 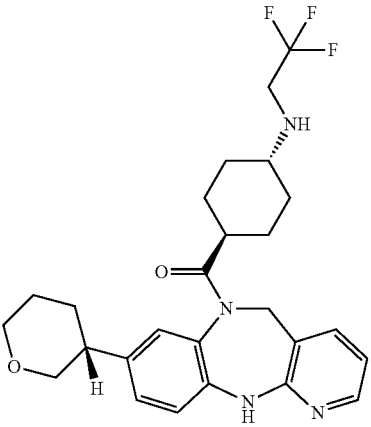 Isomer 2 | trans-4-({8-[(3R)-tetrahydro-2H-pyran-3-yl]-5,11-dihydro-6H-pyrido[2,3-b][1,5]benzodiazepin-6-yl}carbonyl)-N-(2,2,2-trifluoroethyl)cyclohexanamine | 489 |

| Ex. No. | Structure | Chemical Name | [M + H]+ |
|---|---|---|---|
| 377 | 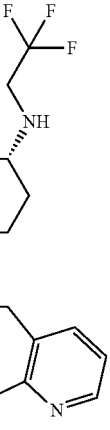<br>Isomer 3 | cis-4-({8-[(3S)-tetrahydro-2H-pyran-3-yl]-5,11-dihydro-6H-pyrido[2,3-b][1,5]benzodiazepin-6-yl}carbonyl)-N-(2,2,2-trifluoroethyl)cyclohexanamine | 489 |
| 378 | 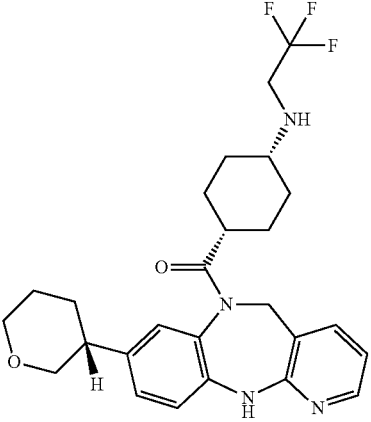<br>Isomer 4 | cis-4-({8-[(3R)-tetrahydro-2H-pyran-3-yl]-5,11-dihydro-6H-pyrido[2,3-b][1,5]benzodiazepin-6-yl}carbonyl)-N-(2,2,2-trifluoroethyl)cyclohexanamine | 489 |
| 379 | 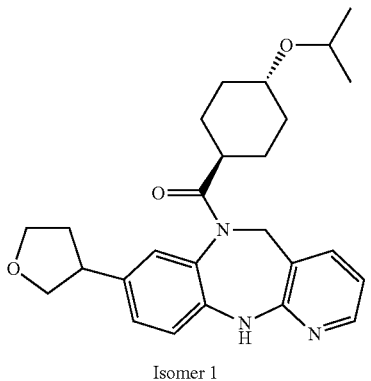 [SMILES: CC(C)O[C@H]1CC[C@H](C(=O)N2Cc3cccnc3Nc3ccc(C4CCOC4)cc32)CC1]<br>Isomer 1 | 6-{[trans-4-(1-methylethoxy)cyclohexyl]carbonyl}-8-[tetrahydrofuran-3-yl]-6,11-dihydro-5H-pyrido[2,3-b][1,5]benzodiazepine | 436 |

| Ex. No. | Structure | Chemical Name | [M + H]+ |
|---|---|---|---|
| 380 | 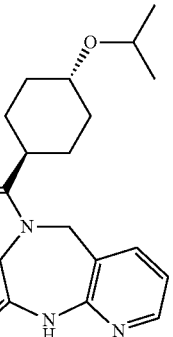 Isomer 2 | 6-{[trans-4-(1-methylethoxy)cyclohexyl]carbonyl}-8-[tetrahydrofuran-3-yl]-6,11-dihydro-5H-pyrido[2,3-b][1,5]benzodiazepine | 436 |
| 381 | 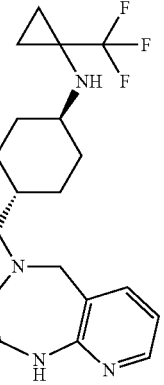 | trans-4-{[8-(tetrahydro-2H-pyran-4-yl)-5,11-dihydro-6H-pyrido[2,3-b][1,5]benzodiazepin-6-yl]carbonyl}-N-[1-(trifluoromethyl)cyclopropyl]cyclohexanamine | 515 |
| 382 | 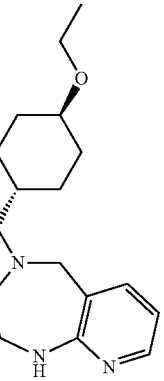 | 6-[(trans-4-ethoxycyclohexyl)carbonyl]-8-(tetrahydro-2H-pyran-4-yl)-6,11-dihydro-5H-pyrido[2,3-b][1,5]benzodiazepine | 436 |
| 383 | 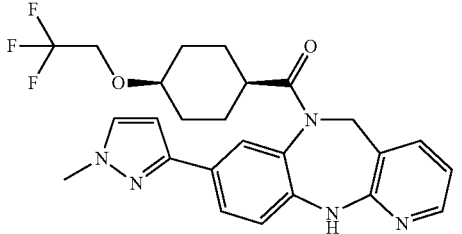 [SMILES: Cn1ccc(-c2ccc3c(c2)N(C(=O)[C@H]2CC[C@@H](OCC(F)(F)F)CC2)Cc2cccnc2N3)n1] | 8-(1-methyl-1H-pyrazol-3-yl)-6-{[cis-4-(2,2,2-trifluoroethoxy)cyclohexyl]carbonyl}-6,11-dihydro-5H-pyrido[2,3-b][1,5]benzodiazepine | 486 |

| Ex. No. | Structure | Chemical Name | [M + H]+ |
|---|---|---|---|
| 384 | 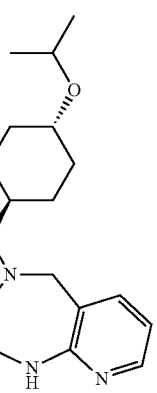<br>Isomer 1 | 8-[1,4-dioxan-2-yl]-6-{[trans-4-(1-methylethoxy)cyclohexyl]carbonyl}-6,11-dihydro-5H-pyrido[2,3-b][1,5]benzodiazepine | 452 |
| 385 | 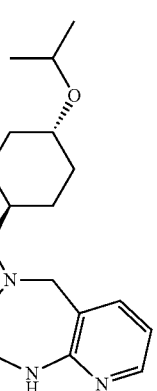<br>Isomer 2 | 8-[1,4-dioxan-2-yl]-6-{[trans-4-(1-methylethoxy)cyclohexyl]carbonyl}-6,11-dihydro-5H-pyrido[2,3-b][1,5]benzodiazepine | 452 |
| 386 | 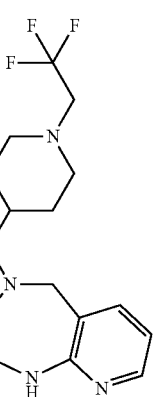<br>Isomer 1 | 8-[1,4-dioxan-2-yl]-6-{[1-(2,2,2-trifluoroethyl)piperidin-4-yl]carbonyl}-6,11-dihydro-5H-pyrido[2,3-b][1,5]benzodiazepine | 477 |

| Ex. No. | Structure | Chemical Name | [M + H]+ |
|---|---|---|---|
| 387 | 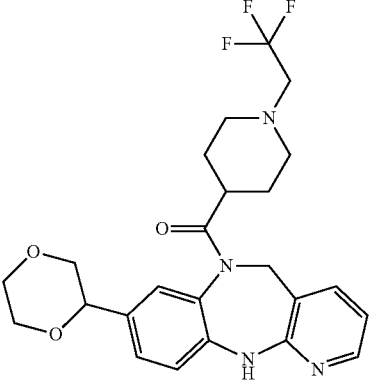<br>Isomer 2 | 8-[1,4-dioxan-2-yl]-6-{[1-(2,2,2-trifluoroethyl)piperidin-4-yl]carbonyl}-6,11-dihydro-5H-pyrido[2,3-b][1,5]benzodiazepine | 477 |
| 388 | 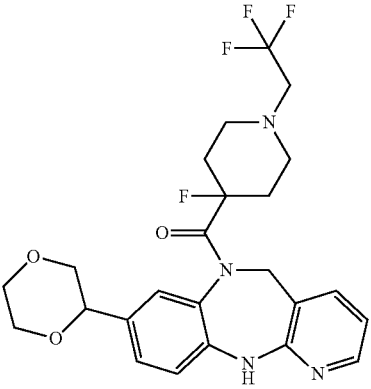<br>Isomer 1 | 8-(1,4-dioxan-2-yl)-6-{[4-fluoro-1-(2,2,2-trifluoroethyl)piperidin-4-yl]carbonyl}-6,11-dihydro-5H-pyrido[2,3-b][1,5]benzodiazepine | 495 |
| 389 | 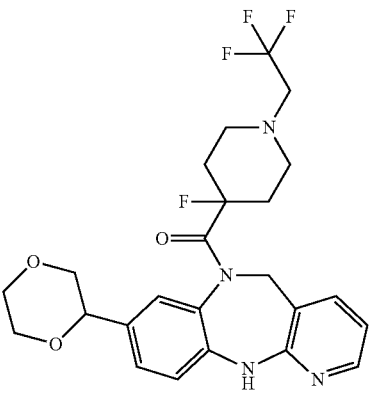<br>Isomer 2 | 8-(1,4-dioxan-2-yl)-6-{[4-fluoro-1-(2,2,2-trifluoroethyl)piperidin-4-yl]carbonyl}-6,11-dihydro-5H-pyrido[2,3-b][1,5]benzodiazepine | 495 |

-continued

| Ex. No. | Structure | Chemical Name | [M + H]+ |
|---|---|---|---|
| 390 | 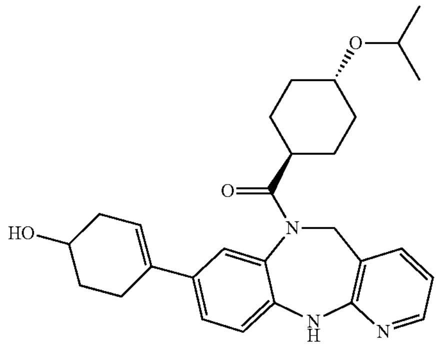 [SMILES: CC(C)O[C@H]1CC[C@H](C(=O)N2Cc3cccnc3Nc3ccc(C4=CCC(O)CC4)cc32)CC1] | 4-(6-{[trans-4-(1-methylethoxy)cyclohexyl]carbonyl}-6,11-dihydro-5H-pyrido[2,3-b][1,5]benzodiazepin-8-yl)cyclohex-3-en-1-ol | 462 |
| 391 | 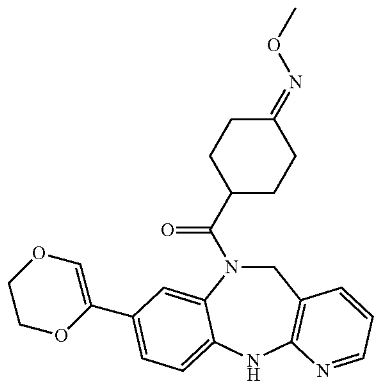 [SMILES: CON=C1CCC(C(=O)N2Cc3cccnc3Nc3ccc(C4=COCCO4)cc32)CC1] | 4-{[8-(5,6-dihydro-1,4-dioxin-2-yl)-5,11-dihydro-6H-pyrido[2,3-b][1,5]benzodiazepin-6-yl]carbonyl}cyclohexanone O-methyloxime | 435 |
| 392 | 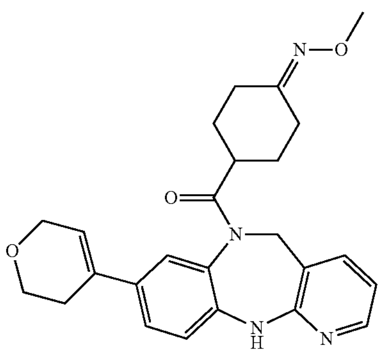 [SMILES: CON=C1CCC(C(=O)N2Cc3cccnc3Nc3ccc(C4=CCOCC4)cc32)CC1] | 4-{[8-(3,6-dihydro-2H-pyran-4-yl)-5,11-dihydro-6H-pyrido[2,3-b][1,5]benzodiazepin-6-yl]carbonyl}cyclohexanone O-methyloxime | 433 |
| 393 | And enantiomer | 4-{[8-(2,4-dioxan-2-yl)-5,11-dihydro-6H-pyrido[2,3-b][1,5]benzodiazepin-6-yl]carbonyl}cyclohexanone O-methyloxime | 437 |

| Ex. No. | Structure | Chemical Name | [M + H]+ |
|---|---|---|---|
| 394 | 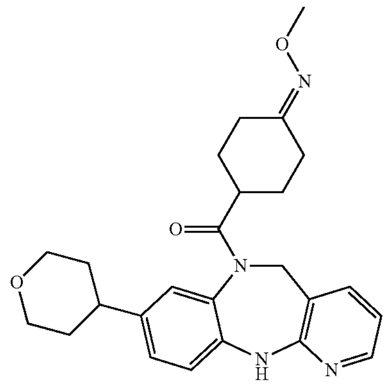 [SMILES: CON=C1CCC(C(=O)N2Cc3cccnc3Nc3ccc(C4CCOCC4)cc32)CC1] | 4-{[8-(tetrahdyro-2H-pyran-4-yl)-5,11-dihydro-6H-pyrido[2,3-b][1,5]benzodiazepin-6-yl]carbonyl}cyclohexanone O-methyloxime | 435 |
| 395 | Isomer 1 | 4-(6-{[trans-4-(1-methylethoxy)cyclohexyl]carbonyl}-6,11-dihydro-5H-pyrido[2,3-b][1,5]benzodiazepin-8-yl)cyclohexanol | 464 |
| 396 | Isomer 2 | 4-(6-{[trans-4-(1-methylethoxy)cyclohexyl]carbonyl}-6,11-dihydro-5H-pyrido[2,3-b][1,5]benzodiazepin-8-yl)cyclohexanol | 464 |
| 397 | 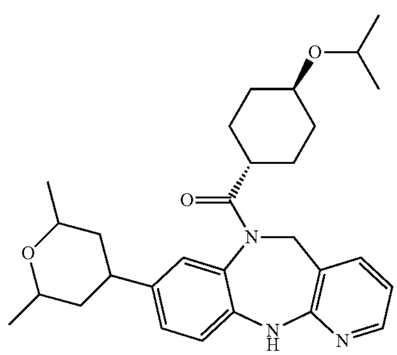 [SMILES: CC1CC(c2ccc3c(c2)N(C(=O)[C@H]2CC[C@H](OC(C)C)CC2)Cc2cccnc2N3)CC(C)O1] | 8-(2,6-dimethyltetrahydro-2H-pyran-4-yl)-6-{[trans-4-(1-methylethoxy)cyclohexyl]carbonyl}-6,11-dihydro-5H-pyrido[2,3-b][1,5]benzodiazepine | 478 |

| Ex. No. | Structure | Chemical Name | [M + H]+ |
|---|---|---|---|
| 398 | 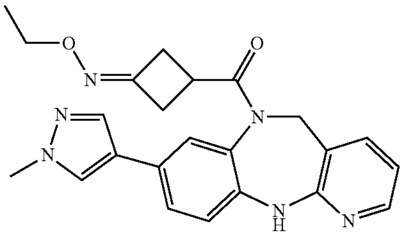 [SMILES: CCON=C1CC(C(=O)N2Cc3cccnc3Nc3ccc(-c4cnn(C)c4)cc32)C1] | 3-{[8-(1-methyl-1H-pyrazol-4-yl)-5,11-dihydro-6H-pyrido[2,3-b][1,5]benzodiazepin-6-yl]carbonyl}cyclobutanone O-ethyloxime | 417 |
| 399 | 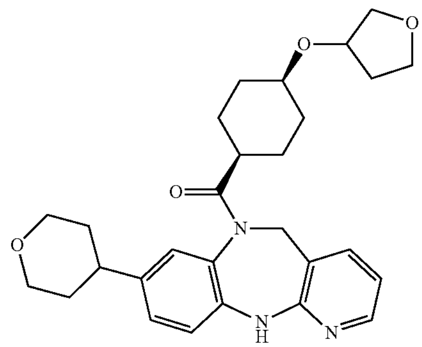 [SMILES: O=C([C@H]1CC[C@@H](OC2CCOC2)CC1)N1Cc2cccnc2Nc2ccc(C3CCOCC3)cc21] | 6-({cis-4-[tetrahydrofuran-3-yloxy]cyclohexyl}carbonyl)-8-(tetrahydro-2H-pyran-4-yl)-6,11-dihydro-5H-pyrido[2,3-b][1,5]benzodiazepine | 478 |

Example 400: 6-[(Trans-4-methoxycyclohexyl)carbonyl]-8-pyrimidin-5-yl-6,11-dihydro-5H-pyrido[2,3-b][1,5]benzodiazepine

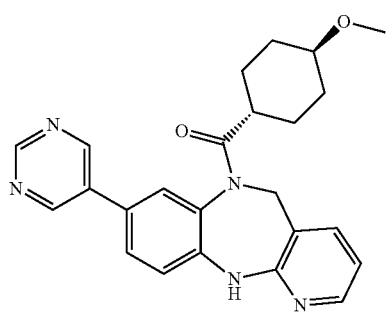 [SMILES: CO[C@H]1CC[C@H](C(=O)N2Cc3cccnc3Nc3ccc(-c4cncnc4)cc32)CC1]

To a microwave vial containing pyrimidin-5-ylboronic acid (10 mg, 0.079 mmol) was added 1,1'-bis(diphenylphosphino)ferrocene-palladium(II)dichloride dichloromethane complex (6 mg, 7 μmol), (8-bromo-5,11-dihydro-6H-pyrido[2,3-b][1,5]benzodiazepin-6-yl)(trans-4-methoxycyclohexyl)methanone, HCl (25 mg, 0.055 mmol), DMA (0.9 mL), and potassium phosphate tribasic (1.0 M in water, 0.29 mL, 0.29 mmol). The mixture was heated to 80° C. for 16 h. The mixture was allowed to cool to room temperature and diluted with 50:50 MeOH:DMSO (1 mL). The mixture was filtered and purified by mass triggered reverse phase HPLC (ACN/water with 0.1% TFA modifier) to afford the title compound as a solid TFA salt. MS: 416 (M+1). $^1$H NMR (500 MHz, DMSO-$d_6$) δ 9.74 (s, 1H), 9.18-9.10 (m, 3H), 8.07 (d, J=4.9 Hz, 1H), 7.86-7.81 (m, 1H), 7.74 (dd, J=8.5, 1.9 Hz, 1H), 7.53 (d, J=7.3 Hz, 1H), 7.47 (d, J=8.5 Hz, 1H), 6.81-6.73 (m, 1H), 5.20 (t, J=13.4 Hz, 1H), 3.95 (d, J=14.9 Hz, 1H), 3.09 (s, 3H), 2.95-2.87 (m, 1H), 2.51-2.47 (m, 1H), 2.00-1.89 (m, 2H), 1.77-1.68 (m, 1H), 1.50-1.38 (m, 1H), 1.24-1.13 (m, 1H), 1.00-0.82 (m, 2H), 0.66-0.57 (m, 1H).

The compounds in the following table were prepared using the methodology herein and the general procedure described in Example 400.

| Ex. No. | Structure | Chemical Name | [M + H]+ |
|---|---|---|---|
| 401 | 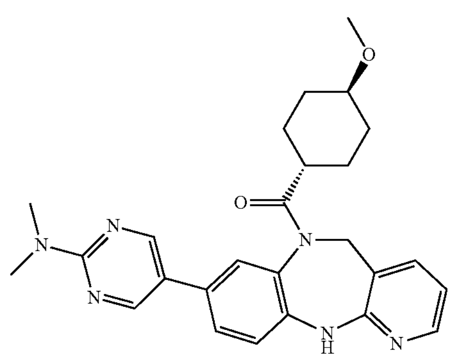 [SMILES: CO[C@H]1CC[C@H](C(=O)N2Cc3cccnc3Nc3ccc(-c4cnc(N(C)C)nc4)cc32)CC1] | 5-{6-[(trans-4-methoxycyclohexyl)carbonyl]-6,11-dihydro-5H-pyrido[2,3-b][1,5]benzodiazepin-8-yl}-N,N-dimethylpyrimidin-2-amine | 459 |

-continued

| Ex. No. | Structure | Chemical Name | [M + H]+ |
|---|---|---|---|
| 402 | 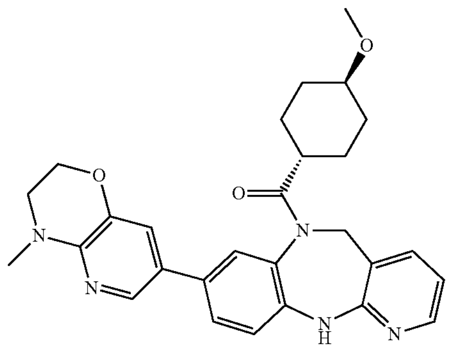 [SMILES: CO[C@H]1CC[C@H](C(=O)N2Cc3cccnc3Nc3ccc(-c4cnc5c(c4)OCCN5C)cc32)CC1] | 6-[(trans-4-methoxycyclohexyl)carbonyl]-8-(4-methyl-3,4-dihydro-2H-pyrido[3,2-b][1,4]oxazin-7-yl)-6,11-dihydro-5H-pyrido[2,3-b][1,5]benzodiazepine | 486 |
| 403 | 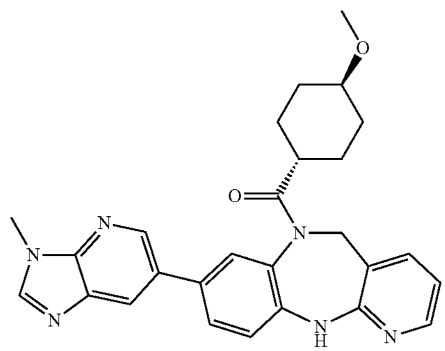 [SMILES: CO[C@H]1CC[C@H](C(=O)N2Cc3cccnc3Nc3ccc(-c4cnc5c(c4)ncn5C)cc32)CC1] | 6-[(trans-4-methoxycyclohexyl)carbonyl]-8-(3-methyl-3H-imidazo[4,5-b]pyridin-6-yl)-6,11-dihydro-5H-pyrido[2,3-b][1,5]benzodiazepine | 469 |
| 404 | 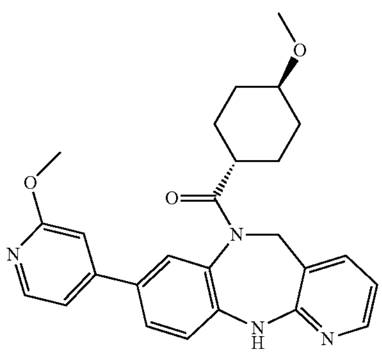 [SMILES: COc1cc(-c2ccc3c(c2)N(C(=O)[C@H]2CC[C@H](OC)CC2)Cc2cccnc2N3)ccn1] | 6-[(trans-4-methoxycyclohexyl)carbonyl]-8-(2-methoxypyridin-4-yl)-6,11-dihydro-5H-pyrido[2,3-b][1,5]benzodiazepine | 445 |
| 405 | 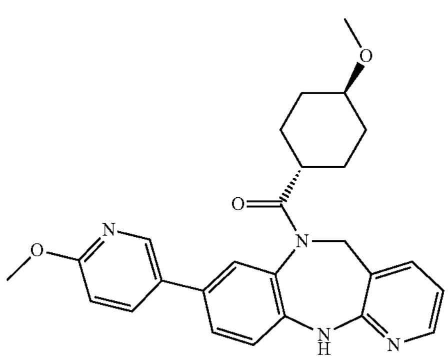 [SMILES: COc1ccc(-c2ccc3c(c2)N(C(=O)[C@H]2CC[C@H](OC)CC2)Cc2cccnc2N3)cn1] | 6-[(trans-4-methoxycyclohexyl)carbonyl]-8-(6-methoxypyridin-3-yl)-6,11-dihydro-5H-pyrido[2,3-b][1,5]benzodiazpine | 445 |

-continued

| Ex. No. | Structure | Chemical Name | [M + H]+ |
|---|---|---|---|
| 406 | 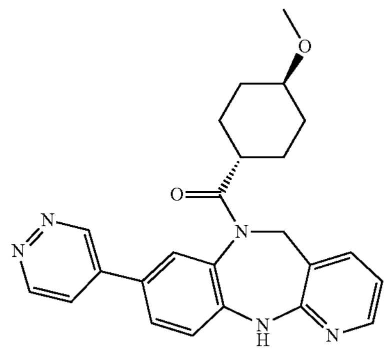 [SMILES: CO[C@H]1CC[C@H](C(=O)N2Cc3cccnc3Nc3ccc(-c4ccnnc4)cc32)CC1] | 6-[(trans-4-methoxycyclohexyl)carbonyl]-8-pyridazin-4-yl-6,11-dihydro-5H-pyrido[2,3-b][1,5]benzodiazepine | 416 |
| 407 | 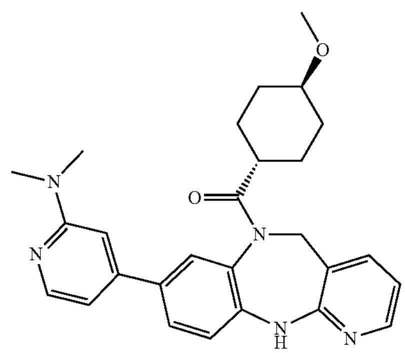 [SMILES: CO[C@H]1CC[C@H](C(=O)N2Cc3cccnc3Nc3ccc(-c4ccnc(N(C)C)c4)cc32)CC1] | 4-{6-[(trans-4-methoxycyclohexyl)carbonyl]-6,11-dihydro-5H-pyrido[2,3-b[1,5]benzodiazepin-8-yl}-N,N-dimethylpyridin-2-amine | 458 |
| 408 | 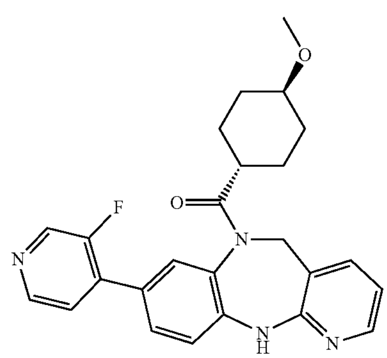 [SMILES: CO[C@H]1CC[C@H](C(=O)N2Cc3cccnc3Nc3ccc(-c4ccncc4F)cc32)CC1] | 8-(3-fluoropyridin-4-yl)-6-[(trans-4-methoxycyclohexyl)carbonyl]-6,11-dihydro-5H-pyrido[2,3-b][1,5]benzodiazepine | 433 |
| 409 | 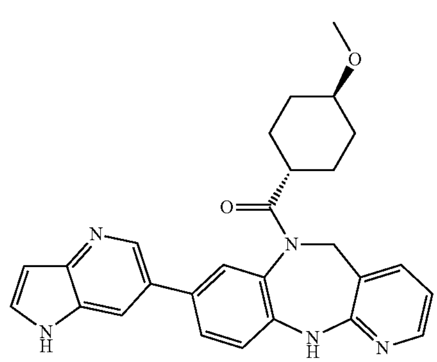 [SMILES: CO[C@H]1CC[C@H](C(=O)N2Cc3cccnc3Nc3ccc(-c4cnc5cc[nH]c5c4)cc32)CC1] | 6-[(trans-4-methoxycyclohexyl)carbonyl]-8-(1H-pyrrolo[3,2-b]pyridin-6-yl)-6,11-dihydro-5H-pyrido[2,3-b][1,5]benzodiazepine | 454 |

| Ex. No. | Structure | Chemical Name | [M + H]+ |
|---|---|---|---|
| 410 | 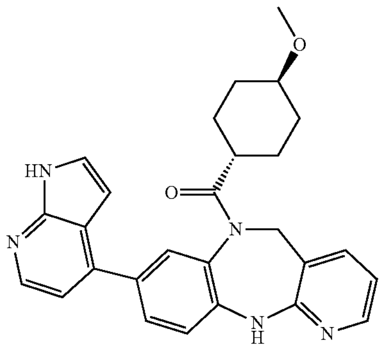 [SMILES: CO[C@H]1CC[C@H](C(=O)N2Cc3cccnc3Nc3ccc(-c4ccnc5[nH]ccc45)cc32)CC1] | 6-[(trans-4-methoxycyclohexyl)carbonyl]-8-(1H-pyrrolo[2,3-b]pyridin-4-yl)-6,11-dihydro-5H-pyrido[2,3-b][1,5]benzodiazepine | 454 |

Example 411: 1-{6-[(Trans-4-methoxycyclohexyl)carbonyl]-6,11-dihydro-5H-pyrido[2,3-b][1,5]benzodiazepin-8-yl}-3-methylazetidine-3-carbonitrile

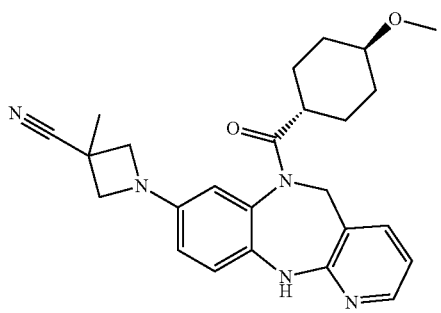 [SMILES: CO[C@H]1CC[C@H](C(=O)N2Cc3cccnc3Nc3ccc(N4CC(C)(C#N)C4)cc32)CC1]

To a microwave vial containing 3-methylazetidine-3-carbonitrile (6.9 mg, 0.072 mmol) was added 2-dicyclohexylphosphino-2',6'-di-isopropoxy-1,1'-biphenyl (1.8 mg, 3.9 µmol), chloro(2-dicyclohexylphosphino-2',6'-di-isopropoxy-1,1'-biphenyl)[2-(2-aminoethylphenyl)]palladium (II), methyl-tert-butylether adduct (3.2 mg, 3.9 µmol), (8-bromo-5,11-dihydro-6H-pyrido[2,3-b][1,5]benzodiazepin-6-yl)(trans-4-methoxycyclohexyl)methanone, HCl (25 mg, 0.055 mmol), sodium tert-butoxide (27 mg, 0.28 mmol), and dioxane (0.5 mL). The mixture was heated to 80° C. for 16 h. The reaction mixture was allowed to cool to room temperature and diluted with 50:50 MeOH:DMSO (1 mL). The mixture was filtered and purified by mass triggered reverse phase HPLC (ACN/water with 0.1% TFA modifier) to afford the title compound as a solid TFA salt. MS: 432 (M+1). $^1$H NMR (500 MHz, DMSO-$d_6$) δ 9.52 (s, 1H), 7.99 (d, J=5.1 Hz, 1H), 7.56 (s, 1H), 7.19 (d, J=8.6 Hz, 1H), 6.77-6.70 (m, 1H), 6.53-6.43 (m, 2H), 5.20 (d, J=15.1 Hz, 1H), 4.14-4.01 (m, 2H), 3.88 (d, J=15.0 Hz, 1H), 3.80-3.68 (m, 2H), 3.13 (s, 3H), 3.00-2.89 (m, 1H), 2.01-1.92 (m, 1H), 1.92-1.82 (m, 1H), 1.82-1.73 (m, 1H), 1.63 (s, 3H), 1.49-1.38 (m, 1H), 1.26-1.18 (m, 2H), 1.08-0.86 (m, 2H), 0.74-0.63 (m, 1H).

The compounds in the following table were prepared using the methodology herein and the general procedure described in Example 411.

| Ex. No. | Structure | Chemical Name | [M + H]+ |
|---|---|---|---|
| 412 | 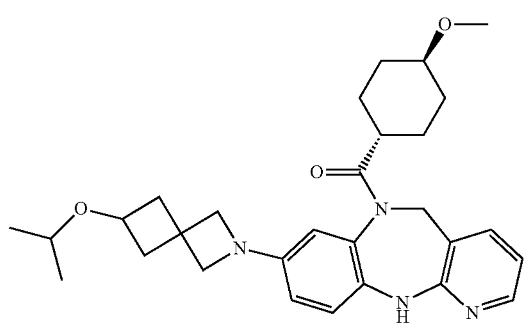 [SMILES: CO[C@H]1CC[C@H](C(=O)N2Cc3cccnc3Nc3ccc(N4CC5(CC(OC(C)C)C5)C4)cc32)CC1] | 6-[(trans-4-methoxycyclohexyl)carbonyl]-8-[6-(1-methylethoxy)-2-azaspiro[3.3]hept-2-yl]-6,11-dihydro-5H-pyrido[2,3-b][1,5]benzodiazepine | 491 |

| Ex. No. | Structure | Chemical Name | [M + H]+ |
| --- | --- | --- | --- |
| 413 | 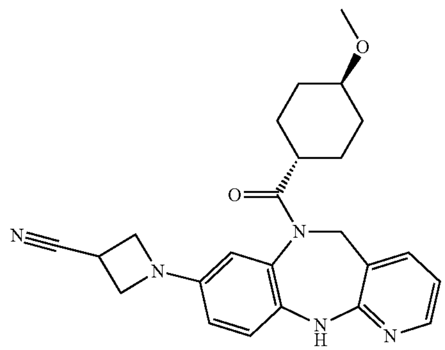 [SMILES: CO[C@H]1CC[C@H](C(=O)N2Cc3cccnc3Nc3ccc(N4CC(C#N)C4)cc32)CC1] | 1-{6-[(trans-4-methoxycyclohexyl)carbonyl]-6,11-dihydro-5H-pyrido[2,3-b][1,5]benzodiazepin-8-yl}azetidine-3-carbonitrile | 418 |
| 414 | 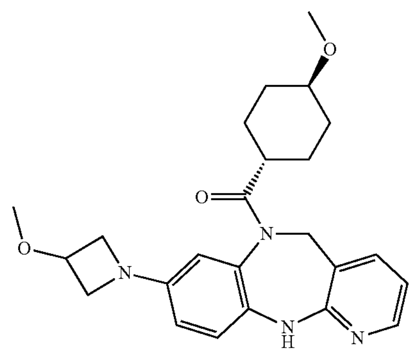 [SMILES: COC1CN(c2ccc3c(c2)N(C(=O)[C@H]2CC[C@H](OC)CC2)Cc2cccnc2N3)C1] | 8-(3-methoxyazetidin-1-yl)-6-[(trans-4-methoxycyclohexyl)carbonyl]-6,11-dihydro-5H-pyrido[2,3-b][1,5]benzodiazepine | 423 |
| 415 | 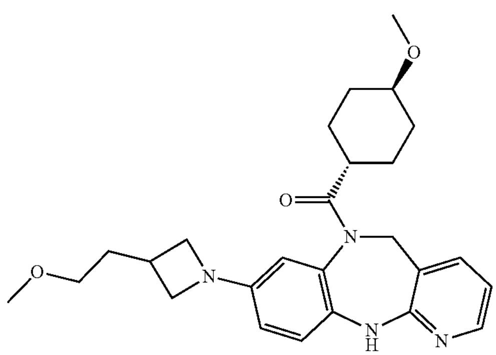 [SMILES: COCCC1CN(c2ccc3c(c2)N(C(=O)[C@H]2CC[C@H](OC)CC2)Cc2cccnc2N3)C1] | 6-[(trans-4-methoxycyclohexyl)carbonyl]-8-[3-(2-methoxyethyl)azetidin-1-yl]-6,11-dihydro-5H-pyrido[2,3-b][1,5]benzodiazepine | 451 |
| 416 | 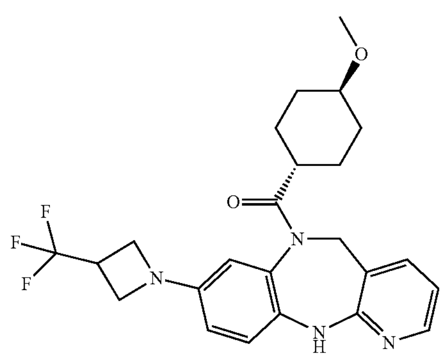 [SMILES: CO[C@H]1CC[C@H](C(=O)N2Cc3cccnc3Nc3ccc(N4CC(C(F)(F)F)C4)cc32)CC1] | 6-[(trans-4-methoxycyclohexyl)carbonyl]-8-[3-(trifluoromethyl)azetidin-1-yl]-6,11-dihydro-5H-pyrido[2,3-b][1,5]benzodiazepine | 461 |

| Ex. No. | Structure | Chemical Name | [M + H]+ |
|---|---|---|---|
| 417 | 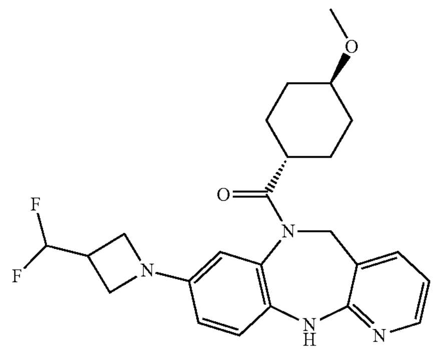 [SMILES: CO[C@H]1CC[C@H](C(=O)N2Cc3cccnc3Nc3ccc(N4CC(C(F)F)C4)cc32)CC1] | 8-[3-(difluoromethyl)azetidin-1-yl]-6-[(trans-4-methoxycyclohexyl)carbonyl]-6,11-dihydro-5H-pyrido[2,3-b][1,5]benzodiazepine | 443 |

Example 418: 6-[(Trans-4-methoxycyclohexyl)carbonyl]-8-(methoxymethyl)-6,11-dihydro-5H-pyrido[2,3-b][1,5]benzodiazepine

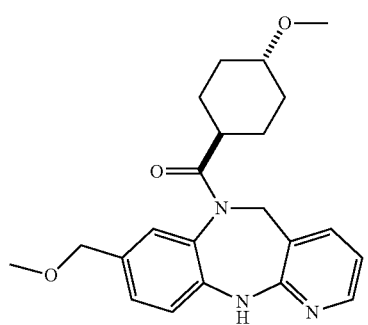

A vial was charged with (8-bromo-5,11-dihydro-6H-pyrido[2,3-b][1,5]benzodiazepin-6-yl)(trans-4-methoxycyclohexyl)methanone (25 mg, 0.060 mmol), potassium trifluoro(methoxymethyl)borate (11 mg, 0.075 mmol), mesylate[(di(1-adamantyl)-n-butylphosphine)-2-(2'-amino-1,1'-biphenyl)]palladium(II), [(di(1-adamantyl)-butylphosphine)-2-(2'-amino-1,1'-biphenyl)]palladium(II) methanesulfonate (4.4 mg, 6.0 μmol) and cesium carbonate (59 mg, 0.18 mmol). The solids were dissolved in 2-methyl-2-butanol (0.5 mL) and water (0.125 mL), the reaction was purged under argon for 5 minutes, and then heated to 70° C. for 18 h. The reaction was then allowed to cool to room temperature and concentrated under reduced pressure. The residue was filtered and purified by mass triggered reverse phase HPLC (ACN/water with 0.1% TFA modifier) to afford the title compound as a solid TFA salt. MS: 382 (M+1). $^1$H NMR (600 MHz, DMSO-$d_6$) δ 9.61 (s, 1H), 8.04-8.00 (m, 1H), 7.51 (d, J=7.1 Hz, 1H), 7.29-7.26 (m, 1H), 7.19-7.16 (m, 2H), 6.76-6.71 (m, 1H), 5.17 (d, J=15.0 Hz, 1H), 4.33 (s, 2H), 3.88 (d, J=14.9 Hz, 1H), 3.20 (s, 3H), 3.09 (s, 3H), 2.95-2.85 (m, 1H), 2.38-2.31 (m, 1H), 1.98-1.90 (m, 1H), 1.84-1.79 (m, 1H), 1.76-1.70 (m, 1H), 1.48-1.37 (m, 1H), 1.17-1.08 (m, 1H), 0.99-0.90 (m, 1H), 0.86-0.76 (m, 1H), 0.62-0.51 (m, 1H).

The compounds in the following table were prepared using the methodology herein and the general procedure described in Example 418.

| Ex. No. | Structure | Chemical Name | [M + H]+ |
|---|---|---|---|
| 419 | Isomer 1 | 6-[(4-methoxycyclohexyl)carbonyl]-8-(2-pyridin-2-ylethyl)-6,11-dihydro-5H-pyrido[2,3-b][1,5]benzodiazepine | 443 |

-continued

| Ex. No. | Structure | Chemical Name | [M + H]+ |
|---|---|---|---|
| 420 | Isomer 1 | 6-[(4-methoxycyclohexyl)carbonyl]-8-[(3S)-tetrahydrofuran-3-ylmethyl]-6,11-dihydro-5H-pyrido[2,3-b][1,5]benzodiazepine | 422 |
| 421 | Isomer 1 | 6-[(4-methoxycyclohexyl)carbonyl]-8-(3-morpholin-4-yl-3-oxopropyl)-6,11-dihydro-5H-pyrido[2,3-b][1,5]benzodiazepine | 479 |
| 422 | Isomer 1 | 8-(3,3-dimethylbutyl)-6-[(4-methoxycyclohexyl)carbonyl]-6,11-dihydro-5H-pyrido[2,3-b][1,5]benzodiazepine | 422 |
| 423 | 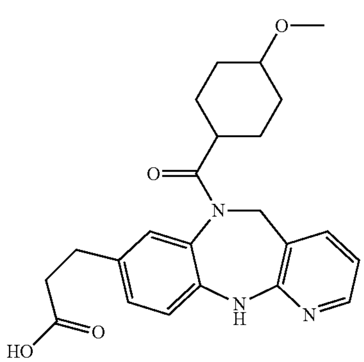 [SMILES: COC1CCC(C(=O)N2Cc3cccnc3Nc3ccc(CCC(=O)O)cc32)CC1] | 3-{6-[(4-methoxycyclohexyl)carbonyl]-6,11-dihydro-5H-pyrido[2,3-b][1,5]benzodiazepin-8-yl}propanoic acid | 410 |

| Ex. No. | Structure | Chemical Name | [M + H]+ |
| --- | --- | --- | --- |
| 424 | 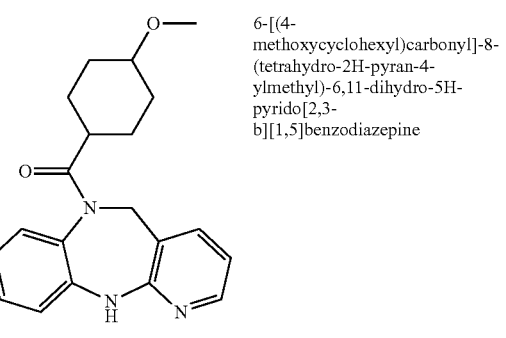
Isomer 1 | 6-[(4-methoxycyclohexyl)carbonyl]-8-(tetrahydro-2H-pyran-4-ylmethyl)-6,11-dihydro-5H-pyrido[2,3-b][1,5]benzodiazepine | 436 |
| 425 | 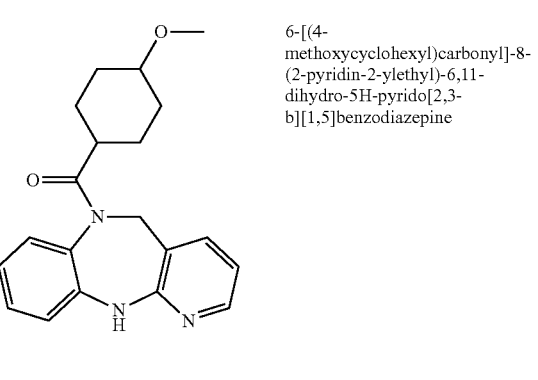
Isomer 2 | 6-[(4-methoxycyclohexyl)carbonyl]-8-(2-pyridin-2-ylethyl)-6,11-dihydro-5H-pyrido[2,3-b][1,5]benzodiazepine | 443 |
| 426 | 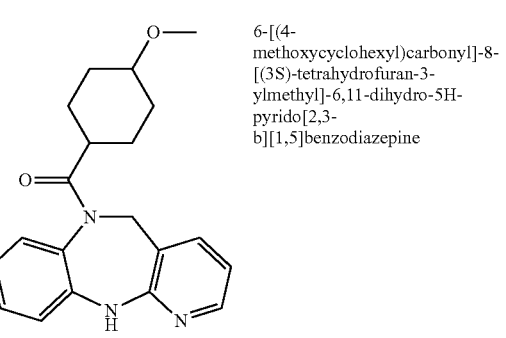
Isomer 2 | 6-[(4-methoxycyclohexyl)carbonyl]-8-[(3S)-tetrahydrofuran-3-ylmethyl]-6,11-dihydro-5H-pyrido[2,3-b][1,5]benzodiazepine | 422 |

-continued
| Ex. No. | Structure | Chemical Name | [M + H]+ |
|---|---|---|---|
| 427 | 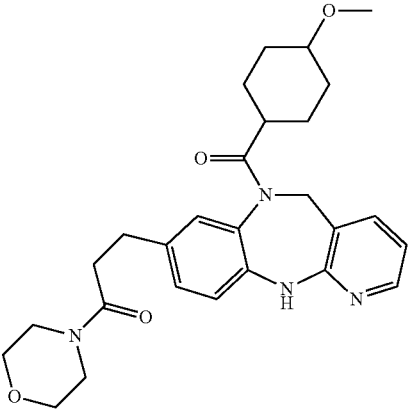<br>Isomer 2 | 6-[(4-methoxycyclohexyl)carbonyl]-8-(3-morpholin-4-yl-3-oxopropyl)-6,11-dihydro-5H-pyrido[2,3-b][1,5]benzodiazepine | 479 |
| 428 | 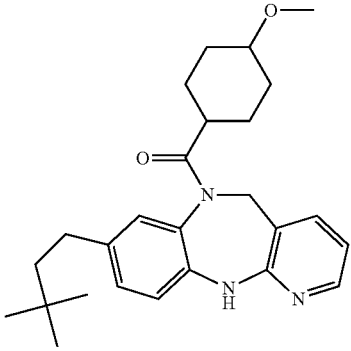<br>Isomer 2 | 8-(3,3-dimethylbutyl)-6-[(4-methoxycyclohexyl)carbonyl]-6,11-dihydro-5H-pyrido[2,3-b][1,5]benzodiazepine | 422 |
| 429 | 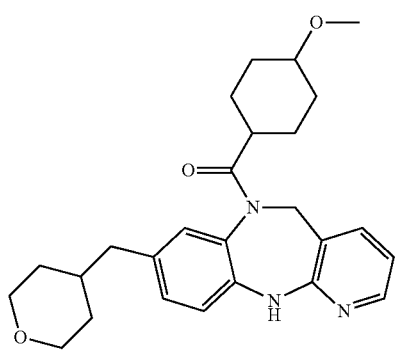<br>Isomer 2 | 6-[(4-methoxycyclohexyl)carbonyl]-8-(tetrahydro-2H-pyran-4-ylmethyl)-6,11-dihydro-5H-pyrido[2,3-b][1,5]benzodiazepine | 436 |

Example 430: (Trans-4-methoxycyclohexyl)[8-(methylsulfonyl)-5,11-dihydro-6H-pyrido[2,3-b][1,5]benzodiazepin-6-yl]methanone

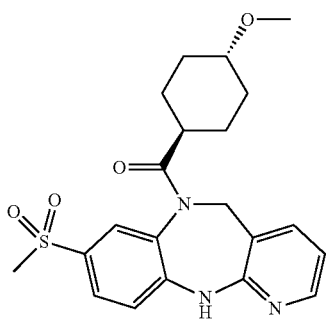 [SMILES: CO[C@H]1CC[C@H](C(=O)N2Cc3cccnc3Nc3ccc(S(C)(=O)=O)cc32)CC1]

To a vial containing (8-bromo-5,11-dihydro-6H-pyrido[2,3-b][1,5]benzodiazepin-6-yl)(trans-4-methoxycyclohexyl)methanone (20 mg, 0.048 mmol) and sodium methanesulfinate (7.3 mg, 0.072 mmol) was added (R)-pyrrolidine-2-carboxylic acid (11 mg, 0.096 mmol), copper(I) iodide (14 mg, 0.072 mmol), and anhydrous DMSO (0.5 mL). The resulting reaction mixture was purged with $N_2$ for 5 minutes and then heated to 120° C. for 16 h. The reaction was allowed to cool to room temperature and then quenched with water (0.5 mL). The resulting mixture was diluted with aqueous ammonium hydroxide (2N, 2 mL) and washed with ethyl acetate (2×4 mL). The combined organic layers were dried over sodium sulfate, filtered, and concentrated under reduced pressure. The residue was purified by reverse phase HPLC (ACN/water with 0.1% TFA modifier) to afford the title compound as a solid TFA salt. MS: 416 (M+1). $^1$H NMR (500 MHz, DMSO-$d_6$) δ: 10.05 (s, 1H), 8.12 (d, J=4.9 Hz, 1H), 7.79 (d, J=2.3 Hz, 1H), 7.72 (dd, J=8.8, 2.1 Hz, 1H), 7.56 (d, J=7.5 Hz, 1H), 7.51 (d, J=8.8 Hz, 1H), 6.84 (dd, J=7.4, 4.8 Hz, 1H) 5.20 (d, J=14.8 Hz, 1H), 3.97 (d, J=14.8 Hz, 1H), 3.20 (s, 3H), 3.13 (s, 3H), 2.96-2.92 (m, 1H), 2.36-2.31 (m, 1H), 2.00-1.95 (m, 2H), 1.93-1.86 (m, 1H), 1.77-1.73 (m, 1H), 1.50-1.41 (m, 1H), 1.11-1.08 (m, 1H), 0.96-0.91 (m, 1H), 0.65-0.63 (m, 1H).

The compounds in the following table were prepared using the methodology herein and the general procedure described in Example 430.

| Ex. No. | Structure | Chemical Name | [M + H]+ |
| --- | --- | --- | --- |
| 431 | | 8-(ethylsulfonyl)-6-[(trans-4-methoxycyclohexyl)carbonyl]-6,11-dihydro-5H-pyrido[2,3-b][1,5]benzodiazepine | 430 |
| 432 | | 8-[(4-fluorophenyl)sulfonyl]-6-[(trans-4-methoxycyclohexyl)carbonyl]-6,11-dihydro-5H-pyrido[2,3-b][1,5]benzodiazepine | 496 |
| 433 | | 8-(cyclopropylsulfonyl)-6-[(trans-4-methoxycyclohexyl)carbonyl]-6,11-dihydro-5H-pyrido[2,3-b][1,5]benzodiazepine | 442 |

Example 434: 6-[(Trans-4-methoxycyclohexyl)carbonyl]-6,11-dihydro-5H-pyrido[2,3-b][1,5]benzodiazepine-8-carbonitrile

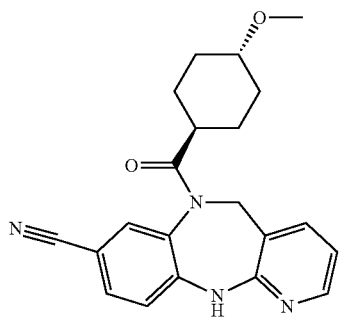 [SMILES: CO[C@H]1CC[C@H](C(=O)N2Cc3cccnc3Nc3ccc(C#N)cc32)CC1]

To a vial containing (8-bromo-5,11-dihydro-6H-pyrido[2,3-b][1,5]benzodiazepin-6-yl)(trans-4-methoxycyclohexyl)methanone (20 mg, 0.048 mmol) and dicyanozinc (5.6 mg, 0.048 mmol) was added tetrakis(triphenylphosphine)Palladium(0) (5.6 mg, 4.8 μmol) and anhydrous DMF (0.5 mL). The resulting reaction mixture was purged with $N_2$ for 5 minutes and then heated to 85° C. for 16 h. The reaction was allowed to cool to room temperature and quenched with water (2 mL). The resulting mixture was washed with ethyl acetate (2×4 mL). The combined organic layers were dried over sodium sulfate, filtered and concentrated under reduced pressure. The residue was purified by reverse phase HPLC (ACN/water with 0.1% TFA modifier) to afford the title compound as the TFA salt. MS: 363 (M+1). $^1$H NMR (500 MHz, DMSO-$d_6$) δ: 10.04 (s, 1H), 8.11 (dd, J=4.9, 1.9 Hz, 1H), 7.85 (d, J=2.0 Hz, 1H), 7.65 (dd, J=8.6, 1.9 Hz, 1H), 7.55 (d, J=7.5 Hz, 1H), 7.45 (d, J=8.5 Hz, 1H), 6.84 (dd, J=7.4 Hz, 4.8, 1H), 5.16 (d, J=14.9 Hz, 1H), 3.94 (d, J=14.8 Hz, 1H), 3.13 (s, 3H), 2.95-2.90 (m, 1H), 2.37-2.32 (m, 1H), 1.98-1.90 (m, 1H), 1.89-1.80 (m, 1H), 1.78-1.70 (m, 1H), 1.50-1.30 (m, 1H), 1.14-1.05 (m, 1H), 0.99-0.90 (m, 1H), 0.89-0.80 (m, 1H), 0.70-0.60 (m, 1H).

Example 435: 2-Methyl-2-[6-({trans-4-[(2,2,2-trifluoroethyl)amino]cyclohexyl}carbonyl)-6,11-dihydro-5H-pyrido[2,3-b][1,5]benzodiazepin-8-yl]propanenitrile

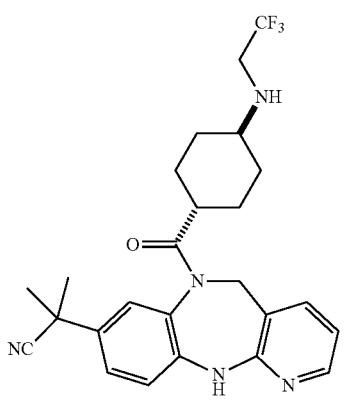

Step 1:

To a vial equipped with a stir bar was added ethyl 4-oxocyclohexanecarboxylate (500 mg, 2.94 mmol), sodium hydroxide (587 mg, 14.7 mmol), and ethanol (12 mL). The reaction was stirred at room temperature for 2 h. The mixture was quenched via the dropwise addition of aqueous HCl (4N) to pH~1-3. The mixture was extracted with ethyl acetate, and the organic layer was washed with brine and dried over sodium sulfate, filtered, and concentrated under reduced pressure to afford 4-oxocyclohexanecarboxylic acid as an oil that was used without further characterization.

Step 2:

To a vial was added 2-(6,11-dihydro-5H-benzo[b]pyrido[2,3-e][1,4]diazepin-8-yl)-2-methylpropanenitrile (80 mg, 0.30 mmol) and PS-PPh$_3$ (2.06 mmol/g loading, 441 mg, 0.908 mmol). A mixture of 4-oxocyclohexanecarboxylic acid (52 mg, 0.36 mmol) in acetonitrile (2 mL) was added followed by trichloroacetonitrile (152 μL, 1.51 mmol). The vial was heated to 100° C. for 10 minutes in a microwave reactor. The reaction mixture was allowed to cool to room temperature, dissolved in MeOH (3 mL), and stirred for 10 minutes. The mixture was filtered and concentrated under reduced pressure. The residue was diluted with ethyl acetate and washed with saturated sodium bicarbonate and then brine. The combined organic layers were dried over magnesium sulfate, filtered, and concentrated under reduced pressure. The residue was purified by column chromatography on silica gel (0-100% EtOAc/hexanes) to afford 2-methyl-2-{6-[(4-oxocyclohexyl)carbonyl]-6,11-dihydro-5H-pyrido[2,3-b][1,5]benzodiazepin-8-yl}propanenitrile as a solid. MS: 389 (M+1).

Step 3:

To a vial equipped with a stir bar was added 2-methyl-2-{6-[(4-oxocyclohexyl)carbonyl]-6,11-dihydro-5H-pyrido[2,3-b][1,5]benzodiazepin-8-yl}propanenitrile (118 mg, 0.304 mmol), 2,2,2-trifluoroethanamine (24 μL, 0.30 mmol), and DCE (1.5 mL). Acetic acid (35 μL, 0.61 mmol) was added, followed by the slow addition of sodium triacetoxyborohydride (103 mg, 0.486 mmol). The reaction was stirred at room temperature for 2.5 h. The crude mixture was diluted with ethyl acetate and washed with saturated sodium bicarbonate and then brine. The organic layer was dried over magnesium sulfate, filtered, and concentrated under reduced pressure. The residue was purified by mass triggered reverse phase HPLC (ACN/water with 0.1% TFA modifier) to afford the title compound as a solid TFA salt. MS: 472 (M+1). $^1$H NMR (600 MHz, DMSO-$d_6$) δ 9.72 (s, 1H), 9.26 (s, 1H), 8.07 (d, J=5.0 Hz, 1H), 7.54 (d, J=7.2 Hz, 1H), 7.45 (s, 1H), 7.38 (s, 2H), 6.81-6.74 (m, 1H), 5.26 (d, J=15.0 Hz, 1H), 4.06-3.87 (m, 3H), 3.08-2.92 (m, 1H), 2.82-2.72 (m, 1H), 2.08-1.93 (m, 2H), 1.77-1.59 (m, 7H), 1.54-1.40 (m, 2H), 1.39-1.18 (m, 2H), 1.13-0.99 (m, 1H).

The compounds in the following table were prepared using the methodology herein and the general procedure described in Example 435.

| Ex. No. | Structure | Chemical Name | [M + H]+ |
|---|---|---|---|
| 436 | 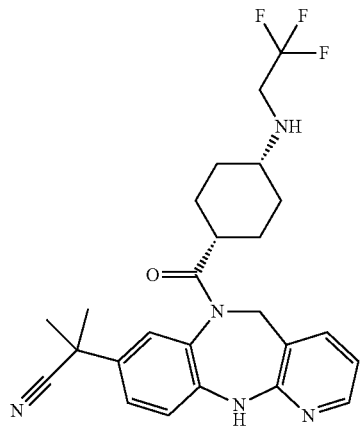 [SMILES: CC(C)(C#N)c1ccc2c(c1)N(C(=O)[C@H]1CC[C@@H](NCC(F)(F)F)CC1)Cc1cccnc1N2] | 2-methyl-2-[6-({cis-4-[(2,2,2-trifluoroethyl)amino]cyclohexyl}carbonyl)-6,11-dihydro-5H-pyrido[2,3-b][1,5]benzodiazepin-8-yl]propanenitrile | 472 |
| 437 | 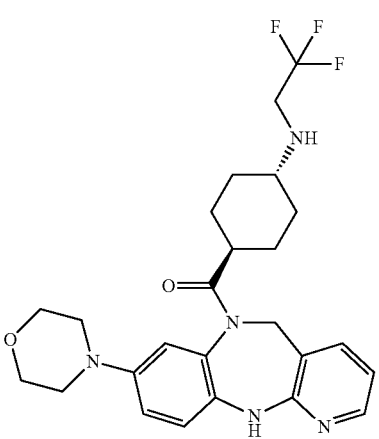 [SMILES: O=C([C@H]1CC[C@H](NCC(F)(F)F)CC1)N1Cc2cccnc2Nc2ccc(N3CCOCC3)cc21] | trans-4-[(8-morpholin-4-yl-5,11-dihydro-6H-pyrido[2,3-b][1,5]benzodiazepin-6-yl)carbonyl]-N-(2,2,2-trifluoroethyl)cyclohexanamine | 490 |
| 438 | 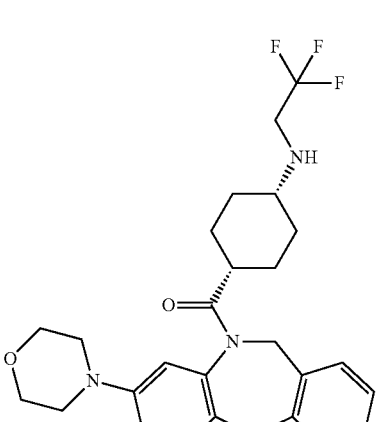 | cis-4-[(8-morpholin-4-yl-5,11-dihydro-6H-pyrido[2,3-b][1,5]benzodiazepin-6-yl)carbonyl]-N-(2,2,2-trifluoroethyl)cyclohexanamine | 490 |

| Ex. No. | Structure | Chemical Name | [M + H]+ |
|---------|-----------|---------------|----------|
| 439 | 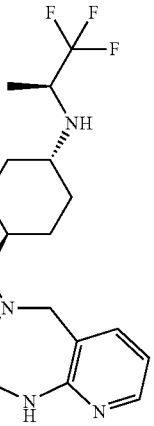 | trans-4-[(8-morpholin-4-yl-5,11-dihydro-6H-pyrido[2,3-b][1,5]benzodiazepin-6-yl)carbonyl]-N-[(1S)-2,2,2-trifluoro-1-methylethyl]cyclohexanamine | 504 |
| 440 | 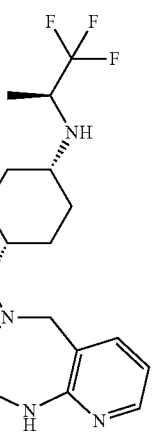 | cis-4-[(8-morpholin-4-yl-5,11-dihydro-6H-pyrido[2,3-b][1,5]benzodiazepin-6-yl)carbonyl]-N-[(1S)-2,2,2-trifluoro-1-methylethyl]cyclohexanamine | 504 |
| 441 | 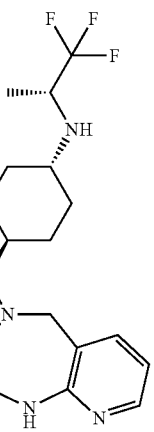 | trans-4-[(8-morpholin-4-yl-5,11-dihydro-6H-pyrido[2,3-b][1,5]benzodiazepin-6-yl)carbonyl]-N-[(1R)-2,2,2-trifluoro-1-methylethyl]cyclohexanamine | 504 |

-continued

| Ex. No. | Structure | Chemical Name | [M + H]+ |
|---|---|---|---|
| 442 | 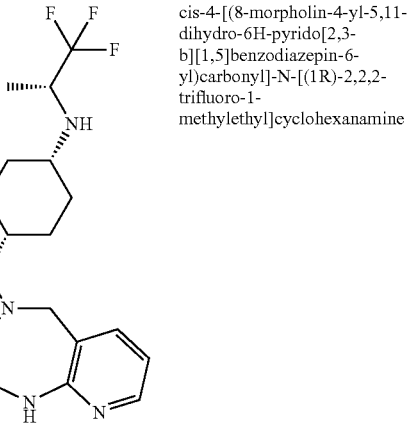 | cis-4-[(8-morpholin-4-yl-5,11-dihydro-6H-pyrido[2,3-b][1,5]benzodiazepin-6-yl)carbonyl]-N-[(1R)-2,2,2-trifluoro-1-methylethyl]cyclohexanamine | 504 |
| 443 | 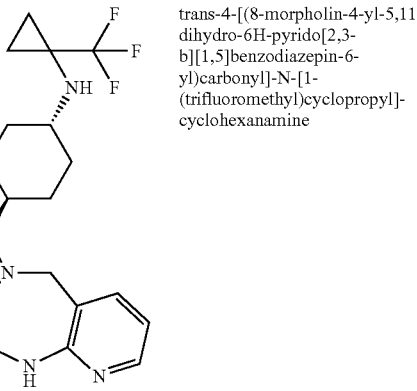 | trans-4-[(8-morpholin-4-yl-5,11-dihydro-6H-pyrido[2,3-b][1,5]benzodiazepin-6-yl)carbonyl]-N-[1-(trifluoromethyl)cyclopropyl]-cyclohexanamine | 516 |
| 444 | 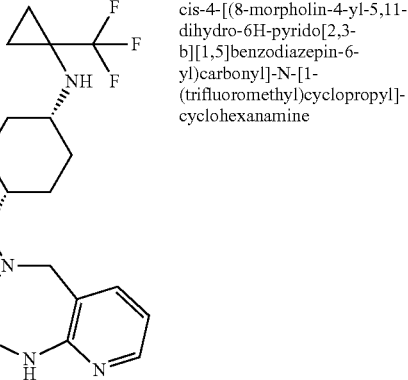 | cis-4-[(8-morpholin-4-yl-5,11-dihydro-6H-pyrido[2,3-b][1,5]benzodiazepin-6-yl)carbonyl]-N-[1-(trifluoromethyl)cyclopropyl]-cyclohexanamine | 516 |

| Ex. No. | Structure | Chemical Name | [M + H]+ |
|---|---|---|---|
| 445 | 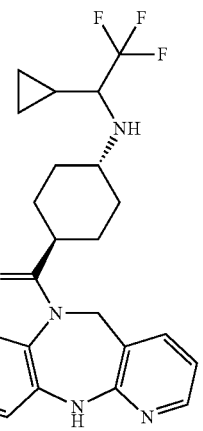 | trans-N-[1-cyclopropyl-2,2,2-trifluoroethyl]-4-[(8-morpholin-4-yl-5,11-dihydro-6H-pyrido[2,3-b][1,5]benzodiazepin-6-yl)carbonyl]cyclohexanamine | 530 |
| 446 | 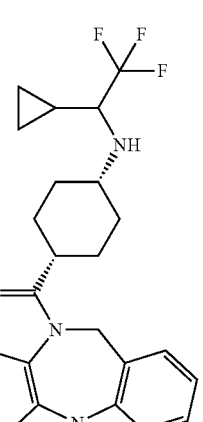 | cis-N-[1-cyclopropyl-2,2,2-trifluormoethyl]-4-[(8-morpholin-4-yl-5,11-dihydro-6H-pyrido[2,3-b][1,5]benzodiazepin-6-yl)carbonyl]cyclohexanamine | 530 |
| 447 | 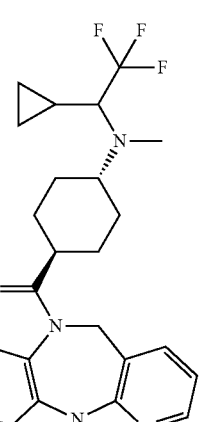 | trans-N-[1-cyclopropyl-2,2,2-trifluoroethyl]-N-methyl-4-[(8-morpholin-4-yl-5,11-dihydro-6H-pyrido[2,3-b][1,5]benzodiazepin-6-yl)carbonyl]cyclohexanamine | 544 |

-continued

| Ex. No. | Structure | Chemical Name | [M + H]+ |
|---|---|---|---|
| 448 | 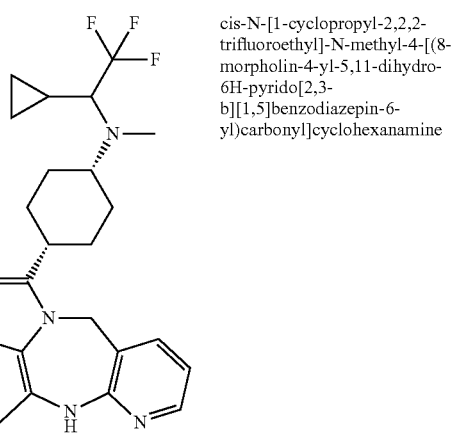 | cis-N-[1-cyclopropyl-2,2,2-trifluoroethyl]-N-methyl-4-[(8-morpholin-4-yl-5,11-dihydro-6H-pyrido[2,3-b][1,5]benzodiazepin-6-yl)carbonyl]cyclohexanamine | 544 |
| 449 | 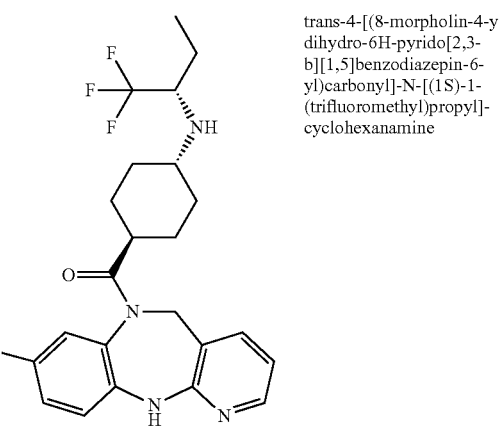 | trans-4-[(8-morpholin-4-yl-5,11-dihydro-6H-pyrido[2,3-b][1,5]benzodiazepin-6-yl)carbonyl]-N-[(1S)-1-(trifluoromethyl)propyl]-cyclohexanamine | 518 |
| 450 | 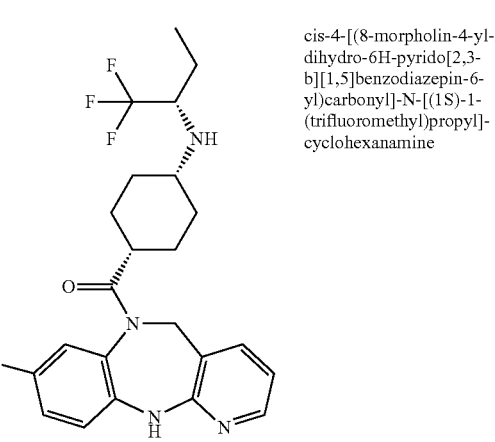 | cis-4-[(8-morpholin-4-yl-5,11-dihydro-6H-pyrido[2,3-b][1,5]benzodiazepin-6-yl)carbonyl]-N-[(1S)-1-(trifluoromethyl)propyl]-cyclohexanamine | 518 |

| Ex. No. | Structure | Chemical Name | [M + H]+ |
|---|---|---|---|
| 451 | 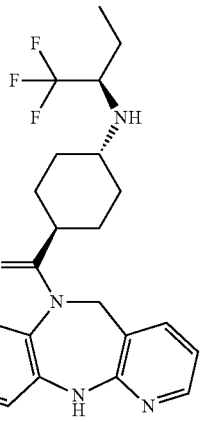 | trans-4-[(8-morpholin-4-yl-5,11-dihydro-6H-pyrido[2,3-b][1,5]benzodiazepin-6-yl)carbonyl]-N-[(1R)-1-(trifluoromethyl)propyl]-cyclohexanamine | 518 |
| 452 | 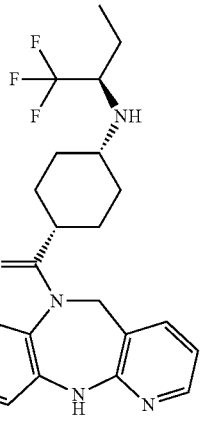 | cis-4-[(8-morpholin-4-yl-5,11-dihydro-6H-pyrido[2,3-b][1,5]benzodiazepin-6-yl)carbonyl]-N-[(1R)-1-(trifluoromethyl)propyl]-cyclohexanamine | 518 |
| 453 | 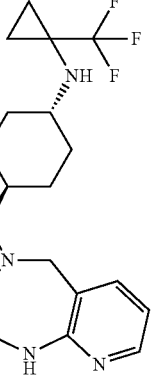 | trans-4-[(8-morpholin-4-yl-5,11-dihydro-6H-pyrido[2,3-b][1,5]benzodiazepin-6-yl)carbonyl]-N-[1-(trifluoromethyl)cyclopropyl]-cyclohexanamine | 516 |

| Ex. No. | Structure | Chemical Name | [M + H]+ |
|---|---|---|---|
| 454 | 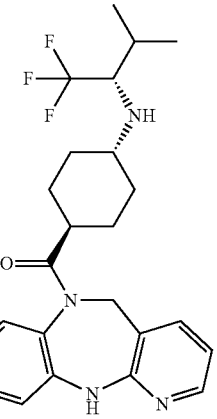 | trans-N-[(1S)-2-methyl-1-(trifluoromethyl)propyl]-4-[(8-morpholin-4-yl-5,11-dihydro-6H-pyrido[2,3-b][1,5]benzodiazepin-6-yl)carbonyl]cyclohexanamine | 532 |
| 455 | 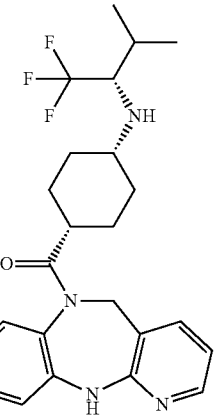 | cis-N-[(1S)-2-methyl-1-(trifluoromethyl)propyl]-4-[(8-morpholin-4-yl-5,11-dihydro-6H-pyrido[2,3-b][1,5]benzodiazepin-6-yl)carbonyl]cyclohexanamine | 532 |
| 456 | 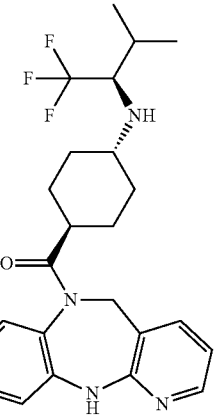 | trans-N-[(1R)-2-methyl-1-(trifluoromethyl)propyl]-4-[(8-morpholin-4-yl-5,11-dihydro-6H-pyrido[2,3-b][1,5]benzodiazepin-6-yl)carbonyl]cyclohexanamine | 532 |

| Ex. No. | Structure | Chemical Name | [M + H]+ |
|---|---|---|---|
| 457 | 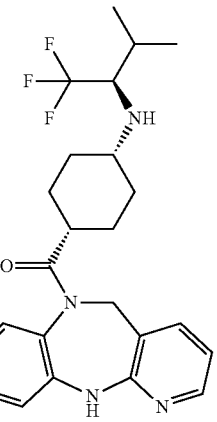 | cis-N-[(1R)-2-methyl-1-(trifluoromethyl)propyl]-4-[(8-morpholin-4-yl-5,11-dihydro-6H-pyrido[2,3-b][1,5]benzodiazepin-6-yl)carbonyl]cyclohexanamine | 532 |
| 458 | 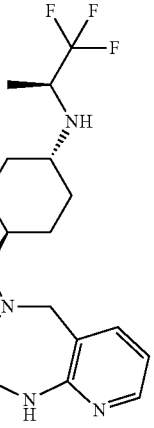 | trans-4-[(8-morpholin-4-yl-5,11-dihydro-6H-pyrido[2,3-b][1,5]benzodiazepin-6-yl)carbonyl]-N-[(1S)-2,2,2-trifluoro-1-methylethyl]cyclohexanamine | 504 |
| 459 | 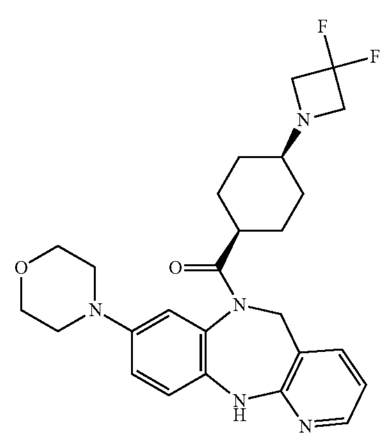 [SMILES: O=C([C@H]1CC[C@@H](N2CC(F)(F)C2)CC1)N1Cc2cccnc2Nc2ccc(C3CCOCC3)cc21] | 6-{(cis-4-(3,3-difluoroazetidin-1-yl)cyclohexyl]carbonyl}-8-morpholin-4-yl-6,11-dihydro-5H-pyrido[2,3-b][1,5]benzodiazepine | 484 |

-continued

| Ex. No. | Structure | Chemical Name | [M + H]+ |
|---|---|---|---|
| 460 | 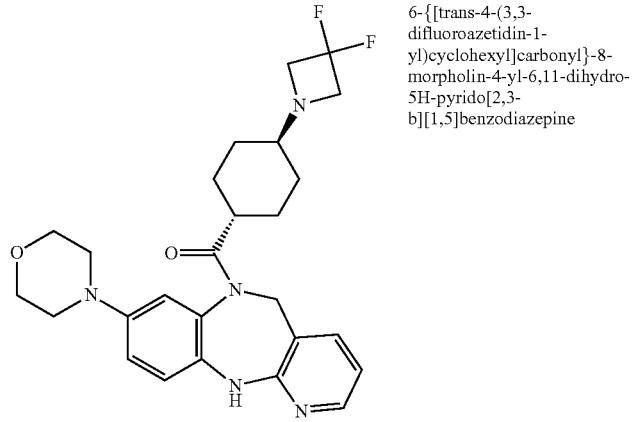 | 6-{[trans-4-(3,3-difluoroazetidin-1-yl)cyclohexyl]carbonyl}-8-morpholin-4-yl-6,11-dihydro-5H-pyrido[2,3-b][1,5]benzodiazepine | 484 |
| 461 | 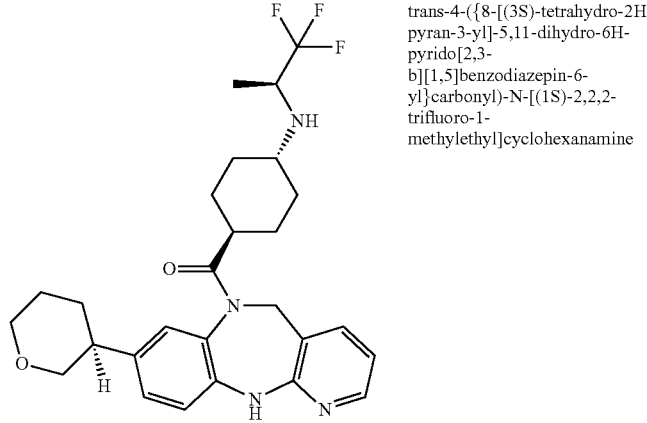 Isomer 1 | trans-4-({8-[(3S)-tetrahydro-2H-pyran-3-yl]-5,11-dihydro-6H-pyrido[2,3-b][1,5]benzodiazepin-6-yl}carbonyl)-N-[(1S)-2,2,2-trifluoro-1-methylethyl]cyclohexanamine | 503 |
| 462 | 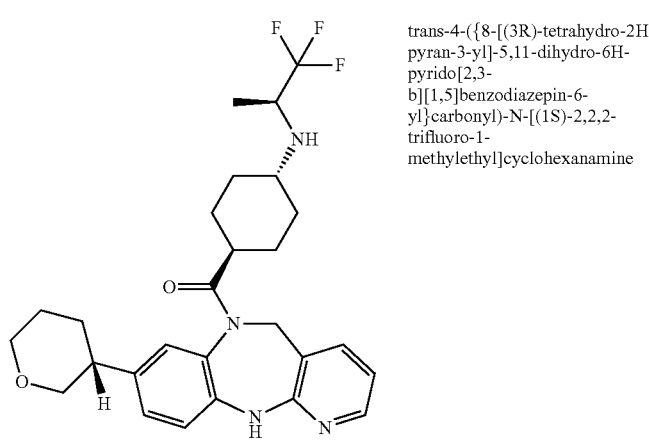 Isomer 2 | trans-4-({8-[(3R)-tetrahydro-2H-pyran-3-yl]-5,11-dihydro-6H-pyrido[2,3-b][1,5]benzodiazepin-6-yl}carbonyl)-N-[(1S)-2,2,2-trifluoro-1-methylethyl]cyclohexanamine | 503 |

-continued

| Ex. No. | Structure | Chemical Name | [M + H]+ |
|---|---|---|---|
| 463 | 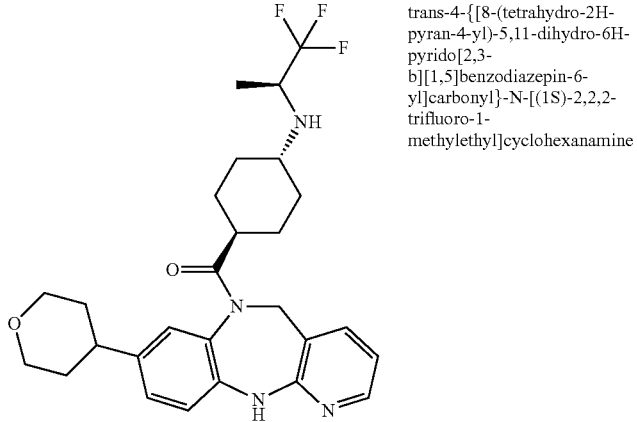 | trans-4-{[8-(tetrahydro-2H-pyran-4-yl)-5,11-dihydro-6H-pyrido[2,3-b][1,5]benzodiazepin-6-yl]carbonyl}-N-[(1S)-2,2,2-trifluoro-1-methylethyl]cyclohexanamine | 503 |
| 464 | 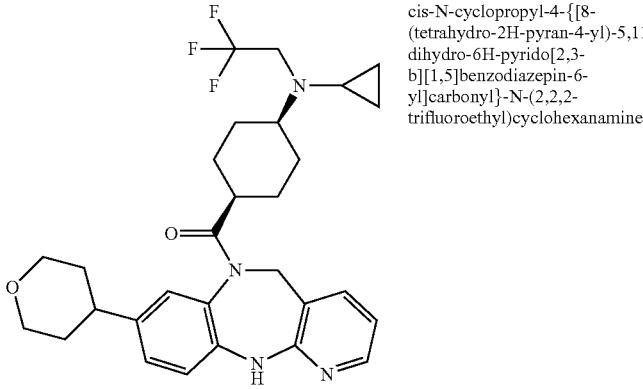 | cis-N-cyclopropyl-4-{[8-(tetrahydro-2H-pyran-4-yl)-5,11-dihydro-6H-pyrido[2,3-b][1,5]benzodiazepin-6-yl]carbonyl}-N-(2,2,2-trifluoroethyl)cyclohexanamine | 529 |
| 465 | 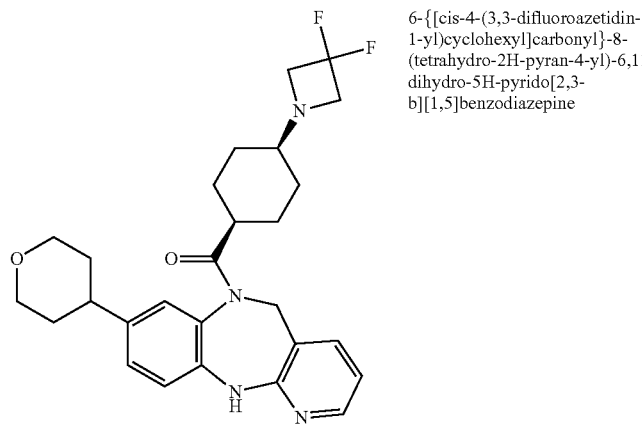 | 6-{[cis-4-(3,3-difluoroazetidin-1-yl)cyclohexyl]carbonyl}-8-(tetrahydro-2H-pyran-4-yl)-6,11-dihydro-5H-pyrido[2,3-b][1,5]benzodiazepine | 483 |

-continued

| Ex. No. | Structure | Chemical Name | [M + H]+ |
|---|---|---|---|
| 466 | 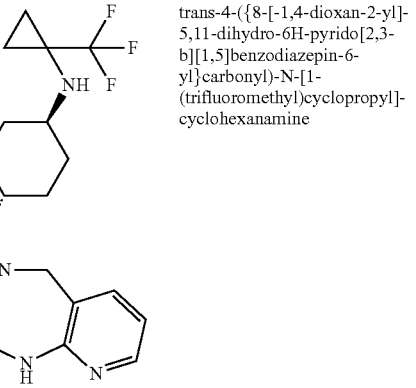 Isomer 1 | trans-4-({8-[-1,4-dioxan-2-yl]-5,11-dihydro-6H-pyrido[2,3-b][1,5]benzodiazepin-6-yl}carbonyl)-N-[1-(trifluoromethyl)cyclopropyl]-cyclohexanamine | 517 |
| 467 | 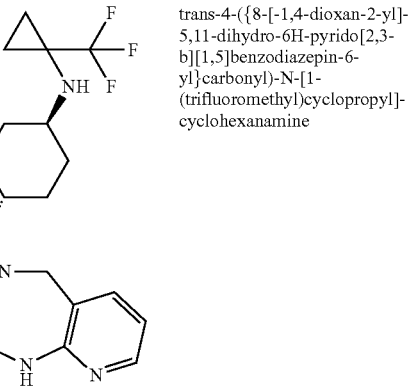 Isomer 2 | trans-4-({8-[-1,4-dioxan-2-yl]-5,11-dihydro-6H-pyrido[2,3-b][1,5]benzodiazepin-6-yl}carbonyl)-N-[1-(trifluoromethyl)cyclopropyl]-cyclohexanamine | 517 |
| 468 | 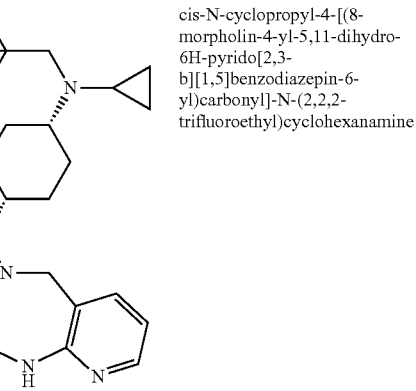 | cis-N-cyclopropyl-4-[(8-morpholin-4-yl-5,11-dihydro-6H-pyrido[2,3-b][1,5]benzodiazepin-6-yl)carbonyl]-N-(2,2,2-trifluoroethyl)cyclohexanamine | 530 |

| Ex. No. | Structure | Chemical Name | [M + H]+ |
|---|---|---|---|
| 469 | 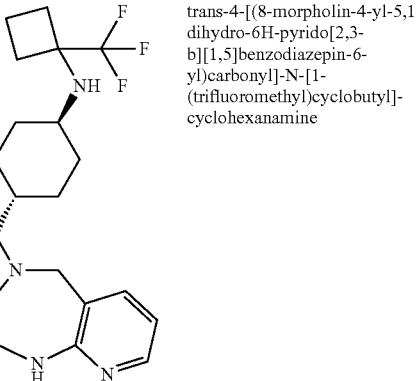 | trans-4-[(8-morpholin-4-yl-5,11-dihydro-6H-pyrido[2,3-b][1,5]benzodiazepin-6-yl)carbonyl]-N-[1-(trifluoromethyl)cyclobutyl]-cyclohexanamine | 530 |
| 470 | 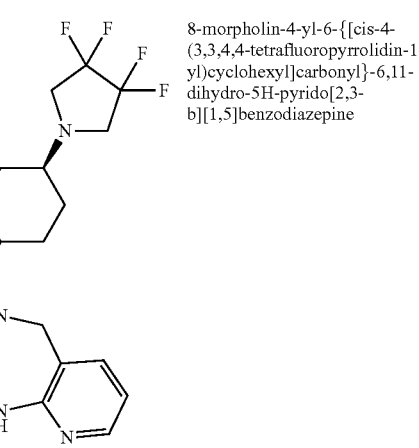 | 8-morpholin-4-yl-6-{[cis-4-(3,3,4,4-tetrafluoropyrrolidin-1-yl)cyclohexyl]carbonyl}-6,11-dihydro-5H-pyrido[2,3-b][1,5]benzodiazepine | 534 |
| 471 | 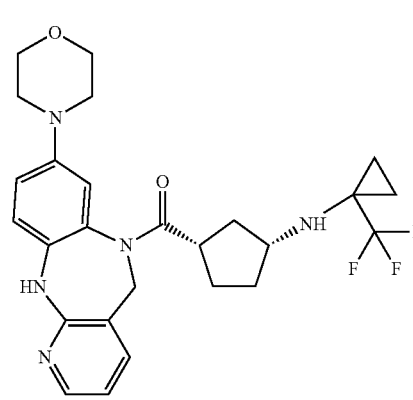

Isomer 1 | (1R,3S)-3-[(8-morpholin-4-yl-5,11-dihydro-6H-pyrido[2,3-b][1,5]benzodiazepin-6-yl)carbonyl]-N-[1-(trifluoromethyl)cyclopropyl]-cyclopentanamine | 502 |

| Ex. No. | Structure | Chemical Name | [M + H]+ |
|---|---|---|---|
| 472 | 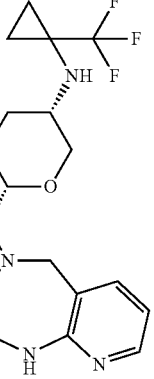  Isomer 1 | (8-morpholino-5,11-dihydro-6H-benzo[b]pyrido[2,3-e][1,4]diazepin-6-yl)((2S,5S)-5-((1-(trifluoromethyl)cyclopropyl)amino)tetrahydro-2H-pyran-2-yl)methanone | 518 |
| 473 | 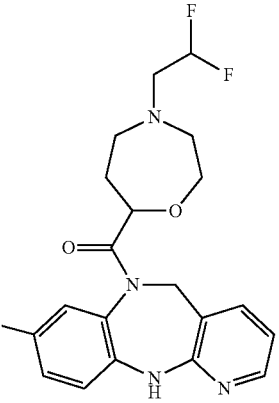 | 6-{[4-(2,2-difluoroethyl)-1,4-oxazepan-7-yl]carbonyl}-8-morpholin-4-yl-6,11-dihydro-5H-pyrido[2,3-b][1,5]benzodiazepine | 474 |
| 474 | 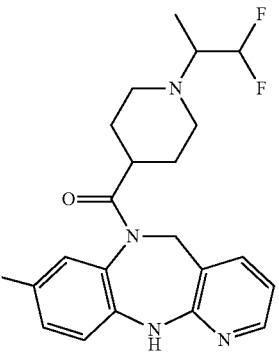  Single enantiomer | 6-{[1-(2,2-difluoro-1-methylethyl)piperidin-4-yl]carbonyl}-8-morpholin-4-yl-6,11-dihydro-5H-pyrido[2,3-b][1,5]benzodiazepine | 472 |

-continued

| Ex. No. | Structure | Chemical Name | [M + H]+ |
|---|---|---|---|
| 475 | 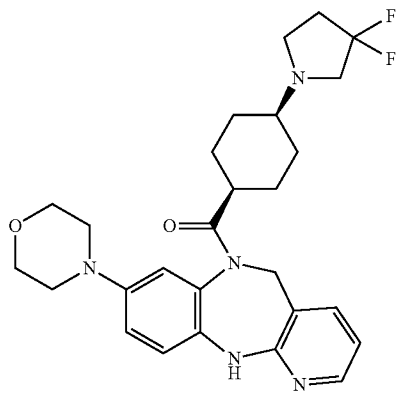 [SMILES: O=C([C@H]1CC[C@@H](N2CCC(F)(F)C2)CC1)N1Cc2cccnc2Nc2ccc(N3CCOCC3)cc21] | 6-{[cis-4-(3,3-difluoropyrrolidin-1-yl)cyclohexyl]carbonyl}-8-morpholin-4-yl-6,11-dihydro-5H-pyrido[2,3-b][1,5]benzodiazepine | 498 |
| 476 | 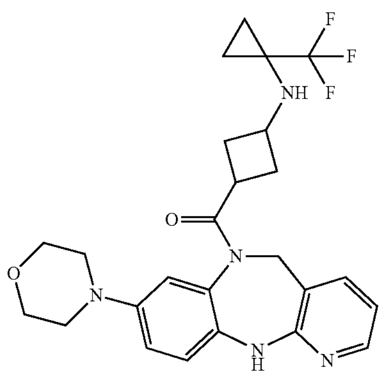 [SMILES: O=C(C1CC(NC2(C(F)(F)F)CC2)C1)N1Cc2cccnc2Nc2ccc(N3CCOCC3)cc21] | 3-[(8-morpholin-4-yl-5,11-dihydro-6H-pyrido[2,3-b][1,5]benzodiazepin-6-yl)carbonyl]-N-[1-(trifluoromethyl)cyclopropyl]-cyclobutanamine | 488 |
| 477 | Isomer 1 | 6-{[(1S,3R)-3-(3,3-difluoroazetidin-1-yl)cyclopentyl]carbonyl}-8-morpholin-4-yl-6,11-dihydro-5H-pyrido[2,3-b][1,5]benzodiazepine | 470 |
| 478 | Isomer 2 | (1S,3S)-3-[(8-morpholin-4-yl-5,11-dihydro-6H-pyrido[2,3-b][1,5]benzodiazepin-6-yl)carbonyl]-N-[1-(trifluoromethyl)cyclopropyl]-cyclopentanamine | 502 |

| Ex. No. | Structure | Chemical Name | [M + H]+ |
|---|---|---|---|
| 479 | 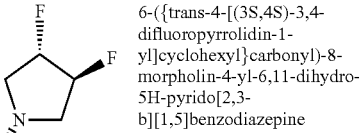 | 6-({trans-4-[(3S,4S)-3,4-difluoropyrrolidin-1-yl]cyclohexyl}carbonyl)-8-morpholin-4-yl-6,11-dihydro-5H-pyrido[2,3-b][1,5]benzodiazepine | 498 |
| 480 | 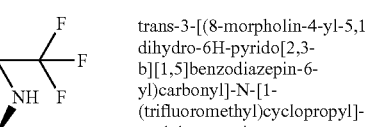 | trans-3-[(8-morpholin-4-yl-5,11-dihydro-6H-pyrido[2,3-b][1,5]benzodiazepin-6-yl)carbonyl]-N-[1-(trifluoromethyl)cyclopropyl]-cyclobutanamine | 488 |
| 481 | 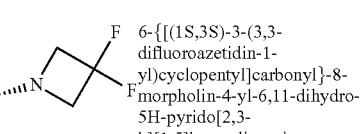   Isomer 2 | 6-{[(1S,3S)-3-(3,3-difluoroazetidin-1-yl)cyclopentyl]carbonyl}-8-morpholin-4-yl-6,11-dihydro-5H-pyrido[2,3-b][1,5]benzodiazepine | 470 |
| 482 | 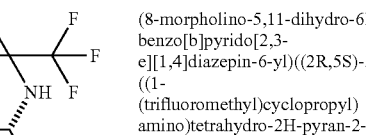   Isomer 2 | (8-morpholino-5,11-dihydro-6H-benzo[b]pyrido[2,3-e][1,4]diazepin-6-yl)((2R,5S)-5-((1-(trifluoromethyl)cyclopropyl)amino)tetrahydro-2H-pyran-2-yl)methanone | 518 |

-continued

| Ex. No. | Structure | Chemical Name | [M + H]+ |
|---|---|---|---|
| 483 | 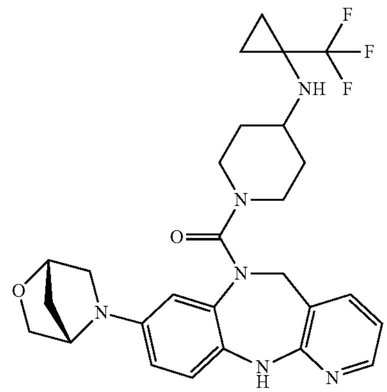 [SMILES: O=C(N1CCC(NC2(C(F)(F)F)CC2)CC1)N1Cc2cccnc2Nc2ccc(N3C[C@@H]4C[C@H]3CO4)cc21] | 1-({8-[(1S,4S)-2-oxa-5-azabicydo[2.2.1]hept-5-yl]-5,11-dihydro-6H-pyrido[2,3-b][1,5]benzodiazepin-6-yl}carbonyl)-N-[1-(trifluoromethyl)cyclopropyl]-piperidin-4-amine | 529 |

Examples 484-485: N-({6-[(Trans-4-methoxycyclohexyl)carbonyl]-6,11-dihydro-5H-pyrido[2,3-b][1,5]benzodiazepin-8-yl}methyl)-1-(trifluoromethyl)cyclopropanamine and N-({6-[(Cis-4-methoxycyclohexyl)carbonyl]-6,11-dihydro-5H-pyrido[2,3-b][1,5]benzodiazepin-8-yl}methyl)-1-(trifluoromethyl)cyclopropanamine

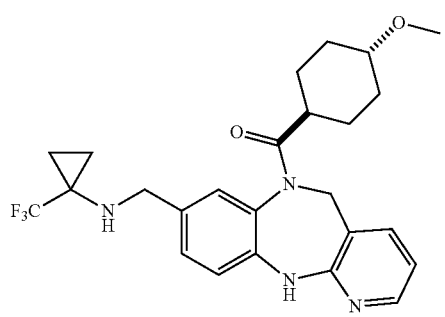

Step 1:

To a solution of tert-butyl 8-formyl-6-(4-methoxycyclohexanecarbonyl)-5H-benzo[b]pyrido[2,3-e][1,4]diazepine-11(6H)-carboxylate (428 mg, 0.922 mmol) in DCM (1 mL) was added TFA (1 mL) at room temperature. The reaction was stirred for 40 minutes and then concentrated under reduced pressure to afford 6-(4-methoxycyclohexanecarbonyl)-6,11-dihydro-5H-benzo[b]pyrido[2,3-e][1,4]diazepine-8-carbaldehyde. MS: 366 (M+1).

Step 2:

To a vial was added 6-(4-methoxycyclohexanecarbonyl)-6,11-dihydro-5H-benzo[b]pyrido[2,3-e][1,4]diazepine-8-carbaldehyde (30 mg, 0.082 mmol) and 1-(trifluoromethyl)cyclopropanamine, HCl (14 mg, 0.086 mmol). The solids were dissolved in DCE (0.8 mL), and then acetic acid (10 μL) and sodium triacetoxyborohydride (40 mg, 0.19 mmol) were added. The reaction was stirred at room temperature for 16 h. The reaction was quenched with saturated aqueous sodium bicarbonate, extracted with ethyl acetate, dried over sodium sulfate, filtered, and concentrated under reduced pressure. The residue was purified by mass triggered reverse phase HPLC (ACN/water with 0.1% NH₄OH) to afford the title compounds as solids.

Trans:

MS: 475 (M+1). ¹H NMR (500 MHz, CH₃OH-d₄): δ 8.03 (s, 1H), 7.51 (d, J=7.3 Hz, 1H), 7.25-7.17 (m, 3H), 6.75 (t, J=6.1 Hz, 1H), 5.31 (d, J=14.9 Hz, 1H), 3.96 (d, J=15.0 Hz, 1H), 3.93 (s, 2H), 3.27 (s, 3H), 3.09-3.03 (m, 1H), 2.55-2.50 (m, 1H), 2.11-2.07 (m, 1H), 1.98-1.93 (m, 1H), 1.89-1.85 (m, 1H), 1.65-1.57 (m, 1H), 1.40-1.36 (m, 1H), 1.17-1.10 (m, 1H), 1.05-1.03 (s, 3H), 0.96-0.91 (m, 2H), 0.81-0.73 (m, 1H).

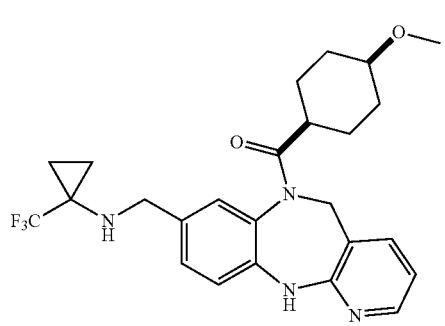

Cis:

MS: 475 (M+1). ¹H NMR (500 MHz, CH₃OH-d₄): δ 8.03 (s, 1H), 7.51 (d, J=7.3 Hz, 1H), 7.24-7.16 (m, 3H), 6.76 (t, J=5.9 Hz, 1H), 5.31 (d, J=14.9 Hz, 1H), 3.96-3.93 (m, 3H), 3.29-3.26 (m, 1H) 3.22 (s, 3H), 2.67-2.60 (m, 1H), 1.97-1.86 (m, 2H), 1.75-1.58 (m, 2H), 1.43-1.33 (m, 2H), 1.06-1.03 (m, 4H), 0.95-0.90 (m, 2H).

The compounds in the following table were prepared using the methodology herein and the general procedure described in Examples 484-485.

| Ex. No. | Structure | Chemical Name | [M + H]+ |
|---|---|---|---|
| 486 | 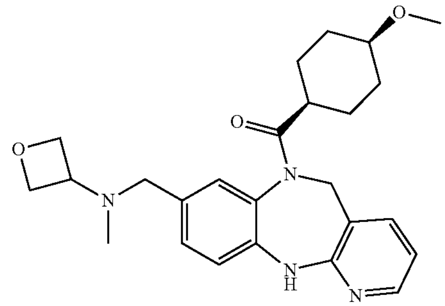 [SMILES: CO[C@H]1CC[C@@H](C(=O)N2Cc3cccnc3Nc3ccc(CN(C)C4COC4)cc32)CC1] | N-({6-[(cis-4-methoxycyclohexyl)carbonyl]-6,11-dihydro-5H-pyrido[2,3-b][1,5]benzodiazepin-8-yl}-methyl)-N-methyloxetan-3-amine | 437 |
| 487 | 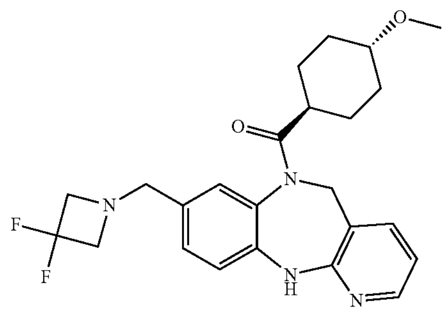 [SMILES: CO[C@H]1CC[C@H](C(=O)N2Cc3cccnc3Nc3ccc(CN4CC(F)(F)C4)cc32)CC1] | 8-[(3,3-difluoroazetidin-1-yl)methyl]-6-[(trans-4-methoxycyclohexyl)carbonyl]-6,11-dihydro-5H-pyrido[2,3-b][1,5]benzodiazepine | 443 |
| 488 | 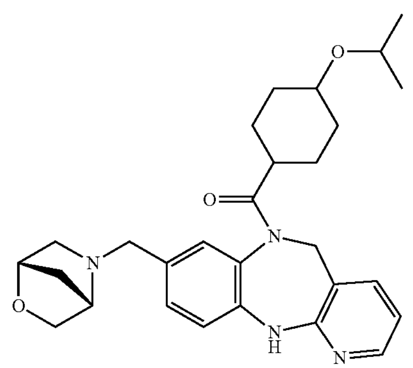 [SMILES: CC(C)OC1CCC(C(=O)N2Cc3cccnc3Nc3ccc(CN4C[C@@H]5C[C@H]4CO5)cc32)CC1] | 6-{[4-(1-methylethoxy)cyclohexyl]carbonyl}-8-[(1S,4S)-2-oxa-5-azabicyclo[2.2.1]hept-5-ylmethyl]-6,11-dihydro-5H-pyrido[2,3-b][1,5]benzodiazepine | 477 |

Example 489: 3-{6-[(Trans-4-methoxycyclohexyl)carbonyl]-6,11-dihydro-5H-pyrido[2,3-b][1,5]benzodiazepin-8-yl}-1,3-oxazolidin-2-one

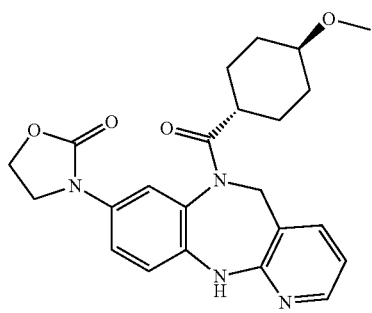

Step 1:

To a vial containing 8-bromo-6,11-dihydro-5H-pyrido[2,3-b][1,5]benzodiazepine, HCl salt (100 mg, 0.320 mmol), copper(I) iodide (3.0 mg, 0.016 mmol), oxazolidin-2-one (28 mg, 0.32 mmol) and potassium carbonate (110 mg, 0.80 mmol) was added a mixture of trans-N,N'-dimethylcyclohexane-1,2-diamine (5.0 mg, 0.032 mmol) in dioxane (1.0 mL). The mixture was evacuated and then purged 5 times with argon. The mixture was heated to 110° C. for 16 h. The mixture was cooled to room temperature and then diluted with ethyl acetate and water. The organic layer was separated, dried over magnesium sulfate, filtered, and concentrated under reduced pressure. The residue was purified by column chromatography on silica gel to afford 3-(6,11-dihydro-5H-benzo[b]pyrido[2,3-e][1,4]diazepin-8-yl)oxazolidin-2-one. MS: 283 (M+1).

Step 2:

To a microwave vial containing trans-4-methoxycyclohexanecarboxylic acid (17 mg, 0.11 mmol) and 3-(6,11-dihydro-5H-benzo[b]pyrido[2,3-e][1,4]diazepin-8-yl)oxazolidin-2-one (25 mg, 0.089 mmol) was added acetonitrile (1.0 mL). PS-PPh$_3$ (1.6 mmol/g loading, 170 mg, 0.272 mmol) and then trichloroacetonitrile (44 μL, 0.44 mmol) were added and the mixture was irradiated in the microwave at 100° C. for 10 minutes. Upon cooling to room temperature, the mixture was filtered, concentrated under reduced pressure, and then purified by reverse phase HPLC (acetonitrile/water with 0.1% TFA modifier) to afford the title compound as a solid TFA salt. MS: 423 (M+1). $^1$H NMR (500 MHz, DMSO-d<sub>6</sub>) δ 9.58 (s, 1H), 8.04 (dd, J=4.9, 1.5 Hz, 1H), 7.53 (d, J=7.1 Hz, 1H), 7.49 (d, J=2.5 Hz, 1H), 7.44 (dd, J=8.9, 2.5 Hz, 1H), 7.34 (d, J=8.9 Hz, 1H), 6.80-6.74 (m, 1H), 5.22 (d, J=15.0 Hz, 1H), 4.45-4.40 (m, 2H), 4.15-4.10 (m, 1H), 3.99-3.88 (m, 2H), 3.13 (s, 3H), 3.02-2.88 (m, 1H), 2.02-1.87 (m, 2H), 1.81-1.73 (m, 1H), 1.55-1.37 (m, 1H), 1.31-1.14 (m, 2H), 1.11-0.88 (m, 2H), 0.78-0.58 (m, 1H).

The compounds in the following table were prepared using the methodology herein and the general procedure described in Example 489.

| Ex. No. | Structure | Chemical Name | [M + H]+ |
| --- | --- | --- | --- |
| 490 | 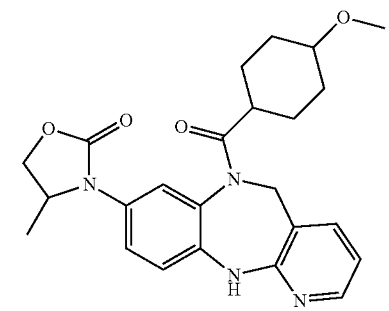 [SMILES: COC1CCC(C(=O)N2Cc3cccnc3Nc3ccc(N4C(=O)OCC4C)cc32)CC1] | 3-{6-[(4-methoxycyclohexyl)carbonyl]-6,11-dihydro-5H-pyrido[2,3-b][1,5]benzodiazepin-8-yl}-4-methyl-1,3-oxazolidin-2-one | 437 |
| 491 | 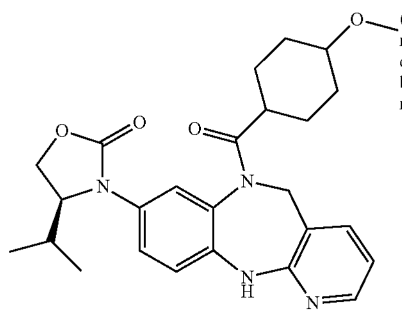 [SMILES: COC1CCC(C(=O)N2Cc3cccnc3Nc3ccc(N4C(=O)OC[C@@H]4C(C)C)cc32)CC1] | (4S)-3-{6-[(4-methoxycyclohexyl)carbonyl]-6,11-dihydro-5H-pyrido[2,3-b][1,5]benzodiazepin-8-yl}-4-(1-methylethyl)-1,3-oxazolidin-2-one | 465 |
| 492 | 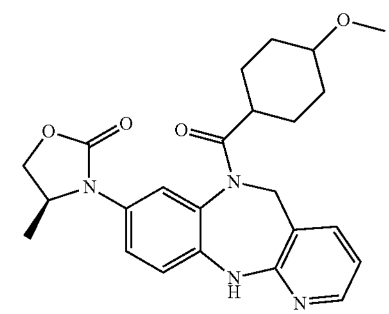 [SMILES: COC1CCC(C(=O)N2Cc3cccnc3Nc3ccc(N4C(=O)OC[C@@H]4C)cc32)CC1] | (I4S)-3-{6-[(4-methoxycyclohexyl)carbonyl]-6,11-dihydro-5H-pyrido[2,3-b][1,5]benzodiazepin-8-yl}-4-methyl-1,3-oxazolidin-2-one | 437 |
| 493 | 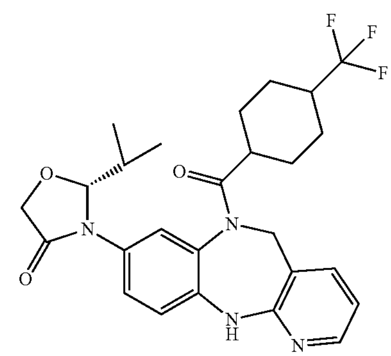 [SMILES: CC(C)[C@H]1OCC(=O)N1c1ccc2c(c1)N(C(=O)C1CCC(C(F)(F)F)CC1)Cc1cccnc1N2] | (4S)-4-(1-methylethy])-3-(6-{[4-(trifluoromethyl)cyclohexyl]-carbonyl}-6,11-dihydro-5H-pyrido[2,3-b][1,5]benzodiazepin-8-yl)-1,3-oxazolidin-2-one | 503 |

-continued

| Ex. No. | Structure | Chemical Name | [M + H]+ |
|---|---|---|---|
| 494 | 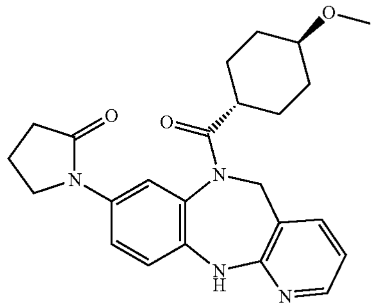 [SMILES: CO[C@H]1CC[C@H](C(=O)N2Cc3cccnc3Nc3ccc(N4CCCC4=O)cc32)CC1] | 1-{6-[(trans-4-methoxycyclohexyl)carbonyl]-6,11-dihydro-5H-pyrido[2,3-b][1,5]benzodiazepin-8-yl}pyrrolidin-2-one | 421 |
| 495 | 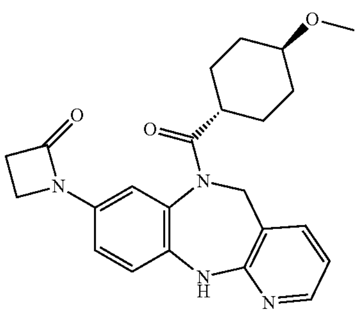 [SMILES: CO[C@H]1CC[C@H](C(=O)N2Cc3cccnc3Nc3ccc(N4CCC4=O)cc32)CC1] | 1-{6-[(trans-4-methoxycyclohexyl)carbonyl]-6,11-dihydro-5H-pyrido[2,3-b][1,5]benzodiazepin-8-yl}azetidin-2-one | 407 |

Example 496: 8-(6-Acryloyl-1,6-diazaspiro[3.3]hept-1-yl)-6-[(3,3-dimethylcyclobutyl)carbonyl]-6,11-dihydro-5H-pyrido[2,3-b][1,5]benzodiazepine

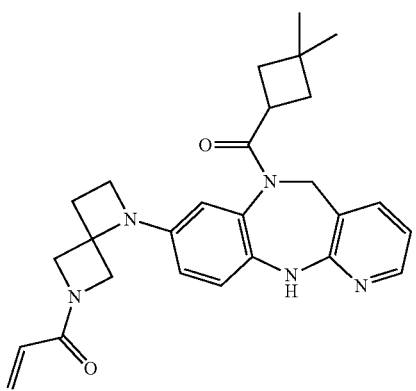 [SMILES: C=CC(=O)N1CC2(CCN2c2ccc3c(c2)N(C(=O)C2CC(C)(C)C2)Cc2cccnc2N3)C1]

To a solution of [8-(1,6-diazaspiro[3.3]hept-1-yl)-5,11-dihydro-6H-pyrido[2,3-b][1,5]benzodiazepin-6-yl](3,3-dimethylcyclobutyl)methanone (30 mg, 0.074 mmol) dissolved in DCM (3 mL) was added DIEA (0.039 mL, 0.22 mmol) and acryloyl chloride (7 µL, 0.09 mmol) (~1 drop). The mixture was stirred for 30 minutes at room temperature. The reaction mixture was concentrated under reduced pressure, dissolved in 1 mL DMSO, and then purified by mass triggered reverse phase HPLC (ACN/water with 0.1% TFA modifier) to afford the title compound as a solid TFA salt. MS: 458 (M+1). $^1$H NMR (500 MHz, CD$_3$OD) δ 7.98 (d, J=4.0 Hz, 1H), 7.49 (d, J=7.3 Hz, 1H), 7.12 (d, J=8.7 Hz, 1H), 6.74-6.68 (m, 1H), 6.61-6.56 (m, 1H), 6.45-6.34 (m, 2H), 6.34-6.26 (m, 1H), 5.81-5.76 (m, 1H), 5.29 (d, J=15.1 Hz, 1H), 4.86-4.76 (m, 1H), 4.63-4.54 (m, 1H), 4.46-4.41 (m, 1H), 4.20-4.15 (m, 1H), 3.98 (d, J=15.0 Hz, 1H), 3.81-3.68 (m, 2H), 3.29-3.18 (m, 1H), 2.69-2.51 (m, 2H), 2.09-2.00 (m, 1H), 1.87-1.75 (m, 1H), 1.72-1.58 (m, 1H), 1.36-1.27 (m, 1H), 1.03 (d, J=5.0 Hz, 3H), 0.93 (d, J=4.4 Hz, 3H).

The compounds in the following table were prepared using the methodology herein and the general procedure described in Example 496.

| Ex. No. | Structure | Chemical Name | [M + H]+ |
|---|---|---|---|
| 497 | 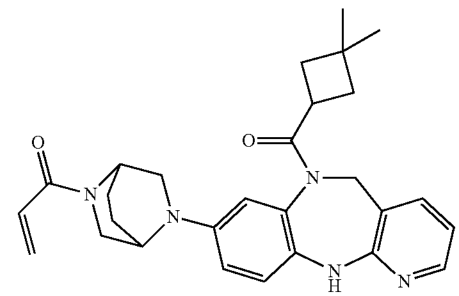 [SMILES: C=CC(=O)N1CC2CCC1CN2c1ccc2c(c1)N(C(=O)C1CC(C)(C)C1)Cc1cccnc1N2] | 8-(5-acryloyl-2,5-diazabicyclo[2.2.2]oct-2-yl)-6-[(3,3-dimethylcyclobutyl)carbonyl]-6,11-dihydro-5H-pyrido[2,3-b][1,5]benzodiazepine | 472 |
| 498 | 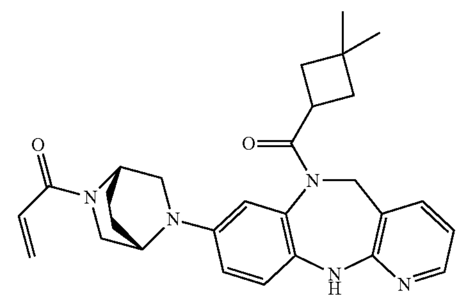 [SMILES: C=CC(=O)N1C[C@@H]2CC[C@H]1CN2c1ccc2c(c1)N(C(=O)C1CC(C)(C)C1)Cc1cccnc1N2] | 8-[(1S,4S)-5-acryloyl-2,5-diazabicyclo[2.2.2]oct-2-yl]-6-[(3,3-dimethylcyclobutyl)carbonyl]-6,11-dihydro-5H-pyrido[2,3-b][1,5]benzodiazepine | 472 |
| 499 | 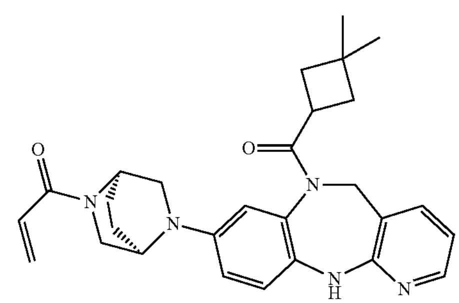 | 8-[(1R,4R)-5-acryloyl-2,5-diazabicyclo[2.2.2]oct-2-yl]-6-[(3,3-dimethylcyclobutyl)carbonyl]-6,11-dihydro-5H-pyrido[2,3-b][1,5]benzodiazepine | 472 |
| 500 | 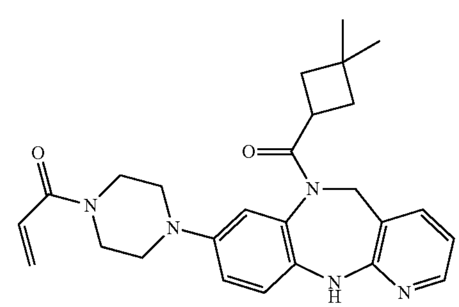 [SMILES: C=CC(=O)N1CCN(c2ccc3c(c2)N(C(=O)C2CC(C)(C)C2)Cc2cccnc2N3)CC1] | 8-(4-acryloylpiperazin-1-yl)-6-[(3,3-dimethylcyclobutyl)carbonyl]-6,11-dihydro-5H-pyrido[2,3-b][1,5]benzodiazepine | 446 |

| Ex. No. | Structure | Chemical Name | [M + H]+ |
|---|---|---|---|
| 501 | 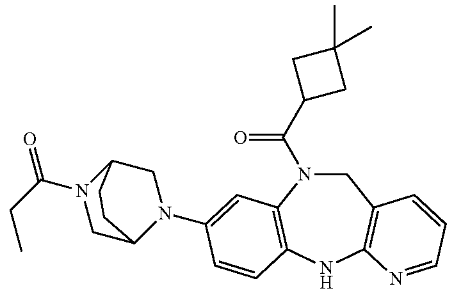 [SMILES: CCC(=O)N1CC2CCC1CN2c1ccc2c(c1)N(C(=O)C1CC(C)(C)C1)Cc1cccnc1N2] | 6-[(3,3-dimethylcyclobutyl)carbonyl]-8-(5-propanoyl-2,5-diazabicyclo[2.2.2]oct-2-yl)-6,11-dihydro-5H-pyrido[2,3-b][1,5]benzodiazepine | 474 |
| 502 | 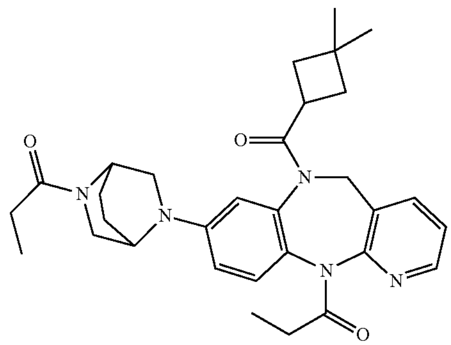 [SMILES: CCC(=O)N1c2ccc(N3CC4CCC3CN4C(=O)CC)cc2N(C(=O)C2CC(C)(C)C2)Cc2cccnc21] | 6-[(3,3-dimethylcyclobutyl)carbonyl]-11-propanoyl-8-(5-propanoyl-2,5-diazabicyclo[2.2.2]oct-2-yl)-6,11-dihydro-5H-pyrido[2,3-b][1,5]benzodiazepine | 530 |

Example 503: Trans-N-methyl-4-[(8-morpholin-4-yl-5,11-dihydro-6H-pyrido[2,3-b][1,5]benzodiazepin-6-yl)carbonyl]-N-[(1)-2,2,2-trifluoro-1-methylethyl]cyclohexanamine

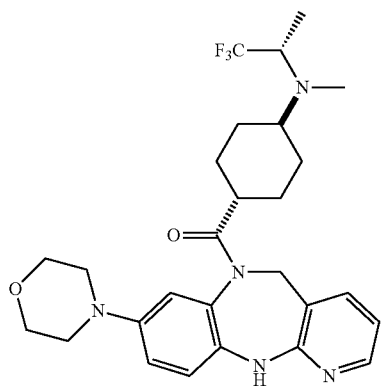

Step 1:

To a vial equipped with a stir bar was added 4-{[8-(morpholin-4-yl)-5,11-dihydro-6H-pyrido[2,3-b][1,5]benzodiazepin-6-yl]carbonyl}cyclohexanone (100 mg, 0.246 mmol), (S)-1,1,1-trifluoropropan-2-amine-HCl (55 mg, 0.37 mmol), and DCE (1.2 mL). Triethylamine (86 µL, 0.62 mmol) was added and the reaction was stirred for 1 h at room temperature. Acetic acid (70 µL, 1.2 mmol) was added, followed by the slow addition of sodium triacetoxyborohydride (83 mg, 0.39 mmol). The mixture was stirred for 1 h, and then quenched with aqueous saturated sodium bicarbonate solution. The mixture was extracted with ethyl acetate and the organic layer was washed with brine, dried over magnesium sulfate, filtered, and concentrated under reduced pressure to afford [8-(morpholin-4-yl)-5,11-dihydro-6H-pyrido[2,3-b][1,5]benzodiazepin-6-yl](4-{[(2S)-1,1,1-trifluoropropan-2-yl]amino}cyclohexyl)methanone as a solid. MS: 504 (M+1).

Step 2:

To a vial equipped with a stir bar was added [8-(morpholin-4-yl)-5,11-dihydro-6H-pyrido[2,3-b][1,5]benzodiazepin-6-yl](4-{[(2S)-1,1,1-trifluoropropan-2-yl]amino}cyclohexyl)methanone (75 mg, 0.074 mmol), formaldehyde (3.0 µL, 0.11 mmol), and DCE (745 µL). Acetic acid (17 µl, 0.30 mmol) was added followed by the slow addition of sodium triacetoxyborohydride (25 mg, 0.12 mmol). The mixture was stirred for 2 h at room temperature, and partial conversion was observed. The reaction was heated to 50° C. for 2 hours. The reaction was cooled to room temperature and quenched with aqueous saturated sodium bicarbonate. The mixture was extracted with ethyl acetate, and the organic layer was washed with brine, dried over magnesium sulfate, filtered, and concentrated under reduced pressure. The residue was purified by mass triggered reverse phase HPLC (ACN/water with 0.1% TFA modifier) to afford the title compound as a solid TFA salt. MS: 518 (M+1). $^1$H NMR (600 MHz, DMSO-$d_6$) δ 9.11 (s, 1H), 7.98 (d, J=3.8 Hz, 1H), 7.40 (d, J=7.5 Hz, 1H), 7.22 (d, J=9.1 Hz, 1H), 6.92 (d, J=7.3 Hz, 1H), 6.78 (s, 1H), 6.68-6.59 (m, 1H), 5.18 (d, J=14.7 Hz, 1H), 3.87 (d, J=14.7 Hz, 1H), 3.73 (s, 4H), 3.15-2.92 (m, 4H), 2.44-2.27 (m, 2H), 2.18 (d, J=2.7 Hz, 3H), 1.95-1.89 (m, 1H), 1.80-1.76 (m, 1H), 1.67-1.54 (m, 1H), 1.54-1.39 (m, 2H), 1.32-1.11 (m, 2H), 1.11-1.06 (m, 3H), 1.02-0.90 (m, 1H), 0.89-0.74 (m, 1H).

The compounds in the following table were prepared using the methodology herein and the general procedure described in Example 503.

| Ex. No. | Structure | Chemical Name | [M + H]+ |
|---|---|---|---|
| 504 | 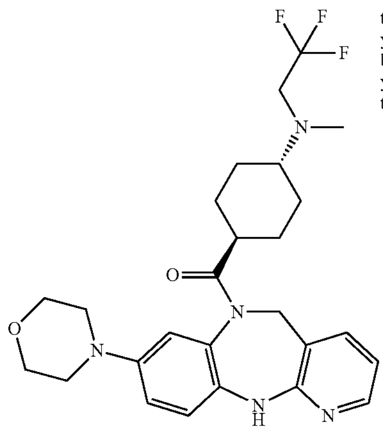 | trans-N-methyl-4-[(8-morpholin-4-yl-5,11-dihydro-6H-pyrido[2,3-b][1,5]benzodiazepin-6-yl)carbonyl]-N-(2,2,2-trifluoroethyl)cyclohexanamine | 504 |
| 505 | 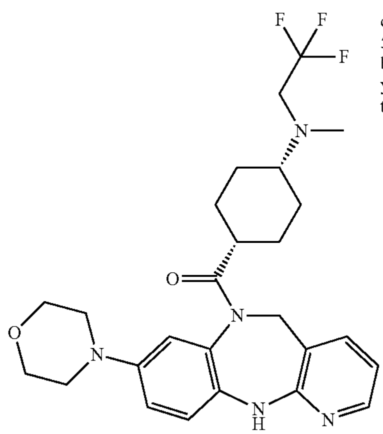 | cis-N-methyl-4-[(8-morpholin-4-yl-5,11-dihydro-6H-pyrido[2,3-b][1,5]benzodiazepin-6-yl)carbonyl]-N-(2,2,2-trifluoroethyl)cyclohexanamine | 504 |
| 506 | 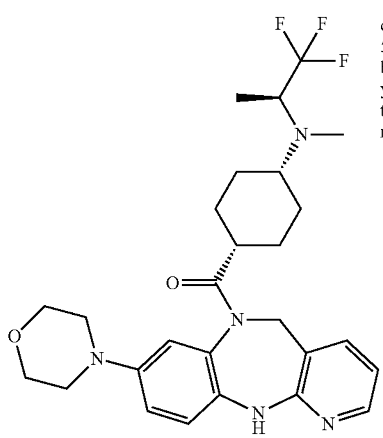 | cis-N-methyl-4-[(8-morpholin-4-yl-5,11-dihydro-6H-pyrido[2,3-b][1,5]benzodiazepin-6-yl)carbonyl]-N-[(1S)-2,2,2-trifluoro-1-methylethyl]cyclohexanamine | 518 |

| Ex. No. | Structure | Chemical Name | [M + H]+ |
|---|---|---|---|
| 507 | 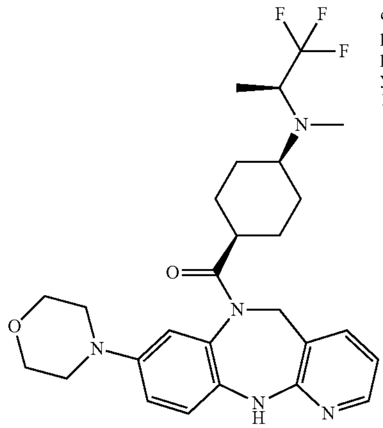 | cis-N-methyl-4-{[8-(tetrahydro-2H-pyran-4-yl)-5,11-dihydro-6H-pyrido[2,3-b][1,5]benzodiazepin-6-yl]carbonyl}-N-[(1S)-2,2,2-trifluoro-1-methylethyl]cyclohexanamine | 517 |
| 508 | 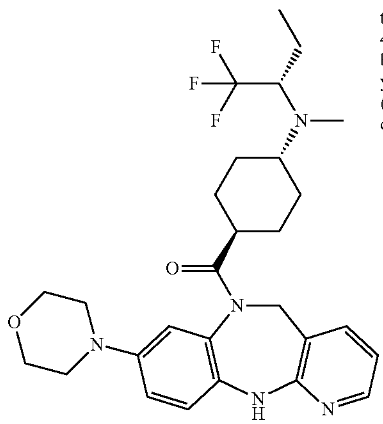 | trans-N-methyl-4-[(8-morpholin-4-yl-5,11-dihydro-6H-pyrido[2,3-b][1,5]benzodiazepin-6-yl)carbonyl]-N-[(1S)-1-(trifluoromethyl)propyl]-cyclohexanamine | 532 |

Examples 509-510: N-(2-Fluorophenyl)-6-[(trans-4-methoxycyclohexyl)carbonyl]-6,11-dihydro-5H-pyrido[2,3-b][1,5]benzodiazepine-8-carboxamide and N-(2-Fluorophenyl)-6-[(cis-4-methoxycyclohexyl)carbonyl]-6,11-dihydro-5H-pyrido[2,3-b][1,5]benzodiazepine-8-carboxamide

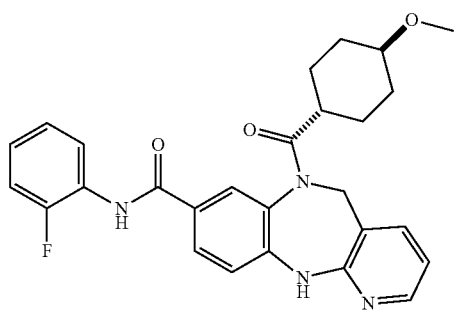

-continued

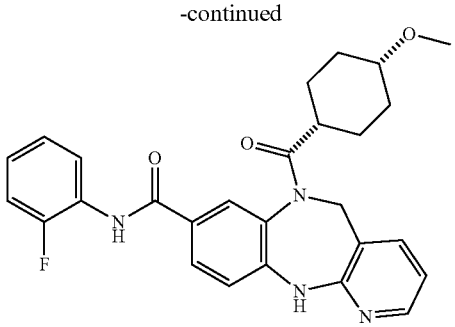

Step 1:

To a flask was added 4-methoxycyclohexanecarboxylic acid (100 mg, 0.632 mmol), and the material was dissolved in DCM (0.9 mL). The mixture was cooled to 0° C. and 1-chloro-N,N,2-trimethylprop-1-en-1-amine (93 µL, 0.70 mmol) was added dropwise. The mixture was warmed to room temperature and stirred for 30 minutes. This mixture was added directly to a solution of 11-tert-butyl 8-methyl 5,6-dihydro-11H-pyrido[2,3-b][1,5]benzodiazepine-8,11-dicarboxylate (200 mg, 0.632 mmol) dissolved in DCM (2.7 mL) and DIEA (0.39 mL, 2.3 mmol). The reaction mixture was stirred at room temperature for 1 h. Another equivalent of the acid chloride was prepared as described above and added to the stirring solution of 11-tert-butyl 8-methyl 5,6-dihydro-11H-pyrido[2,3-b][1,5]benzodiazepine-8,11- dicarboxylate and DIEA in DCM and stirred for 1 h at room temperature. The mixture was quenched with water, and the organic layer was dried over sodium sulfate, filtered, and concentrated under reduced pressure. The residue was purified by column chromatography on silica gel (5-40% EtOAc/DCM) to afford 11-tert-butyl 8-methyl 6-[(4-methoxycyclohexyl)carbonyl]-5,6-dihydro-11H-pyrido[2,3-b][1,5]benzodiazepine-8,11-dicarboxylate as a solid. MS: 496 (M+1).

Step 2:

To 11-tert-butyl 8-methyl 6-[(4-methoxycyclohexyl)carbonyl]-5,6-dihydro-11H-pyrido[2,3-b][1,5]benzodiazepine-8,11-dicarboxylate (279 mg, 0.563 mmol) dissolved in THF (1.87 mL), water (0.47 mL), and MeOH (0.47 mL) was added lithium hydroxide (33.7 mg, 1.41 mmol). The mixture was stirred at room temperature for 5 h. The reaction was quenched with 2 N HCl to pH 5~6 and extracted with EtOAc (2×). The combined organic layers were dried over sodium sulfate, filtered, and concentrated under reduced pressure to afford 11-(tert-butoxycarbonyl)-6-[(4-methoxycyclohexyl)carbonyl]-6,11-dihydro-5H-pyrido[2,3-b][1,5]benzodiazepine-8-carboxylic acid as a solid. MS: 482 (M+1).

Step 3:

To 11-(tert-butoxycarbonyl)-6-[(4-methoxycyclohexyl)carbonyl]-6,11-dihydro-5H-pyrido[2,3-b][1,5]benzodiazepine-8-carboxylic acid (271 mg, 0.563 mmol) dissolved in DMF (2.8 mL) was added DIEA (197 µL, 1.13 mmol), 2-fluoroaniline (69 mg, 0.62 mmol), and 2,4,6-tripropyl-1,3,5,2,4,6-trioxatriphosphinane 2,4,6-trioxide (50% in DMF, 394 µL, 0.675 mmol). The reaction mixture was stirred for 16 h at room temperature. Another equivalent of each reactant was added and then stirred at 45° C. for 4 h. The mixture was quenched with water, and extracted with DCM. The organic layer was washed with water and then brine, and then dried over sodium sulfate, filtered, and concentrated under reduced pressure. The residue was purified by column chromatography on silica gel (5-50% EtOAc:DCM) to afford tert-butyl 8-[(2-fluorophenyl)carbamoyl]-6-[(4-methoxycyclohexyl)carbonyl]-5,6-dihydro-11H-pyrido[2,3-b][1,5]benzodiazepine-11-carboxylate as an oil. MS: 575 (M+1).

Step 4:

To tert-butyl 8-[(2-fluorophenyl)carbamoyl]-6-[(4-methoxycyclohexyl)carbonyl]-5,6-dihydro-11H-pyrido[2,3-b][1,5]benzodiazepine-11-carboxylate (206 mg, 0.358 mmol) was added HCl (4.0 M in dioxane, 2.90 mL, 11.4 mmol). The reaction mixture was stirred at 50° C. for 2 h, and then concentrated under reduced pressure. The residue was purified by mass triggered reverse phase HPLC (ACN/water with 0.1% TFA modifier) to afford:

Peak 1: as a solid TFA salt. MS: 475 (M+1). $^1$H NMR (500 MHz, DMSO-$d_6$) δ 9.93 (s, 1H), 9.89 (s, 1H), 8.11-8.08 (m, 1H), 7.94-7.92 (m, 1H), 7.90-7.86 (m, 1H), 7.63-7.58 (m, 1H), 7.55 (d, J=7.1 Hz, 1H), 7.43 (d, J=8.6 Hz, 1H), 7.33-7.18 (m, 3H), 6.84-6.79 (m, 1H), 5.22 (d, J=15.0 Hz, 1H), 3.97 (d, J=14.8 Hz, 1H), 3.12 (s, 3H), 2.99-2.89 (m, 1H), 2.46-2.37 (m, 1H), 2.02-1.94 (m, 1H), 1.93-1.84 (m, 1H), 1.78-1.70 (m, 1H), 1.54-1.42 (m, 1H), 1.20-1.14 (m, 1H), 1.01-0.83 (m, 2H), 0.69-0.59 (m, 1H).

Peak 2: as a solid TFA salt. MS: 475 (M+1). $^1$H NMR (500 MHz, DMSO-$d_6$) δ 9.97-9.91 (m, 2H), 8.14-8.07 (m, 1H), 7.97-7.91 (m, 1H), 7.91-7.85 (m, 1H), 7.62-7.56 (m, 2H), 7.43 (d, J=8.6 Hz, 1H), 7.32-7.19 (m, 3H), 6.83 (dd, J=5.0, 7.3 Hz, 1H), 5.23 (d, J=15.0 Hz, 1H), 3.96 (d, J=14.8 Hz, 1H), 3.24-3.18 (m, 1H), 3.09 (s, 3H), 2.55-2.51 (m, 1H), 1.85-1.68 (m, 2H), 1.57-1.45 (m, 1H), 1.27-1.09 (m, 2H), 1.01-0.92 (m, 1H), 0.92-0.82 (m, 1H).

Example 511: [8-(4-Hydroxytetrahydro-2H-pyran-4-yl)-5,11-dihydro-6H-pyrido[2,3-b][1,5]benzodiazepin-6-yl](trans-4-methoxycyclohexyl)methanone

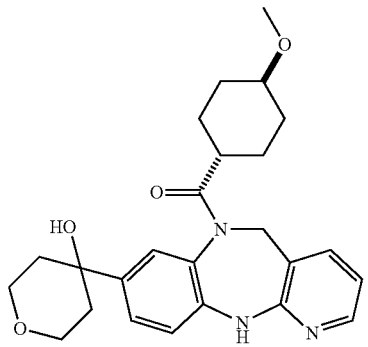

To a solution of (8-bromo-5,11-dihydro-6H-pyrido[2,3-b][1,5]benzodiazepin-6-yl)(trans-4-methoxycyclohexyl)methanone (47 mg, 0.11 mmol) in THF (2 mL) at −78° C. under a nitrogen atmosphere was added N-butyllithium (2.5 M in hexanes, 0.145 mL, 0.361 mmol). The mixture was stirred at −78° C. under a nitrogen atmosphere for 15 minutes. Tetrahydro-4H-pyran-4-one (0.031 mL, 0.34 mmol) was added dropwise and the reaction mixture was allowed to slowly warm to room temperature and stir under a nitrogen atmosphere for 1 h. The reaction was quenched with saturated ammonium chloride and extracted with EtOAc (2×). The combined organic layers were washed with brine, dried over sodium sulfate, filtered, and concentrated under reduced pressure. The residue was purified by column chromatography on silica gel (0-50% 3:1 EtOAc:EtOH/Hexanes) to afford the title compound as a solid. MS: 438 (M+1). $^1$H NMR (500 MHz, DMSO-$d_6$) δ 9.53 (s, 1H), 8.07-8.02 (m, 1H), 7.51 (d, J=7.2 Hz, 1H), 7.39-7.26 (m, 3H), 6.77-6.71 (m, 1H), 5.20 (d, J=15.0 Hz, 1H), 3.90 (d, J=14.6 Hz, 1H), 3.84-3.66 (m, 4H), 3.13 (s, 3H), 3.00-2.87 (m, 1H), 2.42-2.34 (m, 2H), 2.03-1.84 (m, 4H), 1.79-1.72 (m, 1H), 1.56-1.38 (m, 3H), 1.18-1.09 (m, 1H), 1.06-0.93 (m, 1H), 0.93-0.81 (m, 1H), 0.67-0.53 (m, 1H).

Example 512: [8-(3-hydroxyoxetan-3-yl)-5,11-dihydro-6H-pyrido[2,3-b][1,5]benzodiazepin-6-yl][trans-4-(propan-2-yloxy)cyclohexyl]methanone

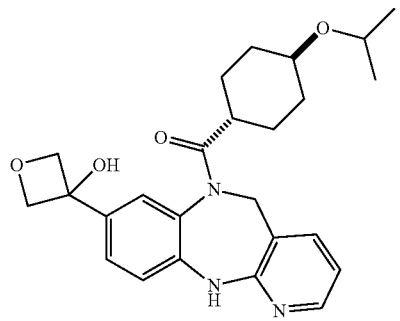

Example 512 was prepared using the procedure described for Example 511. MS: 438 (M+1).

Examples 513-514: 6-[(Trans-4-methoxycyclo-hexyl)carbonyl]-8-(tetrahydro-2H-pyran-4-yl)-6,11-dihydro-5H-pyrido[2,3-b][1,5]benzodiazepine and 8-(3,6-Dihydro-2H-pyran-4-yl)-6-[(trans-4-methoxy-cyclohexyl)carbonyl]-6,11-dihydro-5H-pyrido[2,3-b][1,5]benzodiazepine

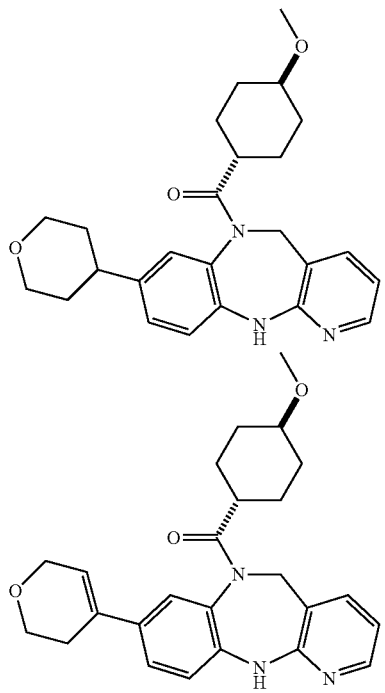

Step 1:

To a solution of (8-bromo-5,11-dihydro-6H-pyrido[2,3-b][1,5]benzodiazepin-6-yl)(trans-4-methoxycyclohexyl)methanone (47 mg, 0.11 mmol) in THF (2 mL) at −78° C. under a nitrogen atmosphere was added N-butyllithium (2.5 M in hexanes, 0.145 mL, 0.361 mmol). The mixture was stirred at −78° C. under a nitrogen atmosphere for 15 minutes. Tetrahydro-4H-pyran-4-one (0.031 mL, 0.34 mmol) was added dropwise and the reaction mixture was allowed to slowly warm to room temperature and stir under a nitrogen atmosphere for 1 h. The reaction was quenched with saturated ammonium chloride and extracted with EtOAc (2×). The combined organic layers were washed with brine, dried over sodium sulfate, filtered, and concentrated under reduced pressure. The residue was purified by column chromatography on silica gel (0-50% 3:1 EtOAc:EtOH/Hexanes) to afford [8-(4-hydroxytetrahydro-2H-pyran-4-yl)-5,11-dihydro-6H-pyrido[2,3-b][1,5]benzodiazepin-6-yl](trans-4-methoxycyclohexyl)methanone as a solid. MS: 438 (M+1).

Step 2:

A solution of [8-(4-hydroxytetrahydro-2H-pyran-4-yl)-5,11-dihydro-6H-pyrido[2,3-b][1,5]benzodiazepin-6-yl](trans-4-methoxycyclohexyl)methanone (34 mg, 0.078 mmol) and triethylsilane (19 μL, 0.12 mmol) in DCM (0.78 mL) was cooled to 0° C. Trifluoroacetic acid (60 μL, 0.78 mmol) was added dropwise, and the reaction mixture was allowed to slowly warm to room temperature and was stirred for 16 h. Another 18 μL of triethylsilane was added and the mixture was stirred for 4 h. The reaction was quenched with 1 N NaOH to pH 8-9, and the mixture was extracted with DCM (3×). The combined organic layers was washed with brine, dried over sodium sulfate, filtered, and concentrated under reduced pressure. The residue was purified by mass triggered reverse phase HPLC (ACN/water with 0.1% TFA modifier) to afford:

Peak 1: as a solid TFA salt. MS: 422 (M+1). $^1$H NMR (500 MHz, DMSO-$d_6$) δ 9.43 (s, 1H), 8.04-8.01 (m, 1H), 7.49 (d, J=7.4 Hz, 1H), 7.29-7.24 (m, 1H), 7.16-7.11 (m, 2H), 6.75-6.69 (m, 1H), 5.19 (d, J=14.9 Hz, 1H), 4.00-3.86 (m, 4H), 3.13 (s, 3H), 2.98-2.90 (m, 1H), 2.78-2.67 (m, 1H), 2.41-2.30 (m, 1H), 2.07-1.95 (m, 1H), 1.94-1.86 (m, 1H), 1.80-1.72 (m, 1H), 1.72-1.57 (m, 5H), 1.50-1.35 (m, 1H), 1.19-1.07 (m, 1H), 1.07-0.93 (m, 1H), 0.93-0.78 (m, 1H), 0.66-0.51 (m, 1H).

Peak 2: as a solid TFA salt. MS: 420 (M+1). $^1$H NMR (500 MHz, DMSO-$d_6$) δ 9.51 (s, 1H), 8.06-8.01 (m, 1H), 7.48 (d, J=6.9 Hz, 1H), 7.40-7.35 (m, 1H), 7.31 (s, 1H), 7.29 (s, 1H), 6.75-6.70 (m, 1H), 6.22 (s, 1H), 5.19 (d, J=14.7 Hz, 1H), 4.21 (s, 2H), 3.90 (d, J=14.7 Hz, 1H), 3.83-3.79 (m, 2H), 3.12 (s, 3H), 2.98-2.91 (m, 1H), 2.42-2.28 (m, 3H), 2.04-1.94 (m, 1H), 1.93-1.85 (m, 1H), 1.81-1.72 (m, 1H), 1.52-1.39 (m, 1H), 1.24-1.13 (m, 1H), 1.04-0.92 (m, 1H), 0.92-0.81 (m, 1H), 0.67-0.56 (m, 1H).

The compounds in the following table were prepared using the methodology herein and the general procedure described in Examples 513-514.

| Ex. No. | Structure | Compound Name | [M + H]+ |
| --- | --- | --- | --- |
| 515 | 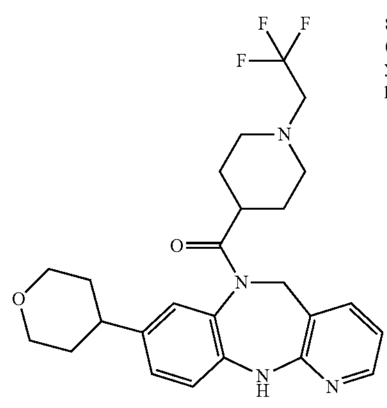 | 8-(tetrahydro-2H-pyran-4-yl)-6-{[1-(2,2,2-trifluoroethyl)piperidin-4-yl]carbonyl}-6,11-dihydro-5H-pyrido[2,3-b][1,5]benzodiazepine | 475 |

| Ex. No. | Structure | Compound Name | [M + H]+ |
|---|---|---|---|
| 516 | 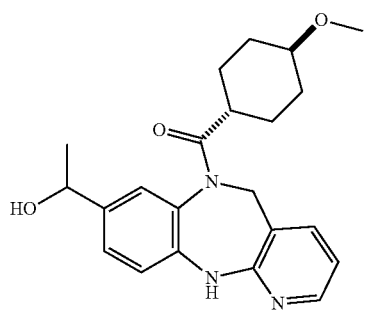 | 8-(3,6-dihydro-2H-pyran-4-yl)-6-{[1-(2,2,2-trifluoroethyl)piperidin-4-yl]carbonyl}-6,11-dihydro-5H-pyrido[2,3-b][1,5]benzodiazepine | 473 |

Example 517: [8-(1-Hydroxyethyl)-5,11-dihydro-6H-pyrido[2,3-b][1,5]benzodiazepin-6-yl](trans-4-methoxycyclohexyl)methanone Step 1:

To a flask was added trans-4-methoxycyclohexanecarboxylic acid (100 mg, 0.645 mmol), and the material was dissolved in DCM (1.0 mL). The mixture was cooled to 0° C. and 1-chloro-N,N,2-trimethylprop-1-en-1-amine (98 µL, 0.74 mmol) was added dropwise. The mixture was warmed to room temperature and stirred for 30 minutes. This mixture was added directly to a solution of tert-butyl 8-formyl-5,6-dihydro-11H-pyrido[2,3-b][1,5]benzodiazepine-11-carboxylate (200 mg, 0.615 mmol) dissolved in DCM (3.0 mL) and DIEA (0.430 mL, 2.46 mmol). The reaction mixture was stirred at room temperature for 1 h. The mixture was quenched with water, and the organic layer was dried over sodium sulfate, filtered, and concentrated under reduced pressure. The residue was purified by column chromatography on silica gel (5-40% EtOAc/DCM) to afford tert-butyl 8-formyl-6-[(trans-4-methoxycyclohexyl)carbonyl]-5,6-dihydro-11H-pyrido[2,3-b][1,5]benzodiazepine-11-carboxylate as a solid. MS: 466 (M+1).

Step 2:

Methylmagnesium bromide (3.0 M in diethyl ether, 142 µL, 0.425 mmol) was added dropwise to a −78° C. solution of tert-butyl 8-formyl-6-[(trans-4-methoxycyclohexyl)carbonyl]-5,6-dihydro-11H-pyrido[2,3-b][1,5]benzodiazepine-11-carboxylate (132 mg, 0.284 mmol) in THF (1.4 mL) under a nitrogen atmosphere. The reaction was stirred for 30 minutes at −78° C., and then quenched with saturated ammonium chloride (5 mL). This mixture was stirred for 10 minutes at room temperature, and then partitioned between EtOAc and water. The organic layer was washed with brine, dried over sodium sulfate, filtered, and concentrated under reduced pressure. The residue was purified by column chromatography on silica gel (5-40% EtOAc/DCM) to afford tert-butyl 8-(1-hydroxyethyl)-6-[(trans-4-methoxycyclohexyl)carbonyl]-5,6-dihydro-11H-pyrido[2,3-b][1,5]benzodiazepine-11-carboxylate as a solid. MS: 482 (M+1).

Step 3:

To tert-butyl 8-(1-hydroxyethyl)-6-[(trans-4-methoxycyclohexyl)carbonyl]-5,6-dihydro-11H-pyrido[2,3-b][1,5]benzodiazepine-11-carboxylate (45 mg, 0.093 mmol) was added HCl (4.0 M in dioxane, 1.65 mL, 71.4 mmol). The reaction mixture was stirred at 50° C. for 2 h, and then concentrated under reduced pressure. The residue was purified by mass triggered reverse phase HPLC (ACN/water with 0.1% TFA modifier) to afford the title compound as a solid TFA salt. MS: 382 (M+1). $^1$H NMR (500 MHz, DMSO-$d_6$) δ 9.57 (s, 1H), 8.04 (d, J=3.5 Hz, 1H), 7.54 (d, J=7.3 Hz, 1H), 7.30-7.15 (m, 3H), 6.79-6.72 (m, 1H), 5.20 (d, J=14.8 Hz, 1H), 4.74-4.65 (m, 1H), 3.90 (d, J=14.8 Hz, 1H), 3.13 (s, 3H), 3.00-2.90 (m, 1H), 2.43-2.34 (m, 1H), 1.99 (s, 1H), 1.93-1.82 (m, 1H), 1.82-1.72 (m, 1H), 1.53-1.37 (m, 1H), 1.30 (d, J=6.4 Hz, 3H), 1.20-1.12 (m, 1H), 1.06-0.96 (m, 1H), 0.96-0.83 (m, 1H), 0.69-0.56 (m, 1H).

Example 518: [Trans-4-(propan-2-yloxy)cyclohexyl][8-(trifluoromethyl)-5,11-dihydro-6H-pyrido[2,3-b][1,5]benzodiazepin-6-yl]methanone

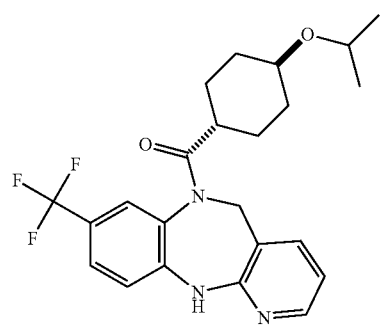

Step 1:

To a flask was added trans-4-(propan-2-yloxy)cyclohexanecarboxylic acid (54 mg, 0.29 mmol), and the material was dissolved in DCM (0.44 mL). The mixture was cooled to 0° C. and 1-chloro-N,N,2-trimethylprop-1-en-1-amine (44 µL, 0.33 mmol) was added dropwise. The mixture was warmed to room temperature and stirred for 30 minutes. This mixture was added directly to a solution of tert-butyl 8-(trifluoromethyl)-5,6-dihydro-11H-pyrido[2,3-b][1,5]benzodiazepine-11-carboxylate (100 mg, 0.274 mmol) dissolved in DCM (1.33 mL) and DIEA (0.191 mL, 1.09 mmol). The reaction mixture was stirred at room temperature for 1 h. The mixture was quenched with water, and the organic layer was dried over sodium sulfate, filtered, and concentrated under reduced pressure. The residue was purified by column chromatography on silica gel (5-40% EtOAc/DCM) to afford tert-butyl 6-{[trans-4-(propan-2-yloxy)cyclohexyl]carbonyl}-8-(trifluoromethyl)-5,6-dihydro-11H-pyrido[2,3-b][1,5]benzodiazepine-11-carboxylate as an oil. MS: 534 (M+1).

Step 2:

To tert-butyl 6-{[trans-4-(propan-2-yloxy)cyclohexyl]carbonyl}-8-(trifluoromethyl)-5,6-dihydro-11H-pyrido[2,3-b][1,5]benzodiazepine-11-carboxylate (60 mg, 0.11 mmol) was added HCl (4.0 M in dioxane, 2.0 mL, 71 mmol). The reaction mixture was stirred at 50° C. for 2 h, and then concentrated under reduced pressure. The residue was purified by mass triggered reverse phase HPLC (ACN/water with 0.1% TFA modifier) to afford the title compound as a solid TFA salt. MS: 434 (M+1). $^1$H NMR (500 MHz, DMSO-$d_6$) δ 9.92 (s, 1H), 8.15-8.06 (m, 1H), 7.66 (s, 1H), 7.61-7.46 (m, 3H), 6.85-6.78 (m, 1H), 5.18 (d, J=15.0 Hz, 1H), 3.97 (d, J=14.9 Hz, 1H), 3.60-3.52 (m, 1H), 3.16-3.06 (m, 1H), 2.33-2.22 (m, 1H), 1.92-1.82 (m, 2H), 1.69-1.63 (m, 1H), 1.50-1.39 (m, 1H), 1.12-1.01 (m, 1H), 0.98-0.93 (m, 6H), 0.93-0.80 (m, 2H), 0.66-0.55 (m, 1H).

Example 519: (Trans)-4-isopropoxycyclohexyl)(8-methoxy-5,11-dihydro-6H-benzo[b]pyrido[2,3-e][1,4]diazepin-6-yl)methanone

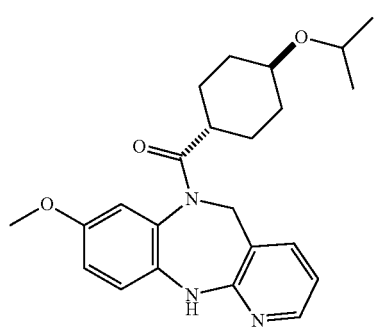

Step 1:

To a flask was added trans-4-(propan-2-yloxy)cyclohexanecarboxylic acid (60 mg, 0.32 mmol), and the material was dissolved in DCM (0.5 mL). The mixture was cooled to 0° C. and 1-chloro-N,N,2-trimethylprop-1-en-1-amine (49 µL, 0.37 mmol) was added dropwise. The mixture was warmed to room temperature and stirred for 30 minutes. This mixture was added directly to a solution of tert-butyl 8-methoxy-5,6-dihydro-11H-pyrido[2,3-b][1,5]benzodiazepine-11-carboxylate (100 mg, 0.305 mmol) dissolved in DCM (1.5 mL) and DIEA (0.213 mL, 1.22 mmol). The reaction mixture was stirred at room temperature for 1 h. The mixture was quenched with water, and the organic layer was dried over sodium sulfate, filtered, and concentrated under reduced pressure. The residue was purified by column chromatography on silica gel (5-40% EtOAc/DCM) to afford tert-butyl 8-methoxy-6-{[trans-4-(propan-2-yloxy)cyclohexyl]carbonyl}-5,6-dihydro-11H-pyrido[2,3-b][1,5]benzodiazepine-11-carboxylate as a solid. MS: 496 (M+1).

Step 2:

To tert-butyl 8-methoxy-6-{[trans-4-(propan-2-yloxy)cyclohexyl]carbonyl}-5,6-dihydro-11H-pyrido[2,3-b][1,5]benzodiazepine-11-carboxylate (124 mg, 0.250 mmol) was added HCl (4.0 M in dioxane, 2.0 mL, 32 mmol). The reaction mixture was stirred at 50° C. for 2 h, and then concentrated under reduced pressure to afford the title compound as a solid HCl salt. MS: 396 (M+1). $^1$H NMR (500 MHz, DMSO-$d_6$) δ 10.38 (s, 1H), 8.10 (d, J=5.5 Hz, 1H), 7.83-7.75 (m, 1H), 7.28 (d, J=8.8 Hz, 1H), 7.04-6.95 (m, 2H), 6.92-6.84 (m, 1H), 5.25 (d, J=15.2 Hz, 1H), 3.97 (d, J=15.1 Hz, 1H), 3.63-3.54 (m, 3H), 3.20-3.08 (m, 1H), 2.46-2.38 (m, 1H), 1.92-1.89 (m, 2H), 1.71-1.67 (m, 1H), 1.54-1.41 (m, 1H), 1.22-1.14 (m, 1H), 1.10-1.00 (m, 2H), 1.00-0.95 (m, 6H), 0.95-0.89 (m, 1H), 0.77-0.63 (m, 1H).

Example 520: [Trans-4-(propan-2-yloxy)cyclohexyl][2-(tetrahydro-2H-pyran-4-yl)-5,10-dihydro-11H-dipyrido[2,3-b:2',3'-e][1,4]diazepin-11-yl]methanone

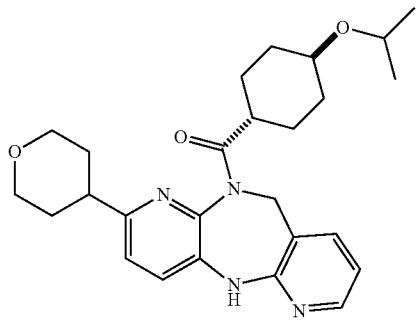

Step 1:

To an oven-dried, nitrogen-cooled vial was added 2-bromo-10,11-dihydro-5H-dipyrido[2,3-b:2',3'-e][1,4]diazepine (101 mg, 0.289 mmol), 4-(4,4,5,5-tetramethyl-1,3,2-dioxaborolan-2-yl)-3,6-dihydro-2H-pyran (73 mg, 0.35 mmol), and 3$^{rd}$ generation x-phos palladacycle (24 mg, 0.029 mmol). THF (1.5 mL) was added, followed by potassium phosphate, tribasic (0.5 M in water, 2.89 mL, 1.45 mmol), and the reaction mixture was heated to 50° C. for 16 h. The reaction was cooled to room temperature and diluted with EtOAc. The mixture was washed with water, and the organic layer was dried over sodium sulfate, filtered, and concentrated under reduced pressure. The residue was purified by column chromatography on silica gel (0-100% 3:1 EtOAc:EtOH/Hexanes) to afford 2-(3,6-dihydro-2H-pyran-4-yl)-10,11-dihydro-5H-dipyrido[2,3-b:2',3'-e][1,4]diazepine as a solid. MS: 281 (M+1).

Step 2:

To a flask containing palladium (10% on carbon, 23 mg, 0.021 mmol) and MeOH (3.2 mL) was added 2-(3,6-dihydro-2H-pyran-4-yl)-10,11-dihydro-5H-dipyrido[2,3-b:2', 3'-e][1,4]diazepine (60 mg, 0.21 mmol). The flask was evacuated and back filled 3× with hydrogen gas via a balloon, and the reaction was stirred under a hydrogen atmosphere at room temperature for 16 h. The reaction mixture was filtered over a pad of celite and the filtrate was concentrated under reduced pressure to afford 2-(tetrahydro-2H-pyran-4-yl)-10,11-dihydro-5H-dipyrido[2,3-b:2',3'-e][1,4]diazepine as an oil. MS: 283 (M+1).

Step 3:

To a flask was added trans-4-(propan-2-yloxy)cyclohexanecarboxylic acid (45 mg, 0.24 mmol), and the material was dissolved in DCM (0.34 mL). A drop of DMF was added, followed by oxalyl chloride (22 μL, 0.25 mmol), and the mixture was stirred at room temperature for 1 h. The mixture was concentrated to afford trans-4-(propan-2-yloxy) cyclohexanecarbonyl chloride, which was immediately dissolved in THF (0.9 mL) and added to a 0° C. solution of 2-(tetrahydro-2H-pyran-4-yl)-10,11-dihydro-5H-dipyrido [2,3-b:2',3'-e][1,4]diazepine (65 mg, 0.23 mmol) and NaHMDS (1.0 M in THF, 0.483 mL, 0.483 mmol) dissolved in THF (0.9 mL). The reaction mixture was stirred at 0° C. for 1 h. The mixture was quenched with water, and extracted with EtOAc (2×). The combined organic layers were dried over sodium sulfate, filtered, and concentrated under reduced pressure. The residue was purified by mass triggered reverse phase HPLC (ACN/water with 0.1% TFA modifier) to afford the title compound as a solid TFA salt. MS: 451 (M+1). $^1$H NMR (500 MHz, DMSO-d$_6$) δ 9.55 (s, 1H), 8.09-8.03 (m, 1H), 7.67 (d, J=8.3 Hz, 1H), 7.49 (d, J=7.3 Hz, 1H), 7.21 (d, J=8.3 Hz, 1H), 6.77-6.72 (m, 1H), 5.22 (s, 1H), 3.97-3.89 (m, 2H), 3.64-3.54 (m, 2H), 3.47-3.39 (m, 2H), 3.20-3.09 (m, 1H), 2.91-2.80 (m, 1H), 1.92-1.63 (m, 7H), 1.60-1.02 (m, 5H), 0.98 (d, J=6.1 Hz, 6H), 0.90-0.64 (m, 2H).

Example 521: [Trans-4-(2-hydroxypropan-2-yl)cyclohexyl][8-(morpholin-4-yl)-5,11-dihydro-6H-pyrido[2,3-b][1,5]benzodiazepin-6-yl]methanone

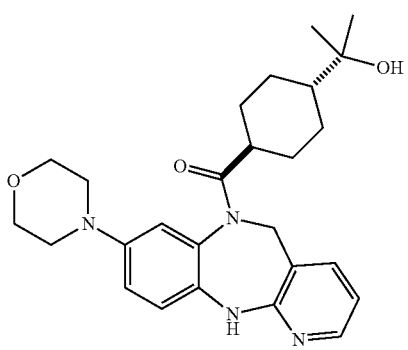

Step 1:

To a vial was added 8-(morpholin-4-yl)-6,11-dihydro-5H-pyrido[2,3-b][1,5]benzodiazepine (76 mg, 0.27 mmol), PS-PPh$_3$ (2.06 mmol/g loading, 392 mg, 0.808 mmol), trans-4-(methoxycarbonyl)cyclohexanecarboxylic acid (50 mg, 0.27 mmol), and acetonitrile (4.5 mL). Trichloroacetonitrile (0.135 mL, 1.35 mmol) was added and the reaction mixture was heated to 100° C. for 15 min in a microwave reactor. The material was filtered and concentrated under reduced pressure. The residue was purified by column chromatography on silica gel (0-100% 3:1 EtOAc:EtOH/Hexanes) to afford methyl trans-4-{[8-(morpholin-4-yl)-5,11-dihydro-6H-pyrido[2,3-b][1,5]benzodiazepin-6-yl]carbonyl}cyclohexanecarboxylate as a solid. MS: 451 (M+1).

Step 2:

Methylmagnesium bromide (3.0 M in diethyl ether, 91 μL, 0.27 mmol) was added dropwise to a 0° C. solution of methyl trans-4-{[8-(morpholin-4-yl)-5,11-dihydro-6H-pyrido[2,3-b][1,5]benzodiazepin-6-yl]carbonyl}cyclohexanecarboxylate (41 mg, 0.091 mmol) in THF (0.91 mL) under a nitrogen atmosphere. The reaction was allowed to slowly warmed to room temperature and was stirred for 16 h. The mixture was quenched with water and extracted with EtOAc. The organic layer was dried over sodium sulfate, filtered, and concentrated under reduced pressure. The residue was purified by mass triggered reverse phase HPLC (ACN/water with 0.1% TFA modifier) to afford the title compound as a solid TFA salt. MS: 451 (M+1). $^1$H NMR (500 MHz, DMSO-d$_6$) δ 9.42 (s, 1H), 8.01 (d, J=5.0 Hz, 1H), 7.53 (d, J=7.0 Hz, 1H), 7.22 (d, J=8.9 Hz, 1H), 6.94 (dd, J=2.7, 8.9 Hz, 1H), 6.84-6.80 (m, 1H), 6.76-6.68 (m, 1H), 5.20 (d, J=15.1 Hz, 1H), 3.90 (d, J=15.0 Hz, 1H), 3.77-3.69 (m, 4H), 3.14-3.04 (m, 2H), 3.04-2.95 (m, 2H), 2.41-2.31 (m, 1H), 1.97-1.88 (m, 1H), 1.81-1.73 (m, 1H), 1.61-1.54 (m, 1H), 1.43-1.31 (m, 2H), 1.28-1.19 (m, 1H), 1.08-0.95 (m, 2H), 0.92 (d, J=1.9 Hz, 6H), 0.85-0.73 (m, 1H), 0.65-0.49 (m, 1H).

Example 522: Cyclohex-3-en-1-yl[8-(morpholin-4-yl)-5,11-dihydro-6H-pyrido[2,3-b][1,5]benzodiazepin-6-yl]methanone

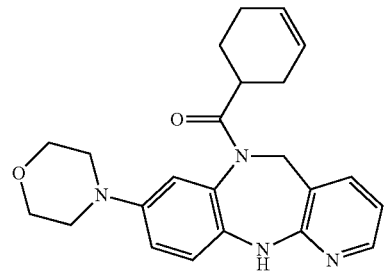 [SMILES: O=C(C1CC=CCC1)N1Cc2cccnc2Nc2ccc(N3CCOCC3)cc21]

To a flask was added 8-(morpholin-4-yl)-6,11-dihydro-5H-pyrido[2,3-b][1,5]benzodiazepine (60 mg, 0.21 mmol), PS-PPh$_3$ (2.06 mmol/g loading, 309 mg, 0.638 mmol), trans-4-(difluoromethoxy)cyclohexanecarboxylic acid (41 mg, 0.21 mmol), and acetonitrile (3.5 mL). Trichloroacetonitrile (0.107 mL, 1.06 mmol) was added and the reaction mixture was heated to 100° C. for 15 min in a microwave reactor. The material was filtered and concentrated under reduced pressure. The residue was purified by mass triggered reverse phase HPLC (ACN/water with 0.1% TFA modifier) to afford the title compound as a solid TFA salt. MS: 391 (M+1). $^1$H NMR (500 MHz, DMSO-d$_6$) δ 9.57 (s, 1H), 8.02 (d, J=4.0 Hz, 1H), 7.59 (s, 1H), 7.22 (dd, J=3.4, 8.9 Hz, 1H), 6.95 (d, J=8.9 Hz, 1H), 6.93-6.88 (m, 1H), 6.79-6.72 (m, 1H), 5.67-5.40 (m, 2H), 5.24 (d, J=14.9 Hz, 1H), 3.94 (d, J=15.0 Hz, 1H), 3.75-3.68 (m, 3H), 3.14-3.05 (m, 2H), 3.05-2.98 (m, 2H), 2.78-2.60 (m, 1H), 2.27-2.07 (m, 1H), 2.07-1.91 (m, 1H), 1.90-1.64 (m, 2H), 1.59-1.45 (m, 2H), 1.28-1.08 (m, 1H).

Example 523 and 524: [8-(4-Hydroxytetrahydro-2H-pyran-4-yl)-5,11-dihydro-6H-pyrido[2,3-b][1,5]benzodiazepin-6-yl][trans-4-(propan-2-yloxy)cyclohexyl]methanone and [8-(4-methoxytetrahydro-2H-pyran-4-yl)-5,11-dihydro-6H-pyrido[2,3-b][1,5]benzodiazepin-6-yl][trans-4-(propan-2-yloxy)cyclohexyl]methanone

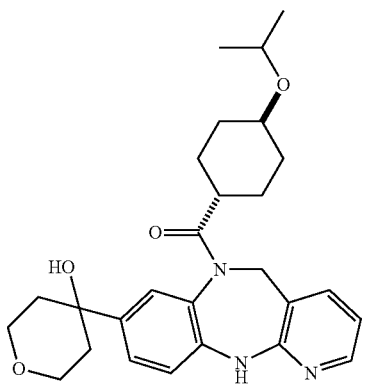

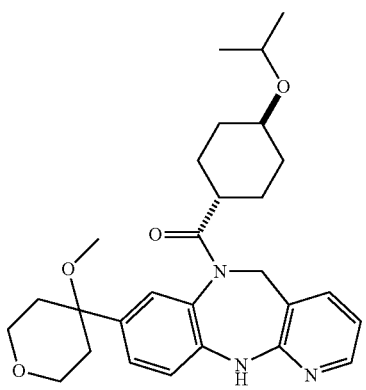

Step 1:

To a solution of (8-bromo-5,11-dihydro-6H-pyrido[2,3-b][1,5]benzodiazepin-6-yl)[trans-4-(propan-2-yloxy)cyclohexyl]methanone (100 mg, 0.23 mmol) in THF (4.5 mL) at −78° C. under a nitrogen atmosphere was added N-butyllithium (2.5 M, 0.29 mL, 0.73 mol). The reaction was stirred at −78° C. under a nitrogen atmosphere for 30 min, and then tetrahydro-4H-pyran-4-one (63 µL, 0.68 mmol) was added. The reaction mixture was allowed to slowly warm to room temperature and stir under an atmosphere of nitrogen for 1 h. The material was quenched with saturated aqueous ammonium chloride and extracted with EtOAc (2×). The combined organic layers were washed with brine, dried over sodium sulfate, filtered, and concentrated under reduced pressure. The residue was purified by column chromatography on silica gel (5-60% 3:1 EtOAc:EtOH/hexanes) to afford [8-(4-hydroxytetrahydro-2H-pyran-4-yl)-5,11-dihydro-6H-pyrido[2,3-b][1,5]benzodiazepin-6-yl][trans-4-(propan-2-yloxy)cyclohexyl]methanone as a solid. MS: 466 (M+1).

Step 2:

A solution of [8-(4-hydroxytetrahydro-2H-pyran-4-yl)-5,11-dihydro-6H-pyrido[2,3-b][1,5]benzodiazepin-6-yl][trans-4-(propan-2-yloxy)cyclohexyl]methanone (62 mg, 0.13 mmol) in DCM (3.3 mL) was cooled to −78° C. Diethylaminosulfur trifluoride (21 µL, 0.16 mmol) was added and the mixture was stirred at −78° C. for 30 min and then warmed to room temperature and stirred for 4 h. The reaction was quenched with saturated aqueous sodium bicarbonate (1 mL) and extracted with DCM (3×). The combined organic layers were washed with brine, dried over sodium sulfate, filtered, and concentrated to afford and 80:20 mixture of [8-(4-fluorotetrahydro-2H-pyran-4-yl)-5,11-dihydro-6H-pyrido[2,3-b][1,5]benzodiazepin-6-yl][trans-4-(propan-2-yloxy)cyclohexyl]methanone and [8-(3,6-dihydro-2H-pyran-4-yl)-5,11-dihydro-6H-pyrido[2,3-b][1,5]benzodiazepin-6-yl][trans-4-(propan-2-yloxy)cyclohexyl]methanone as a solid: MS: 468 and 448, respectively (M+1).

Step 3:

To an 80:20 mixture of [8-(4-fluorotetrahydro-2H-pyran-4-yl)-5,11-dihydro-6H-pyrido[2,3-b][1,5]benzodiazepin-6-yl][trans-4-(propan-2-yloxy)cyclohexyl]methanone and [8-(3,6-dihydro-2H-pyran-4-yl)-5, 11-dihydro-6H-pyrido[2,3-b][1,5]benzodiazepin-6-yl][trans-4-(propan-2-yloxy)cyclohexyl]methanone (59 mg, 0.13 mmol) dissolved in MeOH (0.63 mL) was added sodium methoxide (5.4 M in MeOH, 47 µL, 0.25 mmol). The mixture was stirred at room temperature for 1 h, and then quenched with water. The aqueous layer was extracted with EtOAc (2×), and the combined organic layers were washed with brine, dried over sodium sulfate, filtered, and concentrated under reduced pressure. The residue purified by mass triggered reverse phase HPLC (acetonitrile/water with 0.1% TFA modifier) to afford the two title compounds as a solids as follows:

[8-(4-methoxytetrahydro-2H-pyran-4-yl)-5,11-dihydro-6H-pyrido[2,3-b][1,5]benzodiazepin-6-yl][trans-4-(propan-2-yloxy)cyclohexyl]methanone. MS: 480 (M+1). $^1$H NMR (499 MHz, DMSO-$d_6$) δ 9.47 (s, 1H), 8.03 (dd, J=4.8, 1.7 Hz, 1H), 7.49-7.43 (m, 1H), 7.34 (d, J=8.5 Hz, 1H), 7.25 (dd, J=8.5, 2.1 Hz, 1H), 7.20 (d, J=2.1 Hz, 1H), 6.72 (dd, J=7.3, 4.8 Hz, 1H), 5.19 (d, J=14.9 Hz, 1H), 3.92 (d, J=14.8 Hz, 1H), 3.73-3.61 (m, 4H), 3.61-3.51 (m, 1H), 3.14-3.04 (m, 1H), 2.88 (s, 3H), 2.40-2.30 (m, 1H), 1.99-1.79 (m, 6H), 1.66 (d, J=11.9 Hz, 1H), 1.53-1.40 (m, 1H), 1.15-1.07 (m, 1H), 1.06-0.98 (m, 1H), 0.96 (dd, J=8.7, 6.1 Hz, 6H), 0.88-0.78 (m, 1H), 0.63-0.51 (m, 1H).

[8-(4-hydroxytetrahydro-2H-pyran-4-yl)-5,11-dihydro-6H-pyrido[2,3-b][1,5]benzodiazepin-6-yl][trans-4-(propan-2-yloxy)cyclohexyl]methanone. MS: 466 (M+1). $^1$H NMR (499 MHz, DMSO-$d_6$) δ 9.38 (s, 1H), 8.02 (dd, J=4.8, 1.7 Hz, 1H), 7.44 (d, J=7.2 Hz, 1H), 7.32 (dd, J=8.6, 2.0 Hz, 1H), 7.29-7.24 (m, 2H), 6.70 (dd, J=7.2, 4.8 Hz, 1H), 5.19 (d, J=14.9 Hz, 1H), 5.02 (s, 1H), 3.88 (d, J=14.8 Hz, 1H), 3.81-3.73 (m, 2H), 3.72-3.65 (m, 2H), 3.62-3.41 (m, 1H), 3.16-3.10 (m, 1H), 2.41-2.32 (m, 1H), 2.02-1.81 (m, 3H), 1.69-1.62 (m, 1H), 1.57-1.40 (m, 2H), 1.30-1.20 (m, 2H), 1.16-1.08 (m, 1H), 1.06-0.99 (m, 1H), 0.96 (dd, J=8.4, 6.1 Hz, 6H), 0.93-0.81 (m, 1H), 0.67-0.57 (m, 1H).

Example 525: [8-(Cyclopropylsulfonyl)-5,11-dihydro-6H-pyrido[2,3-b][1,5]benzodiazepin-6-yl][trans-4-(propan-2-yloxy)cyclohexyl]methanone

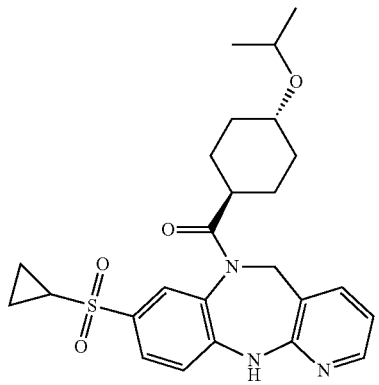 [SMILES: CC(C)O[C@H]1CC[C@H](C(=O)N2Cc3cccnc3Nc3ccc(S(=O)(=O)C4CC4)cc32)CC1]

Step 1:

To a vial was added (8-bromo-5,11-dihydro-6H-pyrido[2,3-b][1,5]benzodiazepin-6-yl)[trans-4-(propan-2-yloxy)cyclohexyl]methanone (2.0 g, 4.5 mmol), sodium iodide (1.3 g, 9.0 mmol), (1R,2R)—N,N'-dimethylcyclohexane-1,2-diamine (64 mg, 0.45 mmol), copper(I) iodide (43 mg, 0.23 mmol), and dioxane (22 mL). The mixture was purged with nitrogen for 5 minutes, sealed, and heated to 110° C. for 16 h. The reaction mixture was cooled to room temperature and another portion of copper(I) iodide (43 mg, 0.23 mmol) was added. The mixture was purged with nitrogen, sealed and heated to 110° C. for 12 h. The mixture was cooled, diluted with EtOAc, and washed with saturated aqueous sodium bicarbonate and brine. The organic layer was dried over magnesium sulfate, filtered, and concentrated under reduced pressure. The residue was purified by column chromatography on silica gel (0-100% EtOAc/hexanes) to afford (8-iodo-5,11-dihydro-6H-pyrido[2,3-b][1,5]benzodiazepin-6-yl)[trans-4-(propan-2-yloxy)cyclohexyl]methanone as a solid. MS: 492 (M+H)

Step 2:

To a vial was added sodium cyclopropanesulfinate (18 mg, 0.14 mmol), copper(I) trifluoromethanesulfonate benzene complex (3.6 mg, 0.0071 mmol), trans-N,N'-dimethylcyclohexane-1,2-diamine (1.7 μL, 0.011 mmol), sodium iodide (5.3 mg, 0.036 mmol), (8-iodo-5,11-dihydro-6H-pyrido[2,3-b][1,5]benzodiazepin-6-yl)[trans-4-(propan-2-yloxy)cyclohexyl]methanone (35 mg, 0.071 mmol). DMSO (0.8 mL) was added, and the vial was purged with nitrogen for 5 minutes. The reaction mixture was stirred at 120° C. under an atmosphere of nitrogen overnight. The reaction mixture was diluted with DMSO and filtered. The filtrate solution was purified by reverse phase HPLC (acetonitrile/water with 0.01% ammonia modifier) to afford the title compound as a solid. MS: 470 (M+H). $^1$H NMR (500 MHz, CDCl$_3$) δ 8.21 (s, 1H), 7.86 (s, 1H), 7.75 (dd, J=8.5, 2.1 Hz, 1H), 7.69 (d, J=2.1 Hz, 1H), 7.58 (d, J=7.3 Hz, 1H), 7.12 (d, J=8.5 Hz, 1H), 6.90 (s, 1H), 5.42 (d, J=14.9 Hz, 1H), 3.90 (d, J=14.8 Hz, 1H), 3.61 (hept, J=6.1 Hz, 1H), 3.16 (tt, J=10.8, 4.1 Hz, 1H), 2.46 (tt, J=7.9, 4.8 Hz, 1H), 2.36 (tt, J=11.7, 3.6 Hz, 1H), 2.06-1.91 (m, 2H), 1.82-1.63 (m, 2H), 1.39 (ddd, J=10.6, 4.8, 1.6 Hz, 1H), 1.30 (s, 1H), 1.36-1.17 (m, 2H), 1.13-0.99 (m, 9H), 0.90-0.78 (m, 1H).

Example 526: [Trans-4-(propan-2-yloxy)cyclohexyl][8-(tetrahydrofuran-2-yl)-5,11-dihydro-6H-pyrido[2,3-b][1,5]benzodiazepin-6-yl]methanone

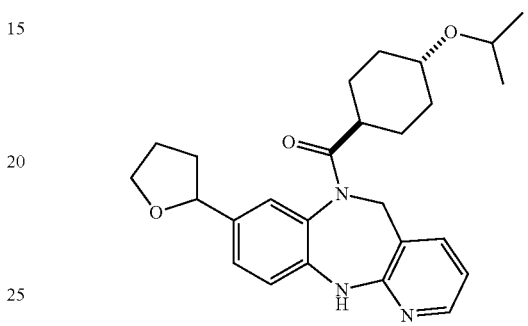

Step 1:

To a vial was added tert-butyl 8-bromo-6-{[trans-4-(propan-2-yloxy)cyclohexyl]carbonyl}-5,6-dihydro-11H-pyrido[2,3-b][1,5]benzodiazepine-11-carboxylate (0.040 g, 0.073 mmol), DTBBPY (2.9 mg, 0.011 mmol), and tetrahydrofuran-2-carboxylic acid (0.017 g, 0.15 mmol). The vial was moved to a glove box and then nickel chloride dimethoxyethane adduct (3.2 mg, 0.015 mmol), potassium phosphate tribasic (0.047 g, 0.22 mmol), Ir[dF(CF$_3$)ppy]$_2$(dtbbpy)PF$_6$ (2.1 mg, 1.8 μmol) and DMF (0.37 mL) were added. The reaction mixture was stirred under blue LED lamps for 3 days. The mixture was diluted with ethyl acetate and washed with saturated aqueous sodium bicarbonate and then brine. The organic layer was dried over sodium sulfate, filtered, and concentrated under reduced pressure. The residue was purified by reverse phase HPLC (acetonitrile/water, with 0.1% TFA modifier) to offer tert-butyl 6-{[trans-4-(propan-2-yloxy)cyclohexyl]carbonyl}-8-(tetrahydrofuran-2-yl)-5,6-dihydro-11H-pyrido[2,3-b][1,5]benzodiazepine-11-carboxylate as a solid. MS: 536 (M+1).

Step 2:

To a solution of tert-butyl 6-{[trans-4-(propan-2-yloxy)cyclohexyl]carbonyl}-8-(tetrahydrofuran-2-yl)-5,6-dihydro-11H-pyrido[2,3-b][1,5]benzodiazepine-11-carboxylate (7.6 mg, 0.014 mmol) in DCM (50 μL) was added TFA (50 μL, 0.71 mmol). The reaction was stirred at room temperature for 1 h. The mixture was concentrated under reduced pressure to the title compound as a solid. MS: 436 (M+1). $^1$H NMR (500 MHz, CD$_3$OD) δ 8.04 (d, J=5.5 Hz, 2H), 7.39 (d, J=5.4 Hz, 2H), 7.30 (s, 1H), 7.10 (t, J=6.9 Hz, 1H), 5.42 (d, J=15.3 Hz, 1H), 4.09 (qd, J=8.8, 5.7, 3.6 Hz, 2H), 3.99-3.89 (m, 1H), 3.68 (p, J=6.1 Hz, 1H), 3.28-3.12 (m, 3H), 2.53-2.22 (m, 2H), 2.10-1.96 (m, 4H), 1.80-1.50 (m, 3H), 1.32 (d, J=13.8 Hz, 1H), 1.27-1.16 (m, 1H), 1.06 (dd, J=9.5, 6.1 Hz, 6H), 0.91-0.78 (m, 1H).

Example 527: E and Z {8-[3-(Methoxyimino)cyclopentyl]-5,11-dihydro-6H-pyrido[2,3-b][1,5]benzodiazepin-6-yl}[trans-4-(propan-2-yloxy)cyclohexyl]methanone

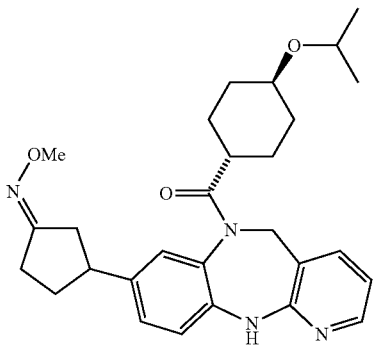

Step 1:
To a vial containing (8-bromo-5,11-dihydro-6H-pyrido[2,3-b][1,5]benzodiazepin-6-yl)[trans-4-(propan-2-yloxy)cyclohexyl]methanone (100 mg, 0.225 mmol), cyclopent-2-enone (37.0 mg, 0.450 mmol), diacetoxypalladium (2.5 mg, 0.011 mmol) and sodium carbonate (71.6 mg, 0.675 mmol) was added DMF (2 mL). The mixture was degassed and heated at 130° C. overnight. The mixture was cooled to room temperature, quenched with water, and extracted with EtOAc. The organic layer was washed with water and then brine, dried over sodium sulfate, filtered, and concentrated under reduced pressure. The residue was purified by column chromatography on silica gel (0-100% EtOAc/Hexanes) to afford 3-(6-{[trans-4-(propan-2-yloxy)cyclohexyl]carbonyl}-6,11-dihydro-5H-pyrido[2,3-b][1,5]benzodiazepin-8-yl)cyclopent-2-en-1-one as a solid. MS: 446 (M+H).

Step 2:
To a solution of 3-(6-{[trans-4-(propan-2-yloxy)cyclohexyl]carbonyl}-6,11-dihydro-5H-pyrido[2,3-b][1,5]benzodiazepin-8-yl)cyclopent-2-en-1-one (96 mg, 0.22 mmol) in EtOAc (2 mL) and methanol (2 mL) was added 10% Pd/C (23 mg, 0.022 mmol). The mixture was stirred at room temperature under an atmosphere of hydrogen for 16 h. The reaction was filtered and the filtrate was concentrated under reduced pressure. The residue was purified by column chromatography on silica gel (0-100% EtOAc/Hexanes) to afford 3-(6-{[trans-4-(propan-2-yloxy)cyclohexyl]carbonyl}-6,11-dihydro-5H-pyrido[2,3-b][1,5]benzodiazepin-8-yl)cyclopentanone as a solid. MS: 448 (M+H).

Step 3:
To a solution of 3-(6-{[trans-4-(propan-2-yloxy)cyclohexyl]carbonyl}-6,11-dihydro-5H-pyrido[2,3-b][1,5]benzodiazepin-8-yl)cyclopentanone (30 mg, 0.067 mmol) in pyridine (0.5 mL) was added O-methylhydroxylamine hydrochloride (11.2 mg, 0.13 mmol). The mixture was stirred at room temperature overnight. Saturated aqueous sodium bicarbonate was added and the mixture was diluted with water and then extracted with EtOAc (3×). The organic layer was washed with water and then brine, dried over sodium sulfate, filtered and concentrated under reduced pressure. The residue was purified by reverse phase HPLC (acetonitrile/water, with 0.15 TFA modifier) to afford the title compound as a mixture of E/Z isomers. MS: 477 (M+H). $^1$H NMR (500 MHz, CDCl$_3$) δ 12.5 (d, J=8.3 Hz 1H), 7.8 (dd, J=13.6, 6.8 Hz, 2H), 7.5 (m, 1H), 7.2 (m, 1H), 7.1 (s, 1H), 6.88 (m, 1H), 5.4 (d, J=15, 1H), 3.9 (s, 1H), 3.87 (s, 3H), 3.63 (m, 1H), 3.2 (m, 1H) 1.2-3.0 (m, 14H), 1.08 (t, J=6.3, 5.8 Hz, 6H).

Example 528: {8-[1-(Methylsulfonyl)piperidin-4-yl]-5,11-dihydro-6H-pyrido[2,3-b][1,5]benzodiazepin-6-yl}[trans-4-(propan-2-yloxy)cyclohexyl]methanone

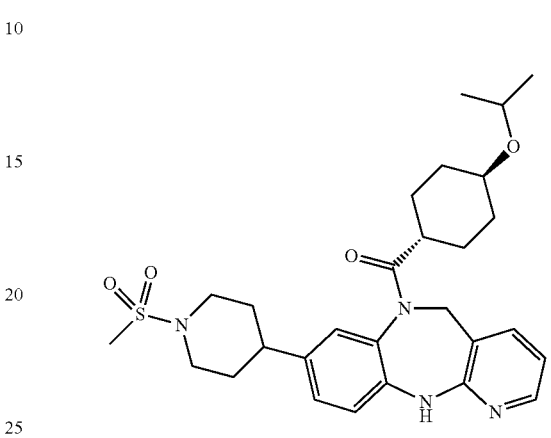

Step 1:
To a vial containing tert-butyl 4-(4,4,5,5-tetramethyl-1,3-dioxolan-2-yl)-5,6-dihydropyridine-1(2H)-carboxylate (210 mg, 0.675 mmol), (8-bromo-5,11-dihydro-6H-pyrido[2,3-b][1,5]benzodiazepin-6-yl)[trans-4-(propan-2-yloxy)cyclohexyl]methanone (200 mg, 0.450 mmol), and methanesulfonato(2-dicyclohexylphosphino-2',4',6'-tri-i-propyl-1,1'-biphenyl)(2'-amino-1,1'-biphenyl-2-yl)palladium(II) (38 mg, 0.045 mmol) was added THF (1 mL). The mixture was degassed, potassium phosphate (1.0 M in water, 2.25 ml, 2.25 mmol) was added, and the mixture was stirred at 80° C. overnight. Upon cooling to room temperature, the reaction mixture was filtered and the filtrate was concentrated under reduced pressure. The residue was purified by column chromatography on silica gel (0-100% EtOAc/Hexanes) to afford tert-butyl 4-(6-{[trans-4-(propan-2-yloxy)cyclohexyl]carbonyl}-6,11-dihydro-5H-pyrido[2,3-b][1,5]benzodiazepin-8-yl)-3,6-dihydropyridine-1(2H)-carboxylate as a solid. MS: 547 (M+H).

Step 2:
A solution of tert-butyl 4-(6-{[trans-4-(propan-2-yloxy)cyclohexyl]carbonyl}-6,11-dihydro-5H-pyrido[2,3-b][1,5]benzodiazepin-8-yl)-3,6-dihydropyridine-1(2H)-carboxylate (125 mg, 0.229 mmol) in EtOAc (2 mL) and methanol (2 mL) was added 10% Pd—C (24 mg, 0.023 mmol). The mixture was stirred at room temperature under an atmosphere of hydrogen for 16 h. The reaction was filtered and the filtrate was concentrated under reduced pressure. The residue was purified reverse phase HPLC (acetonitrile/water, with 0.1% TFA modifier) to afford tert-butyl 4-(6-{[trans-4-(propan-2-yloxy)cyclohexyl]carbonyl}-6,11-dihydro-5H-pyrido[2,3-b][1,5]benzodiazepin-8-yl)piperidine-1-carboxylate as a solid. MS: 549 (M+H).

Step 3:
To a solution of tert-butyl 4-(6-{[trans-4-(propan-2-yloxy)cyclohexyl]carbonyl}-6,11-dihydro-5H-pyrido[2,3-b][1,5]benzodiazepin-8-yl)piperidine-1-carboxylate (80 mg, 0.15 mmol) in DCM (2 mL) was added TFA (2 mL). The reaction mixture was stirred at room temperature for 1 h. The reaction mixture was concentrated under reduced pressure and the residue was purified by reverse phase HPLC (acetonitrile/ water, with 0.1% TFA modifier) to afford [8-(piperidin-4-yl)-5,11-dihydro-6H-pyrido[2,3-b][1,5]benzodiazepin-6-yl][trans-4-(propan-2-yloxy)cyclohexyl]methanone. The product above (10 mg, 0.018 mmol) was dissolved in DCM (0.5 mL), and then Hunig's base (16 µL, 0.089 mmol) and methanesulfonyl chloride (1.5 µL, 0.020 mmol) were added. The mixture was stirred at room temperature for 2 h. The reaction mixture was filtered and concentrated under reduced pressure. The residue was purified by reverse phase HPLC (acetonitrile/water, with 0.1% TFA modifier) to afford the title compound as a solid TFA salt. MS: 527 (M+H).

Examples 529 and 530: A mixture of trans isomers ((2R,5S)-5-Isopropoxytetrahydro-2H-pyran-2-yl)(8-(2-methyltetrahydrofuran-3-yl)-5,11-dihydro-6H-benzo[b]pyrido[2,3-e][1,4]diazepin-6-yl)methanone and ((2R,5S)-5-isopropoxytetrahydro-2H-pyran-2-yl)(8-(2-methyltetrahydrofuran-3-yl)-5,11-dihydro-6H-benzo[b]pyrido[2,3-e][1,4]diazepin-6-yl)methanone

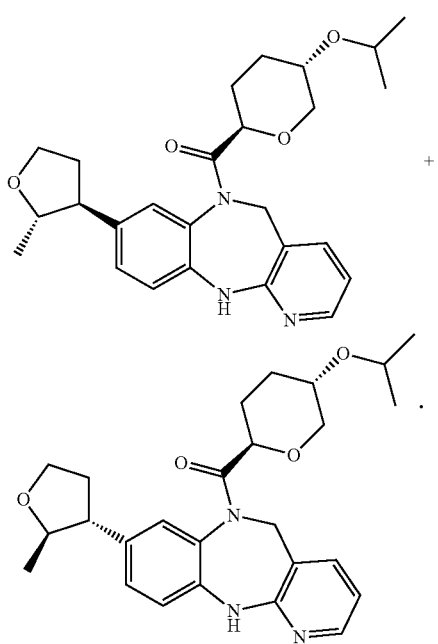

Example 530: Cis ((2R,5S)-5-isopropoxytetrahydro-2H-pyran-2-yl)(8-(2-methyltetrahydrofuran-3-yl)-5,11-dihydro-6H-benzo[b]pyrido[2,3-e][1,4]diazepin-6-yl)methanone

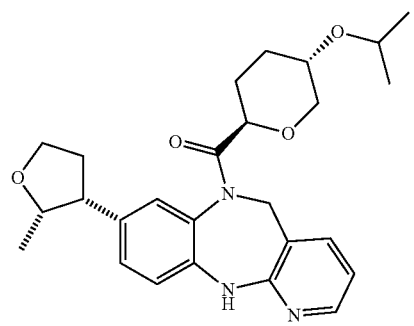

Example 531: Cis ((2R,5S)-5-isopropoxytetrahydro-2H-pyran-2-yl)(8-(2-methyltetrahydrofuran-3-yl)-5,11-dihydro-6H-benzo[b]pyrido[2,3-e][1,4]diazepin-6-yl)methanone

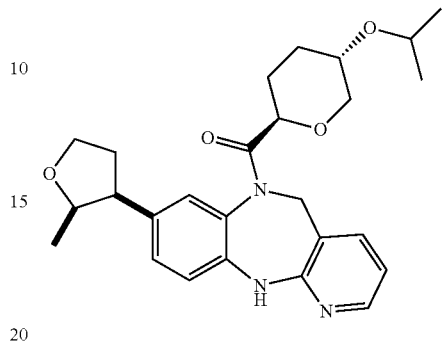

Step 1:
To an oven-dried vial was added 4,4,5,5-tetramethyl-2-(2-methylfuran-3-yl)-1,3,2-dioxaborolane (62 mg, 0.30 mmol), 8-bromo-6,11-dihydro-5H-benzo[b]pyrido[2,3-e][1,4]diazepine (55 mg, 0.20 mmol), and 3$^{rd}$ Generation X-Phos precatalyst (17 mg, 0.020 mmol). THF (1 mL) was added, followed by aqueous $K_3PO_4$ (0.5M, 1.2 mL, 0.60 mmol). The reaction was stirred at 50° C. for 4 h, then quenched with water and extracted with EtOAc (3×). The combined organic layers were dried over sodium sulfate, filtered, and concentrated under reduced pressure. The residue was purified by column chromatography on silica gel (5-50% EtOAc/EtOH [3:1 v/v] and hexanes) to afford 8-(2-methylfuran-3-yl)-6,11-dihydro-5H-benzo[b]pyrido[2,3-e][1,4]diazepine. MS: 278 (M+1).

Step 2:
(2R,5S)-5-Isopropoxytetrahydro-2H-pyran-2-carboxylic acid (39 mg, 0.21 mmol) was dissolved in dichloromethane (1.5 mL) and one drop of DMF. Oxalyl chloride (0.019 mL, 0.22 mmol) was added at room temperature and after 10 minutes of stirring, the reaction was evaporated and dried under vacuum. To a separate vial was added 8-(2-methylfuran-3-yl)-6,11-dihydro-5H-benzo[b]pyrido[2,3-e][1,4]diazepine (52 mg, 0.19 mmol) and DCE (1.5 mL). The mixture was heated at 80° C., followed by the addition of the above acid chloride dissolved in DCE (1.5 mL) and DMAP (23 mg, 0.19 mmol). The reaction was heated for 3 h, then quenched with saturated aqueous sodium bicarbonate and extracted with IPA/CHCl$_3$ (1:3 v/v; 3×). The combined organic layer was dried over sodium sulfate, filtered, and concentrated under reduced pressure. The residue was purified by reverse phase HPLC (ACN/water, with 0.1% TFA modifier) to afford ((2R,5S)-5-isopropoxytetrahydro-2H-pyran-2-yl)(8-(2-methylfuran-3-yl)-5,11-dihydro-6H-benzo[b]pyrido[2,3-e][1,4]diazepin-6-yl)methanone. MS: 448 (M+1).

Step 3:
((2R,5S)-5-isopropoxytetrahydro-2H-pyran-2-yl)(8-(2-methylfuran-3-yl)-5,11-dihydro-6H-benzo[b]pyrido[2,3-e][1,4]diazepin-6-yl)methanone (40 mg, 0.089 mmol) was added to a reaction vessel containing dihydroxypalladium (20 wt %, 13 mg, 0.019 mmol) and EtOH (2 mL) under argon. The flask was purged 3× with hydrogen gas and the reaction mixture was stirred at 50° C. for 3 h under 1 atm of hydrogen. Upon completion, the reaction mixture was filtered over Celite, rinsing with MeOH. The filtrate was concentrated under reduce pressure, and the residue was purified by reverse phase HPLC (ACN/water, with 0.1% TFA modifier) to afford racemic ((2R,5S)-5-isopropoxytetrahydro-2H-pyran-2-yl)(8-(2-methyltetrahydrofuran-3-yl)-5,11-dihydro-6H-benzo[b]pyrido[2,3-e][1,4]diazepin-6-yl)methanone. MS: 452 (M+H). The material was purified by chiral SFC to separate the enantiomers as follows: Chiralpak AD-H, 21×250 mm, isopropanol modifier with 0.25% dimethyl ethyl amine and 255 modifier in $CO_2$.

Peak 1 (Mixture of Trans Isomers):

((2R,5S)-5-isopropoxytetrahydro-2H-pyran-2-yl)(8-((2S, 3S and 2R,3R)-2-methyltetrahydrofuran-3-yl)-5H-benzo[b]pyrido[2,3-e][1,4]diazepin-6(11H)-yl)methanone. MS: 452 (M+1). $^1$H NMR (500 MHz, DMSO-$d_6$) δ 8.03 (s, 1H), 7.89 (s, 1H), 7.46 (d, J=8 Hz, 1H), 7.28-7.06 (m, 2H), 6.72 (m, 1H), 5.29 (d, J=15 Hz, 1H), 3.95 (m, 3H), 3.76 (m, 1H), 3.64 (m, 1H), 3.58 (m, 1H), 3.34 (m, 1H), 3.26 (m, 1H), 2.80 (m, 2H), 2.50 (m, 1H), 2.35 (m, 1H), 2.07 (m, 2H), 1.90 (m, 1H), 1.51 (m, 1H), 1.28 (m, 1H), 1.17 (m, 3H), 1.02-0.98 (m, 6H). Amide rotamers also observed in NMR.

Peak 2:

((2R,5S)-5-isopropoxytetrahydro-2H-pyran-2-yl)(8-((2S, 3R or 2R,3S)-2-methyltetrahydrofuran-3-yl)-5H-benzo[b]pyrido[2,3-e][1,4]diazepin-6(11H)-yl)methanone. MS: 452 (M+1). $^1$H NMR (500 MHz, DMSO-$d_6$) δ 9.5 (s, 1H), 8.04 (s, 1H), 7.50 (m, 1H), 7.26 (m, 1H), 7.04 (m, 2H), 6.71 (m, 1H), 5.21 (t, J=15 Hz, 1H), 4.04 (m, 2H), 3.93 (m, 3H), 3.72 (m, 1H), 3.64 (m, 1H), 3.32 (m, 2H), 2.75 (m, 3H), 2.14 (m, 1H), 2.10-1.81 (m, 1H) 1.04 (m, 1H), 1.00 (d, J=6.5 Hz, 6H), 0.96 (d, J=6.5 Hz, 1H), 0.77 (m, 3H). Amide rotamers also observed in NMR.

Peak 3:

((2R,5S)-5-isopropoxytetrahydro-2H-pyran-2-yl)(8-((2S, 3R or 2R,3S)-2-methyltetrahydrofuran-3-yl)-5H-benzo[b]pyrido[2,3-e][1,4]diazepin-6(11H)-yl)methanone. MS: 452 (M+1). $^1$H NMR (500 MHz, DMSO-$d_6$) δ 9.4 (s, 1H), 8.04 (s, 1H), 7.48 (m, 1H), 7.27 (m, 1H), 7.1 (s, 1H), 7.04 (m, 1H), 6.71 (m, 1H), 5.21 (t, J=15 Hz, 1H), 4.04 (m, 2H), 3.93 (m, 3H), 3.72 (m, 1H), 3.64 (m, 1H), 3.32 (m, 3H), 2.31 (m, 1H), 2.14 (m, 2H), 1.35 (m, 1H) 1.04 (d, J=6.5 Hz, 1H), 1.00 (d, J=6.5 Hz, 6H), 0.96 (d, J=6.5 Hz, 1H), 0.77 (d, J=6.5 Hz, 3H). Amide rotamers also observed in NMR.

The compounds in the following table were prepared using the methodology herein and the general procedure described in Example 531.

| Ex. No. | Structure | Compound Name | [M + H]+ |
|---|---|---|---|
| 532 | Cis/Trans Mixture | ((2R,5S)-5-isopropoxytetrahydro-2H-pyran-2-yl)(8-(4-methyltetrahydrofuran-3-yl)-5,11-dihydro-6H-benzo[b]pyrido[2,3-e][1,4]diazepin-6-yl)methanone | 452 |
| 533 | And diastereomer | ((2R,5S)-5-isopropoxytetrahydro-2H-pyran-2-yl)(8-(5-methyltetrahydrofuran-2-yl)-5,11-dihydro-6H-benzo[b]pyrido[2,3-e][1,4]diazepin-6-yl)methanone | 452 |
| 534 | Isomer 1, cis | ((2R,5S)-5-isopropoxytetrahydro-2H-pyran-2-yl)(8-((2R,5R)-5-methyltetrahydrofuran-2-yl)-5,11-dihydro-6H-benzo[b]pyrido[2,3-e][1,4]diazepin-6-yl)methanone | 452 |

| Ex. No. | Structure | Compound Name | [M + H]+ |
|---|---|---|---|
| 535 | Isomer 2, cis | ((2R,5S)-5-isopropoxytetrahydro-2H-pyran-2-yl)(8-((2S,5S)-5-methyltetrahydrofuran-2-yl)-5,11-dihydro-6H-benzo[b]pyrido[2,3-e][1,4]diazepin-6-yl)methanone | 452 |
| 536 | Isomer 1, cis | ((2R,5S)-5-isopropoxytetrahydro-2H-pyran-2-yl)(8-((3S,4S)-4-methyltetrahydrofuran-3-yl)-5,11-dihydro-6H-benzo[b]pyrido[2,3-e][1,4]diazepin-6-yl)methanone | 452 |
| 537 | Isomer 2, cis | ((2R,5S)-5-isopropoxytetrahydro-2H-pyran-2-yl)(8-((3R,4R)-4-methyltetrahydrofuran-3-yl)-5,11-dihydro-6H-benzo[b]pyrido[2,3-e][1,4]diazepin-6-yl)methanone | 452 |
| 538 | Isomer 3, trans | ((2R,5S)-5-isopropoxytetrahydro-2H-pyran-2-yl)(8-((3S,4R)-4-methyltetrahydrofuran-3-yl)-5,11-dihydro-6H-benzo[b]pyrido[2,3-e][1,4]diazepin-6-yl)methanone | 452 |
| 539 | Isomer 4, trans | ((2R,5S)-5-isopropoxytetrahydro-2H-pyran-2-yl)(8-((3R,4S)-4-methyltetrahydrofuran-3-yl)-5,11-dihydro-6H-benzo[b]pyrido[2,3-e][1,4]diazepin-6-yl)methanone | 452 |

Example 540: (8-(4-Fluorotetrahydrofuran-2-yl)-5,11-dihydro-6H-benzo[b]pyrido[2,3-e][1,4]diazepin-6-yl)((2R,5S)-5-isopropoxytetrahydro-2H-pyran-2-yl)methanone

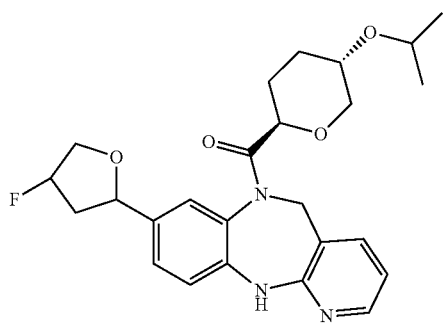 [SMILES: CC(C)O[C@H]1CC[C@H](C(=O)N2Cc3cccnc3Nc3ccc(C4CC(F)CO4)cc32)OC1]

To a solution of (8-(4-hydroxytetrahydrofuran-2-yl)-5,11-dihydro-6H-benzo[b]pyrido[2,3-e][1,4]diazepin-6-yl)((2R,5S)-5-isopropoxytetrahydro-2H-pyran-2-yl)methanone (6.8 mg, 0.015 mmol) in DCM (0.2 mL) was added DAST (5.9 μL, 0.045 mmol) at −78° C. The mixture was warmed to room temperature and stirred overnight. The mixture was concentrated under reduced pressure and purified by reverse phase HPLC (acetonitrile/water with 0.1% TFA modifier) to afford the title compound. MS: 456 (M+1). $^1$H NMR (500 MHz, Methanol-d4) δ 8.10-7.98 (m, 2H), 7.63-7.54 (m, 1H), 7.49-7.31 (m, 2H), 7.13-7.04 (m, 1H), 5.52-5.37 (m, 2H), 5.19-4.97 (m, 1H), 4.33 (td, J=23.3, 11.6 Hz, 1H), 4.09 (s, 1H), 4.17-3.81 (m, 3H), 3.75-3.56 (m, 1H), 3.39 (dp, J=16.4, 5.5 Hz, 1H), 2.98 (ddd, J=15.3, 10.8, 5.8 Hz, 1H), 2.81-2.74 (m, 1H), 2.69-2.55 (m, 1H), 2.19-2.09 (m, 1H), 2.09 (s, 1H), 1.74 (td, J=10.2, 3.4 Hz, 1H), 1.62-1.44 (m, 1H), 1.40-1.25 (m, 1H), 1.12-1.00 (m, 6H).

Example 541: (8-{1-[2-(Cyclobutyloxy)ethoxy]ethyl}-5,11-dihydro-6H-pyrido[2,3-b][1,5]benzodiazepin-6-yl)[trans-4-(propan-2-yloxy)cyclohexyl]methanone

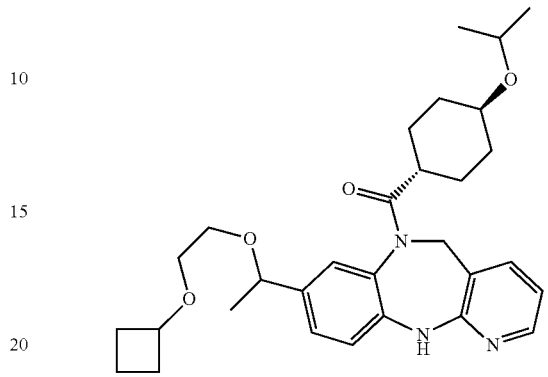

To a vial containing 2-cyclobutoxyethan-1-ol (120 mg, 1.03 mmol) was added [8-(1-chloroethyl)-5,11-dihydro-6H-pyrido[2,3-b][1,5]benzodiazepin-6-yl][trans-4-(propan-2-yloxy)cyclohexyl]methanone (25 mg, 0.058 mmol) and 1,4-dioxane (0.2 mL). The resulting reaction mixture was stirred at 90° C. for 16 h. The reaction was cooled to room temperature and concentrated under reduced pressure. The residue was purified by reverse phase HPLC (acetonitrile/water with 0.1% TFA modifier) to afford the title compound as a TFA salt. MS: 508 (M+1). $^1$H NMR (500 MHz, DMSO-d$_6$): δ 9.57 (d, J=8.1 Hz, 1H), 8.05 (s, 1H), 7.54 (d, J=7.2 Hz, 1H), 7.31 (t, J=10.1 Hz, 1H), 7.22-7.19 (m, 2H), 6.77 (t, J=6.1 Hz, 1H), 5.21 (d, J=15.0 Hz, 1H), 4.44 (dd, J=11.8, 6.2 Hz, 1H), 3.94-3.87 (m, 3H), 3.58 (t, J=6.2 Hz, 1H), 3.38-3.33 (m, 3H), 3.17-3.12 (m, 1H), 2.54 (s, 1H), 2.40-2.36 (m, 1H), 2.17-2.11 (m, 2H), 1.88-1.83 (m, 2H), 1.82-1.78 (m, 2H), 1.67-1.60 (m, 2H), 1.55-1.40 (m, 2H), 1.36-1.31 (m, 4H), 1.30-1.02 (m, 2H), 0.97 (t, J=7.0 Hz, 6H).

The compounds in the following table were prepared using the methodology herein and the general procedure described in Example 541.

| Ex. No. | Structure | Compound Name | [M + H]+ |
| --- | --- | --- | --- |
| 542 | 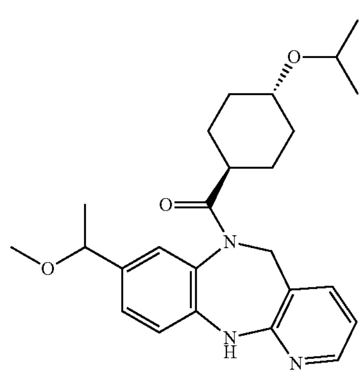 [SMILES: COC(C)c1ccc2c(c1)N(C(=O)[C@H]1CC[C@H](OC(C)C)CC1)Cc1cccnc1N2] | 8-(1-methoxyethyl)-6-{[trans-4-(1-methylethoxy)cyclohexyl]carbonyl}-6,11-dihydro-5H-pyrido[2,3-b][1,5]benzodiazepine | 424 |

| Ex. No. | Structure | Compound Name | [M + H]+ |
|---|---|---|---|
| 543 | 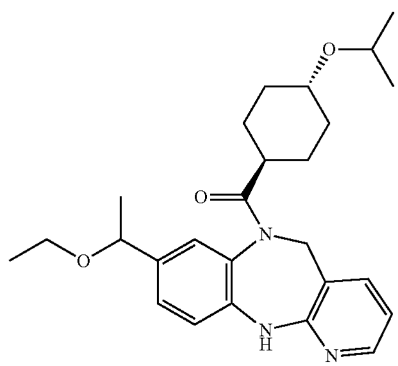 [SMILES: CCOC(C)c1ccc2c(c1)N(C(=O)[C@H]1CC[C@H](OC(C)C)CC1)Cc1cccnc1N2] | 8-(1-ethoxyethyl)-6-{[trans-4-(1-methylethoxy)cyclohexyl]carbonyl}-6,11-dihydro-5H-pyrido[2,3-b][1,5]benzodiazepine | 438 |
| 544 | 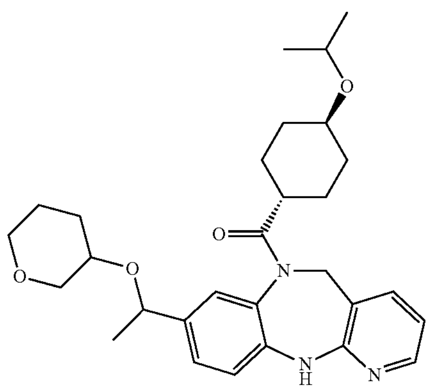 [SMILES: CC(C)O[C@H]1CC[C@H](C(=O)N2Cc3cccnc3Nc3ccc(C(C)OC4CCCOC4)cc32)CC1] | 6-{[trans-4-(1-methylethoxy)cyclohexyl]carbonyl}-8-[1-(tetrahydro-2H-pyran-3-yloxy)ethyl]-6,11-dihydro-5H-pyrido[2,3-b][1,5]benzodiazepine | 494 |
| 545 | 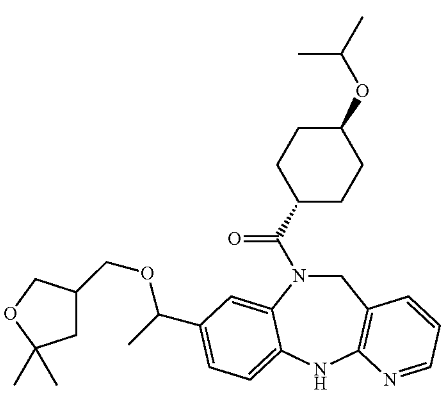 [SMILES: CC(C)O[C@H]1CC[C@H](C(=O)N2Cc3cccnc3Nc3ccc(C(C)OCC4COC(C)(C)C4)cc32)CC1] | 8-{1-[(5,5-dimethyltetrahydrofuran-3-yl)methoxy]ethyl}-6-{[trans-4-(1-methylethoxy)cyclohexyl]carbonyl}-6,11-dihydro-5H-pyrido[2,3-b][1,5]benzodiazepine | 522 |
| 546 | 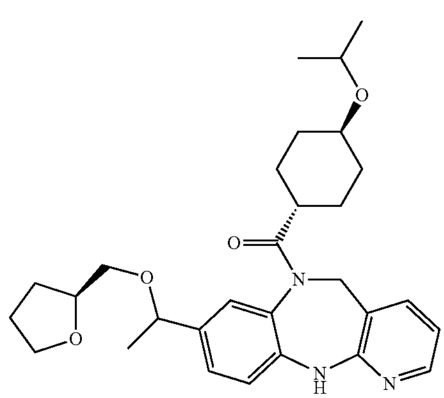 [SMILES: CC(C)O[C@H]1CC[C@H](C(=O)N2Cc3cccnc3Nc3ccc(C(C)OC[C@@H]4CCCO4)cc32)CC1] | 6-{[trans-4-(1-methylethoxy)cyclohexyl]carbonyl}-8-{1-[(2S)-tetrahydrofuran-2-ylmethoxy]ethyl}-6,11-dihydro-5H-pyrido[2,3-b][1,5]benzodiazepine | 494 |

Example 547: [Trans-4-(difluoromethoxy)cyclohexyl][8-(morpholin-4-yl)-5,11-dihydro-6H-pyrido[2,3-b][1,5]benzodiazepin-6-yl]methanone

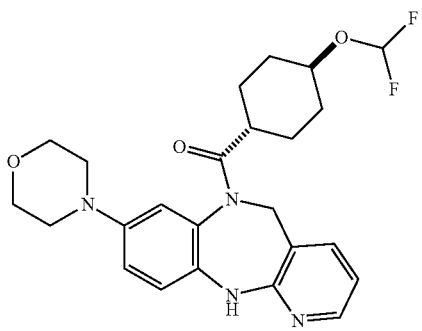

Step 1:

To a solution of trans-4-(difluoromethoxy)cyclohexanecarboxylic acid (73 mg, 0.37 mmol) in 1,2-dichloroethane (0.600 mL) was added 1-chloro-N,N,2-trimethylprop-1-en-1-amine (50 μL, 0.37 mmol). The reaction was stirred for 30 minutes at room temperature, and then added to a solution of 8-(morpholin-4-yl)-6,11-dihydro-5H-pyrido[2,3-b][1,5]benzodiazepine (100 mg, 0.354 mmol) dissolved in 1,2-dichloroethane (2 mL) and N,N-diisopropylethylamine (250 uL, 1.4 mmol). The reaction was stirred for 1 h at room temperature and then heated to reflux for 16 h. The reaction was quenched with water, and the organic layer was collected, dried over sodium sulfate, filtered, and concentrated under reduced pressure. The residue purified by mass triggered reverse phase HPLC (acetonitrile/water with 0.1% TFA modifier) to afford the title compound as a solid. MS: 459 (M+1). $^1$H NMR (499 MHz, DMSO-$d_6$) δ 9.12 (s, 1H), 7.98 (dd, J=5.0, 1.8 Hz, 1H), 7.44-7.37 (m, 1H), 7.22 (d, J=8.9 Hz, 1H), 6.92 (dd, J=9.0, 2.8 Hz, 1H), 6.81 (d, J=2.8 Hz, 1H), 6.69 and 6.55 (t, 1H), 6.64 (dd, J=7.3, 4.8 Hz, 1H), 5.17 (d, J=14.9 Hz, 1H), 3.94-3.83 (m, 2H), 3.76-3.68 (m, 4H), 3.13-3.03 (m, 2H), 3.03-2.91 (m, 2H), 2.01-1.86 (m, 3H), 1.80-1.63 (m, 2H), 1.58-1.33 (m, 2H), 1.20-1.01 (m, 1H), 1.00-0.88 (m, 1H).

Example 548: (Trans-4-tert-butoxycyclohexyl)[8-(6-methoxy-2-azaspiro[3.3]hept-2-yl)-5,11-dihydro-6H-pyrido[2,3-b][1,5]benzodiazepin-6-yl]methanone

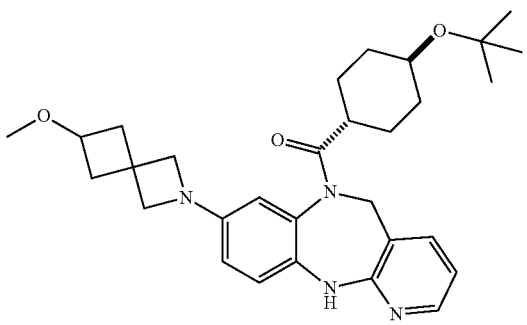

Step 1:

To a vial was added 6-methoxy-2-azaspiro[3.3]heptane, TFA (24 mg, 0.098 mmol), (8-bromo-5,11-dihydro-6H-pyrido[2,3-b][1,5]benzodiazepin-6-yl)(trans-4-tert-butoxycyclohexyl)methanone (30 mg, 0.065 mmol), and $3^{rd}$ gen t-Bu-XPhos PreCat (5.2 mg, 6.5 mol). Added NMP (0.75 mL) in a glovebox, and then added N'''—[P,P-bis(dimethylamino)-N-ethylphosphorimidoyl]-N,N,N',N',N'',N''-hexamethylphosphorimidic triamide (65 μL, 0.20 mmol) dissolved in NMP (0.375 mL) to the reaction mixture in a glovebox. The vial was capped, removed from the glovebox, and stirred at room temperature for 16 h. Added 4 volumes of 2-MeTHF and 4 volumes of saturated aqueous ammonium chloride, and the material was agitated and the organic layer was separated. The aqueous layer was back extracted with 4 volumes of 2-MeTHF and the combined organic layers were dried over sodium sulfate, filtered, and concentrated under reduced pressure. The residue purified by mass triggered reverse phase HPLC (acetonitrile/water with 0.1% TFA modifier) and then basified by washing with saturated aqueous sodium bicarbonate to afford the title compound as a solid. MS: 505 (M+1). $^1$H NMR (499 MHz, DMSO-$d_6$) δ 9.29 (s, 1H), 8.03-7.92 (m, 1H), 7.51 (d, J=7.2 Hz, 1H), 7.16 (d, J=8.7 Hz, 1H), 6.73-6.67 (m, 1H), 6.45-6.38 (m, 1H), 6.31 (s, 1H), 5.19 (d, J=15.0 Hz, 1H), 3.87 (d, J=15.0 Hz, 1H), 3.82-3.65 (m, 4H), 3.31-3.22 (m, 1H), 3.12 (s, 3H), 2.47-2.42 (m, 1H), 2.40-2.32 (m, 1H), 2.18 (s, 1H), 2.08-1.99 (m, 2H), 1.82 (d, J=13.4 Hz, 1H), 1.73 (d, J=12.6 Hz, 1H), 1.58-1.40 (m, 3H), 1.33-1.26 (m, 1H), 1.20-1.07 (m, 2H), 1.05 (s, 8H), 1.01-0.90 (m, 1H), 0.89-0.66 (m, 1H).

Example 549: [4-(Methoxyimino)cyclohexyl][8-(8-oxa-3-azabicyclo[3.2.1]oct-3-yl)-5,11-dihydro-6H-pyrido[2,3-b][1,5]benzodiazepin-6-yl]methanone

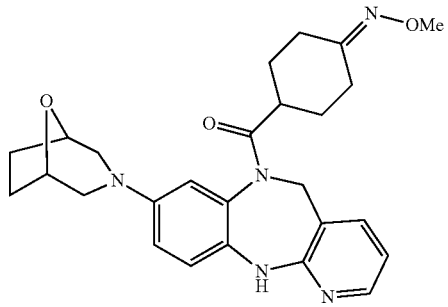 [SMILES: CON=C1CCC(C(=O)N2Cc3cccnc3Nc3ccc(N4CC5CCC(C4)O5)cc32)CC1]

To a vial containing of 4-{[8-(8-oxa-3-azabicyclo[3.2.1]oct-3-yl)-5,11-dihydro-6H-pyrido[2,3-b][1,5]benzodiazepin-6-yl]carbonyl}cyclohexanone (30 mg, 0.069 mmol) and O-methylhydroxylamine hydrochloride (5.8 mg, 0.069 mmol) was added pyridine (5 mL). The mixture was stirred overnight at room temperature. Saturated aqueous sodium bicarbonate was added and the mixture was diluted with water and then extracted with EtOAc (3×). The organic layer was washed with water and then brine, dried over sodium sulfate, filtered and concentrated under reduced pressure. The residue was purified by reverse phase HPLC (acetonitrile/water, with 0.1% TFA modifier) to the title compound as a solid. MS: 462 (M+H). $^1$H NMR (500 MHz, CDCl$_3$) δ 12 (s, 1H), 7.8 (m, 2H), 7.5 (d, J=9.2, 1H), 6.84 (m, 2H), 6.58 (s, 1H), 5.44 (d, J=15, 1H), 4.56 (s, 2H), 3.94 (d, J=15 Hz, 1H), 3.79 and 3.80 (two s, 3H), 1.5-3.4 (m, 17H).

The compounds in the following table were prepared using the methodology herein and the general procedure described in Examples 548-549.

| Ex. No. | Structure | Compound Name | [M + H]+ |
|---|---|---|---|
| 550 | 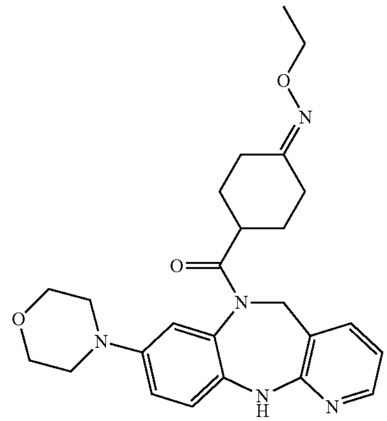 [SMILES: CCON=C1CCC(C(=O)N2Cc3cccnc3Nc3ccc(N4CCOCC4)cc32)CC1] | 4-[(8-morpholin-4-yl-5,11-dihydro-6H-pyrido[2,3-b][1,5]benzodiazepin-6-yl)carbonyl]cyclohexanone O-ethyloxime | 450 |
| 551 | 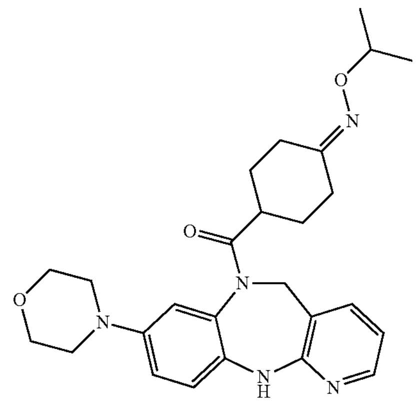 [SMILES: CC(C)ON=C1CCC(C(=O)N2Cc3cccnc3Nc3ccc(N4CCOCC4)cc32)CC1] | 4-[(8-morpholin-4-yl-5,11-dihydro-6H-pyrido[2,3-b][1,5]benzodiazepin-6-yl)carbonyl]cyclohexanone O-(1-methylethyl)oxime | 464 |

Example 552: [1-(2,2-Difluoroethyl)piperidin-4-yl][8-(morpholin-4-yl)-5,11-dihydro-6H-pyrido[2,3-b][1,5]benzodiazepin-6-yl]methanone

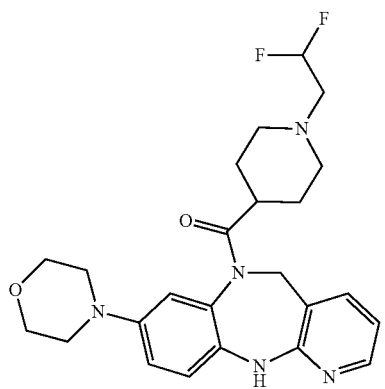 [SMILES: O=C(C1CCN(CC(F)F)CC1)N1Cc2cccnc2Nc2ccc(N3CCOCC3)cc21]

To a vial containing 2-bromo-1,1-difluoroethane (18 mg, 0.12 mmol) was added [8-(morpholin-4-yl)-5,11-dihydro-6H-pyrido[2,3-b][1,5]benzodiazepin-6-yl](piperidin-4-yl)methanone (25 mg, 0.064 mmol), NMP (1.5 mL), and sodium bicarbonate (16 mg, 0.19 mmol). The resulting reaction mixture was stirred at 110° C. for 16 h. The reaction was cooled to room temperature and filtered. The filtrate was purified by reverse phase HPLC (acetonitrile/water with 0.1% TFA modifier) to afford the title compound as a TFA salt. MS: 458 (M+1). $^1$H NMR (500 MHz, DMSO-$d_6$): δ 9.33 (s, 1H), 8.02 (d, J=4.9 Hz, 1H), 7.50 (d, J=7.3 Hz, 1H), 7.26 (d, J=8.9 Hz, 1H), 6.97 (d, J=9.2 Hz, 1H), 6.89 (s, 1H), 6.71 (dd, J=7.3, 5.0 Hz, 1H), 6.44 (t, J=53.6 Hz, 1H), 5.23 (d, J=15.0 Hz, 1H), 3.96 (d, J=14.9 Hz, 1H), 3.74 (m, 4H), 3.12-3.03 (m, 4H), 2.73-2.54 (m, 7H), 2.01-1.96 (m, 2H), 1.51-1.34 (m, 2H).

Example 553: (8-Morpholino-5,11-dihydro-6H-benzo[b]pyrido[2,3-e][1,4]diazepin-6-yl)(4-(2,2,2-trifluoroethyl)piperazin-1-yl)methanone

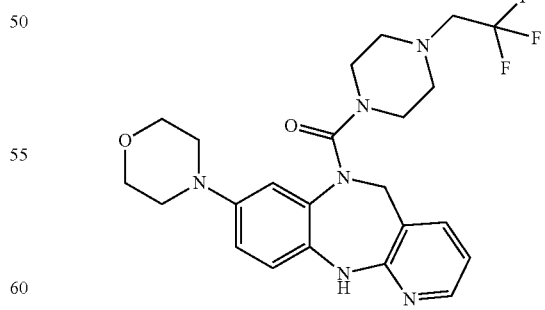

To a mixture of 3-methyl-1-(8-morpholino-6,11-dihydro-5H-benzo[b]pyrido[2,3-e][1,4]diazepine-6-carbonyl)-1H-imidazol-3-ium iodide (75 mg, 0.14 mmol) in DMF (1.0 mL) was added 1-(2,2,2-trifluoroethyl)piperazine (32 mg, 0.19 mmol) and ethyldiisopropylamine (34 μL, 0.19 mmol). The mixture was heated to 55° C. for 3 hours. Upon cooling to room temperature, the mixture was diluted with ethyl acetate and water. The organic layer was separated, dried over magnesium sulfate, filtered and concentrated under reduced pressure. The residue was purified by HPLC (acetonitrile gradient in water with a TFA modifier) to afford the title compound as the TFA salt. MS: 477 (M+H). $^1$H NMR (499 MHz, DMSO-$d_6$) δ 9.48 (s, 1H), 8.01 (dd, J=5.2, 1.7 Hz, 1H), 7.48 (d, J=7.1 Hz, 1H), 7.17 (d, J=8.9 Hz, 1H), 6.82 (dd, J=8.9, 2.7 Hz, 1H), 6.69 (dd, J=7.2, 5.2 Hz, 1H), 6.52 (d, J=2.7 Hz, 1H), 4.87-4.51 (m, 2H), 3.79-3.66 (m, 4H), 3.17-3.06 (m, 2H), 3.06-2.96 (m, 8H), 2.43-2.32 (m, 4H).

The compounds in the following table were prepared using the methodology herein and the general procedure described in Example 668.

Step 1:

A mixture of 4-(6,11-dihydro-5H-benzo[b]pyrido[2,3-e][1,4]diazepin-8-yl)morpholine (0.230 g, 0.815 mmol), polymer supported triphenylphosphine (0.64 g, 2.4 mmol). 4-(tert-butoxycarbonyl)-1,4-oxazepane-7-carboxylic acid (0.20 g, 0.82 mmol), trichloroacetonitrile (0.41 ml, 4.1 mmol), and triethylamine (0.34 ml, 2.4 mmol) in acetonitrile (8.2 ml) was stirred at 100° C. for 1 h under microwave irradiation. Upon cooling to room temperature, the reaction was filtered and rinsed with DCM. The filtrate was concentrated under reduced pressure and the residue was purified by column chromatography on silica gel (0-70% 3:1 EtOAc/EtOH in hexanes) to afford tert-butyl 7-{[8-(morpholin-4-

| Ex. No. | Structure | Compound Name | [M + H]+ |
|---|---|---|---|
| 554 | 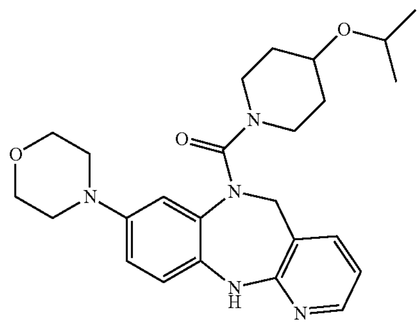 [SMILES: CC(C)OC1CCN(C(=O)N2Cc3cccnc3Nc3ccc(N4CCOCC4)cc32)CC1] | 6-{[4-(1-methylethoxy)piperidin-1-yl]carbonyl}-8-morpholin-4-yl-6,11-dihydro-5H-pyrido[2,3-b][1,5]benzodiazepine | 452 |
| 555 | 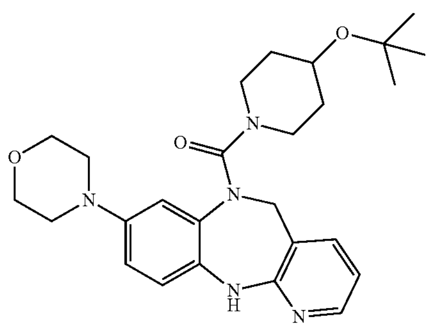 [SMILES: CC(C)(C)OC1CCN(C(=O)N2Cc3cccnc3Nc3ccc(N4CCOCC4)cc32)CC1] | 6-[(4-tert-butoxypiperidin-1-yl)carbonyl]-8-morpholin-4-yl-6,11-dihydro-5H-pyrido[2,3-b][1,5]benzodiazepine | 466 |

Example 556: (8-Morpholino-5,11-dihydro-6H-benzo[b]pyrido[2,3-e][1,4]diazepin-6-yl)(4-(2,2,2-trifluoroethyl)-1,4-oxazepan-7-yl)methanone

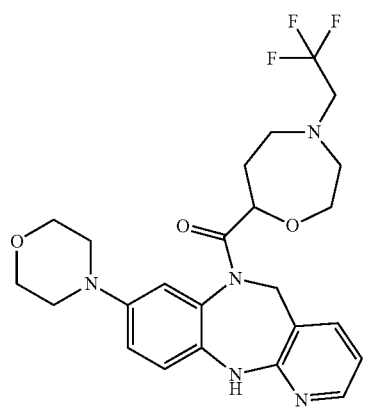 [SMILES: O=C(C1CCN(CC(F)(F)F)CCO1)N1Cc2cccnc2Nc2ccc(N3CCOCC3)cc21]

yl)-5,11-dihydro-6H-pyrido[2,3-b][1,5]benzodiazepin-6-yl]carbonyl}-1,4-oxazepane-4-carboxylate as a solid. MS: 510 (M+1).

Step 2:

To the solution of tert-butyl 7-{[8-(morpholin-4-yl)-5,11-dihydro-6H-pyrido[2,3-b][1,5]benzodiazepin-6-yl]carbonyl}-1,4-oxazepane-4-carboxylate (0.073 g, 0.14 mmol) in DCM (0.72 mL) was added HCl (4.0 M in 1,4-dioxane, 0.54 ml, 2.1 mmol). The mixture was stirred at room temperature for 1 h, and then concentrated under reduced pressure. The residue was diluted with DCM and washed with saturated aqueous sodium bicarbonate. The organic layer was dried over magnesium sulfate, filtered, and concentrated under reduced pressure to afford [8-(morpholin-4-yl)-5,11-dihydro-6H-pyrido[2,3-b][1,5]benzodiazepin-6-yl](1,4-oxazepan-7-yl)methanone, which was subsequently dissolved in DMF (0.72 mL). To the solution was added potassium carbonate (0.040 g, 0.29 mmol) and 2,2,2-trifluoroethyl trifluoromethanesulfonate (0.021 mL, 0.14 mmol). The reaction mixture was stirred at room temperature for 2 h and then was filtered and concentrated under reduced pressure. The residue was purified by reverse phase HPCL to the title compound. MS: 492 (M+1), $^1$H NMR (400 MHz, CDCl$_3$) δ 12.28 (s, 1H), 7.90 (dd, J=21.6, 6.7 Hz, 2H), 7.55 (m, 1H), 7.10 (t, J=10.6 Hz, 1H), 7.03 (s, 1H), 6.94 (t, J=6.7 Hz, 1H), 5.49-5.36 (m, 2H), 4.46-3.80 (m, 10H), 3.65-3.22 (m, 5H), 3.18 (d, J=11.7 Hz, 1H), 2.77 (s, 1H), 2.35 (m, 1H), 1.95 (m, 1H).

R132H IDH1 Enzymatic Assay

Each test compound (10 mM stock in DMSO) is diluted in DMSO to make a 10-point, 3-fold dilution series. 125 nL of each dilution or DMSO alone is dispensed to a 384-well Greiner Lumitrac 200 assay plate using an Echo® Liquid Handler. To each well of the plate is added 20 uL of enzyme in assay buffer or assay buffer alone. Assay buffer consists of 50 mM sodium phosphate, pH 7.0, 50 mM magnesium chloride, 50 mM sodium chloride, and 0.01% (w/v) bovine serum albumin. When present, the R132H mutant IDH1 enzyme is at a working concentration of 1.875 nM (final concentration in assay of 1.5 nM). The assay plate is allowed to incubate for 30 minutes at room temperature and 5 uL of 5× substrate mixture (2.5 uM nicotinamide adenine dinucleotide phosphate, 100 uM adenosine diphosphate, 7.5 mM glyceraldehyde-3-phosphate, 7.5 ug/mL of spinach glyceraldehyde-3-phosphate dehydrogenase, 25 nM phosphoglycerate kinase, and 5 mM alpha-ketoglutarate in assay buffer) is added to all wells. The reaction plate is incubated for 60 minutes followed by addition of 25 uL of Promega Kinase-GLO reagent to all wells and 10-minute incubation.

Luminescence is measured using a PerkinElmer Envision plate reader. The percent activity of each dilution is determined as the ratio of background corrected signal to the background corrected signal of wells receiving only DMSO. IC$_{50}$ values are determined by fitting percent activity data to a four-parameter logistic dose response equation. The IC$_{50}$ values of the exemplified compounds are included in the table below.

Using the above biological assay, all compounds in the examples have IC$_{50}$ of about 1 nM to about 25,000 nM, or more specifically, about 5 nM to about 20,000 nM, or even more specifically, about 10 nM to about 15,000 nM, or even more specifically, about 10 nM to about 10,000 nM, or still more specifically, about 10 nM to about 5,000 nM. Such a result is indicative of the intrinsic activity of the compounds in use as an inhibitor of a mutant IDH1 enzyme. Specific IC$_{50}$ activity data for the exemplified compounds disclosed herein is provided in the following table.

| Ex. No. | IC$_{50}$, nM |
| --- | --- |
| 1 | 73 |
| 2 | 76 |
| 3 | 273 |
| 4 | 152 |
| 5 | 283 |
| 6 | 151 |
| 7 | 182 |
| 8 | 76 |
| 9 | 206 |
| 10 | 396 |
| 11 | 934 |
| 12 | 42 |
| 13 | 58 |
| 14 | 16 |
| 15 | 20 |
| 16 | 19 |
| 17 | 52 |
| 18 | 54 |
| 19 | 18 |
| 20 | 72 |
| 21 | 77 |
| 22 | 9 |
| 23 | 6 |
| 24 | 87 |
| 25 | 45 |
| 26 | 15 |
| 27 | 10 |
| 28 | 7 |
| 29 | 36 |
| 30 | 30 |
| 31 | 36 |
| 32 | 16 |
| 33 | 46 |
| 34 | 29 |
| 35 | 69 |
| 36 | 12 |
| 37 | 21 |
| 38 | 49 |
| 39 | 16 |
| 40 | 17 |
| 41 | 22 |
| 42 | 50 |
| 43 | 76 |
| 44 | 35 |
| 45 | 72 |
| 46 | 57 |
| 47 | 54 |
| 48 | 26 |
| 49 | 5 |
| 50 | 686 |
| 51 | 662 |
| 52 | 654 |
| 53 | 771 |
| 54 | 562 |
| 55 | 286 |
| 56 | 492 |
| 57 | 337 |
| 58 | 458 |
| 59 | 931 |
| 60 | 70 |
| 61 | 595 |
| 62 | 112 |
| 63 | 487 |
| 64 | 154 |
| 65 | 346 |
| 66 | 113 |
| 67 | 354 |
| 68 | 53 |
| 69 | 344 |
| 70 | 36 |
| 71 | 975 |
| 72 | 561 |
| 73 | 927 |
| 74 | 330 |
| 75 | 83 |
| 76 | 489 |
| 77 | 676 |
| 78 | 82 |
| 79 | 168 |
| 80 | 404 |
| 81 | 527 |
| 82 | 52 |
| 83 | 81 |
| 84 | 636 |
| 85 | 807 |
| 86 | 801 |
| 87 | 204 |
| 88 | 980 |
| 89 | 104 |
| 90 | 104 |
| 91 | 126 |
| 92 | 282 |
| 93 | 218 |
| 94 | 561 |
| 95 | 78 |
| 96 | 111 |
| 97 | 94 |
| 98 | 469 |

| Ex. No. | IC$_{50}$, nM | | Ex. No. | IC$_{50}$, nM |
|---|---|---|---|---|
| 99 | 61 | | 176 | 286 |
| 100 | 75 | | 177 | 69 |
| 101 | 620 | | 178 | 152 |
| 102 | 120 | | 179 | 41 |
| 103 | 69 | | 180 | 212 |
| 104 | 75 | | 181 | 105 |
| 105 | 59 | | 182 | 164 |
| 106 | 155 | | 183 | 139 |
| 107 | 31 | | 184 | 556 |
| 108 | 505 | | 185 | 107 |
| 109 | 488 | | 186 | 617 |
| 110 | 50 | | 187 | 203 |
| 111 | 34 | | 188 | 99 |
| 112 | 84 | | 189 | 28 |
| 113 | 194 | | 190 | 3715 |
| 114 | 204 | | 191 | 39 |
| 115 | 440 | | 192 | 38 |
| 116 | 155 | | 193 | 125 |
| 117 | 91 | | 194 | 1040 |
| 118 | 30 | | 195 | 194 |
| 119 | 68 | | 196 | 614 |
| 120 | 298 | | 197 | 220 |
| 121 | 153 | | 198 | 761 |
| 122 | 740 | | 199 | 627 |
| 123 | 59 | | 200 | 663 |
| 124 | 120 | | 201 | 283 |
| 125 | 61 | | 202 | 564 |
| 126 | 126 | | 203 | 560 |
| 127 | 40 | | 204 | 732 |
| 128 | 71 | | 205 | 270 |
| 129 | 82 | | 206 | 205 |
| 130 | 155 | | 207 | 70 |
| 131 | 103 | | 208 | 103 |
| 132 | 64 | | 209 | 651 |
| 133 | 40 | | 210 | 250 |
| 134 | 546 | | 211 | 152 |
| 135 | 175 | | 212 | 286 |
| 136 | 19 | | 213 | 321 |
| 137 | 15 | | 214 | 327 |
| 138 | 4 | | 215 | 266 |
| 139 | 91 | | 216 | 332 |
| 140 | 14 | | 217 | 318 |
| 141 | 15 | | 218 | 198 |
| 142 | 26 | | 219 | 200 |
| 143 | 82 | | 220 | 165 |
| 144 | 11 | | 221 | 440 |
| 145 | 82 | | 222 | 491 |
| 146 | 26 | | 223 | 810 |
| 147 | 38 | | 224 | 846 |
| 148 | 19 | | 225 | 474 |
| 149 | 75 | | 226 | 475 |
| 150 | 125 | | 227 | 613 |
| 151 | 36 | | 228 | 618 |
| 152 | 46 | | 229 | 303 |
| 153 | 65 | | 230 | 312 |
| 154 | 56 | | 231 | 223 |
| 155 | 55 | | 232 | 686 |
| 156 | 38 | | 233 | 310 |
| 157 | 13 | | 234 | 724 |
| 158 | 24 | | 235 | 961 |
| 159 | 25 | | 236 | 195 |
| 160 | 15 | | 237 | 130 |
| 161 | 18 | | 238 | 989 |
| 162 | 49 | | 239 | 910 |
| 163 | 117 | | 240 | 181 |
| 164 | 1332 | | 241 | 165 |
| 165 | 954 | | 242 | 177 |
| 166 | 557 | | 243 | 83 |
| 167 | 167 | | 244 | 300 |
| 168 | 272 | | 245 | 286 |
| 169 | 51 | | 246 | 459 |
| 170 | 70 | | 247 | 342 |
| 171 | 121 | | 248 | 159 |
| 172 | 168 | | 249 | 69 |
| 173 | 144 | | 250 | 374 |
| 174 | 120 | | 251 | 326 |
| 175 | 16 | | 252 | 23 |

| Ex. No. | IC$_{50}$, nM |
|---|---|
| 253 | 295 |
| 254 | 894 |
| 255 | 567 |
| 256 | 215 |
| 257 | 221 |
| 258 | 266 |
| 259 | 660 |
| 260 | 153 |
| 261 | 191 |
| 262 | 722 |
| 263 | 105 |
| 264 | 286 |
| 265 | 150 |
| 266 | 141 |
| 267 | 749 |
| 268 | 623 |
| 269 | 334 |
| 270 | 251 |
| 271 | 689 |
| 272 | 546 |
| 273 | 272 |
| 274 | 224 |
| 275 | 287 |
| 276 | 819 |
| 277 | 519 |
| 278 | 597 |
| 279 | 231 |
| 280 | 447 |
| 281 | 94 |
| 282 | 211 |
| 283 | 285 |
| 284 | 223 |
| 285 | 271 |
| 286 | 223 |
| 287 | 404 |
| 288 | 865 |
| 289 | 498 |
| 290 | 115 |
| 291 | 123 |
| 292 | 678 |
| 293 | 589 |
| 294 | 846 |
| 295 | 428 |
| 296 | 698 |
| 297 | 564 |
| 298 | 54 |
| 299 | 55 |
| 300 | 48 |
| 301 | 116 |
| 302 | 46 |
| 303 | 37 |
| 304 | 13 |
| 305 | 77 |
| 306 | 24 |
| 307 | 16 |
| 308 | 64 |
| 309 | 100 |
| 310 | 26 |
| 311 | 175 |
| 312 | 30 |
| 313 | 43 |
| 314 | 95 |
| 315 | 79 |
| 316 | 88 |
| 317 | 39 |
| 318 | 43 |
| 319 | 18 |
| 320 | 9 |
| 321 | 35 |
| 322 | 6 |
| 323 | 12 |
| 324 | 18 |
| 325 | 20 |
| 326 | 14 |
| 327 | 32 |
| 328 | 19 |
| 329 | 12 |
| 330 | 12 |
| 331 | 3 |
| 332 | 3 |
| 333 | 6 |
| 334 | 43 |
| 335 | 59 |
| 336 | 18 |
| 337 | 14 |
| 338 | 43 |
| 339 | 30 |
| 340 | 30 |
| 341 | 27 |
| 342 | 26 |
| 343 | 24 |
| 344 | 9 |
| 345 | 13 |
| 346 | 5 |
| 347 | 5 |
| 348 | 12 |
| 349 | 17 |
| 350 | 68 |
| 351 | 13 |
| 352 | 138 |
| 353 | 67 |
| 354 | 95 |
| 355 | 224 |
| 356 | 55 |
| 357 | 107 |
| 358 | 44 |
| 359 | 40 |
| 360 | 52 |
| 361 | 97 |
| 362 | 307 |
| 363 | 187 |
| 364 | 44 |
| 365 | 127 |
| 366 | 291 |
| 367 | 110 |
| 368 | 276 |
| 369 | 203 |
| 370 | 149 |
| 371 | 68 |
| 372 | 20 |
| 373 | 145 |
| 374 | 11 |
| 375 | 62 |
| 376 | 59 |
| 377 | 48 |
| 378 | 63 |
| 379 | 20 |
| 380 | 29 |
| 381 | 15 |
| 382 | 46 |
| 383 | 83 |
| 384 | 28 |
| 385 | 39 |
| 386 | 18 |
| 387 | 33 |
| 388 | 26 |
| 389 | 21 |
| 390 | 11 |
| 391 | 36 |
| 392 | 26 |
| 393 | 98 |
| 394 | 30 |
| 395 | 4 |
| 396 | 4 |
| 397 | 20 |
| 398 | 36 |
| 399 | 287 |
| 400 | 582 |
| 401 | 219 |
| 402 | 73 |
| 403 | 53 |
| 404 | 83 |
| 405 | 91 |
| 406 | 648 |

| Ex. No. | IC$_{50}$, nM |
|---|---|
| 407 | 123 |
| 408 | 107 |
| 409 | 44 |
| 410 | 31 |
| 411 | 618 |
| 412 | 577 |
| 413 | 300 |
| 414 | 725 |
| 415 | 686 |
| 416 | 292 |
| 417 | 555 |
| 418 | 768 |
| 419 | 107 |
| 420 | 93 |
| 421 | 582 |
| 422 | 104 |
| 423 | 385 |
| 424 | 44 |
| 425 | 87 |
| 426 | 59 |
| 427 | 599 |
| 428 | 75 |
| 429 | 14 |
| 430 | 889 |
| 431 | 594 |
| 432 | 52 |
| 433 | 189 |
| 434 | 1392 |
| 435 | 73 |
| 436 | 62 |
| 437 | 534 |
| 438 | 890 |
| 439 | 237 |
| 440 | 920 |
| 441 | 449 |
| 442 | 691 |
| 443 | 56 |
| 444 | 155 |
| 445 | 95 |
| 446 | 203 |
| 447 | 45 |
| 448 | 123 |
| 449 | 83 |
| 450 | 221 |
| 451 | 128 |
| 452 | 139 |
| 453 | 33 |
| 454 | 115 |
| 455 | 175 |
| 456 | 108 |
| 457 | 90 |
| 458 | 87 |
| 459 | 237 |
| 460 | 870 |
| 461 | 36 |
| 462 | 43 |
| 463 | 48 |
| 464 | 85 |
| 465 | 48 |
| 466 | 43 |
| 467 | 46 |
| 468 | 44 |
| 469 | 40 |
| 470 | 64 |
| 471 | 51 |
| 472 | 57 |
| 473 | 21 |
| 474 | 251 |
| 475 | 191 |
| 476 | 480 |
| 477 | 918 |
| 478 | 185 |
| 479 | 843 |
| 480 | 576 |
| 481 | 568 |
| 482 | 506 |
| 483 | 123 |
| 484 | 209 |
| 485 | 102 |
| 486 | 418 |
| 487 | 308 |
| 488 | 378 |
| 489 | 876 |
| 490 | 529 |
| 491 | 19 |
| 492 | 974 |
| 493 | 4 |
| 494 | 763 |
| 495 | 543 |
| 496 | 3342 |
| 497 | 76 |
| 498 | 42 |
| 499 | 125 |
| 500 | 463 |
| 501 | 98 |
| 502 | 574 |
| 503 | 73 |
| 504 | 273 |
| 505 | 502 |
| 506 | 164 |
| 507 | 43 |
| 508 | 39 |
| 509 | 233 |
| 510 | 206 |
| 511 | 277 |
| 512 | 47 |
| 513 | 54 |
| 514 | 90 |
| 515 | 6 |
| 516 | 8 |
| 517 | 822 |
| 518 | 55 |
| 519 | 72 |
| 520 | 200 |
| 521 | 133 |
| 522 | 669 |
| 523 | 68 |
| 524 | 39 |
| 525 | 8 |
| 526 | 26 |
| 527 | 9 |
| 528 | 11 |
| 529 | 6 |
| 530 | 29 |
| 531 | 13 |
| 532 | 5 |
| 533 | 17 |
| 534 | 65 |
| 535 | 34 |
| 536 | 35 |
| 537 | 11 |
| 538 | 5 |
| 539 | 9 |
| 540 | 59 |
| 541 | 13 |
| 542 | 22 |
| 543 | 21 |
| 544 | 20 |
| 545 | 11 |
| 546 | 17 |
| 547 | 18 |
| 548 | 21 |
| 549 | 31 |
| 550 | 145 |
| 551 | 137 |
| 552 | 930 |
| 553 | 280 |
| 554 | 294 |
| 555 | 178 |
| 556 | 390 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:
1. A compound of Formula I:

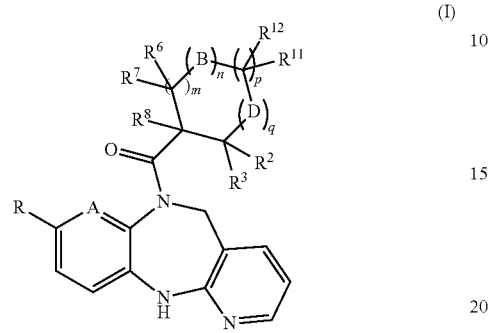

(I)

wherein
A is —C($R^1$)= or N=, and $R^1$ is hydrogen or hydroxyl;
B is C($R^9$)($R^{10}$)—, —N($R^{10}$)—, —O—, —S— or —S(O)$_2$—;
D is —C($R^4$)($R^5$)—, —N($R^5$)—, —O— or —S—;
m is 0, 1 or 2; n is 0 or 1; p is 0, 1 or 2; q is 0 or 1; with the proviso that at least one of m, n, p and q is not 0;
R is selected from the group consisting of:
 (1) halogen,
 (2) —CN,
 (3) —(C=O)$_t$—$R^a$, wherein t is 0 or 1, and
 (4) —S(O)$_2R^a$;
each occurrence of $R^2$, $R^3$, $R^4$, $R^6$, $R^7$ and $R^9$ is independently selected from the group consisting of:
 (1) halogen,
 (2) —CN, and
 (3) —(C=O)$_t$—$R^a$, wherein t is 0 or 1;
each occurrence of $R^5$ and $R^{10}$ is independently selected from the group consisting of:
 (1) hydrogen,
 (2) $C_{1-6}$alkyl, optionally substituted with one to four substituents independently selected from $R^b$; and
 (3) $C_{3-7}$cycloalkyl, optionally substituted with one to four substituents independently selected from $R^b$;
$R^8$ is selected from the group consisting of:
 (1) hydrogen,
 (2) halogen,
 (3) —CN,
 (4) —O—$R^a$,
 (5) —(C=O)—NR$^j$R$^k$, wherein each of R$^j$ and R$^k$ is independently selected from the group consisting of hydrogen and $C_{1-6}$alkyl,
 (6) $C_{1-6}$alkyl, optionally substituted with one to four substituents independently selected from $R^b$,
 (7) $C_{2-6}$ alkenyl, and
 (8) phenyl, optionally substituted with one to four substituents independently selected from $R^b$;
$R^{11}$ and $R^{12}$ together form an oxo; or alternatively, each occurrence of $R^{11}$ and $R^{12}$ is independently selected from the group consisting of:
 (1) halogen,
 (2) —CN, and
 (3) —(C=O)$_t$—$R^a$, wherein t is 0 or 1;
each occurrence of $R^a$ is independently selected from the group consisting of:
 (1) hydrogen,
 (2) —(O)$_t$—$R^d$, wherein t is 0 or 1; $R^d$ is selected from the group consisting of (a) hydrogen, (b) $C_{1-6}$alkyl, (c) $C_{3-7}$cycloalkyl, and (d) phenyl;
  wherein each of the $C_{1-6}$alkyl of (b) and $C_{3-7}$cycloalkyl of (c) is optionally substituted with one to four substituents independently selected from $R^b$,
 (3) —NR$^x$R$^y$, wherein each of R$^x$ and R$^y$ is independently selected from the group consisting of (a) hydrogen, (b) $C_{1-6}$alkyl, (c) $C_{3-6}$cycloalkyl, (d) —O—$C_{1-6}$alkyl, (e) phenyl optionally substituted with one to four halogens, and (f) heterocyclyl;
  wherein the $C_{1-6}$alkyl of (b) is optionally substituted with one to four substituents independently selected from halogen, —O—$C_{1-4}$alkyl, $C_{3-6}$cycloalkyl, and heterocyclyl; and
  the $C_{3-6}$cycloalkyl of (c) is optionally substituted with one to four substituents independently selected from halogen, —O—$C_{1-4}$alkyl, $C_{3-6}$cycloalkyl, heterocyclyl, and $C_{1-4}$alkyl, which is optionally substituted with one to four halogens,
  the heterocyclyl of (f) is optionally substituted with one to four substituents independently selected from halogen, $C_{1-4}$alkyl, —O—$C_{1-4}$alkyl, $C_{3-6}$cycloalkyl, and heterocyclyl,
 (4) $C_{2-6}$alkenyl, optionally substituted with one to four substituents independently selected from $R^b$,
 (5) $C_{5-6}$cycloalkenyl, optionally substituted with one to four substituents independently selected from $R^b$,
 (6) aryl, optionally substituted with one to four substituents independently selected from $R^b$, and
 (7) heterocyclyl, optionally substituted with one to four substituents independently selected from $R^b$;
each occurrence of $R^b$ is independently selected from the group consisting of:
 (1) halogen,
 (2) —CN,
 (3) oxo,
 (4) —(O)$_t$—$R^d$, wherein t is 0 or 1; $R^d$ is selected from the group consisting of (a) hydrogen, (b) $C_{1-6}$alkyl, (c) $C_{3-7}$cycloalkyl, and (d) heterocyclyl;
  wherein the $C_{1-6}$alkyl of (b) is optionally substituted with one to four substituents independently selected from (i) halogen, (ii) hydroxyl, (iii) —O—$C_{1-6}$alkyl, (iv) $C_{3-6}$cycloalkyl optionally substituted with 1-3 halogens, (v) —NR$^x$R$^y$, wherein each of R$^x$ and R$^y$ is independently selected from the group consisting of hydrogen, $C_{1-6}$alkyl, $C_{3-6}$cycloalkyl, phenyl optionally substituted with one to four halogens, and heterocyclyl, and (vi) heterocyclyl;
  the $C_{3-7}$cycloalkyl of (c) is optionally substituted with one to four substituents independently selected from (i) halogen, and (ii) $C_{1-6}$ alkyl, which is optionally substituted with one to four halogens, and (iii) —CN; and
  the heterocyclyl of (d) is optionally substituted with one to four substituents independently selected from (i) halogen, (ii) hydroxyl, (iii) oxo, (iv) $C_{1-6}$ alkyl optionally substituted with one to four halogens, (v) —O—$C_{1-6}$alkyl, (vi) heterocyclyl optionally substituted with halogen or hydroxyl, and (vii) —NR$^j$R$^k$, wherein each of R$^j$ and R$^k$ is independently selected from the group consisting of hydrogen and $C_{1-6}$alkyl,

473

(5) —(C=O)$_t$—R$^c$, wherein t is 0 or 1; R$^c$ is selected from the group consisting of hydrogen, hydroxyl, C$_{1-6}$alkyl, C$_{2-6}$alkenyl, —O—C$_{1-6}$6 alkyl, —NR$^x$R$^y$, and heterocyclyl;
   wherein each of R$^x$ and R$^y$ is independently selected from the group consisting of (a) hydrogen, (b) C$_{1-6}$alkyl, (c) C$_{2-6}$alkenyl, (d) C$_{3-6}$cycloalkyl, (e) phenyl optionally substituted with one to four halogens, and (f) heterocyclyl;
   wherein the C$_{1-6}$alkyl of (b) is optionally substituted with one to four substituents independently selected from halogen, —O—C$_{1-4}$alkyl, C$_{3-6}$cycloalkyl, heterocyclyl, and —(C=O)—NR$^j$R$^k$, wherein each of R$^j$ and R$^k$ is independently hydrogen or C$_{1-6}$alkyl;
   the C$_{3-6}$cyclolkyl of (d) is optionally substituted with one to four substituents independently selected from halogen and C$_{1-4}$alkyl, which is optionally substituted with one to four halogens; and
   the heterocyclyl of (f) is optionally substituted with one to four substituents independently selected from halogen, —CN, C$_{1-6}$alkyl, and —O—C$_{1-6}$alkyl,
(6) —(P=O)R$^j$R$^k$, wherein each of R$^j$ and R$^k$ is independently hydrogen or C$_{1-6}$alkyl,
(7) C$_{2-6}$alkenyl, and
(8) phenyl, optionally substituted with one to four substituents independently selected from halogen, C$_{1-6}$alkyl, and —O—C$_{1-6}$alkyl;
or a pharmaceutically acceptable salt thereof.

2. The compound of claim 1 of formula (Ia):

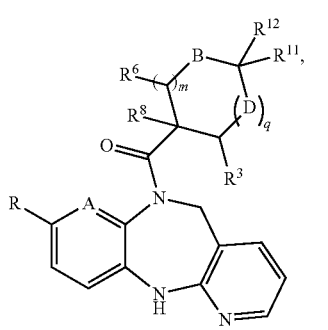

(Ia)

or a pharmaceutically acceptable salt thereof.
3. The compound of claim 2, wherein:
A is —CH= or —N=;
B is —CH(R$^9$)—, —O— or —N(R$^{10}$)—;
D is —CH(R$^5$)— or —N(R$^5$)—;
m is 0, 1 or 2; q is 0 or 1; and
R$^8$ is selected from the group consisting of hydrogen, C$_{1-4}$alkyl, —CN, and phenyl;
or a pharmaceutically acceptable salt thereof.
4. The compound of claim 3, wherein:
R is selected from the group consisting of:
   (1) hydrogen,
   (2) halogen,
   (3) —CN,
   (4) —S(O)$_2$—R$^f$, wherein R$^f$ is selected from the group consisting of (a) C$_{1-4}$alkyl optionally substituted with —NH$_2$, (b) C$_{3-6}$cycloalkyl, and (c) phenyl optionally substituted with one to three halogens,
   (5) C$_{1-6}$alkyl, optionally substituted with one to four substituents independently selected from (a) halo-

474 gen, (b) —CN, (c) —OR$^d$, (d) —(C=O)—R$^e$, (e) —NR$^x$R$^y$, and (f) heterocyclyl; wherein R$^d$ is hydrogen or C$_{1-4}$alkyl optionally substituted with heterocyclyl; R$^e$ is hydroxyl or heterocyclyl;
   each of R$^x$ and R$^y$ is independently selected from the group consisting of hydrogen, C$_{1-6}$alkyl, and C$_{3-6}$cycloalkyl; wherein the C$_{3-6}$cycloalkyl is optionally substituted with one to four substituents independently selected from halogen and C$_{1-4}$alkyl optionally substituted with one to four halogens; and
   the heterocyclyl of (f) is optionally substituted with one to three substituents independently selected from halogen and C$_{1-6}$alkyl,
(6) —O—C$_{1-6}$alkyl,
(7) —NR$^x$R$^y$, wherein each of R$^x$ and R$^y$ is independently selected from the group consisting of (a) hydrogen, (b) (c) C$_{3-6}$cycloalkyl, (d)$_{1-6}$alkyl, (e) phenyl optionally substituted with one to four halogens, and (f) heterocyclyl optionally substituted with C$_{1-4}$alkyl; wherein the C$_{1-6}$alkyl of (b) is optionally substituted with one to four substituents independently selected from halogen, —O—C$_{1-4}$alkyl, C$_{3-6}$cycloalkyl, and heterocyclyl,
(8) —(C=O)—NR$^x$R$^y$, wherein each of R$^x$ and R$^y$ is independently selected from the group consisting of (a) hydrogen, (b) C$_{1-6}$alkyl, and (c) phenyl optionally substituted with one to three halogens,
(9) —(C=O)-heterocyclyl, wherein the heterocyclyl is optionally substituted with one to four substituents independently selected from halogen and C$_{1-6}$alkyl, and
(10) heterocyclyl, which is optionally substituted with one to four substituents independently selected from (a) halogen, (b) hydroxyl, (c) —CN, (d) oxo, (e) C$_{1-6}$alkyl optionally substituted with one to four substituents independently selected from halogen, —O—C$_{1-6}$alkyl, and heterocyclyl, (f) —O—C$_{1-6}$alkyl, (g) —(C=O)—NH$_2$, (h) (i) —(C=O)—C$_{2-6}$alkenyl, (j) C$_{3-6}$cycloalkyl optionally substituted with one to four halogens, (k) —NR$^j$R$^k$, wherein each of R$^j$ and R$^k$ is independently selected from hydrogen and C$_{1-6}$alkyl optionally substituted with —(C=O)—N(C$_{1-6}$alkyl)(C$_{1-6}$alkyl), (l) phenyl optionally substituted with halogen or —O$_{1-6}$alkyl, and (m) heterocyclyl optionally substituted with halogen or C$_{1-6}$alkyl;
or a pharmaceutically acceptable salt thereof.
5. The compound of claim 1, wherein:
each occurrence of R$^3$, R$^4$, R$^6$, R$^7$ and R$^9$, when present, is independently selected from the group consisting of:
   (1) hydrogen,
   (2) —O—C$_{1-6}$alkyl,
   (3) C$_{1-6}$alkyl, optionally substituted with one to four halogens,
   (4) C$_{3-7}$cycloalkyl,
   (5) —(C=O)—O—C$_{1-6}$alkyl, and
   (6) phenyl, optionally substituted with one to four halogens;
or a pharmaceutically acceptable salt thereof.
6. The compound of claim 5, wherein:
each occurrence of R$^5$ and R$^{10}$, when present, is independently selected from the group consisting of:
   (1) hydrogen,
   (2) C$_{1-4}$alkyl, optionally substituted with one to three halogens, and (3) C$_{3-7}$cycloalkyl, optionally substituted with one to three halogens;

or a pharmaceutically acceptable salt thereof.

7. The compound of claim 6, wherein:

R$^8$ is selected from the group consisting of:
(1) hydrogen,
(2) —CN,
(3) C$_{1-4}$alkyl, and
(4) phenyl;

or a pharmaceutically acceptable salt thereof.

8. The compound of claim 7, wherein:

R$^{11}$ and R$^{12}$ together form an oxo; or alternatively, each occurrence of R$^{11}$ and R$^{12}$ is independently selected from the group consisting of:
(1) hydrogen,
(2) halogen,
(3) —O—C$_{1-6}$alkyl, optionally substituted with one to three halogens,
(4) —O—C$_{3-6}$cycloalkyl, optionally substituted with one to three halogens,
(5) —NR$^x$R$^y$, wherein each of R$^x$ and R$^y$ is independently selected from the group consisting of (a) hydrogen, (b) C$_{1-6}$alkyl, and (c) C$_{3-6}$cycloalkyl; wherein the C$_{1-6}$alkyl of (b) is optionally substituted with one to four substituents independently selected from halogen, —O—C$_{1-6}$alkyl, and C$_{3-6}$cycloalkyl; and
the C$_{3-6}$cycloalkyl of (c) is optionally substituted with one to four substituents independently selected from halogen and C$_{1-4}$alkyl optionally substituted with one to four halogens,
(6) C$_{1-6}$alkyl, optionally substituted with one to four substituents independently selected from halogen, hydroxyl, —O—C$_{1-6}$alkyl, and C$_{3-6}$cycloalkyl,
(7) —CN,
(8) hydroxyl,
(9) —(C═O)—C$_{1-6}$alkyl,
(10) C$_{2-6}$alkenyl,
(11) phenyl, and
(12) heterocyclyl, optionally substituted with one to four substituents independently selected from halogen and C$_{1-6}$alkyl;

or a pharmaceutically acceptable salt thereof.

9. The compound of claim 8, wherein:

each occurrence of R$^b$ is independently selected from the group consisting of:
(1) halogen,
(2) hydroxyl,
(3) —CN,
(4) oxo,
(5) —O—C$_{1-6}$alkyl, wherein the alkyl is optionally substituted with one to four substituents independently selected from halogen, and C$_{3-6}$cycloalkyl,
(6) C$_{1-6}$alkyl, optionally substituted with one to four substituents independently selected from (a) halogen, (b) hydroxyl, (c) —O—C$_{1-4}$alkyl, (d) C$_{3-6}$cycloalkyl, and (e) —NR$^x$R$^y$, wherein each of R$^x$ and R$^y$ is independently selected from the group consisting of hydrogen, C$_{1-6}$alkyl, C$_{3-6}$cycloalkyl, phenyl optionally substituted with one to four halogens, and heterocyclyl,
(7) C$_{3-7}$cycloalkyl, optionally substituted with one to four substituents independently selected from halogen and C$_{1-6}$alkyl,
(8) phenyl, optionally substituted with one to four halogens, and
(9) heterocyclyl, optionally substituted with one to four substituents independently selected halogen, C$_{1-6}$alkyl, and —O—C$_{1-6}$alkyl;

or a pharmaceutically acceptable salt thereof.

10. The compound of claim 9, wherein:

each occurrence of the heterocyclyl is independently a monocyclic or bicyclic saturated, partially unsaturated or aromatic ring moiety having at least one ring heteroatom and at least one ring carbon atom, wherein the heteroatom is selected from the group consisting of oxygen, sulfur, and nitrogen; and wherein the bicyclic ring moiety is a fused, spirocycle or bridged bicyclic ring moiety;

or a pharmaceutically acceptable salt thereof.

11. The compound of claim 9, wherein:

each occurrence of the heterocyclyl is independently a 7-12 membered fused bicyclic ring moiety, wherein:
a 4-6 membered heterocyclic ring comprising 1-4 heteroatoms selected from oxygen, sulfur and nitrogen and a 5-7 membered heterocyclic ring comprising 1-4 heteroatoms selected from oxygen, sulfur and nitrogen are connected through two ring atoms;
or alternatively, a 4-6 membered heterocyclic ring comprising 1-4 heteroatoms selected from oxygen, sulfur and nitrogen and a C$_{5-10}$ carbocyclic ring are connected through two ring carbon atoms;

or a pharmaceutically acceptable salt thereof.

12. The compound of claim 9, wherein:

each occurrence of the heterocyclyl is independently a 7-12 membered spirocycle ("spiro") bicyclic moiety, wherein two 3-7 membered rings are connected through one common ring atom, and either or both of the 3-7 membered rings comprise at least one heteroatom selected from oxygen, sulfur and nitrogen;

or a pharmaceutically acceptable salt thereof.

13. The compound of claim 9, wherein:

each occurrence of the heterocyclyl is independently selected from the group consisting of: 8-azabicyclo[3.2.1]octanyl, 2-azaspiro[3.3]heptanyl, azaindolyl, azetidinyl, 2,5-diazabicyclo[2.2.2]octanyl, 1,6-diazaspiro[3.3]heptanyl, 2,6-diazaspiro[3.3]heptanyl, 2,3-dihydro-1,4-dioxinyl, 3,6-dihydro-pyranyl, 3,4-dihydro-2H-pyrido[3,2-b][1,4]oxazinyl, 5,6-dihydro-4H-pyrrolo[1,2-b]pyrazolyl, 3,9-dioxa-7-azabicyclo[3.3.1]nonanyl, 2,5-dioxabicyclo[4.1.0]heptanyl, 1,4-dioxanyl, hexahydro-1H-furo[3,4-c]pyrrolyl, 1,2,4,5,6,6a-hexahydropyrrolo[3,4-b]pyrrolyl, imidazolyl, 1H-imidazo[4,5-b]pyridinyl, isoindolinyl, isoxazolyl, morpholinyl, octahydrocyclopenta[1,4]oxazinyl, octahydro-1H-imidazo[4,5-c]pyridinyl, 2-oxa-5-azabicyclo[2.2.1]heptanyl, 3-oxa-6-azabicyclo[3.2.0]heptanyl, 6-oxa-3-azabicyclo[3.1.1]heptanyl, 2-oxa-5-azabicyclo[2.2.2]octanyl, 3-oxa-8-azabicyclo[3.2.1]octanyl, 8-oxa-3-azabicyclo[3.2.1]octanyl, 1-oxa-8-azaspiro[4.5]decanyl, 2-oxa-6-azaspiro[3.3]heptanyl, 4-oxa-7-azaspiro[2.5]octanyl, 6-oxa-2-azaspiro[3.4]octanyl, 7-oxa-2,5-diazaspiro[3.4]octanyl, 3-oxa-1,7-diazaspiro[4.4]nonanyl, 1,4-oxazepanyl, oxazolidinyl, oxetanyl, piperazinyl, piperidinyl, pyrazolo[1,5-b]pyridazinyl, pyrazolyl, pyridazinyl, pyridinyl, pyrimidinyl, pyrrolidinyl, pyrrolyl, tetrahydrofuranyl, 5,6,7,8-tetrahydroimidazo[1,5-a]pyrazinyl, tetrahydropyranyl, 4,5,6,7-tetrahydropyrazolo[1,5-a]pyrazinyl, 4,5,6,7-tetrahydro-2H-pyrazolo[4,3-c]pyridinyl, 1,2,3,6-tetrahydropyridinyl, 1,2,3,4-tetrahydropyrrolo[1,2-a]pyrazinyl, 4,5,6,7-tetrahydro-[1,2,3]triazolo[1,5-a]pyrazinyl, 5,6,7,8-tetrahydro-[1,2,4]triazolo[4,3-a]

pyrazinyl, 5,6,7,8-tetrahydro-[1,2,4]triazolo[1,5-a]pyrazinyl, thiazolyl, and thiophenyl;
or a pharmaceutically acceptable salt thereof.

14. The compound of claim 1 of formula Ib:

(Ib)

wherein:
A is —CH= or —N=;
B is —CH($R^9$)—, —O— or —N($R^{10}$)—;
m is 0, 1 or 2;
q is 0 or 1;
R is selected from the group consisting of:
  (1) hydrogen,
  (2) halogen,
  (3) $C_{1-6}$alkyl, optionally substituted with one to three substituents independently selected from halogen, —$OR^d$, —CN, —(C=O)—$R^e$, —$NR^xR^y$, and heterocyclyl optionally substituted with $C_{1-4}$alkyl; wherein $R^d$ is hydrogen or $C_{1-4}$alkyl optionally substituted with heterocyclyl; $R^e$ is hydroxyl or heterocyclyl;
    each of $R^x$ and $R^y$ is independently selected from the group consisting of (a) hydrogen, (b) $C_{1-6}$alkyl, (c) $C_{3-6}$cycloalkyl, (d) phenyl optionally substituted with one to four halogens, and (e) heterocyclyl;
    wherein the $C_{1-6}$alkyl of (b) is optionally substituted with one to four substituents independently selected from halogen, —O—$C_{1-4}$alkyl, $C_{3-6}$cycloalkyl, and heterocyclyl; and
    the $C_{3-6}$cycloalkyl of (c) is optionally substituted with one to four substituents independently selected from halogen and $C_{1-4}$alkyl, which is optionally substituted with one to four halogens,
  (4) —(C=O)$_t$—$NR^xR^y$, wherein t is 0 or 1; each of $R^x$ and $R^y$ is independently selected from the group consisting of hydrogen, $C_{1-6}$alkyl, $C_{3-6}$cycloalkyl, phenyl optionally substituted with one to four halogens, and heterocyclyl; wherein each of the alkyl, cycloalkyl and heterocyclyl is optionally substituted with one to four substituents independently selected from halogen, —O—$C_{1-4}$alkyl, $C_{3-6}$cycloalkyl, and heterocyclyl, and
  (5) —(C=O)$_t$-heterocyclyl, wherein t is 0 or 1; and the heterocyclyl is optionally substituted with one to four substituents independently selected from $R^b$;
each of $R^4$, $R^9$, $R^{11}$ and $R^{12}$ is independently selected from the group consisting of:
  (1) hydrogen,
  (2) halogen,
  (3) —(O)$_t$—$R^d$, wherein t is 0 or 1; $R^d$ is (a) $C_{1-6}$alkyl or (b) $C_{3-6}$cycloalkyl, the alkyl of (a) is optionally substituted with one to four substituents independently selected from halogen, hydroxyl, —O—$C_{1-4}$alkyl and $C_{3-6}$cycloalkyl; and the cycloalkyl of (b) is optionally substituted with one to three halogens,
  (4) —$NR^xR^y$, wherein each of $R^x$ and $R^y$ is independently selected from the group consisting of (a) hydrogen, (b) $C_{1-6}$alkyl, (c) $C_{3-6}$cycloalkyl, (d) phenyl optionally substituted with one to four halogens, and (e) heterocyclyl;
    wherein the $C_{1-6}$alkyl of (b) is optionally substituted with one to four substituents independently selected from halogen, —O—$C_{1-4}$alkyl, $C_{3-6}$cycloalkyl, and heterocyclyl, and
    the $C_{3-6}$cycloalkyl of (c) is optionally substituted with one to four substituents independently selected from halogen and $C_{1-4}$alkyl, which is optionally substituted with one to four halogens;
  (5) phenyl; and
  (6) —(C=O)$_t$-heterocyclyl, wherein t is 0 or 1; and the heterocyclyl is optionally substituted with one to four substituents independently selected from $R^b$;
$R^8$ is hydrogen or $C_{1-4}$alkyl;
$R^{10}$ is selected from the group consisting of:
  (1) hydrogen,
  (2) $C_{1-4}$alkyl, optionally substituted with one to three halogens, and
  (3) $C_{3-7}$cycloalkyl, optionally substituted with one to three halogens;
each occurrence of $R^b$ is independently selected from the group consisting of:
  (1) halogen,
  (2) hydroxyl,
  (3) —CN,
  (4) oxo,
  (5) —O—$C_{1-6}$alkyl, wherein the alkyl is optionally substituted with one to four substituents independently selected from halogen and $C_{3-6}$cycloalkyl,
  (6) —(C=O)$_t$—$C_{1-6}$alkyl, wherein t is 0 or 1, and
  (7) —(C=O)$_t$-heterocyclyl, wherein t is 0 or 1; and
wherein each occurrence of the heterocyclyl in this claim is independently selected from the group consisting of azaindolyl, azetidinyl, 1,4-dioxanyl, imidazolyl, isoindolinyl, morpholinyl, oxazolidinyl, oxetanyl, piperazinyl, piperidinyl, pyrazolyl, pyridinyl, pyrimidinyl, pyrrolidinyl, tetrahydrofuranyl, tetrahydropyranyl, thiazolyl, 2-azaspiro[3.3]heptanyl, 2,5-diazabicyclo[2.2.2]octanyl, 1,6-diazaspiro[3.3]heptanyl, 2,6-diazaspiro[3.3]heptanyl, 2,3-dihydro-1,4-dioxinyl, 3,9-dioxa-7-azabicyclo[3.3.1]nonanyl, 2,5-dioxabicyclo[4.1.0]heptanyl, 2-oxa-5-azabicyclo[2.2.2]octanyl, 1-oxa-8-azaspiro[4.5]decanyl, 2-oxa-6-azaspiro[3.3]heptanyl, 4-oxa-7-azaspiro[2.5]octanyl, 6-oxa-2-azaspiro[3.4]octanyl, 7-oxa-2,5-diazaspiro[3.4]octanyl, 3-oxa-1,7-diazaspiro[4.4]nonanyl, 3,6-dihydropyranyl, 3,4-dihydro-2H-pyrido[3,2-b][1,4]oxazinyl, 5,6-dihydro-4H-pyrrolo[1,2-b]pyrazolyl, hexahydro-1H-furo[3,4-c]pyrrolyl, 1,2,4,5,6,6a-hexahydropyrrolo[3,4-b]pyrrolyl, 1H-imidazo[4,5-b]pyridinyl, octahydrocyclopenta[1,4]oxazinyl, octahydro-1H-imidazo[4,5-c]pyridinyl, 3-oxa-6-azabicyclo[3.2.0]heptanyl, pyrazolo[1,5-b]pyridazinyl, 5,6,7,8-tetrahydroimidazo[1,5-a]pyrazinyl, 4,5,6,7-tetrahydropyrazolo[1,5-a]pyrazinyl, 4,5,6,7-tetrahydro-2H-pyrazolo[4,3-c]pyridinyl, 1,2,3,4-tetrahydropyrrolo[1,2-a]pyrazinyl, 4,5,6,7-tetrahydro-[1,2,3]triazolo[1,5-a]pyrazinyl, 5,6,7,8-tetrahydro-[1,2,4]triazolo[4,3-a]pyrazinyl, and 5,6,7,8-tetrahydro-[1,2,4]triazolo[1,5-a]pyrazinyl;
or a pharmaceutically acceptable salt thereof.

15. The compound of claim 1 selected from the group consisting of
- ((2R,5S)-5-isopropoxytetrahydro-2H-pyran-2-yl)(8-(tetrahydro-2H-pyran-4-yl)-5,11-dihydro-6H-benzo[b]pyrido[2,3-e][1,4]diazepin-6-yl)methanone,
- 8-morpholin-4-yl-6-({1-[1-(trifluoromethyl)cyclopropyl]piperidin-4-yl}carbonyl)-6,11-dihydro-5H-pyrido[2,3-b][1,5]benzodiazepine,
- 8-morpholin-4-yl-6-{[1-(2,2,2-trifluoro-1,1-dimethylethyl)piperidin-4-yl]carbonyl}-6,11-dihydro-5H-pyrido[2,3-b][1,5]benzodiazepine,
- 8-morpholin-4-yl-6-({1-[1-(trifluoromethyl)cyclobutyl]piperidin-4-yl}carbonyl)-6,11-dihydro-5H-pyrido[2,3-b][1,5]benzodiazepine,
- (8-((1S,4S)-2-oxa-5-azabicyclo[2.2.2]octan-5-yl)-5,11-dihydro-6H-benzo[b]pyrido[2,3-e][1,4]diazepin-6-yl)((2R,5S)-5-isopropoxytetrahydro-2H-pyran-2-yl)methanone,
- (8-((1R,4R)-2-oxa-5-azabicyclo[2.2.2]octan-5-yl)-5,11-dihydro-6H-benzo[b]pyrido[2,3-e][1,4]diazepin-6-yl)((2R,5S)-5-isopropoxytetrahydro-2H-pyran-2-yl)methanone,
- (8-(6-oxa-2-azaspiro[3.5]nonan-2-yl)-5,11-dihydro-6H-benzo[b]pyrido[2,3-e][1,4]diazepin-6-yl)((2R,5S)-5-isopropoxytetrahydro-2H-pyran-2-yl)methanone,
- (8-(3,9-dioxa-7-azabicyclo[3.3.1]nonan-7-yl)-5,11-dihydro-6H-benzo[b]pyrido[2,3-e][1,4]diazepin-6-yl)((2R,5S)-5-isopropoxytetrahydro-2H-pyran-2-yl)methanone,
- ((2R,5S)-5-isopropoxytetrahydro-2H-pyran-2-yl)(8-((1S,4S)-1-methyl-2-oxa-5-azabicyclo[2.2.1]heptan-5-yl)-5,11-dihydro-6H-benzo[b]pyrido[2,3-e][1,4]diazepin-6-yl)methanone,
- 6-[(Trans-4-methoxycyclohexyl)carbonyl]-8-morpholin-4-yl-6,11-dihydro-5H-pyrido[2,3-b][1,5]benzodiazepine,
- 6-[(Cis-4-methoxycyclohexyl)carbonyl]-8-morpholin-4-yl-6,11-dihydro-5H-pyrido[2,3-b][1,5]benzodiazepine,
- 6-{[(1S,3R)-3-ethoxycyclopentyl]carbonyl}-8-(8-oxa-3-azabicyclo[3.2.1]oct-3-yl)-6,11-dihydro-5H-pyrido[2,3-b][1,5]benzodiazepine,
- 6-{[(1R,3S,4S)-3-ethoxy-4-fluorocyclopentyl]carbonyl}-8-[(1S,4S)-2-oxa-5-azabicyclo[2.2.2]oct-5-yl]-6,11-dihydro-5H-pyrido[2,3-b][1,5]benzodiazepine,
- 6-{[(1R,3S,4S)-3-ethoxy-4-fluorocyclopentyl]carbonyl}-8-[(1R,4R)-2-oxa-5-azabicyclo[2.2.2]oct-5-yl]-6,11-dihydro-5H-pyrido[2,3-b][1,5]benzodiazepine,
- (8-(8-oxa-3-azabicyclo[3.2.1]octan-3-yl)-5,11-dihydro-6H-benzo[b]pyrido[2,3-e][1,4]diazepin-6-yl)((2R,5S)-5-isopropoxytetrahydro-2H-pyran-2-yl)methanone,
- ((2R,5S)-5-isopropoxytetrahydro-2H-pyran-2-yl)(8-((1R,3R,5S)-3-methoxy-8-azabicyclo[3.2.1]octan-8-yl)-5,11-dihydro-6H-benzo[b]pyrido[2,3-e][1,4]diazepin-6-yl)methanone,
- (8-(3-oxa-8-azabicyclo[3.2.1]octan-8-yl)-5,11-dihydro-6H-benzo[b]pyrido[2,3-e][1,4]diazepin-6-yl)((2R,5S)-5-isopropoxytetrahydro-2H-pyran-2-yl)methanone,
- 6-{[Trans-4-(1-methylethoxy)cyclohexyl]carbonyl}-8-(2-oxa-5-azabicyclo[2.2.2]oct-5-yl)-6,1-dihydro-5H-pyrido[2,3-b][1,5]benzodiazepine,
- 6-[(trans-4-ethoxycyclohexyl)carbonyl]-8-(2-oxa-5-azabicyclo[2.2.2]oct-5-yl)-6,11-dihydro-5H-pyrido[2,3-b][1,5]benzodiazepine,
- 6-{[trans-4-(1-methylethoxy)cyclohexyl]carbonyl}-8-(6-oxa-2-azaspiro[3.5]non-2-yl)-6,11-dihydro-5H-pyrido[2,3-b][1,5]benzodiazepine,
- 8-(2-oxa-5-azabicyclo[2.2.2]oct-5-yl)-6-{[1-(2,2,2-trifluoroethyl)piperidin-4-yl]carbonyl}-6,11-dihydro-5H-pyrido[2,3-b][1,5]benzodiazepine,
- 8-(6-oxa-2-azaspiro[3.5]non-2-yl)-6-{[1-(2,2,2-trifluoroethyl)piperidin-4-yl]carbonyl}-6,11-dihydro-5H-pyrido[2,3-b][1,5]benzodiazepine, and
- 8-[(3-endo)-3-methoxy-8-azabicyclo[3.2.1]oct-8-yl]-6-{[1-(2,2,2-trifluoroethyl)azepan-4-yl]carbonyl}-6,11-dihydro-5H-pyrido[2,3-b][1,5]benzodiazepine.

16. A composition which comprises an inert carrier and a compound of claim 1 or a pharmaceutically acceptable salt thereof.

* * * * *

UNITED STATES PATENT AND TRADEMARK OFFICE
CERTIFICATE OF CORRECTION

PATENT NO. : 10,442,819 B2
APPLICATION NO. : 15/532549
DATED : October 15, 2019
INVENTOR(S) : Christian Fischer et al.

Page 1 of 1

It is certified that error appears in the above-identified patent and that said Letters Patent is hereby corrected as shown below:

On the Title Page

(71) appears as follows:
(71) Applicants: Christian Fischer, et al.

(71) should appear as follows:
(71) Applicant: Merck Sharp & Dohme Corp.,
Rahway, NJ (US)

Signed and Sealed this
Thirty-first Day of December, 2019

Andrei Iancu
*Director of the United States Patent and Trademark Office*